US007314925B2

(12) United States Patent
Sablon et al.

(10) Patent No.: US 7,314,925 B2
(45) Date of Patent: Jan. 1, 2008

(54) CONSTRUCTS AND METHODS FOR EXPRESSION OF RECOMBINANT HCV ENVELOPE PROTEINS

(75) Inventors: Erwin Sablon, Merchtem (BE); Annie Van Broekhoven, Berchem (BE); Fons Bosman, Opwijk (BE); Erik Depla, Destelbergen (BE); Geert Deschamps, Aalter (BE)

(73) Assignee: Innogenetics N.V., Ghent (BE)

( * ) Notice: Subject to any disclaimer, the term of this patent is extended or adjusted under 35 U.S.C. 154(b) by 769 days.

(21) Appl. No.: 10/128,587

(22) Filed: Apr. 24, 2002

(65) Prior Publication Data

US 2003/0152940 A1 Aug. 14, 2003

Related U.S. Application Data

(60) Provisional application No. 60/305,604, filed on Jul. 17, 2001.

(30) Foreign Application Priority Data

Apr. 24, 2001 (EP) ................................ 01870088

(51) Int. Cl.

| | |
|---|---|
| ***C07H 21/00*** | (2006.01) |
| ***C12P 21/00*** | (2006.01) |
| ***C12N 15/00*** | (2006.01) |
| ***C12N 15/09*** | (2006.01) |
| ***C12N 15/51*** | (2006.01) |
| *A61K 39/00* | (2006.01) |
| *A61K 39/29* | (2006.01) |

(52) U.S. Cl. ................ 536/23.72; 536/23.4; 536/23.5; 435/69.1; 435/69.3; 435/69.7; 435/69.8; 435/70.1; 435/71.1; 435/320.1; 424/184.1; 424/185.1; 424/189.1; 424/192.1

(58) Field of Classification Search .............. 435/69.1, 435/69.3, 69.7, 69.8, 69.9, 71.1, 243, 254.1, 435/254.11, 254.2, 255.1, 255.6, 320.1; 424/184.1, 424/188.1, 192.1, 205.1, 225.1, 228.1; 536/23.1, 536/23.4, 23.72

See application file for complete search history.

(56) References Cited

U.S. PATENT DOCUMENTS

| | | | | |
|---|---|---|---|---|
| 5,135,854 A | | 8/1992 | Mackay et al. | |
| 5,503,993 A | * | 4/1996 | Hayasuke et al. | 435/69.8 |
| 5,585,257 A | * | 12/1996 | De Baetselier et al. | 435/320.1 |
| 5,629,203 A | * | 5/1997 | Shuster | 435/320.1 |
| 5,935,824 A | * | 8/1999 | Sgarlato | 435/69.7 |
| 6,613,333 B1 | | 9/2003 | Leroux-Roels et al. | |

FOREIGN PATENT DOCUMENTS

| | | | |
|---|---|---|---|
| EP | 0288198 | | 10/1988 |
| EP | WO95/12677 | * | 5/1995 |
| WO | WO94/01132 | | 1/1994 |
| WO | WO 09/512677 | | 5/1995 |
| WO | WO96/04385 | | 2/1996 |
| WO | WO97/22706 | * | 6/1997 |
| WO | WO98/28429 | * | 7/1998 |
| WO | WO99/37793 | * | 7/1999 |
| WO | WO99/54735 | | 10/1999 |
| WO | WO99/67285 | | 12/1999 |
| WO | WO 01/30815 | | 5/2001 |
| WO | WO 02/055548 | | 7/2002 |
| WO | WO 03/051912 | | 6/2003 |

OTHER PUBLICATIONS

Yamamoto et al., Biochemical and Biophysical Research Communications, vol. 149 No. 2, pp. 431-436 (Dec. 1987).*

Hopp et al., BIO/TECHNOLOGY, vol. 6, pp. 1204-1210 (Oct. 1988).*

Jigami et al., Gene, vol. 43 No. 3, pp. 273-279 (1986).*

Gellissen et al., Biotechnology Advances, vol. 10 No. 2, pp. 179-189 (1992).*

Weydemann et al., Applied Microbiology and Biotechnology, Voume 44 No. 3-4, pp. 377-385 (Oct. 1995).*

Bowie et al., Science, vol. 247 No. 4948, pp. 1306-1310 (Mar. 1990).*

Oka et al. "Human lysozyme secretion increased by alpha-factor pro-sequence in *Pichia pastoris*," Bioscience, Biotechnology, and Biochemistry, vol. 63 No. 11, pp. 1977-1983 (Nov. 1999).*

Kuroda et al, The Journal of Biological Chemistry, 1992, vol. 267, No. 3, issue of Jan. 25, pp. 1953-1961.

Kuroda et al, Applied Microbiology Biotechnology, 1993, 40:333-340.

Helenius, Molecular Biology of the Cell, 1994, vol. 5, 253-265, March.

Liang et al, Ann Intern Med, 2000, 132:296-305.

Rosa et al, PNAS, 1996, 93, pp. 1759-1763, March.

Ralston et al, J. Virology, 1993, No. pp. 6753-6761, vol. 67, No. 11.

Fransca et al, The Journal of Immunology, 1999, 163: 650-658.

Lechmann et al, Hepatology, 1996, 24:790-795.

Klenerman et al, Science, 2000, vol. 289, Sep. 22, p. 2003a.

Mustilli et al, Res Microbiol, 1999, 150 (1999) 179-187.

Diminsky etal, Vaccine, Apr.-May 1997; 15(6-7):637-47.

Sarobe, Journal of Virology, 2003, p. 10862-10871, vol. 77, No. 20.

Choo et al, PNAS, 1994, pp. 1294-1298.

Ghany, Hepatology, 2003, 38, 1092-1094.

Lerous-Roels et al, Hepatology, 2003, 34, 449A.

(Continued)

*Primary Examiner*—Zachariah Lucas
(74) *Attorney, Agent, or Firm*—Nixon & Vanderhye P.C.

(57) ABSTRACT

The current invention relates to vectors and methods for efficient expression of HCV envelope proteins in eukaryotic cells. More particularly said vectors comprise the coding sequence for an avian lysozyme signal peptide or a functional equivalent thereof joined to a HCV envelope protein or a part thereof. Said avian lysozyme signal peptide is efficiently removed when the protein comprising said avian lysozyme signal peptide joined to a HCV envelope protein or a part thereof is expressed in a eukaryotic cell. Suitable eukaryotic cells include yeast cells such as *Saccharomyces* or *Hansenula* cells.

32 Claims, 54 Drawing Sheets

OTHER PUBLICATIONS

Figure 1:
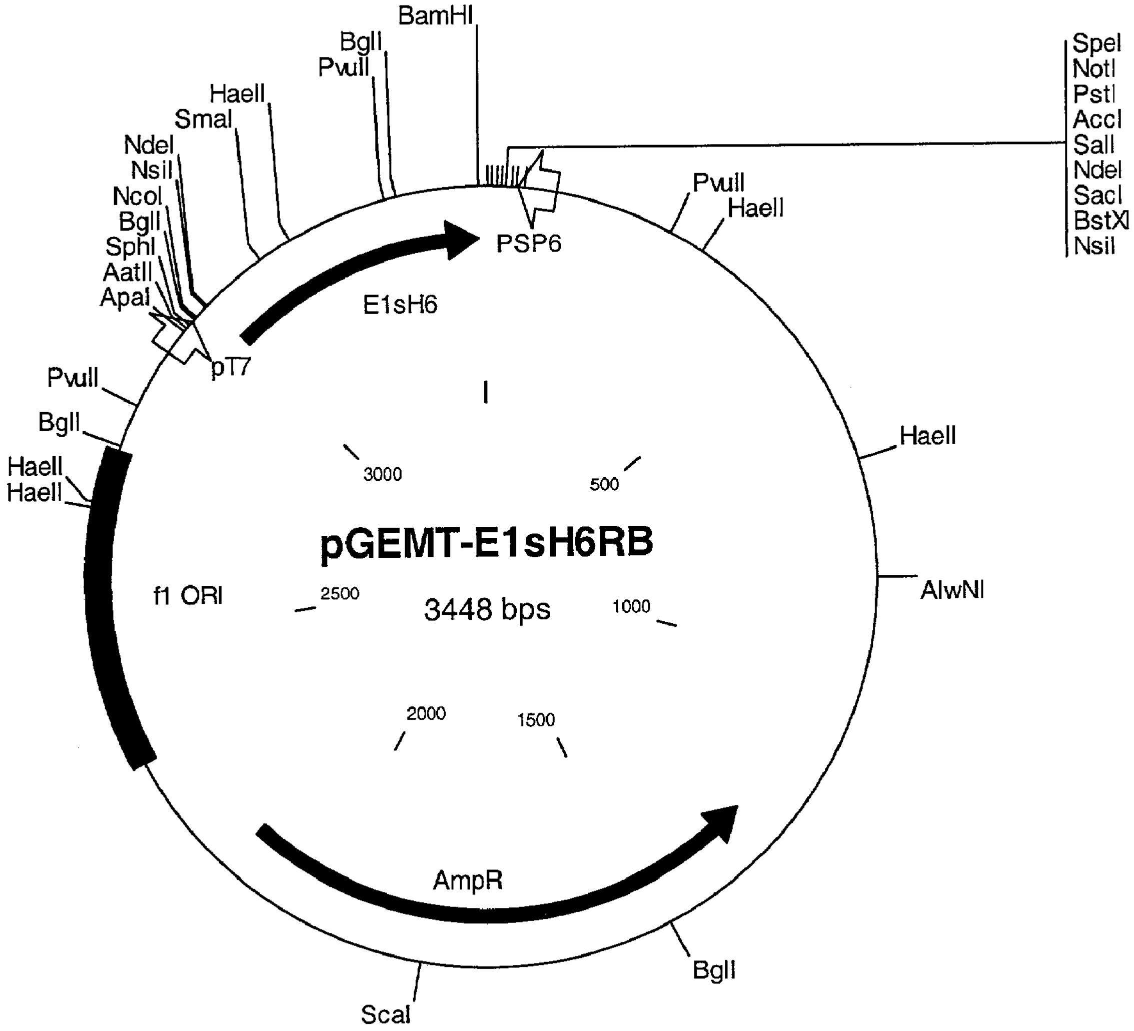

Nevens et al, Hepatology, 2003, 38, 1289-1296.
Pawlotsky, Hepatology, 2003, 39, 554-567.
Forns, J. Hepatol, 2002, 37, 684-395.
Major, J. Virology, 2002, 76, 6586-6595.
Bassett, Hepatology, 2001, 33, 1479-1487.
Weiner, J. Virology, 2001,75, 7142-7148.
Mehta, Lancet, 2002, 359, 1478-1483.
Herscovics, FASEB, 1993, 7, 540-550.
Botarelli et al, Gastroenterology, 1993, 104:580-587.
Houghton et al, Prospects for Prophylactic and Therapeutic Hepatitis C Virus Vaccines, 1995, pp. 237-243.

* cited by examiner

SEQUENCE LISTING

```
<160> NUMBER OF SEQ ID NOS: 98

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence:
      avian lysozyme signal peptide
<220> FEATURE:
<221> NAME/KEY: MISC_FEATURE
<222> LOCATION: (2)..(2)
<223> OTHER INFORMATION: Xaa is Arg, Lys or Val
<220> FEATURE:
<221> NAME/KEY: MISC_FEATURE
<222> LOCATION: (3)..(3)
<223> OTHER INFORMATION: Xaa is Ser, Ala, Val, Arg or Met
<220> FEATURE:
<221> NAME/KEY: MISC_FEATURE
```

-continued

<222> LOCATION: (4)..(4)
<223> OTHER INFORMATION: Xaa is Leu or Phe
<220> FEATURE:
<221> NAME/KEY: MISC_FEATURE
<222> LOCATION: (5)..(5)
<223> OTHER INFORMATION: Xaa is Leu or Ala
<220> FEATURE:
<221> NAME/KEY: MISC_FEATURE
<222> LOCATION: (6)..(6)
<223> OTHER INFORMATION: Xaa is Ile, Thr, Phe or Val
<220> FEATURE:
<221> NAME/KEY: MISC_FEATURE
<222> LOCATION: (7)..(7)
<223> OTHER INFORMATION: Xaa is Leu, Phe or Ala
<220> FEATURE:
<221> NAME/KEY: MISC_FEATURE
<222> LOCATION: (8)..(8)
<223> OTHER INFORMATION: Xaa is Val, Ile, Ala, Leu or Cys
<220> FEATURE:
<221> NAME/KEY: MISC_FEATURE
<222> LOCATION: (9)..(9)
<223> OTHER INFORMATION: Xaa is Leu, Phe, Ala or Ile
<220> FEATURE:
<221> NAME/KEY: MISC_FEATURE
<222> LOCATION: (10)..(10)
<223> OTHER INFORMATION: Xaa is Cys, Phe, Ser or Leu
<220> FEATURE:
<221> NAME/KEY: MISC_FEATURE
<222> LOCATION: (11)..(11)
<223> OTHER INFORMATION: Xaa is Phe, Leu, Ser or Pro
<220> FEATURE:
<221> NAME/KEY: MISC_FEATURE
<222> LOCATION: (12)..(12)
<223> OTHER INFORMATION: Xaa is Leu, Ala or Met
<220> FEATURE:
<221> NAME/KEY: MISC_FEATURE
<222> LOCATION: (13)..(13)
<223> OTHER INFORMATION: Xaa is Pro, Ala or Ile
<220> FEATURE:
<221> NAME/KEY: MISC_FEATURE
<222> LOCATION: (14)..(14)
<223> OTHER INFORMATION: Xaa is Leu or Ala
<220> FEATURE:
<221> NAME/KEY: MISC_FEATURE
<222> LOCATION: (15)..(15)
<223> OTHER INFORMATION: Xaa is Ala, Val, Ser or Met
<220> FEATURE:
<221> NAME/KEY: MISC_FEATURE
<222> LOCATION: (16)..(16)
<223> OTHER INFORMATION: Xaa is Ala, Lys or Ser
<220> FEATURE:
<221> NAME/KEY: MISC_FEATURE
<222> LOCATION: (17)..(17)
<223> OTHER INFORMATION: Xaa is Leu, Pro, Gln or Ile

<400> SEQUENCE: 1

```
Met Xaa Xaa Xaa Xaa Xaa Xaa Xaa Xaa Xaa Xaa Xaa Xaa Xaa Xaa Xaa
1               5                   10                  15

Xaa Gly
```

<210> SEQ ID NO 2
<211> LENGTH: 135
<212> TYPE: PRT
<213> ORGANISM: Artificial Sequence
<220> FEATURE:
<223> OTHER INFORMATION: Description of Artificial Sequence: hepatitis C virus

<400> SEQUENCE: 2

```
Tyr Glu Val Arg Asn Val Ser Gly Met Tyr His Val Thr Asn Asp Cys
1               5                   10                  15

Ser Asn Ser Ser Ile Val Tyr Glu Ala Ala Asp Met Ile Met His Thr
            20                  25                  30
```

-continued

```
Pro Gly Cys Val Pro Cys Val Arg Glu Asn Asn Ser Ser Arg Cys Trp
        35                  40                  45

Val Ala Leu Thr Pro Thr Leu Ala Ala Arg Asn Ala Ser Val Pro Thr
    50                  55                  60

Thr Thr Ile Arg Arg His Val Asp Leu Leu Val Gly Ala Ala Ala Phe
65                  70                  75                  80

Cys Ser Ala Met Tyr Val Gly Asp Leu Cys Gly Ser Val Phe Leu Val
                85                  90                  95

Ser Gln Leu Phe Thr Ile Ser Pro Arg Arg His Glu Thr Val Gln Asp
            100                 105                 110

Cys Asn Cys Ser Ile Tyr Pro Gly His Ile Thr Gly His Arg Met Ala
        115                 120                 125

Trp Asp Met Met Met Asn Trp
    130                 135


<210> SEQ ID NO 3
<211> LENGTH: 290
<212> TYPE: PRT
<213> ORGANISM: hepatitis C virus

<400> SEQUENCE: 3

His Thr Arg Val Ser Gly Gly Ala Ala Ala Ser Asp Thr Arg Gly Leu
1               5                   10                  15

Val Ser Leu Phe Ser Pro Gly Ser Ala Gln Lys Ile Gln Leu Val Asn
            20                  25                  30

Thr Asn Gly Ser Trp His Ile Asn Arg Thr Ala Leu Asn Cys Asn Asp
        35                  40                  45

Ser Leu Gln Thr Gly Phe Phe Ala Ala Leu Phe Tyr Lys His Lys Phe
    50                  55                  60

Asn Ser Ser Gly Cys Pro Glu Arg Leu Ala Ser Cys Arg Ser Ile Asp
65                  70                  75                  80

Lys Phe Ala Gln Gly Trp Gly Pro Leu Thr Tyr Thr Glu Pro Asn Ser
                85                  90                  95

Ser Asp Gln Arg Pro Tyr Cys Trp His Tyr Ala Pro Arg Pro Cys Gly
            100                 105                 110

Ile Val Pro Ala Ser Gln Val Cys Gly Pro Val Tyr Cys Phe Thr Pro
        115                 120                 125

Ser Pro Val Val Val Gly Thr Thr Asp Arg Phe Gly Val Pro Thr Tyr
    130                 135                 140

Asn Trp Gly Ala Asn Asp Ser Asp Val Leu Ile Leu Asn Asn Thr Arg
145                 150                 155                 160

Pro Pro Arg Gly Asn Trp Phe Gly Cys Thr Trp Met Asn Gly Thr Gly
                165                 170                 175

Phe Thr Lys Thr Cys Gly Gly Pro Pro Cys Asn Ile Gly Gly Ala Gly
            180                 185                 190

Asn Asn Thr Leu Thr Cys Pro Thr Asp Cys Phe Arg Lys His Pro Glu
        195                 200                 205

Ala Thr Tyr Ala Arg Cys Gly Ser Gly Pro Trp Leu Thr Pro Arg Cys
    210                 215                 220

Met Val His Tyr Pro Tyr Arg Leu Trp His Tyr Pro Cys Thr Val Asn
225                 230                 235                 240

Phe Thr Ile Phe Lys Val Arg Met Tyr Val Gly Gly Val Glu His Arg
                245                 250                 255

Phe Glu Ala Ala Cys Asn Trp Thr Arg Gly Glu Arg Cys Asp Leu Glu
            260                 265                 270
```

-continued

```
Asp Arg Asp Arg Ser Glu Leu Ser Pro Leu Leu Leu Ser Thr Thr Glu
        275                 280                 285

Trp Gln
    290
```

<210> SEQ ID NO 4
<211> LENGTH: 141
<212> TYPE: PRT
<213> ORGANISM: hepatitis C virus

<400> SEQUENCE: 4

```
Tyr Glu Val Arg Asn Val Ser Gly Met Tyr His Val Thr Asn Asp Cys
1               5                   10                  15

Ser Asn Ser Ser Ile Val Tyr Glu Ala Ala Asp Met Ile Met His Thr
            20                  25                  30

Pro Gly Cys Val Pro Cys Val Arg Glu Asn Asn Ser Ser Arg Cys Trp
        35                  40                  45

Val Ala Leu Thr Pro Thr Leu Ala Ala Arg Asn Ala Ser Val Pro Thr
    50                  55                  60

Thr Thr Ile Arg Arg His Val Asp Leu Leu Val Gly Ala Ala Ala Phe
65                  70                  75                  80

Cys Ser Ala Met Tyr Val Gly Asp Leu Cys Gly Ser Val Phe Leu Val
                85                  90                  95

Ser Gln Leu Phe Thr Ile Ser Pro Arg Arg His Glu Thr Val Gln Asp
            100                 105                 110

Cys Asn Cys Ser Ile Tyr Pro Gly His Ile Thr Gly His Arg Met Ala
        115                 120                 125

Trp Asp Met Met Met Asn Trp His His His His His His
    130                 135                 140
```

<210> SEQ ID NO 5
<211> LENGTH: 301
<212> TYPE: PRT
<213> ORGANISM: hepatitis C virus

<400> SEQUENCE: 5

```
His Thr Arg Val Ser Gly Gly Ala Ala Ala Ser Asp Thr Arg Gly Leu
1               5                   10                  15

Val Ser Leu Phe Ser Pro Gly Ser Ala Gln Lys Ile Gln Leu Val Asn
            20                  25                  30

Thr Asn Gly Ser Trp His Ile Asn Arg Thr Ala Leu Asn Cys Asn Asp
        35                  40                  45

Ser Leu Gln Thr Gly Phe Phe Ala Ala Leu Phe Tyr Lys His Lys Phe
    50                  55                  60

Asn Ser Ser Gly Cys Pro Glu Arg Leu Ala Ser Cys Arg Ser Ile Asp
65                  70                  75                  80

Lys Phe Ala Gln Gly Trp Gly Pro Leu Thr Tyr Thr Glu Pro Asn Ser
                85                  90                  95

Ser Asp Gln Arg Pro Tyr Cys Trp His Tyr Ala Pro Arg Pro Cys Gly
            100                 105                 110

Ile Val Pro Ala Ser Gln Val Cys Gly Pro Val Tyr Cys Phe Thr Pro
        115                 120                 125

Ser Pro Val Val Val Gly Thr Thr Asp Arg Phe Gly Val Pro Thr Tyr
    130                 135                 140

Asn Trp Gly Ala Asn Asp Ser Asp Val Leu Ile Leu Asn Asn Thr Arg
145                 150                 155                 160
```

-continued

```
Pro Pro Arg Gly Asn Trp Phe Gly Cys Thr Trp Met Asn Gly Thr Gly
                165                 170                 175

Phe Thr Lys Thr Cys Gly Gly Pro Pro Cys Asn Ile Gly Gly Ala Gly
            180                 185                 190

Asn Asn Thr Leu Thr Cys Pro Thr Asp Cys Phe Arg Lys His Pro Glu
        195                 200                 205

Ala Thr Tyr Ala Arg Cys Gly Ser Gly Pro Trp Leu Thr Pro Arg Cys
    210                 215                 220

Met Val His Tyr Pro Tyr Arg Leu Trp His Tyr Pro Cys Thr Val Asn
225                 230                 235                 240

Phe Thr Ile Phe Lys Val Arg Met Tyr Val Gly Gly Val Glu His Arg
                245                 250                 255

Phe Glu Ala Ala Cys Asn Trp Thr Arg Gly Glu Arg Cys Asp Leu Glu
            260                 265                 270

Asp Arg Asp Arg Ser Glu Leu Ser Pro Leu Leu Leu Ser Thr Thr Glu
        275                 280                 285

Trp Gln Val Ile Glu Gly Arg His His His His His His
    290                 295                 300


<210> SEQ ID NO 6
<211> LENGTH: 3448
<212> TYPE: DNA
<213> ORGANISM: Artificial Sequence
<220> FEATURE:
<223> OTHER INFORMATION: Description of Artificial Sequence:
      vector pGEMTE1sH6

<400> SEQUENCE: 6

aatcactagt gcggccgcct gcaggtcgac catatgggag agctcccaac gcgttggatg      60

catagcttga gtattctata gtgtcaccta aatagcttgg cgtaatcatg gtcatagctg     120

tttcctgtgt gaaattgtta tccgctcaca attccacaca acatacgagc cggaagcata     180

aagtgtaaag cctggggtgc ctaatgagtg agctaactca cattaattgc gttgcgctca     240

ctgcccgctt tccagtcggg aaacctgtcg tgccagctgc attaatgaat cggccaacgc     300

gcggggagag gcggtttgcg tattgggcgc tcttccgctt cctcgctcac tgactcgctg     360

cgctcggtcg ttcggctgcg gcgagcggta tcagctcact caaaggcggt aatacggtta     420

tccacagaat caggggataa cgcaggaaag aacatgtgag caaaaggcca gcaaaaggcc     480

aggaaccgta aaaaggccgc gttgctggcg tttttcgata ggctccgccc ccctgacgag     540

catcacaaaa atcgacgctc aagtcagagg tggcgaaacc cgacaggact ataaagatac     600

caggcgtttc cccctggaag ctccctcgtg cgctctcctg ttccgaccct gccgcttacc     660

ggatacctgt ccgcctttct cccttcggga agcgtggcgc tttctcatag ctcacgctgt     720

aggtatctca gttcggtgta ggtcgttcgc tccaagctgg gctgtgtgca cgaacccccc     780

gttcagcccg accgctgcgc cttatccggt aactatcgtc ttgagtccaa cccggtaaga     840

cacgacttat cgccactggc agcagccact ggtaacagga ttagcagagc gaggtatgta     900

ggcggtgcta cagagttctt gaagtggtgg cctaactacg gctacactag aaggacagta     960

tttggtatct gcgctctgct gaagccagtt accttcggaa aaagagttgg tagctcttga    1020

tccggcaaac aaaccaccgc tggtagcggt ggtttttttg tttgcaagca gcagattacg    1080

cgcagaaaaa aaggatctca agaagatcct ttgatctttt ctacggggtc tgacgctcag    1140

tggaacgaaa actcacgtta agggattttg gtcatgagat tatcaaaaag gatcttcacc    1200
```

-continued

```
tagatccttt taaattaaaa atgaagtttt aaatcaatct aaagtatata tgagtaaact   1260
tggtctgaca gttaccaatg cttaatcagt gaggcaccta tctcagcgat ctgtctattt   1320
cgttcatcca tagttgcctg actccccgtc gtgtagataa ctacgatacg ggagggctta   1380
ccatctggcc ccagtgctgc aatgataccg cgagacccac gctcaccggc tccagattta   1440
tcagcaataa accagccagc cggaagggcc gagcgcagaa gtggtcctgc aactttatcc   1500
gcctccatcc agtctattaa ttgttgccgg gaagctagag taagtagttc gccagttaat   1560
agtttgcgca acgttgttgg cattgctaca ggcatcgtgg tgtcacgctc gtcgtttggt   1620
atggcttcat tcagctccgg ttcccaacga tcaaggcgag ttacatgatc ccccatgttg   1680
tgcaaaaaag cggttagctc cttcggtcct ccgatcgttg tcagaagtaa gttggccgca   1740
gtgttatcac tcatggttat ggcagcactg cataattctc ttactgtcat gccatccgta   1800
agatgctttt ctgtgactgg tgagtactca accaagtcat tctgagaata ccgcgcccgg   1860
cgaccgagtt gctcttgccc ggcgtcaata cgggataata gtgtatgaca tagcagaact   1920
ttaaaagtgc tcatcattgg aaaacgttct tcggggcgaa aactctcaag gatcttaccg   1980
ctgttgagat ccagttcgat gtaacccact cgtgcaccca actgatcttc agcatctttt   2040
actttcacca gcgtttctgg gtgagcaaaa acaggaaggc aaaatgccgc aaaaaaggga   2100
ataagggcga cacggaaatg ttgaatactc atactcttcc tttttcaata ttattgaagc   2160
atttatcagg gttattgtct catgagcgga tacatatttg aatgtattta gaaaaataaa   2220
caaatagggg ttccgcgcac atttccccga aaagtgccac ctgtatgcgg tgtgaaatac   2280
cgcacagatg cgtaaggaga aaataccgca tcaggcgaaa ttgtaaacgt taatattttg   2340
ttaaaattcg cgttaaatat ttgttaaatc agctcatttt ttaaccaata ggccgaaatc   2400
ggcaaaatcc cttataaatc aaaagaatag accgagatag ggttgagtgt tgttccagtt   2460
tggaacaaga gtccactatt aaagaacgtg gactccaacg tcaaagggcg aaaaaccgtc   2520
tatcagggcg atggcccact acgtgaacca tcacccaaat caagtttttt gcggtcgagg   2580
tgccgtaaag ctctaaatcg gaaccctaaa gggagccccc gatttagagc ttgacgggga   2640
aagccggcga acgtggcgag aaaggaaggg aagaaagcga aaggagcggg cgctagggcg   2700
ctggcaagtg tagcggtcac gctgcgcgta accaccacac ccgccgcgct taatgcgccg   2760
ctacagggcg cgtccattcg ccattcaggc tgcgcaactg ttgggaaggg cgatcggtgc   2820
gggcctcttc gctattacgc cagctggcga aagggggatg tgctgcaagg cgattaagtt   2880
gggtaacgcc agggttttcc cagtcacgac gttgtaaaac gacggccagt gaattgtaat   2940
acgactcact atagggcgaa ttgggcccga cgtcgcatgc tcccggccgc catggccgcg   3000
ggattccaat gcatatgagg tgcgcaacgt gtccgggatg taccatgtca cgaacgactg   3060
ctccaactca agcattgtgt atgaggcagc ggacatgatc atgcacaccc ccgggtgcgt   3120
gccctgcgtt cgggagaaca actcttcccg ctgctgggta gcgctcaccc ccacgctcgc   3180
agctaggaac gccagcgtcc ccactacgac aatacgacgc cacgtcgatt tgctcgttgg   3240
ggcggctgct ttctgttccg ctatgtacgt gggggatctc tgcggatctg tcttcctcgt   3300
ctcccagctg ttcaccatct cgcctcgccg gcatgagacg gtgcaggact gcaattgctc   3360
aatctatccc ggccacataa caggtcaccg tatggcttgg gatatgatga tgaactggca   3420
ccaccaccat caccattaag gatccaag                                      3448
```

<210> SEQ ID NO 7
<211> LENGTH: 37

-continued

<212> TYPE: DNA
<213> ORGANISM: Artificial Sequence
<220> FEATURE:
<223> OTHER INFORMATION: Description of Artificial Sequence: CHHE1-F

<400> SEQUENCE: 7
agttactctt caaggtatga ggtgcgcaac gtgtccg 37

<210> SEQ ID NO 8
<211> LENGTH: 47
<212> TYPE: DNA
<213> ORGANISM: Artificial Sequence
<220> FEATURE:
<223> OTHER INFORMATION: Description of Artificial Sequence: CHHE1-R

<400> SEQUENCE: 8
agttactctt cacagggatc ctccttaatg gtgatggtgg tggtgcc 47

<210> SEQ ID NO 9
<211> LENGTH: 3067
<212> TYPE: DNA
<213> ORGANISM: Artificial Sequence
<220> FEATURE:
<223> OTHER INFORMATION: Description of Artificial Sequence:
vector pCHH-Hir

<400> SEQUENCE: 9
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg ccaagcttgc 240
atgcctgcag gtcgacccta gatctctatt actgcaggta ttcttccggg atttcttcga 300
agtcgccgtc gttgtgagac tgcggacgcg gggtaccttc gccagtaacg cactggttac 360
gttcgccttt agagcccagg atgcatttgt tgccctggcc gcaaacgtta gagccttcgc 420
acaggcacag gttctgaccg gattcagtgc agtcagtgta aacaaccctc ttttccaacg 480
ggtgtgtagt tccattctcc accgctaggg ctgcgctggg ctccattggc gaggttttca 540
aggccgctag gatgcgatcc atgcgtccgt agccttgcgt ggagcgtgcg tgtgcgtgcg 600
ggagtgcgca taggtaggct acggtgatga ttgctagcat ggcgggaata gttttgctat 660
acatgaattc actggccgtc gttttacaac gtcgtgactg ggaaaaccct ggcgttaccc 720
aacttaatcg ccttgcagca catcccccttt tcgccagctg gcgtaatagc gaagaggccc 780
gcaccgatcg cccttcccaa cagttgcgca gcctgaatgg cgaatggcgc ctgatgcggt 840
attttctcct tacgcatctg tgcggtattt cacaccgcat atggtgcact ctcagtacaa 900
tctgctctga tgccgcatag ttaagccagc cccgacaccc gccaacaccc gctgacgcgc 960
cctgacgggc ttgtctgctc ccggcatccg cttacagaca agctgtgacc gtctccggga 1020
gctgcatgtg tcagaggttt tcaccgtcat caccgaaacg cgcgagacga aagggcctcg 1080
tgatacgcct atttttatag gttaatgtca tgataataat ggtttcttag acgtcaggtg 1140
gcacttttcg gggaaatgtg cgcggaaccc ctatttgttt atttttctaa atacattcaa 1200
atatgtatcc gctcatgaga caataaccct gataaatgct tcaataatat tgaaaaagga 1260
agagtatgag tattcaacat ttccgtgtcg cccttattcc cttttttgcg gcattttgcc 1320
ttcctgtttt tgctcaccca gaaacgctgg tgaaagtaaa agatgctgaa gatcagttgg 1380
gtgcacgagt gggttacatc gaactggatc tcaacagcgg taagatcctt gagagttttc 1440

-continued gccccgaaga acgttttcca atgatgagca cttttaaagt tctgctatgt ggcgcggtat 1500
tatcccgtat tgacgccggg caagagcaac tcggtcgccg catacactat tctcagaatg 1560
acttggttga gtactcacca gtcacagaaa agcatcttac ggatggcatg acagtaagag 1620
aattatgcag tgctgccata accatgagtg ataacactgc ggccaactta cttctgacaa 1680
cgatcggagg accgaaggag ctaaccgctt ttttgcacaa catgggggat catgtaactc 1740
gccttgatcg ttgggaaccg gagctgaatg aagccatacc aaacgacgag cgtgacacca 1800
cgatgcctgt agcaatggca acaacgttgc gcaaactatt aactggcgaa ctacttactc 1860
tagcttcccg gcaacaatta atagactgga tggaggcgga taaagttgca ggaccacttc 1920
tgcgctcggc ccttccggct ggctggttta ttgctgataa atctggagcc ggtgagcgtg 1980
ggtctcgcgg tatcattgca gcactggggc cagatggtaa gccctcccgt atcgtagtta 2040
tctacacgac ggggagtcag gcaactatgg atgaacgaaa tagacagatc gctgagatag 2100
gtgcctcact gattaagcat tggtaactgt cagaccaagt ttactcatat atactttaga 2160
ttgatttaaa acttcatttt taatttaaaa ggatctaggt gaagatcctt tttgataatc 2220
tcatgaccaa aatcccttaa cgtgagtttt cgttccactg agcgtcagac cccgtagaaa 2280
agatcaaagg atcttcttga gatccttttt ttctgcgcgt aatctgctgc ttgcaaacaa 2340
aaaaaccacc gctaccagcg gtggtttgtt tgccggatca agagctacca actctttttc 2400
cgaaggtaac tggcttcagc agagcgcaga taccaaatac tgtccttcta gtgtagccgt 2460
agttaggcca ccacttcaag aactctgtag caccgcctac atacctcgct ctgctaatcc 2520
tgttaccagt ggctgctgcc agtggcgata agtcgtgtct taccgggttg gactcaagac 2580
gatagttacc ggataaggcg cagcggtcgg gctgaacggg gggttcgtgc acacagccca 2640
gcttggagcg aacgacctac accgaactga gatacctaca gcgtgagcta tgagaaagcg 2700
ccacgcttcc cgaagggaga aaggcggaca ggtatccggt aagcggcagg gtcggaacag 2760
gagagcgcac gagggagctt ccagggggaa acgcctggta tctttatagt cctgtcgggt 2820
ttcgccacct ctgacttgag cgtcgatttt tgtgatgctc gtcagggggg cggagcctat 2880
ggaaaaacgc cagcaacgcg gcctttttac ggttcctggc cttttgctgg ccttttgctc 2940
acatgttctt tcctgcgtta tcccctgatt ctgtggataa ccgtattacc gcctttgagt 3000
gagctgatac cgctcgccgc agccgaacga ccgagcgcag cgagtcagtg agcgaggaag 3060
cggaaga 3067

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: CHH-links

<400> SEQUENCE: 10
agttactctt cacctctttt ccaacgggtg tgtag 35

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence:
vector pCHH-Hir

<400> SEQUENCE: 11

-continued agtcactctt cactgcaggc atgcaagctt ggcg 34

<210> SEQ ID NO 12
<211> LENGTH: 6973
<212> TYPE: DNA
<213> ORGANISM: Artificial Sequence
<220> FEATURE:
<223> OTHER INFORMATION: Description of Artificial Sequence:
vector pFPMT121

<400> SEQUENCE: 12
ggtaccctgc tcaatctccg gaatggtgat ctgatcgttc ctgaaaacct cgacattggc 60
tccctcctga cacaggtact cgtacaggtt ccaggtaaac gagtcgtagt tgtcgatcat 120
gacaacgttc ttagaagcgg ccggcatttt gaaggtgact aatagcctaa gaaaatattt 180
aatttaattt tcattaaatt ttcctatact cgctatttca gcttttcatc tcatcacttc 240
ataaacgata taaaccagaa aaagaactat tttcaaacac gcttctcaaa agcggtatgt 300
ccttccacgt ctccttagaa tctggcaagt ccgcgagggg gatccagatc tgaattcccg 360
atgaagcaga gagcgcagga ggcggtattt atagtgccat tcccctctct gagagacccg 420
gatggtagtc gagtgtatcg gagacagctt gatgtagact ccgtgcctgc cggctcctct 480
tattggcgga caccagtgag acaccccgga acttgctgtt tttctgcaaa atccggggtg 540
accagtggga gcctatttgc acacacgagc gggacacccc actctggtga agagtgccaa 600
agtcattctt tttcccgttg cggggcagcc gattgcatgt tttaggaaaa tattaccttt 660
gctacaccct gtcagattta ccctccacac atatatattc cgtcacctcc agggactatt 720
attcgtcgtt gcgccgccag cggaagatat ccagaagctg ttttccgaga gactcggttg 780
gcgcctggta tatttgatgg atgtcgcgct gcctcacgtc ccggtaccca ggaacgcggt 840
gggatctcgg gcccatcgaa gactgtgctc cagactgctc gcccagcagg tgtttcttga 900
tcgccgcctc taaattgtcc gcgcatcgcc ggtaacattt ttccagctcg gagtttgcgt 960
ttagatacag tttctgcgat gccaaaggag cctgcagatt ataacctcgg atgctgtcat 1020
tcagcgcttt taatttgacc tccagatagt tgctgtattt ctgttcccat tggctgctgc 1080
gcagcttcgt ataactcgag ttattgttgc gctctgcctc ggcgtactgg ctcatgatct 1140
ggatcttgtc cgtgtcgctt ttcttcgagt gtttctcgca aacgatgtgc acggcctgca 1200
gtgtccaatc ggagtcgagc tggcgccgaa actggcggat ctgagcctcc acactgccct 1260
gtttctctat ccacggcgga accgcctcct gccgtttcag aatgttgttc aagtggtact 1320
ctgtgcggtc aatgaaggcg ttattgccgg tgaaatcttt gggaagcggt tttcctcggg 1380
gaagattacg aaattccccg cgtcgttgcg cttcctggat ctcgaggaga tcgttctccg 1440
cgtcgaggag atcgttctcc gcgtcgacac cattccttgc ggcggcggtg ctcaacggcc 1500
tcaacctact actgggctgc ttcctaatgc aggagtcgca taagggagag cgtcgacaaa 1560
cccgcgtttg agaacttgct caagcttctg gtaaacgttg tagtactctg aaacaaggcc 1620
ctagcactct gatctgtttc tcttgggtag cggtgagtgg tttattggag ttcactggtt 1680
tcagcacatc tgtcatctag acaatattgt tactaaattt ttttgaacta caattgttcg 1740
taattcatct attattatac atcctcgtca gcaatttctg gcagacggag tttactaacg 1800
tcttgagtat gaggccgaga atccagctct gtggccatac tcagtcttga cagcctgctg 1860
atgtggctgc gttcaacgca ataagcgtgt cctccgactc cgagttgtgc tcgttatcgt 1920
cgttctcatc ctcggaaaaa tcacacgaaa gaacatactc accagtaggc tttctggtcc 1980

-continued

```
ctggggcacg gctgtttctg acgtattccg gcgttgataa tagctcgaaa gtgaacgccg   2040
agtcgcggga gtcgaccgat gcccttgaga gccttcaacc cagtcagctc cttccggtgg   2100
gcgcggggca tgactatcgt cgccgcactt atgactgtct tctttatcat gcaactcgta   2160
ggacaggtgc cggcagcgct ctgggtcatt ttcggcgagg accgctttcg ctggagcgcg   2220
acgatgatcg gcctgtcgct tgcggtattc ggaatcttgc acgccctcgc tcaagccttc   2280
gtcactggtc ccgccaccaa acgtttcggc gagaagcagg ccattatcgc cggcatggcg   2340
gccgacgcgc tgggctacgt cttgctggcg ttcgcgacgc gaggctggat ggccttcccc   2400
attatgattc ttctcgcttc cggcggcatc gggatgcccg cgttgcaggc catgctgtcc   2460
aggcaggtag atgacgacca tcagggacag cttcaaggat cgctcgcggc tcttaccagc   2520
ctaacttcga tcactggacc gctgatcgtc acggcgattt atgccgcctc ggcgagcaca   2580
tggaacgggt tggcatggat tgtaggcgcc gccctatacc ttgtctgcct ccccgcgttg   2640
cgtcgcggtg catggagccg ggccacctcg acctgaatgg aagccggcgg cacctcgcta   2700
acggattcac cactccaaga attggagcca atcaattctt gcggagaact gtgaatgcgc   2760
aaaccaaccc ttggcagaac atatccatcg cgtccgccat ctccagcagc cgcacgcggc   2820
gcatcggggg gggggggggg gggggggggc aaacaattca tcattttttt tttattcttt   2880
tttttgattt cggtttcttt gaaatttttt tgattcggta atctccgaac agaaggaaga   2940
acgaaggaag gagcacagac ttagattggt atatatacgc atatgtagtg ttgaagaaac   3000
atgaaattgc ccagtattct taacccaact gcacagaaca aaaacctgca ggaaacgaag   3060
ataaatcatg tcgaaagcta catataagga acgtgctgct actcatccta gtcctgttgc   3120
tgccaagcta tttaatatca tgcacgaaaa gcaaacaaac ttgtgtgctt cattggatgt   3180
tcgtaccacc aaggaattac tggagttagt tgaagcatta ggtcccaaaa tttgtttact   3240
aaaaacacat gtggatatct tgactgattt ttccatggag ggcacagtta agccgctaaa   3300
ggcattatcc gccaagtaca atttttttact cttcgaagac agaaaatttg ctgacattgg   3360
taatacagtc aaattgcagt actctgcggg tgtatacaga atagcagaat gggcagacat   3420
tacgaatgca cacggtgtgg tgggcccagg tattgttagc ggtttgaagc aggcggcaga   3480
agaagtaaca aaggaaccta gaggcctttt gatgttagca gaattgtcat gcaagggctc   3540
cctatctact ggagaatata ctaagggtac tgttgacatt gcgaagagcg acaaagattt   3600
tgttatcggc tttattgctc aaagagacat gggtggaaga gatgaaggtt acgattggtt   3660
gattatgaca cccggtgtgg gtttagatga caagggagac gcattgggtc aacagtatag   3720
aaccgtggat gatgtggtct ctacaggatc tgacattatt attgttggaa gaggactatt   3780
tgcaaaggga agggatgcta aggtagaggg tgaacgttac agaaaagcag gctgggaagc   3840
atatttgaga agatgcggcc agcaaaacta aaaaactgta ttataagtaa atgcatgtat   3900
actaaactca caaattagag cttcaattta attatatcag ttattacccg ggaatctcgg   3960
tcgtaatgat tttataatg acgaaaaaaa aaaaattgga aagaaaagcc cccccccccc   4020
cccccccccc cccccccccc ccgcagcgtt gggtcctggc cacgggtgcg catgatcgtg   4080
ctcctgtcgt tgaggacccg gctaggctgg cggggttgcc ttactggtta gcagaatgaa   4140
tcaccgatac gcgagcgaac gtgaagcgac tgctgctgca aaacgtctgc gacctgagca   4200
acaacatgaa tggtcttcgg tttccgtgtt tcgtaaagtc tggaaacgcg gaagtcagcg   4260
ccctgcacca ttatgttccg gatctgcatc gcaggatgct gctggctacc ctgtggaaca   4320
```

-continued

```
cctacatctg tattaacgaa gcgctggcat tgaccctgag tgatttttct ctggtcccgc   4380
cgcatccata ccgccagttg tttaccctca caacgttcca gtaaccgggc atgttcatca   4440
tcagtaaccc gtatcgtgag catcctctct cgtttcatcg gtatcattac ccccatgaac   4500
agaaattccc ccttacacgg aggcatcaag tgaccaaaca ggaaaaaacc gcccttaaca   4560
tggcccgctt tatcagaagc cagacattaa cgcttctgga gaaactcaac gagctggacg   4620
cggatgaaca ggcagacatc tgtgaatcgc ttcacgacca cgctgatgag ctttaccgca   4680
gctgcctcgc gcgtttcggt gatgacggtg aaaacctctg acacatgcag ctcccggaga   4740
cggtcacagc ttgtctgtaa gcggatgccg ggagcagaca agcccgtcag ggcgcgtcag   4800
cgggtgttgg cgggtgtcgg ggcgcagcca tgacccagtc acgtagcgat agcggagtgt   4860
atactggctt aactatgcgg catcagagca gattgtactg agagtgcacc atatgcggtg   4920
tgaaataccg cacagatgcg taaggagaaa ataccgcatc aggcgctctt ccgcttcctc   4980
gctcactgac tcgctgcgct cggtcgttcg gctgcggcga gcggtatcag ctcactcaaa   5040
ggcggtaata cggttatcca cagaatcagg ggataacgca ggaaagaaca tgtgagcaaa   5100
aggccagcaa aaggccagga accgtaaaaa ggccgcgttg ctggcgtttt tccataggct   5160
ccgcccccct gacgagcatc acaaaaatcg acgctcaagt cagaggtggc gaaacccgac   5220
aggactataa agataccagg cgtttccccc tggaagctcc ctcgtgcgct ctcctgttcc   5280
gaccctgccg cttaccggat acctgtccgc ctttctccct tcgggaagcg tggcgctttc   5340
tcatagctca cgctgtaggt atctcagttc ggtgtaggtc gttcgctcca agctgggctg   5400
tgtgcacgaa ccccccgttc agcccgaccg ctgcgcctta tccggtaact atcgtcttga   5460
gtccaacccg gtaagacacg acttatcgcc actggcagca gccactggta acaggattag   5520
cagagcgagg tatgtaggcg gtgctacaga gttcttgaag tggtggccta actacggcta   5580
cactagaagg acagtatttg gtatctgcgc tctgctgaag ccagttacct tcggaaaaag   5640
agttggtagc tcttgatccg gcaaacaaac caccgctggt agcggtggtt tttttgtttg   5700
caagcagcag attacgcgca gaaaaaaagg atctcaagaa gatcctttga tcttttctac   5760
ggggtctgac gctcagtgga acgaaaactc acgttaaggg attttggtca tgagattatc   5820
aaaaaggatc ttcacctaga tccttttaaa ttaaaaatga agttttaaat caatctaaag   5880
tatatatgag taaacttggt ctgacagtta ccaatgctta atcagtgagg cacctatctc   5940
agcgatctgt ctatttcgtt catccatagt tgcctgactc cccgtcgtgt agataactac   6000
gatacgggag ggcttaccat ctggccccag tgctgcaatg ataccgcgag acccacgctc   6060
accggctcca gatttatcag caataaacca gccagccgga agggccgagc gcagaagtgg   6120
tcctgcaact ttatccgcct ccatccagtc tattaattgt tgccgggaag ctagagtaag   6180
tagttcgcca gttaatagtt tgcgcaacgt tgttgccatt gctgcaggca tcgtggtgtc   6240
acgctcgtcg tttggtatgg cttcattcag ctccggttcc caacgatcaa ggcgagttac   6300
atgatccccc atgttgtgca aaaaagcggt tagctccttc ggtcctccga tcgttgtcag   6360
aagtaagttg gccgcagtgt tatcactcat ggttatggca gcactgcata attctcttac   6420
tgtcatgcca tccgtaagat gcttttctgt gactggtgag tactcaacca agtcattctg   6480
agaatagtgt atgcggcgac cgagttgctc ttgcccggcg tcaacacggg ataataccgc   6540
gccacatagc agaactttaa aagtgctcat cattggaaaa cgttcttcgg ggcgaaaact   6600
ctcaaggatc ttaccgctgt tgagatccag ttcgatgtaa cccactcgtg cacccaactg   6660
atcttcagca tcttttactt tcaccagcgt ttctgggtga gcaaaaacag gaaggcaaaa   6720
```

-continued

```
tgccgcaaaa aagggaataa gggcgacacg gaaatgttga atactcatac tcttcctttt   6780

tcaatattat tgaagcattt atcagggtta ttgtctcatg agcggataca tatttgaatg   6840

tatttagaaa aataaacaaa taggggttcc gcgcacattt ccccgaaaag tgccacctga   6900

cgtctaagaa accattatta tcatgacatt aacctataaa aataggcgta tcacgaggcc   6960

ctttcgtctt caa                                                      6973
```

<210> SEQ ID NO 13
<211> LENGTH: 7591
<212> TYPE: DNA
<213> ORGANISM: Artificial Sequence
<220> FEATURE:
<223> OTHER INFORMATION: Description of Artificial Sequence:
vector pFPMT-CHH-E1H6

<400> SEQUENCE: 13

```
ggtaccctgc tcaatctccg gaatggtgat ctgatcgttc ctgaaaacct cgacattggc     60

tccctcctga cacaggtact cgtacaggtt ccaggtaaac gagtcgtagt tgtcgatcat    120

gacaacgttc ttagaagcgg ccggcatttt gaaggtgact aatagcctaa gaaaatattt    180

aatttaattt tcattaaatt ttcctatact cgctatttca gcttttcatc tcatcacttc    240

ataaacgata taaaccagaa aaagaactat tttcaaacac gcttctcaaa agcggtatgt    300

ccttccacgt ctccttagaa tctggcaagt ccgcgagggg gatccttaat ggtgatggtg    360

gtggtgccag ttcatcatca tatcccaagc catacggtga cctgttatgt ggccgggata    420

gattgagcaa ttgcagtcct gcaccgtctc atgccggcga ggcgagatgg tgaacagctg    480

ggagacgagg aagacagatc cgcagagatc ccccacgtac atagcggaac agaaagcagc    540

cgccccaacc agcaaatcga cgtggcgtcg tattgtcgta gtggggacgc tggcgttcct    600

agctgcgagc gtgggggtga gcgctaccca gcagcgggaa gagttgttct cccgaacgca    660

gggcacgcac ccgggggtgt gcatgatcat gtccgctgcc tcatacacaa tgcttgagtt    720

ggagcagtcg ttcgtgacat ggtacatccc ggacacgttg cgcacctcat acctcttttc    780

caacgggtgt gtagttccat tctccaccgc tagggctgcg ctgggctcca ttggcgaggt    840

tttcaaggcc gctaggatgc gatccatgcg tccgtagcct tgcgtggagc gtgcgtgtgc    900

gtgcgggagt gcgcataggt aggctacggt gatgattgct agcatggcgg gaatagtttt    960

gctatacatg aattcccgat gaagcagaga gcgcaggagg cggtatttat agtgccattc   1020

ccctctctga gagacccgga tggtagtcga gtgtatcgga gacagcttga tgtagactcc   1080

gtgcctgccg gctcctctta ttggcggaca ccagtgagac accccggaac ttgctgtttt   1140

tctgcaaaat ccggggtgac cagtgggagc ctatttgcac acacgagcgg gacaccccac   1200

tctggtgaag agtgccaaag tcattctttt tcccgttgcg gggcagccga ttgcatgttt   1260

taggaaaata ttacctttgc tacaccctgt cagatttacc ctccacacat atatattccg   1320

tcacctccag ggactattat tcgtcgttgc gccgccagcg gaagatatcc agaagctgtt   1380

ttccgagaga ctcggttggc gcctggtata tttgatggat gtcgcgctgc ctcacgtccc   1440

ggtacccagg aacgcggtgg gatctcgggc ccatcgaaga ctgtgctcca gactgctcgc   1500

ccagcaggtg tttcttgatc gccgcctcta aattgtccgc gcatcgccgg taacattttt   1560

ccagctcgga gtttgcgttt agatacagtt tctgcgatgc caaaggagcc tgcagattat   1620

aacctcggat gctgtcattc agcgctttta atttgacctc cagatagttg ctgtatttct   1680

gttcccattg gctgctgcgc agcttcgtat aactcgagtt attgttgcgc tctgcctcgg   1740
```

-continued

```
cgtactggct catgatctgg atcttgtccg tgtcgctttt cttcgagtgt ttctcgcaaa   1800
cgatgtgcac ggcctgcagt gtccaatcgg agtcgagctg gcgccgaaac tggcggatct   1860
gagcctccac actgccctgt ttctctatcc acggcggaac cgcctcctgc cgtttcagaa   1920
tgttgttcaa gtggtactct gtgcggtcaa tgaaggcgtt attgccggtg aaatctttgg   1980
gaagcggttt tcctcgggga agattacgaa attccccgcg tcgttgcgct tcctggatct   2040
cgaggagatc gttctccgcg tcgaggagat cgttctccgc gtcgacacca ttccttgcgg   2100
cggcggtgct caacggcctc aacctactac tgggctgctt cctaatgcag gagtcgcata   2160
agggagagcg tcgacaaacc cgcgtttgag aacttgctca agcttctggt aaacgttgta   2220
gtactctgaa acaaggccct agcactctga tctgtttctc ttgggtagcg gtgagtggtt   2280
tattggagtt cactggtttc agcacatctg tcatctagac aatattgtta ctaaattttt   2340
ttgaactaca attgttcgta attcatctat tattatacat cctcgtcagc aatttctggc   2400
agacggagtt tactaacgtc ttgagtatga ggccgagaat ccagctctgt ggccatactc   2460
agtcttgaca gcctgctgat gtggctgcgt tcaacgcaat aagcgtgtcc tccgactccg   2520
agttgtgctc gttatcgtcg ttctcatcct cggaaaaatc acacgaaaga acatactcac   2580
cagtaggctt tctggtccct ggggcacggc tgtttctgac gtattccggc gttgataata   2640
gctcgaaagt gaacgccgag tcgcgggagt cgaccgatgc ccttgagagc cttcaaccca   2700
gtcagctcct tccggtgggc gcggggcatg actatcgtcg ccgcacttat gactgtcttc   2760
tttatcatgc aactcgtagg acaggtgccg gcagcgctct gggtcatttt cggcgaggac   2820
cgctttcgct ggagcgcgac gatgatcggc ctgtcgcttg cggtattcgg aatcttgcac   2880
gccctcgctc aagccttcgt cactggtccc gccaccaaac gtttcggcga gaagcaggcc   2940
attatcgccg gcatggcggc cgacgcgctg ggctacgtct tgctggcgtt cgcgacgcga   3000
ggctggatgg ccttccccat tatgattctt ctcgcttccg gcggcatcgg gatgcccgcg   3060
ttgcaggcca tgctgtccag gcaggtagat gacgaccatc agggacagct tcaaggatcg   3120
ctcgcggctc ttaccagcct aacttcgatc actggaccgc tgatcgtcac ggcgatttat   3180
gccgcctcgg cgagcacatg gaacgggttg gcatggattg taggcgccgc cctatacctt   3240
gtctgcctcc ccgcgttgcg tcgcggtgca tggagccggg ccacctcgac ctgaatggaa   3300
gccggcggca cctcgctaac ggattcacca ctccaagaat tggagccaat caattcttgc   3360
ggagaactgt gaatgcgcaa accaaccctt ggcagaacat atccatcgcg tccgccatct   3420
ccagcagccg cacgcggcgc atcggggggg gggggggggg ggggggcaa acaattcatc   3480
attttttttt tattcttttt tttgatttcg gtttctttga aatttttttg attcggtaat   3540
ctccgaacag aaggaagaac gaaggaagga gcacagactt agattggtat atatacgcat   3600
atgtagtgtt gaagaaacat gaaattgccc agtattctta acccaactgc acagaacaaa   3660
aacctgcagg aaacgaagat aaatcatgtc gaaagctaca tataaggaac gtgctgctac   3720
tcatcctagt cctgttgctg ccaagctatt taatatcatg cacgaaaagc aaacaaactt   3780
gtgtgcttca ttggatgttc gtaccaccaa ggaattactg gagttagttg aagcattagg   3840
tcccaaaatt tgtttactaa aaacacatgt ggatatcttg actgattttt ccatggaggg   3900
cacagttaag ccgctaaagg cattatccgc caagtacaat tttttactct tcgaagacag   3960
aaaatttgct gacattggta atacagtcaa attgcagtac tctgcgggtg tatacagaat   4020
agcagaatgg gcagacatta cgaatgcaca cggtgtggtg ggcccaggta ttgttagcgg   4080
```

-continued

```
tttgaagcag gcggcagaag aagtaacaaa ggaacctaga ggccttttga tgttagcaga   4140
attgtcatgc aagggctccc tatctactgg agaatatact aagggtactg ttgacattgc   4200
gaagagcgac aaagatttg ttatcggctt tattgctcaa agagacatgg gtggaagaga   4260
tgaaggttac gattggttga ttatgacacc cggtgtgggt ttagatgaca agggagacgc   4320
attgggtcaa cagtatagaa ccgtggatga tgtggtctct acaggatctg acattattat   4380
tgttggaaga ggactatttg caaagggaag ggatgctaag gtagagggtg aacgttacag   4440
aaaagcaggc tgggaagcat atttgagaag atgcggccag caaaactaaa aaactgtatt   4500
ataagtaaat gcatgtatac taaactcaca aattagagct tcaatttaat tatatcagtt   4560
attacccggg aatctcggtc gtaatgattt ttataatgac gaaaaaaaaa aaattggaaa   4620
gaaaagcccc cccccccccc cccccccccc cccccccccc gcagcgttgg gtcctggcca   4680
cgggtgcgca tgatcgtgct cctgtcgttg aggacccggc taggctggcg gggttgcctt   4740
actggttagc agaatgaatc accgatacgc gagcgaacgt gaagcgactg ctgctgcaaa   4800
acgtctgcga cctgagcaac aacatgaatg gtcttcggtt tccgtgtttc gtaaagtctg   4860
gaaacgcgga agtcagcgcc ctgcaccatt atgttccgga tctgcatcgc aggatgctgc   4920
tggctaccct gtggaacacc tacatctgta ttaacgaagc gctggcattg accctgagtg   4980
atttttctct ggtcccgccg catccatacc gccagttgtt taccctcaca acgttccagt   5040
aaccgggcat gttcatcatc agtaacccgt atcgtgagca tcctctctcg tttcatcggt   5100
atcattaccc ccatgaacag aaattccccc ttacacggag gcatcaagtg accaaacagg   5160
aaaaaaccgc ccttaacatg gcccgcttta tcagaagcca gacattaacg cttctggaga   5220
aactcaacga gctggacgcg gatgaacagg cagacatctg tgaatcgctt cacgaccacg   5280
ctgatgagct ttaccgcagc tgcctcgcgc gtttcggtga tgacggtgaa aacctctgac   5340
acatgcagct cccggagacg gtcacagctt gtctgtaagc ggatgccggg agcagacaag   5400
cccgtcaggg cgcgtcagcg ggtgttggcg ggtgtcgggg cgcagccatg acccagtcac   5460
gtagcgatag cggagtgtat actggcttaa ctatgcggca tcagagcaga ttgtactgag   5520
agtgcaccat atgcggtgtg aaataccgca cagatgcgta aggagaaaat accgcatcag   5580
gcgctcttcc gcttcctcgc tcactgactc gctgcgctcg gtcgttcggc tgcggcgagc   5640
ggtatcagct cactcaaagg cggtaatacg gttatccaca gaatcagggg ataacgcagg   5700
aaagaacatg tgagcaaaag gccagcaaaa ggccaggaac cgtaaaaagg ccgcgttgct   5760
ggcgtttttc cataggctcc gcccccctga cgagcatcac aaaaatcgac gctcaagtca   5820
gaggtggcga aacccgacag gactataaag ataccaggcg tttccccctg gaagctccct   5880
cgtgcgctct cctgttccga ccctgccgct taccggatac ctgtccgcct ttctcccttc   5940
gggaagcgtg gcgctttctc atagctcacg ctgtaggtat ctcagttcgg tgtaggtcgt   6000
tcgctccaag ctgggctgtg tgcacgaacc ccccgttcag cccgaccgct gcgccttatc   6060
cggtaactat cgtcttgagt ccaacccggt aagacacgac ttatcgccac tggcagcagc   6120
cactggtaac aggattagca gagcgaggta tgtaggcggt gctacagagt tcttgaagtg   6180
gtggcctaac tacggctaca ctagaaggac agtatttggt atctgcgctc tgctgaagcc   6240
agttaccttc ggaaaaagag ttggtagctc ttgatccggc aaacaaacca ccgctggtag   6300
cggtggtttt tttgtttgca agcagcagat tacgcgcaga aaaaaaggat ctcaagaaga   6360
tcctttgatc ttttctacgg ggtctgacgc tcagtggaac gaaaactcac gttaagggat   6420
tttggtcatg agattatcaa aaaggatctt cacctagatc cttttaaatt aaaaatgaag   6480
```

-continued ttttaaatca atctaaagta tatatgagta aacttggtct gacagttacc aatgcttaat 6540
cagtgaggca cctatctcag cgatctgtct atttcgttca tccatagttg cctgactccc 6600
cgtcgtgtag ataactacga tacgggaggg cttaccatct ggccccagtg ctgcaatgat 6660
accgcgagac ccacgctcac cggctccaga tttatcagca ataaaccagc cagccggaag 6720
ggccgagcgc agaagtggtc ctgcaacttt atccgcctcc atccagtcta ttaattgttg 6780
ccgggaagct agagtaagta gttcgccagt taatagtttg cgcaacgttg ttgccattgc 6840
tgcaggcatc gtggtgtcac gctcgtcgtt tggtatggct tcattcagct ccggttccca 6900
acgatcaagg cgagttacat gatcccccat gttgtgcaaa aaagcggtta gctccttcgg 6960
tcctccgatc gttgtcagaa gtaagttggc cgcagtgtta tcactcatgg ttatggcagc 7020
actgcataat tctcttactg tcatgccatc cgtaagatgc ttttctgtga ctggtgagta 7080
ctcaaccaag tcattctgag aatagtgtat gcggcgaccg agttgctctt gcccggcgtc 7140
aacacgggat aataccgcgc cacatagcag aactttaaaa gtgctcatca ttggaaaacg 7200
ttcttcgggg cgaaaactct caaggatctt accgctgttg agatccagtt cgatgtaacc 7260
cactcgtgca cccaactgat cttcagcatc ttttactttc accagcgttt ctgggtgagc 7320
aaaaacagga aggcaaaatg ccgcaaaaaa gggaataagg gcgacacgga aatgttgaat 7380
actcatactc ttcctttttc aatattattg aagcatttat cagggttatt gtctcatgag 7440
cggatacata tttgaatgta tttagaaaaa taaacaaata ggggttccgc gcacatttcc 7500
ccgaaaagtg ccacctgacg tctaagaaac cattattatc atgacattaa cctataaaaa 7560
taggcgtatc acgaggccct ttcgtcttca a 7591

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence:
primer MFa-E1 f-Hi

<400> SEQUENCE: 14
aggggtaagc ttggataaaa ggtatgaggt gcgcaacgtg tccgggatgt 50

<210> SEQ ID NO 15
<211> LENGTH: 42
<212> TYPE: DNA
<213> ORGANISM: Artificial Sequence
<220> FEATURE:
<223> OTHER INFORMATION: Description of Artificial Sequence:
primer E1 back-Bam

<400> SEQUENCE: 15
agttacggat ccttaatggt gatggtggtg gtgccagttc at 42

<210> SEQ ID NO 16
<211> LENGTH: 7648
<212> TYPE: DNA
<213> ORGANISM: Artificial Sequence
<220> FEATURE:
<223> OTHER INFORMATION: Description of Artificial Sequence:
vector pFPMT-Mfalfa-E1-H6

<400> SEQUENCE: 16
ggtaccctgc tcaatctccg gaatggtgat ctgatcgttc ctgaaaacct cgacattggc 60
tccctcctga cacaggtact cgtacaggtt ccaggtaaac gagtcgtagt tgtcgatcat 120

-continued

```
gacaacgttc ttagaagcgg ccggcatttt gaaggtgact aatagcctaa gaaaatattt    180
aatttaattt tcattaaatt ttcctatact cgctatttca gcttttcatc tcatcacttc    240
ataaacgata taaaccagaa aaagaactat tttcaaacac gcttctcaaa agcggtatgt    300
ccttccacgt ctccttagaa tctggcaagt ccgcgagggg gatccttaat ggtgatggtg    360
gtggtgccag ttcatcatca tatcccaagc catacggtga cctgttatgt ggccgggata    420
gattgagcaa ttgcagtcct gcaccgtctc atgccggcga ggcgagatgg tgaacagctg    480
ggagacgagg aagacagatc cgcagagatc cccccacgtac atagcggaac agaaagcagc    540
cgccccaacg agcaaatcga cgtggcgtcg tattgtcgta gtggggacgc tggcgttcct    600
agctgcgagc gtgggggtga gcgctaccca gcagcgggaa gagttgttct cccgaacgca    660
gggcacgcac ccgggggtgt gcatgatcat gtccgctgcc tcatacacaa tgcttgagtt    720
ggagcagtcg ttcgtgacat ggtacatccc ggacacgttg cgcacctcat accttttatc    780
caagcttacc ccttcttctt tagcagcaat gctggcaata gtagtattta taaacaataa    840
cccgttattt gtgctgttgg aaaatggcaa aacagcaaca tcgaaatccc cttctaaatc    900
tgagtaaccg atgacagctt cagccggaat ttgtgccgtt tcatcttctg ttgtagtgtt    960
gactggagca gctaatgcgg aggatgctgc gaataaaact gcagtaaaaa ttgaaggaaa   1020
tctcatgaat tcccgatgaa gcagagagcg caggaggcgg tatttatagt gccattcccc   1080
tctctgagag acccggatgg tagtcgagtg tatcggagac agcttgatgt agactccgtg   1140
cctgccggct cctcttattg gcggacacca gtgagacacc ccggaacttg ctgtttttct   1200
gcaaaatccg gggtgaccag tgggagccta tttgcacaca cgagcgggac accccactct   1260
ggtgaagagt gccaaagtca ttctttttcc cgttgcgggg cagccgattg catgttttag   1320
gaaaatatta cctttgctac accctgtcag atttaccctc cacacatata tattccgtca   1380
cctccaggga ctattattcg tcgttgcgcc gccagcggaa gatatccaga agctgttttc   1440
cgagagactc ggttggcgcc tggtatattt gatggatgtc gcgctgcctc acgtcccggt   1500
acccaggaac gcggtgggat ctcgggccca tcgaagactg tgctccagac tgctcgccca   1560
gcaggtgttt cttgatcgcc gcctctaaat tgtccgcgca tcgccggtaa catttttcca   1620
gctcggagtt tgcgtttaga tacagtttct gcgatgccaa aggagcctgc agattataac   1680
ctcggatgct gtcattcagc gcttttaatt tgacctccag atagttgctg tatttctgtt   1740
cccattggct gctgcgcagc ttcgtataac tcgagttatt gttgcgctct gcctcggcgt   1800
actggctcat gatctggatc ttgtccgtgt cgcttttctt cgagtgtttc tcgcaaacga   1860
tgtgcacggc ctgcagtgtc caatcggagt cgagctggcg ccgaaactgg cggatctgag   1920
cctccacact gccctgtttc tctatccacg gcggaaccgc ctcctgccgt ttcagaatgt   1980
tgttcaagtg gtactctgtg cggtcaatga aggcgttatt gccggtgaaa tctttgggaa   2040
gcggttttcc tcggggaaga ttacgaaatt ccccgcgtcg ttgcgcttcc tggatctcga   2100
ggagatcgtt ctccgcgtcg aggagatcgt tctccgcgtc gacaccattc cttgcggcgg   2160
cggtgctcaa cggcctcaac ctactactgg gctgcttcct aatgcaggag tcgcataagg   2220
gagagcgtcg acaaacccgc gtttgagaac ttgctcaagc ttctggtaaa cgttgtagta   2280
ctctgaaaca aggccctagc actctgatct gtttctcttg ggtagcggtg agtggtttat   2340
tggagttcac tggtttcagc acatctgtca tctagacaat attgttacta aattttttttg   2400
aactacaatt gttcgtaatt catctattat tatacatcct cgtcagcaat ttctggcaga   2460
```

-continued

```
cggagtttac taacgtcttg agtatgaggc cgagaatcca gctctgtggc catactcagt   2520

cttgacagcc tgctgatgtg gctgcgttca acgcaataag cgtgtcctcc gactccgagt   2580

tgtgctcgtt atcgtcgttc tcatcctcgg aaaaatcaca cgaaagaaca tactcaccag   2640

taggctttct ggtccctggg gcacggctgt ttctgacgta ttccggcgtt gataatagct   2700

cgaaagtgaa cgccgagtcg cgggagtcga ccgatgccct tgagagcctt caacccagtc   2760

agctccttcc ggtgggcgcg gggcatgact atcgtcgccg cacttatgac tgtcttcttt   2820

atcatgcaac tcgtaggaca ggtgccggca gcgctctggg tcattttcgg cgaggaccgc   2880

tttcgctgga gcgcgacgat gatcggcctg tcgcttgcgg tattcggaat cttgcacgcc   2940

ctcgctcaag ccttcgtcac tggtcccgcc accaaacgtt tcggcgagaa gcaggccatt   3000

atcgccggca tggcggccga cgcgctgggc tacgtcttgc tggcgttcgc gacgcgaggc   3060

tggatggcct tccccattat gattcttctc gcttccggcg gcatcgggat gcccgcgttg   3120

caggccatgc tgtccaggca ggtagatgac gaccatcagg gacagcttca aggatcgctc   3180

gcggctctta ccagcctaac ttcgatcact ggaccgctga tcgtcacggc gatttatgcc   3240

gcctcggcga gcacatggaa cgggttggca tggattgtag gcgccgccct ataccttgtc   3300

tgcctccccg cgttgcgtcg cggtgcatgg agccgggcca cctcgacctg aatggaagcc   3360

ggcggcacct cgctaacgga ttcaccactc caagaattgg agccaatcaa ttcttgcgga   3420

gaactgtgaa tgcgcaaacc aacccttggc agaacatatc catcgcgtcc gccatctcca   3480

gcagccgcac gcggcgcatc gggggggggg gggggggggg ggggcaaaca attcatcatt   3540

ttttttttat tctttttttt gatttcggtt tctttgaaat ttttttgatt cggtaatctc   3600

cgaacagaag gaagaacgaa ggaaggagca cagacttaga ttggtatata tacgcatatg   3660

tagtgttgaa gaaacatgaa attgcccagt attcttaacc caactgcaca gaacaaaaac   3720

ctgcaggaaa cgaagataaa tcatgtcgaa agctacatat aaggaacgtg ctgctactca   3780

tcctagtcct gttgctgcca agctatttaa tatcatgcac gaaaagcaaa caaacttgtg   3840

tgcttcattg gatgttcgta ccaccaagga attactggag ttagttgaag cattaggtcc   3900

caaaatttgt ttactaaaaa cacatgtgga tatcttgact gatttttcca tggagggcac   3960

agttaagccg ctaaaggcat tatccgccaa gtacaatttt ttactcttcg aagacagaaa   4020

atttgctgac attggtaata cagtcaaatt gcagtactct gcgggtgtat acagaatagc   4080

agaatgggca gacattacga atgcacacgg tgtggtgggc ccaggtattg ttagcggttt   4140

gaagcaggcg gcagaagaag taacaaagga acctagaggc cttttgatgt tagcagaatt   4200

gtcatgcaag ggctccctat ctactggaga atatactaag ggtactgttg acattgcgaa   4260

gagcgacaaa gattttgtta tcggctttat tgctcaaaga gacatgggtg gaagagatga   4320

aggttacgat tggttgatta tgacacccgg tgtgggttta gatgacaagg gagacgcatt   4380

gggtcaacag tatagaaccg tggatgatgt ggtctctaca ggatctgaca ttattattgt   4440

tggaagagga ctatttgcaa agggaaggga tgctaaggta gagggtgaac gttacagaaa   4500

agcaggctgg gaagcatatt tgagaagatg cggccagcaa aactaaaaaa ctgtattata   4560

agtaaatgca tgtatactaa actcacaaat tagagcttca atttaattat atcagttatt   4620

acccgggaat ctcggtcgta atgattttta taatgacgaa aaaaaaaaaa ttggaaagaa   4680

aagccccccc cccccccccc cccccccccc cccccccgca gcgttgggtc ctggccacgg   4740

gtgcgcatga tcgtgctcct gtcgttgagg acccggctag gctggcgggg ttgccttact   4800

ggttagcaga atgaatcacc gatacgcgag cgaacgtgaa gcgactgctg ctgcaaaacg   4860
```

-continued

```
tctgcgacct gagcaacaac atgaatggtc ttcggtttcc gtgtttcgta aagtctggaa   4920
acgcggaagt cagcgccctg caccattatg ttccggatct gcatcgcagg atgctgctgg   4980
ctaccctgtg gaacacctac atctgtatta acgaagcgct ggcattgacc ctgagtgatt   5040
tttctctggt cccgccgcat ccataccgcc agttgtttac cctcacaacg ttccagtaac   5100
cgggcatgtt catcatcagt aacccgtatc gtgagcatcc tctctcgttt catcggtatc   5160
attaccccca tgaacagaaa ttcccccta cacggaggca tcaagtgacc aaacaggaaa   5220
aaaccgccct taacatggcc cgctttatca gaagccagac attaacgctt ctggagaaac   5280
tcaacgagct ggacgcggat gaacaggcag acatctgtga atcgcttcac gaccacgctg   5340
atgagcttta ccgcagctgc ctcgcgcgtt tcggtgatga cggtgaaaac ctctgacaca   5400
tgcagctccc ggagacggtc acagcttgtc tgtaagcgga tgccgggagc agacaagccc   5460
gtcagggcgc gtcagcgggt gttggcgggt gtcggggcgc agccatgacc cagtcacgta   5520
gcgatagcgg agtgtatact ggcttaacta tgcggcatca gagcagattg tactgagagt   5580
gcaccatatg cggtgtgaaa taccgcacag atgcgtaagg agaaaatacc gcatcaggcg   5640
ctcttccgct tcctcgctca ctgactcgct gcgctcggtc gttcggctgc ggcgagcggt   5700
atcagctcac tcaaaggcgg taatacggtt atccacagaa tcaggggata acgcaggaaa   5760
gaacatgtga gcaaaaggcc agcaaaaggc caggaaccgt aaaaaggccg cgttgctggc   5820
gtttttccat aggctccgcc cccctgacga gcatcacaaa aatcgacgct caagtcagag   5880
gtggcgaaac ccgacaggac tataaagata ccaggcgttt ccccctggaa gctccctcgt   5940
gcgctctcct gttccgaccc tgccgcttac cggatacctg tccgcctttc tcccttcggg   6000
aagcgtggcg ctttctcata gctcacgctg taggtatctc agttcggtgt aggtcgttcg   6060
ctccaagctg ggctgtgtgc acgaaccccc cgttcagccc gaccgctgcg ccttatccgg   6120
taactatcgt cttgagtcca acccggtaag acacgactta tcgccactgg cagcagccac   6180
tggtaacagg attagcagag cgaggtatgt aggcggtgct acagagttct tgaagtggtg   6240
gcctaactac ggctacacta gaaggacagt atttggtatc tgcgctctgc tgaagccagt   6300
taccttcgga aaaagagttg gtagctcttg atccggcaaa caaaccaccg ctggtagcgg   6360
tggttttttt gtttgcaagc agcagattac gcgcagaaaa aaaggatctc aagaagatcc   6420
tttgatcttt tctacggggt ctgacgctca gtggaacgaa aactcacgtt aagggatttt   6480
ggtcatgaga ttatcaaaaa ggatcttcac ctagatcctt ttaaattaaa aatgaagttt   6540
taaatcaatc taaagtatat atgagtaaac ttggtctgac agttaccaat gcttaatcag   6600
tgaggcacct atctcagcga tctgtctatt tcgttcatcc atagttgcct gactccccgt   6660
cgtgtagata actacgatac gggagggctt accatctggc cccagtgctg caatgatacc   6720
gcgagaccca cgctcaccgg ctccagattt atcagcaata aaccagccag ccggaagggc   6780
cgagcgcaga agtggtcctg caactttatc cgcctccatc cagtctatta attgttgccg   6840
ggaagctaga gtaagtagtt cgccagttaa tagtttgcgc aacgttgttg ccattgctgc   6900
aggcatcgtg gtgtcacgct cgtcgtttgg tatggcttca ttcagctccg gttcccaacg   6960
atcaaggcga gttacatgat cccccatgtt gtgcaaaaaa gcggttagct ccttcggtcc   7020
tccgatcgtt gtcagaagta agttggccgc agtgttatca ctcatggtta tggcagcact   7080
gcataattct cttactgtca tgccatccgt aagatgcttt tctgtgactg gtgagtactc   7140
aaccaagtca ttctgagaat agtgtatgcg gcgaccgagt tgctcttgcc cggcgtcaac   7200
```

-continued

```
acgggataat accgcgccac atagcagaac tttaaaagtg ctcatcattg gaaaacgttc   7260

ttcggggcga aaactctcaa ggatcttacc gctgttgaga tccagttcga tgtaacccac   7320

tcgtgcaccc aactgatctt cagcatcttt tactttcacc agcgtttctg ggtgagcaaa   7380

aacaggaagg caaaatgccg caaaaaaggg aataagggcg acacggaaat gttgaatact   7440

catactcttc ctttttcaat attattgaag catttatcag ggttattgtc tcatgagcgg   7500

atacatattt gaatgtattt agaaaaataa acaaataggg gttccgcgca catttccccg   7560

aaaagtgcca cctgacgtct aagaaaccat tattatcatg acattaacct ataaaaatag   7620

gcgtatcacg aggccctttc gtcttcaa                                      7648
```

<210> SEQ ID NO 17
<211> LENGTH: 4453
<212> TYPE: DNA
<213> ORGANISM: Artificial Sequence
<220> FEATURE:
<223> OTHER INFORMATION: Description of Artificial Sequence:
vector pUC18-FMD-MFalfa-E1-H6
<220> FEATURE:
<221> NAME/KEY: misc_feature
<222> LOCATION: (1207)..(1208)
<223> OTHER INFORMATION: N is any nucleotide
<220> FEATURE:
<221> NAME/KEY: misc_feature
<222> LOCATION: (1386)..(1387)
<223> OTHER INFORMATION: N is any nucleotide

<400> SEQUENCE: 17

```
gcgcccaata cgcaaaccgc ctctccccgc gcgttggccg attcattaat gcagctggca     60

cgacaggttt cccgactgga aagcgggcag tgagcgcaac gcaattaatg tgagttagct    120

cactcattag gcaccccagg ctttacactt tatgcttccg gctcgtatgt tgtgtggaat    180

tgtgagcgga taacaatttc acacaggaaa cagctatgac catgattacg aattcgagct    240

cggtacccgg ggatccttaa tggtgatggt ggtggtgcca gttcatcatc atatcccaag    300

ccatacggtg acctgttatg tggccgggat agattgagca attgcagtcc tgcaccgtct    360

catgccggcg aggcgagatg gtgaacagct gggagacgag gaagacagat ccgcagagat    420

cccccacgta catagcggaa cagaaagcag ccgccccaac gagcaaatcg acgtggcgtc    480

gtattgtcgt agtggggacg ctggcgttcc tagctgcgag cgtgggggtg agcgctaccc    540

agcagcggga agagttgttc tcccgaacgc agggcacgca cccgggggtg tgcatgatca    600

tgtccgctgc ctcatacaca atgcttgagt tggagcagtc gttcgtgaca tggtacatcc    660

cggacacgtt gcgcacctca taccttttat ccaagcttac cccttcttct ttagcagcaa    720

tgctggcaat agtagtattt ataaacaata acccgttatt tgtgctgttg gaaaatggca    780

aaacagcaac atcgaaatcc ccttctaaat ctgagtaacc gatgacagct tcagccggaa    840

tttgtgccgt ttcatcttct gttgtagtgt tgactggagc agctaatgcg gaggatgctg    900

cgaataaaac tgcagtaaaa attgaaggaa atctcatgaa ttcccgatga aggcagagag    960

cgcaaggagg cggtatttat agtgccattc ccctctctga gagacccgga tggtagtcga   1020

gtgttatcgg agacagcttg atgtagactc cgtgcctgcc ggtcctctta ttggcggaca   1080

ccagtgagac accccggaac ttgctgtttt tctgcaaaat ccggggtgac cagtgggagc   1140

ctatttgcac acacgagcgg gacaccccac tctggtgaag agtgccaaag tcattctttt   1200

tcccgtnncg gggcagccga ttgcatgttt taggaaaata ttacctttgc tacaccctgt   1260

cagatttacc ctccacacat atatattccg tcacctccag ggactattct tggctcgttg   1320
```

-continued

```
cgccgccgcg gaagatatcc agaagctgtg ttttccgaga gactcggttg gcgcctggta   1380
tatttnnagg atgtcgcgct gcctcacgtc ccggtaccca ggaacgcggt gggatctcgg   1440
gcccatcgaa gactgtgctc cagactgctc gcccagcagg tgtttcttga ttgccgcctc   1500
taaatagtcc gcgcatcgcc ggtaacattt ttccagctcg gagtttgcgt ttagatacat   1560
ttctgcgatg ccaaaggagc ctgcagatta taacctcgga tgctgtcatt cagcgctttt   1620
aatttgacct ccagatagtt gctgtatttc tgttccattg gctgctggac gttcgtataa   1680
ctcgagttat tgttgcgctc tgcctcggcg tactggctca tgactgactg cggtcgcttc   1740
tcgagtgttc tcgcaacagg acgcctgcag gtcatcgagt cgagctggcg ccgaaactgg   1800
cggatctgac ctccacactg ccctgtatct ctatccaccg ggaaccgcct cctgccgttc   1860
cagaatgttg ttcaagtggt agctctgtgc ggtcaatgaa ggcgttattg ccggtgaaat   1920
ctttgggaag cggtttatcc tcggggaaga ttacgaaatt cccgcgcgtc gttgcgcttc   1980
ctggatctcg aggaagatcg ttctccgcgt cgaggagatc gttctccgcg tcgacctgca   2040
ggcatgcaag cttggcactg gccgtcgttt tacaacgtcg tgactgggaa aaccctggcg   2100
ttacccaact taatcgcctt gcagcacatc ccccttcgc cagctggcgt aatagcgaag   2160
aggcccgcac cgatcgccct tcccaacagt tgcgcagcct gaatggcgaa tggcgcctga   2220
tgcggtattt tctccttacg catctgtgcg gtatttcaca ccgcatatgg tgcactctca   2280
gtacaatctg ctctgatgcc gcatagttaa gccagccccg acacccgcca acacccgctg   2340
acgcgccctg acgggcttgt ctgctcccgg catccgctta cagacaagct gtgaccgtct   2400
ccgggagctg catgtgtcag aggttttcac cgtcatcacc gaaacgcgcg agacgaaagg   2460
gcctcgtgat acgcctattt ttataggtta atgtcatgat aataatggtt tcttagacgt   2520
caggtggcac ttttcgggga aatgtgcgcg gaacccctat ttgtttattt ttctaaatac   2580
attcaaatat gtatccgctc atgagacaat aaccctgata aatgcttcaa taatattgaa   2640
aaaggaagag tatgagtatt caacatttcc gtgtcgccct tattcccttt tttgcggcat   2700
tttgccttcc tgtttttgct cacccagaaa cgctggtgaa agtaaaagat gctgaagatc   2760
agttgggtgc acgagtgggt tacatcgaac tggatctcaa cagcggtaag atccttgaga   2820
gttttcgccc cgaagaacgt tttccaatga tgagcacttt taaagttctg ctatgtggcg   2880
cggtattatc ccgtattgac gccgggcaag agcaactcgg tcgccgcata cactattctc   2940
agaatgactt ggttgagtac tcaccagtca cagaaaagca tcttacggat ggcatgacag   3000
taagagaatt atgcagtgct gccataacca tgagtgataa cactgcggcc aacttacttc   3060
tgacaacgat cggaggaccg aaggagctaa ccgctttttt gcacaacatg ggggatcatg   3120
taactcgcct tgatcgttgg gaaccggagc tgaatgaagc cataccaaac gacgagcgtg   3180
acaccacgat gcctgtagca atggcaacaa cgttgcgcaa actattaact ggcgaactac   3240
ttactctagc ttcccggcaa caattaatag actggatgga ggcggataaa gttgcaggac   3300
cacttctgcg ctcggccctt ccggctggct ggtttattgc tgataaatct ggagccggtg   3360
agcgtgggtc tcgcggtatc attgcagcac tggggccaga tggtaagccc tcccgtatcg   3420
tagttatcta cacgacgggg agtcaggcaa ctatggatga acgaaataga cagatcgctg   3480
agataggtgc ctcactgatt aagcattggt aactgtcaga ccaagtttac tcatatatac   3540
tttagattga tttaaaactt catttttaat ttaaaaggat ctaggtgaag atcctttttg   3600
ataatctcat gaccaaaatc ccttaacgtg agttttcgtt ccactgagcg tcagaccccg   3660
tagaaaagat caaaggatct tcttgagatc cttttttct gcgcgtaatc tgctgcttgc   3720
```

-continued aaacaaaaaa accaccgcta ccagcggtgg tttgtttgcc ggatcaagag ctaccaactc 3780
tttttccgaa ggtaactggc ttcagcagag cgcagatacc aaatactgtc cttctagtgt 3840
agccgtagtt aggccaccac ttcaagaact ctgtagcacc gcctacatac ctcgctctgc 3900
taatcctgtt accagtggct gctgccagtg gcgataagtc gtgtcttacc gggttggact 3960
caagacgata gttaccggat aaggcgcagc ggtcgggctg aacggggggt tcgtgcacac 4020
agcccagctt ggagcgaacg acctacaccg aactgagata cctacagcgt gagctatgag 4080
aaagcgccac gcttcccgaa gggagaaagg cggacaggta tccggtaagc ggcagggtcg 4140
gaacaggaga gcgcacgagg gagcttccag ggggaaacgc ctggtatctt tatagtcctg 4200
tcgggtttcg ccacctctga cttgagcgtc gatttttgtg atgctcgtca ggggggcgga 4260
gcctatggaa aaacgccagc aacgcggcct ttttacggtt cctggccttt tgctggcctt 4320
ttgctcacat gttctttcct gcgttatccc ctgattctgt ggataaccgt attaccgcct 4380
ttgagtgagc tgataccgct cgccgcagcc gaacgaccga gcgcagcgag tcagtgagcg 4440
aggaagcgga aga 4453

<210> SEQ ID NO 18
<211> LENGTH: 51
<212> TYPE: DNA
<213> ORGANISM: Artificial Sequence
<220> FEATURE:
<223> OTHER INFORMATION: Description of Artificial Sequence:
primer CL hin

<400> SEQUENCE: 18
tgcttcctac cactagcagc actaggatat gaggtgcgca acgtgtccgg g 51

<210> SEQ ID NO 19
<211> LENGTH: 52
<212> TYPE: DNA
<213> ORGANISM: Artificial Sequence
<220> FEATURE:
<223> OTHER INFORMATION: Description of Artificial Sequence:
primer CL her neu

<400> SEQUENCE: 19
tagtactagt attagtaggc ttcgcatgaa ttcccgatga aggcagagag cg 52

<210> SEQ ID NO 20
<211> LENGTH: 4252
<212> TYPE: DNA
<213> ORGANISM: Artificial Sequence
<220> FEATURE:
<223> OTHER INFORMATION: Description of Artificial Sequence:
vector pUC18-FMD-CL-E1-H6
<220> FEATURE:
<221> NAME/KEY: misc_feature
<222> LOCATION: (1006)..(1007)
<223> OTHER INFORMATION: N is any nucleotide
<220> FEATURE:
<221> NAME/KEY: misc_feature
<222> LOCATION: (1185)..(1186)
<223> OTHER INFORMATION: N is any nucleotide

<400> SEQUENCE: 20
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg aattcgagct 240

-continued

```
cggtacccgg ggatccttaa tggtgatggt ggtggtgcca gttcatcatc atatcccaag    300
ccatacggtg acctgttatg tggccgggat agattgagca attgcagtcc tgcaccgtct    360
catgccggcg aggcgagatg gtgaacagct gggagacgag gaagacagat ccgcagagat    420
cccccacgta catagcggaa cagaaagcag ccgccccaac gagcaaatcg acgtggcgtc    480
gtattgtcgt agtggggacg ctggcgttcc tagctgcgag cgtgggggtg agcgctaccc    540
agcagcggga agagttgttc tcccgaacgc agggcacgca cccgggggtg tgcatgatca    600
tgtccgctgc ctcatacaca atgcttgagt tggagcagtc gttcgtgaca tggtacatcc    660
cggacacgtt gcgcacctca tatcctagtg ctgctagtgg taggaagcat agtactagta    720
ttagtaggct tcgcatgaat tcccgatgaa ggcagagagc gcaaggaggc ggtatttata    780
gtgccattcc cctctctgag agacccggat ggtagtcgag tgttatcgga gacagcttga    840
tgtagactcc gtgcctgccg gtcctcttat tggcggacac cagtgagaca ccccggaact    900
tgctgttttt ctgcaaaatc cggggtgacc agtgggagcc tatttgcaca cacgagcggg    960
acaccccact ctggtgaaga gtgccaaagt cattcttttt cccgtnncgg ggcagccgat   1020
tgcatgtttt aggaaaatat tacctttgct acaccctgtc agatttaccc tccacacata   1080
tatattccgt cacctccagg gactattctt ggctcgttgc gccgccgcgg aagatatcca   1140
gaagctgtgt tttccgagag actcggttgg cgcctggtat atttnnagga tgtcgcgctg   1200
cctcacgtcc cggtacccag gaacgcggtg ggatctcggg cccatcgaag actgtgctcc   1260
agactgctcg cccagcaggt gtttcttgat tgccgcctct aaatagtccg cgcatcgccg   1320
gtaacatttt tccagctcgg agtttgcgtt tagatacatt tctgcgatgc caaaggagcc   1380
tgcagattat aacctcggat gctgtcattc agcgctttta atttgacctc cagatagttg   1440
ctgtatttct gttccattgg ctgctggacg ttcgtataac tcgagttatt gttgcgctct   1500
gcctcggcgt actggctcat gactgactgc ggtcgcttct cgagtgttct cgcaacagga   1560
cgcctgcagg tcatcgagtc gagctggcgc cgaaactggc ggatctgacc tccacactgc   1620
cctgtatctc tatccaccgg gaaccgcctc ctgccgttcc agaatgttgt tcaagtggta   1680
gctctgtgcg gtcaatgaag gcgttattgc cggtgaaatc tttgggaagc ggtttatcct   1740
cggggaagat tacgaaattc ccgcgcgtcg ttgcgcttcc tggatctcga ggaagatcgt   1800
tctccgcgtc gaggagatcg ttctccgcgt cgacctgcag gcatgcaagc ttggcactgg   1860
ccgtcgtttt acaacgtcgt gactgggaaa accctggcgt tacccaactt aatcgccttg   1920
cagcacatcc ccctttcgcc agctggcgta atagcgaaga ggcccgcacc gatcgccctt   1980
cccaacagtt gcgcagcctg aatggcgaat ggcgcctgat gcggtatttt ctccttacgc   2040
atctgtgcgg tatttcacac cgcatatggt gcactctcag tacaatctgc tctgatgccg   2100
catagttaag ccagccccga cacccgccaa cacccgctga cgcgccctga cgggcttgtc   2160
tgctcccggc atccgcttac agacaagctg tgaccgtctc cgggagctgc atgtgtcaga   2220
ggttttcacc gtcatcaccg aaacgcgcga gacgaaaggg cctcgtgata cgcctatttt   2280
tataggttaa tgtcatgata ataatggttt cttagacgtc aggtggcact tttcggggaa   2340
atgtgcgcgg aacccctatt tgtttatttt tctaaataca ttcaaatatg tatccgctca   2400
tgagacaata accctgataa atgcttcaat aatattgaaa aaggaagagt atgagtattc   2460
aacatttccg tgtcgccctt attccctttt ttgcggcatt ttgccttcct gtttttgctc   2520
acccagaaac gctggtgaaa gtaaaagatg ctgaagatca gttgggtgca cgagtgggtt   2580
```

-continued

```
acatcgaact ggatctcaac agcggtaaga tccttgagag ttttcgcccc gaagaacgtt   2640
ttccaatgat gagcactttt aaagttctgc tatgtggcgc ggtattatcc cgtattgacg   2700
ccgggcaaga gcaactcggt cgccgcatac actattctca gaatgacttg gttgagtact   2760
caccagtcac agaaaagcat cttacggatg gcatgacagt aagagaatta tgcagtgctg   2820
ccataaccat gagtgataac actgcggcca acttacttct gacaacgatc ggaggaccga   2880
aggagctaac cgcttttttg cacaacatgg gggatcatgt aactcgcctt gatcgttggg   2940
aaccggagct gaatgaagcc ataccaaacg acgagcgtga caccacgatg cctgtagcaa   3000
tggcaacaac gttgcgcaaa ctattaactg gcgaactact tactctagct tcccggcaac   3060
aattaataga ctggatggag gcggataaag ttgcaggacc acttctgcgc tcggcccttc   3120
cggctggctg gtttattgct gataaatctg gagccggtga gcgtgggtct cgcggtatca   3180
ttgcagcact ggggccagat ggtaagccct cccgtatcgt agttatctac acgacgggga   3240
gtcaggcaac tatggatgaa cgaaatagac agatcgctga gataggtgcc tcactgatta   3300
agcattggta actgtcagac caagtttact catatatact ttagattgat ttaaaacttc   3360
atttttaatt taaaaggatc taggtgaaga tcctttttga taatctcatg accaaaatcc   3420
cttaacgtga gttttcgttc cactgagcgt cagaccccgt agaaaagatc aaaggatctt   3480
cttgagatcc tttttttctg cgcgtaatct gctgcttgca aacaaaaaaa ccaccgctac   3540
cagcggtggt ttgtttgccg gatcaagagc taccaactct ttttccgaag gtaactggct   3600
tcagcagagc gcagatacca aatactgtcc ttctagtgta gccgtagtta ggccaccact   3660
tcaagaactc tgtagcaccg cctacatacc tcgctctgct aatcctgtta ccagtggctg   3720
ctgccagtgg cgataagtcg tgtcttaccg ggttggactc aagacgatag ttaccggata   3780
aggcgcagcg gtcgggctga acggggggtt cgtgcacaca gcccagcttg gagcgaacga   3840
cctacaccga actgagatac ctacagcgtg agctatgaga aagcgccacg cttcccgaag   3900
ggagaaaggc ggacaggtat ccggtaagcg gcagggtcgg aacaggagag cgcacgaggg   3960
agcttccagg gggaaacgcc tggtatcttt atagtcctgt cgggtttcgc cacctctgac   4020
ttgagcgtcg atttttgtga tgctcgtcag gggggcggag cctatggaaa aacgccagca   4080
acgcggcctt tttacggttc ctggcctttt gctggccttt tgctcacatg ttctttcctg   4140
cgttatcccc tgattctgtg gataaccgta ttaccgcctt tgagtgagct gataccgctc   4200
gccgcagccg aacgaccgag cgcagcgagt cagtgagcga ggaagcggaa ga           4252
```

<210> SEQ ID NO 21
<211> LENGTH: 7447
<212> TYPE: DNA
<213> ORGANISM: Artificial Sequence
<220> FEATURE:
<223> OTHER INFORMATION: Description of Artificial Sequence:
vector pFPMT-CL-E1-H6

<400> SEQUENCE: 21

```
ggtaccctgc tcaatctccg gaatggtgat ctgatcgttc ctgaaaacct cgacattggc     60
tccctcctga cacaggtact cgtacaggtt ccaggtaaac gagtcgtagt tgtcgatcat    120
gacaacgttc ttagaagcgg ccggcatttt gaaggtgact aatagcctaa gaaaatattt    180
aatttaattt tcattaaatt ttcctatact cgctatttca gcttttcatc tcatcacttc    240
ataaacgata taaaccagaa aaagaactat tttcaaacac gcttctcaaa agcggtatgt    300
ccttccacgt ctccttagaa tctggcaagt ccgcgagggg gatccttaat ggtgatggtg    360
```

-continued

```
gtggtgccag ttcatcatca tatcccaagc catacggtga cctgttatgt ggccgggata    420
gattgagcaa ttgcagtcct gcaccgtctc atgccggcga ggcgagatgg tgaacagctg    480
ggagacgagg aagacagatc cgcagagatc ccccacgtac atagcggaac agaaagcagc    540
cgccccaacg agcaaatcga cgtggcgtcg tattgtcgta gtggggacgc tggcgttcct    600
agctgcgagc gtgggggtga gcgctaccca gcagcgggaa gagttgttct cccgaacgca    660
gggcacgcac ccgggggtgt gcatgatcat gtccgctgcc tcatacacaa tgcttgagtt    720
ggagcagtcg ttcgtgacat ggtacatccc ggacacgttg cgcacctcat atcctagtgc    780
tgctagtggt aggaagcata gtactagtat tagtaggctt cgcatgaatt cccgatgaag    840
cagagagcgc aggaggcggt atttatagtg ccattcccct ctctgagaga cccggatggt    900
agtcgagtgt atcggagaca gcttgatgta gactccgtgc ctgccggctc ctcttattgg    960
cggacaccag tgagacaccc cggaacttgc tgtttttctg caaaatccgg ggtgaccagt   1020
gggagcctat ttgcacacac gagcgggaca ccccactctg gtgaagagtg ccaaagtcat   1080
tctttttccc gttgcggggc agccgattgc atgttttagg aaaatattac ctttgctaca   1140
ccctgtcaga tttaccctcc acacatatat attccgtcac ctccagggac tattattcgt   1200
cgttgcgccg ccagcggaag atatccagaa gctgttttcc gagagactcg gttggcgcct   1260
ggtatatttg atggatgtcg cgctgcctca cgtcccggta cccaggaacg cggtgggatc   1320
tcgggcccat cgaagactgt gctccagact gctcgcccag caggtgtttc ttgatcgccg   1380
cctctaaatt gtccgcgcat cgccggtaac atttttccag ctcggagttt gcgtttagat   1440
acagtttctg cgatgccaaa ggagcctgca gattataacc tcggatgctg tcattcagcg   1500
cttttaattt gacctccaga tagttgctgt atttctgttc ccattggctg ctgcgcagct   1560
tcgtataact cgagttattg ttgcgctctg cctcggcgta ctggctcatg atctggatct   1620
tgtccgtgtc gcttttcttc gagtgtttct cgcaaacgat gtgcacggcc tgcagtgtcc   1680
aatcggagtc gagctggcgc cgaaactggc ggatctgagc ctccacactg ccctgtttct   1740
ctatccacgg cggaaccgcc tcctgccgtt tcagaatgtt gttcaagtgg tactctgtgc   1800
ggtcaatgaa ggcgttattg ccggtgaaat ctttgggaag cggttttcct cggggaagat   1860
tacgaaattc cccgcgtcgt tgcgcttcct ggatctcgag gagatcgttc tccgcgtcga   1920
ggagatcgtt ctccgcgtcg acaccattcc ttgcggcggc ggtgctcaac ggcctcaacc   1980
tactactggg ctgcttccta atgcaggagt cgcataaggg agagcgtcga caaacccgcg   2040
tttgagaact tgctcaagct tctggtaaac gttgtagtac tctgaaacaa ggccctagca   2100
ctctgatctg tttctcttgg gtagcggtga gtggtttatt ggagttcact ggtttcagca   2160
catctgtcat ctagacaata ttgttactaa attttttttga actacaattg ttcgtaattc   2220
atctattatt atacatcctc gtcagcaatt tctggcagac ggagtttact aacgtcttga   2280
gtatgaggcc gagaatccag ctctgtggcc atactcagtc ttgacagcct gctgatgtgg   2340
ctgcgttcaa cgcaataagc gtgtcctccg actccgagtt gtgctcgtta tcgtcgttct   2400
catcctcgga aaaatcacac gaaagaacat actcaccagt aggctttctg gtccctgggg   2460
cacggctgtt tctgacgtat tccggcgttg ataatagctc gaaagtgaac gccgagtcgc   2520
gggagtcgac cgatgccctt gagagccttc aacccagtca gctccttccg gtgggcgcgg   2580
ggcatgacta tcgtcgccgc acttatgact gtcttcttta tcatgcaact cgtaggacag   2640
gtgccggcag cgctctgggt cattttcggc gaggaccgct ttcgctggag cgcgacgatg   2700
atcggcctgt cgcttgcggt attcggaatc ttgcacgccc tcgctcaagc cttcgtcact   2760
```

-continued

```
ggtcccgcca ccaaacgttt cggcgagaag caggccatta tcgccggcat ggcggccgac   2820
gcgctgggct acgtcttgct ggcgttcgcg acgcgaggct ggatggcctt ccccattatg   2880
attcttctcg cttccggcgg catcgggatg cccgcgttgc aggccatgct gtccaggcag   2940
gtagatgacg accatcaggg acagcttcaa ggatcgctcg cggctcttac cagcctaact   3000
tcgatcactg gaccgctgat cgtcacggcg atttatgccg cctcggcgag cacatggaac   3060
gggttggcat ggattgtagg cgccgcccta taccttgtct gcctccccgc gttgcgtcgc   3120
ggtgcatgga gccgggccac ctcgacctga atggaagccg gcggcacctc gctaacggat   3180
tcaccactcc aagaattgga gccaatcaat tcttgcggag aactgtgaat gcgcaaacca   3240
acccttggca gaacatatcc atcgcgtccg ccatctccag cagccgcacg cggcgcatcg   3300
gggggggggg gggggggggg gggcaaacaa ttcatcattt tttttttatt cttttttttg   3360
atttcggttt ctttgaaatt tttttgattc ggtaatctcc gaacagaagg aagaacgaag   3420
gaaggagcac agacttagat tggtatatat acgcatatgt agtgttgaag aaacatgaaa   3480
ttgcccagta ttcttaaccc aactgcacag aacaaaaacc tgcaggaaac gaagataaat   3540
catgtcgaaa gctacatata aggaacgtgc tgctactcat cctagtcctg ttgctgccaa   3600
gctatttaat atcatgcacg aaaagcaaac aaacttgtgt gcttcattgg atgttcgtac   3660
caccaaggaa ttactggagt tagttgaagc attaggtccc aaaatttgtt tactaaaaac   3720
acatgtggat atcttgactg atttttccat ggagggcaca gttaagccgc taaaggcatt   3780
atccgccaag tacaattttt tactcttcga agacagaaaa tttgctgaca ttggtaatac   3840
agtcaaattg cagtactctg cgggtgtata cagaatagca gaatgggcag acattacgaa   3900
tgcacacggt gtggtgggcc caggtattgt tagcggtttg aagcaggcgg cagaagaagt   3960
aacaaaggaa cctagaggcc ttttgatgtt agcagaattg tcatgcaagg gctccctatc   4020
tactggagaa tatactaagg gtactgttga cattgcgaag agcgacaaag attttgttat   4080
cggctttatt gctcaaagag acatgggtgg aagagatgaa ggttacgatt ggttgattat   4140
gacacccggt gtgggtttag atgacaaggg agacgcattg ggtcaacagt atagaaccgt   4200
ggatgatgtg gtctctacag gatctgacat tattattgtt ggaagaggac tatttgcaaa   4260
gggaagggat gctaaggtag agggtgaacg ttacagaaaa gcaggctggg aagcatattt   4320
gagaagatgc ggccagcaaa actaaaaaac tgtattataa gtaaatgcat gtatactaaa   4380
ctcacaaatt agagcttcaa tttaattata tcagttatta cccgggaatc tcggtcgtaa   4440
tgatttttat aatgacgaaa aaaaaaaaat tggaaagaaa agcccccccc cccccccccc   4500
cccccccccc ccccccgcag cgttgggtcc tggccacggg tgcgcatgat cgtgctcctg   4560
tcgttgagga cccggctagg ctggcggggt tgccttactg gttagcagaa tgaatcaccg   4620
atacgcgagc gaacgtgaag cgactgctgc tgcaaaacgt ctgcgacctg agcaacaaca   4680
tgaatggtct tcggtttccg tgtttcgtaa agtctggaaa cgcggaagtc agcgccctgc   4740
accattatgt tccggatctg catcgcagga tgctgctggc taccctgtgg aacacctaca   4800
tctgtattaa cgaagcgctg gcattgaccc tgagtgattt ttctctggtc ccgccgcatc   4860
cataccgcca gttgtttacc ctcacaacgt tccagtaacc gggcatgttc atcatcagta   4920
acccgtatcg tgagcatcct ctctcgtttc atcggtatca ttacccccat gaacagaaat   4980
tcccccttac acggaggcat caagtgacca aacaggaaaa aaccgccctt aacatggccc   5040
gctttatcag aagccagaca ttaacgcttc tggagaaact caacgagctg gacgcggatg   5100
```

-continued

```
aacaggcaga catctgtgaa tcgcttcacg accacgctga tgagctttac cgcagctgcc   5160
tcgcgcgttt cggtgatgac ggtgaaaacc tctgacacat gcagctcccg gagacggtca   5220
cagcttgtct gtaagcggat gccgggagca gacaagcccg tcagggcgcg tcagcgggtg   5280
ttggcgggtg tcggggcgca gccatgaccc agtcacgtag cgatagcgga gtgtatactg   5340
gcttaactat gcggcatcag agcagattgt actgagagtg caccatatgc ggtgtgaaat   5400
accgcacaga tgcgtaagga gaaaataccg catcaggcgc tcttccgctt cctcgctcac   5460
tgactcgctg cgctcggtcg ttcggctgcg gcgagcggta tcagctcact caaaggcggt   5520
aatacggtta tccacagaat caggggataa cgcaggaaag aacatgtgag caaaaggcca   5580
gcaaaaggcc aggaaccgta aaaaggccgc gttgctggcg tttttccata ggctccgccc   5640
ccctgacgag catcacaaaa atcgacgctc aagtcagagg tggcgaaacc cgacaggact   5700
ataaagatac caggcgtttc cccctggaag ctccctcgtg cgctctcctg ttccgaccct   5760
gccgcttacc ggatacctgt ccgcctttct cccttcggga agcgtggcgc tttctcatag   5820
ctcacgctgt aggtatctca gttcggtgta ggtcgttcgc tccaagctgg gctgtgtgca   5880
cgaacccccc gttcagcccg accgctgcgc cttatccggt aactatcgtc ttgagtccaa   5940
cccggtaaga cacgacttat cgccactggc agcagccact ggtaacagga ttagcagagc   6000
gaggtatgta ggcggtgcta cagagttctt gaagtggtgg cctaactacg gctacactag   6060
aaggacagta tttggtatct gcgctctgct gaagccagtt accttcggaa aaagagttgg   6120
tagctcttga tccggcaaac aaaccaccgc tggtagcggt ggtttttttg tttgcaagca   6180
gcagattacg cgcagaaaaa aaggatctca agaagatcct ttgatctttt ctacggggtc   6240
tgacgctcag tggaacgaaa actcacgtta agggattttg gtcatgagat tatcaaaaag   6300
gatcttcacc tagatccttt taaattaaaa atgaagtttt aaatcaatct aaagtatata   6360
tgagtaaact tggtctgaca gttaccaatg cttaatcagt gaggcaccta tctcagcgat   6420
ctgtctattt cgttcatcca tagttgcctg actccccgtc gtgtagataa ctacgatacg   6480
ggagggctta ccatctggcc ccagtgctgc aatgataccg cgagacccac gctcaccggc   6540
tccagattta tcagcaataa accagccagc cggaagggcc gagcgcagaa gtggtcctgc   6600
aactttatcc gcctccatcc agtctattaa ttgttgccgg gaagctagag taagtagttc   6660
gccagttaat agtttgcgca acgttgttgc cattgctgca ggcatcgtgg tgtcacgctc   6720
gtcgtttggt atggcttcat tcagctccgg ttcccaacga tcaaggcgag ttacatgatc   6780
ccccatgttg tgcaaaaaag cggttagctc cttcggtcct ccgatcgttg tcagaagtaa   6840
gttggccgca gtgttatcac tcatggttat ggcagcactg cataattctc ttactgtcat   6900
gccatccgta agatgctttt ctgtgactgg tgagtactca accaagtcat tctgagaata   6960
gtgtatgcgg cgaccgagtt gctcttgccc ggcgtcaaca cgggataata ccgcgccaca   7020
tagcagaact ttaaaagtgc tcatcattgg aaaacgttct tcggggcgaa aactctcaag   7080
gatcttaccg ctgttgagat ccagttcgat gtaacccact cgtgcaccca actgatcttc   7140
agcatctttt actttcacca gcgtttctgg gtgagcaaaa acaggaaggc aaaatgccgc   7200
aaaaaaggga ataagggcga cacggaaatg ttgaatactc atactcttcc tttttcaata   7260
ttattgaagc atttatcagg gttattgtct catgagcgga tacatatttg aatgtattta   7320
gaaaaataaa caaatagggg ttccgcgcac atttccccga aaagtgccac ctgacgtcta   7380
agaaaccatt attatcatga cattaaccta taaaaatagg cgtatcacga ggccctttcg   7440
tcttcaa                                                             7447
```

-continued

<210> SEQ ID NO 22
<211> LENGTH: 3730
<212> TYPE: DNA
<213> ORGANISM: Artificial Sequence
<220> FEATURE:
<223> OTHER INFORMATION: Description of Artificial Sequence:
vector pSP72E2H6

<400> SEQUENCE: 22
gaactcgagc agctgaagct tgaattcatg agatttcctt caatttttac tgcagtttta 60
ttcgcagcat cctccgcatt agctgctcca gtcaacacta caacagaaga tgaaacggca 120
caaattccgg ctgaagctgt catcggttac tcagatttag aaggggattt cgatgttgct 180
gttttgccat tttccaacag cacaaataac gggttattgt ttataaatac tactattgcc 240
agcattgctg ctaaagaaga aggggtatct ctagataaaa ggcatacccg cgtgtcagga 300
ggggcagcag cctccgatac caggggcctt gtgtccctct ttagccccgg gtcggctcag 360
aaaatccagc tcgtaaacac caacggcagt tggcacatca acaggactgc cctgaactgc 420
aacgactccc tccaaacagg gttctttgcc gcactattct acaaacacaa attcaactcg 480
tctggatgcc cagagcgctt ggccagctgt cgctccatcg acaagttcgc tcaggggtgg 540
ggtcccctca cttacactga gcctaacagc tcggaccaga ggccctactg ctggcactac 600
gcgcctcgac cgtgtggtat tgtacccgcg tctcaggtgt gcggtccagt gtattgcttc 660
accccgagcc ctgttgtggt ggggacgacc gatcggtttg gtgtccccac gtataactgg 720
ggggcgaacg actcggatgt gctgattctc aacaacacgc ggccgccgcg aggcaactgg 780
ttcggctgta catggatgaa tggcactggg ttcaccaaga cgtgtggggg cccccccgtgc 840 aacatcgggg gggccggcaa caacaccttg acctgcccca ctgactgttt tcggaagcac 900
cccgaggcca cttacgccag atgcggttct gggccctggc tgacacctag gtgtatggtt 960
cattacccat ataggctctg gcactacccc tgcactgtca acttcaccat cttcaaggtt 1020
aggatgtacg tgggggggcgt ggagcacagg ttcgaagccg catgcaattg gactcgagga 1080
gagcgttgtg acttggagga cagggataga tcagagctta gctcgctgct gctgtctaca 1140
acagagtggc aggtgatcga gggcagacac catcaccacc atcactaata gttaattaac 1200
gatctcgact tggttgaaca cgttgccaag gcttaagtga atttacttta aagtcttgca 1260
tttaaataaa ttttcttttt atagctttat gacttagttt caatttatat actattttaa 1320
tgacattttc gattcattga ttgaaagcta tcagatctgc cggtctccct atagtgagtc 1380
gtattaattt cgataagcca ggttaacctg cattaatgaa tcggccaacg cgcggggaga 1440
ggcggtttgc gtattgggcg ctcttccgct tcctcgctca ctgactcgct gcgctcggtc 1500
gttcggctgc ggcgagcggt atcagctcac tcaaaggcgg taatacggtt atccacagaa 1560
tcaggggata acgcaggaaa gaacatgtga gcaaaaggcc agcaaaaggc caggaaccgt 1620
aaaaaggccg cgttgctggc gtttttccat aggctccgcc cccctgacga gcatcacaaa 1680
aatcgacgct caagtcagag gtggcgaaac ccgacaggac tataaagata ccaggcgttt 1740
ccccctggaa gctccctcgt gcgctctcct gttccgaccc tgccgcttac cggatacctg 1800
tccgcctttc tcccttcggg aagcgtggcg ctttctcaat gctcacgctg taggtatctc 1860
agttcggtgt aggtcgttcg ctccaagctg ggctgtgtgc acgaaccccc cgttcagccc 1920
gaccgctgcg ccttatccgg taactatcgt cttgagtcca acccggtaag acacgactta 1980
tcgccactgg cagcagccac tggtaacagg attagcagag cgaggtatgt aggcggtgct 2040

-continued acagagttct tgaagtggtg gcctaactac ggctacacta gaaggacagt atttggtatc 2100
tgcgctctgc tgaagccagt taccttcgga aaaagagttg gtagctcttg atccggcaaa 2160
caaaccaccg ctggtagcgg tggttttttt gtttgcaagc agcagattac gcgcagaaaa 2220
aaaggatctc aagaagatcc tttgatcttt tctacggggt ctgacgctca gtggaacgaa 2280
aactcacgtt aagggatttt ggtcatgaga ttatcaaaaa ggatcttcac ctagatcctt 2340
ttaaattaaa aatgaagttt taaatcaatc taaagtatat atgagtaaac ttggtctgac 2400
agttaccaat gcttaatcag tgaggcacct atctcagcga tctgtctatt tcgttcatcc 2460
atagttgcct gactccccgt cgtgtagata actacgatac gggagggctt accatctggc 2520
cccagtgctg caatgatacc gcgagaccca cgctcaccgg ctccagattt atcagcaata 2580
aaccagccag ccggaagggc cgagcgcaga agtggtcctg caactttatc cgcctccatc 2640
cagtctatta attgttgccg ggaagctaga gtaagtagtt cgccagttaa tagtttgcgc 2700
aacgttgttg ccattgctac aggcatcgtg gtgtcacgct cgtcgtttgg tatggcttca 2760
ttcagctccg gttcccaacg atcaaggcga gttacatgat cccccatgtt gtgcaaaaaa 2820
gcggttagct ccttcggtcc tccgatcgtt gtcagaagta agttggccgc agtgttatca 2880
ctcatggtta tggcagcact gcataattct cttactgtca tgccatccgt aagatgcttt 2940
tctgtgactg gtgagtactc aaccaagtca ttctgagaat agtgtatgcg gcgaccgagt 3000
tgctcttgcc cggcgtcaat acgggataat accgcgccac atagcagaac tttaaaagtg 3060
ctcatcattg gaaaacgttc ttcggggcga aaactctcaa ggatcttacc gctgttgaga 3120
tccagttcga tgtaacccac tcgtgcaccc aactgatctt cagcatcttt tactttcacc 3180
agcgtttctg ggtgagcaaa aacaggaagg caaaatgccg caaaaaaggg aataagggcg 3240
acacggaaat gttgaatact catactcttc ctttttcaat attattgaag catttatcag 3300
ggttattgtc tcatgagcgg atacatattt gaatgtattt agaaaaataa acaaataggg 3360
gttccgcgca catttccccg aaaagtgcca cctgacgtct aagaaaccat tattatcatg 3420
acattaacct ataaaaatag gcgtatcacg aggccctttc gtctcgcgcg tttcggtgat 3480
gacggtgaaa acctctgaca catgcagctc ccggagacgg tcacagcttg tctgtaagcg 3540
gatgccggga gcagacaagc ccgtcagggc gcgtcagcgg gtgttggcgg gtgtcggggc 3600
tggcttaact atgcggcatc agagcagatt gtactgagag tgcaccatat ggacatattg 3660
tcgttagaac gcggctacaa ttaatacata accttatgta tcatacacat acgatttagg 3720
tgacactata 3730

<210> SEQ ID NO 23
<211> LENGTH: 7370
<212> TYPE: DNA
<213> ORGANISM: Artificial Sequence
<220> FEATURE:
<223> OTHER INFORMATION: Description of Artificial Sequence:
vector pMPT121
<220> FEATURE:
<221> NAME/KEY: misc_feature
<222> LOCATION: (778)..(778)
<223> OTHER INFORMATION: N is any nucleotide

<400> SEQUENCE: 23
ggtaccctgc tcaatctccg gaatggtgat ctgatcgttc ctgaaaacct cgacattggc 60
tccctcctga cacaggtact cgtacaggtt ccaggtaaac gagtcgtagt tgtcgatcat 120
gacaacgttc ttagaagcgg ccggcatttt gaaggtgact aatagcctaa gaaaatattt 180

-continued

```
aatttaattt tcattaaatt ttcctatact cgctatttca gcttttcatc tcatcacttc    240
ataaacgata taaaccagaa aaagaactat tttcaaacac gcttctcaaa agcggtatgt    300
ccttccacgt ctccttagaa tctggcaagt ccgcgagggg gatccagatc tgaattcgtt    360
tttgtacttt agattgatgt caccaccgtg cactggcagc agtatttata gatggaccgt    420
gtggggacgg ttgggtacac ttagcggcag cgctgacccc atctgtgatc aagtagggca    480
aaaactgggg atgtcggagt cgctgcacgg tagcataaga atttactttc tggccggttc    540
acccgcattt gcactgtgga gaaacagcct gtccgacacc ccaccagttg ccacatcggc    600
cctctgctgc tctggtgatt ttctggtagc aggcacagac agcagtgggt agcgccgtcc    660
ggttaggcaa ggtcacgttg taggctaccc cagcaaacag agcctcacat gacaccatcc    720
agctgcgtcc tcgaagcgaa aagttcggtt gcggctgcag aaccccctca gttgccanat    780
tcacaagttt tacgcgacgg ctaaagcgag tgggttttaa aacttgcgg tgcaaggatg    840
catgcggcaa caattaattg gtgcatccag cacagcaagc ccagtctcga gatgtccagt    900
cgctacagag tggagtacgc actcaaggaa caccgtcgag atggcctcat agaatggatc    960
aagggcctgc tggccacgcc gttcgtcctg tacgcggtga agagcaacgg catctctgca   1020
gtggacgacc tcatggtaaa ctctgaggca aaacgccgct acgcggaaat cttccacgac   1080
ctcgaactcc tcatcgacga caacattgaa atgaccaaag ccggcacccc cgaattgtct   1140
cggctcgtgc agctggttcc gagcgttggc agcttcttca cgagactgcc tctggaaaag   1200
gccttctaca tcgaggacga gcgccgcgcc atcagcaaac gccggcttgt ggccccctcg   1260
ttcaacgacg tccggctcat tctcaacacg gcccagctgt tggagatgtc gcggttcttc   1320
cattccaaaa ccatccgaga tcgcaagctg cagctcatta cattcgatgg tgacatcaca   1380
ctgtacgacg acggcaaaaa tttcgatgcc gagtcgccca tcctgcccca cctcatcaaa   1440
ctaatggcca aggacctcta tgtgggtatc gtcaccgcgg ccggctacag cgacggaaca   1500
agtactacga gcgcctcaag ggcctcatcg acgccgtcca gacgtccccg ctgctcacag   1560
gccaccagaa agagaacctg ttcattatgg gcggcgaggc aaactacctc ttccggtaca   1620
gtaacgagga gcagagatta cgcttctact ccaaagacag atggctgctc gagaacatgc   1680
tgaattggtc cgaggaggac attcatctga cactggactt tgcgcaggac gttctaaacg   1740
acctcgttca caaactgggc tcgccagcca ccgtggtccg caaggagcgt cgcgtcggcc   1800
tggttccatt accgggccac aagctgatcc gcgagcagct cgaggagatc gttctccgcg   1860
tcgacaccat tccttgcggc ggcggtgctc aacggcctca acctactact gggctgcttc   1920
ctaatgcagg agtcgcataa gggagagcgt cgactcccgc gactcggcgt tcactttcga   1980
gctattatca acgccggaat acgtcagaaa cagccgtgcc ccagggacca gaaagcctac   2040
tggtgagtat gttctttcgt gtgatttttc cgaggatgag aacgacgata acgagcacaa   2100
ctcggagtcg gaggacacgc ttattgcgtt gaacgcagcc acatcagcag gctgtcaaga   2160
ctgagtatgg ccacagagct ggattctcgg cctcatactc aagacgttag taaactccgt   2220
ctgccagaaa ttgctgacga ggatgtataa taatagatga attacgaaca attgtagttc   2280
aaaaaaattt agtaacaata ttgtctagat gacagatgtg ctgaaaccag tgaactccaa   2340
taaaccactc accgctaccc aagagaaaca gatcagagtg ctagggcctt gtttcagagt   2400
actacaacgt ttaccagaag cttgagcaag ttctcaaacg cgggtttgtc gaccgatgcc   2460
cttgagagcc ttcaacccag tcagctcctt ccggtgggcg cggggcatga ctatcgtcgc   2520
```

-continued

```
cgcacttatg actgtcttct ttatcatgca actcgtagga caggtgccgg cagcgctctg   2580
ggtcattttc ggcgaggacc gctttcgctg gagcgcgacg atgatcggcc tgtcgcttgc   2640
ggtattcgga atcttgcacg ccctcgctca agccttcgtc actggtcccg ccaccaaacg   2700
tttcggcgag aagcaggcca ttatcgccgg catggcggcc gacgcgctgg gctacgtctt   2760
gctggcgttc gcgacgcgag gctggatggc cttccccatt atgattcttc tcgcttccgg   2820
cggcatcggg atgcccgcgt tgcaggccat gctgtccagg caggtagatg acgaccatca   2880
gggacagctt caaggatcgc tcgcggctct taccagccta acttcgatca ctggaccgct   2940
gatcgtcacg gcgatttatg ccgcctcggc gagcacatgg aacgggttgg catggattgt   3000
aggcgccgcc ctataccttg tctgcctccc cgcgttgcgt cgcggtgcat ggagccgggc   3060
cacctcgacc tgaatggaag ccggcggcac ctcgctaacg gattcaccac tccaagaatt   3120
ggagccaatc aattcttgcg gagaactgtg aatgcgcaaa ccaacccttg gcagaacata   3180
tccatcgcgt ccgccatctc cagcagccgc acgcggcgca tcgggggggg gggggggggg   3240
ggggggcaaa caattcatca tttttttttt attctttttt ttgatttcgg tttctttgaa   3300
atttttttga ttcggtaatc tccgaacaga aggaagaacg aaggaaggag cacagactta   3360
gattggtata tatacgcata tgtagtgttg aagaaacatg aaattgccca gtattcttaa   3420
cccaactgca cagaacaaaa acctgcagga aacgaagata aatcatgtcg aaagctacat   3480
ataaggaacg tgctgctact catcctagtc ctgttgctgc caagctattt aatatcatgc   3540
acgaaaagca aacaaacttg tgtgcttcat tggatgttcg taccaccaag gaattactgg   3600
agttagttga agcattaggt cccaaaattt gtttactaaa aacacatgtg gatatcttga   3660
ctgatttttc catggagggc acagttaagc cgctaaaggc attatccgcc aagtacaatt   3720
ttttactctt cgaagacaga aaatttgctg acattggtaa tacagtcaaa ttgcagtact   3780
ctgcgggtgt atacagaata gcagaatggg cagacattac gaatgcacac ggtgtggtgg   3840
gcccaggtat tgttagcggt ttgaagcagg cggcagaaga agtaacaaag gaacctagag   3900
gcctttttgat gttagcagaa ttgtcatgca agggctccct atctactgga gaatatacta   3960
agggtactgt tgacattgcg aagagcgaca aagattttgt tatcggcttt attgctcaaa   4020
gagacatggg tggaagagat gaaggttacg attggttgat tatgacaccc ggtgtgggtt   4080
tagatgacaa gggagacgca ttgggtcaac agtatagaac cgtggatgat gtggtctcta   4140
caggatctga cattattatt gttggaagag gactatttgc aaagggaagg gatgctaagg   4200
tagagggtga acgttacaga aaagcaggct gggaagcata tttgagaaga tgcggccagc   4260
aaaactaaaa aactgtatta taagtaaatg catgtatact aaactcacaa attagagctt   4320
caatttaatt atatcagtta ttacccggga atctcggtcg taatgatttt tataatgacg   4380
aaaaaaaaaa aattggaaag aaaagccccc cccccccccc cccccccccc cccccccccg   4440
cagcgttggg tcctggccac gggtgcgcat gatcgtgctc ctgtcgttga ggacccggct   4500
aggctggcgg ggttgcctta ctggttagca gaatgaatca ccgatacgcg agcgaacgtg   4560
aagcgactgc tgctgcaaaa cgtctgcgac ctgagcaaca acatgaatgg tcttcggttt   4620
ccgtgtttcg taaagtctgg aaacgcggaa gtcagcgccc tgcaccatta tgttccggat   4680
ctgcatcgca ggatgctgct ggctaccctg tggaacacct acatctgtat taacgaagcg   4740
ctggcattga ccctgagtga tttttctctg gtcccgccgc atccataccg ccagttgttt   4800
accctcacaa cgttccagta accgggcatg ttcatcatca gtaacccgta tcgtgagcat   4860
cctctctcgt ttcatcggta tcattacccc catgaacaga aattccccct tacacggagg   4920
```

-continued catcaagtga ccaaacagga aaaaaccgcc cttaacatgg cccgctttat cagaagccag 4980
acattaacgc ttctggagaa actcaacgag ctggacgcgg atgaacaggc agacatctgt 5040
gaatcgcttc acgaccacgc tgatgagctt taccgcagct gcctcgcgcg tttcggtgat 5100
gacggtgaaa acctctgaca catgcagctc ccggagacgg tcacagcttg tctgtaagcg 5160
gatgccggga gcagacaagc ccgtcagggc gcgtcagcgg gtgttggcgg gtgtcggggc 5220
gcagccatga cccagtcacg tagcgatagc ggagtgtata ctggcttaac tatgcggcat 5280
cagagcagat tgtactgaga gtgcaccata tgcggtgtga aataccgcac agatgcgtaa 5340
ggagaaaata ccgcatcagg cgctcttccg cttcctcgct cactgactcg ctgcgctcgg 5400
tcgttcggct gcggcgagcg gtatcagctc actcaaaggc ggtaatacgg ttatccacag 5460
aatcagggga taacgcagga aagaacatgt gagcaaaagg ccagcaaaag gccaggaacc 5520
gtaaaaaggc cgcgttgctg gcgtttttcc ataggctccg cccccctgac gagcatcaca 5580
aaaatcgacg ctcaagtcag aggtggcgaa acccgacagg actataaaga taccaggcgt 5640
ttccccctgg aagctccctc gtgcgctctc ctgttccgac cctgccgctt accggatacc 5700
tgtccgcctt tctcccttcg ggaagcgtgg cgctttctca tagctcacgc tgtaggtatc 5760
tcagttcggt gtaggtcgtt cgctccaagc tgggctgtgt gcacgaaccc cccgttcagc 5820
ccgaccgctg cgccttatcc ggtaactatc gtcttgagtc caacccggta agacacgact 5880
tatcgccact ggcagcagcc actggtaaca ggattagcag agcgaggtat gtaggcggtg 5940
ctacagagtt cttgaagtgg tggcctaact acggctacac tagaaggaca gtatttggta 6000
tctgcgctct gctgaagcca gttaccttcg gaaaaagagt tggtagctct tgatccggca 6060
aacaaaccac cgctggtagc ggtggttttt ttgtttgcaa gcagcagatt acgcgcagaa 6120
aaaaaggatc tcaagaagat cctttgatct tttctacggg gtctgacgct cagtggaacg 6180
aaaactcacg ttaagggatt ttggtcatga gattatcaaa aaggatcttc acctagatcc 6240
ttttaaatta aaaatgaagt tttaaatcaa tctaaagtat atatgagtaa acttggtctg 6300
acagttacca atgcttaatc agtgaggcac ctatctcagc gatctgtcta tttcgttcat 6360
ccatagttgc ctgactcccc gtcgtgtaga taactacgat acgggagggc ttaccatctg 6420
gccccagtgc tgcaatgata ccgcgagacc cacgctcacc ggctccagat ttatcagcaa 6480
taaaccagcc agccggaagg gccgagcgca gaagtggtcc tgcaacttta tccgcctcca 6540
tccagtctat taattgttgc cgggaagcta gagtaagtag ttcgccagtt aatagtttgc 6600
gcaacgttgt tgccattgct gcaggcatcg tggtgtcacg ctcgtcgttt ggtatggctt 6660
cattcagctc cggttcccaa cgatcaaggc gagttacatg atcccccatg ttgtgcaaaa 6720
aagcggttag ctccttcggt cctccgatcg ttgtcagaag taagttggcc gcagtgttat 6780
cactcatggt tatggcagca ctgcataatt ctcttactgt catgccatcc gtaagatgct 6840
tttctgtgac tggtgagtac tcaaccaagt cattctgaga atagtgtatg cggcgaccga 6900
gttgctcttg cccggcgtca acacgggata ataccgcgcc acatagcaga actttaaaag 6960
tgctcatcat tggaaaacgt tcttcggggc gaaaactctc aaggatctta ccgctgttga 7020
gatccagttc gatgtaaccc actcgtgcac ccaactgatc ttcagcatct tttactttca 7080
ccagcgtttc tgggtgagca aaaacaggaa ggcaaaatgc cgcaaaaaag ggaataaggg 7140
cgacacggaa atgttgaata ctcatactct tcctttttca atattattga agcatttatc 7200
agggttattg tctcatgagc ggatacatat ttgaatgtat ttagaaaaat aaacaaatag 7260

-continued gggttccgcg cacatttccc cgaaaagtgc cacctgacgt ctaagaaacc attattatca 7320
tgacattaac ctataaaaat aggcgtatca cgaggccctt tcgtcttcaa 7370

<210> SEQ ID NO 24
<211> LENGTH: 8298
<212> TYPE: DNA
<213> ORGANISM: Artificial Sequence
<220> FEATURE:
<223> OTHER INFORMATION: Description of Artificial Sequence:
vector pFMPT-MFalfa-E2-H6

<400> SEQUENCE: 24
ggtaccctgc tcaatctccg gaatggtgat ctgatcgttc ctgaaaacct cgacattggc 60
tccctcctga cacaggtact cgtacaggtt ccaggtaaac gagtcgtagt tgtcgatcat 120
gacaacgttc ttagaagcgg ccggcatttt gaaggtgact aatagcctaa gaaaatattt 180
aatttaattt tcattaaatt ttcctatact cgctatttca gcttttcatc tcatcacttc 240
ataaacgata taaaccagaa aaagaactat tttcaaacac gcttctcaaa agcggtatgt 300
ccttccacgt ctccttagaa tctggcaagt ccgcgagggg gatccagatc tgatagcttt 360
caatcaatga atcgaaaatg tcattaaaat agtatataaa ttgaaactaa gtcataaagc 420
tataaaaaga aaatttattt aaatgcaaga ctttaaagta aattcactta agccttggca 480
acgtgttcaa ccaagtcgag atcgttaatt aactattagt gatggtggtg atggtgtctg 540
ccctcgatca cctgccactc tgttgtagac agcagcagcg agctaagctc tgatctatcc 600
ctgtcctcca agtcacaacg ctctcctcga gtccaattgc atgcggcttc gaacctgtgc 660
tccacgcccc ccacgtacat cctaaccttg aagatggtga agttgacagt gcaggggtag 720
tgccagagcc tatatgggta atgaaccata cacctaggtg tcagccaggg cccagaaccg 780
catctggcgt aagtggcctc ggggtgcttc cgaaaacagt cagtggggca ggtcaaggtg 840
ttgttgccgg cccccccgat gttgcacggg gggcccccac acgtcttggt gaacccagtg 900
ccattcatcc atgtacagcc gaaccagttg cctcgcggcg gccgcgtgtt gttgagaatc 960
agcacatccg agtcgttcgc cccccagtta tacgtgggga caccaaaccg atcggtcgtc 1020
cccaccacaa cagggctcgg ggtgaagcaa tacactggac cgcacacctg agacgcgggt 1080
acaataccac acggtcgagg cgcgtagtgc cagcagtagg gcctctggtc cgagctgtta 1140
ggctcagtgt aagtgagggg accccacccc tgagcgaact tgtcgatgga gcgacagctg 1200
gccaagcgct ctgggcatcc agacgagttg aatttgtgtt tgtagaatag tgcggcaaag 1260
aaccctgttt ggagggagtc gttgcagttc agggcagtcc tgttgatgtg ccaactgccg 1320
ttggtgttta cgagctggat ttctgagcc gacccggggc taaagaggga cacaaggccc 1380
ctggtatcgg aggctgctgc ccctcctgac acgcgggtat gccttttatc tagagatacc 1440
ccttcttctt tagcagcaat gctggcaata gtagtattta taaacaataa cccgttattt 1500
gtgctgttgg aaaatggcaa aacagcaaca tcgaaatccc cttctaaatc tgagtaaccg 1560
atgacagctt cagccggaat ttgtgccgtt tcatcttctg ttgtagtgtt gactggagca 1620
gctaatgcgg aggatgctgc gaataaaact gcagtaaaaa ttgaaggaaa tctcatgaat 1680
tcccgatgaa gcagagagcg caggaggcgg tatttatagt gccattcccc tctctgagag 1740
acccggatgg tagtcgagtg tatcggagac agcttgatgt agactccgtg cctgccggct 1800
cctcttattg gcggacacca gtgagacacc ccggaacttg ctgtttttct gcaaaatccg 1860
gggtgaccag tgggagccta tttgcacaca cgagcgggac accccactct ggtgaagagt 1920

-continued gccaaagtca ttctttttcc cgttgcgggg cagccgattg catgttttag gaaaatatta 1980
cctttgctac accctgtcag atttaccctc cacacatata tattccgtca cctccaggga 2040
ctattattcg tcgttgcgcc gccagcggaa gatatccaga agctgttttc cgagagactc 2100
ggttggcgcc tggtatattt gatggatgtc gcgctgcctc acgtcccggt acccaggaac 2160
gcggtgggat ctcgggccca tcgaagactg tgctccagac tgctcgccca gcaggtgttt 2220
cttgatcgcc gcctctaaat tgtccgcgca tcgccggtaa catttttcca gctcggagtt 2280
tgcgtttaga tacagtttct gcgatgccaa aggagcctgc agattataac ctcggatgct 2340
gtcattcagc gcttttaatt tgacctccag atagttgctg tatttctgtt cccattggct 2400
gctgcgcagc ttcgtataac tcgagttatt gttgcgctct gcctcggcgt actggctcat 2460
gatctggatc ttgtccgtgt cgcttttctt cgagtgtttc tcgcaaacga tgtgcacggc 2520
ctgcagtgtc caatcggagt cgagctggcg ccgaaactgg cggatctgag cctccacact 2580
gccctgtttc tctatccacg gcggaaccgc ctcctgccgt ttcagaatgt tgttcaagtg 2640
gtactctgtg cggtcaatga aggcgttatt gccggtgaaa tctttgggaa gcggttttcc 2700
tcggggaaga ttacgaaatt ccccgcgtcg ttgcgcttcc tggatctcga ggagatcgtt 2760
ctccgcgtcg aggagatcgt tctccgcgtc gacaccattc cttgcggcgg cggtgctcaa 2820
cggcctcaac ctactactgg gctgcttcct aatgcaggag tcgcataagg gagagcgtcg 2880
acaaacccgc gtttgagaac ttgctcaagc ttctggtaaa cgttgtagta ctctgaaaca 2940
aggccctagc actctgatct gtttctcttg ggtagcggtg agtggtttat tggagttcac 3000
tggtttcagc acatctgtca tctagacaat attgttacta aatttttttg aactacaatt 3060
gttcgtaatt catctattat tatacatcct cgtcagcaat ttctggcaga cggagtttac 3120
taacgtcttg agtatgaggc cgagaatcca gctctgtggc catactcagt cttgacagcc 3180
tgctgatgtg gctgcgttca acgcaataag cgtgtcctcc gactccgagt tgtgctcgtt 3240
atcgtcgttc tcatcctcgg aaaaatcaca cgaaagaaca tactcaccag taggctttct 3300
ggtccctggg gcacggctgt ttctgacgta ttccggcgtt gataatagct cgaaagtgaa 3360
cgccgagtcg cgggagtcga ccgatgccct tgagagcctt caacccagtc agctccttcc 3420
ggtgggcgcg gggcatgact atcgtcgccg cacttatgac tgtcttcttt atcatgcaac 3480
tcgtaggaca ggtgccggca gcgctctggg tcattttcgg cgaggaccgc tttcgctgga 3540
gcgcgacgat gatcggcctg tcgcttgcgg tattcggaat cttgcacgcc ctcgctcaag 3600
ccttcgtcac tggtcccgcc accaaacgtt tcggcgagaa gcaggccatt atcgccggca 3660
tggcggccga cgcgctgggc tacgtcttgc tggcgttcgc gacgcgaggc tggatggcct 3720
tccccattat gattcttctc gcttccggcg gcatcgggat gcccgcgttg caggccatgc 3780
tgtccaggca ggtagatgac gaccatcagg gacagcttca aggatcgctc gcggctctta 3840
ccagcctaac ttcgatcact ggaccgctga tcgtcacggc gatttatgcc gcctcggcga 3900
gcacatggaa cgggttggca tggattgtag gcgccgccct ataccttgtc tgcctccccg 3960
cgttgcgtcg cggtgcatgg agccgggcca cctcgacctg aatggaagcc ggcggcacct 4020
cgctaacgga ttcaccactc caagaattgg agccaatcaa ttcttgcgga gaactgtgaa 4080
tgcgcaaacc aacccttggc agaacatatc catcgcgtcc gccatctcca gcagccgcac 4140
gcggcgcatc gggggggggg gggggggggg ggggcaaaca attcatcatt tttttttttat 4200
tcttttttttt gatttcggtt tctttgaaat tttttttgatt cggtaatctc cgaacagaag 4260
gaagaacgaa ggaaggagca cagacttaga ttggtatata tacgcatatg tagtgttgaa 4320

-continued

```
gaaacatgaa attgcccagt attcttaacc caactgcaca gaacaaaaac ctgcaggaaa   4380
cgaagataaa tcatgtcgaa agctacatat aaggaacgtg ctgctactca tcctagtcct   4440
gttgctgcca agctatttaa tatcatgcac gaaaagcaaa caaacttgtg tgcttcattg   4500
gatgttcgta ccaccaagga attactggag ttagttgaag cattaggtcc caaaatttgt   4560
ttactaaaaa cacatgtgga tatcttgact gatttttcca tggagggcac agttaagccg   4620
ctaaaggcat tatccgccaa gtacaatttt ttactcttcg aagacagaaa atttgctgac   4680
attggtaata cagtcaaatt gcagtactct gcgggtgtat acagaatagc agaatgggca   4740
gacattacga atgcacacgg tgtggtgggc ccaggtattg ttagcggttt gaagcaggcg   4800
gcagaagaag taacaaagga acctagaggc cttttgatgt tagcagaatt gtcatgcaag   4860
ggctccctat ctactggaga atatactaag ggtactgttg acattgcgaa gagcgacaaa   4920
gattttgtta tcggctttat tgctcaaaga gacatgggtg gaagagatga aggttacgat   4980
tggttgatta tgacacccgg tgtgggttta gatgacaagg gagacgcatt gggtcaacag   5040
tatagaaccg tggatgatgt ggtctctaca ggatctgaca ttattattgt tggaagagga   5100
ctatttgcaa agggaaggga tgctaaggta gagggtgaac gttacagaaa agcaggctgg   5160
gaagcatatt tgagaagatg cggccagcaa aactaaaaaa ctgtattata agtaaatgca   5220
tgtatactaa actcacaaat tagagcttca atttaattat atcagttatt acccgggaat   5280
ctcggtcgta atgattttta taatgacgaa aaaaaaaaaa ttggaaagaa aagccccccc   5340
cccccccccc cccccccccc cccccccgca gcgttgggtc ctggccacgg gtgcgcatga   5400
tcgtgctcct gtcgttgagg acccggctag gctggcgggg ttgccttact ggttagcaga   5460
atgaatcacc gatacgcgag cgaacgtgaa gcgactgctg ctgcaaaacg tctgcgacct   5520
gagcaacaac atgaatggtc ttcggtttcc gtgtttcgta aagtctggaa acgcggaagt   5580
cagcgccctg caccattatg ttccggatct gcatcgcagg atgctgctgg ctaccctgtg   5640
gaacacctac atctgtatta acgaagcgct ggcattgacc ctgagtgatt tttctctggt   5700
cccgccgcat ccataccgcc agttgtttac cctcacaacg ttccagtaac cgggcatgtt   5760
catcatcagt aacccgtatc gtgagcatcc tctctcgttt catcggtatc attaccccca   5820
tgaacagaaa ttcccccctta cacggaggca tcaagtgacc aaacaggaaa aaaccgccct   5880
taacatggcc cgctttatca gaagccagac attaacgctt ctggagaaac tcaacgagct   5940
ggacgcggat gaacaggcag acatctgtga atcgcttcac gaccacgctg atgagcttta   6000
ccgcagctgc ctcgcgcgtt tcggtgatga cggtgaaaac ctctgacaca tgcagctccc   6060
ggagacggtc acagcttgtc tgtaagcgga tgccgggagc agacaagccc gtcagggcgc   6120
gtcagcgggt gttggcgggt gtcggggcgc agccatgacc cagtcacgta gcgatagcgg   6180
agtgtatact ggcttaacta tgcggcatca gagcagattg tactgagagt gcaccatatg   6240
cggtgtgaaa taccgcacag atgcgtaagg agaaaatacc gcatcaggcg ctcttccgct   6300
tcctcgctca ctgactcgct gcgctcggtc gttcggctgc ggcgagcggt atcagctcac   6360
tcaaaggcgg taatacggtt atccacagaa tcaggggata acgcaggaaa gaacatgtga   6420
gcaaaaggcc agcaaaaggc caggaaccgt aaaaaggccg cgttgctggc gtttttccat   6480
aggctccgcc cccctgacga gcatcacaaa aatcgacgct caagtcagag gtggcgaaac   6540
ccgacaggac tataaagata ccaggcgttt ccccctggaa gctccctcgt gcgctctcct   6600
gttccgaccc tgccgcttac cggatacctg tccgcctttc tcccttcggg aagcgtggcg   6660
```

-continued

```
ctttctcata gctcacgctg taggtatctc agttcggtgt aggtcgttcg ctccaagctg   6720

ggctgtgtgc acgaaccccc cgttcagccc gaccgctgcg ccttatccgg taactatcgt   6780

cttgagtcca acccggtaag acacgactta tcgccactgg cagcagccac tggtaacagg   6840

attagcagag cgaggtatgt aggcggtgct acagagttct tgaagtggtg gcctaactac   6900

ggctacacta gaaggacagt atttggtatc tgcgctctgc tgaagccagt taccttcgga   6960

aaaagagttg gtagctcttg atccggcaaa caaaccaccg ctggtagcgg tggttttttt   7020

gtttgcaagc agcagattac gcgcagaaaa aaaggatctc aagaagatcc tttgatcttt   7080

tctacggggt ctgacgctca gtggaacgaa aactcacgtt aagggatttt ggtcatgaga   7140

ttatcaaaaa ggatcttcac ctagatcctt ttaaattaaa aatgaagttt taaatcaatc   7200

taaagtatat atgagtaaac ttggtctgac agttaccaat gcttaatcag tgaggcacct   7260

atctcagcga tctgtctatt tcgttcatcc atagttgcct gactccccgt cgtgtagata   7320

actacgatac gggagggctt accatctggc cccagtgctg caatgatacc gcgagaccca   7380

cgctcaccgg ctccagattt atcagcaata aaccagccag ccggaagggc cgagcgcaga   7440

agtggtcctg caactttatc cgcctccatc cagtctatta attgttgccg ggaagctaga   7500

gtaagtagtt cgccagttaa tagtttgcgc aacgttgttg ccattgctgc aggcatcgtg   7560

gtgtcacgct cgtcgtttgg tatggcttca ttcagctccg gttcccaacg atcaaggcga   7620

gttacatgat cccccatgtt gtgcaaaaaa gcggttagct ccttcggtcc tccgatcgtt   7680

gtcagaagta agttggccgc agtgttatca ctcatggtta tggcagcact gcataattct   7740

cttactgtca tgccatccgt aagatgcttt tctgtgactg gtgagtactc aaccaagtca   7800

ttctgagaat agtgtatgcg gcgaccgagt tgctcttgcc cggcgtcaac acgggataat   7860

accgcgccac atagcagaac tttaaaagtg ctcatcattg gaaaacgttc ttcggggcga   7920

aaactctcaa ggatcttacc gctgttgaga tccagttcga tgtaacccac tcgtgcaccc   7980

aactgatctt cagcatcttt tactttcacc agcgtttctg ggtgagcaaa aacaggaagg   8040

caaaatgccg caaaaaaggg aataagggcg acacggaaat gttgaatact catactcttc   8100

ctttttcaat attattgaag catttatcag ggttattgtc tcatgagcgg atacatattt   8160

gaatgtattt agaaaaataa acaaataggg gttccgcgca catttccccg aaaagtgcca   8220

cctgacgtct aagaaaccat tattatcatg acattaacct ataaaaatag gcgtatcacg   8280

aggccctttc gtcttcaa                                                 8298
```

<210> SEQ ID NO 25
<211> LENGTH: 8695
<212> TYPE: DNA
<213> ORGANISM: Artificial Sequence
<220> FEATURE:
<223> OTHER INFORMATION: Description of Artificial Sequence:
      vector pMPT-Mfalfa-E2-H6
<220> FEATURE:
<221> NAME/KEY: misc_feature
<222> LOCATION: (2103)..(2103)
<223> OTHER INFORMATION: N is any nucleotide

<400> SEQUENCE: 25

```
ggtaccctgc tcaatctccg gaatggtgat ctgatcgttc ctgaaaacct cgacattggc     60

tccctcctga cacaggtact cgtacaggtt ccaggtaaac gagtcgtagt tgtcgatcat    120

gacaacgttc ttagaagcgg ccggcatttt gaaggtgact aatagcctaa gaaaatattt    180

aatttaattt tcattaaatt ttcctatact cgctatttca gcttttcatc tcatcacttc    240
```

-continued

```
ataaacgata taaaccagaa aaagaactat tttcaaacac gcttctcaaa agcggtatgt    300
ccttccacgt ctccttagaa tctggcaagt ccgcgagggg gatccagatc tgatagcttt    360
caatcaatga atcgaaaatg tcattaaaat agtatataaa ttgaaactaa gtcataaagc    420
tataaaaaga aaatttattt aaatgcaaga ctttaaagta aattcactta agccttggca    480
acgtgttcaa ccaagtcgag atcgttaatt aactattagt gatggtggtg atggtgtctg    540
ccctcgatca cctgccactc tgttgtagac agcagcagcg agctaagctc tgatctatcc    600
ctgtcctcca agtcacaacg ctctcctcga gtccaattgc atgcggcttc gaacctgtgc    660
tccacgcccc ccacgtacat cctaaccttg aagatggtga agttgacagt gcaggggtag    720
tgccagagcc tatatgggta atgaaccata cacctaggtg tcagccaggg cccagaaccg    780
catctggcgt aagtggcctc ggggtgcttc cgaaaacagt cagtggggca ggtcaaggtg    840
ttgttgccgg ccccccccgat gttgcacggg gggcccccac acgtcttggt gaacccagtg    900
ccattcatcc atgtacagcc gaaccagttg cctcgcggcg gccgcgtgtt gttgagaatc    960
agcacatccg agtcgttcgc cccccagtta tacgtgggga caccaaaccg atcggtcgtc   1020
cccaccacaa cagggctcgg ggtgaagcaa tacactggac cgcacacctg agacgcgggt   1080
acaataccac acggtcgagg cgcgtagtgc cagcagtagg gcctctggtc cgagctgtta   1140
ggctcagtgt aagtgagggg accccacccc tgagcgaact tgtcgatgga gcgacagctg   1200
gccaagcgct ctgggcatcc agacgagttg aatttgtgtt tgtagaatag tgcggcaaag   1260
aaccctgttt ggagggagtc gttgcagttc agggcagtcc tgttgatgtg ccaactgccg   1320
ttggtgttta cgagctggat tttctgagcc gacccggggc taaagaggga cacaaggccc   1380
ctggtatcgg aggctgctgc ccctcctgac acgcgggtat gccttttatc tagagatacc   1440
ccttcttctt tagcagcaat gctggcaata gtagtattta taaacaataa cccgttattt   1500
gtgctgttgg aaaatggcaa aacagcaaca tcgaaatccc cttctaaatc tgagtaaccg   1560
atgacagctt cagccggaat ttgtgccgtt tcatcttctg ttgtagtgtt gactggagca   1620
gctaatgcgg aggatgctgc gaataaaact gcagtaaaaa ttgaaggaaa tctcatgaat   1680
tcgtttttgt actttagatt gatgtcacca ccgtgcactg gcagcagtat ttatagatgg   1740
accgtgtggg gacggttggg tacacttagc ggcagcgctg accccatctg tgatcaagta   1800
gggcaaaaac tggggatgtc ggagtcgctg cacggtagca taagaattta ctttctggcc   1860
ggttcacccg catttgcact gtggagaaac agcctgtccg acaccccacc agttgccaca   1920
tcggccctct gctgctctgg tgattttctg gtagcaggca cagacagcag tgggtagcgc   1980
cgtccggtta ggcaaggtca cgttgtaggc taccccagca aacagagcct cacatgacac   2040
catccagctg cgtcctcgaa gcgaaaagtt cggttgcggc tgcagaaccc cctcagttgc   2100
canattcaca agttttacgc gacggctaaa gcgagtgggt tttaaaaact tgcggtgcaa   2160
ggatgcatgc ggcaacaatt aattggtgca tccagcacag caagcccagt ctcgagatgt   2220
ccagtcgcta cagagtggag tacgcactca aggaacaccg tcgagatggc ctcatagaat   2280
ggatcaaggg cctgctggcc acgccgttcg tcctgtacgc ggtgaagagc aacggcatct   2340
ctgcagtgga cgacctcatg gtaaactctg aggcaaaacg ccgctacgcg gaaatcttcc   2400
acgacctcga actcctcatc gacgacaaca ttgaaatgac caaagccggc acccccgaat   2460
tgtctcggct cgtgcagctg gttccgagcg ttggcagctt cttcacgaga ctgcctctgg   2520
aaaaggcctt ctacatcgag gacgagcgcc gcgccatcag caaacgccgg cttgtggccc   2580
cctcgttcaa cgacgtccgg ctcattctca acacggccca gctgttggag atgtcgcggt   2640
```

-continued

```
tcttccattc caaaaccatc cgagatcgca agctgcagct cattacattc gatggtgaca   2700
tcacactgta cgacgacggc aaaaatttcg atgccgagtc gcccatcctg ccccacctca   2760
tcaaactaat ggccaaggac ctctatgtgg gtatcgtcac cgcggccggc tacagcgacg   2820
gaacaagtac tacgagcgcc tcaagggcct catcgacgcc gtccagacgt ccccgctgct   2880
cacaggccac cagaaagaga acctgttcat tatgggcggc gaggcaaact acctcttccg   2940
gtacagtaac gaggagcaga gattacgctt ctactccaaa gacagatggc tgctcgagaa   3000
catgctgaat tggtccgagg aggacattca tctgacactg gactttgcgc aggacgttct   3060
aaacgacctc gttcacaaac tgggctcgcc agccaccgtg gtccgcaagg agcgtcgcgt   3120
cggcctggtt ccattaccgg gccacaagct gatccgcgag cagctcgagg agatcgttct   3180
ccgcgtcgac accattcctt gcggcggcgg tgctcaacgg cctcaaccta ctactgggct   3240
gcttcctaat gcaggagtcg cataagggag agcgtcgact cccgcgactc ggcgttcact   3300
ttcgagctat tatcaacgcc ggaatacgtc agaaacagcc gtgccccagg gaccagaaag   3360
cctactggtg agtatgttct ttcgtgtgat ttttccgagg atgagaacga cgataacgag   3420
cacaactcgg agtcggagga cacgcttatt gcgttgaacg cagccacatc agcaggctgt   3480
caagactgag tatggccaca gagctggatt ctcggcctca tactcaagac gttagtaaac   3540
tccgtctgcc agaaattgct gacgaggatg tataataata gatgaattac gaacaattgt   3600
agttcaaaaa aatttagtaa caatattgtc tagatgacag atgtgctgaa accagtgaac   3660
tccaataaac cactcaccgc tacccaagag aaacagatca gagtgctagg gccttgtttc   3720
agagtactac aacgtttacc agaagcttga gcaagttctc aaacgcgggt ttgtcgaccg   3780
atgcccttga gagccttcaa cccagtcagc tccttccggt gggcgcgggg catgactatc   3840
gtcgccgcac ttatgactgt cttctttatc atgcaactcg taggacaggt gccggcagcg   3900
ctctgggtca ttttcggcga ggaccgcttt cgctggagcg cgacgatgat cggcctgtcg   3960
cttgcggtat tcggaatctt gcacgccctc gctcaagcct tcgtcactgg tcccgccacc   4020
aaacgtttcg gcgagaagca ggccattatc gccggcatgg cggccgacgc gctgggctac   4080
gtcttgctgg cgttcgcgac gcgaggctgg atggccttcc ccattatgat tcttctcgct   4140
tccggcggca tcgggatgcc cgcgttgcag gccatgctgt ccaggcaggt agatgacgac   4200
catcagggac agcttcaagg atcgctcgcg gctcttacca gcctaacttc gatcactgga   4260
ccgctgatcg tcacggcgat ttatgccgcc tcggcgagca catggaacgg gttggcatgg   4320
attgtaggcg ccgccctata ccttgtctgc ctccccgcgt tgcgtcgcgg tgcatggagc   4380
cgggccacct cgacctgaat ggaagccggc ggcacctcgc taacggattc accactccaa   4440
gaattggagc caatcaattc ttgcggagaa ctgtgaatgc gcaaaccaac ccttggcaga   4500
acatatccat cgcgtccgcc atctccagca gccgcacgcg gcgcatcggg gggggggggg   4560
gggggggggg gcaaacaatt catcattttt tttttattct ttttttttgat ttcggtttct   4620
ttgaaatttt tttgattcgg taatctccga acagaaggaa gaacgaagga aggagcacag   4680
acttagattg gtatatatac gcatatgtag tgttgaagaa acatgaaatt gcccagtatt   4740
cttaacccaa ctgcacagaa caaaaacctg caggaaacga agataaatca tgtcgaaagc   4800
tacatataag gaacgtgctg ctactcatcc tagtcctgtt gctgccaagc tatttaatat   4860
catgcacgaa aagcaaacaa acttgtgtgc ttcattggat gttcgtacca ccaaggaatt   4920
actggagtta gttgaagcat taggtcccaa aatttgttta ctaaaaacac atgtggatat   4980
```

-continued

```
cttgactgat ttttccatgg agggcacagt taagccgcta aaggcattat ccgccaagta   5040
caatttttta ctcttcgaag acagaaaatt tgctgacatt ggtaatacag tcaaattgca   5100
gtactctgcg ggtgtataca gaatagcaga atgggcagac attacgaatg cacacggtgt   5160
ggtgggccca ggtattgtta gcggtttgaa gcaggcggca gaagaagtaa caaaggaacc   5220
tagaggcctt ttgatgttag cagaattgtc atgcaagggc tccctatcta ctggagaata   5280
tactaagggt actgttgaca ttgcgaagag cgacaaagat tttgttatcg gctttattgc   5340
tcaaagagac atgggtggaa gagatgaagg ttacgattgg ttgattatga cacccggtgt   5400
gggtttagat gacaagggag acgcattggg tcaacagtat agaaccgtgg atgatgtggt   5460
ctctacagga tctgacatta ttattgttgg aagaggacta tttgcaaagg gaagggatgc   5520
taaggtagag ggtgaacgtt acagaaaagc aggctgggaa gcatatttga gaagatgcgg   5580
ccagcaaaac taaaaaactg tattataagt aaatgcatgt atactaaact cacaaattag   5640
agcttcaatt taattatatc agttattacc cgggaatctc ggtcgtaatg atttttataa   5700
tgacgaaaaa aaaaaaattg gaaagaaaag cccccccccc cccccccccc cccccccccc   5760
ccccgcagcg ttgggtcctg gccacgggtg cgcatgatcg tgctcctgtc gttgaggacc   5820
cggctaggct ggcggggttg ccttactggt tagcagaatg aatcaccgat acgcgagcga   5880
acgtgaagcg actgctgctg caaaacgtct gcgacctgag caacaacatg aatggtcttc   5940
ggtttccgtg tttcgtaaag tctggaaacg cggaagtcag cgccctgcac cattatgttc   6000
cggatctgca tcgcaggatg ctgctggcta ccctgtggaa cacctacatc tgtattaacg   6060
aagcgctggc attgaccctg agtgattttt ctctggtccc gccgcatcca taccgccagt   6120
tgtttaccct cacaacgttc cagtaaccgg gcatgttcat catcagtaac ccgtatcgtg   6180
agcatcctct ctcgtttcat cggtatcatt acccccatga acagaaattc ccccttacac   6240
ggaggcatca agtgaccaaa caggaaaaaa ccgcccttaa catggcccgc tttatcagaa   6300
gccagacatt aacgcttctg gagaaactca acgagctgga cgcggatgaa caggcagaca   6360
tctgtgaatc gcttcacgac cacgctgatg agctttaccg cagctgcctc gcgcgtttcg   6420
gtgatgacgg tgaaaacctc tgacacatgc agctcccgga gacggtcaca gcttgtctgt   6480
aagcggatgc cgggagcaga caagcccgtc agggcgcgtc agcgggtgtt ggcgggtgtc   6540
ggggcgcagc catgacccag tcacgtagcg atagcggagt gtatactggc ttaactatgc   6600
ggcatcagag cagattgtac tgagagtgca ccatatgcgg tgtgaaatac cgcacagatg   6660
cgtaaggaga aaataccgca tcaggcgctc ttccgcttcc tcgctcactg actcgctgcg   6720
ctcggtcgtt cggctgcggc gagcggtatc agctcactca aaggcggtaa tacggttatc   6780
cacagaatca ggggataacg caggaaagaa catgtgagca aaaggccagc aaaaggccag   6840
gaaccgtaaa aaggccgcgt tgctggcgtt tttccatagg ctccgccccc ctgacgagca   6900
tcacaaaaat cgacgctcaa gtcagaggtg gcgaaacccg acaggactat aaagatacca   6960
ggcgtttccc cctggaagct ccctcgtgcg ctctcctgtt ccgaccctgc cgcttaccgg   7020
atacctgtcc gcctttctcc cttcgggaag cgtggcgctt tctcatagct cacgctgtag   7080
gtatctcagt tcggtgtagg tcgttcgctc caagctgggc tgtgtgcacg aaccccccgt   7140
tcagcccgac cgctgcgcct tatccggtaa ctatcgtctt gagtccaacc cggtaagaca   7200
cgacttatcg ccactggcag cagccactgg taacaggatt agcagagcga ggtatgtagg   7260
cggtgctaca gagttcttga agtggtggcc taactacggc tacactagaa ggacagtatt   7320
tggtatctgc gctctgctga agccagttac cttcggaaaa agagttggta gctcttgatc   7380
```

-continued

```
cggcaaacaa accaccgctg gtagcggtgg tttttttgtt tgcaagcagc agattacgcg   7440

cagaaaaaaa ggatctcaag aagatccttt gatcttttct acggggtctg acgctcagtg   7500

gaacgaaaac tcacgttaag ggattttggt catgagatta tcaaaaagga tcttcaccta   7560

gatcctttta aattaaaaat gaagttttaa atcaatctaa agtatatatg agtaaacttg   7620

gtctgacagt taccaatgct taatcagtga ggcacctatc tcagcgatct gtctatttcg   7680

ttcatccata gttgcctgac tccccgtcgt gtagataact acgatacggg agggcttacc   7740

atctggcccc agtgctgcaa tgataccgcg agacccacgc tcaccggctc cagatttatc   7800

agcaataaac cagccagccg gaagggccga gcgcagaagt ggtcctgcaa ctttatccgc   7860

ctccatccag tctattaatt gttgccggga agctagagta agtagttcgc cagttaatag   7920

tttgcgcaac gttgttgcca ttgctgcagg catcgtggtg tcacgctcgt cgtttggtat   7980

ggcttcattc agctccggtt cccaacgatc aaggcgagtt acatgatccc ccatgttgtg   8040

caaaaaagcg gttagctcct tcggtcctcc gatcgttgtc agaagtaagt tggccgcagt   8100

gttatcactc atggttatgg cagcactgca taattctctt actgtcatgc catccgtaag   8160

atgcttttct gtgactggtg agtactcaac caagtcattc tgagaatagt gtatgcggcg   8220

accgagttgc tcttgcccgg cgtcaacacg ggataatacc gcgccacata gcagaacttt   8280

aaaagtgctc atcattggaa aacgttcttc ggggcgaaaa ctctcaagga tcttaccgct   8340

gttgagatcc agttcgatgt aacccactcg tgcacccaac tgatcttcag catcttttac   8400

tttcaccagc gtttctgggt gagcaaaaac aggaaggcaa aatgccgcaa aaaagggaat   8460

aagggcgaca cggaaatgtt gaatactcat actcttcctt tttcaatatt attgaagcat   8520

ttatcagggt tattgtctca tgagcggata catatttgaa tgtatttaga aaaataaaca   8580

aataggggtt ccgcgcacat ttccccgaaa agtgccacct gacgtctaag aaaccattat   8640

tatcatgaca ttaacctata aaaataggcg tatcacgagg ccctttcgtc ttcaa        8695
```

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence:
primer MF30E2/F

<400> SEQUENCE: 26
agtcactctt caaggcatac ccgcgtgtca ggaggg 36

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence:
primer MF30E2/R

<400> SEQUENCE: 27
agtcactctt cacagggatc cttagtgatg gtggtgatg 39

<210> SEQ ID NO 28
<211> LENGTH: 4190
<212> TYPE: DNA
<213> ORGANISM: Artificial Sequence
<220> FEATURE:
<223> OTHER INFORMATION: Description of Artificial Sequence:
vector pMF30

-continued

<400> SEQUENCE: 28
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg ccaagcttgc 240
atgcctgcag ttgattgcag atgccagatc ccgaaagaac agaggacgga gcgtaaactt 300
gtggcattcc accagaaatt gatacagata agcttccgga gtcaccagct aaaacggaat 360
tgcaagaaat aatatcgata actttatcac cactagaata gccggtgttg ctgacagtaa 420
tatcctgtga cccgtttgaa cctaaattat taaaaatgga aatcaattga ttagcatcgc 480
tacccttcct agtggctata tagtggtctg aagaagaaac aactgaggat ttgtaagttg 540
aataggcaga atccttctta atagcttgat ttcttatttg atttagttta ctgattagct 600
cgtagtattc tgaatcggta ttatatccac ttaaccataa agcttctcta ttggcaggat 660
cggaaccacc attgagacct tgttcttggc cataataaat aattgggata ccatcaccca 720
aaattataaa agccatgtca ttcttaatca aggatgtgtc tgaggtaact gatggaaatc 780
taacttggtc atggttttca ataaagtttc ccaacaaaga gacgtccgaa caagatgact 840
gtaacgtgga gatcattgaa gttaactcac tggaagtcgc cgaagtatca ctgaagaatc 900
tatatactgg atagtataat ggatagttgg taactccttt catataattc tgatatggac 960
aagtataagt tggatctcct tgataaactt cacctaagtt ataaacacca gaagcgtcct 1020
caaacttcgt taatgaagcg gtatctacgt gctttgcact atcaattctt aaaccatcga 1080
ttgaatagtt ttgaacaaaa tctgacaccc aagtttgaaa tactcctata acttcattat 1140
cctcggtact taaatctgga agggagactt cagtatcacc ttcccaacaa tcttcaacat 1200
tggtttgatc attataattt gtaatcaaac aataatcgtg gaagtaagat tgttgattga 1260
atggagtgaa actagaataa tctacgcttg aaccatctcc gttccaagca taatggttgt 1320
aaacaacgtc gaccatcaat aacatgcttc tggaatgcaa ttcgctagct aattgtttca 1380
attcatcagc ggtaccaaaa ttagtgttca attcatcaat atttttcatc caataaccat 1440
ggtaagcata accataagca gtattgtcag gaatttgctc aacaactggg gagatccaga 1500
tcgcagtgaa acccatacct tgaatataat ccaacttgtc gataatccct ttataagatc 1560
caccacagta cttgcgatca ctcactaaac agtcagctgt ggtcgagcca tcagatctgg 1620
caaacctatc agtaacgatt tgataaatcg attggtcttt ccatttatca gctgacgagc 1680
taacatccct cttgtcaaaa ataatcggtt gagcagatac caatcttgag aatgctaaaa 1740
ttgctgcaac aactttactt gtaaatcctt cagttgaaaa tctcattgaa ttcactggcc 1800
gtcgttttac aacgtcgtga ctgggaaaac cctggcgtta cccaacttaa tcgccttgca 1860
gcacatcccc ctttcgccag ctggcgtaat agcgaagagg cccgcaccga tcgcccttcc 1920
caacagttgc gcagcctgaa tggcgaatgg cgcctgatgc ggtattttct ccttacgcat 1980
ctgtgcggta tttcacaccg catatggtgc actctcagta caatctgctc tgatgccgca 2040
tagttaagcc agccccgaca cccgccaaca cccgctgacg cgccctgacg ggcttgtctg 2100
ctcccggcat ccgcttacag acaagctgtg accgtctccg ggagctgcat gtgtcagagg 2160
ttttcaccgt catcaccgaa acgcgcgaga cgaaagggcc tcgtgatacg cctattttta 2220
taggttaatg tcatgataat aatggtttct tagacgtcag gtggcacttt tcggggaaat 2280

-continued gtgcgcggaa cccctatttg tttattttc taaatacatt caaatatgta tccgctcatg 2340
agacaataac cctgataaat gcttcaataa tattgaaaaa ggaagagtat gagtattcaa 2400
catttccgtg tcgcccttat tccctttttt gcggcatttt gccttcctgt ttttgctcac 2460
ccagaaacgc tggtgaaagt aaaagatgct gaagatcagt tgggtgcacg agtgggttac 2520
atcgaactgg atctcaacag cggtaagatc cttgagagtt ttcgccccga agaacgtttt 2580
ccaatgatga gcacttttaa agttctgcta tgtggcgcgg tattatcccg tattgacgcc 2640
gggcaagagc aactcggtcg ccgcatacac tattctcaga atgacttggt tgagtactca 2700
ccagtcacag aaaagcatct tacggatggc atgacagtaa gagaattatg cagtgctgcc 2760
ataaccatga gtgataacac tgcggccaac ttacttctga caacgatcgg aggaccgaag 2820
gagctaaccg cttttttgca caacatgggg gatcatgtaa ctcgccttga tcgttgggaa 2880
ccggagctga atgaagccat accaaacgac gagcgtgaca ccacgatgcc tgtagcaatg 2940
gcaacaacgt tgcgcaaact attaactggc gaactactta ctctagcttc ccggcaacaa 3000
ttaatagact ggatggaggc ggataaagtt gcaggaccac ttctgcgctc ggcccttccg 3060
gctggctggt ttattgctga taaatctgga gccggtgagc gtgggtctcg cggtatcatt 3120
gcagcactgg ggccagatgg taagccctcc cgtatcgtag ttatctacac gacggggagt 3180
caggcaacta tggatgaacg aaatagacag atcgctgaga taggtgcctc actgattaag 3240
cattggtaac tgtcagacca agtttactca tatatacttt agattgattt aaaacttcat 3300
ttttaattta aaaggatcta ggtgaagatc ctttttgata atctcatgac caaaatccct 3360
taacgtgagt tttcgttcca ctgagcgtca gaccccgtag aaaagatcaa aggatcttct 3420
tgagatcctt tttttctgcg cgtaatctgc tgcttgcaaa caaaaaaacc accgctacca 3480
gcggtggttt gtttgccgga tcaagagcta ccaactcttt ttccgaaggt aactggcttc 3540
agcagagcgc agataccaaa tactgtcctt ctagtgtagc cgtagttagg ccaccacttc 3600
aagaactctg tagcaccgcc tacatacctc gctctgctaa tcctgttacc agtggctgct 3660
gccagtggcg ataagtcgtg tcttaccggg ttggactcaa gacgatagtt accggataag 3720
gcgcagcggt cgggctgaac ggggggttcg tgcacacagc ccagcttgga gcgaacgacc 3780
tacaccgaac tgagatacct acagcgtgag ctatgagaaa gcgccacgct tcccgaaggg 3840
agaaaggcgg acaggtatcc ggtaagcggc agggtcggaa caggagagcg cacgagggag 3900
cttccagggg gaaacgcctg gtatctttat agtcctgtcg ggtttcgcca cctctgactt 3960
gagcgtcgat ttttgtgatg ctcgtcaggg gggcggagcc tatggaaaaa cgccagcaac 4020
gcggcctttt tacggttcct ggccttttgc tggccttttg ctcacatgtt ctttcctgcg 4080
ttatcccctg attctgtgga taaccgtatt accgcctttg agtgagctga taccgctcgc 4140
cgcagccgaa cgaccgagcg cagcgagtca gtgagcgagg aagcggaaga 4190

<210> SEQ ID NO 29
<211> LENGTH: 38
<212> TYPE: DNA
<213> ORGANISM: Artificial Sequence
<220> FEATURE:
<223> OTHER INFORMATION: Description of Artificial Sequence:
primer MF30-Links

<400> SEQUENCE: 29
agtcactctt cacctcttgt caaaaataat cggttgag 38

<210> SEQ ID NO 30

-continued

<211> LENGTH: 52
<212> TYPE: DNA
<213> ORGANISM: Artificial Sequence
<220> FEATURE:
<223> OTHER INFORMATION: Description of Artificial Sequence:
primer CL2 hin

<400> SEQUENCE: 30
tgcttcctac cactagcagc actaggacat acccgcgtgt caggaggggc ag 52

<210> SEQ ID NO 31
<211> LENGTH: 57
<212> TYPE: DNA
<213> ORGANISM: Artificial Sequence
<220> FEATURE:
<223> OTHER INFORMATION: Description of Artificial Sequence:
primer CL2 her

<400> SEQUENCE: 31
tagtactagt attagtaggc ttcgcatgga attcactggc cgtcgtttta caacgtc 57

<210> SEQ ID NO 32
<211> LENGTH: 7927
<212> TYPE: DNA
<213> ORGANISM: Artificial Sequence
<220> FEATURE:
<223> OTHER INFORMATION: Description of Artificial Sequence:
vector pFMPT-CL-E2-H6

<400> SEQUENCE: 32
ggtaccctgc tcaatctccg gaatggtgat ctgatcgttc ctgaaaacct cgacattggc 60
tccctcctga cacaggtact cgtacaggtt ccaggtaaac gagtcgtagt tgtcgatcat 120
gacaacgttc ttagaagcgg ccggcatttt gaaggtgact aatagcctaa gaaaatattt 180
aatttaattt tcattaaatt ttcctatact cgctatttca gcttttcatc tcatcacttc 240
ataaacgata taaaccagaa aaagaactat tttcaaacac gcttctcaaa agcggtatgt 300
ccttccacgt ctccttagaa tctggcaagt ccgcgagggg gatccttagt gatggtggtg 360
atggtgtctg ccctcgatca cctgccactc tgttgtagac agcagcagcg agctaagctc 420
tgatctatcc ctgtcctcca agtcacaacg ctctcctcga gtccaattgc atgcggcttc 480
gaacctgtgc tccacgcccc ccacgtacat cctaaccttg aagatggtga agttgacagt 540
gcaggggtag tgccagagcc tatatgggta atgaaccata cacctaggtg tcagccaggg 600
cccagaaccg catctggcgt aagtggcctc ggggtgcttc cgaaaacagt cagtggggca 660
ggtcaaggtg ttgttgccgg cccccccgat gttgcacggg gggcccccac acgtcttggt 720
gaacccagtg ccattcatcc atgtacagcc gaaccagttg cctcgcggcg gccgcgtgtt 780
gttgagaatc agcacatccg agtcgttcgc cccccagtta tacgtgggga caccaaaccg 840
atcggtcgtc cccaccacaa cagggctcgg ggtgaagcaa tacactggac cgcacacctg 900
agacgcgggt acaataccac acggtcgagg cgcgtagtgc cagcagtagg gcctctggtc 960
cgagctgtta ggctcagtgt aagtgagggg accccacccc tgagcgaact tgtcgatgga 1020
gcgacagctg gccaagcgct ctgggcatcc agacgagttg aatttgtgtt tgtagaatag 1080
tgcggcaaag aaccctgttt ggagggagtc gttgcagttc agggcagtcc tgttgatgtg 1140
ccaactgccg ttggtgttta cgagctggat tttctgagcc gacccggggc taaagaggga 1200
cacaaggccc ctggtatcgg aggctgctgc ccctcctgac acgcgggtat gtcctagtgc 1260
tgctagtggt aggaagcata gtactagtat tagtaggctg cgcatgaatt cccgatgaag 1320

-continued cagagagcgc aggaggcggt atttatagtg ccattcccct ctctgagaga cccggatggt 1380
agtcgagtgt atcggagaca gcttgatgta gactccgtgc ctgccggctc ctcttattgg 1440
cggacaccag tgagacaccc cggaacttgc tgtttttctg caaaatccgg ggtgaccagt 1500
gggagcctat ttgcacacac gagcgggaca ccccactctg gtgaagagtg ccaaagtcat 1560
tctttttccc gttgcggggc agccgattgc atgttttagg aaaatattac ctttgctaca 1620
ccctgtcaga tttaccctcc acacatatat attccgtcac ctccagggac tattattcgt 1680
cgttgcgccg ccagcggaag atatccagaa gctgttttcc gagagactcg gttggcgcct 1740
ggtatatttg atggatgtcg cgctgcctca cgtcccggta cccaggaacg cggtgggatc 1800
tcgggcccat cgaagactgt gctccagact gctcgcccag caggtgtttc ttgatcgccg 1860
cctctaaatt gtccgcgcat cgccggtaac atttttccag ctcggagttt gcgtttagat 1920
acagtttctg cgatgccaaa ggagcctgca gattataacc tcggatgctg tcattcagcg 1980
cttttaattt gacctccaga tagttgctgt atttctgttc ccattggctg ctgcgcagct 2040
tcgtataact cgagttattg ttgcgctctg cctcggcgta ctggctcatg atctggatct 2100
tgtccgtgtc gcttttcttc gagtgtttct cgcaaacgat gtgcacggcc tgcagtgtcc 2160
aatcggagtc gagctggcgc cgaaactggc ggatctgagc ctccacactg ccctgtttct 2220
ctatccacgg cggaaccgcc tcctgccgtt tcagaatgtt gttcaagtgg tactctgtgc 2280
ggtcaatgaa ggcgttattg ccggtgaaat ctttgggaag cggtttttcct cggggaagat 2340 tacgaaattc cccgcgtcgt tgcgcttcct ggatctcgag gagatcgttc tccgcgtcga 2400
ggagatcgtt ctccgcgtcg acaccattcc ttgcggcggc ggtgctcaac ggcctcaacc 2460
tactactggg ctgcttccta atgcaggagt cgcataaggg agagcgtcga caaacccgcg 2520
tttgagaact tgctcaagct tctggtaaac gttgtagtac tctgaaacaa ggccctagca 2580
ctctgatctg tttctcttgg gtagcggtga gtggtttatt ggagttcact ggtttcagca 2640
catctgtcat ctagacaata ttgttactaa attttttga actacaattg ttcgtaattc 2700
atctattatt atacatcctc gtcagcaatt tctggcagac ggagtttact aacgtcttga 2760
gtatgaggcc gagaatccag ctctgtggcc atactcagtc ttgacagcct gctgatgtgg 2820
ctgcgttcaa cgcaataagc gtgtcctccg actccgagtt gtgctcgtta tcgtcgttct 2880
catcctcgga aaaatcacac gaaagaacat actcaccagt aggctttctg gtccctgggg 2940
cacggctgtt tctgacgtat tccggcgttg ataatagctc gaaagtgaac gccgagtcgc 3000
gggagtcgac cgatgccctt gagagccttc aacccagtca gctccttccg gtgggcgcgg 3060
ggcatgacta tcgtcgccgc acttatgact gtcttcttta tcatgcaact cgtaggacag 3120
gtgccggcag cgctctgggt cattttcggc gaggaccgct ttcgctggag cgcgacgatg 3180
atcggcctgt cgcttgcggt attcggaatc ttgcacgccc tcgctcaagc cttcgtcact 3240
ggtcccgcca ccaaacgttt cggcgagaag caggccatta tcgccggcat ggcggccgac 3300
gcgctgggct acgtcttgct ggcgttcgcg acgcgaggct ggatggcctt ccccattatg 3360
attcttctcg cttccggcgg catcgggatg cccgcgttgc aggccatgct gtccaggcag 3420
gtagatgacg accatcaggg acagcttcaa ggatcgctcg cggctcttac cagcctaact 3480
tcgatcactg gaccgctgat cgtcacggcg atttatgccg cctcggcgag cacatggaac 3540
gggttggcat ggattgtagg cgccgcccta taccttgtct gcctccccgc gttgcgtcgc 3600
ggtgcatgga gccgggccac ctcgacctga atggaagccg gcggcacctc gctaacggat 3660
tcaccactcc aagaattgga gccaatcaat tcttgcggag aactgtgaat gcgcaaacca 3720

-continued

```
accccttggca gaacatatcc atcgcgtccg ccatctccag cagccgcacg cggcgcatcg   3780
gggggggggg gggggggggg gggcaaacaa ttcatcattt tttttttatt cttttttttg   3840
atttcggttt ctttgaaatt tttttgattc ggtaatctcc gaacagaagg aagaacgaag   3900
gaaggagcac agacttagat tggtatatat acgcatatgt agtgttgaag aaacatgaaa   3960
ttgcccagta ttcttaaccc aactgcacag aacaaaaacc tgcaggaaac gaagataaat   4020
catgtcgaaa gctacatata aggaacgtgc tgctactcat cctagtcctg ttgctgccaa   4080
gctatttaat atcatgcacg aaaagcaaac aaacttgtgt gcttcattgg atgttcgtac   4140
caccaaggaa ttactggagt tagttgaagc attaggtccc aaaatttgtt tactaaaaac   4200
acatgtggat atcttgactg atttttccat ggagggcaca gttaagccgc taaaggcatt   4260
atccgccaag tacaattttt tactcttcga agacagaaaa tttgctgaca ttggtaatac   4320
agtcaaattg cagtactctg cgggtgtata cagaatagca gaatgggcag acattacgaa   4380
tgcacacggt gtggtgggcc caggtattgt tagcggtttg aagcaggcgg cagaagaagt   4440
aacaaaggaa cctagaggcc ttttgatgtt agcagaattg tcatgcaagg gctccctatc   4500
tactggagaa tatactaagg gtactgttga cattgcgaag agcgacaaag attttgttat   4560
cggctttatt gctcaaagag acatgggtgg aagagatgaa ggttacgatt ggttgattat   4620
gacacccggt gtgggtttag atgacaaggg agacgcattg ggtcaacagt atagaaccgt   4680
ggatgatgtg gtctctacag gatctgacat tattattgtt ggaagaggac tatttgcaaa   4740
gggaagggat gctaaggtag agggtgaacg ttacagaaaa gcaggctggg aagcatattt   4800
gagaagatgc ggccagcaaa actaaaaaac tgtattataa gtaaatgcat gtatactaaa   4860
ctcacaaatt agagcttcaa tttaattata tcagttatta cccgggaatc tcggtcgtaa   4920
tgatttttat aatgacgaaa aaaaaaaaat tggaaagaaa agcccccccc cccccccccc   4980
cccccccccc ccccccgcag cgttgggtcc tggccacggg tgcgcatgat cgtgctcctg   5040
tcgttgagga cccggctagg ctggcggggt tgccttactg gttagcagaa tgaatcaccg   5100
atacgcgagc gaacgtgaag cgactgctgc tgcaaaacgt ctgcgacctg agcaacaaca   5160
tgaatggtct tcggtttccg tgtttcgtaa agtctggaaa cgcggaagtc agcgccctgc   5220
accattatgt tccggatctg catcgcagga tgctgctggc taccctgtgg aacacctaca   5280
tctgtattaa cgaagcgctg gcattgaccc tgagtgattt ttctctggtc ccgccgcatc   5340
cataccgcca gttgtttacc ctcacaacgt tccagtaacc gggcatgttc atcatcagta   5400
acccgtatcg tgagcatcct ctctcgtttc atcggtatca ttacccccat gaacagaaat   5460
tccccccttac acggaggcat caagtgacca aacaggaaaa aaccgccctt aacatggccc   5520
gctttatcag aagccagaca ttaacgcttc tggagaaact caacgagctg gacgcggatg   5580
aacaggcaga catctgtgaa tcgcttcacg accacgctga tgagctttac cgcagctgcc   5640
tcgcgcgttt cggtgatgac ggtgaaaacc tctgacacat gcagctcccg gagacggtca   5700
cagcttgtct gtaagcggat gccgggagca gacaagcccg tcagggcgcg tcagcgggtg   5760
ttggcgggtg tcggggcgca gccatgaccc agtcacgtag cgatagcgga gtgtatactg   5820
gcttaactat gcggcatcag agcagattgt actgagagtg caccatatgc ggtgtgaaat   5880
accgcacaga tgcgtaagga gaaaataccg catcaggcgc tcttccgctt cctcgctcac   5940
tgactcgctg cgctcggtcg ttcggctgcg gcgagcggta tcagctcact caaaggcggt   6000
aatacggtta tccacagaat caggggataa cgcaggaaag aacatgtgag caaaaggcca   6060
```

-continued

```
gcaaaaggcc aggaaccgta aaaaggccgc gttgctggcg tttttccata ggctccgccc   6120

ccctgacgag catcacaaaa atcgacgctc aagtcagagg tggcgaaacc cgacaggact   6180

ataaagatac caggcgtttc cccctggaag ctccctcgtg cgctctcctg ttccgaccct   6240

gccgcttacc ggatacctgt ccgcctttct cccttcggga agcgtggcgc tttctcatag   6300

ctcacgctgt aggtatctca gttcggtgta ggtcgttcgc tccaagctgg gctgtgtgca   6360

cgaacccccc gttcagcccg accgctgcgc cttatccggt aactatcgtc ttgagtccaa   6420

cccggtaaga cacgacttat cgccactggc agcagccact ggtaacagga ttagcagagc   6480

gaggtatgta ggcggtgcta cagagttctt gaagtggtgg cctaactacg gctacactag   6540

aaggacagta tttggtatct gcgctctgct gaagccagtt accttcggaa aaagagttgg   6600

tagctcttga tccggcaaac aaaccaccgc tggtagcggt ggtttttttg tttgcaagca   6660

gcagattacg cgcagaaaaa aaggatctca agaagatcct ttgatctttt ctacggggtc   6720

tgacgctcag tggaacgaaa actcacgtta agggattttg gtcatgagat tatcaaaaag   6780

gatcttcacc tagatccttt taaattaaaa atgaagtttt aaatcaatct aaagtatata   6840

tgagtaaact tggtctgaca gttaccaatg cttaatcagt gaggcaccta tctcagcgat   6900

ctgtctattt cgttcatcca tagttgcctg actccccgtc gtgtagataa ctacgatacg   6960

ggagggctta ccatctggcc ccagtgctgc aatgataccg cgagacccac gctcaccggc   7020

tccagattta tcagcaataa accagccagc cggaagggcc gagcgcagaa gtggtcctgc   7080

aactttatcc gcctccatcc agtctattaa ttgttgccgg gaagctagag taagtagttc   7140

gccagttaat agtttgcgca acgttgttgc cattgctgca ggcatcgtgg tgtcacgctc   7200

gtcgtttggt atggcttcat tcagctccgg ttcccaacga tcaaggcgag ttacatgatc   7260

ccccatgttg tgcaaaaaag cggttagctc cttcggtcct ccgatcgttg tcagaagtaa   7320

gttggccgca gtgttatcac tcatggttat ggcagcactg cataattctc ttactgtcat   7380

gccatccgta agatgctttt ctgtgactgg tgagtactca accaagtcat tctgagaata   7440

gtgtatgcgg cgaccgagtt gctcttgccc ggcgtcaaca cgggataata ccgcgccaca   7500

tagcagaact ttaaaagtgc tcatcattgg aaaacgttct tcggggcgaa aactctcaag   7560

gatcttaccg ctgttgagat ccagttcgat gtaacccact cgtgcaccca actgatcttc   7620

agcatctttt actttcacca gcgtttctgg gtgagcaaaa acaggaaggc aaaatgccgc   7680

aaaaaaggga ataagggcga cacggaaatg ttgaatactc atactcttcc tttttcaata   7740

ttattgaagc atttatcagg gttattgtct catgagcgga tacatatttg aatgtattta   7800

gaaaaataaa caaatagggg ttccgcgcac atttccccga aaagtgccac ctgacgtcta   7860

agaaaccatt attatcatga cattaaccta taaaaatagg cgtatcacga ggccctttcg   7920

tcttcaa                                                             7927
```

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: probe seq 33

<400> SEQUENCE: 33

```
taaggatccc cgggtaccga gctc                                            24
```

<210> SEQ ID NO 34
<211> LENGTH: 25

-continued

<212> TYPE: DNA
<213> ORGANISM: Artificial Sequence
<220> FEATURE:
<223> OTHER INFORMATION: Description of Artificial Sequence: probe seq 34

<400> SEQUENCE: 34
ccagttcatc atcatatccc aagcc 25

<210> SEQ ID NO 35
<211> LENGTH: 4234
<212> TYPE: DNA
<213> ORGANISM: Artificial Sequence
<220> FEATURE:
<223> OTHER INFORMATION: Description of Artificial Sequence:
vector pUC18-FMD-CL-E1
<220> FEATURE:
<221> NAME/KEY: misc_feature
<222> LOCATION: (988)..(989)
<223> OTHER INFORMATION: N is any nucleotide
<220> FEATURE:
<221> NAME/KEY: misc_feature
<222> LOCATION: (1167)..(1168)
<223> OTHER INFORMATION: N is any nucleotide
<400> SEQUENCE: 35
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg aattcgagct 240
cggtacccgg ggatccttac cagttcatca tcatatccca agccatacgg tgacctgtta 300
tgtggccggg atagattgag caattgcagt cctgcaccgt ctcatgccgg cgaggcgaga 360
tggtgaacag ctgggagacg aggaagacag atccgcagag atcccccacg tacatagcgg 420
aacagaaagc agccgcccca acgagcaaat cgacgtggcg tcgtattgtc gtagtgggga 480
cgctggcgtt cctagctgcg agcgtggggg tgagcgctac ccagcagcgg gaagagttgt 540
tctcccgaac gcagggcacg cacccggggg tgtgcatgat catgtccgct gcctcataca 600
caatgcttga gttggagcag tcgttcgtga catggtacat cccggacacg ttgcgcacct 660
catatcctag tgctgctagt ggtaggaagc atagtactag tattagtagg cttcgcatga 720
attcccgatg aaggcagaga gcgcaaggag gcggtattta tagtgccatt cccctctctg 780
agagacccgg atggtagtcg agtgttatcg gagacagctt gatgtagact ccgtgcctgc 840
cggtcctctt attggcggac accagtgaga caccccggaa cttgctgttt ttctgcaaaa 900
tccggggtga ccagtgggag cctatttgca cacacgagcg ggacacccca ctctggtgaa 960
gagtgccaaa gtcattcttt ttcccgtnnc ggggcagccg attgcatgtt ttaggaaaat 1020
attacctttg ctacaccctg tcagatttac cctccacaca tatatattcc gtcacctcca 1080
gggactattc ttggctcgtt gcgccgccgc ggaagatatc cagaagctgt gttttccgag 1140
agactcggtt ggcgcctggt atatttnnag gatgtcgcgc tgcctcacgt cccggtaccc 1200
aggaacgcgg tgggatctcg ggcccatcga agactgtgct ccagactgct cgcccagcag 1260
gtgtttcttg attgccgcct ctaaatagtc cgcgcatcgc cggtaacatt tttccagctc 1320
ggagtttgcg tttagataca tttctgcgat gccaaaggag cctgcagatt ataacctcgg 1380
atgctgtcat tcagcgcttt taatttgacc tccagatagt tgctgtattt ctgttccatt 1440
ggctgctgga cgttcgtata actcgagtta ttgttgcgct ctgcctcggc gtactggctc 1500
atgactgact gcggtcgctt ctcgagtgtt ctcgcaacag gacgcctgca ggtcatcgag 1560

-continued

```
tcgagctggc gccgaaactg gcggatctga cctccacact gccctgtatc tctatccacc   1620
gggaaccgcc tcctgccgtt ccagaatgtt gttcaagtgg tagctctgtg cggtcaatga   1680
aggcgttatt gccggtgaaa tctttgggaa gcggtttatc ctcggggaag attacgaaat   1740
tcccgcgcgt cgttgcgctt cctggatctc gaggaagatc gttctccgcg tcgaggagat   1800
cgttctccgc gtcgacctgc aggcatgcaa gcttggcact ggccgtcgtt ttacaacgtc   1860
gtgactggga aaaccctggc gttacccaac ttaatcgcct tgcagcacat ccccctttcg   1920
ccagctggcg taatagcgaa gaggcccgca ccgatcgccc ttcccaacag ttgcgcagcc   1980
tgaatggcga atggcgcctg atgcggtatt ttctccttac gcatctgtgc ggtatttcac   2040
accgcatatg gtgcactctc agtacaatct gctctgatgc cgcatagtta agccagcccc   2100
gacacccgcc aacacccgct gacgcgccct gacgggcttg tctgctcccg gcatccgctt   2160
acagacaagc tgtgaccgtc tccgggagct gcatgtgtca gaggttttca ccgtcatcac   2220
cgaaacgcgc gagacgaaag ggcctcgtga tacgcctatt tttataggtt aatgtcatga   2280
taataatggt ttcttagacg tcaggtggca cttttcgggg aaatgtgcgc ggaaccccta   2340
tttgtttatt tttctaaata cattcaaata tgtatccgct catgagacaa taaccctgat   2400
aaatgcttca ataatattga aaaaggaaga gtatgagtat tcaacatttc cgtgtcgccc   2460
ttattccctt ttttgcggca ttttgccttc ctgtttttgc tcacccagaa acgctggtga   2520
aagtaaaaga tgctgaagat cagttgggtg cacgagtggg ttacatcgaa ctggatctca   2580
acagcggtaa gatccttgag agttttcgcc ccgaagaacg ttttccaatg atgagcactt   2640
ttaaagttct gctatgtggc gcggtattat cccgtattga cgccgggcaa gagcaactcg   2700
gtcgccgcat acactattct cagaatgact tggttgagta ctcaccagtc acagaaaagc   2760
atcttacgga tggcatgaca gtaagagaat tatgcagtgc tgccataacc atgagtgata   2820
acactgcggc caacttactt ctgacaacga tcggaggacc gaaggagcta accgcttttt   2880
tgcacaacat gggggatcat gtaactcgcc ttgatcgttg ggaaccggag ctgaatgaag   2940
ccataccaaa cgacgagcgt gacaccacga tgcctgtagc aatggcaaca acgttgcgca   3000
aactattaac tggcgaacta cttactctag cttcccggca acaattaata gactggatgg   3060
aggcggataa agttgcagga ccacttctgc gctcggccct tccggctggc tggtttattg   3120
ctgataaatc tggagccggt gagcgtgggt ctcgcggtat cattgcagca ctggggccag   3180
atggtaagcc ctcccgtatc gtagttatct acacgacggg gagtcaggca actatggatg   3240
aacgaaatag acagatcgct gagataggtg cctcactgat taagcattgg taactgtcag   3300
accaagttta ctcatatata ctttagattg atttaaaact tcatttttaa tttaaaagga   3360
tctaggtgaa gatccttttt gataatctca tgaccaaaat cccttaacgt gagttttcgt   3420
tccactgagc gtcagacccc gtagaaaaga tcaaaggatc ttcttgagat cctttttttc   3480
tgcgcgtaat ctgctgcttg caaacaaaaa aaccaccgct accagcggtg gtttgtttgc   3540
cggatcaaga gctaccaact ctttttccga aggtaactgg cttcagcaga gcgcagatac   3600
caaatactgt ccttctagtg tagccgtagt taggccacca cttcaagaac tctgtagcac   3660
cgcctacata cctcgctctg ctaatcctgt taccagtggc tgctgccagt ggcgataagt   3720
cgtgtcttac cgggttggac tcaagacgat agttaccgga taaggcgcag cggtcgggct   3780
gaacgggggg ttcgtgcaca cagcccagct tggagcgaac gacctacacc gaactgagat   3840
acctacagcg tgagctatga gaaagcgcca cgcttcccga agggagaaag gcggacaggt   3900
```

-continued

```
atccggtaag cggcagggtc ggaacaggag agcgcacgag ggagcttcca gggggaaacg   3960

cctggtatct ttatagtcct gtcgggtttc gccacctctg acttgagcgt cgatttttgt   4020

gatgctcgtc aggggggcgg agcctatgga aaaacgccag caacgcggcc tttttacggt   4080

tcctggcctt ttgctggcct tttgctcaca tgttctttcc tgcgttatcc cctgattctg   4140

tggataaccg tattaccgcc tttgagtgag ctgataccgc tcgccgcagc cgaacgaccg   4200

agcgcagcga gtcagtgagc gaggaagcgg aaga                               4234
```

<210> SEQ ID NO 36
<211> LENGTH: 7429
<212> TYPE: DNA
<213> ORGANISM: Artificial Sequence
<220> FEATURE:
<223> OTHER INFORMATION: Description of Artificial Sequence:
vector pFPMT-CL-E1

<400> SEQUENCE: 36

```
ggtaccctgc tcaatctccg gaatggtgat ctgatcgttc ctgaaaacct cgacattggc     60

tccctcctga cacaggtact cgtacaggtt ccaggtaaac gagtcgtagt tgtcgatcat    120

gacaacgttc ttagaagcgg ccggcatttt gaaggtgact aatagcctaa gaaaatattt    180

aatttaattt tcattaaatt ttcctatact cgctatttca gcttttcatc tcatcacttc    240

ataaacgata taaaccagaa aaagaactat tttcaaacac gcttctcaaa agcggtatgt    300

ccttccacgt ctccttagaa tctggcaagt ccgcgagggg gatccttacc agttcatcat    360

catatcccaa gccatacggt gacctgttat gtggccggga tagattgagc aattgcagtc    420

ctgcaccgtc tcatgccggc gaggcgagat ggtgaacagc tgggagacga ggaagacaga    480

tccgcagaga tcccccacgt acatagcgga acagaaagca gccgccccaa cgagcaaatc    540

gacgtggcgt cgtattgtcg tagtggggac gctggcgttc ctagctgcga gcgtgggggt    600

gagcgctacc cagcagcggg aagagttgtt ctcccgaacg cagggcacgc acccgggggt    660

gtgcatgatc atgtccgctg cctcatacac aatgcttgag ttggagcagt cgttcgtgac    720

atggtacatc ccggacacgt tgcgcacctc atatcctagt gctgctagtg gtaggaagca    780

tagtactagt attagtaggc ttcgcatgaa ttcccgatga agcagagagc gcaggaggcg    840

gtatttatag tgccattccc ctctctgaga gacccggatg gtagtcgagt gtatcggaga    900

cagcttgatg tagactccgt gcctgccggc tcctcttatt ggcggacacc agtgagacac    960

cccggaactt gctgtttttc tgcaaaatcc ggggtgacca gtgggagcct atttgcacac   1020

acgagcggga caccccactc tggtgaagag tgccaaagtc attctttttc ccgttgcggg   1080

gcagccgatt gcatgtttta ggaaaatatt acctttgcta caccctgtca gatttaccct   1140

ccacacatat atattccgtc acctccaggg actattattc gtcgttgcgc cgccagcgga   1200

agatatccag aagctgtttt ccgagagact cggttggcgc ctggtatatt tgatggatgt   1260

cgcgctgcct cacgtcccgg tacccaggaa cgcggtggga tctcgggccc atcgaagact   1320

gtgctccaga ctgctcgccc agcaggtgtt tcttgatcgc cgcctctaaa ttgtccgcgc   1380

atcgccggta acatttttcc agctcggagt ttgcgtttag atacagtttc tgcgatgcca   1440

aaggagcctg cagattataa cctcggatgc tgtcattcag cgcttttaat ttgacctcca   1500

gatagttgct gtatttctgt tcccattggc tgctgcgcag cttcgtataa ctcgagttat   1560

tgttgcgctc tgcctcggcg tactggctca tgatctggat cttgtccgtg tcgcttttct   1620

tcgagtgttt ctcgcaaacg atgtgcacgg cctgcagtgt ccaatcggag tcgagctggc   1680
```

-continued

```
gccgaaactg gcggatctga gcctccacac tgccctgttt ctctatccac ggcggaaccg   1740
cctcctgccg tttcagaatg ttgttcaagt ggtactctgt gcggtcaatg aaggcgttat   1800
tgccggtgaa atctttggga agcggttttc ctcggggaag attacgaaat tccccgcgtc   1860
gttgcgcttc ctggatctcg aggagatcgt tctccgcgtc gaggagatcg ttctccgcgt   1920
cgacaccatt ccttgcggcg gcggtgctca acggcctcaa cctactactg ggctgcttcc   1980
taatgcagga gtcgcataag ggagagcgtc gacaaacccg cgtttgagaa cttgctcaag   2040
cttctggtaa acgttgtagt actctgaaac aaggccctag cactctgatc tgtttctctt   2100
gggtagcggt gagtggttta ttggagttca ctggtttcag cacatctgtc atctagacaa   2160
tattgttact aaattttttt gaactacaat tgttcgtaat tcatctatta ttatacatcc   2220
tcgtcagcaa tttctggcag acggagttta ctaacgtctt gagtatgagg ccgagaatcc   2280
agctctgtgg ccatactcag tcttgacagc ctgctgatgt ggctgcgttc aacgcaataa   2340
gcgtgtcctc cgactccgag ttgtgctcgt tatcgtcgtt ctcatcctcg gaaaaatcac   2400
acgaaagaac atactcacca gtaggctttc tggtccctgg ggcacggctg tttctgacgt   2460
attccggcgt tgataatagc tcgaaagtga acgccgagtc gcgggagtcg accgatgccc   2520
ttgagagcct tcaacccagt cagctccttc cggtgggcgc ggggcatgac tatcgtcgcc   2580
gcacttatga ctgtcttctt tatcatgcaa ctcgtaggac aggtgccggc agcgctctgg   2640
gtcattttcg gcgaggaccg ctttcgctgg agcgcgacga tgatcggcct gtcgcttgcg   2700
gtattcggaa tcttgcacgc cctcgctcaa gccttcgtca ctggtcccgc caccaaacgt   2760
ttcggcgaga agcaggccat tatcgccggc atggcggccg acgcgctggg ctacgtcttg   2820
ctggcgttcg cgacgcgagg ctggatggcc ttccccatta tgattcttct cgcttccggc   2880
ggcatcggga tgcccgcgtt gcaggccatg ctgtccaggc aggtagatga cgaccatcag   2940
ggacagcttc aaggatcgct cgcggctctt accagcctaa cttcgatcac tggaccgctg   3000
atcgtcacgg cgatttatgc cgcctcggcg agcacatgga acgggttggc atggattgta   3060
ggcgccgccc tataccttgt ctgcctcccc gcgttgcgtc gcggtgcatg gagccgggcc   3120
acctcgacct gaatggaagc cggcggcacc tcgctaacgg attcaccact ccaagaattg   3180
gagccaatca attcttgcgg agaactgtga atgcgcaaac caacccttgg cagaacatat   3240
ccatcgcgtc cgccatctcc agcagccgca cgcggcgcat cggggggggg gggggggggg   3300
gggggcaaac aattcatcat tttttttta ttcttttttt tgatttcggt ttctttgaaa   3360
tttttttgat tcggtaatct ccgaacagaa ggaagaacga aggaaggagc acagacttag   3420
attggtatat atacgcatat gtagtgttga agaaacatga aattgcccag tattcttaac   3480
ccaactgcac agaacaaaaa cctgcaggaa acgaagataa atcatgtcga aagctacata   3540
taaggaacgt gctgctactc atcctagtcc tgttgctgcc aagctattta atatcatgca   3600
cgaaaagcaa acaaacttgt gtgcttcatt ggatgttcgt accaccaagg aattactgga   3660
gttagttgaa gcattaggtc ccaaaatttg tttactaaaa acacatgtgg atatcttgac   3720
tgatttttcc atggagggca cagttaagcc gctaaaggca ttatccgcca agtacaattt   3780
tttactcttc gaagacagaa aatttgctga cattggtaat acagtcaaat tgcagtactc   3840
tgcgggtgta tacagaatag cagaatgggc agacattacg aatgcacacg gtgtggtggg   3900
cccaggtatt gttagcggtt tgaagcaggc ggcagaagaa gtaacaaagg aacctagagg   3960
ccttttgatg ttagcagaat tgtcatgcaa gggctcccta tctactggag aatatactaa   4020
gggtactgtt gacattgcga agagcgacaa agattttgtt atcggcttta ttgctcaaag   4080
```

-continued agacatgggt ggaagagatg aaggttacga ttggttgatt atgacacccg gtgtgggttt 4140
agatgacaag ggagacgcat tgggtcaaca gtatagaacc gtggatgatg tggtctctac 4200
aggatctgac attattattg ttggaagagg actatttgca aagggaaggg atgctaaggt 4260
agagggtgaa cgttacagaa aagcaggctg ggaagcatat ttgagaagat gcggccagca 4320
aaactaaaaa actgtattat aagtaaatgc atgtatacta aactcacaaa ttagagcttc 4380
aatttaatta tatcagttat tacccgggaa tctcggtcgt aatgattttt ataatgacga 4440
aaaaaaaaaa attggaaaga aaagcccccc cccccccccc cccccccccc cccccccgc 4500 agcgttgggt cctggccacg ggtgcgcatg atcgtgctcc tgtcgttgag gacccggcta 4560
ggctggcggg gttgccttac tggttagcag aatgaatcac cgatacgcga gcgaacgtga 4620
agcgactgct gctgcaaaac gtctgcgacc tgagcaacaa catgaatggt cttcggtttc 4680
cgtgtttcgt aaagtctgga aacgcggaag tcagcgccct gcaccattat gttccggatc 4740
tgcatcgcag gatgctgctg gctaccctgt ggaacaccta catctgtatt aacgaagcgc 4800
tggcattgac cctgagtgat ttttctctgg tcccgccgca tccataccgc cagttgttta 4860
ccctcacaac gttccagtaa ccgggcatgt tcatcatcag taacccgtat cgtgagcatc 4920
ctctctcgtt tcatcggtat cattaccccc atgaacagaa attccccctt acacggaggc 4980
atcaagtgac caaacaggaa aaaaccgccc ttaacatggc ccgctttatc agaagccaga 5040
cattaacgct tctggagaaa ctcaacgagc tggacgcgga tgaacaggca gacatctgtg 5100
aatcgcttca cgaccacgct gatgagcttt accgcagctg cctcgcgcgt ttcggtgatg 5160
acggtgaaaa cctctgacac atgcagctcc cggagacggt cacagcttgt ctgtaagcgg 5220
atgccgggag cagacaagcc cgtcagggcg cgtcagcggg tgttggcggg tgtcggggcg 5280
cagccatgac ccagtcacgt agcgatagcg gagtgtatac tggcttaact atgcggcatc 5340
agagcagatt gtactgagag tgcaccatat gcggtgtgaa ataccgcaca gatgcgtaag 5400
gagaaaatac cgcatcaggc gctcttccgc ttcctcgctc actgactcgc tgcgctcggt 5460
cgttcggctg cggcgagcgg tatcagctca ctcaaaggcg gtaatacggt tatccacaga 5520
atcaggggat aacgcaggaa agaacatgtg agcaaaaggc cagcaaaagg ccaggaaccg 5580
taaaaaggcc gcgttgctgg cgtttttcca taggctccgc ccccctgacg agcatcacaa 5640
aaatcgacgc tcaagtcaga ggtggcgaaa cccgacagga ctataaagat accaggcgtt 5700
tccccctgga agctccctcg tgcgctctcc tgttccgacc ctgccgctta ccggatacct 5760
gtccgccttt ctcccttcgg gaagcgtggc gctttctcat agctcacgct gtaggtatct 5820
cagttcggtg taggtcgttc gctccaagct gggctgtgtg cacgaacccc ccgttcagcc 5880
cgaccgctgc gccttatccg gtaactatcg tcttgagtcc aacccggtaa gacacgactt 5940
atcgccactg gcagcagcca ctggtaacag gattagcaga gcgaggtatg taggcggtgc 6000
tacagagttc ttgaagtggt ggcctaacta cggctacact agaaggacag tatttggtat 6060
ctgcgctctg ctgaagccag ttaccttcgg aaaaagagtt ggtagctctt gatccggcaa 6120
acaaaccacc gctggtagcg gtggtttttt tgtttgcaag cagcagatta cgcgcagaaa 6180
aaaaggatct caagaagatc ctttgatctt ttctacgggg tctgacgctc agtggaacga 6240
aaactcacgt taagggattt tggtcatgag attatcaaaa aggatcttca cctagatcct 6300
tttaaattaa aaatgaagtt ttaaatcaat ctaaagtata tatgagtaaa cttggtctga 6360
cagttaccaa tgcttaatca gtgaggcacc tatctcagcg atctgtctat ttcgttcatc 6420

-continued

```
catagttgcc tgactccccg tcgtgtagat aactacgata cgggagggct taccatctgg   6480

ccccagtgct gcaatgatac cgcgagaccc acgctcaccg gctccagatt tatcagcaat   6540

aaaccagcca gccggaaggg ccgagcgcag aagtggtcct gcaactttat ccgcctccat   6600

ccagtctatt aattgttgcc gggaagctag agtaagtagt tcgccagtta atagtttgcg   6660

caacgttgtt gccattgctg caggcatcgt ggtgtcacgc tcgtcgtttg gtatggcttc   6720

attcagctcc ggttcccaac gatcaaggcg agttacatga tcccccatgt tgtgcaaaaa   6780

agcggttagc tccttcggtc ctccgatcgt tgtcagaagt aagttggccg cagtgttatc   6840

actcatggtt atggcagcac tgcataattc tcttactgtc atgccatccg taagatgctt   6900

ttctgtgact ggtgagtact caaccaagtc attctgagaa tagtgtatgc ggcgaccgag   6960

ttgctcttgc ccggcgtcaa cacgggataa taccgcgcca catagcagaa ctttaaaagt   7020

gctcatcatt ggaaaacgtt cttcggggcg aaaactctca aggatcttac cgctgttgag   7080

atccagttcg atgtaaccca ctcgtgcacc caactgatct tcagcatctt ttactttcac   7140

cagcgtttct gggtgagcaa aaacaggaag gcaaaatgcc gcaaaaaagg gaataagggc   7200

gacacggaaa tgttgaatac tcatactctt cctttttcaa tattattgaa gcatttatca   7260

gggttattgt ctcatgagcg gatacatatt tgaatgtatt tagaaaaata aacaaatagg   7320

ggttccgcgc acatttcccc gaaaagtgcc acctgacgtc taagaaacca ttattatcat   7380

gacattaacc tataaaaata ggcgtatcac gaggcccttt cgtcttcaa              7429


<210> SEQ ID NO 37
<211> LENGTH: 39
<212> TYPE: DNA
<213> ORGANISM: Artificial Sequence
<220> FEATURE:
<223> OTHER INFORMATION: Description of Artificial Sequence:
      Primer H6K hin neu

<400> SEQUENCE: 37

catcacaaat atgaggtgcg caacgtgtcc gggatgtac                           39


<210> SEQ ID NO 38
<211> LENGTH: 42
<212> TYPE: DNA
<213> ORGANISM: Artificial Sequence
<220> FEATURE:
<223> OTHER INFORMATION: Description of Artificial Sequence:
      Primer H6KRK her neu

<400> SEQUENCE: 38

gtgatggtgg tgtcctagtg ctgctagtgg taggaagcat ag                       42


<210> SEQ ID NO 39
<211> LENGTH: 4273
<212> TYPE: DNA
<213> ORGANISM: Artificial Sequence
<220> FEATURE:
<223> OTHER INFORMATION: Description of Artificial Sequence:
      vector pUC18-FMD-CL-E1-H-K6
<220> FEATURE:
<221> NAME/KEY: misc_feature
<222> LOCATION: (1027)..(1028)
<223> OTHER INFORMATION: N is any nucleotide
<220> FEATURE:
<221> NAME/KEY: misc_feature
<222> LOCATION: (1206)..(1207)
<223> OTHER INFORMATION: N is any nucleotide

<400> SEQUENCE: 39
```

-continued

```
gcgcccaata cgcaaaccgc ctctccccgc gcgttggccg attcattaat gcagctggca     60
cgacaggttt cccgactgga aagcgggcag tgagcgcaac gcaattaatg tgagttagct    120
cactcattag gcaccccagg ctttacactt tatgcttccg gctcgtatgt tgtgtggaat    180
tgtgagcgga taacaatttc acacaggaaa cagctatgac catgattacg aattcgagct    240
cggtacccgg ggatccttaa tggtgatggt ggtggtgcca gttcatcatc atatcccaag    300
ccatacggtg acctgttatg tggccgggat agattgagca attgcagtcc tgcaccgtct    360
catgccggcg aggcgagatg gtgaacagct gggagacgag gaagacagat ccgcagagat    420
cccccacgta catagcggaa cagaaagcag ccgccccaac gagcaaatcg acgtggcgtc    480
gtattgtcgt agtggggacg ctggcgttcc tagctgcgag cgtgggggtg agcgctaccc    540
agcagcggga agagttgttc tcccgaacgc agggcacgca cccgggggtg tgcatgatca    600
tgtccgctgc ctcatacaca atgcttgagt tggagcagtc gttcgtgaca tggtacatcc    660
cggacacgtt gcgcacctca tatttgtgat ggtgatggtg gtgtcctagt gctgctagtg    720
gtaggaagca tagtactagt attagtaggc ttcgcatgaa ttcccgatga aggcagagag    780
cgcaaggagg cggtatttat agtgccattc ccctctctga gagacccgga tggtagtcga    840
gtgttatcgg agacagcttg atgtagactc cgtgcctgcc ggtcctctta ttggcggaca    900
ccagtgagac accccggaac ttgctgtttt tctgcaaaat ccggggtgac cagtgggagc    960
ctatttgcac acacgagcgg gacaccccac tctggtgaag agtgccaaag tcattctttt   1020
tcccgtnncg gggcagccga ttgcatgttt taggaaaata ttacctttgc tacaccctgt   1080
cagatttacc ctccacacat atatattccg tcacctccag ggactattct tggctcgttg   1140
cgccgccgcg gaagatatcc agaagctgtg ttttccgaga gactcggttg gcgcctggta   1200
tatttnnagg atgtcgcgct gcctcacgtc ccggtaccca ggaacgcggt gggatctcgg   1260
gcccatcgaa gactgtgctc cagactgctc gcccagcagg tgtttcttga ttgccgcctc   1320
taaatagtcc gcgcatcgcc ggtaacattt ttccagctcg gagtttgcgt ttagatacat   1380
ttctgcgatg ccaaaggagc ctgcagatta taacctcgga tgctgtcatt cagcgctttt   1440
aatttgacct ccagatagtt gctgtatttc tgttccattg gctgctggac gttcgtataa   1500
ctcgagttat tgttgcgctc tgcctcggcg tactggctca tgactgactg cggtcgcttc   1560
tcgagtgttc tcgcaacagg acgcctgcag gtcatcgagt cgagctggcg ccgaaactgg   1620
cggatctgac ctccacactg ccctgtatct ctatccaccg ggaaccgcct cctgccgttc   1680
cagaatgttg ttcaagtggt agctctgtgc ggtcaatgaa ggcgttattg ccggtgaaat   1740
ctttgggaag cggtttatcc tcggggaaga ttacgaaatt cccgcgcgtc gttgcgcttc   1800
ctggatctcg aggaagatcg ttctccgcgt cgaggagatc gttctccgcg tcgacctgca   1860
ggcatgcaag cttggcactg gccgtcgttt tacaacgtcg tgactgggaa aaccctggcg   1920
ttacccaact taatcgcctt gcagcacatc ccccttttcgc cagctggcgt aatagcgaag   1980
aggcccgcac cgatcgccct tcccaacagt tgcgcagcct gaatggcgaa tggcgcctga   2040
tgcggtattt tctccttacg catctgtgcg gtatttcaca ccgcatatgg tgcactctca   2100
gtacaatctg ctctgatgcc gcatagttaa gccagccccg acacccgcca acacccgctg   2160
acgcgccctg acgggcttgt ctgctcccgg catccgctta cagacaagct gtgaccgtct   2220
ccgggagctg catgtgtcag aggttttcac cgtcatcacc gaaacgcgcg agacgaaagg   2280
gcctcgtgat acgcctattt ttataggtta atgtcatgat aataatggtt tcttagacgt   2340
caggtggcac ttttcgggga aatgtgcgcg gaacccctat ttgtttattt ttctaaatac   2400
```

-continued

```
attcaaatat gtatccgctc atgagacaat aaccctgata aatgcttcaa taatattgaa   2460
aaaggaagag tatgagtatt caacatttcc gtgtcgccct tattcccttt tttgcggcat   2520
tttgccttcc tgtttttgct cacccagaaa cgctggtgaa agtaaaagat gctgaagatc   2580
agttgggtgc acgagtgggt tacatcgaac tggatctcaa cagcggtaag atccttgaga   2640
gttttcgccc cgaagaacgt tttccaatga tgagcacttt taaagttctg ctatgtggcg   2700
cggtattatc ccgtattgac gccgggcaag agcaactcgg tcgccgcata cactattctc   2760
agaatgactt ggttgagtac tcaccagtca cagaaaagca tcttacggat ggcatgacag   2820
taagagaatt atgcagtgct gccataacca tgagtgataa cactgcggcc aacttacttc   2880
tgacaacgat cggaggaccg aaggagctaa ccgctttttt gcacaacatg ggggatcatg   2940
taactcgcct tgatcgttgg gaaccggagc tgaatgaagc cataccaaac gacgagcgtg   3000
acaccacgat gcctgtagca atggcaacaa cgttgcgcaa actattaact ggcgaactac   3060
ttactctagc ttcccggcaa caattaatag actggatgga ggcggataaa gttgcaggac   3120
cacttctgcg ctcggccctt ccggctggct ggtttattgc tgataaatct ggagccggtg   3180
agcgtgggtc tcgcggtatc attgcagcac tggggccaga tggtaagccc tcccgtatcg   3240
tagttatcta cacgacgggg agtcaggcaa ctatggatga acgaaataga cagatcgctg   3300
agataggtgc ctcactgatt aagcattggt aactgtcaga ccaagtttac tcatatatac   3360
tttagattga tttaaaactt catttttaat ttaaaaggat ctaggtgaag atcctttttg   3420
ataatctcat gaccaaaatc ccttaacgtg agttttcgtt ccactgagcg tcagaccccg   3480
tagaaaagat caaaggatct tcttgagatc ctttttttct gcgcgtaatc tgctgcttgc   3540
aaacaaaaaa accaccgcta ccagcggtgg tttgtttgcc ggatcaagag ctaccaactc   3600
tttttccgaa ggtaactggc ttcagcagag cgcagatacc aaatactgtc cttctagtgt   3660
agccgtagtt aggccaccac ttcaagaact ctgtagcacc gcctacatac ctcgctctgc   3720
taatcctgtt accagtggct gctgccagtg gcgataagtc gtgtcttacc gggttggact   3780
caagacgata gttaccggat aaggcgcagc ggtcgggctg aacggggggt tcgtgcacac   3840
agcccagctt ggagcgaacg acctacaccg aactgagata cctacagcgt gagctatgag   3900
aaagcgccac gcttcccgaa gggagaaagg cggacaggta tccggtaagc ggcagggtcg   3960
gaacaggaga gcgcacgagg gagcttccag ggggaaacgc ctggtatctt tatagtcctg   4020
tcgggtttcg ccacctctga cttgagcgtc gatttttgtg atgctcgtca ggggggcgga   4080
gcctatggaa aaacgccagc aacgcggcct ttttacggtt cctggccttt tgctggcctt   4140
ttgctcacat gttctttcct gcgttatccc ctgattctgt ggataaccgt attaccgcct   4200
ttgagtgagc tgataccgct cgccgcagcc gaacgaccga gcgcagcgag tcagtgagcg   4260
aggaagcgga aga                                                      4273
```

<210> SEQ ID NO 40
<211> LENGTH: 7330
<212> TYPE: DNA
<213> ORGANISM: Artificial Sequence
<220> FEATURE:
<223> OTHER INFORMATION: Description of Artificial Sequence:
      vector pFPMT-CL-H6-K-E1
<220> FEATURE:
<221> NAME/KEY: misc_feature
<222> LOCATION: (1098)..(1099)
<223> OTHER INFORMATION: N is any nucleotide
<220> FEATURE:
<221> NAME/KEY: misc_feature -continued

```
<222> LOCATION: (1277)..(1278)
<223> OTHER INFORMATION: N is any nucleotide

<400> SEQUENCE: 40

ggtaccctgc tcaatctccg gaatggtgat ctgatcgttc ctgaaaacct cgacattggc     60

tccctcctga cacaggtact cgtacaggtt ccaggtaaac gagtcgtagt tgtcgatcat    120

gacaacgttc ttagaagcgg ccggcatttt gaaggtgact aatagcctaa gaaaatattt    180

aatttaattt tcattaaatt ttcctatact cgctatttca gcttttcatc tcatcacttc    240

ataaacgata taaaccagaa aaagaactat tttcaaacac gcttctcaaa agcggtatgt    300

ccttccacgt ctccttagaa tctggcaagt ccgcgagggg gatccttacc agttcatcat    360

catatcccaa gccatacggt gacctgttat gtggccggga tagattgagc aattgcagtc    420

ctgcaccgtc tcatgccggc gaggcgagat ggtgaacagc tgggagacga ggaagacaga    480

tccgcagaga tcccccacgt acatagcgga acagaaagca gccgccccaa cgagcaaatc    540

gacgtggcgt cgtattgtcg tagtggggac gctggcgttc ctagctgcga gcgtgggggt    600

gagcgctacc cagcagcggg aagagttgtt ctcccgaacg cagggcacgc acccgggggt    660

gtgcatgatc atgtccgctg cctcatacac aatgcttgag ttggagcagt cgttcgtgac    720

atggtacatc ccggacacgt tgcgcacctc atatttgtga tggtgatggt ggtgtcctag    780

tgctgctagt ggtaggaagc atagtactag tattagtagg cttcgcatga attcccgatg    840

aaggcagaga gcgcaaggag gcggtattta tagtgccatt cccctctctg agagacccgg    900

atggtagtcg agtgttatcg gagacagctt gatgtagact ccgtgcctgc cggtcctctt    960

attggcggac accagtgaga caccccggaa cttgctgttt ttctgcaaaa tccggggtga   1020

ccagtgggag cctatttgca cacacgagcg ggacacccca ctctggtgaa gagtgccaaa   1080

gtcattcttt ttcccgtnnc ggggcagccg attgcatgtt ttaggaaaat attacctttg   1140

ctacaccctg tcagatttac cctccacaca tatatattcc gtcacctcca gggactattc   1200

ttggctcgtt gcgccgccgc ggaagatatc cagaagctgt gttttccgag agactcggtt   1260

ggcgcctggt atatttnnag gatgtcgcgc tgcctcacgt cccggtaccc aggaacgcgg   1320

tgggatctcg ggcccatcga agactgtgct ccagactgct cgcccagcag gtgtttcttg   1380

attgccgcct ctaaatagtc cgcgcatcgc cggtaacatt tttccagctc ggagtttgcg   1440

tttagataca tttctgcgat gccaaaggag cctgcagatt ataacctcgg atgctgtcat   1500

tcagcgcttt taatttgacc tccagatagt tgctgtattt ctgttccatt ggctgctgga   1560

cgttcgtata actcgagtta ttgttgcgct ctgcctcggc gtactggctc atgactgact   1620

gcggtcgctt ctcgagtgtt ctcgcaacag gacgcctgca ggtcatcgag tcgagctggc   1680

gccgaaactg gcggatctga cctccacact gccctgtatc tctatccacc gggaaccgcc   1740

tcctgccgtt ccagaatgtt gttcaagtgg tagctctgtg cggtcaatga aggcgttatt   1800

gccggtgaaa tctttgggaa gcggtttatc ctcggggaag attacgaaat tcccgcgcgt   1860

cgttgcgctt cctggatctc gaggaagatc gttctccgcg tcgaggagat cgttctccgc   1920

gtcgacctgc aggcatgcaa gcttctggta aacgttgtag tactctgaaa caaggcccta   1980

gcactctgat ctgtttctct tgggtagcgg tgagtggttt attggagttc actggtttca   2040

gcacatctgt catctagaca atattgttac taaatttttt tgaactacaa ttgttcgtaa   2100

ttcatctatt attatacatc ctcgtcagca atttctggca gacggagttt actaacgtct   2160

tgagtatgag gccgagaatc cagctctgtg gccatactca gtcttgacag cctgctgatg   2220
```

-continued tggctgcgtt caacgcaata agcgtgtcct ccgactccga gttgtgctcg ttatcgtcgt 2280
tctcatcctc ggaaaaatca cacgaaagaa catactcacc agtaggcttt ctggtccctg 2340
gggcacggct gtttctgacg tattccggcg ttgataatag ctcgaaagtg aacgccgagt 2400
cgcgggagtc gaccgatgcc cttgagagcc ttcaacccag tcagctcctt ccggtgggcg 2460
cggggcatga ctatcgtcgc cgcacttatg actgtcttct ttatcatgca actcgtagga 2520
caggtgccgg cagcgctctg ggtcattttc ggcgaggacc gctttcgctg gagcgcgacg 2580
atgatcggcc tgtcgcttgc ggtattcgga atcttgcacg ccctcgctca agccttcgtc 2640
actggtcccg ccaccaaacg tttcggcgag aagcaggcca ttatcgccgg catggcggcc 2700
gacgcgctgg gctacgtctt gctggcgttc gcgacgcgag gctggatggc cttccccatt 2760
atgattcttc tcgcttccgg cggcatcggg atgcccgcgt tgcaggccat gctgtccagg 2820
caggtagatg acgaccatca gggacagctt caaggatcgc tcgcggctct taccagccta 2880
acttcgatca ctggaccgct gatcgtcacg gcgatttatg ccgcctcggc gagcacatgg 2940
aacgggttgg catggattgt aggcgccgcc ctataccttg tctgcctccc cgcgttgcgt 3000
cgcggtgcat ggagccgggc cacctcgacc tgaatggaag ccggcggcac ctcgctaacg 3060
gattcaccac tccaagaatt ggagccaatc aattcttgcg gagaactgtg aatgcgcaaa 3120
ccaacccttg gcagaacata tccatcgcgt ccgccatctc cagcagccgc acgcggcgca 3180
tcgggggggg gggggggggg ggggggcaaa caattcatca tttttttttt attctttttt 3240
ttgatttcgg tttctttgaa atttttttga ttcggtaatc tccgaacaga aggaagaacg 3300
aaggaaggag cacagactta gattggtata tatacgcata tgtagtgttg aagaaacatg 3360
aaattgccca gtattcttaa cccaactgca cagaacaaaa acctgcagga aacgaagata 3420
aatcatgtcg aaagctacat ataaggaacg tgctgctact catcctagtc ctgttgctgc 3480
caagctattt aatatcatgc acgaaaagca aacaaacttg tgtgcttcat tggatgttcg 3540
taccaccaag gaattactgg agttagttga agcattaggt cccaaaattt gtttactaaa 3600
aacacatgtg gatatcttga ctgatttttc catggagggc acagttaagc cgctaaaggc 3660
attatccgcc aagtacaatt ttttactctt cgaagacaga aaatttgctg acattggtaa 3720
tacagtcaaa ttgcagtact ctgcgggtgt atacagaata gcagaatggg cagacattac 3780
gaatgcacac ggtgtggtgg gcccaggtat tgttagcggt ttgaagcagg cggcagaaga 3840
agtaacaaag gaacctagag gccttttgat gttagcagaa ttgtcatgca agggctccct 3900
atctactgga gaatatacta agggtactgt tgacattgcg aagagcgaca aagattttgt 3960
tatcggcttt attgctcaaa gagacatggg tggaagagat gaaggttacg attggttgat 4020
tatgacaccc ggtgtgggtt tagatgacaa gggagacgca ttgggtcaac agtatagaac 4080
cgtggatgat gtggtctcta caggatctga cattattatt gttggaagag gactatttgc 4140
aaagggaagg gatgctaagg tagagggtga acgttacaga aaagcaggct gggaagcata 4200
tttgagaaga tgcggccagc aaaactaaaa aactgtatta taagtaaatg catgtatact 4260
aaactcacaa attagagctt caatttaatt atatcagtta ttacccggga atctcggtcg 4320
taatgatttt tataatgacg aaaaaaaaaa aattggaaag aaaagccccc cccccccccc 4380
cccccccccc cccccccccg cagcgttggg tcctggccac gggtgcgcat gatcgtgctc 4440
ctgtcgttga ggacccggct aggctggcgg ggttgcctta ctggttagca gaatgaatca 4500
ccgatacgcg agcgaacgtg aagcgactgc tgctgcaaaa cgtctgcgac ctgagcaaca 4560
acatgaatgg tcttcggttt ccgtgtttcg taaagtctgg aaacgcggaa gtcagcgccc 4620

-continued

```
tgcaccatta tgttccggat ctgcatcgca ggatgctgct ggctaccctg tggaacacct   4680
acatctgtat taacgaagcg ctggcattga ccctgagtga tttttctctg gtcccgccgc   4740
atccataccg ccagttgttt accctcacaa cgttccagta accgggcatg ttcatcatca   4800
gtaacccgta tcgtgagcat cctctctcgt ttcatcggta tcattacccc catgaacaga   4860
aattcccct tacacggagg catcaagtga ccaaacagga aaaaaccgcc cttaacatgg   4920
cccgctttat cagaagccag acattaacgc ttctggagaa actcaacgag ctggacgcgg   4980
atgaacaggc agacatctgt gaatcgcttc acgaccacgc tgatgagctt taccgcagct   5040
gcctcgcgcg tttcggtgat gacggtgaaa acctctgaca catgcagctc ccggagacgg   5100
tcacagcttg tctgtaagcg gatgccggga gcagacaagc ccgtcagggc gcgtcagcgg   5160
gtgttggcgg gtgtcggggc gcagccatga cccagtcacg tagcgatagc ggagtgtata   5220
ctggcttaac tatgcggcat cagagcagat tgtactgaga gtgcaccata tgcggtgtga   5280
aataccgcac agatgcgtaa ggagaaaata ccgcatcagg cgctcttccg cttcctcgct   5340
cactgactcg ctgcgctcgg tcgttcggct gcggcgagcg gtatcagctc actcaaaggc   5400
ggtaatacgg ttatccacag aatcagggga taacgcagga aagaacatgt gagcaaaagg   5460
ccagcaaaag gccaggaacc gtaaaaaggc cgcgttgctg gcgtttttcc ataggctccg   5520
cccccctgac gagcatcaca aaaatcgacg ctcaagtcag aggtggcgaa acccgacagg   5580
actataaaga taccaggcgt ttccccctgg aagctccctc gtgcgctctc ctgttccgac   5640
cctgccgctt accggatacc tgtccgcctt tctcccttcg ggaagcgtgg cgctttctca   5700
tagctcacgc tgtaggtatc tcagttcggt gtaggtcgtt cgctccaagc tgggctgtgt   5760
gcacgaaccc cccgttcagc ccgaccgctg cgccttatcc ggtaactatc gtcttgagtc   5820
caacccggta agacacgact tatcgccact ggcagcagcc actggtaaca ggattagcag   5880
agcgaggtat gtaggcggtg ctacagagtt cttgaagtgg tggcctaact acggctacac   5940
tagaaggaca gtatttggta tctgcgctct gctgaagcca gttaccttcg gaaaaagagt   6000
tggtagctct tgatccggca aacaaaccac cgctggtagc ggtggttttt ttgtttgcaa   6060
gcagcagatt acgcgcagaa aaaaaggatc tcaagaagat cctttgatct tttctacggg   6120
gtctgacgct cagtggaacg aaaactcacg ttaagggatt ttggtcatga gattatcaaa   6180
aaggatcttc acctagatcc ttttaaatta aaaatgaagt tttaaatcaa tctaaagtat   6240
atatgagtaa acttggtctg acagttacca atgcttaatc agtgaggcac ctatctcagc   6300
gatctgtcta tttcgttcat ccatagttgc ctgactcccc gtcgtgtaga taactacgat   6360
acgggagggc ttaccatctg gccccagtgc tgcaatgata ccgcgagacc cacgctcacc   6420
ggctccagat ttatcagcaa taaaccagcc agccggaagg gccgagcgca gaagtggtcc   6480
tgcaacttta tccgcctcca tccagtctat taattgttgc cgggaagcta gagtaagtag   6540
ttcgccagtt aatagtttgc gcaacgttgt tgccattgct gcaggcatcg tggtgtcacg   6600
ctcgtcgttt ggtatggctt cattcagctc cggttcccaa cgatcaaggc gagttacatg   6660
atcccccatg ttgtgcaaaa aagcggttag ctccttcggt cctccgatcg ttgtcagaag   6720
taagttggcc gcagtgttat cactcatggt tatggcagca ctgcataatt ctcttactgt   6780
catgccatcc gtaagatgct tttctgtgac tggtgagtac tcaaccaagt cattctgaga   6840
atagtgtatg cggcgaccga gttgctcttg cccggcgtca acacgggata ataccgcgcc   6900
acatagcaga actttaaaag tgctcatcat tggaaaacgt tcttcggggc gaaaactctc   6960
```

-continued

```
aaggatctta ccgctgttga gatccagttc gatgtaaccc actcgtgcac ccaactgatc   7020

ttcagcatct tttactttca ccagcgtttc tgggtgagca aaaacaggaa ggcaaaatgc   7080

cgcaaaaaag ggaataaggg cgacacggaa atgttgaata ctcatactct tcctttttca   7140

atattattga agcatttatc agggttattg tctcatgagc ggatacatat ttgaatgtat   7200

ttagaaaaat aaacaaatag gggttccgcg cacatttccc cgaaaagtgc cacctgacgt   7260

ctaagaaacc attattatca tgacattaac ctataaaaat aggcgtatca cgaggccctt   7320

tcgtcttcaa                                                          7330
```

<210> SEQ ID NO 41
<211> LENGTH: 5202
<212> TYPE: DNA
<213> ORGANISM: Artificial Sequence
<220> FEATURE:
<223> OTHER INFORMATION: Description of Artificial Sequence: vector pYIG5

<400> SEQUENCE: 41

```
agcgcccaat acgcaaaccg cctctccccg cgcgttggcc gattcattaa tgcagctggc     60

acgacaggtt tcccgactgg aaagcgggca gtgagcgcaa cgcaattaat gtgagttagc    120

tcactcatta ggcaccccag gctttacact ttatgcttcc ggctcgtatg ttgtgtggaa    180

ttgtgagcgg ataacaattt cacacaggaa acagctatga ccatgattac gaatttaata    240

cgactcacta tagggaattc gaggatcctt caatatgcgc acatacgctg ttatgttcaa    300

ggtcccttcg tttaagaacg aaagcggtct tccttttgag ggatgtttca agttgttcaa    360

atctatcaaa tttgcaaatc cccagtctgt atctagagcg ttgaatcggt gatgcgattt    420

gttaattaaa ttgatggtgt caccattacc aggtctagat ataccaatgg caaactgagc    480

acaacaatac cagtccggat caactggcac catctctccc gtagtctcat ctaatttttc    540

ttccggatga ggttccagat ataccgcaac acctttatta tggtttccct gagggaataa    600

tagaatgtcc cattcgaaat caccaattct aaacctgggc gaattgtatt tcgggtttgt    660

taactcgttc cagtcaggaa tgttccacgt gaagctatct tccagcaaag tctccacttc    720

ttcatcaaat tgtggagaat actcccaatg ctcttatcta tgggacttcc gggaaacaca    780

gtaccgatac ttcccaattc gtcttcagag ctcattgttt gtttgaagag actaatcaaa    840

gaatcgtttt ctcaaaaaaa ttaatatctt aactgatagt ttgatcaaag ggcaaaacg    900

taggggcaaa caaacggaaa aatcgtttct caaattttct gatgccaaga actctaacca    960

gtcttatcta aaaattgcct tatgatccgt ctctccggtt acagcctgtg taactgatta   1020

atcctgcctt tctaatcacc attctaatgt tttaattaag ggattttgtc ttcattaacg   1080

gctttcgctc ataaaaatgt tatgacgttt tgcccgcagg cgggaaacca tccacttcac   1140

gagactgatc tcctctgccg gaacaccggg catctccaac ttataagttg gagaaataag   1200

agaatttcag attgagagaa tgaaaaaaaa aaaccctgaa aaaaaaggtt gaaaccagtt   1260

ccctgaaatt attcccctac ttgactaata agtatataaa gacggtaggt attgattgta   1320

attctgtaaa tctatttctt aaacttctta aattctactt ttatagttag tcttttttttt   1380

agttttaaaa caccaagaac ttagtttcga ataaacacac ataaacaaac accatgagat   1440

ttccttcaat tttactgca gttttattcg cagcatcctc cgcattagct gctccagtca   1500

acactacaac agaagatgaa acggcacaaa ttccggctga agctgtcatc ggttactcag   1560

atttagaagg ggatttcgat gttgctgttt tgccattttc caacagcaca aataacgggt   1620

tattgtttat aaatactact attgccagca ttgctgctaa agaagaaggg gtatctctag   1680
```

-continued

```
ataaaaggcc tgtcgacggt accagatctc gacttggttg aacacgttgc caaggcttaa   1740
gtgaatttac tttaaagtct tgcatttaaa taaattttct ttttatagct ttatgactta   1800
gtttcaattt atatactatt ttaatgacat tttcgattca ttgattgaaa gctttgtgtt   1860
ttttcttgat gcgctattgc attgttcttg tctttttcgc cacatgtaat atctgtagta   1920
gatacctgat acattgtgga tgctgagtga aattttagtt aataatggag gcgctcttaa   1980
taattttggg gatattggct ttttttttta aagtttacaa atgaattttt tccgccagga   2040
taacgattct gaagttactc ttagcgttcc tatcggtaca gccatcaaat catgcctata   2100
aatcatgcct atatttgcgt gcagtcagta tcatctacat gaaaaaaact cccgcaattt   2160
cttatagaat acgttgaaaa ttaaatgtac gcgccaagat aagataacat atatctagct   2220
agatgcagta atatacacag attcccgcgg acgtgggaag gaaaaaatta gataacaaaa   2280
tctgagtgat atggaaattc cgctgtatag ctcatatctt tcccttcaac accagaaatg   2340
taaaaatctt gttacgaagg atctttttgc taatgtttct cgctcaatcc tcatttcttc   2400
cctacgaaga gtcaaatcta cttgttttct gccggtatca agatccatat cttctagttt   2460
caccatcaaa gtccaatttc tagtatacag tttatgtccc aacgtaacag acaatcaaaa   2520
ttggaaagga taagtatcct tcaaagaatg attctgcgct ggctcctgaa ccgcctaatg   2580
ggaacagaga agtccaaaac gatgctataa gaaccagaaa taaaacgata aaaccatacc   2640
aggatccaag cttggcactg gccgtcgttt tacaacgtcg tgactgggaa aaccctggcg   2700
ttacccaact taatcgcctt gcagcacatc cccctttcgc cagctggcgt aatagcgaag   2760
aggcccgcac cgatcgccct tcccaacagt tgcgcagcct gaatggcgaa tgggaaattg   2820
taaacgttaa tattttgtta aaattcgcgt taaatttttg ttaaatcagc tcatttttta   2880
accaataggc cgaaatcggc aaaatccctt ataaatcaaa agaatagacc gagatagggt   2940
tgagtgttgt tccagtttgg aacaagagtc cactattaaa gaacgtggac tccaacgtca   3000
aagggcgaaa aaccgtctat cagggcgatg gcccactacg tgaaccatca ccctaatcaa   3060
gtttttgggg gtcgaggtgc cgtaaagcac taaatcggaa ccctaaaggg agcccccgat   3120
ttagagcttg acggggaaag ccggcgaacg tggcgagaaa ggaagggaag aaagcgaaag   3180
gagcgggcgc tagggcgctg gcaagtgtag cggtcacgct gcgcgtaacc accacacccg   3240
ccgcgcttaa tgcgccgcta cagggcgcgt caggtggcac ttttcgggga aatgtgcgcg   3300
gaacccctat ttgtttattt ttctaaatac attcaaatat gtatccgctc atgagacaat   3360
aaccctgata aatgcttcaa taatattgaa aaaggaagag tatgagtatt caacatttcc   3420
gtgtcgccct tattcccttt tttgcggcat tttgccttcc tgtttttgct cacccagaaa   3480
cgctggtgaa agtaaaagat gctgaagatc agttgggtgc acgagtgggt tacatcgaac   3540
tggatctcaa cagcggtaag atccttgaga gttttcgccc cgaagaacgt tttccaatga   3600
tgagcacttt taaagttctg ctatgtggcg cggtattatc ccgtattgac gccgggcaag   3660
agcaactcgg tcgccgcata cactattctc agaatgactt ggttgagtac tcaccagtca   3720
cagaaaagca tcttacggat ggcatgacag taagagaatt atgcagtgct gccataacca   3780
tgagtgataa cactgcggcc aacttacttc tgacaacgat cggaggaccg aaggagctaa   3840
ccgctttttt gcacaacatg ggggatcatg taactcgcct tgatcgttgg gaaccggagc   3900
tgaatgaagc cataccaaac gacgagcgtg acaccacgat gcctgtagca atggcaacaa   3960
cgttgcgcaa actattaact ggcgaactac ttactctagc ttcccggcaa caattaatag   4020
```

-continued

```
actggatgga ggcggataaa gttgcaggac cacttctgcg ctcggccctt ccggctggct   4080

ggtttattgc tgataaatct ggagccggtg agcgtgggtc tcgcggtatc attgcagcac   4140

tggggccaga tggtaagccc tcccgtatcg tagttatcta cacgacgggg agtcaggcaa   4200

ctatggatga acgaaataga cagatcgctg agataggtgc ctcactgatt aagcattggt   4260

aactgtcaga ccaagtttac tcatatatac tttagattga tttaaaactt catttttaat   4320

ttaaaaggat ctaggtgaag atcctttttg ataatctcat gaccaaaatc ccttaacgtg   4380

agttttcgtt ccactgagcg tcagaccccg tagaaaagat caaaggatct tcttgagatc   4440

cttttttct gcgcgtaatc tgctgcttgc aaacaaaaaa accaccgcta ccagcggtgg   4500

tttgtttgcc ggatcaagag ctaccaactc tttttccgaa ggtaactggc ttcagcagag   4560

cgcagatacc aaatactgtc cttctagtgt agccgtagtt aggccaccac ttcaagaact   4620

ctgtagcacc gcctacatac ctcgctctgc taatcctgtt accagtggct gctgccagtg   4680

gcgataagtc gtgtcttacc gggttggact caagacgata gttaccggat aaggcgcagc   4740

ggtcgggctg aacggggggt tcgtgcacac agcccagctt ggagcgaacg acctacaccg   4800

aactgagata cctacagcgt gagcattgag aaagcgccac gcttcccgaa gggagaaagg   4860

cggacaggta tccggtaagc ggcagggtcg gaacaggaga gcgcacgagg gagcttccag   4920

ggggaaacgc ctggtatctt tatagtcctg tcgggtttcg ccacctctga cttgagcgtc   4980

gatttttgtg atgctcgtca ggggggcgga gcctatggaa aaacgccagc aacgcggcct   5040

ttttacggtt cctggccttt tgctggcctt ttgctcacat gttctttcct gcgttatccc   5100

ctgattctgt ggataaccgt attaccgcct ttgagtgagc tgataccgct cgccgcagcc   5160

gaacgaccga gcgcagcgag tcagtgagcg aggaagcgga ag                      5202
```

```
<210> SEQ ID NO 42
<211> LENGTH: 5613
<212> TYPE: DNA
<213> ORGANISM: Artificial Sequence
<220> FEATURE:
<223> OTHER INFORMATION: Description of Artificial Sequence:
      vector pYIG5E1H6

<400> SEQUENCE: 42
```

```
ggatccttca atatgcgcac atacgctgtt atgttcaagg tcccttcgtt taagaacgaa     60

agcggtcttc cttttgaggg atgtttcaag ttgttcaaat ctatcaaatt tgcaaatccc    120

cagtctgtat ctagagcgtt gaatcggtga tgcgatttgt taattaaatt gatggtgtca    180

ccattaccag gtctagatat accaatggca aactgagcac aacaatacca gtccggatca    240

actggcacca tctctcccgt agtctcatct aatttttctt ccggatgagg ttccagatat    300

accgcaacac ctttattatg gtttccctga gggaataata gaatgtccca ttcgaaatca    360

ccaattctaa acctgggcga attgtatttc gggtttgtta actcgttcca gtcaggaatg    420

ttccacgtga agctatcttc cagcaaagtc tccacttctt catcaaattg tggagaatac    480

tcccaatgct cttatctatg ggacttccgg gaaacacagt accgatactt cccaattcgt    540

cttcagagct cattgtttgt ttgaagagac taatcaaaga atcgttttct caaaaaaatt    600

aatatcttaa ctgatagttt gatcaaaggg gcaaaacgta ggggcaaaca aacggaaaaa    660

tcgtttctca aattttctga tgccaagaac tctaaccagt cttatctaaa aattgcctta    720

tgatccgtct ctccggttac agcctgtgta actgattaat cctgcctttc taatcaccat    780

tctaatgttt taattaaggg attttgtctt cattaacggc tttcgctcat aaaaatgtta    840
```

-continued

```
tgacgttttg cccgcaggcg ggaaaccatc cacttcacga gactgatctc ctctgccgga    900
acaccgggca tctccaactt ataagttgga gaaataagag aatttcagat tgagagaatg    960
aaaaaaaaaa accctgaaaa aaaaggttga aaccagttcc ctgaaattat tcccctactt   1020
gactaataag tatataaaga cggtaggtat tgattgtaat tctgtaaatc tatttcttaa   1080
acttcttaaa ttctactttt atagttagtc tttttttag ttttaaaaca ccaagaactt   1140
agtttcgaat aaacacacat aaacaaacac catgagattt ccttcaattt ttactgcagt   1200
tttattcgca gcatcctccg cattagctgc tccagtcaac actacaacag aagatgaaac   1260
ggcacaaatt ccggctgaag ctgtcatcgg ttacttagat ttagaagggg atttcgatgt   1320
tgctgttttg ccattttcca acagcacaaa taacgggtta ttgtttataa atactactat   1380
tgccagcatt gctgctaaag aagaaggggt atctctagat aaaaggtatg aggtgcgcaa   1440
cgtgtccggg atgtaccatg tcacgaacga ctgctccaac tcaagcattg tgtatgaggc   1500
agcggacatg atcatgcaca cccccgggtg cgtgccctgc gttcgggaga acaactcttc   1560
ccgctgctgg gtagcgctca cccccacgct cgcagctagg aacgccagcg tccccactac   1620
gacaatacga cgccacgtcg atttgctcgt tggggcggct gctttctgtt ccgctatgta   1680
cgtgggggat ctctgcggat ctgtcttcct cgtctcccag ctgttcacca tctcgcctcg   1740
ccggcatgag acggtgcagg actgcaattg ctcaatctat cccggccaca taacaggtca   1800
ccgtatggct tgggatatga tgatgaactg gcaccaccac catcaccatt aaagatctcg   1860
acttggttga acacgttgcc aaggcttaag tgaatttact ttaaagtctt gcatttaaat   1920
aaattttctt tttatagctt tatgacttag tttcaattta tatactattt taatgacatt   1980
ttcgattcat tgattgaaag ctttgtgttt tttcttgatg cgctattgca ttgttcttgt   2040
ctttttcgcc acatgtaata tctgtagtag atacctgata cattgtggat gctgagtgaa   2100
attttagtta ataatggagg cgctcttaat aattttgggg atattggctt ttttttttaa   2160
agtttacaaa tgaatttttt ccgccaggat aacgattctg aagttactct tagcgttcct   2220
atcggtacag ccatcaaatc atgcctataa atcatgccta tatttgcgtg cagtcagtat   2280
catctacatg aaaaaaactc ccgcaatttc ttatagaata cgttgaaaat taaatgtacg   2340
cgccaagata agataacata tatctagcta gatgcagtaa tatacacaga ttcccgcgga   2400
cgtgggaagg aaaaaattag ataacaaaat ctgagtgata tggaaattcc gctgtatagc   2460
tcatatcttt cccttcaaca ccagaaatgt aaaaatcttg ttacgaagga tctttttgct   2520
aatgtttctc gctcaatcct catttcttcc ctacgaagag tcaaatctac ttgttttctg   2580
ccggtatcaa gatccatatc ttctagtttc accatcaaag tccaatttct agtatacagt   2640
ttatgtccca acgtaacaga caatcaaaat tggaaaggat aagtatcctt caaagaatga   2700
ttctgcgctg gctcctgaac cgcctaatgg gaacagagaa gtccaaaacg atgctataag   2760
aaccagaaat aaaacgataa aaccatacca ggatccaagc ttggcactgg ccgtcgtttt   2820
acaacgtcgt gactgggaaa accctggcgt tacccaactt aatcgccttg cagcacatcc   2880
ccctttcgcc agctggcgta atagcgaaga ggcccgcacc gatcgccctt cccaacagtt   2940
gcgcagcctg aatggcgaat gggaaattgt aaacgttaat attttgttaa aattcgcgtt   3000
aaatttttgt taaatcagct cattttttaa ccaataggcc gaaatcggca aaatccctta   3060
taaatcaaaa gaatagaccg agatagggtt gagtgttgtt ccagtttgga acaagagtcc   3120
actattaaag aacgtggact ccaacgtcaa agggcgaaaa accgtctatc agggcgatgg   3180
cccactacgt gaaccatcac cctaatcaag ttttttgggg tcgaggtgcc gtaaagcact   3240
```

-continued

```
aaatcggaac cctaaaggga gcccccgatt tagagcttga cggggaaagc cggcgaacgt   3300
ggcgagaaag gaagggaaga aagcgaaagg agcgggcgct agggcgctgg caagtgtagc   3360
ggtcacgctg cgcgtaacca ccacacccgc cgcgcttaat gcgccgctac agggcgcgtc   3420
aggtggcact tttcggggaa atgtgcgcgg aacccctatt tgtttatttt tctaaataca   3480
ttcaaatatg tatccgctca tgagacaata accctgataa atgcttcaat aatattgaaa   3540
aaggaagagt atgagtattc aacatttccg tgtcgccctt attccctttt ttgcggcatt   3600
ttgccttcct gtttttgctc acccagaaac gctggtgaaa gtaaaagatg ctgaagatca   3660
gttgggtgca cgagtgggtt acatcgaact ggatctcaac agcggtaaga tccttgagag   3720
ttttcgcccc gaagaacgtt ttccaatgat gagcactttt aaagttctgc tatgtggcgc   3780
ggtattatcc cgtattgacg ccgggcaaga gcaactcggt cgccgcatac actattctca   3840
gaatgacttg gttgagtact caccagtcac agaaaagcat cttacggatg gcatgacagt   3900
aagagaatta tgcagtgctg ccataaccat gagtgataac actgcggcca acttacttct   3960
gacaacgatc ggaggaccga aggagctaac cgcttttttg cacaacatgg gggatcatgt   4020
aactcgcctt gatcgttggg aaccggagct gaatgaagcc ataccaaacg acgagcgtga   4080
caccacgatg cctgtagcaa tggcaacaac gttgcgcaaa ctattaactg gcgaactact   4140
tactctagct tcccggcaac aattaataga ctggatggag gcggataaag ttgcaggacc   4200
acttctgcgc tcggcccttc cggctggctg gtttattgct gataaatctg gagccggtga   4260
gcgtgggtct cgcggtatca ttgcagcact ggggccagat ggtaagccct cccgtatcgt   4320
agttatctac acgacgggga gtcaggcaac tatggatgaa cgaaatagac agatcgctga   4380
gataggtgcc tcactgatta agcattggta actgtcagac caagtttact catatatact   4440
ttagattgat ttaaaacttc atttttaatt taaaaggatc taggtgaaga tcctttttga   4500
taatctcatg accaaaatcc cttaacgtga gttttcgttc cactgagcgt cagaccccgt   4560
agaaaagatc aaaggatctt cttgagatcc tttttttctg cgcgtaatct gctgcttgca   4620
aacaaaaaaa ccaccgctac cagcggtggt ttgtttgccg gatcaagagc taccaactct   4680
ttttccgaag gtaactggct tcagcagagc gcagatacca aatactgtcc ttctagtgta   4740
gccgtagtta ggccaccact tcaagaactc tgtagcaccg cctacatacc tcgctctgct   4800
aatcctgtta ccagtggctg ctgccagtgg cgataagtcg tgtcttaccg ggttggactc   4860
aagacgatag ttaccggata aggcgcagcg gtcgggctga acggggggtt cgtgcacaca   4920
gcccagcttg gagcgaacga cctacaccga actgagatac ctacagcgtg agcattgaga   4980
aagcgccacg cttcccgaag ggagaaaggc ggacaggtat ccggtaagcg gcagggtcgg   5040
aacaggagag cgcacgaggg agcttccagg gggaaacgcc tggtatcttt atagtcctgt   5100
cgggtttcgc cacctctgac ttgagcgtcg atttttgtga tgctcgtcag gggggcggag   5160
cctatggaaa aacgccagca acgcggcctt tttacggttc ctggcctttt gctggccttt   5220
tgctcacatg ttctttcctg cgttatcccc tgattctgtg gataaccgta ttaccgcctt   5280
tgagtgagct gataccgctc gccgcagccg aacgaccgag cgcagcgagt cagtgagcga   5340
ggaagcggaa gagcgcccaa tacgcaaacc gcctctcccc gcgcgttggc cgattcatta   5400
atgcagctgg cacgacaggt ttcccgactg gaaagcgggc agtgagcgca acgcaattaa   5460
tgtgagttag ctcactcatt aggcacccca ggctttacac tttatgcttc cggctcgtat   5520
gttgtgtgga attgtgagcg gataacaatt tcacacagga aacagctatg accatgatta   5580
```

-continued

```
cgaatttaat acgactcact atagggaatt cga                              5613


<210> SEQ ID NO 43
<211> LENGTH: 13020
<212> TYPE: DNA
<213> ORGANISM: Artificial Sequence
<220> FEATURE:
<223> OTHER INFORMATION: Description of Artificial Sequence:
      vector pSY1

<400> SEQUENCE: 43

atcgataagc ttttcaattc aattcatcat ttttttttta ttcttttttt tgatttcggt     60

ttctttgaaa tttttttgat tcggtaatct ccgaacagaa ggaagaacga aggaaggagc    120

acagacttag attggtatat atacgcatat gtagtgttga agaaacatga aattgcccag    180

tattcttaac ccaactgcac agaacaaaaa cctgcaggaa acgaagataa atcatgtcga    240

aagctacata taaggaacgt gctgctactc atcctagtcc tgttgctgcc aagctattta    300

atatcatgca cgaaaagcaa acaaacttgt gtgcttcatt ggatgttcgt accaccaagg    360

aattactgga gttagttgaa gcattaggtc ccaaaatttg tttactaaaa acacatgtgg    420

atatcttgac tgatttttcc atggagggca cagttaagcc gctaaaggca ttatccgcca    480

agtacaattt tttactcttc gaagacagaa aatttgctga cattggtaat acagtcaaat    540

tgcagtactc tgcgggtgta tacagaatag cagaatgggc agacattacg aatgcacacg    600

gtgtggtggg cccaggtatt gttagcggtt tgaagcaggc ggcagaagaa gtaacaaagg    660

aacctagagg cctttgatg ttagcagaat tgtcatgcaa gggctcccta tctactggag     720

aatatactaa gggtactgtt gacattgcga agagcgacaa agattttgtt atcggcttta    780

ttgctcaaag agacatgggt ggaagagatg aaggttacga ttggttgatt atgacacccg    840

gtgtgggttt agatgacaag ggagacgcat tgggtcaaca gtatagaacc gtggatgatg    900

tggtctctac aggatctgac attattattg ttggaagagg actatttgca aagggaaggg    960

atgctaaggt agagggtgaa cgttacagaa aagcaggctg ggaagcatat ttgagaagat   1020

gcggccagca aaactaaaaa actgtattat aagtaaatgc atgtatacta aactcacaaa   1080

ttagagcttc aatttaatta tatcagttat tacccgggaa tctcggtcgt aatgattttt   1140

ataatgacga aaaaaaaaaa attggaaaga aaaagcttta atgcggtagt ttatcacagt   1200

taaattgcta acgcagtcag gcaccgtgta tgaaatctaa caatgcgctc atcgtcatcc   1260

tcggcaccgt caccctggat gctgtaggca taggcttggt tatgccggta ctgccgggcc   1320

tcttgcggga tatcgtccat tccgacagca tcgccagtca ctatggcgtg ctgctagcgc   1380

tatatgcgtt gatgcaattt ctatgcgcac ccgttctcgg agcactgtcc gaccgctttg   1440

gccgccgccc agtcctgctc gcttcgctac ttggagccac tatcgactac gcgatcatgg   1500

cgaccacacc cgtcctgtgg atcctctacg ccggacgcat cgtggccggc atcaccggcg   1560

ccacaggtgc ggttgctggc ccctatatcg ccgacatcac cgatggggaa gatcgggctc   1620

gccacttcgg gctcatgagc gcttgtttcg gcgtgggtat ggtggcaggc cccgtggccg   1680

ggggactgtt gggcgccatc tccttgcatg caccattcct tgcggcggcg gtgctcaacg   1740

gcctcaacct actactgggc tgcttcctaa tgcaggagtc gcataaggga gagcgtcgac   1800

cgatgccctt gagagccttc aacccagtca gctccttccg gtgggcgcgg ggcatgacta   1860

tcgtcgccgc acttatgact gtcttcttta tcatgcaact cgtaggacag gtgccggcag   1920

cgctctgggt cattttcggc gaggaccgct ttcgctggag cgcgacgatg atcggcctgt   1980
```

-continued

```
cgcttgcggt attcggaatc ttgcacgccc tcgctcaagc cttcgtcact ggtcccgcca   2040
ccaaacgttt cggcgagaag caggccatta tcgccggcat ggcggccgac gcgctgggct   2100
acgtcttgct ggcgttcgcg acgcgaggct ggatggcctt ccccattatg attcttctcg   2160
cttccggcgg catcgggatg cccgcgttgc aggccatgct gtccaggcag gtagatgacg   2220
accatcaggg acagcttcaa ggatcgctcg cggctcttac cagcctaact tcgatcactg   2280
gaccgctgat cgtcacggcg atttatgccg cctcggcgag cacatggaac gggttggcat   2340
ggattgtagg cgccgcccta taccttgtct gcctccccgc gttgcgtcgc ggtgcatgga   2400
gccgggccac ctcgacctga atggaagccg gcggcacctc gctaacggat tcaccactcc   2460
aagaattgga gccaatcaat tcttgcggag aactgtgaat gcgcaaacca acccttggca   2520
gaacatatcc atcgcgtccg ccatctccag cagccgcacg cggcgcatct cgggcagcgt   2580
tgggtcctgg ccacgggtgc gcatgatcgt gctcctgtcg ttgaggaccc ggctaggctg   2640
gcggggttgc cttactggtt agcagaatga atcaccgata cgcgagcgaa cgtgaagcga   2700
ctgctgctgc aaaacgtctg cgacctgagc aacaacatga atggtcttcg gtttccgtgt   2760
ttcgtaaagt ctggaaacgc ggaagtcagc gccctgcacc attatgttcc ggatctgcat   2820
cgcaggatgc tgctggctac cctgtggaac acctacatct gtattaacga agcgctggca   2880
ttgaccctga gtgatttttc tctggtcccg ccgcatccat accgccagtt gtttaccctc   2940
acaacgttcc agtaaccggg catgttcatc atcagtaacc cgtatcgtga gcatcctctc   3000
tcgtttcatc ggtatcatta cccccatgaa cagaaattcc cccttacacg gaggcatcaa   3060
gtgaccaaac aggaaaaaac cgcccttaac atggcccgct ttatcagaag ccagacatta   3120
acgcttctgg agaaactcaa cgagctggac gcggatgaac aggcagacat ctgtgaatcg   3180
cttcacgacc acgctgatga gctttaccgc agctgcctcg cgcgtttcgg tgatgacggt   3240
gaaaacctct gacacatgca gctcccggag acggtcacag cttgtctgta agcggtgccg   3300
ggagcagaca agcccgtcag ggcgcgtcag cgggtgttgg cgggtgtcgg ggcgcagcca   3360
tgacccagtc acgtagcgat agcggagtgt atactggctt aactatgcgg catcagagca   3420
gattgtactg agagtgcacc atatgcggtg tgaaataccg cacagatgcg taaggagaaa   3480
ataccgcatc aggcgctctt ccgcttcctc gctcactgac tcgctgcgct cggtcgttcg   3540
gctgcggcga gcggtatcag ctcactcaaa ggcggtaata cggttatcca cagaatcagg   3600
ggataacgca ggaaagaaca tgtgagcaaa aggccagcaa aaggccagga accgtaaaaa   3660
ggccgcgttg ctggcgtttt tccataggct ccgcccccct gacgagcatc acaaaaatcg   3720
acgctcaagt cagaggtggc gaaacccgac aggactataa agataccagg cgtttccccc   3780
tggaagctcc ctcgtgcgct ctcctgttcc gaccctgccg cttaccggat acctgtccgc   3840
ctttctccct tcgggaagcg tggcgctttc tcatagctca cgctgtaggt atctcagttc   3900
ggtgtaggtc gttcgctcca agctgggctg tgtgcacgaa ccccccgttc agcccgaccg   3960
ctgcgcctta tccggtaact atcgtcttga gtccaacccg gtaagacacg acttatcgcc   4020
actggcagca gccactggta acaggattag cagagcgagg tatgtaggcg gtgctacaga   4080
gttcttgaag tggtggccta actacggcta cactagaagg acagtatttg gtatctgcgc   4140
tctgctgaag ccagttacct tcggaaaaag agttggtagc tcttgatccg gcaaacaaac   4200
caccgctggt agcggtggtt tttttgtttg caagcagcag attacgcgca gaaaaaaagg   4260
atctcaagaa gatcctttga tcttttctac ggggtctgac gctcagtgga acgaaaactc   4320
acgttaaggg attttggtca tgagattatc aaaaaggatc ttcacctaga tccttttaaa   4380
```

-continued ttaaaaatga agttttaaat caatctaaag tatatatgag taaacttggt ctgacagtta 4440
ccaatgctta atcagtgagg cacctatctc agcgatctgt ctatttcgtt catccatagt 4500
tgcctgactc cccgtcgtgt agataactac gatacgggag ggcttaccat ctggccccag 4560
tgctgcaatg ataccgcgag acccacgctc accggctcca gatttatcag caataaacca 4620
gccagccgga agggccgagc gcagaagtgg tcctgcaact ttatccgcct ccatccagtc 4680
tattaattgt tgccgggaag ctagagtaag tagttcgcca gttaatagtt tgcgcaacgt 4740
tgttgccatt gctgcaggca tcgtggtgtc acgctcgtcg tttggtatgg cttcattcag 4800
ctccggttcc caacgatcaa ggcgagttac atgatccccc atgttgtgca aaaaagcggt 4860
tagctccttc ggtcctccga tcgttgtcag aagtaagttg gccgcagtgt tatcactcat 4920
ggttatggca gcactgcata attctcttac tgtcatgcca tccgtaagat gcttttctgt 4980
gactggtgag tactcaacca agtcattctg agaatagtgt atgcggcgac cgagttgctc 5040
ttgcccggcg tcaacacggg ataataccgc gccacatagc agaactttaa aagtgctcat 5100
cattggaaaa cgttcttcgg ggcgaaaact ctcaaggatc ttaccgctgt tgagatccag 5160
ttcgatgtaa cccactcgtg cacccaactg atcttcagca tcttttactt tcaccagcgt 5220
ttctgggtga gcaaaaacag gaaggcaaaa tgccgcaaaa aagggaataa gggcgacacg 5280
gaaatgttga atactcatac tcttcctttt tcaatattat tgaagcattt atcagggtta 5340
ttgtctcatg agcggataca tatttgaatg tatttagaaa aataaacaaa taggggttcc 5400
gcgcacattt ccccgaaaag tgccacctga cgtctaagaa accattatta tcatgacatt 5460
aacctataaa aataggcgt atcacgaggc cctttcgtct tcaagaattc tcatgtttga 5520
cagcttatca tcgatccact tgtatatttg gatgaatttt tgaggaattc tgaaccagtc 5580
ctaaaacgag taaataggac cggcaattct tcaagcaata aacaggaata ccaattatta 5640
aaagataact tagtcagatc gtacaataaa gctttgaaga aaaatgcgcc ttattcaatc 5700
tttgcataaa aaaatggccc aaaatctcac attggaagac atttgatgac ctcatttctt 5760
tcaatgaagg gcctaacgga gttgactaat gttgtgggaa attggaccga taagcgtgct 5820
tctgccgtgg ccaggacaac gtatactcat cagataacag caatacctga tcactacttc 5880
gcactagttt ctcggtacta tgcatatgat ccaatatcaa aggaaatgat agcattgaag 5940
gatgagacta atccaattga ggagtggcag catatagaac agctaaaggg tagtgctgaa 6000
ggaagcatac gataccccgc atggaatggg ataatatcac aggaggtact agactacctt 6060
tcatcctaca taaatagacg catataagta cgcatttaag cataaacacg cactatgccg 6120
ttcttctcat gtatatatat atacaggcaa cacgcagata taggtgcgac gtgaacagtg 6180
agctgtatgt gcgcagctcg cgttgcattt tcggaagcgc tcgttttcgg aaacgctttg 6240
aagttcctat tccgaagttc ctattctcta gaaagtatag gaacttcaga gcgcttttga 6300
aaaccaaaag cgctctgaag acgcactttc aaaaaaccaa aaacgcaccg gactgtaacg 6360
agctactaaa atattgcgaa taccgcttcc acaaacattg ctcaaaagta tctctttgct 6420
atatatctct gtgctatatc cctatataac catcccatcc acctttcgct ccttgaactt 6480
gcatctaaac tcgacctcta catttttat gtttatctct agtattacct cttagacaaa 6540
aaaattgtag taagaactat tcatagagtt aatcgaaaac aatacgaaaa tgtaaacatt 6600
tcctatacgt agtatataga gacaaaatag aagaaaccgt tcataatttt ctgaccaatg 6660
aagaatcatc aacgctatca ctttctgttc acaaagtatg cgcaatccac atcggtatag 6720

-continued

```
aatataatcg gggatgcctt tatcttgaaa aaatgcaccc gcagcttcgc tagtaatcag   6780
taaacgcggg aagtggagtc aggctttttt tatggaagag aaaatagaca ccaaagtagc   6840
cttcttctaa ccttaacgga cctacagtgc aaaaagttat caagagactg cattatagag   6900
cgcacaaagg agaaaaaaag taatctaaga tgctttgtta gaaaaatagc gctctcggga   6960
tgcatttttg tagaacaaaa aagaagtata gattcttgtt ggtaaaatag cgctctcgcg   7020
ttgcatttct gttctgtaaa aatgcagctc agattctttg tttgaaaaat tagcgctctc   7080
gcgttgcatt tttgttttac aaaaatgaag cacagattct tcgttggtaa aatagcgctt   7140
tcgcgttgca tttctgttct gtaaaaatgc agctcagatt ctttgtttga aaaattagcg   7200
ctctcgcgtt gcatttttgt tctacaaaat gaagcacaga tgcttcgtta acaaagatat   7260
gctattgaag tgcaagatgg aaacgcagaa aatgaaccgg ggatgcgacg tgcaagatta   7320
cctatgcaat agatgcaata gtttctccag gaaccgaaat acatacattg tcttccgtaa   7380
agcgctagac tatatattat tatacaggtt caaatatact atctgtttca gggaaaactc   7440
ccaggttcgg atgttcaaaa ttcaatgatg ggtaacaagt acgatcgtaa atctgtaaaa   7500
cagtttgtcg gatattaggc tgtatctcct caaagcgtat tcgaatatca ttgagaagct   7560
gcattttttt tttttttttt tttttttttt tttttatata tatttcaagg atataccatt   7620
gtaatgtctg cccctaagaa gatcgtcgtt ttgccaggtg accacgttgg tcaagaaatc   7680
acagccgaag ccattaaggt tcttaaagct atttctgatg ttcgttccaa tgtcaagttc   7740
gatttcgaaa atcatttaat tggtggtgct gctatcgatg ctacaggtgt cccacttcca   7800
gatgaggcgc tggaagcctc caagaaggtt gatgccgttt tgttaggtgc tgtgggtggt   7860
cctaaatggg gtaccggtag tgttagacct gaacaaggtt tactaaaaat ccgtaaagaa   7920
cttcaattgt acgccaactt aagaccatgt aactttgcat ccgactctct tttagactta   7980
tctccaatca agccacaatt tgctaaaggt actgacttcg ttgttgtcag agaattagtg   8040
ggaggtattt actttggtaa gagaaaggaa gacgatggtg atggtgtcgc ttgggatagt   8100
gaacaataca ccgttccaga agtgcaaaga atcacaagaa tggccgcttt catggcccta   8160
caacatgagc caccattgcc tatttggtcc ttggataaag ctaatgtttt ggcctcttca   8220
agattatgga gaaaaactgt ggaggaaacc atcaagaacg aattccctac attgaaggtt   8280
caacatcaat tgattgattc tgccgccatg atcctagtta agaacccaac ccacctaaat   8340
ggtattataa tcaccagcaa catgtttggt gatatcatct ccgatgaagc ctccgttatc   8400
ccaggttcct tgggtttgtt gccatctgcg tccttggcct ctttgccaga caagaacacc   8460
gcatttggtt tgtacgaacc atgccacggt tctgctccag atttgccaaa gaataaggtt   8520
gaccctatcg ccactatctt gtctgctgca atgatgttga aattgtcatt gaacttgcct   8580
gaagaaggta aggccattga agatgcagtt aaaaaggttt tggatgcagg tatcagaact   8640
ggtgatttag gtggttccaa cagtaccacc gaagtcggtg atgctgtcgc cgaagaagtt   8700
aagaaaatcc ttgcttaaaa agattctctt tttttatgat atttgtacaa aaaaaaaaaa   8760
aaaaaaaaaa aaaaaaaaaa aaaaaaaaaa aaaatgcagc gtcacatcgg ataataatga   8820
tggcagccat tgtagaagtg ccttttgcat ttctagtctc tttctcggtc tagctagttt   8880
tactacatcg cgaagataga atcttagatc acactgcctt tgctgagctg gatcatatga   8940
gtaacaaaag agtggtaagg cctcgttaaa ggacaaggac ctgagcggaa gtgtatcgta   9000
aagtagacgg agtatactag tatagtctat agtccgtgga attctaagtg ccagctttat   9060
aatgtcattc tccttactac agacccgcct gaaagtagac acatcatcat cagtaagctt   9120
```

-continued

```
tgacaaaaag cattgagtag ctaactcttc tatgcaatct atagctgttt tataaggcat   9180
tcaatggaca gattgaggtt tttgaaacat actagtgaaa ttagccttaa tcccttctcg   9240
aagttaatca tgcattatgg tgtaaaaaat gcaactcgcg ttgctctact ttttcccgaa   9300
tttccaaata cgcagctggg gtgattgctc gatttcgtaa cgaaagtttt gtttataaaa   9360
accgcgaaaa ccttctgtaa cagatagatt tttacagcgc tgatatacaa tgacatcagc   9420
tgtaatggaa aataactgaa atatgaatgg cgagagactg cttgcttgta ttaagcaatg   9480
tattatgcag cacttccaac ctatggtgta cgatgaaagt aggtgtgtaa tcgagacgac   9540
aaggggact  tttccagttc ctgatcatta taagaaatac aaaacgttag catttgcatt   9600
tgttggacat gtactgaata cagacgacac accggtaatt gaaaaagaac tggattggcc   9660
tgatcctgca ctagtgtaca atacaattgt cgatcgaatc ataaatcacc cagaattatc   9720
acagtttata tcggttgcat ttattagtca gttaaaggcc accatcggag agggtttaga   9780
tattaatgta aaaggcacgc taaaccgcag gggaaagggt atcagaaggc ctaaaggcgt   9840
attttttaga tacatggaat ctccatttgt caatacaaag gtcactgcat tcttctctta   9900
tcttcgagat tataataaaa ttgcctcaga atatcacaat aatactaaat tcattctcac   9960
gttttcatgt caagcatatt gggcatctgg cccaaacttc tccgccttga agaatgttat  10020
ttggtgctcc ataattcatg aatacatttc taagtttgtg gaaagagaac aggataaagg  10080
tcatatagga gatcaggagc taccgcctga agaggaccct tctcgtgaac taaacaatgt  10140
acaacatgaa gtcaatagtt taacggaaca agatgcggag gcggatgaag gattgtgggg  10200
tgaaatagat tcattatgtg aaaaatggca gtctgaagcg gagagtcaaa ctgaggcgga  10260
gataatagcc gacaggataa ttggaaatag ccagaggatg gcgaacctca aaattcgtcg  10320
tacaaagttc aaaagtgtct tgtatcatat actaaaggaa ctaattcaat ctcagggaac  10380
cgtaaaggtt tatcgcggta gtagtttttc acacgattcg ataaagataa gcttacatta  10440
tgaagagcag catattacag ccgtatgggt ctacttgata gtaaaatttg aagagcattg  10500
gaagcctgtt gatgtagagg tcgagtttag atgcaagttc aaggagcgaa aggtggatgg  10560
gtaggttata tagggatata gcacagagat atatagcaaa gagatacttt tgaggcaatg  10620
tttgtggaag cggtattcgc aatattttag tagctcgtta cagtccggtg cgtttttggt  10680
tttttgaaag tgcgtcttca gagcgctttt ggttttcaaa agcgctctga agttcctata  10740
ctttctagag aataggaact tcggaatagg aacttcaaag cgtttccgaa aacgagcgct  10800
tccgaaaatg caacgcgagc tgcgcacata cagctcactg ttcacgtcgc acctatatct  10860
gcgtgttgcc tgtatatata tatacatgag aagaacggca tagtgcgtgt ttatgcttaa  10920
atgcgtactt atatgcgtct atttatgtag gatgaaaggt agtctagtac ctcctgtgat  10980
attatcccat tccatgcggg gtatcgtatg cttccttcag cactaccctt tagctgttct  11040
atatgctgcc actcctcaat tggattagtc tcatccttca atgcattcat ttcctttgat  11100
attggatcat accctagaag tattacgtga ttttctgccc cttaccctcg ttgctactct  11160
ccttttttc  gtgggaaccg ctttagggcc ctcagtgatg gtgttttgta atttatatgc  11220
tcctcttgca tttgtgtctc tacttcttgt tcgcctggag ggaacttctt catttgtatt  11280
agcatggttc acttcagtcc ttccttccaa ctcactcttt ttttgctgta aacgattctc  11340
tgccgccagt tcattgaaac tattgaatat atcctttaga gattccggga tgaataaatc  11400
acctattaaa gcagcttgac gatctggtgg aactaaagta agcaattggg taacgacgct  11460
```

-continued

```
tacgagcttc ataacatctt cttccgttgg agctggtggg actaataact gtgtacaatc  11520
catttttctc atgagcattt cggtagctct cttcttgtct ttctcgggca atcttcctat  11580
tattatagca atagatttgt atagttgctt tctattgtct aacagcttgt tattctgtag  11640
catcaaatct atggcagcct gacttgcttc ttgtgaagag agcataccat ttccaatcga  11700
agatacgctg gaatcttctg cgctagaatc aagaccatac ggcctaccgg ttgtgagaga  11760
ttccatgggc cttatgacat atcctggaaa gagtagctca tcagacttac gtttactctc  11820
tatatcaata tctacatcag gagcaatcat ttcaataaac agccgacata catcccagac  11880
gctataagct gtacgtgctt ttaccgtcag attcttggct gtttcaatgt cgtccatttt  11940
ggttttcttt taccagtatt gttcgtttga taatgtattc ttgcttatta cattataaaa  12000
tctgtgcaga tcacatgtca aaacaacttt ttatcacaag atagtaccgc aaaacgaacc  12060
tgcgggccgt ctaaaaatta aggaaaagca gcaaaggtgc atttttaaaa tatgaaatga  12120
agataccgca gtaccaatta ttttcgcagt acaaataatg cgcggccggt gcatttttcg  12180
aaagaacgcg agacaaacag gacaattaaa gttagttttt cgagttagcg tgtttgaata  12240
ctgcaagata caagataaat agagtagttg aaactagata tcaattgcac acaagatcgg  12300
cgctaagcat gccacaattt ggtatattat gtaaaacacc acctaaggtg cttgttcgtc  12360
agtttgtgga aaggtttgaa agaccttcag gtgagaaaat agcattatgt gctgctgaac  12420
taacctattt atgttggatg attacacata acggaacagc aatcaagaga gccacattca  12480
tgagctataa tactatcata agcaattcgc tgagtttcga tattgtcaat aaatcactcc  12540
agtttaaata caagacgcaa aaagcaacaa ttctggaagc ctcattaaag aaattgattc  12600
ctgcttggga atttacaatt attccttact atggacaaaa acatcaatct gatatcactg  12660
atattgtaag tagtttgcaa ttacagttcg aatcatcgga agaagcagat aagggaaata  12720
gccacagtaa aaaaatgcta aagcacttct aagtgagggt gaaagcatct gggagatcac  12780
tgagaaaata ctaaattcgt ttgagtatac ttcgagattt acaaaaacaa aaactttata  12840
ccaattcctc ttcctagcta ctttcatcaa ttgtggaaga ttcagcgata ttaagaacgt  12900
tgatccgaaa tcatttaaat tagtccaaaa taagtatctg ggagtaataa tccagtgttt  12960
agtgacagag acaaagacaa gcgttagtag gcacatatac ttctttagcg caaggggtag  13020
```

<210> SEQ ID NO 44
<211> LENGTH: 15810
<212> TYPE: DNA
<213> ORGANISM: Artificial Sequence
<220> FEATURE:
<223> OTHER INFORMATION: Description of Artificial Sequence:
vector pSY1aMFE1sH6a

<400> SEQUENCE: 44

```
atcgataagc ttttcaattc aattcatcat ttttttttta ttcttttttt tgatttcggt     60
ttctttgaaa tttttttgat tcggtaatct ccgaacagaa ggaagaacga aggaaggagc    120
acagacttag attggtatat atacgcatat gtagtgttga agaaacatga aattgcccag    180
tattcttaac ccaactgcac agaacaaaaa cctgcaggaa acgaagataa atcatgtcga    240
aagctacata taaggaacgt gctgctactc atcctagtcc tgttgctgcc aagctattta    300
atatcatgca cgaaaagcaa acaaacttgt gtgcttcatt ggatgttcgt accaccaagg    360
aattactgga gttagttgaa gcattaggtc ccaaaatttg tttactaaaa acacatgtgg    420
atatcttgac tgatttttcc atggagggca cagttaagcc gctaaaggca ttatccgcca    480
```

-continued

```
agtacaattt tttactcttc gaagacagaa aatttgctga cattggtaat acagtcaaat    540
tgcagtactc tgcgggtgta tacagaatag cagaatgggc agacattacg aatgcacacg    600
gtgtggtggg cccaggtatt gttagcggtt tgaagcaggc ggcagaagaa gtaacaaagg    660
aacctagagg ccttttgatg ttagcagaat tgtcatgcaa gggctcccta tctactggag    720
aatatactaa gggtactgtt gacattgcga agagcgacaa agattttgtt atcggcttta    780
ttgctcaaag agacatgggt ggaagagatg aaggttacga ttggttgatt atgacacccg    840
gtgtgggttt agatgacaag ggagacgcat tgggtcaaca gtatagaacc gtggatgatg    900
tggtctctac aggatctgac attattattg ttggaagagg actatttgca aagggaaggg    960
atgctaaggt agagggtgaa cgttacagaa aagcaggctg ggaagcatat ttgagaagat   1020
gcggccagca aaactaaaaa actgtattat aagtaaatgc atgtatacta aactcacaaa   1080
ttagagcttc aatttaatta tatcagttat tacccgggaa tctcggtcgt aatgattttt   1140
ataatgacga aaaaaaaaaa attggaaaga aaaagcttta atgcggtagt ttatcacagt   1200
taaattgcta acgcagtcag gcaccgtgta tgaaatctaa caatgcgctc atcgtcatcc   1260
tcggcaccgt caccctggat gctgtaggca taggcttggt tatgccggta ctgccgggcc   1320
tcttgcggga tatcgtccat tccgacagca tcgccagtca ctatggcgtg ctgctagcgc   1380
tatatgcgtt gatgcaattt ctatgcgcac ccgttctcgg agcactgtcc gaccgctttg   1440
gccgccgccc agtcctgctc gcttcgctac ttggagccac tatcgactac gcgatcatgg   1500
cgaccacacc cgtcctgtgg atccttcaat atgcgcacat acgctgttat gttcaaggtc   1560
ccttcgttta agaacgaaag cggtcttcct tttgagggat gtttcaagtt gttcaaatct   1620
atcaaatttg caaatcccca gtctgtatct agagcgttga atcggtgatg cgatttgtta   1680
attaaattga tggtgtcacc attaccaggt ctagatatac caatggcaaa ctgagcacaa   1740
caataccagt ccggatcaac tggcaccatc tctcccgtag tctcatctaa tttttcttcc   1800
ggatgaggtt ccagatatac cgcaacacct ttattatggt ttccctgagg gaataataga   1860
atgtcccatt cgaaatcacc aattctaaac ctgggcgaat tgtatttcgg gtttgttaac   1920
tcgttccagt caggaatgtt ccacgtgaag ctatcttcca gcaaagtctc cacttcttca   1980
tcaaattgtg gagaatactc ccaatgctct tatctatggg acttccggga aacacagtac   2040
cgatacttcc caattcgtct tcagagctca ttgtttgttt gaagagacta atcaaagaat   2100
cgttttctca aaaaaattaa tatcttaact gatagtttga tcaaaggggc aaaacgtagg   2160
ggcaaacaaa cggaaaaatc gtttctcaaa ttttctgatg ccaagaactc taaccagtct   2220
tatctaaaaa ttgccttatg atccgtctct ccggttacag cctgtgtaac tgattaatcc   2280
tgcctttcta atcaccattc taatgtttta attaagggat tttgtcttca ttaacggctt   2340
tcgctcataa aaatgttatg acgttttgcc cgcaggcggg aaaccatcca cttcacgaga   2400
ctgatctcct ctgccggaac accgggcatc tccaacttat aagttggaga aataagagaa   2460
tttcagattg agagaatgaa aaaaaaaaac cctgaaaaaa aaggttgaaa ccagttccct   2520
gaaattattc ccctacttga ctaataagta tataaagacg gtaggtattg attgtaattc   2580
tgtaaatcta tttcttaaac ttcttaaatt ctacttttat agttagtctt ttttttagtt   2640
ttaaaacacc aagaacttag tttcgaataa acacacataa acaaacacca tgagatttcc   2700
ttcaattttt actgcagttt tattcgcagc atcctccgca ttagctgctc cagtcaacac   2760
tacaacagaa gatgaaacgg cacaaattcc ggctgaagct gtcatcggtt actcagattt   2820
agaaggggat ttcgatgttg ctgttttgcc attttccaac agcacaaata acgggttatt   2880
```

-continued

```
gtttataaat actactattg ccagcattgc tgctaaagaa gaaggggtat ctctagataa   2940
aaggtatgag gtgcgcaacg tgtccgggat gtaccatgtc acgaacgact gctccaactc   3000
aagcattgtg tatgaggcag cggacatgat catgcacacc cccgggtgcg tgccctgcgt   3060
tcgggagaac aactcttccc gctgctgggt agcgctcacc cccacgctcg cagctaggaa   3120
cgccagcgtc cccactacga caatacgacg ccacgtcgat ttgctcgttg ggcggctgc    3180
tttctgttcc gctatgtacg tgggggatct ctgcggatct gtcttcctcg tctcccagct   3240
gttcaccatc tcgcctcgcc ggcatgagac ggtgcaggac tgcaattgct caatctatcc   3300
cggccacata acgggtcacc gtatggcttg ggatatgatg atgaactggc accaccacca   3360
tcaccattaa agatctcgac ttggttgaac acgttgccaa ggcttaagtg aatttacttt   3420
aaagtcttgc atttaaataa attttctttt tatagcttta tgacttagtt tcaatttata   3480
tactatttta atgacatttt cgattcattg attgaaagct ttgtgttttt tcttgatgcg   3540
ctattgcatt gttcttgtct ttttcgccac atgtaatatc tgtagtagat acctgataca   3600
ttgtggatgc tgagtgaaat tttagttaat aatggaggcg ctcttaataa ttttggggat   3660
attggctttt ttttttaaag tttacaaatg aattttttcc gccaggataa cgattctgaa   3720
gttactctta gcgttcctat cggtacagcc atcaaatcat gcctataaat catgcctata   3780
tttgcgtgca gtcagtatca tctacatgaa aaaaactccc gcaatttctt atagaatacg   3840
ttgaaaatta aatgtacgcg ccaagataag ataacatata tctagctaga tgcagtaata   3900
tacacagatt cccgcggacg tgggaaggaa aaaattagat aacaaaatct gagtgatatg   3960
gaaattccgc tgtatagctc atatctttcc cttcaacacc agaaatgtaa aaatcttgtt   4020
acgaaggatc tttttgctaa tgtttctcgc tcaatcctca tttcttccct acgaagagtc   4080
aaatctactt gttttctgcc ggtatcaaga tccatatctt ctagtttcac catcaaagtc   4140
caatttctag tatacagttt atgtcccaac gtaacagaca atcaaaattg gaaaggataa   4200
gtatccttca aagaatgatt ctgcgctggc tcctgaaccg cctaatggga acagagaagt   4260
ccaaaacgat gctataagaa ccagaaataa aacgataaaa ccataccagg atcctctacg   4320
ccggacgcat cgtggccggc atcaccggcg ccacaggtgc ggttgctggc ccctatatcg   4380
ccgacatcac cgatggggaa gatcgggctc gccacttcgg gctcatgagc gcttgtttcg   4440
gcgtgggtat ggtggcaggc cccgtggccg ggggactgtt gggcgccatc tccttgcatg   4500
caccattcct tgcggcggcg gtgctcaacg gcctcaacct actactgggc tgcttcctaa   4560
tgcaggagtc gcataaggga gagcgtcgac cgatgccctt gagagccttc aacccagtca   4620
gctccttccg gtgggcgcgg ggcatgacta tcgtcgccgc acttatgact gtcttcttta   4680
tcatgcaact cgtaggacag gtgccggcag cgctctgggt cattttcggc gaggaccgct   4740
ttcgctggag cgcgacgatg atcggcctgt cgcttgcggt attcggaatc ttgcacgccc   4800
tcgctcaagc cttcgtcact ggtcccgcca ccaaacgttt cggcgagaag caggccatta   4860
tcgccggcat ggcggccgac gcgctgggct acgtcttgct ggcgttcgcg acgcgaggct   4920
ggatggcctt ccccattatg attcttctcg cttccggcgg catcgggatg cccgcgttgc   4980
aggccatgct gtccaggcag gtagatgacg accatcaggg acagcttcaa ggatcgctcg   5040
cggctcttac cagcctaact tcgatcactg gaccgctgat cgtcacggcg atttatgccg   5100
cctcggcgag cacatggaac gggttggcat ggattgtagg cgccgcccta taccttgtct   5160
gcctccccgc gttgcgtcgc ggtgcatgga gccgggccac ctcgacctga atggaagccg   5220
```

-continued

```
gcggcacctc gctaacggat tcaccactcc aagaattgga gccaatcaat tcttgcggag   5280
aactgtgaat gcgcaaacca acccttggca gaacatatcc atcgcgtccg ccatctccag   5340
cagccgcacg cggcgcatct cgggcagcgt tgggtcctgg ccacgggtgc gcatgatcgt   5400
gctcctgtcg ttgaggaccc ggctaggctg gcggggttgc cttactggtt agcagaatga   5460
atcaccgata cgcgagcgaa cgtgaagcga ctgctgctgc aaaacgtctg cgacctgagc   5520
aacaacatga atggtcttcg gtttccgtgt ttcgtaaagt ctggaaacgc ggaagtcagc   5580
gccctgcacc attatgttcc ggatctgcat cgcaggatgc tgctggctac cctgtggaac   5640
acctacatct gtattaacga agcgctggca ttgaccctga gtgatttttc tctggtcccg   5700
ccgcatccat accgccagtt gtttaccctc acaacgttcc agtaaccggg catgttcatc   5760
atcagtaacc cgtatcgtga gcatcctctc tcgtttcatc ggtatcatta cccccatgaa   5820
cagaaattcc cccttacacg gaggcatcaa gtgaccaaac aggaaaaaac cgcccttaac   5880
atggcccgct ttatcagaag ccagacatta acgcttctgg agaaactcaa cgagctggac   5940
gcggatgaac aggcagacat ctgtgaatcg cttcacgacc acgctgatga gctttaccgc   6000
agctgcctcg cgcgtttcgg tgatgacggt gaaaacctct gacacatgca gctcccggag   6060
acggtcacag cttgtctgta agcggtgccg ggagcagaca agcccgtcag ggcgcgtcag   6120
cgggtgttgg cgggtgtcgg ggcgcagcca tgacccagtc acgtagcgat agcggagtgt   6180
atactggctt aactatgcgg catcagagca gattgtactg agagtgcacc atatgcggtg   6240
tgaaataccg cacagatgcg taaggagaaa ataccgcatc aggcgctctt ccgcttcctc   6300
gctcactgac tcgctgcgct cggtcgttcg gctgcggcga gcggtatcag ctcactcaaa   6360
ggcggtaata cggttatcca cagaatcagg ggataacgca ggaaagaaca tgtgagcaaa   6420
aggccagcaa aaggccagga accgtaaaaa ggccgcgttg ctggcgtttt tccataggct   6480
ccgcccccct gacgagcatc acaaaaatcg acgctcaagt cagaggtggc gaaacccgac   6540
aggactataa agataccagg cgtttccccc tggaagctcc ctcgtgcgct ctcctgttcc   6600
gaccctgccg cttaccggat acctgtccgc ctttctccct tcgggaagcg tggcgctttc   6660
tcatagctca cgctgtaggt atctcagttc ggtgtaggtc gttcgctcca agctgggctg   6720
tgtgcacgaa ccccccgttc agcccgaccg ctgcgcctta tccggtaact atcgtcttga   6780
gtccaacccg gtaagacacg acttatcgcc actggcagca gccactggta acaggattag   6840
cagagcgagg tatgtaggcg gtgctacaga gttcttgaag tggtggccta actacggcta   6900
cactagaagg acagtatttg gtatctgcgc tctgctgaag ccagttacct tcggaaaaag   6960
agttggtagc tcttgatccg gcaaacaaac caccgctggt agcggtggtt tttttgtttg   7020
caagcagcag attacgcgca gaaaaaaagg atctcaagaa gatcctttga tcttttctac   7080
ggggtctgac gctcagtgga acgaaaactc acgttaaggg attttggtca tgagattatc   7140
aaaaaggatc ttcacctaga tccttttaaa ttaaaaatga agttttaaat caatctaaag   7200
tatatatgag taaacttggt ctgacagtta ccaatgctta atcagtgagg cacctatctc   7260
agcgatctgt ctatttcgtt catccatagt tgcctgactc cccgtcgtgt agataactac   7320
gatacgggag ggcttaccat ctggccccag tgctgcaatg ataccgcgag acccacgctc   7380
accggctcca gatttatcag caataaacca gccagccgga agggccgagc gcagaagtgg   7440
tcctgcaact ttatccgcct ccatccagtc tattaattgt tgccgggaag ctagagtaag   7500
tagttcgcca gttaatagtt tgcgcaacgt tgttgccatt gctgcaggca tcgtggtgtc   7560
acgctcgtcg tttggtatgg cttcattcag ctccggttcc caacgatcaa ggcgagttac   7620
```

-continued

```
atgatccccc atgttgtgca aaaaagcggt tagctccttc ggtcctccga tcgttgtcag   7680
aagtaagttg gccgcagtgt tatcactcat ggttatggca gcactgcata attctcttac   7740
tgtcatgcca tccgtaagat gcttttctgt gactggtgag tactcaacca agtcattctg   7800
agaatagtgt atgcggcgac cgagttgctc ttgcccggcg tcaacacggg ataataccgc   7860
gccacatagc agaactttaa aagtgctcat cattggaaaa cgttcttcgg ggcgaaaact   7920
ctcaaggatc ttaccgctgt tgagatccag ttcgatgtaa cccactcgtg cacccaactg   7980
atcttcagca tcttttactt tcaccagcgt ttctgggtga gcaaaaacag gaaggcaaaa   8040
tgccgcaaaa aagggaataa gggcgacacg gaaatgttga atactcatac tcttcctttt   8100
tcaatattat tgaagcattt atcagggtta ttgtctcatg agcggataca tatttgaatg   8160
tatttagaaa aataaacaaa taggggttcc gcgcacattt ccccgaaaag tgccacctga   8220
cgtctaagaa accattatta tcatgacatt aacctataaa aataggcgt atcacgaggc   8280
cctttcgtct tcaagaattc tcatgtttga cagcttatca tcgatccact tgtatatttg   8340
gatgaatttt tgaggaattc tgaaccagtc ctaaaacgag taaataggac cggcaattct   8400
tcaagcaata aacaggaata ccaattatta aaagataact tagtcagatc gtacaataaa   8460
gctttgaaga aaaatgcgcc ttattcaatc tttgcataaa aaaatggccc aaaatctcac   8520
attggaagac atttgatgac ctcatttctt tcaatgaagg gcctaacgga gttgactaat   8580
gttgtgggaa attggaccga taagcgtgct tctgccgtgg ccaggacaac gtatactcat   8640
cagataacag caatacctga tcactacttc gcactagttt ctcggtacta tgcatatgat   8700
ccaatatcaa aggaaatgat agcattgaag gatgagacta atccaattga ggagtggcag   8760
catatagaac agctaaaggg tagtgctgaa ggaagcatac gataccccgc atggaatggg   8820
ataatatcac aggaggtact agactacctt tcatcctaca taaatagacg catataagta   8880
cgcatttaag cataaacacg cactatgccg ttcttctcat gtatatatat atacaggcaa   8940
cacgcagata taggtgcgac gtgaacagtg agctgtatgt gcgcagctcg cgttgcattt   9000
tcggaagcgc tcgttttcgg aaacgctttg aagttcctat tccgaagttc ctattctcta   9060
gaaagtatag gaacttcaga gcgcttttga aaaccaaaag cgctctgaag acgcactttc   9120
aaaaaaccaa aaacgcaccg gactgtaacg agctactaaa atattgcgaa taccgcttcc   9180
acaaacattg ctcaaaagta tctctttgct atatatctct gtgctatatc cctatataac   9240
catcccatcc acctttcgct ccttgaactt gcatctaaac tcgacctcta catttttat   9300
gtttatctct agtattacct cttagacaaa aaaattgtag taagaactat tcatagagtt   9360
aatcgaaaac aatacgaaaa tgtaaacatt tcctatacgt agtatataga gacaaaatag   9420
aagaaaccgt tcataatttt ctgaccaatg aagaatcatc aacgctatca ctttctgttc   9480
acaaagtatg cgcaatccac atcggtatag aatataatcg gggatgcctt tatcttgaaa   9540
aaatgcaccc gcagcttcgc tagtaatcag taaacgcggg aagtggagtc aggctttttt   9600
tatggaagag aaaatagaca ccaaagtagc cttcttctaa ccttaacgga cctacagtgc   9660
aaaaagttat caagagactg cattatagag cgcacaaagg agaaaaaaag taatctaaga   9720
tgctttgtta gaaaaatagc gctctcggga tgcatttttg tagaacaaaa aagaagtata   9780
gattcttgtt ggtaaaatag cgctctcgcg ttgcatttct gttctgtaaa aatgcagctc   9840
agattctttg tttgaaaaat tagcgctctc gcgttgcatt tttgttttac aaaaatgaag   9900
cacagattct tcgttggtaa aatagcgctt tcgcgttgca tttctgttct gtaaaaatgc   9960
```

-continued

```
agctcagatt ctttgtttga aaaattagcg ctctcgcgtt gcatttttgt tctacaaaat  10020
gaagcacaga tgcttcgtta acaaagatat gctattgaag tgcaagatgg aaacgcagaa  10080
aatgaaccgg ggatgcgacg tgcaagatta cctatgcaat agatgcaata gtttctccag  10140
gaaccgaaat acatacattg tcttccgtaa agcgctagac tatatattat tatacaggtt  10200
caaatatact atctgtttca gggaaaactc ccaggttcgg atgttcaaaa ttcaatgatg  10260
ggtaacaagt acgatcgtaa atctgtaaaa cagtttgtcg gatattaggc tgtatctcct  10320
caaagcgtat tcgaatatca ttgagaagct gcattttttt tttttttttt tttttttttt  10380
tttttatata tatttcaagg atataccatt gtaatgtctg cccctaagaa gatcgtcgtt  10440
ttgccaggtg accacgttgg tcaagaaatc acagccgaag ccattaaggt tcttaaagct  10500
atttctgatg ttcgttccaa tgtcaagttc gatttcgaaa atcatttaat tggtggtgct  10560
gctatcgatg ctacaggtgt cccacttcca gatgaggcgc tggaagcctc caagaaggtt  10620
gatgccgttt tgttaggtgc tgtgggtggt cctaaatggg gtaccggtag tgttagacct  10680
gaacaaggtt tactaaaaat ccgtaaagaa cttcaattgt acgccaactt aagaccatgt  10740
aactttgcat ccgactctct tttagactta tctccaatca agccacaatt tgctaaaggt  10800
actgacttcg ttgttgtcag agaattagtg ggaggtattt actttggtaa gagaaaggaa  10860
gacgatggtg atggtgtcgc ttgggatagt gaacaataca ccgttccaga agtgcaaaga  10920
atcacaagaa tggccgcttt catggcccta caacatgagc caccattgcc tatttggtcc  10980
ttggataaag ctaatgtttt ggcctcttca agattatgga gaaaaactgt ggaggaaacc  11040
atcaagaacg aattccctac attgaaggtt caacatcaat tgattgattc tgccgccatg  11100
atcctagtta agaacccaac ccacctaaat ggtattataa tcaccagcaa catgtttggt  11160
gatatcatct ccgatgaagc ctccgttatc ccaggttcct tgggtttgtt gccatctgcg  11220
tccttggcct ctttgccaga caagaacacc gcatttggtt tgtacgaacc atgccacggt  11280
tctgctccag atttgccaaa gaataaggtt gaccctatcg ccactatctt gtctgctgca  11340
atgatgttga aattgtcatt gaacttgcct gaagaaggta aggccattga agatgcagtt  11400
aaaaaggttt tggatgcagg tatcagaact ggtgatttag gtggttccaa cagtaccacc  11460
gaagtcggtg atgctgtcgc cgaagaagtt aagaaaatcc ttgcttaaaa agattctctt  11520
tttttatgat atttgtacaa aaaaaaaaaa aaaaaaaaaa aaaaaaaaaa aaaaaaaaaa  11580
aaaatgcagc gtcacatcgg ataataatga tggcagccat tgtagaagtg ccttttgcat  11640
ttctagtctc tttctcggtc tagctagttt tactacatcg cgaagataga atcttagatc  11700
acactgcctt tgctgagctg gatcatatga gtaacaaaag agtggtaagg cctcgttaaa  11760
ggacaaggac ctgagcggaa gtgtatcgta aagtagacgg agtatactag tatagtctat  11820
agtccgtgga attctaagtg ccagctttat aatgtcattc tccttactac agacccgcct  11880
gaaagtagac acatcatcat cagtaagctt tgacaaaaag cattgagtag ctaactcttc  11940
tatgcaatct atagctgttt tataaggcat tcaatggaca gattgaggtt tttgaaacat  12000
actagtgaaa ttagccttaa tcccttctcg aagttaatca tgcattatgg tgtaaaaaat  12060
gcaactcgcg ttgctctact ttttcccgaa tttccaaata cgcagctggg gtgattgctc  12120
gatttcgtaa cgaaagtttt gtttataaaa accgcgaaaa ccttctgtaa cagatagatt  12180
tttacagcgc tgatatacaa tgacatcagc tgtaatggaa aataactgaa atatgaatgg  12240
cgagagactg cttgcttgta ttaagcaatg tattatgcag cacttccaac ctatggtgta  12300
cgatgaaagt aggtgtgtaa tcgagacgac aagggggact tttccagttc ctgatcatta  12360
```

-continued

```
taagaaatac aaaacgttag catttgcatt tgttggacat gtactgaata cagacgacac  12420
accggtaatt gaaaaagaac tggattggcc tgatcctgca ctagtgtaca atacaattgt  12480
cgatcgaatc ataaatcacc cagaattatc acagtttata tcggttgcat ttattagtca  12540
gttaaaggcc accatcggag agggtttaga tattaatgta aaaggcacgc taaaccgcag  12600
gggaaagggt atcagaaggc ctaaaggcgt attttttaga tacatggaat ctccatttgt  12660
caatacaaag gtcactgcat tcttctctta tcttcgagat tataataaaa ttgcctcaga  12720
atatcacaat aatactaaat tcattctcac gttttcatgt caagcatatt gggcatctgg  12780
cccaaacttc tccgccttga agaatgttat ttggtgctcc ataattcatg aatacatttc  12840
taagtttgtg gaaagagaac aggataaagg tcatatagga gatcaggagc taccgcctga  12900
agaggaccct tctcgtgaac taaacaatgt acaacatgaa gtcaatagtt taacggaaca  12960
agatgcggag gcggatgaag gattgtgggg tgaaatagat tcattatgtg aaaaatggca  13020
gtctgaagcg gagagtcaaa ctgaggcgga gataatagcc gacaggataa ttggaaatag  13080
ccagaggatg gcgaacctca aaattcgtcg tacaaagttc aaaagtgtct tgtatcatat  13140
actaaaggaa ctaattcaat ctcagggaac cgtaaaggtt tatcgcggta gtagtttttc  13200
acacgattcg ataaagataa gcttacatta tgaagagcag catattacag ccgtatgggt  13260
ctacttgata gtaaaatttg aagagcattg gaagcctgtt gatgtagagg tcgagtttag  13320
atgcaagttc aaggagcgaa aggtggatgg gtaggttata tagggatata gcacagagat  13380
atatagcaaa gagatacttt tgaggcaatg tttgtggaag cggtattcgc aatattttag  13440
tagctcgtta cagtccggtg cgtttttggt tttttgaaag tgcgtcttca gagcgctttt  13500
ggttttcaaa agcgctctga agttcctata ctttctagag aataggaact tcggaatagg  13560
aacttcaaag cgtttccgaa aacgagcgct tccgaaaatg caacgcgagc tgcgcacata  13620
cagctcactg ttcacgtcgc acctatatct gcgtgttgcc tgtatatata tatacatgag  13680
aagaacggca tagtgcgtgt ttatgcttaa atgcgtactt atatgcgtct atttatgtag  13740
gatgaaaggt agtctagtac ctcctgtgat attatcccat tccatgcggg gtatcgtatg  13800
cttccttcag cactaccctt tagctgttct atatgctgcc actcctcaat tggattagtc  13860
tcatccttca atgcattcat ttcctttgat attggatcat accctagaag tattacgtga  13920
ttttctgccc cttaccctcg ttgctactct cctttttttc gtgggaaccg ctttagggcc  13980
ctcagtgatg gtgttttgta atttatatgc tcctcttgca tttgtgtctc tacttcttgt  14040
tcgcctggag ggaacttctt catttgtatt agcatggttc acttcagtcc ttccttccaa  14100
ctcactcttt ttttgctgta aacgattctc tgccgccagt tcattgaaac tattgaatat  14160
atcctttaga gattccggga tgaataaatc acctattaaa gcagcttgac gatctggtgg  14220
aactaaagta agcaattggg taacgacgct tacgagcttc ataacatctt cttccgttgg  14280
agctggtggg actaataact gtgtacaatc catttttctc atgagcattt cggtagctct  14340
cttcttgtct ttctcgggca atcttcctat tattatagca atagatttgt atagttgctt  14400
tctattgtct aacagcttgt tattctgtag catcaaatct atggcagcct gacttgcttc  14460
ttgtgaagag agcataccat ttccaatcga agatacgctg gaatcttctg cgctagaatc  14520
aagaccatac ggcctaccgg ttgtgagaga ttccatgggc cttatgacat atcctggaaa  14580
gagtagctca tcagacttac gtttactctc tatatcaata tctacatcag gagcaatcat  14640
ttcaataaac agccgacata catcccagac gctataagct gtacgtgctt ttaccgtcag  14700
```

-continued

```
attcttggct gtttcaatgt cgtccatttt ggttttcttt taccagtatt gttcgtttga  14760

taatgtattc ttgcttatta cattataaaa tctgtgcaga tcacatgtca aaacaacttt  14820

ttatcacaag atagtaccgc aaaacgaacc tgcgggccgt ctaaaaatta aggaaaagca  14880

gcaaaggtgc atttttaaaa tatgaaatga agataccgca gtaccaatta ttttcgcagt  14940

acaaataatg cgcggccggt gcatttttcg aaagaacgcg agacaaacag gacaattaaa  15000

gttagttttt cgagttagcg tgtttgaata ctgcaagata caagataaat agagtagttg  15060

aaactagata tcaattgcac acaagatcgg cgctaagcat gccacaattt ggtatattat  15120

gtaaaacacc acctaaggtg cttgttcgtc agtttgtgga aaggtttgaa agaccttcag  15180

gtgagaaaat agcattatgt gctgctgaac taacctattt atgttggatg attacacata  15240

acggaacagc aatcaagaga gccacattca tgagctataa tactatcata agcaattcgc  15300

tgagtttcga tattgtcaat aaatcactcc agtttaaata caagacgcaa aaagcaacaa  15360

ttctggaagc ctcattaaag aaattgattc ctgcttggga atttacaatt attccttact  15420

atggacaaaa acatcaatct gatatcactg atattgtaag tagtttgcaa ttacagttcg  15480

aatcatcgga agaagcagat aagggaaata gccacagtaa aaaaatgcta aagcacttct  15540

aagtgagggt gaaagcatct gggagatcac tgagaaaata ctaaattcgt ttgagtatac  15600

ttcgagattt acaaaaacaa aaactttata ccaattcctc ttcctagcta ctttcatcaa  15660

ttgtggaaga ttcagcgata ttaagaacgt tgatccgaaa tcatttaaat tagtccaaaa  15720

taagtatctg ggagtaataa tccagtgttt agtgacagag acaaagacaa gcgttagtag  15780

gcacatatac ttctttagcg caaggggtag                                   15810
```

<210> SEQ ID NO 45
<211> LENGTH: 3928
<212> TYPE: DNA
<213> ORGANISM: Artificial Sequence
<220> FEATURE:
<223> OTHER INFORMATION: Description of Artificial Sequence:
vector pBKS-E2sH6

<400> SEQUENCE: 45

```
cacctaaatt gtaagcgtta atattttgtt aaaattcgcg ttaaattttt gttaaatcag     60

ctcatttttt aaccaatagg ccgaaatcgg caaaatccct tataaatcaa aagaatagac    120

cgagataggg ttgagtgttg ttccagtttg gaacaagagt ccactattaa agaacgtgga    180

ctccaacgtc aaagggcgaa aaaccgtcta tcagggcgat ggcccactac gtgaaccatc    240

accctaatca agttttttgg ggtcgaggtg ccgtaaagca ctaaatcgga accctaaagg    300

gagcccccga tttagagctt gacggggaaa gccggcgaac gtggcgagaa aggaagggaa    360

gaaagcgaaa ggagcgggcg ctagggcgct ggcaagtgta gcggtcacgc tgcgcgtaac    420

caccacaccc gccgcgctta atgcgccgct acagggcgcg tcccattcgc cattcaggct    480

gcgcaactgt tgggaagggc gatcggtgcg ggcctcttcg ctattacgcc agctggcgaa    540

agggggatgt gctgcaaggc gattaagttg ggtaacgcca gggttttccc agtcacgacg    600

ttgtaaaacg acggccagtg aattgtaata cgactcacta tagggcgaat tgggtaccgg    660

gccccccctc gaggtcgacg gtatcgataa gcttgcatgc ctgcagttaa ttaactatta    720

gtgatggtgg tgatggtgtc tgccctcgat cacctgccac tctgttgtag acagcagcag    780

cgggctaagc tctgatctat ccctgtcctc caagtcacaa cgctctcctc gagtccaatt    840

gcatgcggct tcgaacctgt gctccacgcc ccccacgtac atcctaacct tgaagatggt    900
```

-continued

```
gaagttgaca gtgcaggggt agtgccagag cctatatggg taatgaacca tacacctagg    960
tgtcagccag ggcccagaac cgcatctggc gtaggtggcc tcggggtgct tccgaaaaca   1020
gtcagtgggg caggtcaagg tgttgttgcc ggcccccccg atgttgcacg gggggccccc   1080
acacgtcttg gtgaacccag tgccattcat ccatgtacag ccgaaccagt tgcctcgcgg   1140
cggccgcgtg ttgttgagaa tcagcacatc cgagtcgttc gccccccagt tatacgtggg   1200
gacaccaaac cgatcggtcg tccccaccac aacagggctc ggggtgaagc aatacactgg   1260
accgcacacc tgagacgcgg gtacaatacc acacggtcga ggcgcgtagt gccagcagta   1320
gggcctctgg tccgagctgt taggctcagt gtaagtgagg ggaccccacc cctgagcgaa   1380
cttgtcgatg gagcgacagc tggccaagcg ctctgggcat ccagacgagt tgaatttgtg   1440
tttgtagaat agtgcggcaa agaaccctgt ttggagggag tcgttgcagt tcagggcagt   1500
cctgttgatg tgccaactgc cgttggtgtt tacgagctgg attttctgag ccgacccggg   1560
gctaaagagg gacacaaggc cctggtatc ggaggctgct gcccctcctg acacgcgggt   1620
atggtaccgg gccccccctc gaggtcgacg gtatcgataa gcttgatatc gaattcctgc   1680
agcccggggg atccactagt tctagagcgg ccgccaccgc ggtggagctc cagcttttgt   1740
tccctttagt gagggttaat ttcgagcttg gcgtaatcat ggtcatagct gtttcctgtg   1800
tgaaattgtt atccgctcac aattccacac aacatacgag ccggaagcat aaagtgtaaa   1860
gcctggggtg cctaatgagt gagctaactc acattaattg cgttgcgctc actgcccgct   1920
ttccagtcgg gaaacctgtc gtgccagctg cattaatgaa tcggccaacg cgcggggaga   1980
ggcggtttgc gtattgggcg ctcttccgct tcctcgctca ctgactcgct gcgctcggtc   2040
gttcggctgc ggcgagcggt atcagctcac tcaaaggcgg taatacggtt atccacagaa   2100
tcaggggata acgcaggaaa gaacatgtga gcaaaaggcc agcaaaaggc caggaaccgt   2160
aaaaaggccg cgttgctggc gtttttccat aggctccgcc cccctgacga gcatcacaaa   2220
aatcgacgct caagtcagag gtggcgaaac ccgacaggac tataaagata ccaggcgttt   2280
ccccctggaa gctccctcgt gcgctctcct gttccgaccc tgccgcttac cggatacctg   2340
tccgcctttc tcccttcggg aagcgtggcg ctttctcata gctcacgctg taggtatctc   2400
agttcggtgt aggtcgttcg ctccaagctg ggctgtgtgc acgaaccccc cgttcagccc   2460
gaccgctgcg ccttatccgg taactatcgt cttgagtcca acccggtaag acacgactta   2520
tcgccactgg cagcagccac tggtaacagg attagcagag cgaggtatgt aggcggtgct   2580
acagagttct tgaagtggtg gcctaactac ggctacacta gaaggacagt atttggtatc   2640
tgcgctctgc tgaagccagt taccttcgga aaaagagttg gtagctcttg atccggcaaa   2700
caaaccaccg ctggtagcgg tggttttttt gtttgcaagc agcagattac gcgcagaaaa   2760
aaaggatctc aagaagatcc tttgatcttt tctacggggt ctgacgctca gtggaacgaa   2820
aactcacgtt aagggatttt ggtcatgaga ttatcaaaaa ggatcttcac ctagatcctt   2880
ttaaattaaa aatgaagttt taaatcaatc taaagtatat atgagtaaac ttggtctgac   2940
agttaccaat gcttaatcag tgaggcacct atctcagcga tctgtctatt tcgttcatcc   3000
atagttgcct gactccccgt cgtgtagata actacgatac gggagggctt accatctggc   3060
cccagtgctg caatgatacc gcgagaccca cgctcaccgg ctccagattt atcagcaata   3120
aaccagccag ccggaagggc cgagcgcaga agtggtcctg caactttatc cgcctccatc   3180
cagtctatta attgttgccg ggaagctaga gtaagtagtt cgccagttaa tagtttgcgc   3240
aacgttgttg ccattgctac aggcatcgtg gtgtcacgct cgtcgtttgg tatggcttca   3300
```

-continued

```
ttcagctccg gttcccaacg atcaaggcga gttacatgat cccccatgtt gtgcaaaaaa   3360

gcggttagct ccttcggtcc tccgatcgtt gtcagaagta agttggccgc agtgttatca   3420

ctcatggtta tggcagcact gcataattct cttactgtca tgccatccgt aagatgcttt   3480

tctgtgactg gtgagtactc aaccaagtca ttctgagaat agtgtatgcg gcgaccgagt   3540

tgctcttgcc cggcgtcaat acgggataat accgcgccac atagcagaac tttaaaagtg   3600

ctcatcattg gaaaacgttc ttcggggcga aaactctcaa ggatcttacc gctgttgaga   3660

tccagttcga tgtaacccac tcgtgcaccc aactgatctt cagcatcttt tactttcacc   3720

agcgtttctg ggtgagcaaa aacaggaagg caaaatgccg caaaaaaggg aataagggcg   3780

acacggaaat gttgaatact catactcttc ctttttcaat attattgaag catttatcag   3840

ggttattgtc tcatgagcgg atacatattt gaatgtattt agaaaaataa acaaataggg   3900

gttccgcgca catttccccg aaaagtgc                                      3928
```

```
<210> SEQ ID NO 46
<211> LENGTH: 6104
<212> TYPE: DNA
<213> ORGANISM: Artificial Sequence
<220> FEATURE:
<223> OTHER INFORMATION: Description of Artificial Sequence:
      vector pYIG5HCCL-22aH6

<400> SEQUENCE: 46
```

```
agcgcccaat acgcaaaccg cctctccccg cgcgttggcc gattcattaa tgcagctggc     60

acgacaggtt tcccgactgg aaagcgggca gtgagcgcaa cgcaattaat gtgagttagc    120

tcactcatta ggcaccccag gctttacact ttatgcttcc ggctcgtatg ttgtgtggaa    180

ttgtgagcgg ataacaattt cacacaggaa acagctatga ccatgattac gaatttaata    240

cgactcacta tagggaattc gaggatcctt caatatgcgc acatacgctg ttatgttcaa    300

ggtcccttcg tttaagaacg aaagcggtct tccttttgag ggatgtttca agttgttcaa    360

atctatcaaa tttgcaaatc cccagtctgt atctagagcg ttgaatcggt gatgcgattt    420

gttaattaaa ttgatggtgt caccattacc aggtctagat ataccaatgg caaactgagc    480

acaacaatac cagtccggat caactggcac catctctccc gtagtctcat ctaatttttc    540

ttccggatga ggttccagat ataccgcaac acctttatta tggtttccct gagggaataa    600

tagaatgtcc cattcgaaat caccaattct aaacctgggc gaattgtatt tcgggtttgt    660

taactcgttc cagtcaggaa tgttccacgt gaagctatct tccagcaaag tctccacttc    720

ttcatcaaat tgtggagaat actcccaatg ctcttatcta tgggacttcc gggaaacaca    780

gtaccgatac ttcccaattc gtcttcagag ctcattgttt gtttgaagag actaatcaaa    840

gaatcgtttt ctcaaaaaaa ttaatatctt aactgatagt ttgatcaaag gggcaaaacg    900

taggggcaaa caaacggaaa aatcgtttct caaattttct gatgccaaga actctaacca    960

gtcttatcta aaaattgcct tatgatccgt ctctccggtt acagcctgtg taactgatta   1020

atcctgcctt tctaatcacc attctaatgt tttaattaag ggattttgtc ttcattaacg   1080

gctttcgctc ataaaaatgt tatgacgttt tgcccgcagg cgggaaacca tccacttcac   1140

gagactgatc tcctctgccg gaacaccggg catctccaac ttataagttg gagaaataag   1200

agaatttcag attgagagaa tgaaaaaaaa aaaccctgaa aaaaaaggtt gaaaccagtt   1260

ccctgaaatt attcccctac ttgactaata agtatataaa gacggtaggt attgattgta   1320

attctgtaaa tctatttctt aaacttctta aattctactt ttatagttag tctttttttt   1380
```

-continued

```
agttttaaaa caccaagaac ttagtttcga ataaacacac ataaacaaac accatgagat   1440
ttccttcaat ttttactgca gttttattcg cagcatcctc cgcattagct gctccagtca   1500
acactacaac agaagatgaa acggcacaaa ttccggctga agctgtcatc ggttactcag   1560
atttagaagg ggatttcgat gttgctgttt tgccattttc caacagcaca aataacgggt   1620
tattgtttat aaatactact attgccagca ttgctgctaa agaagaaggg gtatctctag   1680
ataaaaggca tacccgcgtg tcaggagggg cagcagcctc cgataccagg ggccttgtgt   1740
ccctctttag ccccgggtcg gctcagaaaa tccagctcgt aaacaccaac ggcagttggc   1800
acatcaacag gactgccctg aactgcaacg actccctcca aacagggttc tttgccgcac   1860
tattctacaa acacaaattc aactcgtctg gatgcccaga gcgcttggcc agctgtcgct   1920
ccatcgacaa gttcgctcag gggtggggtc ccctcactta cactgagcct aacagctcgg   1980
accagaggcc ctactgctgg cactacgcgc ctcgaccgtg tggtattgta cccgcgtctc   2040
aggtgtgcgg tccagtgtat tgcttcaccc cgagccctgt tgtggtgggg acgaccgatc   2100
ggtttggtgt ccccacgtat aactgggggg cgaacgactc ggatgtgctg attctcaaca   2160
acacgcggcc gccgcgaggc aactggttcg gctgtacatg gatgaatggc actgggttca   2220
ccaagacgtg tgggggcccc ccgtgcaaca tcgggggggc cggcaacaac accttgacct   2280
gccccactga ctgttttcgg aagcaccccg aggccactta cgccagatgc ggttctgggc   2340
cctggctgac acctaggtgt atggttcatt acccatatag gctctggcac tacccctgca   2400
ctgtcaactt caccatcttc aaggttagga tgtacgtggg gggcgtggag cacaggttcg   2460
aagccgcatg caattggact cgaggagagc gttgtgactt ggaggacagg gatagatcag   2520
agcttagctc gctgctgctg tctacaacag agtggcaggt gatcgagggc agacaccatc   2580
accaccatca ctaatagtta attaacgatc tcgacttggt tgaacacgtt gccaaggctt   2640
aagtgaattt actttaaagt cttgcattta aataaatttt ctttttatag ctttatgact   2700
tagtttcaat ttatatacta ttttaatgac attttcgatt cattgattga aagctttgtg   2760
tttttcttg atgcgctatt gcattgttct tgtctttttc gccacatgta atatctgtag   2820
tagatacctg atacattgtg gatgctgagt gaaattttag ttaataatgg aggcgctctt   2880
aataattttg ggatattgg cttttttttt taaagtttac aaatgaattt tttccgccag   2940
gataacgatt ctgaagttac tcttagcgtt cctatcggta cagccatcaa atcatgccta   3000
taaatcatgc ctatatttgc gtgcagtcag tatcatctac atgaaaaaaa ctcccgcaat   3060
ttcttataga atacgttgaa aattaaatgt acgcgccaag ataagataac atatatctag   3120
ctagatgcag taatatacac agattcccgc ggacgtggga aggaaaaaat tagataacaa   3180
aatctgagtg atatggaaat tccgctgtat agctcatatc tttcccttca acaccagaaa   3240
tgtaaaaatc ttgttacgaa ggatcttttt gctaatgttt ctcgctcaat cctcatttct   3300
tccctacgaa gagtcaaatc tacttgtttt ctgccggtat caagatccat atcttctagt   3360
ttcaccatca aagtccaatt tctagtatac agtttatgtc ccaacgtaac agacaatcaa   3420
aattggaaag gataagtatc cttcaaagaa tgattctgcg ctggctcctg aaccgcctaa   3480
tgggaacaga gaagtccaaa acgatgctat aagaaccaga aataaaacga taaaaccata   3540
ccaggatcca agcttggcac tggccgtcgt tttacaacgt cgtgactggg aaaaccctgg   3600
cgttacccaa cttaatcgcc ttgcagcaca tccccctttc gccagctggc gtaatagcga   3660
agaggcccgc accgatcgcc cttcccaaca gttgcgcagc ctgaatggcg aatgggaaat   3720
```

-continued

```
tgtaaacgtt aatattttgt taaaattcgc gttaaatttt tgttaaatca gctcattttt   3780
taaccaatag gccgaaatcg gcaaaatccc ttataaatca aaagaataga ccgagatagg   3840
gttgagtgtt gttccagttt ggaacaagag tccactatta aagaacgtgg actccaacgt   3900
caaagggcga aaaaccgtct atcagggcga tggcccacta cgtgaaccat caccctaatc   3960
aagttttttg gggtcgaggt gccgtaaagc actaaatcgg aaccctaaag ggagcccccg   4020
atttagagct tgacggggaa agccggcgaa cgtggcgaga aaggaaggga agaaagcgaa   4080
aggagcgggc gctagggcgc tggcaagtgt agcggtcacg ctgcgcgtaa ccaccacacc   4140
cgccgcgctt aatgcgccgc tacagggcgc gtcaggtggc acttttcggg gaaatgtgcg   4200
cggaacccct atttgtttat ttttctaaat acattcaaat atgtatccgc tcatgagaca   4260
ataaccctga taaatgcttc aataatattg aaaaaggaag agtatgagta ttcaacattt   4320
ccgtgtcgcc cttattccct tttttgcggc attttgcctt cctgtttttg ctcacccaga   4380
aacgctggtg aaagtaaaag atgctgaaga tcagttgggt gcacgagtgg gttacatcga   4440
actggatctc aacagcggta agatccttga gagttttcgc cccgaagaac gttttccaat   4500
gatgagcact tttaaagttc tgctatgtgg cgcggtatta tcccgtattg acgccgggca   4560
agagcaactc ggtcgccgca tacactattc tcagaatgac ttggttgagt actcaccagt   4620
cacagaaaag catcttacgg atggcatgac agtaagagaa ttatgcagtg ctgccataac   4680
catgagtgat aacactgcgg ccaacttact tctgacaacg atcggaggac cgaaggagct   4740
aaccgctttt ttgcacaaca tgggggatca tgtaactcgc cttgatcgtt gggaaccgga   4800
gctgaatgaa gccataccaa acgacgagcg tgacaccacg atgcctgtag caatggcaac   4860
aacgttgcgc aaactattaa ctggcgaact acttactcta gcttcccggc aacaattaat   4920
agactggatg gaggcggata aagttgcagg accacttctg cgctcggccc ttccggctgg   4980
ctggtttatt gctgataaat ctggagccgg tgagcgtggg tctcgcggta tcattgcagc   5040
actggggcca gatggtaagc cctcccgtat cgtagttatc tacacgacgg ggagtcaggc   5100
aactatggat gaacgaaata gacagatcgc tgagataggt gcctcactga ttaagcattg   5160
gtaactgtca gaccaagttt actcatatat actttagatt gatttaaaac ttcattttta   5220
atttaaaagg atctaggtga agatcctttt tgataatctc atgaccaaaa tcccttaacg   5280
tgagttttcg ttccactgag cgtcagaccc cgtagaaaag atcaaaggat cttcttgaga   5340
tccttttttt ctgcgcgtaa tctgctgctt gcaaacaaaa aaaccaccgc taccagcggt   5400
ggtttgtttg ccggatcaag agctaccaac tctttttccg aaggtaactg gcttcagcag   5460
agcgcagata ccaaatactg tccttctagt gtagccgtag ttaggccacc acttcaagaa   5520
ctctgtagca ccgcctacat acctcgctct gctaatcctg ttaccagtgg ctgctgccag   5580
tggcgataag tcgtgtctta ccgggttgga ctcaagacga tagttaccgg ataaggcgca   5640
gcggtcgggc tgaacggggg gttcgtgcac acagcccagc ttggagcgaa cgacctacac   5700
cgaactgaga tacctacagc gtgagcattg agaaagcgcc acgcttcccg aagggagaaa   5760
ggcggacagg tatccggtaa gcggcagggt cggaacagga gagcgcacga gggagcttcc   5820
agggggaaac gcctggtatc tttatagtcc tgtcgggttt cgccacctct gacttgagcg   5880
tcgatttttg tgatgctcgt caggggggcg gagcctatgg aaaaacgcca gcaacgcggc   5940
ctttttacgg ttcctggcct tttgctggcc ttttgctcac atgttctttc ctgcgttatc   6000
ccctgattct gtggataacc gtattaccgc ctttgagtga gctgataccg ctcgccgcag   6060
ccgaacgacc gagcgcagcg agtcagtgag cgaggaagcg gaag                    6104
```

-continued

<210> SEQ ID NO 47
<211> LENGTH: 16301
<212> TYPE: DNA
<213> ORGANISM: Artificial Sequence
<220> FEATURE:
<223> OTHER INFORMATION: Description of Artificial Sequence: vector pYYIGSE2H6

<400> SEQUENCE: 47

```
atcgataagc ttttcaattc aattcatcat ttttttttta ttcttttttt tgatttcggt     60
ttctttgaaa tttttttgat tcggtaatct ccgaacagaa ggaagaacga aggaaggagc    120

acagacttag attggtatat atacgcatat gtagtgttga agaaacatga aattgcccag    180

tattcttaac ccaactgcac agaacaaaaa cctgcaggaa acgaagataa atcatgtcga    240

aagctacata taaggaacgt gctgctactc atcctagtcc tgttgctgcc aagctattta    300

atatcatgca cgaaaagcaa acaaacttgt gtgcttcatt ggatgttcgt accaccaagg    360

aattactgga gttagttgaa gcattaggtc ccaaaatttg tttactaaaa acacatgtgg    420

atatcttgac tgatttttcc atggagggca cagttaagcc gctaaaggca ttatccgcca    480

agtacaattt tttactcttc gaagacagaa aatttgctga cattggtaat acagtcaaat    540

tgcagtactc tgcgggtgta tacagaatag cagaatgggc agacattacg aatgcacacg    600

gtgtggtggg cccaggtatt gttagcggtt tgaagcaggc ggcagaagaa gtaacaaagg    660

aacctagagg ccttttgatg ttagcagaat tgtcatgcaa gggctcccta tctactggag    720

aatatactaa gggtactgtt gacattgcga agagcgacaa agattttgtt atcggcttta    780

ttgctcaaag agacatgggt ggaagagatg aaggttacga ttggttgatt atgacacccg    840

gtgtgggttt agatgacaag ggagacgcat tgggtcaaca gtatagaacc gtggatgatg    900

tggtctctac aggatctgac attattattg ttggaagagg actatttgca aagggaaggg    960

atgctaaggt agagggtgaa cgttacagaa aagcaggctg ggaagcatat ttgagaagat   1020

gcggccagca aaactaaaaa actgtattat aagtaaatgc atgtatacta aactcacaaa   1080

ttagagcttc aatttaatta tatcagttat tacccgggaa tctcggtcgt aatgattttt   1140

ataatgacga aaaaaaaaaa attggaaaga aaaagcttta atgcggtagt ttatcacagt   1200

taaattgcta acgcagtcag gcaccgtgta tgaaatctaa caatgcgctc atcgtcatcc   1260

tcggcaccgt caccctggat gctgtaggca taggcttggt tatgccggta ctgccgggcc   1320

tcttgcggga tatcgtccat tccgacagca tcgccagtca ctatggcgtg ctgctagcgc   1380

tatatgcgtt gatgcaattt ctatgcgcac ccgttctcgg agcactgtcc gaccgctttg   1440

gccgccgccc agtcctgctc gcttcgctac ttggagccac tatcgactac gcgatcatgg   1500

cgaccacacc cgtcctgtgg atccttcaat atgcgcacat acgctgttat gttcaaggtc   1560

ccttcgttta agaacgaaag cggtcttcct tttgagggat gtttcaagtt gttcaaatct   1620

atcaaatttg caaatcccca gtctgtatct agagcgttga atcggtgatg cgatttgtta   1680

attaaattga tggtgtcacc attaccaggt ctagatatac caatggcaaa ctgagcacaa   1740

caataccagt ccggatcaac tggcaccatc tctcccgtag tctcatctaa tttttcttcc   1800

ggatgaggtt ccagatatac cgcaacacct ttattatggt ttccctgagg gaataataga   1860

atgtcccatt cgaaatcacc aattctaaac ctgggcgaat tgtatttcgg gtttgttaac   1920

tcgttccagt caggaatgtt ccacgtgaag ctatcttcca gcaaagtctc cacttcttca   1980

tcaaattgtg gagaatactc ccaatgctct tatctatggg acttccggga aacacagtac   2040
```

-continued

```
cgatacttcc caattcgtct tcagagctca ttgtttgttt gaagagacta atcaaagaat   2100
cgttttctca aaaaaattaa tatcttaact gatagtttga tcaaaggggc aaaacgtagg   2160
ggcaaacaaa cggaaaaatc gtttctcaaa ttttctgatg ccaagaactc taaccagtct   2220
tatctaaaaa ttgccttatg atccgtctct ccggttacag cctgtgtaac tgattaatcc   2280
tgcctttcta atcaccattc taatgtttta attaagggat tttgtcttca ttaacggctt   2340
tcgctcataa aaatgttatg acgttttgcc cgcaggcggg aaaccatcca cttcacgaga   2400
ctgatctcct ctgccggaac accgggcatc tccaacttat aagttggaga aataagagaa   2460
tttcagattg agagaatgaa aaaaaaaaac cctgaaaaaa aaggttgaaa ccagttccct   2520
gaaattattc ccctacttga ctaataagta tataaagacg gtaggtattg attgtaattc   2580
tgtaaatcta tttcttaaac ttcttaaatt ctacttttat agttagtctt ttttttagtt   2640
ttaaaacacc aagaacttag tttcgaataa acacacataa acaaacacca tgagatttcc   2700
ttcaattttt actgcagttt tattcgcagc atcctccgca ttagctgctc cagtcaacac   2760
tacaacagaa gatgaaacgg cacaaattcc ggctgaagct gtcatcggtt actcagattt   2820
agaaggggat ttcgatgttg ctgttttgcc attttccaac agcacaaata acgggttatt   2880
gtttataaat actactattg ccagcattgc tgctaaagaa gaaggggtat ctctagataa   2940
aaggcatacc cgcgtgtcag gaggggcagc agcctccgat accaggggcc ttgtgtccct   3000
ctttagcccc gggtcggctc agaaaatcca gctcgtaaac accaacggca gttggcacat   3060
caacaggact gccctgaact gcaacgactc cctccaaaca gggttctttg ccgcactatt   3120
ctacaaacac aaattcaact cgtctggatg cccagagcgc ttggccagct gtcgctccat   3180
cgacaagttc gctcaggggt ggggtcccct cacttacact gagcctaaca gctcggacca   3240
gaggccctac tgctggcact acgcgcctcg accgtgtggt attgtacccg cgtctcaggt   3300
gtgcggtcca gtgtattgct tcaccccgag ccctgttgtg gtggggacga ccgatcggtt   3360
tggtgtcccc acgtataact ggggggcgaa cgactcggat gtgctgattc tcaacaacac   3420
gcggccgccg cgaggcaact ggttcggctg tacatggatg aatggcactg ggttcaccaa   3480
gacgtgtggg ggcccccgt gcaacatcgg gggggccggc aacaacacct tgacctgccc   3540
cactgactgt tttcggaagc accccgaggc cacttacgcc agatgcggtt ctgggccctg   3600
gctgacacct aggtgtatgg ttcattaccc atataggctc tggcactacc cctgcactgt   3660
caacttcacc atcttcaagg ttaggatgta cgtgggggc gtggagcaca ggttcgaagc   3720
cgcatgcaat tggactcgag gagagcgttg tgacttggag gacagggata gatcagagct   3780
tagctcgctg ctgctgtcta caacagagtg gcaggtgatc gagggcagac accatcacca   3840
ccatcactaa tagttaatta acgatctcga cttggttgaa cacgttgcca aggcttaagt   3900
gaatttactt taaagtcttg catttaaata aattttcttt ttatagcttt atgacttagt   3960
ttcaatttat atactatttt aatgacattt tcgattcatt gattgaaagc tttgtgtttt   4020
ttcttgatgc gctattgcat tgttcttgtc tttttcgcca catgtaatat ctgtagtaga   4080
tacctgatac attgtggatg ctgagtgaaa ttttagttaa taatggaggc gctcttaata   4140
attttgggga tattggcttt tttttttaaa gtttacaaat gaatttttttc cgccaggata   4200
acgattctga agttactctt agcgttccta tcggtacagc catcaaatca tgcctataaa   4260
tcatgcctat atttgcgtgc agtcagtatc atctacatga aaaaaactcc cgcaatttct   4320
tatagaatac gttgaaaatt aaatgtacgc gccaagataa gataacatat atctagctag   4380
atgcagtaat atacacagat tcccgcggac gtgggaagga aaaaattaga taacaaaatc   4440
```

-continued

```
tgagtgatat ggaaattccg ctgtatagct catatctttc ccttcaacac cagaaatgta   4500
aaaatcttgt tacgaaggat ctttttgcta atgtttctcg ctcaatcctc atttcttccc   4560
tacgaagagt caaatctact tgttttctgc cggtatcaag atccatatct tctagtttca   4620
ccatcaaagt ccaatttcta gtatacagtt tatgtcccaa cgtaacagac aatcaaaatt   4680
ggaaaggata agtatccttc aaagaatgat tctgcgctgg ctcctgaacc gcctaatggg   4740
aacagagaag tccaaaacga tgctataaga accagaaata aaacgataaa accataccag   4800
gatcctctac gccggacgca tcgtggccgg catcaccggc gccacaggtg cggttgctgg   4860
cccctatatc gccgacatca ccgatgggga agatcgggct cgccacttcg ggctcatgag   4920
cgcttgtttc ggcgtgggta tggtggcagg ccccgtggcc gggggactgt tgggcgccat   4980
ctccttgcat gcaccattcc ttgcggcggc ggtgctcaac ggcctcaacc tactactggg   5040
ctgcttccta atgcaggagt cgcataaggg agagcgtcga ccgatgccct tgagagcctt   5100
caacccagtc agctccttcc ggtgggcgcg gggcatgact atcgtcgccg cacttatgac   5160
tgtcttcttt atcatgcaac tcgtaggaca ggtgccggca gcgctctggg tcattttcgg   5220
cgaggaccgc tttcgctgga gcgcgacgat gatcggcctg tcgcttgcgg tattcggaat   5280
cttgcacgcc ctcgctcaag ccttcgtcac tggtcccgcc accaaacgtt tcggcgagaa   5340
gcaggccatt atcgccggca tggcggccga cgcgctgggc tacgtcttgc tggcgttcgc   5400
gacgcgaggc tggatggcct tccccattat gattcttctc gcttccggcg gcatcgggat   5460
gcccgcgttg caggccatgc tgtccaggca ggtagatgac gaccatcagg gacagcttca   5520
aggatcgctc gcggctctta ccagcctaac ttcgatcact ggaccgctga tcgtcacggc   5580
gatttatgcc gcctcggcga gcacatggaa cgggttggca tggattgtag gcgccgccct   5640
ataccttgtc tgcctccccg cgttgcgtcg cggtgcatgg agccgggcca cctcgacctg   5700
aatggaagcc ggcggcacct cgctaacgga ttcaccactc caagaattgg agccaatcaa   5760
ttcttgcgga gaactgtgaa tgcgcaaacc aacccttggc agaacatatc catcgcgtcc   5820
gccatctcca gcagccgcac gcggcgcatc tcgggcagcg ttgggtcctg gccacgggtg   5880
cgcatgatcg tgctcctgtc gttgaggacc cggctaggct ggcggggttg ccttactggt   5940
tagcagaatg aatcaccgat acgcgagcga acgtgaagcg actgctgctg caaaacgtct   6000
gcgacctgag caacaacatg aatggtcttc ggtttccgtg tttcgtaaag tctggaaacg   6060
cggaagtcag cgccctgcac cattatgttc cggatctgca tcgcaggatg ctgctggcta   6120
ccctgtggaa cacctacatc tgtattaacg aagcgctggc attgaccctg agtgattttt   6180
ctctggtccc gccgcatcca taccgccagt tgtttaccct cacaacgttc cagtaaccgg   6240
gcatgttcat catcagtaac ccgtatcgtg agcatcctct ctcgtttcat cggtatcatt   6300
acccccatga acagaaattc ccccttacac ggaggcatca agtgaccaaa caggaaaaaa   6360
ccgcccttaa catggcccgc tttatcagaa gccagacatt aacgcttctg gagaaactca   6420
acgagctgga cgcggatgaa caggcagaca tctgtgaatc gcttcacgac cacgctgatg   6480
agctttaccg cagctgcctc gcgcgtttcg gtgatgacgg tgaaaacctc tgacacatgc   6540
agctcccgga gacggtcaca gcttgtctgt aagcggtgcc gggagcagac aagcccgtca   6600
gggcgcgtca gcgggtgttg gcgggtgtcg gggcgcagcc atgacccagt cacgtagcga   6660
tagcggagtg tatactggct taactatgcg gcatcagagc agattgtact gagagtgcac   6720
catatgcggt gtgaaatacc gcacagatgc gtaaggagaa aataccgcat caggcgctct   6780
```

-continued

```
tccgcttcct cgctcactga ctcgctgcgc tcggtcgttc ggctgcggcg agcggtatca   6840
gctcactcaa aggcggtaat acggttatcc acagaatcag gggataacgc aggaaagaac   6900
atgtgagcaa aaggccagca aaaggccagg aaccgtaaaa aggccgcgtt gctggcgttt   6960
ttccataggc tccgcccccc tgacgagcat cacaaaaatc gacgctcaag tcagaggtgg   7020
cgaaacccga caggactata aagataccag gcgtttcccc ctggaagctc cctcgtgcgc   7080
tctcctgttc cgaccctgcc gcttaccgga tacctgtccg cctttctccc ttcgggaagc   7140
gtggcgcttt ctcatagctc acgctgtagg tatctcagtt cggtgtaggt cgttcgctcc   7200
aagctgggct gtgtgcacga accccccgtt cagcccgacc gctgcgcctt atccggtaac   7260
tatcgtcttg agtccaaccc ggtaagacac gacttatcgc cactggcagc agccactggt   7320
aacaggatta gcagagcgag gtatgtaggc ggtgctacag agttcttgaa gtggtggcct   7380
aactacggct acactagaag gacagtattt ggtatctgcg ctctgctgaa gccagttacc   7440
ttcggaaaaa gagttggtag ctcttgatcc ggcaaacaaa ccaccgctgg tagcggtggt   7500
tttttgttt gcaagcagca gattacgcgc agaaaaaaag gatctcaaga agatcctttg    7560
atcttttcta cggggtctga cgctcagtgg aacgaaaact cacgttaagg gattttggtc   7620
atgagattat caaaaaggat cttcacctag atccttttaa attaaaaatg aagttttaaa   7680
tcaatctaaa gtatatatga gtaaacttgg tctgacagtt accaatgctt aatcagtgag   7740
gcacctatct cagcgatctg tctatttcgt tcatccatag ttgcctgact ccccgtcgtg   7800
tagataacta cgatacggga gggcttacca tctggcccca gtgctgcaat gataccgcga   7860
gacccacgct caccggctcc agatttatca gcaataaacc agccagccgg aagggccgag   7920
cgcagaagtg gtcctgcaac tttatccgcc tccatccagt ctattaattg ttgccgggaa   7980
gctagagtaa gtagttcgcc agttaatagt ttgcgcaacg ttgttgccat tgctgcaggc   8040
atcgtggtgt cacgctcgtc gtttggtatg gcttcattca gctccggttc ccaacgatca   8100
aggcgagtta catgatcccc catgttgtgc aaaaaagcgg ttagctcctt cggtcctccg   8160
atcgttgtca gaagtaagtt ggccgcagtg ttatcactca tggttatggc agcactgcat   8220
aattctctta ctgtcatgcc atccgtaaga tgcttttctg tgactggtga gtactcaacc   8280
aagtcattct gagaatagtg tatgcggcga ccgagttgct cttgcccggc gtcaacacgg   8340
gataataccg cgccacatag cagaacttta aaagtgctca tcattggaaa acgttcttcg   8400
gggcgaaaac tctcaaggat cttaccgctg ttgagatcca gttcgatgta acccactcgt   8460
gcacccaact gatcttcagc atcttttact ttcaccagcg tttctgggtg agcaaaaaca   8520
ggaaggcaaa atgccgcaaa aaagggaata agggcgacac ggaaatgttg aatactcata   8580
ctcttccttt ttcaatatta ttgaagcatt tatcagggtt attgtctcat gagcggatac   8640
atatttgaat gtatttagaa aaataaacaa ataggggttc cgcgcacatt tccccgaaaa   8700
gtgccacctg acgtctaaga aaccattatt atcatgacat taacctataa aaataggcg    8760
tatcacgagg ccctttcgtc ttcaagaatt ctcatgtttg acagcttatc atcgatccac   8820
ttgtatattt ggatgaattt ttgaggaatt ctgaaccagt cctaaaacga gtaaatagga   8880
ccggcaattc ttcaagcaat aaacaggaat accaattatt aaaagataac ttagtcagat   8940
cgtacaataa agctttgaag aaaaatgcgc cttattcaat ctttgcataa aaaaatggcc   9000
caaaatctca cattggaaga catttgatga cctcatttct ttcaatgaag ggcctaacgg   9060
agttgactaa tgttgtggga aattggaccg ataagcgtgc ttctgccgtg gccaggacaa   9120
cgtatactca tcagataaca gcaatacctg atcactactt cgcactagtt tctcggtact   9180
```

-continued atgcatatga tccaatatca aaggaaatga tagcattgaa ggatgagact aatccaattg 9240
aggagtggca gcatatagaa cagctaaagg gtagtgctga aggaagcata cgatacccg 9300
catggaatgg gataatatca caggaggtac tagactacct ttcatcctac ataaatagac 9360
gcatataagt acgcatttaa gcataaacac gcactatgcc gttcttctca tgtatatata 9420
tatacaggca acacgcagat ataggtgcga cgtgaacagt gagctgtatg tgcgcagctc 9480
gcgttgcatt ttcggaagcg ctcgttttcg gaaacgcttt gaagttccta ttccgaagtt 9540
cctattctct agaaagtata ggaacttcag agcgcttttg aaaaccaaaa gcgctctgaa 9600
gacgcacttt caaaaaacca aaaacgcacc ggactgtaac gagctactaa aatattgcga 9660
ataccgcttc cacaaacatt gctcaaaagt atctctttgc tatatatctc tgtgctatat 9720
ccctatataa ccatcccatc cacctttcgc tccttgaact tgcatctaaa ctcgacctct 9780
acatttttta tgtttatctc tagtattacc tcttagacaa aaaaattgta gtaagaacta 9840
ttcatagagt taatcgaaaa caatacgaaa atgtaaacat ttcctatacg tagtatatag 9900
agacaaaata gaagaaaccg ttcataattt tctgaccaat gaagaatcat caacgctatc 9960
actttctgtt cacaaagtat gcgcaatcca catcggtata gaatataatc ggggatgcct 10020
ttatcttgaa aaaatgcacc cgcagcttcg ctagtaatca gtaaacgcgg gaagtggagt 10080
caggcttttt ttatggaaga gaaaatagac accaaagtag ccttcttcta accttaacgg 10140
acctacagtg caaaaagtta tcaagagact gcattataga gcgcacaaag gagaaaaaaa 10200
gtaatctaag atgctttgtt agaaaaatag cgctctcggg atgcattttt gtagaacaaa 10260
aaagaagtat agattcttgt tggtaaaata gcgctctcgc gttgcatttc tgttctgtaa 10320
aaatgcagct cagattcttt gtttgaaaaa ttagcgctct cgcgttgcat ttttgtttta 10380
caaaaatgaa gcacagattc ttcgttggta aaatagcgct ttcgcgttgc atttctgttc 10440
tgtaaaaatg cagctcagat tctttgtttg aaaaattagc gctctcgcgt tgcatttttg 10500
ttctacaaaa tgaagcacag atgcttcgtt aacaaagata tgctattgaa gtgcaagatg 10560
gaaacgcaga aaatgaaccg gggatgcgac gtgcaagatt acctatgcaa tagatgcaat 10620
agtttctcca ggaaccgaaa tacatacatt gtcttccgta aagcgctaga ctatatatta 10680
ttatacaggt tcaaatatac tatctgtttc agggaaaact cccaggttcg gatgttcaaa 10740
attcaatgat gggtaacaag tacgatcgta aatctgtaaa acagtttgtc ggatattagg 10800
ctgtatctcc tcaaagcgta ttcgaatatc attgagaagc tgcatttttt tttttttttt 10860
tttttttttt ttttttatat atatttcaag gatataccat tgtaatgtct gcccctaaga 10920
agatcgtcgt tttgccaggt gaccacgttg gtcaagaaat cacagccgaa gccattaagg 10980
ttcttaaagc tatttctgat gttcgttcca atgtcaagtt cgatttcgaa aatcatttaa 11040
ttggtggtgc tgctatcgat gctacaggtg tcccacttcc agatgaggcg ctggaagcct 11100
ccaagaaggt tgatgccgtt ttgttaggtg ctgtgggtgg tcctaaatgg ggtaccggta 11160
gtgttagacc tgaacaaggt ttactaaaaa tccgtaaaga acttcaattg tacgccaact 11220
taagaccatg taactttgca tccgactctc ttttagactt atctccaatc aagccacaat 11280
ttgctaaagg tactgacttc gttgttgtca gagaattagt gggaggtatt tactttggta 11340
agagaaagga agacgatggt gatggtgtcg cttgggatag tgaacaatac accgttccag 11400
aagtgcaaag aatcacaaga atggccgctt tcatggccct acaacatgag ccaccattgc 11460
ctatttggtc cttggataaa gctaatgttt tggcctcttc aagattatgg agaaaaactg 11520

-continued

```
tggaggaaac catcaagaac gaattcccta cattgaaggt tcaacatcaa ttgattgatt  11580
ctgccgccat gatcctagtt aagaacccaa cccacctaaa tggtattata atcaccagca  11640
acatgtttgg tgatatcatc tccgatgaag cctccgttat cccaggttcc ttgggtttgt  11700
tgccatctgc gtccttggcc tctttgccag acaagaacac cgcatttggt ttgtacgaac  11760
catgccacgg ttctgctcca gatttgccaa agaataaggt tgaccctatc gccactatct  11820
tgtctgctgc aatgatgttg aaattgtcat tgaacttgcc tgaagaaggt aaggccattg  11880
aagatgcagt taaaaaggtt ttggatgcag gtatcagaac tggtgattta ggtggttcca  11940
acagtaccac cgaagtcggt gatgctgtcg ccgaagaagt taagaaaatc cttgcttaaa  12000
aagattctct ttttttatga tatttgtaca aaaaaaaaaa aaaaaaaaaa aaaaaaaaaa  12060
aaaaaaaaaa aaaaatgcag cgtcacatcg gataataatg atggcagcca ttgtagaagt  12120
gccttttgca tttctagtct ctttctcggt ctagctagtt ttactacatc gcgaagatag  12180
aatcttagat cacactgcct ttgctgagct ggatcatatg agtaacaaaa gagtggtaag  12240
gcctcgttaa aggacaagga cctgagcgga agtgtatcgt aaagtagacg gagtatacta  12300
gtatagtcta tagtccgtgg aattctaagt gccagcttta taatgtcatt ctccttacta  12360
cagacccgcc tgaaagtaga cacatcatca tcagtaagct ttgacaaaaa gcattgagta  12420
gctaactctt ctatgcaatc tatagctgtt ttataaggca ttcaatggac agattgaggt  12480
ttttgaaaca tactagtgaa attagcctta atcccttctc gaagttaatc atgcattatg  12540
gtgtaaaaaa tgcaactcgc gttgctctac tttttcccga atttccaaat acgcagctgg  12600
ggtgattgct cgatttcgta acgaaagttt tgtttataaa aaccgcgaaa accttctgta  12660
acagatagat ttttacagcg ctgatataca atgacatcag ctgtaatgga aaataactga  12720
aatatgaatg gcgagagact gcttgcttgt attaagcaat gtattatgca gcacttccaa  12780
cctatggtgt acgatgaaag taggtgtgta atcgagacga caagggggac ttttccagtt  12840
cctgatcatt ataagaaata caaaacgtta gcatttgcat ttgttggaca tgtactgaat  12900
acagacgaca caccggtaat tgaaaaagaa ctggattggc ctgatcctgc actagtgtac  12960
aatacaattg tcgatcgaat cataaatcac ccagaattat cacagtttat atcggttgca  13020
tttattagtc agttaaaggc caccatcgga gagggtttag atattaatgt aaaaggcacg  13080
ctaaaccgca ggggaaaggg tatcagaagg cctaaaggcg tattttttag atacatggaa  13140
tctccatttg tcaatacaaa ggtcactgca ttcttctctt atcttcgaga ttataataaa  13200
attgcctcag aatatcacaa taatactaaa ttcattctca cgttttcatg tcaagcatat  13260
tgggcatctg gcccaaactt ctccgccttg aagaatgtta tttggtgctc cataattcat  13320
gaatacattt ctaagtttgt ggaaagagaa caggataaag gtcatatagg agatcaggag  13380
ctaccgcctg aagaggaccc ttctcgtgaa ctaaacaatg tacaacatga agtcaatagt  13440
ttaacggaac aagatgcgga ggcggatgaa ggattgtggg gtgaaataga ttcattatgt  13500
gaaaaatggc agtctgaagc ggagagtcaa actgaggcgg agataatagc cgacaggata  13560
attggaaata gccagaggat ggcgaacctc aaaattcgtc gtacaaagtt caaaagtgtc  13620
ttgtatcata tactaaagga actaattcaa tctcagggaa ccgtaaaggt ttatcgcggt  13680
agtagttttt cacacgattc gataaagata agcttacatt atgaagagca gcatattaca  13740
gccgtatggg tctacttgat agtaaaattt gaagagcatt ggaagcctgt tgatgtagag  13800
gtcgagttta gatgcaagtt caaggagcga aaggtggatg ggtaggttat atagggatat  13860
agcacagaga tatatagcaa agagatactt ttgaggcaat gtttgtggaa gcggtattcg  13920
```

-continued

```
caatatttta gtagctcgtt acagtccggt gcgtttttgg ttttttgaaa gtgcgtcttc  13980
agagcgcttt tggttttcaa aagcgctctg aagttcctat actttctaga gaataggaac  14040
ttcggaatag gaacttcaaa gcgtttccga aaacgagcgc ttccgaaaat gcaacgcgag  14100
ctgcgcacat acagctcact gttcacgtcg cacctatatc tgcgtgttgc ctgtatatat  14160
atatacatga gaagaacggc atagtgcgtg tttatgctta aatgcgtact tatatgcgtc  14220
tatttatgta ggatgaaagg tagtctagta cctcctgtga tattatccca ttccatgcgg  14280
ggtatcgtat gcttccttca gcactaccct ttagctgttc tatatgctgc cactcctcaa  14340
ttggattagt ctcatccttc aatgcattca tttcctttga tattggatca taccctagaa  14400
gtattacgtg attttctgcc ccttaccctc gttgctactc tcctttttt cgtgggaacc  14460
gctttagggc cctcagtgat ggtgttttgt aatttatatg ctcctcttgc atttgtgtct  14520
ctacttcttg ttcgcctgga gggaacttct tcatttgtat tagcatggtt cacttcagtc  14580
cttccttcca actcactctt tttttgctgt aaacgattct ctgccgccag ttcattgaaa  14640
ctattgaata tatcctttag agattccggg atgaataaat cacctattaa agcagcttga  14700
cgatctggtg gaactaaagt aagcaattgg gtaacgacgc ttacgagctt cataacatct  14760
tcttccgttg gagctggtgg gactaataac tgtgtacaat ccatttttct catgagcatt  14820
tcggtagctc tcttcttgtc tttctcgggc aatcttccta ttattatagc aatagatttg  14880
tatagttgct ttctattgtc taacagcttg ttattctgta gcatcaaatc tatggcagcc  14940
tgacttgctt cttgtgaaga gagcatacca tttccaatcg aagatacgct ggaatcttct  15000
gcgctagaat caagaccata cggcctaccg gttgtgagag attccatggg ccttatgaca  15060
tatcctggaa agagtagctc atcagactta cgtttactct ctatatcaat atctacatca  15120
ggagcaatca tttcaataaa cagccgacat acatcccaga cgctataagc tgtacgtgct  15180
tttaccgtca gattcttggc tgtttcaatg tcgtccattt tggttttctt ttaccagtat  15240
tgttcgtttg ataatgtatt cttgcttatt acattataaa atctgtgcag atcacatgtc  15300
aaaacaactt tttatcacaa gatagtaccg caaaacgaac ctgcgggccg tctaaaaatt  15360
aaggaaaagc agcaaaggtg catttttaaa atatgaaatg aagataccgc agtaccaatt  15420
attttcgcag tacaaataat gcgcggccgg tgcatttttc gaaagaacgc gagacaaaca  15480
ggacaattaa agttagtttt tcgagttagc gtgtttgaat actgcaagat acaagataaa  15540
tagagtagtt gaaactagat atcaattgca cacaagatcg gcgctaagca tgccacaatt  15600
tggtatatta tgtaaaacac cacctaaggt gcttgttcgt cagtttgtgg aaaggtttga  15660
aagaccttca ggtgagaaaa tagcattatg tgctgctgaa ctaacctatt tatgttggat  15720
gattacacat aacggaacag caatcaagag agccacattc atgagctata atactatcat  15780
aagcaattcg ctgagtttcg atattgtcaa taaatcactc cagtttaaat acaagacgca  15840
aaaagcaaca attctggaag cctcattaaa gaaattgatt cctgcttggg aatttacaat  15900
tattccttac tatggacaaa aacatcaatc tgatatcact gatattgtaa gtagtttgca  15960
attacagttc gaatcatcgg aagaagcaga taagggaaat agccacagta aaaaaatgct  16020
aaagcacttc taagtgaggg tgaaagcatc tgggagatca ctgagaaaat actaaattcg  16080
tttgagtata cttcgagatt tacaaaaaca aaaactttat accaattcct cttcctagct  16140
actttcatca attgtggaag attcagcgat attaagaacg ttgatccgaa atcatttaaa  16200
ttagtccaaa ataagtatct gggagtaata atccagtgtt tagtgacaga gacaaagaca  16260
```

-continued agcgttagta ggcacatata cttctttagc gcaaggggta g 16301

<210> SEQ ID NO 48
<211> LENGTH: 4989
<212> TYPE: DNA
<213> ORGANISM: Artificial Sequence
<220> FEATURE:
<223> OTHER INFORMATION: Description of Artificial Sequence: vector pYIG7

<400> SEQUENCE: 48
agcgcccaat acgcaaaccg cctctccccg cgcgttggcc gattcattaa tgcagctggc 60
acgacaggtt tcccgactgg aaagcgggca gtgagcgcaa cgcaattaat gtgagttagc 120
tcactcatta ggcaccccag gctttacact ttatgcttcc ggctcgtatg ttgtgtggaa 180
ttgtgagcgg ataacaattt cacacaggaa acagctatga ccatgattac gaatttaata 240
cgactcacta tagggaattc ggatccttca atatgcgcac atacgctgtt atgttcaagg 300
tcccttcgtt taagaacgaa agcggtcttc cttttgaggg atgtttcaag ttgttcaaat 360
ctatcaaatt tgcaaatccc cagtctgtat ctagagcgtt gaatcggtga tgcgatttgt 420
taattaaatt gatggtgtca ccattaccag gtctagatat accaatggca aactgagcac 480
aacaatacca gtccggatca actggcacca tctctcccgt agtctcatct aatttttctt 540
ccggatgagg ttccagatat accgcaacac ctttattatg gtttccctga gggaataata 600
gaatgtccca ttcgaaatca ccaattctaa acctgggcga attgtatttc gggtttgtta 660
actcgttcca gtcaggaatg ttccacgtga agctatcttc cagcaaagtc tccacttctt 720
catcaaattg tggagaatac tcccaatgct cttatctatg ggacttccgg gaaacacagt 780
accgatactt cccaattcgt cttcagagct cattgtttgt ttgaagagac taatcaaaga 840
atcgttttct caaaaaaatt aatatcttaa ctgatagttt gatcaaaggg gcaaaacgta 900
ggggcaaaca aacggaaaaa tcgtttctca aattttctga tgccaagaac tctaaccagt 960
cttatctaaa aattgcctta tgatccgtct ctccggttac agcctgtgta actgattaat 1020
cctgcctttc taatcaccat tctaatgttt taattaaggg attttgtctt cattaacggc 1080
tttcgctcat aaaaatgtta tgacgttttg cccgcaggcg ggaaaccatc cacttcacga 1140
gactgatctc ctctgccgga acaccgggca tctccaactt ataagttgga gaaataagag 1200
aatttcagat tgagagaatg aaaaaaaaaa accctgaaaa aaaaggttga aaccagttcc 1260
ctgaaattat tcccctactt gactaataag tatataaaga cggtaggtat tgattgtaat 1320
tctgtaaatc tatttcttaa acttcttaaa ttctactttt atagttagtc ttttttttag 1380
ttttaaaaca ccaagaactt agtttcgaat aaacacacat aaacaaacac catgaggtct 1440
ttgctaatac tagtgctttg cttcctgccc ctggctgctc tgggggtacc agatctcgac 1500
ttggttgaac acgttgccaa ggcttaagtg aatttacttt aaagtcttgc atttaaataa 1560
attttctttt tatagcttta tgacttagtt tcaatttata tactatttta atgacatttt 1620
cgattcattg attgaaagct ttgtgttttt tcttgatgcg ctattgcatt gttcttgtct 1680
ttttcgccac atgtaatatc tgtagtagat acctgataca ttgtggatgc tgagtgaaat 1740
tttagttaat aatggaggcg ctcttaataa ttttggggat attggctttt ttttttaaag 1800
tttacaaatg aattttttcc gccaggataa cgattctgaa gttactctta gcgttcctat 1860
cggtacagcc atcaaatcat gcctataaat catgcctata tttgcgtgca gtcagtatca 1920
tctacatgaa aaaaactccc gcaatttctt atagaatacg ttgaaaatta aatgtacgcg 1980

-continued ccaagataag ataacatata tctagctaga tgcagtaata tacacagatt cccgcggacg 2040
tgggaaggaa aaaattagat aacaaaatct gagtgatatg gaaattccgc tgtatagctc 2100
atatctttcc cttcaacacc agaaatgtaa aaatcttgtt acgaaggatc tttttgctaa 2160
tgtttctcgc tcaatcctca tttcttccct acgaagagtc aaatctactt gttttctgcc 2220
ggtatcaaga tccatatctt ctagtttcac catcaaagtc caatttctag tatacagttt 2280
atgtcccaac gtaacagaca atcaaaattg gaaaggataa gtatccttca aagaatgatt 2340
ctgcgctggc tcctgaaccg cctaatggga acagagaagt ccaaaacgat gctataagaa 2400
ccagaaataa aacgataaaa ccataccagg atccaagctt ggcactggcc gtcgttttac 2460
aacgtcgtga ctgggaaaac cctggcgtta cccaacttaa tcgccttgca gcacatcccc 2520
ctttcgccag ctggcgtaat agcgaagagg cccgcaccga tcgcccttcc caacagttgc 2580
gcagcctgaa tggcgaatgg gaaattgtaa acgttaatat tttgttaaaa ttcgcgttaa 2640
atttttgtta aatcagctca ttttttaacc aataggccga aatcggcaaa atcccttata 2700
aatcaaaaga atagaccgag atagggttga gtgttgttcc agtttggaac aagagtccac 2760
tattaaagaa cgtggactcc aacgtcaaag ggcgaaaaac cgtctatcag ggcgatggcc 2820
cactacgtga accatcaccc taatcaagtt ttttggggtc gaggtgccgt aaagcactaa 2880
atcggaaccc taaagggagc ccccgattta gagcttgacg gggaaagccg gcgaacgtgg 2940
cgagaaagga agggaagaaa gcgaaaggag cgggcgctag ggcgctggca agtgtagcgg 3000
tcacgctgcg cgtaaccacc acacccgccg cgcttaatgc gccgctacag ggcgcgtcag 3060
gtggcacttt tcggggaaat gtgcgcggaa cccctatttg tttatttttc taaatacatt 3120
caaatatgta tccgctcatg agacaataac cctgataaat gcttcaataa tattgaaaaa 3180
ggaagagtat gagtattcaa catttccgtg tcgcccttat tccctttttt gcggcatttt 3240
gccttcctgt ttttgctcac ccagaaacgc tggtgaaagt aaaagatgct gaagatcagt 3300
tgggtgcacg agtgggttac atcgaactgg atctcaacag cggtaagatc cttgagagtt 3360
ttcgccccga agaacgtttt ccaatgatga gcacttttaa agttctgcta tgtggcgcgg 3420
tattatcccg tattgacgcc gggcaagagc aactcggtcg ccgcatacac tattctcaga 3480
atgacttggt tgagtactca ccagtcacag aaaagcatct tacggatggc atgacagtaa 3540
gagaattatg cagtgctgcc ataaccatga gtgataacac tgcggccaac ttacttctga 3600
caacgatcgg aggaccgaag gagctaaccg cttttttgca caacatgggg gatcatgtaa 3660
ctcgccttga tcgttgggaa ccggagctga atgaagccat accaaacgac gagcgtgaca 3720
ccacgatgcc tgtagcaatg gcaacaacgt tgcgcaaact attaactggc gaactactta 3780
ctctagcttc ccggcaacaa ttaatagact ggatggaggc ggataaagtt gcaggaccac 3840
ttctgcgctc ggcccttccg gctggctggt ttattgctga taaatctgga gccggtgagc 3900
gtgggtctcg cggtatcatt gcagcactgg ggccagatgg taagccctcc cgtatcgtag 3960
ttatctacac gacggggagt caggcaacta tggatgaacg aaatagacag atcgctgaga 4020
taggtgcctc actgattaag cattggtaac tgtcagacca agtttactca tatatacttt 4080
agattgattt aaaacttcat ttttaattta aaaggatcta ggtgaagatc ctttttgata 4140
atctcatgac caaaatccct taacgtgagt tttcgttcca ctgagcgtca gaccccgtag 4200
aaaagatcaa aggatcttct tgagatcctt tttttctgcg cgtaatctgc tgcttgcaaa 4260
caaaaaaacc accgctacca gcggtggttt gtttgccgga tcaagagcta ccaactcttt 4320
ttccgaaggt aactggcttc agcagagcgc agataccaaa tactgtcctt ctagtgtagc 4380

-continued cgtagttagg ccaccacttc aagaactctg tagcaccgcc tacatacctc gctctgctaa 4440
tcctgttacc agtggctgct gccagtggcg ataagtcgtg tcttaccggg ttggactcaa 4500
gacgatagtt accggataag gcgcagcggt cgggctgaac ggggggttcg tgcacacagc 4560
ccagcttgga gcgaacgacc tacaccgaac tgagatacct acagcgtgag cattgagaaa 4620
gcgccacgct tcccgaaggg agaaaggcgg acaggtatcc ggtaagcggc agggtcggaa 4680
caggagagcg cacgagggag cttccagggg gaaacgcctg gtatctttat agtcctgtcg 4740
ggtttcgcca cctctgactt gagcgtcgat ttttgtgatg ctcgtcaggg gggcggagcc 4800
tatggaaaaa cgccagcaac gcggcctttt tacggttcct ggccttttgc tggccttttg 4860
ctcacatgtt ctttcctgcg ttatcccctg attctgtgga taaccgtatt accgcctttg 4920
agtgagctga taccgctcgc cgcagccgaa cgaccgagcg cagcgagtca gtgagcgagg 4980
aagcggaag 4989

<210> SEQ ID NO 49
<211> LENGTH: 5422
<212> TYPE: DNA
<213> ORGANISM: Artificial Sequence
<220> FEATURE:
<223> OTHER INFORMATION: Description of Artificial Sequence: vector pYIG7E1

<400> SEQUENCE: 49
agcgcccaat acgcaaaccg cctctccccg cgcgttggcc gattcattaa tgcagctggc 60
acgacaggtt tcccgactgg aaagcgggca gtgagcgcaa cgcaattaat gtgagttagc 120
tcactcatta ggcaccccag gctttacact ttatgcttcc ggctcgtatg ttgtgtggaa 180
ttgtgagcgg ataacaattt cacacaggaa acagctatga ccatgattac gaatttaata 240
cgactcacta tagggaattc ggatccttca atatgcgcac atacgctgtt atgttcaagg 300
tcccttcgtt taagaacgaa agcggtcttc cttttgaggg atgtttcaag ttgttcaaat 360
ctatcaaatt tgcaaatccc cagtctgtat ctagagcgtt gaatcggtga tgcgatttgt 420
taattaaatt gatggtgtca ccattaccag gtctagatat accaatggca aactgagcac 480
aacaatacca gtccggatca actggcacca tctctcccgt agtctcatct aatttttctt 540
ccggatgagg ttccagatat accgcaacac ctttattatg gtttccctga gggaataata 600
gaatgtccca ttcgaaatca ccaattctaa acctgggcga attgtatttc gggtttgtta 660
actcgttcca gtcaggaatg ttccacgtga agctatcttc cagcaaagtc tccacttctt 720
catcaaattg tggagaatac tcccaatgct cttatctatg ggacttccgg gaaacacagt 780
accgatactt cccaattcgt cttcagagct cattgtttgt ttgaagagac taatcaaaga 840
atcgttttct caaaaaaatt aatatcttaa ctgatagttt gatcaaaggg gcaaaacgta 900
ggggcaaaca aacggaaaaa tcgtttctca aatttctga tgccaagaac tctaaccagt 960
cttatctaaa aattgcctta tgatccgtct ctccggttac agcctgtgta actgattaat 1020
cctgcctttc taatcaccat tctaatgttt taattaaggg attttgtctt cattaacggc 1080
tttcgctcat aaaaatgtta tgacgttttg cccgcaggcg ggaaaccatc cacttcacga 1140
gactgatctc ctctgccgga acaccgggca tctccaactt ataagttgga gaaataagag 1200
aatttcagat tgagagaatg aaaaaaaaaa accctgaaaa aaaaggttga aaccagttcc 1260
ctgaaattat tcccctactt gactaataag tatataaaga cggtaggtat tgattgtaat 1320
tctgtaaatc tatttcttaa acttcttaaa ttctactttt atagttagtc ttttttttag 1380

-continued ttttaaaaca ccaagaactt agtttcgaat aaacacacat aaacaaacac catgaggtct 1440
ttgctaatac tagtgctttg cttcctgccc ctggctgctc tggggtatga ggtgcgcaac 1500
gtgtccggga tgtaccatgt cacgaacgac tgctccaact caagcattgt gtatgaggca 1560
gcggacatga tcatgcacac ccccgggtgc gtgccctgcg ttcgggagaa caactcttcc 1620
cgctgctggg tagcgctcac cccccacgctc gcagctagga acgccagcgt ccccaccacg 1680
acaatacgac gccacgtcga tttgctcgtt ggggcggctg ctttctgttc cgctatgtac 1740
gtgggggacc tctgcggatc tgtcttcctc gtctcccagc tgttcaccat ctcgcctcgc 1800
cggcatgaga cggtgcagga ctgcaattgc tcaatctatc ccggccacat aacgggtcac 1860
cgtatggctt gggatatgat gatgaactgg taatagaccc ttctcacctc ggccgataag 1920
ctcagatctc gacttggttg aacacgttgc caaggcttaa gtgaatttac tttaaagtct 1980
tgcatttaaa taaattttct ttttatagct ttatgactta gtttcaattt atatactatt 2040
ttaatgacat tttcgattca ttgattgaaa gctttgtgtt ttttcttgat gcgctattgc 2100
attgttcttg tctttttcgc cacatgtaat atctgtagta gatacctgat acattgtgga 2160
tgctgagtga aattttagtt aataatggag gcgctcttaa taattttggg gatattggct 2220
ttttttttta aagtttacaa atgaattttt tccgccagga taacgattct gaagttactc 2280
ttagcgttcc tatcggtaca gccatcaaat catgcctata aatcatgcct atatttgcgt 2340
gcagtcagta tcatctacat gaaaaaaact cccgcaattt cttatagaat acgttgaaaa 2400
ttaaatgtac gcgccaagat aagataacat atatctagct agatgcagta atatacacag 2460
attcccgcgg acgtgggaag gaaaaaatta gataacaaaa tctgagtgat atggaaattc 2520
cgctgtatag ctcatatctt tcccttcaac accagaaatg taaaaatctt gttacgaagg 2580
atctttttgc taatgtttct cgctcaatcc tcatttcttc cctacgaaga gtcaaatcta 2640
cttgttttct gccggtatca agatccatat cttctagttt caccatcaaa gtccaatttc 2700
tagtatacag tttatgtccc aacgtaacag acaatcaaaa ttggaaagga taagtatcct 2760
tcaaagaatg attctgcgct ggctcctgaa ccgcctaatg ggaacagaga agtccaaaac 2820
gatgctataa gaaccagaaa taaaacgata aaaccatacc aggatccaag cttggcactg 2880
gccgtcgttt tacaacgtcg tgactgggaa aaccctggcg ttacccaact taatcgcctt 2940
gcagcacatc ccccttttcgc cagctggcgt aatagcgaag aggcccgcac cgatcgccct 3000
tcccaacagt tgcgcagcct gaatggcgaa tgggaaattg taaacgttaa tattttgtta 3060
aaattcgcgt taaatttttg ttaaatcagc tcatttttta accaataggc cgaaatcggc 3120
aaaatccctt ataaatcaaa agaatagacc gagatagggt tgagtgttgt tccagtttgg 3180
aacaagagtc cactattaaa gaacgtggac tccaacgtca aagggcgaaa aaccgtctat 3240
cagggcgatg gcccactacg tgaaccatca ccctaatcaa gttttttggg gtcgaggtgc 3300
cgtaaagcac taaatcggaa ccctaaaggg agcccccgat ttagagcttg acggggaaag 3360
ccggcgaacg tggcgagaaa ggaagggaag aaagcgaaag gagcgggcgc tagggcgctg 3420
gcaagtgtag cggtcacgct gcgcgtaacc accacacccg ccgcgcttaa tgcgccgcta 3480
cagggcgcgt caggtggcac ttttcgggga aatgtgcgcg gaacccctat ttgtttattt 3540
ttctaaatac attcaaatat gtatccgctc atgagacaat aaccctgata aatgcttcaa 3600
taatattgaa aaaggaagag tatgagtatt caacatttcc gtgtcgccct tattcccttt 3660
tttgcggcat tttgccttcc tgtttttgct cacccagaaa cgctggtgaa agtaaaagat 3720
gctgaagatc agttgggtgc acgagtgggt tacatcgaac tggatctcaa cagcggtaag 3780

-continued atccttgaga gttttcgccc cgaagaacgt tttccaatga tgagcacttt taaagttctg 3840
ctatgtggcg cggtattatc ccgtattgac gccgggcaag agcaactcgg tcgccgcata 3900
cactattctc agaatgactt ggttgagtac tcaccagtca cagaaaagca tcttacggat 3960
ggcatgacag taagagaatt atgcagtgct gccataacca tgagtgataa cactgcggcc 4020
aacttacttc tgacaacgat cggaggaccg aaggagctaa ccgctttttt gcacaacatg 4080
ggggatcatg taactcgcct tgatcgttgg gaaccggagc tgaatgaagc cataccaaac 4140
gacgagcgtg acaccacgat gcctgtagca atggcaacaa cgttgcgcaa actattaact 4200
ggcgaactac ttactctagc ttcccggcaa caattaatag actggatgga ggcggataaa 4260
gttgcaggac cacttctgcg ctcggccctt ccggctggct ggtttattgc tgataaatct 4320
ggagccggtg agcgtgggtc tcgcggtatc attgcagcac tggggccaga tggtaagccc 4380
tcccgtatcg tagttatcta cacgacgggg agtcaggcaa ctatggatga acgaaataga 4440
cagatcgctg agataggtgc ctcactgatt aagcattggt aactgtcaga ccaagtttac 4500
tcatatatac tttagattga tttaaaactt catttttaat ttaaaaggat ctaggtgaag 4560
atcctttttg ataatctcat gaccaaaatc ccttaacgtg agttttcgtt ccactgagcg 4620
tcagaccccg tagaaaagat caaaggatct tcttgagatc ctttttttct gcgcgtaatc 4680
tgctgcttgc aaacaaaaaa accaccgcta ccagcggtgg tttgtttgcc ggatcaagag 4740
ctaccaactc tttttccgaa ggtaactggc ttcagcagag cgcagatacc aaatactgtc 4800
cttctagtgt agccgtagtt aggccaccac ttcaagaact ctgtagcacc gcctacatac 4860
ctcgctctgc taatcctgtt accagtggct gctgccagtg gcgataagtc gtgtcttacc 4920
gggttggact caagacgata gttaccggat aaggcgcagc ggtcgggctg aacggggggt 4980
tcgtgcacac agcccagctt ggagcgaacg acctacaccg aactgagata cctacagcgt 5040
gagcattgag aaagcgccac gcttcccgaa gggagaaagg cggacaggta tccggtaagc 5100
ggcagggtcg gaacaggaga gcgcacgagg gagcttccag ggggaaacgc ctggtatctt 5160
tatagtcctg tcgggtttcg ccacctctga cttgagcgtc gatttttgtg atgctcgtca 5220
ggggggcgga gcctatggaa aaacgccagc aacgcggcct ttttacggtt cctggccttt 5280
tgctggcctt ttgctcacat gttctttcct gcgttatccc ctgattctgt ggataaccgt 5340
attaccgcct ttgagtgagc tgataccgct cgccgcagcc gaacgaccga gcgcagcgag 5400
tcagtgagcg aggaagcgga ag 5422

<210> SEQ ID NO 50
<211> LENGTH: 15621
<212> TYPE: DNA
<213> ORGANISM: Artificial Sequence
<220> FEATURE:
<223> OTHER INFORMATION: Description of Artificial Sequence:
vector pSY1YIG7E1s

<400> SEQUENCE: 50
atcgataagc ttttcaattc aattcatcat ttttttttta ttcttttttt tgatttcggt 60
ttctttgaaa tttttttgat tcggtaatct ccgaacagaa ggaagaacga aggaaggagc 120
acagacttag attggtatat atacgcatat gtagtgttga agaaacatga aattgcccag 180
tattcttaac ccaactgcac agaacaaaaa cctgcaggaa acgaagataa atcatgtcga 240
aagctacata taaggaacgt gctgctactc atcctagtcc tgttgctgcc aagctattta 300
atatcatgca cgaaaagcaa acaaacttgt gtgcttcatt ggatgttcgt accaccaagg 360

-continued

```
aattactgga gttagttgaa gcattaggtc ccaaaatttg tttactaaaa acacatgtgg    420
atatcttgac tgatttttcc atggagggca cagttaagcc gctaaaggca ttatccgcca    480
agtacaattt tttactcttc gaagacagaa aatttgctga cattggtaat acagtcaaat    540
tgcagtactc tgcgggtgta tacagaatag cagaatgggc agacattacg aatgcacacg    600
gtgtggtggg cccaggtatt gttagcggtt tgaagcaggc ggcagaagaa gtaacaaagg    660
aacctagagg ccttttgatg ttagcagaat tgtcatgcaa gggctcccta tctactggag    720
aatatactaa gggtactgtt gacattgcga agagcgacaa agattttgtt atcggcttta    780
ttgctcaaag agacatgggt ggaagagatg aaggttacga ttggttgatt atgacacccg    840
gtgtgggttt agatgacaag ggagacgcat tgggtcaaca gtatagaacc gtggatgatg    900
tggtctctac aggatctgac attattattg ttggaagagg actatttgca aagggaaggg    960
atgctaaggt agagggtgaa cgttacagaa aagcaggctg ggaagcatat ttgagaagat   1020
gcggccagca aaactaaaaa actgtattat aagtaaatgc atgtatacta aactcacaaa   1080
ttagagcttc aatttaatta tatcagttat tacccgggaa tctcggtcgt aatgattttt   1140
ataatgacga aaaaaaaaaa attggaaaga aaaagcttta atgcggtagt ttatcacagt   1200
taaattgcta acgcagtcag gcaccgtgta tgaaatctaa caatgcgctc atcgtcatcc   1260
tcggcaccgt caccctggat gctgtaggca taggcttggt tatgccggta ctgccgggcc   1320
tcttgcggga tatcgtccat tccgacagca tcgccagtca ctatggcgtg ctgctagcgc   1380
tatatgcgtt gatgcaattt ctatgcgcac ccgttctcgg agcactgtcc gaccgctttg   1440
gccgccgccc agtcctgctc gcttcgctac ttggagccac tatcgactac gcgatcatgg   1500
cgaccacacc cgtcctgtgg atcctggtat ggttttatcg ttttatttct ggttcttata   1560
gcatcgtttt ggacttctct gttcccatta ggcggttcag gagccagcgc agaatcattc   1620
tttgaaggat acttatcctt tccaattttg attgtctgtt acgttgggac ataaactgta   1680
tactagaaat tggactttga tggtgaaact agaagatatg gatcttgata ccggcagaaa   1740
acaagtagat ttgactcttc gtagggaaga aatgaggatt gagcgagaaa cattagcaaa   1800
aagatccttc gtaacaagat ttttacattt ctggtgttga agggaaagat atgagctata   1860
cagcggaatt tccatatcac tcagattttg ttatctaatt ttttccttcc cacgtccgcg   1920
ggaatctgtg tatattactg catctagcta gatatatgtt atcttatctt ggcgcgtaca   1980
tttaatttc aacgtattct ataagaaatt gcgggagttt ttttcatgta gatgatactg    2040
actgcacgca aatataggca tgatttatag gcatgatttg atggctgtac cgataggaac   2100
gctaagagta acttcagaat cgttatcctg gcggaaaaaa ttcatttgta aactttaaaa   2160
aaaaaagcca atatccccaa aattattaag agcgcctcca ttattaacta aaatttcact   2220
cagcatccac aatgtatcag gtatctacta cagatattac atgtggcgaa aaagacaaga   2280
acaatgcaat agcgcatcaa gaaaaaacac aaagctttca atcaatgaat cgaaaatgtc   2340
attaaaatag tatataaatt gaaactaagt cataaagcta taaaaagaaa atttatttaa   2400
atgcaagact ttaaagtaaa ttcacttaag ccttggcaac gtgttcaacc aagtcgagat   2460
ctgagcttat cggccgaggt gagaagggtc tattaccagt tcatcatcat atcccaagcc   2520
atacggtgac ccgttatgtg gccgggatag attgagcaat tgcagtcctg caccgtctca   2580
tgccggcgag gcgagatggt gaacagctgg gagacgagga agacagatcc gcagaggtcc   2640
cccacgtaca tagcggaaca gaaagcagcc gccccaacga gcaaatcgac gtggcgtcgt   2700
```

-continued

```
attgtcgtgg tggggacgct ggcgttccta gctgcgagcg tgggggtgag cgctacccag   2760
cagcgggaag agttgttctc ccgaacgcag ggcacgcacc cgggggtgtg catgatcatg   2820
tccgctgcct catacacaat gcttgagttg gagcagtcgt tcgtgacatg gtacatcccg   2880
gacacgttgc gcacctcata ccccagagca gccaggggca ggaagcaaag cactagtatt   2940
agcaaagacc tcatggtgtt tgtttatgtg tgtttattcg aaactaagtt cttggtgttt   3000
taaaactaaa aaaaagacta actataaaag tagaatttaa gaagtttaag aaatagattt   3060
acagaattac aatcaatacc taccgtcttt atatacttat tagtcaagta ggggaataat   3120
ttcagggaac tggtttcaac cttttttttc agggtttttt tttttcattc tctcaatctg   3180
aaattctctt atttctccaa cttataagtt ggagatgccc ggtgttccgg cagaggagat   3240
cagtctcgtg aagtggatgg tttcccgcct gcgggcaaaa cgtcataaca tttttatgag   3300
cgaaagccgt taatgaagac aaaatccctt aattaaaaca ttagaatggt gattagaaag   3360
gcaggattaa tcagttacac aggctgtaac cggagagacg gatcataagg caatttttag   3420
ataagactgg ttagagttct tggcatcaga aaatttgaga aacgattttt ccgtttgttt   3480
gcccctacgt tttgcccctt tgatcaaact atcagttaag atattaattt ttttgagaaa   3540
acgattcttt gattagtctc ttcaaacaaa caatgagctc tgaagacgaa ttgggaagta   3600
tcggtactgt gtttcccgga agtcccatag ataagagcat tgggagtatt ctccacaatt   3660
tgatgaagaa gtggagactt tgctggaaga tagcttcacg tggaacattc ctgactggaa   3720
cgagttaaca aacccgaaat acaattcgcc caggtttaga attggtgatt tcgaatggga   3780
cattctatta ttccctcagg gaaaccataa taaaggtgtt gcggtatatc tggaacctca   3840
tccggaagaa aaattagatg agactacggg agagatggtg ccagttgatc cggactggta   3900
ttgttgtgct cagtttgcca ttggtatatc tagacctggt aatggtgaca ccatcaattt   3960
aattaacaaa tcgcatcacc gattcaacgc tctagataca gactggggat ttgcaaattt   4020
gatagatttg aacaacttga aacatccctc aaaaggaaga ccgctttcgt tcttaaacga   4080
agggaccttg aacataacag cgtatgtgcg catattgaag gatcctctac gccggacgca   4140
tcgtggccgg catcaccggc gccacaggtg cggttgctgg cccctatatc gccgacatca   4200
ccgatgggga agatcgggct cgccacttcg ggctcatgag cgcttgtttc ggcgtgggta   4260
tggtggcagg ccccgtggcc gggggactgt tgggcgccat ctccttgcat gcaccattcc   4320
ttgcggcggc ggtgctcaac ggcctcaacc tactactggg ctgcttccta atgcaggagt   4380
cgcataaggg agagcgtcga ccgatgccct tgagagcctt caacccagtc agctccttcc   4440
ggtgggcgcg gggcatgact atcgtcgccg cacttatgac tgtcttcttt atcatgcaac   4500
tcgtaggaca ggtgccggca gcgctctggg tcattttcgg cgaggaccgc tttcgctgga   4560
gcgcgacgat gatcggcctg tcgcttgcgg tattcggaat cttgcacgcc ctcgctcaag   4620
ccttcgtcac tggtcccgcc accaaacgtt tcggcgagaa gcaggccatt atcgccggca   4680
tggcggccga cgcgctgggc tacgtcttgc tggcgttcgc gacgcgaggc tggatggcct   4740
tccccattat gattcttctc gcttccggcg gcatcgggat gcccgcgttg caggccatgc   4800
tgtccaggca ggtagatgac gaccatcagg gacagcttca aggatcgctc gcggctctta   4860
ccagcctaac ttcgatcact ggaccgctga tcgtcacggc gatttatgcc gcctcggcga   4920
gcacatggaa cgggttggca tggattgtag gcgccgccct ataccttgtc tgcctccccg   4980
cgttgcgtcg cggtgcatgg agccgggcca cctcgacctg aatggaagcc ggcggcacct   5040
cgctaacgga ttcaccactc caagaattgg agccaatcaa ttcttgcgga gaactgtgaa   5100
```

-continued

```
tgcgcaaacc aacccttggc agaacatatc catcgcgtcc gccatctcca gcagccgcac   5160
gcggcgcatc tcgggcagcg ttgggtcctg gccacgggtg cgcatgatcg tgctcctgtc   5220
gttgaggacc cggctaggct ggcggggttg ccttactggt tagcagaatg aatcaccgat   5280
acgcgagcga acgtgaagcg actgctgctg caaaacgtct gcgacctgag caacaacatg   5340
aatggtcttc ggtttccgtg tttcgtaaag tctggaaacg cggaagtcag cgccctgcac   5400
cattatgttc cggatctgca tcgcaggatg ctgctggcta ccctgtggaa cacctacatc   5460
tgtattaacg aagcgctggc attgaccctg agtgattttt ctctggtccc gccgcatcca   5520
taccgccagt tgtttaccct cacaacgttc cagtaaccgg gcatgttcat catcagtaac   5580
ccgtatcgtg agcatcctct ctcgtttcat cggtatcatt acccccatga acagaaattc   5640
cccttacac ggaggcatca agtgaccaaa caggaaaaaa ccgcccttaa catggcccgc   5700
tttatcagaa gccagacatt aacgcttctg gagaaactca acgagctgga cgcggatgaa   5760
caggcagaca tctgtgaatc gcttcacgac cacgctgatg agctttaccg cagctgcctc   5820
gcgcgtttcg gtgatgacgg tgaaaacctc tgacacatgc agctcccgga gacggtcaca   5880
gcttgtctgt aagcggtgcc gggagcagac aagcccgtca gggcgcgtca gcgggtgttg   5940
gcgggtgtcg gggcgcagcc atgacccagt cacgtagcga tagcggagtg tatactggct   6000
taactatgcg gcatcagagc agattgtact gagagtgcac catatgcggt gtgaaatacc   6060
gcacagatgc gtaaggagaa aataccgcat caggcgctct tccgcttcct cgctcactga   6120
ctcgctgcgc tcggtcgttc ggctgcggcg agcggtatca gctcactcaa aggcggtaat   6180
acggttatcc acagaatcag gggataacgc aggaaagaac atgtgagcaa aaggccagca   6240
aaaggccagg aaccgtaaaa aggccgcgtt gctggcgttt ttccataggc tccgcccccc   6300
tgacgagcat cacaaaaatc gacgctcaag tcagaggtgg cgaaacccga caggactata   6360
aagataccag gcgtttcccc ctggaagctc cctcgtgcgc tctcctgttc cgaccctgcc   6420
gcttaccgga tacctgtccg cctttctccc ttcgggaagc gtggcgcttt ctcatagctc   6480
acgctgtagg tatctcagtt cggtgtaggt cgttcgctcc aagctgggct gtgtgcacga   6540
accccccgtt cagcccgacc gctgcgcctt atccggtaac tatcgtcttg agtccaaccc   6600
ggtaagacac gacttatcgc cactggcagc agccactggt aacaggatta gcagagcgag   6660
gtatgtaggc ggtgctacag agttcttgaa gtggtggcct aactacggct acactagaag   6720
gacagtattt ggtatctgcg ctctgctgaa gccagttacc ttcggaaaaa gagttggtag   6780
ctcttgatcc ggcaaacaaa ccaccgctgg tagcggtggt ttttttgttt gcaagcagca   6840
gattacgcgc agaaaaaaag gatctcaaga agatcctttg atcttttcta cggggtctga   6900
cgctcagtgg aacgaaaact cacgttaagg gattttggtc atgagattat caaaaaggat   6960
cttcacctag atccttttaa attaaaaatg aagttttaaa tcaatctaaa gtatatatga   7020
gtaaacttgg tctgacagtt accaatgctt aatcagtgag gcacctatct cagcgatctg   7080
tctatttcgt tcatccatag ttgcctgact ccccgtcgtg tagataacta cgatacggga   7140
gggcttacca tctggcccca gtgctgcaat gataccgcga gacccacgct caccggctcc   7200
agatttatca gcaataaacc agccagccgg aagggccgag cgcagaagtg gtcctgcaac   7260
tttatccgcc tccatccagt ctattaattg ttgccgggaa gctagagtaa gtagttcgcc   7320
agttaatagt ttgcgcaacg ttgttgccat tgctgcaggc atcgtggtgt cacgctcgtc   7380
gtttggtatg gcttcattca gctccggttc ccaacgatca aggcgagtta catgatcccc   7440
```

-continued catgttgtgc aaaaaagcgg ttagctcctt cggtcctccg atcgttgtca gaagtaagtt 7500
ggccgcagtg ttatcactca tggttatggc agcactgcat aattctctta ctgtcatgcc 7560
atccgtaaga tgcttttctg tgactggtga gtactcaacc aagtcattct gagaatagtg 7620
tatgcggcga ccgagttgct cttgcccggc gtcaacacgg gataataccg cgccacatag 7680
cagaacttta aaagtgctca tcattggaaa acgttcttcg gggcgaaaac tctcaaggat 7740
cttaccgctg ttgagatcca gttcgatgta acccactcgt gcacccaact gatcttcagc 7800
atcttttact ttcaccagcg tttctgggtg agcaaaaaca ggaaggcaaa atgccgcaaa 7860
aaagggaata agggcgacac ggaaatgttg aatactcata ctcttccttt ttcaatatta 7920
ttgaagcatt tatcagggtt attgtctcat gagcggatac atatttgaat gtatttagaa 7980
aaataaacaa ataggggttc cgcgcacatt tccccgaaaa gtgccacctg acgtctaaga 8040
aaccattatt atcatgacat taacctataa aaataggcg tatcacgagg ccctttcgtc 8100
ttcaagaatt ctcatgtttg acagcttatc atcgatccac ttgtatattt ggatgaattt 8160
ttgaggaatt ctgaaccagt cctaaaacga gtaaatagga ccggcaattc ttcaagcaat 8220
aaacaggaat accaattatt aaaagataac ttagtcagat cgtacaataa agctttgaag 8280
aaaaatgcgc cttattcaat ctttgcataa aaaaatggcc caaaatctca cattggaaga 8340
catttgatga cctcatttct ttcaatgaag ggcctaacgg agttgactaa tgttgtggga 8400
aattggaccg ataagcgtgc ttctgccgtg gccaggacaa cgtatactca tcagataaca 8460
gcaatacctg atcactactt cgcactagtt tctcggtact atgcatatga tccaatatca 8520
aaggaaatga tagcattgaa ggatgagact aatccaattg aggagtggca gcatatagaa 8580
cagctaaagg gtagtgctga aggaagcata cgataccccg catggaatgg gataatatca 8640
caggaggtac tagactacct ttcatcctac ataaatagac gcatataagt acgcatttaa 8700
gcataaacac gcactatgcc gttcttctca tgtatatata tatacaggca acacgcagat 8760
ataggtgcga cgtgaacagt gagctgtatg tgcgcagctc gcgttgcatt ttcggaagcg 8820
ctcgttttcg gaaacgcttt gaagttccta ttccgaagtt cctattctct agaaagtata 8880
ggaacttcag agcgcttttg aaaaccaaaa gcgctctgaa gacgcacttt caaaaaacca 8940
aaaacgcacc ggactgtaac gagctactaa aatattgcga ataccgcttc cacaaacatt 9000
gctcaaaagt atctctttgc tatatatctc tgtgctatat ccctatataa ccatcccatc 9060
cacctttcgc tccttgaact tgcatctaaa ctcgacctct acattttta tgtttatctc 9120 tagtattacc tcttagacaa aaaaattgta gtaagaacta ttcatagagt taatcgaaaa 9180
caatacgaaa atgtaaacat ttcctatacg tagtatatag agacaaaata gaagaaaccg 9240
ttcataattt tctgaccaat gaagaatcat caacgctatc actttctgtt cacaaagtat 9300
gcgcaatcca catcggtata gaatataatc ggggatgcct ttatcttgaa aaaatgcacc 9360
cgcagcttcg ctagtaatca gtaaacgcgg gaagtggagt caggcttttt ttatggaaga 9420
gaaaatagac accaaagtag ccttcttcta accttaacgg acctacagtg caaaaagtta 9480
tcaagagact gcattataga gcgcacaaag gagaaaaaaa gtaatctaag atgctttgtt 9540
agaaaaatag cgctctcggg atgcattttt gtagaacaaa aaagaagtat agattcttgt 9600
tggtaaaata gcgctctcgc gttgcatttc tgttctgtaa aaatgcagct cagattcttt 9660
gtttgaaaaa ttagcgctct cgcgttgcat ttttgtttta caaaaatgaa gcacagattc 9720
ttcgttggta aaatagcgct ttcgcgttgc atttctgttc tgtaaaaatg cagctcagat 9780
tctttgtttg aaaaattagc gctctcgcgt tgcatttttg ttctacaaaa tgaagcacag 9840

-continued

```
atgcttcgtt aacaaagata tgctattgaa gtgcaagatg gaaacgcaga aaatgaaccg    9900
gggatgcgac gtgcaagatt acctatgcaa tagatgcaat agtttctcca ggaaccgaaa    9960
tacatacatt gtcttccgta aagcgctaga ctatatatta ttatacaggt tcaaatatac   10020
tatctgtttc agggaaaact cccaggttcg gatgttcaaa attcaatgat gggtaacaag   10080
tacgatcgta aatctgtaaa acagtttgtc ggatattagg ctgtatctcc tcaaagcgta   10140
ttcgaatatc attgagaagc tgcatttttt tttttttttt tttttttttt ttttttatat   10200
atatttcaag gatataccat tgtaatgtct gcccctaaga agatcgtcgt tttgccaggt   10260
gaccacgttg gtcaagaaat cacagccgaa gccattaagg ttcttaaagc tatttctgat   10320
gttcgttcca atgtcaagtt cgatttcgaa aatcatttaa ttggtggtgc tgctatcgat   10380
gctacaggtg tcccacttcc agatgaggcg ctggaagcct ccaagaaggt tgatgccgtt   10440
ttgttaggtg ctgtgggtgg tcctaaatgg ggtaccggta gtgttagacc tgaacaaggt   10500
ttactaaaaa tccgtaaaga acttcaattg tacgccaact taagaccatg taactttgca   10560
tccgactctc ttttagactt atctccaatc aagccacaat ttgctaaagg tactgacttc   10620
gttgttgtca gagaattagt gggaggtatt tactttggta agagaaagga agacgatggt   10680
gatggtgtcg cttgggatag tgaacaatac accgttccag aagtgcaaag aatcacaaga   10740
atggccgctt tcatggccct acaacatgag ccaccattgc ctatttggtc cttggataaa   10800
gctaatgttt tggcctcttc aagattatgg agaaaaactg tggaggaaac catcaagaac   10860
gaattcccta cattgaaggt tcaacatcaa ttgattgatt ctgccgccat gatcctagtt   10920
aagaacccaa cccacctaaa tggtattata atcaccagca acatgtttgg tgatatcatc   10980
tccgatgaag cctccgttat cccaggttcc ttgggtttgt tgccatctgc gtccttggcc   11040
tctttgccag acaagaacac cgcatttggt ttgtacgaac catgccacgg ttctgctcca   11100
gatttgccaa agaataaggt tgaccctatc gccactatct tgtctgctgc aatgatgttg   11160
aaattgtcat tgaacttgcc tgaagaaggt aaggccattg aagatgcagt taaaaaggtt   11220
ttggatgcag gtatcagaac tggtgattta ggtggttcca acagtaccac cgaagtcggt   11280
gatgctgtcg ccgaagaagt taagaaaatc cttgcttaaa aagattctct ttttttatga   11340
tatttgtaca aaaaaaaaaa aaaaaaaaaa aaaaaaaaaa aaaaaaaaaa aaaaatgcag   11400
cgtcacatcg gataataatg atggcagcca ttgtagaagt gccttttgca tttctagtct   11460
ctttctcggt ctagctagtt ttactacatc gcgaagatag aatcttagat cacactgcct   11520
ttgctgagct ggatcatatg agtaacaaaa gagtggtaag gcctcgttaa aggacaagga   11580
cctgagcgga agtgtatcgt aaagtagacg gagtatacta gtatagtcta tagtccgtgg   11640
aattctaagt gccagcttta taatgtcatt ctccttacta cagacccgcc tgaaagtaga   11700
cacatcatca tcagtaagct ttgacaaaaa gcattgagta gctaactctt ctatgcaatc   11760
tatagctgtt ttataaggca ttcaatggac agattgaggt ttttgaaaca tactagtgaa   11820
attagcctta atcccttctc gaagttaatc atgcattatg gtgtaaaaaa tgcaactcgc   11880
gttgctctac tttttcccga atttccaaat acgcagctgg ggtgattgct cgatttcgta   11940
acgaaagttt tgtttataaa aaccgcgaaa accttctgta acagatagat ttttacagcg   12000
ctgatataca atgacatcag ctgtaatgga aaataactga aatatgaatg gcgagagact   12060
gcttgcttgt attaagcaat gtattatgca gcacttccaa cctatggtgt acgatgaaag   12120
taggtgtgta atcgagacga caagggggac ttttccagtt cctgatcatt ataagaaata   12180
```

-continued

```
caaaacgtta gcatttgcat ttgttggaca tgtactgaat acagacgaca caccggtaat  12240
tgaaaaagaa ctggattggc ctgatcctgc actagtgtac aatacaattg tcgatcgaat  12300
cataaatcac ccagaattat cacagtttat atcggttgca tttattagtc agttaaaggc  12360
caccatcgga gagggtttag atattaatgt aaaaggcacg ctaaaccgca ggggaaaggg  12420
tatcagaagg cctaaaggcg tattttttag atacatggaa tctccatttg tcaatacaaa  12480
ggtcactgca ttcttctctt atcttcgaga ttataataaa attgcctcag aatatcacaa  12540
taatactaaa ttcattctca cgttttcatg tcaagcatat tgggcatctg gcccaaactt  12600
ctccgccttg aagaatgtta tttggtgctc cataattcat gaatacattt ctaagtttgt  12660
ggaaagagaa caggataaag gtcatatagg agatcaggag ctaccgcctg aagaggaccc  12720
ttctcgtgaa ctaaacaatg tacaacatga agtcaatagt ttaacggaac aagatgcgga  12780
ggcggatgaa ggattgtggg gtgaaataga ttcattatgt gaaaaatggc agtctgaagc  12840
ggagagtcaa actgaggcgg agataatagc cgacaggata attggaaata gccagaggat  12900
ggcgaacctc aaaattcgtc gtacaaagtt caaaagtgtc ttgtatcata tactaaagga  12960
actaattcaa tctcagggaa ccgtaaaggt ttatcgcggt agtagttttt cacacgattc  13020
gataaagata agcttacatt atgaagagca gcatattaca gccgtatggg tctacttgat  13080
agtaaaattt gaagagcatt ggaagcctgt tgatgtagag gtcgagttta gatgcaagtt  13140
caaggagcga aaggtggatg ggtaggttat atagggatat agcacagaga tatatagcaa  13200
agagatactt ttgaggcaat gtttgtggaa gcggtattcg caatatttta gtagctcgtt  13260
acagtccggt gcgtttttgg ttttttgaaa gtgcgtcttc agagcgcttt tggttttcaa  13320
aagcgctctg aagttcctat actttctaga gaataggaac ttcggaatag gaacttcaaa  13380
gcgtttccga aaacgagcgc ttccgaaaat gcaacgcgag ctgcgcacat acagctcact  13440
gttcacgtcg cacctatatc tgcgtgttgc ctgtatatat atatacatga gaagaacggc  13500
atagtgcgtg tttatgctta aatgcgtact tatatgcgtc tatttatgta ggatgaaagg  13560
tagtctagta cctcctgtga tattatccca ttccatgcgg ggtatcgtat gcttccttca  13620
gcactaccct ttagctgttc tatatgctgc cactcctcaa ttggattagt ctcatccttc  13680
aatgcattca tttcctttga tattggatca taccctagaa gtattacgtg attttctgcc  13740
ccttaccctc gttgctactc tcctttttttt cgtgggaacc gctttagggc cctcagtgat  13800
ggtgttttgt aatttatatg ctcctcttgc atttgtgtct ctacttcttg ttcgcctgga  13860
gggaacttct tcatttgtat tagcatggtt cacttcagtc cttccttcca actcactctt  13920
tttttgctgt aaacgattct ctgccgccag ttcattgaaa ctattgaata tatcctttag  13980
agattccggg atgaataaat cacctattaa agcagcttga cgatctggtg gaactaaagt  14040
aagcaattgg gtaacgacgc ttacgagctt cataacatct tcttccgttg gagctggtgg  14100
gactaataac tgtgtacaat ccatttttct catgagcatt tcggtagctc tcttcttgtc  14160
tttctcgggc aatcttccta ttattatagc aatagatttg tatagttgct ttctattgtc  14220
taacagcttg ttattctgta gcatcaaatc tatggcagcc tgacttgctt cttgtgaaga  14280
gagcatacca tttccaatcg aagatacgct ggaatcttct gcgctagaat caagaccata  14340
cggcctaccg gttgtgagag attccatggg ccttatgaca tatcctggaa agagtagctc  14400
atcagactta cgtttactct ctatatcaat atctacatca ggagcaatca tttcaataaa  14460
cagccgacat acatcccaga cgctataagc tgtacgtgct tttaccgtca gattcttggc  14520
tgtttcaatg tcgtccattt tggttttctt ttaccagtat tgttcgtttg ataatgtatt  14580
```

-continued

```
cttgcttatt acattataaa atctgtgcag atcacatgtc aaaacaactt tttatcacaa  14640
gatagtaccg caaaacgaac ctgcgggccg tctaaaaatt aaggaaaagc agcaaaggtg  14700
catttttaaa atatgaaatg aagataccgc agtaccaatt attttcgcag tacaaataat  14760
gcgcggccgg tgcatttttc gaaagaacgc gagacaaaca ggacaattaa agttagtttt  14820
tcgagttagc gtgtttgaat actgcaagat acaagataaa tagagtagtt gaaactagat  14880
atcaattgca cacaagatcg gcgctaagca tgccacaatt tggtatatta tgtaaaacac  14940
cacctaaggt gcttgttcgt cagtttgtgg aaaggtttga aagaccttca ggtgagaaaa  15000
tagcattatg tgctgctgaa ctaacctatt tatgttggat gattacacat aacggaacag  15060
caatcaagag agccacattc atgagctata atactatcat aagcaattcg ctgagtttcg  15120
atattgtcaa taaatcactc cagtttaaat acaagacgca aaaagcaaca attctggaag  15180
cctcattaaa gaaattgatt cctgcttggg aatttacaat tattccttac tatggacaaa  15240
aacatcaatc tgatatcact gatattgtaa gtagtttgca attacagttc gaatcatcgg  15300
aagaagcaga taagggaaat agccacagta aaaaaatgct aaagcacttc taagtgaggg  15360
tgaaagcatc tgggagatca ctgagaaaat actaaattcg tttgagtata cttcgagatt  15420
tacaaaaaca aaaactttat accaattcct cttcctagct actttcatca attgtggaag  15480
attcagcgat attaagaacg ttgatccgaa atcatttaaa ttagtccaaa ataagtatct  15540
gggagtaata atccagtgtt tagtgacaga gacaaagaca agcgttagta ggcacatata  15600
cttctttagc gcaaggggta g                                            15621
```

```
<210> SEQ ID NO 51
<211> LENGTH: 3593
<212> TYPE: DNA
<213> ORGANISM: Artificial Sequence
<220> FEATURE:
<223> OTHER INFORMATION: Description of Artificial Sequence:
      vector pPICZalphaA

<400> SEQUENCE: 51
```

```
agatctaaca tccaaagacg aaaggttgaa tgaaaccttt ttgccatccg acatccacag     60
gtccattctc acacataagt gccaaacgca acaggagggg atacactagc agcagaccgt    120
tgcaaacgca ggacctccac tcctcttctc ctcaacaccc acttttgcca tcgaaaaacc    180
agcccagtta ttgggcttga ttggagctcg ctcattccaa ttccttctat taggctacta    240
acaccatgac tttattagcc tgtctatcct ggcccccctg gcgaggttca tgtttgttta    300
tttccgaatg caacaagctc cgcattacac ccgaacatca ctccagatga gggctttctg    360
agtgtggggt caaatagttt catgttcccc aaatggccca aaactgacag tttaaacgct    420
gtcttggaac ctaatatgac aaaagcgtga tctcatccaa gatgaactaa gtttggttcg    480
ttgaaatgct aacggccagt tggtcaaaaa gaaacttcca aaagtcggca taccgtttgt    540
cttgtttggt attgattgac gaatgctcaa aaataatctc attaatgctt agcgcagtct    600
ctctatcgct tctgaacccc ggtgcacctg tgccgaaacg caaatgggga aacacccgct    660
ttttggatga ttatgcattg tctccacatt gtatgcttcc aagattctgg tgggaatact    720
gctgatagcc taacgttcat gatcaaaatt taactgttct aacccctact tgacagcaat    780
atataaacag aaggaagctg ccctgtctta aacctttttt tttatcatca ttattagctt    840
actttcataa ttgcgactgg ttccaattga caagcttttg attttaacga cttttaacga    900
caacttgaga agatcaaaaa acaactaatt attcgaaacg atgagatttc cttcaatttt    960
```

-continued

```
tactgctgtt ttattcgcag catcctccgc attagctgct ccagtcaaca ctacaacaga   1020
agatgaaacg gcacaaattc cggctgaagc tgtcatcggt tactcagatt tagaagggga   1080
tttcgatgtt gctgttttgc cattttccaa cagcacaaat aacgggttat tgtttataaa   1140
tactactatt gccagcattg ctgctaaaga agaaggggta tctctcgaga aaagagaggc   1200
tgaagctgaa ttcacgtggc ccagccggcc gtctcggatc ggtacctcga gccgcggcgg   1260
ccgccagctt tctagaacaa aaactcatct cagaagagga tctgaatagc gccgtcgacc   1320
atcatcatca tcatcattga gtttgtagcc ttagacatga ctgttcctca gttcaagttg   1380
ggcacttacg agaagaccgg tcttgctaga ttctaatcaa gaggatgtca gaatgccatt   1440
tgcctgagag atgcaggctt catttttgat acttttttat ttgtaaccta tatagtatag   1500
gatttttttt gtcattttgt ttcttctcgt acgagcttgc tcctgatcag cctatctcgc   1560
agctgatgaa tatcttgtgg taggggtttg ggaaaatcat tcgagtttga tgtttttctt   1620
ggtatttccc actcctcttc agagtacaga agattaagtg agaccttcgt ttgtgcggat   1680
cccccacaca ccatagcttc aaaatgtttc tactcctttt ttactcttcc agattttctc   1740
ggactccgcg catcgccgta ccacttcaaa acacccaagc acagcatact aaattttccc   1800
tctttcttcc tctagggtgt cgttaattac ccgtactaaa ggtttggaaa agaaaaaaga   1860
gaccgcctcg tttctttttc ttcgtcgaaa aaggcaataa aaatttttat cacgtttctt   1920
tttcttgaaa tttttttttt tagttttttt ctctttcagt gacctccatt gatatttaag   1980
ttaataaacg gtcttcaatt tctcaagttt cagtttcatt tttcttgttc tattacaact   2040
ttttttactt cttgttcatt agaaagaaag catagcaatc taatctaagg ggcggtgttg   2100
acaattaatc atcggcatag tatatcggca tagtataata cgacaaggtg aggaactaaa   2160
ccatggccaa gttgaccagt gccgttccgg tgctcaccgc gcgcgacgtc gccggagcgg   2220
tcgagttctg gaccgaccgg ctcgggttct cccgggactt cgtggaggac gacttcgccg   2280
gtgtggtccg ggacgacgtg accctgttca tcagcgcggt ccaggaccag gtggtgccgg   2340
acaacaccct ggcctgggtg tgggtgcgcg gcctggacga gctgtacgcc gagtggtcgg   2400
aggtcgtgtc cacgaacttc cgggacgcct ccgggccggc catgaccgag atcggcgagc   2460
agccgtgggg gcgggagttc gccctgcgcg acccggccgg caactgcgtg cacttcgtgg   2520
ccgaggagca ggactgacac gtccgacggc ggcccacggg tcccaggcct cggagatccg   2580
tcccccttt ccttgtcga tatcatgtaa ttagttatgt cacgcttaca ttcacgccct   2640
ccccccacat ccgctctaac cgaaaaggaa ggagttagac aacctgaagt ctaggtccct   2700
atttattttt ttatagttat gttagtatta agaacgttat ttatatttca aatttttctt   2760
ttttttctgt acagacgcgt gtacgcatgt aacattatac tgaaaacctt gcttgagaag   2820
gttttgggac gctcgaaggc tttaatttgc aagctggaga ccaacatgtg agcaaaaggc   2880
cagcaaaagg ccaggaaccg taaaaaggcc gcgttgctgg cgtttttcca taggctccgc   2940
ccccctgacg agcatcacaa aaatcgacgc tcaagtcaga ggtggcgaaa cccgacagga   3000
ctataaagat accaggcgtt tccccctgga agctccctcg tgcgctctcc tgttccgacc   3060
ctgccgctta ccggatacct gtccgccttt ctcccttcgg gaagcgtggc gctttctcaa   3120
tgctcacgct gtaggtatct cagttcggtg taggtcgttc gctccaagct gggctgtgtg   3180
cacgaacccc ccgttcagcc cgaccgctgc gccttatccg gtaactatcg tcttgagtcc   3240
aacccggtaa gacacgactt atcgccactg gcagcagcca ctggtaacag gattagcaga   3300
```

-continued gcgaggtatg taggcggtgc tacagagttc ttgaagtggt ggcctaacta cggctacact 3360
agaaggacag tatttggtat ctgcgctctg ctgaagccag ttaccttcgg aaaaagagtt 3420
ggtagctctt gatccggcaa acaaaccacc gctggtagcg gtggtttttt tgtttgcaag 3480
cagcagatta cgcgcagaaa aaaaggatct caagaagatc ctttgatctt ttctacgggg 3540
tctgacgctc agtggaacga aaactcacgt taagggattt tggtcatgag atc 3593

<210> SEQ ID NO 52
<211> LENGTH: 3547
<212> TYPE: DNA
<213> ORGANISM: Artificial Sequence
<220> FEATURE:
<223> OTHER INFORMATION: Description of Artificial Sequence: vector pPICZalphaD'

<400> SEQUENCE: 52
agatctaaca tccaaagacg aaaggttgaa tgaaaccttt ttgccatccg acatccacag 60
gtccattctc acacataagt gccaaacgca acaggagggg atacactagc agcagaccgt 120
tgcaaacgca ggacctccac tcctcttctc ctcaacaccc acttttgcca tcgaaaaacc 180
agcccagtta ttgggcttga ttggagctcg ctcattccaa ttccttctat taggctacta 240
acaccatgac tttattagcc tgtctatcct ggcccccctg gcgaggttca tgtttgttta 300
tttccgaatg caacaagctc cgcattacac ccgaacatca ctccagatga gggctttctg 360
agtgtggggt caaatagttt catgttcccc aaatggccca aaactgacag tttaaacgct 420
gtcttggaac ctaatatgac aaaagcgtga tctcatccaa gatgaactaa gtttggttcg 480
ttgaaatgct aacggccagt tggtcaaaaa gaaacttcca aaagtcggca taccgtttgt 540
cttgtttggt attgattgac gaatgctcaa aaataatctc attaatgctt agcgcagtct 600
ctctatcgct tctgaacccc ggtgcacctg tgccgaaacg caaatgggga aacacccgct 660
ttttggatga ttatgcattg tctccacatt gtatgcttcc aagattctgg tgggaatact 720
gctgatagcc taacgttcat gatcaaaatt taactgttct aacccctact tgacagcaat 780
atataaacag aaggaagctg ccctgtctta aacctttttt tttatcatca ttattagctt 840
actttcataa ttgcgactgg ttccaattga caagcttttg attttaacga cttttaacga 900
caacttgaga agatcaaaaa acaactaatt attcgaaacg atgagatttc cttcaatttt 960
tactgctgtt ttattcgcag catcctccgc attagctgct ccagtcaaca ctacaacaga 1020
agatgaaacg gcacaaattc cggctgaagc tgtcatcggt tactcagatt tagaaggggga 1080 tttcgatgtt gctgttttgc cattttccaa cagcacaaat aacgggttat tgtttataaa 1140
tactactatt gccagcattg ctgctaaaga agaaggggta tctctcgaga aaaggggccc 1200
gaattcgcat gcggccgcca gctttctaga acaaaaactc atctcagaag aggatctgaa 1260
tagcgccgtc gaccatcatc atcatcatca ttgagtttgt agccttagac atgactgttc 1320
ctcagttcaa gttgggcact tacgagaaga ccggtcttgc tagattctaa tcaagaggat 1380
gtcagaatgc catttgcctg agagatgcag gcttcatttt tgatactttt ttatttgtaa 1440
cctatatagt ataggatttt ttttgtcatt ttgtttcttc tcgtacgagc ttgctcctga 1500
tcagcctatc tcgcagctga tgaatatctt gtggtagggg tttgggaaaa tcattcgagt 1560
ttgatgtttt tcttggtatt tcccactcct cttcagagta cagaagatta agtgagacct 1620
tcgtttgtgc ggatccccca cacaccatag cttcaaaatg tttctactcc ttttttactc 1680
ttccagattt tctcggactc cgcgcatcgc cgtaccactt caaaacaccc aagcacagca 1740

-continued tactaaattt tccctctttc ttcctctagg gtgtcgttaa ttacccgtac taaaggtttg 1800
gaaaagaaaa aagagaccgc ctcgtttctt tttcttcgtc gaaaaaggca ataaaaattt 1860
ttatcacgtt tctttttctt gaaatttttt tttttagttt ttttctcttt cagtgacctc 1920
cattgatatt taagttaata aacggtcttc aatttctcaa gtttcagttt catttttctt 1980
gttctattac aacttttttt acttcttgtt cattagaaag aaagcatagc aatctaatct 2040
aaggggcggt gttgacaatt aatcatcggc atagtatatc ggcatagtat aatacgacaa 2100
ggtgaggaac taaaccatgg ccaagttgac cagtgccgtt ccggtgctca ccgcgcgcga 2160
cgtcgccgga gcggtcgagt tctggaccga ccggctcggg ttctcccggg acttcgtgga 2220
ggacgacttc gccggtgtgg tccgggacga cgtgaccctg ttcatcagcg cggtccagga 2280
ccaggtggtg ccggacaaca ccctggcctg ggtgtgggtg cgcggcctgg acgagctgta 2340
cgccgagtgg tcggaggtcg tgtccacgaa cttccgggac gcctccgggc cggccatgac 2400
cgagatcggc gagcagccgt gggggcggga gttcgccctg cgcgacccgg ccggcaactg 2460
cgtgcacttc gtggccgagg agcaggactg acacgtccga cggcggccca cgggtcccag 2520
gcctcggaga tccgtccccc ttttcctttg tcgatatcat gtaattagtt atgtcacgct 2580
tacattcacg ccctcccccc acatccgctc taaccgaaaa ggaaggagtt agacaacctg 2640
aagtctaggt ccctatttat ttttttatag ttatgttagt attaagaacg ttatttatat 2700
ttcaaatttt tctttttttt ctgtacagac gcgtgtacgc atgtaacatt atactgaaaa 2760
ccttgcttga gaaggttttg ggacgctcga aggctttaat ttgcaagctg gagaccaaca 2820
tgtgagcaaa aggccagcaa aaggccagga accgtaaaaa ggccgcgttg ctggcgtttt 2880
tccataggct ccgcccccct gacgagcatc acaaaaatcg acgctcaagt cagaggtggc 2940
gaaacccgac aggactataa agataccagg cgtttccccc tggaagctcc ctcgtgcgct 3000
ctcctgttcc gaccctgccg cttaccggat acctgtccgc ctttctccct tcgggaagcg 3060
tggcgctttc tcaatgctca cgctgtaggt atctcagttc ggtgtaggtc gttcgctcca 3120
agctgggctg tgtgcacgaa ccccccgttc agcccgaccg ctgcgcctta tccggtaact 3180
atcgtcttga gtccaacccg gtaagacacg acttatcgcc actggcagca gccactggta 3240
acaggattag cagagcgagg tatgtaggcg gtgctacaga gttcttgaag tggtggccta 3300
actacggcta cactagaagg acagtatttg gtatctgcgc tctgctgaag ccagttacct 3360
tcggaaaaag agttggtagc tcttgatccg gcaaacaaac caccgctggt agcggtggtt 3420
tttttgtttg caagcagcag attacgcgca gaaaaaaagg atctcaagaa gatcctttga 3480
tcttttctac ggggtctgac gctcagtgga acgaaaactc acgttaaggg attttggtca 3540
tgagatc 3547

<210> SEQ ID NO 53
<211> LENGTH: 3558
<212> TYPE: DNA
<213> ORGANISM: Artificial Sequence
<220> FEATURE:
<223> OTHER INFORMATION: Description of Artificial Sequence:
vector pPICZalphaE'

<400> SEQUENCE: 53
agatctaaca tccaaagacg aaaggttgaa tgaaaccttt ttgccatccg acatccacag 60
gtccattctc acacataagt gccaaacgca acaggagggg atacactagc agcagaccgt 120
tgcaaacgca ggacctccac tcctcttctc ctcaacaccc acttttgcca tcgaaaaacc 180

-continued

```
agcccagtta ttgggcttga ttggagctcg ctcattccaa ttccttctat taggctacta    240
acaccatgac tttattagcc tgtctatcct ggccccccctg gcgaggttca tgtttgttta   300
tttccgaatg caacaagctc cgcattacac ccgaacatca ctccagatga gggctttctg    360
agtgtggggt caaatagttt catgttcccc aaatggccca aaactgacag tttaaacgct    420
gtcttggaac ctaatatgac aaaagcgtga tctcatccaa gatgaactaa gtttggttcg    480
ttgaaatgct aacggccagt tggtcaaaaa gaaacttcca aaagtcggca taccgtttgt    540
cttgtttggt attgattgac gaatgctcaa aaataatctc attaatgctt agcgcagtct    600
ctctatcgct tctgaacccc ggtgcacctg tgccgaaacg caaatgggga aacacccgct    660
ttttggatga ttatgcattg tctccacatt gtatgcttcc aagattctgg tgggaatact    720
gctgatagcc taacgttcat gatcaaaatt taactgttct aacccctact tgacagcaat    780
atataaacag aaggaagctg ccctgtctta aaccttttttt tttatcatca ttattagctt   840
actttcataa ttgcgactgg ttccaattga caagcttttg attttaacga cttttaacga    900
caacttgaga agatcaaaaa acaactaatt attcgaaacg atgagatttc cttcaatttt    960
tactgctgtt ttattcgcag catcctccgc attagctgct ccagtcaaca ctacaacaga   1020
agatgaaacg gcacaaattc cggctgaagc tgtcatcggt tactcagatt tagaagggga   1080
tttcgatgtt gctgttttgc cattttccaa cagcacaaat aacgggttat tgtttataaa   1140
tactactatt gccagcattg ctgctaaaga agaaggggta tctctcgaga aaagagaggc   1200
tgaagcctgc agcatatgct cgaggccgcc agctttctag aacaaaaact catctcagaa   1260
gaggatctga atagcgccgt cgaccatcat catcatcatc attgagtttg tagccttaga   1320
catgactgtt cctcagttca agttgggcac ttacgagaag accggtcttg ctagattcta   1380
atcaagagga tgtcagaatg ccatttgcct gagagatgca ggcttcattt ttgatacttt   1440
tttatttgta acctatatag tataggattt tttttgtcat tttgtttctt ctcgtacgag   1500
cttgctcctg atcagcctat ctcgcagctg atgaatatct tgtggtaggg gtttgggaaa   1560
atcattcgag tttgatgttt ttcttggtat ttcccactcc tcttcagagt acagaagatt   1620
aagtgagacc ttcgtttgtg cggatccccc acacaccata gcttcaaaat gtttctactc   1680
cttttttact cttccagatt ttctcggact ccgcgcatcg ccgtaccact tcaaaacacc   1740
caagcacagc atactaaatt ttccctcttt cttcctctag ggtgtcgtta attacccgta   1800
ctaaaggttt ggaaaagaaa aaagagaccg cctcgtttct ttttcttcgt cgaaaaaggc   1860
aataaaaatt tttatcacgt ttcttttttct tgaaattttt ttttttagtt tttttctctt  1920
tcagtgacct ccattgatat ttaagttaat aaacggtctt caatttctca agtttcagtt   1980
tcatttttct tgttctatta caacttttttt tacttcttgt tcattagaaa gaaagcatag  2040
caatctaatc taaggggcgg tgttgacaat taatcatcgg catagtatat cggcatagta   2100
taatacgaca aggtgaggaa ctaaaccatg gccaagttga ccagtgccgt tccggtgctc   2160
accgcgcgcg acgtcgccgg agcggtcgag ttctggaccg accggctcgg gttctcccgg   2220
gacttcgtgg aggacgactt cgccggtgtg gtccgggacg acgtgaccct gttcatcagc   2280
gcggtccagg accaggtggt gccggacaac accctggcct gggtgtgggt gcgcggcctg   2340
gacgagctgt acgccgagtg gtcggaggtc gtgtccacga acttccggga cgcctccggg   2400
ccggccatga ccgagatcgg cgagcagccg tgggggcggg agttcgccct gcgcgacccg   2460
gccggcaact gcgtgcactt cgtggccgag gagcaggact gacacgtccg acggcggccc   2520
acgggtccca ggcctcggag atccgtcccc cttttccttt gtcgatatca tgtaattagt   2580
```

-continued

```
tatgtcacgc ttacattcac gccctccccc cacatccgct ctaaccgaaa aggaaggagt   2640

tagacaacct gaagtctagg tccctattta tttttttata gttatgttag tattaagaac   2700

gttatttata tttcaaattt ttcttttttt tctgtacaga cgcgtgtacg catgtaacat   2760

tatactgaaa accttgcttg agaaggtttt gggacgctcg aaggctttaa tttgcaagct   2820

ggagaccaac atgtgagcaa aaggccagca aaaggccagg aaccgtaaaa aggccgcgtt   2880

gctggcgttt ttccataggc tccgcccccc tgacgagcat cacaaaaatc gacgctcaag   2940

tcagaggtgg cgaaacccga caggactata aagataccag gcgtttcccc ctggaagctc   3000

cctcgtgcgc tctcctgttc cgaccctgcc gcttaccgga tacctgtccg cctttctccc   3060

ttcgggaagc gtggcgcttt ctcaatgctc acgctgtagg tatctcagtt cggtgtaggt   3120

cgttcgctcc aagctgggct gtgtgcacga accccccgtt cagcccgacc gctgcgcctt   3180

atccggtaac tatcgtcttg agtccaaccc ggtaagacac gacttatcgc cactggcagc   3240

agccactggt aacaggatta gcagagcgag gtatgtaggc ggtgctacag agttcttgaa   3300

gtggtggcct aactacggct acactagaag gacagtattt ggtatctgcg ctctgctgaa   3360

gccagttacc ttcggaaaaa gagttggtag ctcttgatcc ggcaaacaaa ccaccgctgg   3420

tagcggtggt ttttttgttt gcaagcagca gattacgcgc agaaaaaaag gatctcaaga   3480

agatcctttg atcttttcta cggggtctga cgctcagtgg aacgaaaact cacgttaagg   3540

gattttggtc atgagatc                                                 3558
```

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence: 8822

<400> SEQUENCE: 54

```
tcgagaaaag gggcccgaat tcgcatgc                                        28
```

<210> SEQ ID NO 55
<211> LENGTH: 28
<212> TYPE: DNA
<213> ORGANISM: Artificial Sequence
<220> FEATURE:
<223> OTHER INFORMATION: Description of Artificial Sequence: 8823

<400> SEQUENCE: 55

```
ggccgcatgc gaattcgggc cccttttc                                        28
```

<210> SEQ ID NO 56
<211> LENGTH: 35
<212> TYPE: DNA
<213> ORGANISM: Artificial Sequence
<220> FEATURE:
<223> OTHER INFORMATION: Description of Artificial Sequence: 8649

<400> SEQUENCE: 56

```
tcgagaaaag agaggctgaa gcctgcagca tatgc                                35
```

<210> SEQ ID NO 57
<211> LENGTH: 35
<212> TYPE: DNA
<213> ORGANISM: Artificial Sequence
<220> FEATURE:
<223> OTHER INFORMATION: Description of Artificial Sequence: 8650

-continued

<400> SEQUENCE: 57
ggccgcatat gctgcaggct tcagcctctc ttttc 35

<210> SEQ ID NO 58
<211> LENGTH: 3997
<212> TYPE: DNA
<213> ORGANISM: Artificial Sequence
<220> FEATURE:
<223> OTHER INFORMATION: Description of Artificial Sequence:
vector pPICZalphaD'E1sH6

<400> SEQUENCE: 58
agatctaaca tccaaagacg aaaggttgaa tgaaaccttt ttgccatccg acatccacag 60
gtccattctc acacataagt gccaaacgca acaggagggg atacactagc agcagaccgt 120
tgcaaacgca ggacctccac tcctcttctc ctcaacaccc acttttgcca tcgaaaaacc 180
agcccagtta ttgggcttga ttggagctcg ctcattccaa ttccttctat taggctacta 240
acaccatgac tttattagcc tgtctatcct ggcccccctg gcgaggttca tgtttgttta 300
tttccgaatg caacaagctc cgcattacac ccgaacatca ctccagatga gggctttctg 360
agtgtggggt caaatagttt catgttcccc aaatggccca aaactgacag tttaaacgct 420
gtcttggaac ctaatatgac aaaagcgtga tctcatccaa gatgaactaa gtttggttcg 480
ttgaaatgct aacggccagt tggtcaaaaa gaaacttcca aaagtcggca taccgtttgt 540
cttgtttggt attgattgac gaatgctcaa aaataatctc attaatgctt agcgcagtct 600
ctctatcgct tctgaacccc ggtgcacctg tgccgaaacg caaatgggga aacacccgct 660
ttttggatga ttatgcattg tctccacatt gtatgcttcc aagattctgg tgggaatact 720
gctgatagcc taacgttcat gatcaaaatt taactgttct aacccctact tgacagcaat 780
atataaacag aaggaagctg ccctgtctta aacctttttt tttatcatca ttattagctt 840
actttcataa ttgcgactgg ttccaattga caagcttttg attttaacga cttttaacga 900
caacttgaga agatcaaaaa acaactaatt attcgaaacg atgagatttc cttcaatttt 960
tactgctgtt ttattcgcag catcctccgc attagctgct ccagtcaaca ctacaacaga 1020
agatgaaacg gcacaaattc cggctgaagc tgtcatcggt tactcagatt tagaagggga 1080
tttcgatgtt gctgttttgc cattttccaa cagcacaaat aacgggttat tgtttataaa 1140
tactactatt gccagcattg ctgctaaaga agaaggggta tctctcgaga aaaggtatga 1200
ggtgcgcaac gtgtccggga tgtaccatgt cacgaacgac tgctccaact caagcattgt 1260
gtatgaggca gcggacatga tcatgcacac ccccgggtgc gtgccctgcg ttcgggagaa 1320
caactcttcc cgctgctggg tagcgctcac ccccacgctc gcagctagga acgccagcgt 1380
ccccactacg acaatacgac gccacgtcga tttgctcgtt ggggcggctg ctttctgttc 1440
cgctatgtac gtgggggatc tctgcggatc tgtcttcctc gtctcccagc tgttcaccat 1500
ctcgcctcgc cggcatgaga cggtgcagga ctgcaattgc tcaatctatc ccggccacat 1560
aacaggtcac cgtatggctt gggatatgat gatgaactgg caccaccacc atcaccatta 1620
aagatctaag cttgaatccc gcggccatgc gaattcgcat gcggccgcca gctttctaga 1680
acaaaaactc atctcagaag aggatctgaa tagcgccgtc gaccatcatc atcatcatca 1740
ttgagtttgt agccttagac atgactgttc ctcagttcaa gttgggcact tacgagaaga 1800
ccggtcttgc tagattctaa tcaagaggat gtcagaatgc catttgcctg agagatgcag 1860
gcttcatttt tgatactttt ttatttgtaa cctatatagt ataggatttt ttttgtcatt 1920

-continued

```
ttgtttcttc tcgtacgagc ttgctcctga tcagcctatc tcgcagctga tgaatatctt   1980
gtggtagggg tttgggaaaa tcattcgagt ttgatgtttt tcttggtatt tcccactcct   2040
cttcagagta cagaagatta agtgagacct tcgtttgtgc ggatccccca cacaccatag   2100
cttcaaaatg tttctactcc ttttttactc ttccagattt tctcggactc cgcgcatcgc   2160
cgtaccactt caaaacaccc aagcacagca tactaaattt tccctctttc ttcctctagg   2220
gtgtcgttaa ttacccgtac taaaggtttg gaaaagaaaa aagagaccgc ctcgtttctt   2280
tttcttcgtc gaaaaaggca ataaaaattt ttatcacgtt tctttttctt gaaatttttt   2340
tttttagttt ttttctcttt cagtgacctc cattgatatt taagttaata aacggtcttc   2400
aatttctcaa gtttcagttt catttttctt gttctattac aacttttttt acttcttgtt   2460
cattagaaag aaagcatagc aatctaatct aaggggcggt gttgacaatt aatcatcggc   2520
atagtatatc ggcatagtat aatacgacaa ggtgaggaac taaaccatgg ccaagttgac   2580
cagtgccgtt ccggtgctca ccgcgcgcga cgtcgccgga gcggtcgagt tctggaccga   2640
ccggctcggg ttctcccggg acttcgtgga ggacgacttc gccggtgtgg tccgggacga   2700
cgtgaccctg ttcatcagcg cggtccagga ccaggtggtg ccggacaaca ccctggcctg   2760
ggtgtgggtg cgcggcctgg acgagctgta cgccgagtgg tcggaggtcg tgtccacgaa   2820
cttccgggac gcctccgggc cggccatgac cgagatcggc gagcagccgt gggggcggga   2880
gttcgccctg cgcgacccgg ccggcaactg cgtgcacttc gtggccgagg agcaggactg   2940
acacgtccga cggcggccca cgggtcccag gcctcggaga tccgtccccc ttttcctttg   3000
tcgatatcat gtaattagtt atgtcacgct tacattcacg ccctcccccc acatccgctc   3060
taaccgaaaa ggaaggagtt agacaacctg aagtctaggt ccctatttat ttttttatag   3120
ttatgttagt attaagaacg ttatttatat ttcaaatttt tctttttttt ctgtacagac   3180
gcgtgtacgc atgtaacatt atactgaaaa ccttgcttga gaaggttttg ggacgctcga   3240
aggctttaat ttgcaagctg gagaccaaca tgtgagcaaa aggccagcaa aaggccagga   3300
accgtaaaaa ggccgcgttg ctggcgtttt tccataggct ccgcccccct gacgagcatc   3360
acaaaaatcg acgctcaagt cagaggtggc gaaacccgac aggactataa agataccagg   3420
cgtttccccc tggaagctcc ctcgtgcgct ctcctgttcc gaccctgccg cttaccggat   3480
acctgtccgc ctttctccct tcgggaagcg tggcgctttc tcaatgctca cgctgtaggt   3540
atctcagttc ggtgtaggtc gttcgctcca agctgggctg tgtgcacgaa ccccccgttc   3600
agcccgaccg ctgcgcctta tccggtaact atcgtcttga gtccaacccg gtaagacacg   3660
acttatcgcc actggcagca gccactggta acaggattag cagagcgagg tatgtaggcg   3720
gtgctacaga gttcttgaag tggtggccta actacggcta cactagaagg acagtatttg   3780
gtatctgcgc tctgctgaag ccagttacct tcggaaaaag agttggtagc tcttgatccg   3840
gcaaacaaac caccgctggt agcggtggtt tttttgtttg caagcagcag attacgcgca   3900
gaaaaaaagg atctcaagaa gatcctttga tcttttctac ggggtctgac gctcagtgga   3960
acgaaaactc acgttaaggg attttggtca tgagatc                             3997
```

<210> SEQ ID NO 59
<211> LENGTH: 4004
<212> TYPE: DNA
<213> ORGANISM: Artificial Sequence
<220> FEATURE:
<223> OTHER INFORMATION: Description of Artificial Sequence:
vector pPICZalphaE'E1sH6

-continued

<400> SEQUENCE: 59

```
agatctaaca tccaaagacg aaaggttgaa tgaaaccttt ttgccatccg acatccacag     60
gtccattctc acacataagt gccaaacgca acaggagggg atacactagc agcagaccgt    120
tgcaaacgca ggacctccac tcctcttctc ctcaacaccc acttttgcca tcgaaaaacc    180
agcccagtta ttgggcttga ttggagctcg ctcattccaa ttccttctat taggctacta    240
acaccatgac tttattagcc tgtctatcct ggcccccctg gcgaggttca tgtttgttta    300
tttccgaatg caacaagctc cgcattacac ccgaacatca ctccagatga gggctttctg    360
agtgtggggt caaatagttt catgttcccc aaatggccca aaactgacag tttaaacgct    420
gtcttggaac ctaatatgac aaaagcgtga tctcatccaa gatgaactaa gtttggttcg    480
ttgaaatgct aacggccagt tggtcaaaaa gaaacttcca aaagtcggca taccgtttgt    540
cttgtttggt attgattgac gaatgctcaa aaataatctc attaatgctt agcgcagtct    600
ctctatcgct tctgaacccc ggtgcacctg tgccgaaacg caaatgggga aacacccgct    660
ttttggatga ttatgcattg tctccacatt gtatgcttcc aagattctgg tgggaatact    720
gctgatagcc taacgttcat gatcaaaatt taactgttct aacccctact tgacagcaat    780
atataaacag aaggaagctg ccctgtctta aacctttttt tttatcatca ttattagctt    840
actttcataa ttgcgactgg ttccaattga caagcttttg attttaacga cttttaacga    900
caacttgaga agatcaaaaa acaactaatt attcgaaacg atgagatttc cttcaatttt    960
tactgctgtt ttattcgcag catcctccgc attagctgct ccagtcaaca ctacaacaga   1020
agatgaaacg gcacaaattc cggctgaagc tgtcatcggt tactcagatt tagaagggga   1080
tttcgatgtt gctgttttgc cattttccaa cagcacaaat aacgggttat tgtttataaa   1140
tactactatt gccagcattg ctgctaaaga agaaggggta tctctcgaga aaagagaggc   1200
tgaagcctat gaggtgcgca acgtgtccgg gatgtaccat gtcacgaacg actgctccaa   1260
ctcaagcatt gtgtatgagg cagcggacat gatcatgcac acccccgggt gcgtgccctg   1320
cgttcgggag aacaactctt cccgctgctg ggtagcgctc acccccacgc tcgcagctag   1380
gaacgccagc gtccccacta cgacaatacg acgccacgtc gatttgctcg ttggggcggc   1440
tgctttctgt tccgctatgt acgtggggga tctctgcgga tctgtcttcc tcgtctccca   1500
gctgttcacc atctcgcctc gccggcatga gacggtgcag gactgcaatt gctcaatcta   1560
tcccggccac ataacgggtc accgtatggc ttgggatatg atgatgaact ggcaccacca   1620
ccatcaccat taaagatcta agcttgaatc ccgcggccat ggcatatgcg gccgccagct   1680
ttctagaaca aaaactcatc tcagaagagg atctgaatag cgccgtcgac catcatcatc   1740
atcatcattg agtttgtagc cttagacatg actgttcctc agttcaagtt gggcacttac   1800
gagaagaccg gtcttgctag attctaatca agaggatgtc agaatgccat ttgcctgaga   1860
gatgcaggct tcatttttga tacttttttta tttgtaacct atatagtata ggattttttt   1920
tgtcattttg tttcttctcg tacgagcttg ctcctgatca gcctatctcg cagctgatga   1980
atatcttgtg gtaggggttt gggaaaatca ttcgagtttg atgtttttct tggtatttcc   2040
cactcctctt cagagtacag aagattaagt gagaccttcg tttgtgcgga tcccccacac   2100
accatagctt caaaatgttt ctactccttt tttactcttc cagattttct cggactccgc   2160
gcatcgccgt accacttcaa aacacccaag cacagcatac taaattttcc ctctttcttc   2220
ctctagggtg tcgttaatta cccgtactaa aggtttggaa aagaaaaaag agaccgcctc   2280
gtttcttttt cttcgtcgaa aaaggcaata aaaattttta tcacgtttct ttttcttgaa   2340
```

-continued

```
atttttttt ttagtttttt tctctttcag tgacctccat tgatatttaa gttaataaac   2400
ggtcttcaat ttctcaagtt tcagtttcat ttttcttgtt ctattacaac ttttttttact   2460
tcttgttcat tagaaagaaa gcatagcaat ctaatctaag gggcggtgtt gacaattaat   2520
catcggcata gtatatcggc atagtataat acgacaaggt gaggaactaa accatggcca   2580
agttgaccag tgccgttccg gtgctcaccg cgcgcgacgt cgccggagcg gtcgagttct   2640
ggaccgaccg gctcgggttc tcccgggact tcgtggagga cgacttcgcc ggtgtggtcc   2700
gggacgacgt gaccctgttc atcagcgcgg tccaggacca ggtggtgccg gacaacaccc   2760
tggcctgggt gtgggtgcgc ggcctggacg agctgtacgc cgagtggtcg gaggtcgtgt   2820
ccacgaactt ccgggacgcc tccgggccgg ccatgaccga gatcggcgag cagccgtggg   2880
ggcgggagtt cgccctgcgc gacccggccg gcaactgcgt gcacttcgtg gccgaggagc   2940
aggactgaca cgtccgacgg cggcccacgg gtcccaggcc tcggagatcc gtcccccttt   3000
tcctttgtcg atatcatgta attagttatg tcacgcttac attcacgccc tccccccaca   3060
tccgctctaa ccgaaaagga aggagttaga caacctgaag tctaggtccc tatttatttt   3120
tttatagtta tgttagtatt aagaacgtta tttatatttc aaatttttct tttttttctg   3180
tacagacgcg tgtacgcatg taacattata ctgaaaacct tgcttgagaa ggttttggga   3240
cgctcgaagg ctttaatttg caagctggag accaacatgt gagcaaaagg ccagcaaaag   3300
gccaggaacc gtaaaaaggc cgcgttgctg gcgtttttcc ataggctccg cccccctgac   3360
gagcatcaca aaaatcgacg ctcaagtcag aggtggcgaa acccgacagg actataaaga   3420
taccaggcgt ttccccctgg aagctccctc gtgcgctctc ctgttccgac cctgccgctt   3480
accggatacc tgtccgcctt tctcccttcg ggaagcgtgg cgctttctca atgctcacgc   3540
tgtaggtatc tcagttcggt gtaggtcgtt cgctccaagc tgggctgtgt gcacgaaccc   3600
cccgttcagc ccgaccgctg cgccttatcc ggtaactatc gtcttgagtc caacccggta   3660
agacacgact tatcgccact ggcagcagcc actggtaaca ggattagcag agcgaggtat   3720
gtaggcggtg ctacagagtt cttgaagtgg tggcctaact acggctacac tagaaggaca   3780
gtatttggta tctgcgctct gctgaagcca gttaccttcg gaaaaagagt tggtagctct   3840
tgatccggca aacaaaccac cgctggtagc ggtggttttt ttgtttgcaa gcagcagatt   3900
acgcgcagaa aaaaaggatc tcaagaagat cctttgatct tttctacggg gtctgacgct   3960
cagtggaacg aaaactcacg ttaagggatt ttggtcatga gatc                      4004
```

```
<210> SEQ ID NO 60
<211> LENGTH: 4492
<212> TYPE: DNA
<213> ORGANISM: Artificial Sequence
<220> FEATURE:
<223> OTHER INFORMATION: Description of Artificial Sequence:
      vector pPICZalphaD'E2sH6

<400> SEQUENCE: 60
```

```
agatctaaca tccaaagacg aaaggttgaa tgaaaccttt ttgccatccg acatccacag     60
gtccattctc acacataagt gccaaacgca acaggagggg atacactagc agcagaccgt    120
tgcaaacgca ggacctccac tcctcttctc ctcaacaccc acttttgcca tcgaaaaacc    180
agcccagtta ttgggcttga ttggagctcg ctcattccaa ttccttctat taggctacta    240
acaccatgac tttattagcc tgtctatcct ggcccccctg gcgaggttca tgtttgttta    300
```

-continued

```
tttccgaatg caacaagctc cgcattacac ccgaacatca ctccagatga gggctttctg    360
agtgtggggt caaatagttt catgttcccc aaatggccca aaactgacag tttaaacgct    420
gtcttggaac ctaatatgac aaaagcgtga tctcatccaa gatgaactaa gtttggttcg    480
ttgaaatgct aacggccagt tggtcaaaaa gaaacttcca aaagtcggca taccgtttgt    540
cttgtttggt attgattgac gaatgctcaa aaataatctc attaatgctt agcgcagtct    600
ctctatcgct tctgaacccc ggtgcacctg tgccgaaacg caaatgggga aacacccgct    660
ttttggatga ttatgcattg tctccacatt gtatgcttcc aagattctgg tgggaatact    720
gctgatagcc taacgttcat gatcaaaatt taactgttct aacccctact tgacagcaat    780
atataaacag aaggaagctg ccctgtctta aacctttttt tttatcatca ttattagctt    840
actttcataa ttgcgactgg ttccaattga caagcttttg attttaacga cttttaacga    900
caacttgaga agatcaaaaa acaactaatt attcgaaacg atgagatttc cttcaatttt    960
tactgctgtt ttattcgcag catcctccgc attagctgct ccagtcaaca ctacaacaga   1020
agatgaaacg gcacaaattc cggctgaagc tgtcatcggt tactcagatt tagaagggga   1080
tttcgatgtt gctgttttgc cattttccaa cagcacaaat aacgggttat tgtttataaa   1140
tactactatt gccagcattg ctgctaaaga agaaggggta tctctcgaga aaaggcatac   1200
ccgcgtgtca ggaggggcag cagcctccga taccaggggc cttgtgtccc tctttagccc   1260
cgggtcggct cagaaaatcc agctcgtaaa caccaacggc agttggcaca tcaacaggac   1320
tgccctgaac tgcaacgact ccctccaaac agggttcttt gccgcactat tctacaaaca   1380
caaattcaac tcgtctggat gcccagagcg cttggccagc tgtcgctcca tcgacaagtt   1440
cgctcagggg tggggtcccc tcacttacac tgagcctaac agctcggacc agaggcccta   1500
ctgctggcac tacgcgcctc gaccgtgtgg tattgtaccc gcgtctcagg tgtgcggtcc   1560
agtgtattgc ttcaccccga gccctgttgt ggtggggacg accgatcggt ttggtgtccc   1620
cacgtataac tgggggggcga acgactcgga tgtgctgatt ctcaacaaca cgcggccgcc   1680
gcgaggcaac tggttcggct gtacatggat gaatggcact gggttcacca agacgtgtgg   1740
gggccccccg tgcaacatcg gggggggccgg caacaacacc ttgacctgcc ccactgactg   1800
ttttcggaag caccccgagg ccacctacgc cagatgcggt tctgggccct ggctgacacc   1860
taggtgtatg gttcattacc catataggct ctggcactac ccctgcactg tcaacttcac   1920
catcttcaag gttaggatgt acgtgggggg cgtggagcac aggttcgaag ccgcatgcaa   1980
ttggactcga ggagagcgtt gtgacttgga ggacagggat agatcagagc ttagcccgct   2040
gctgctgtct acaacagagt ggcaggtgat cgagggcaga caccatcacc accatcacta   2100
atagttaatt aactgcaggc atgcaagctt atcgataccg tcgacgaatt cgcatgcggc   2160
cgccagcttt ctagaacaaa aactcatctc agaagaggat ctgaatagcg ccgtcgacca   2220
tcatcatcat catcattgag tttgtagcct tagacatgac tgttcctcag ttcaagttgg   2280
gcacttacga gaagaccggt cttgctagat tctaatcaag aggatgtcag aatgccattt   2340
gcctgagaga tgcaggcttc atttttgata cttttttatt tgtaacctat atagtatagg   2400
atttttttttg tcattttgtt tcttctcgta cgagcttgct cctgatcagc ctatctcgca   2460
gctgatgaat atcttgtggt aggggtttgg gaaaatcatt cgagtttgat gtttttcttg   2520
gtatttccca ctcctcttca gagtacagaa gattaagtga gaccttcgtt tgtgcggatc   2580
ccccacacac catagcttca aaatgtttct actccttttt tactcttcca gattttctcg   2640
gactccgcgc atcgccgtac cacttcaaaa cacccaagca cagcatacta aattttccct   2700
```

-continued

```
ctttcttcct ctagggtgtc gttaattacc cgtactaaag gtttggaaaa gaaaaaagag   2760

accgcctcgt ttcttttct tcgtcgaaaa aggcaataaa aatttttatc acgtttcttt   2820

ttcttgaaat ttttttttt agtttttttc tctttcagtg acctccattg atatttaagt   2880

taataaacgg tcttcaattt ctcaagtttc agtttcattt ttcttgttct attacaactt   2940

tttttacttc ttgttcatta gaaagaaagc atagcaatct aatctaaggg gcggtgttga   3000

caattaatca tcggcatagt atatcggcat agtataatac gacaaggtga ggaactaaac   3060

catggccaag ttgaccagtg ccgttccggt gctcaccgcg cgcgacgtcg ccggagcggt   3120

cgagttctgg accgaccggc tcgggttctc ccgggacttc gtggaggacg acttcgccgg   3180

tgtggtccgg gacgacgtga ccctgttcat cagcgcggtc caggaccagg tggtgccgga   3240

caacaccctg gcctgggtgt gggtgcgcgg cctggacgag ctgtacgccg agtggtcgga   3300

ggtcgtgtcc acgaacttcc gggacgcctc cgggccggcc atgaccgaga tcggcgagca   3360

gccgtggggg cgggagttcg ccctgcgcga cccggccggc aactgcgtgc acttcgtggc   3420

cgaggagcag gactgacacg tccgacggcg gcccacgggt cccaggcctc ggagatccgt   3480

ccccctttc ctttgtcgat atcatgtaat tagttatgtc acgcttacat tcacgccctc   3540

cccccacatc cgctctaacc gaaaaggaag gagttagaca acctgaagtc taggtcccta   3600

tttatttttt tatagttatg ttagtattaa gaacgttatt tatatttcaa atttttcttt   3660

tttttctgta cagacgcgtg tacgcatgta acattatact gaaaaccttg cttgagaagg   3720

ttttgggacg ctcgaaggct ttaatttgca agctggagac caacatgtga gcaaaaggcc   3780

agcaaaaggc caggaaccgt aaaaaggccg cgttgctggc gtttttccat aggctccgcc   3840

cccctgacga gcatcacaaa aatcgacgct caagtcagag gtggcgaaac ccgacaggac   3900

tataaagata ccaggcgttt ccccctggaa gctccctcgt gcgctctcct gttccgaccc   3960

tgccgcttac cggatacctg tccgcctttc tcccttcggg aagcgtggcg ctttctcaat   4020

gctcacgctg taggtatctc agttcggtgt aggtcgttcg ctccaagctg ggctgtgtgc   4080

acgaaccccc cgttcagccc gaccgctgcg ccttatccgg taactatcgt cttgagtcca   4140

acccggtaag acacgactta tcgccactgg cagcagccac tggtaacagg attagcagag   4200

cgaggtatgt aggcggtgct acagagttct tgaagtggtg gcctaactac ggctacacta   4260

gaaggacagt atttggtatc tgcgctctgc tgaagccagt taccttcgga aaaagagttg   4320

gtagctcttg atccggcaaa caaaccaccg ctggtagcgg tggttttttt gtttgcaagc   4380

agcagattac gcgcagaaaa aaaggatctc aagaagatcc tttgatcttt tctacggggt   4440

ctgacgctca gtggaacgaa aactcacgtt aagggatttt ggtcatgaga tc            4492
```

<210> SEQ ID NO 61
<211> LENGTH: 4431
<212> TYPE: DNA
<213> ORGANISM: Artificial Sequence
<220> FEATURE:
<223> OTHER INFORMATION: Description of Artificial Sequence:
vector pPICZalphaE'E2sH6

<400> SEQUENCE: 61

```
agatctaaca tccaaagacg aaaggttgaa tgaaaccttt ttgccatccg acatccacag     60

gtccattctc acacataagt gccaaacgca acaggagggg atacactagc agcagaccgt    120

tgcaaacgca ggacctccac tcctcttctc ctcaacaccc acttttgcca tcgaaaaacc    180

agcccagtta ttgggcttga ttggagctcg ctcattccaa ttccttctat taggctacta    240
```

-continued

```
acaccatgac tttattagcc tgtctatcct ggcccccctg gcgaggttca tgtttgttta    300
tttccgaatg caacaagctc cgcattacac ccgaacatca ctccagatga gggctttctg    360
agtgtggggt caaatagttt catgttcccc aaatggccca aaactgacag tttaaacgct    420
gtcttggaac ctaatatgac aaaagcgtga tctcatccaa gatgaactaa gtttggttcg    480
ttgaaatgct aacggccagt tggtcaaaaa gaaacttcca aaagtcggca taccgtttgt    540
cttgtttggt attgattgac gaatgctcaa aaataatctc attaatgctt agcgcagtct    600
ctctatcgct tctgaacccc ggtgcacctg tgccgaaacg caaatgggga aacacccgct    660
ttttggatga ttatgcattg tctccacatt gtatgcttcc aagattctgg tgggaatact    720
gctgatagcc taacgttcat gatcaaaatt taactgttct aacccctact tgacagcaat    780
atataaacag aaggaagctg ccctgtctta aacctttttt tttatcatca ttattagctt    840
actttcataa ttgcgactgg ttccaattga caagcttttg attttaacga cttttaacga    900
caacttgaga agatcaaaaa acaactaatt attcgaaacg atgagatttc cttcaatttt    960
tactgctgtt ttattcgcag catcctccgc attagctgct ccagtcaaca ctacaacaga   1020
agatgaaacg gcacaaattc cggctgaagc tgtcatcggt tactcagatt tagaagggga   1080
tttcgatgtt gctgttttgc cattttccaa cagcacaaat aacgggttat tgtttataaa   1140
tactactatt gccagcattg ctgctaaaga agaaggggta tctctcgaga aaagagaggc   1200
tgaagcccat acccgcgtgt caggaggggc agcagcctcc gataccaggg gccttgtgtc   1260
cctctttagc cccgggtcgg ctcagaaaat ccagctcgta aacaccaacg gcagttggca   1320
catcaacagg actgccctga actgcaacga ctccctccaa acagggttct ttgccgcact   1380
attctacaaa cacaaattca actcgtctgg atgcccagag cgcttggcca gctgtcgctc   1440
catcgacaag ttcgctcagg ggtggggtcc cctcacttac actgagccta acagctcgga   1500
ccagaggccc tactgctggc actacgcgcc tcgaccgtgt ggtattgtac ccgcgtctca   1560
ggtgtgcggt ccagtgtatt gcttcacccc gagccctgtt gtggtgggga cgaccgatcg   1620
gtttggtgtc cccacgtata actgggggc gaacgactcg gatgtgctga ttctcaacaa    1680
cacgcggccg ccgcgaggca actggttcgg ctgtacatgg atgaatggca ctgggttcac   1740
caagacgtgt gggggccccc cgtgcaacat cggggggggcc ggcaacaaca ccttgacctg  1800
ccccactgac tgttttcgga agcaccccga ggccacctac gccagatgcg gttctgggcc   1860
ctggctgaca cctaggtgta tggttcatta cccatatagg ctctggcact acccctgcac   1920
tgtcaacttc accatcttca aggttaggat gtacgtgggg ggcgtggagc acaggttcga   1980
agccgcatgc aattggactc gaggagagcg ttgtgacttg gaggacaggg atagatcaga   2040
gcttagcccg ctgctgctgt ctacaacaga gtggcaggtg atcgagggca gacaccatca   2100
ccaccatcac taatagttaa ttaactgcag gcatgcaagc ttatcgatac cgtcgaccat   2160
catcatcatc atcattgagt ttgtagcctt agacatgact gttcctcagt tcaagttggg   2220
cacttacgag aagaccggtc ttgctagatt ctaatcaaga ggatgtcaga atgccatttg   2280
cctgagagat gcaggcttca tttttgatac ttttttattt gtaacctata tagtatagga   2340
tttttttttgt cattttgttt cttctcgtac gagcttgctc ctgatcagcc tatctcgcag  2400
ctgatgaata tcttgtggta ggggtttggg aaaatcattc gagtttgatg tttttcttgg   2460
tatttcccac tcctcttcag agtacagaag attaagtgag accttcgttt gtgcggatcc   2520
cccacacacc atagcttcaa aatgtttcta ctcctttttt actcttccag attttctcgg   2580
```

-continued

```
actccgcgca tcgccgtacc acttcaaaac acccaagcac agcatactaa attttccctc   2640

tttcttcctc tagggtgtcg ttaattaccc gtactaaagg tttggaaaag aaaaaagaga   2700

ccgcctcgtt tctttttctt cgtcgaaaaa ggcaataaaa atttttatca cgtttctttt   2760

tcttgaaatt ttttttttta gtttttttct ctttcagtga cctccattga tatttaagtt   2820

aataaacggt cttcaatttc tcaagtttca gtttcatttt tcttgttcta ttacaacttt   2880

ttttacttct tgttcattag aaagaaagca tagcaatcta atctaagggg cggtgttgac   2940

aattaatcat cggcatagta tatcggcata gtataatacg acaaggtgag gaactaaacc   3000

atggccaagt tgaccagtgc cgttccggtg ctcaccgcgc gcgacgtcgc cggagcggtc   3060

gagttctgga ccgaccggct cgggttctcc cgggacttcg tggaggacga cttcgccggt   3120

gtggtccggg acgacgtgac cctgttcatc agcgcggtcc aggaccaggt ggtgccggac   3180

aacaccctgg cctgggtgtg ggtgcgcggc ctggacgagc tgtacgccga gtggtcggag   3240

gtcgtgtcca cgaacttccg ggacgcctcc gggccggcca tgaccgagat cggcgagcag   3300

ccgtgggggc gggagttcgc cctgcgcgac ccggccggca actgcgtgca cttcgtggcc   3360

gaggagcagg actgacacgt ccgacggcgg cccacgggtc ccaggcctcg gagatccgtc   3420

cccctttcc tttgtcgata tcatgtaatt agttatgtca cgcttacatt cacgccctcc   3480

ccccacatcc gctctaaccg aaaaggaagg agttagacaa cctgaagtct aggtccctat   3540

ttattttttt atagttatgt tagtattaag aacgttattt atatttcaaa tttttctttt   3600

ttttctgtac agacgcgtgt acgcatgtaa cattatactg aaaaccttgc ttgagaaggt   3660

tttgggacgc tcgaaggctt taatttgcaa gctggagacc aacatgtgag caaaaggcca   3720

gcaaaaggcc aggaaccgta aaaaggccgc gttgctggcg tttttccata ggctccgccc   3780

ccctgacgag catcacaaaa atcgacgctc aagtcagagg tggcgaaacc cgacaggact   3840

ataaagatac caggcgtttc cccctggaag ctccctcgtg cgctctcctg ttccgaccct   3900

gccgcttacc ggatacctgt ccgcctttct cccttcggga agcgtggcgc tttctcaatg   3960

ctcacgctgt aggtatctca gttcggtgta ggtcgttcgc tccaagctgg gctgtgtgca   4020

cgaacccccc gttcagcccg accgctgcgc cttatccggt aactatcgtc ttgagtccaa   4080

cccggtaaga cacgacttat cgccactggc agcagccact ggtaacagga ttagcagagc   4140

gaggtatgta ggcggtgcta cagagttctt gaagtggtgg cctaactacg gctacactag   4200

aaggacagta tttggtatct gcgctctgct gaagccagtt accttcggaa aaagagttgg   4260

tagctcttga tccggcaaac aaaccaccgc tggtagcggt ggtttttttg tttgcaagca   4320

gcagattacg cgcagaaaaa aaggatctca agaagatcct ttgatctttt ctacggggtc   4380

tgacgctcag tggaacgaaa actcacgtta agggattttg gtcatgagat c            4431
```

```
<210> SEQ ID NO 62
<211> LENGTH: 2880
<212> TYPE: DNA
<213> ORGANISM: Artificial Sequence
<220> FEATURE:
<223> OTHER INFORMATION: Description of Artificial Sequence:
      vector pUC18MFa

<400> SEQUENCE: 62
```

```
gcgcccaata cgcaaaccgc ctctccccgc gcgttggccg attcattaat gcagctggca     60

cgacaggttt cccgactgga aagcgggcag tgagcgcaac gcaattaatg tgagttagct    120

cactcattag gcaccccagg ctttacactt tatgcttccg gctcgtatgt tgtgtggaat    180
```

-continued

```
tgtgagcgga taacaatttc acacaggaaa cagctatgac catgattacg ccaagcttac    240
cccttcttct ttagcagcaa tgctggcaat agtagtattt ataaacaata acccgttatt    300
tgtgctgttg gaaaatggca aaacagcaac atcgaaatcc ccttctaaat ctgagtaacc    360
gatgacagct tcagccggaa tttgtgccgt ttcatcttct gttgtagtgt tgactggagc    420
agctaatgcg gaggatgctg cgaataaaac tgcagtaaaa attgaaggaa atctcatgaa    480
ttcactggcc gtcgttttac aacgtcgtga ctgggaaaac cctggcgtta cccaacttaa    540
tcgccttgca gcacatcccc ctttcgccag ctggcgtaat agcgaagagg cccgcaccga    600
tcgcccttcc caacagttgc gcagcctgaa tggcgaatgg cgcctgatgc ggtattttct    660
ccttacgcat ctgtgcggta tttcacaccg catatggtgc actctcagta caatctgctc    720
tgatgccgca tagttaagcc agccccgaca cccgccaaca cccgctgacg cgccctgacg    780
ggcttgtctg ctcccggcat ccgcttacag acaagctgtg accgtctccg ggagctgcat    840
gtgtcagagg ttttcaccgt catcaccgaa acgcgcgaga cgaaagggcc tcgtgatacg    900
cctattttta taggttaatg tcatgataat aatggtttct tagacgtcag gtggcacttt    960
tcggggaaat gtgcgcggaa cccctatttg tttatttttc taaatacatt caaatatgta   1020
tccgctcatg agacaataac cctgataaat gcttcaataa tattgaaaaa ggaagagtat   1080
gagtattcaa catttccgtg tcgcccttat tccctttttt gcggcatttt gccttcctgt   1140
ttttgctcac ccagaaacgc tggtgaaagt aaaagatgct gaagatcagt tgggtgcacg   1200
agtgggttac atcgaactgg atctcaacag cggtaagatc cttgagagtt ttcgccccga   1260
agaacgtttt ccaatgatga gcacttttaa agttctgcta tgtggcgcgg tattatcccg   1320
tattgacgcc gggcaagagc aactcggtcg ccgcatacac tattctcaga atgacttggt   1380
tgagtactca ccagtcacag aaaagcatct tacggatggc atgacagtaa gagaattatg   1440
cagtgctgcc ataaccatga gtgataacac tgcggccaac ttacttctga caacgatcgg   1500
aggaccgaag gagctaaccg cttttttgca caacatgggg gatcatgtaa ctcgccttga   1560
tcgttgggaa ccggagctga atgaagccat accaaacgac gagcgtgaca ccacgatgcc   1620
tgtagcaatg gcaacaacgt tgcgcaaact attaactggc gaactactta ctctagcttc   1680
ccggcaacaa ttaatagact ggatggaggc ggataaagtt gcaggaccac ttctgcgctc   1740
ggcccttccg gctggctggt ttattgctga taaatctgga gccggtgagc gtgggtctcg   1800
cggtatcatt gcagcactgg ggccagatgg taagccctcc cgtatcgtag ttatctacac   1860
gacggggagt caggcaacta tggatgaacg aaatagacag atcgctgaga taggtgcctc   1920
actgattaag cattggtaac tgtcagacca agtttactca tatatacttt agattgattt   1980
aaaacttcat ttttaattta aaaggatcta ggtgaagatc ctttttgata atctcatgac   2040
caaaatccct taacgtgagt tttcgttcca ctgagcgtca gaccccgtag aaaagatcaa   2100
aggatcttct tgagatcctt tttttctgcg cgtaatctgc tgcttgcaaa caaaaaaacc   2160
accgctacca gcggtggttt gtttgccgga tcaagagcta ccaactcttt ttccgaaggt   2220
aactggcttc agcagagcgc agataccaaa tactgtcctt ctagtgtagc cgtagttagg   2280
ccaccacttc aagaactctg tagcaccgcc tacatacctc gctctgctaa tcctgttacc   2340
agtggctgct gccagtggcg ataagtcgtg tcttaccggg ttggactcaa gacgatagtt   2400
accggataag gcgcagcggt cgggctgaac ggggggttcg tgcacacagc ccagcttgga   2460
gcgaacgacc tacaccgaac tgagatacct acagcgtgag ctatgagaaa gcgccacgct   2520
tcccgaaggg agaaaggcgg acaggtatcc ggtaagcggc agggtcggaa caggagagcg   2580
```

-continued

```
cacgagggag cttccagggg gaaacgcctg gtatctttat agtcctgtcg ggtttcgcca   2640

cctctgactt gagcgtcgat ttttgtgatg ctcgtcaggg gggcggagcc tatggaaaaa   2700

cgccagcaac gcggcctttt tacggttcct ggccttttgc tggccttttg ctcacatgtt   2760

ctttcctgcg ttatcccctg attctgtgga taaccgtatt accgcctttg agtgagctga   2820

taccgctcgc cgcagccgaa cgaccgagcg cagcgagtca gtgagcgagg aagcggaaga   2880


<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence:
      adaptor peptide

<400> SEQUENCE: 63

His His His His His His
1               5


<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence:
      adaptor peptide

<400> SEQUENCE: 64

Glu Glu Gly Glu Pro Lys
1               5


<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence:
      adaptor peptide

<400> SEQUENCE: 65

Glu Glu Ala Glu Pro Lys
1               5


<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence:
      processing site
<220> FEATURE:
<221> NAME/KEY: MISC_FEATURE
<222> LOCATION: (5)..(5)
<223> OTHER INFORMATION: X is any amino acid

<400> SEQUENCE: 66

Ile Glu Gly Arg Xaa
1               5


<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence:
      processing site
```

-continued

<220> FEATURE:
<221> NAME/KEY: MISC_FEATURE
<222> LOCATION: (5)..(5)
<223> OTHER INFORMATION: X is any amino acid

<400> SEQUENCE: 67

Ile Asp Gly Arg Xaa
1               5

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence: processing site
<220> FEATURE:
<221> NAME/KEY: MISC_FEATURE
<222> LOCATION: (5)..(5)
<223> OTHER INFORMATION: X is any amino acid

<400> SEQUENCE: 68

Ala Glu Gly Arg Xaa
1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: adaptor peptide

<400> SEQUENCE: 69

Val Ile Glu Gly Arg
1               5

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: adaptor peptide

<400> SEQUENCE: 70

Ile Glu Gly Arg
1

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence: adaptor peptide

<400> SEQUENCE: 71

Ile Asp Gly Arg
1

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence: adaptor peptide

<400> SEQUENCE: 72

Ala Glu Gly Arg
1

<210> SEQ ID NO 73
<211> LENGTH: 4
<212> TYPE: PRT
<213> ORGANISM: Artificial Sequence
<220> FEATURE:
<223> OTHER INFORMATION: Description of Artificial
equence: HCV E1

<400> SEQUENCE: 73

Asn Asn Ser Ser
1

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequen
e: FLAG epitope

<400> SEQUENCE: 74

Asp Tyr Lys Asp Asp Asp Asp Lys
1 5

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: P
otein C epitope

<400> SEQUENCE: 75

Glu Asp Gln Val Asp Pro Arg Leu Ile Asp Gly Lys
1 5 10

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Seque
ce: VSV epitope

<400> SEQUENCE: 76

Tyr Thr Asp Ile Glu Met Asn Arg Leu Gly Lys
1 5 10

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Se
uence: streptag

<400> SEQUENCE: 77

Ala Trp Arg His Pro Gln Phe Gly Gly
1 5

<210> SEQ ID NO 78
<211> LENGTH: 12
<212> TYPE: PRT

-continued

```
<213> ORGANISM: Artificial Sequence
<220> FEATURE:
<223> OTHER INFORMATION: Description of Artificial Sequence
      Tag100 epitope

<400> SEQUENCE: 78

Glu Glu Thr Ala Arg Phe Gln Pro Gly Tyr Arg Ser
1               5                   10


<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequenc
      : c-myc epitope

<400> SEQUENCE: 79

Glu Gln Lys Leu Ile Ser Glu Glu Asp Leu
1               5                   10


<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequ
      nce: HA epitope

<400> SEQUENCE: 80

Tyr Pro Tyr Asp Val Pro Asp Tyr Ala Ser Leu
1               5                   10


<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequ
      nce: HA epitope

<400> SEQUENCE: 81

Tyr Pro Tyr Asp Val Pro Asp Tyr Ala
1               5


<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: HA epitope

<400> SEQUENCE: 82

Cys Tyr Pro Tyr Asp Val Pro Asp Tyr Ala Ser Leu
1               5                   10


<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence:
      thrombin cleavage site

<400> SEQUENCE: 83

Leu Val Pro Arg Gly Ser
1               5
```

-continued

<210> SEQ ID NO 84
<211> LENGTH: 4
<212> TYPE: PRT
<213> ORGANISM: Artificial Sequence
<220> FEATURE:
<223> OTHER INFORMATION: Description of Artificial Sequence: collagenase recognition site
<220> FEATURE:
<221> NAME/KEY: MISC_FEATURE
<222> LOCATION: (2)..(2)
<223> OTHER INFORMATION: Xaa is any amino acid but most frequently a neutral amino acid

<400> SEQUENCE: 84

```
Pro Xaa Gly Pro
1
```

<210> SEQ ID NO 85
<211> LENGTH: 192
<212> TYPE: PRT
<213> ORGANISM: Artificial Sequence
<220> FEATURE:
<223> OTHER INFORMATION: Description of Artificial Sequence: hepatitis C virus

<400> SEQUENCE: 85

```
Tyr Gln Val Arg Asn Ser Ser Gly Leu Tyr His Val Thr Asn Asp Cys
1               5                   10                  15

Pro Asn Ser Ser Val Val Tyr Glu Ala Ala Asp Ala Ile Leu His Thr
            20                  25                  30

Pro Gly Cys Val Pro Cys Val Arg Glu Gly Asn Ala Ser Arg Cys Trp
        35                  40                  45

Val Ala Val Thr Pro Thr Val Ala Thr Arg Asp Gly Lys Leu Pro Thr
    50                  55                  60

Thr Gln Leu Arg Arg His Ile Asp Leu Leu Val Gly Ser Ala Thr Leu
65                  70                  75                  80

Cys Ser Ala Leu Tyr Val Gly Asp Leu Cys Gly Ser Val Phe Leu Val
                85                  90                  95

Gly Gln Leu Phe Thr Phe Ser Pro Arg His His Trp Thr Thr Gln Asp
            100                 105                 110

Cys Asn Cys Ser Ile Tyr Pro Gly His Ile Thr Gly His Arg Met Ala
        115                 120                 125

Trp Asp Met Met Met Asn Trp Ser Pro Thr Ala Ala Leu Val Val Ala
    130                 135                 140

Gln Leu Leu Arg Ile Pro Gln Ala Ile Met Asp Met Ile Ala Gly Ala
145                 150                 155                 160

His Trp Gly Val Leu Ala Gly Ile Ala Tyr Phe Ser Met Val Gly Asn
                165                 170                 175

Trp Ala Glu Val Leu Val Val Leu Leu Leu Phe Ala Gly Val Asp Ala
            180                 185                 190
```

<210> SEQ ID NO 86
<211> LENGTH: 209
<212> TYPE: PRT
<213> ORGANISM: Artificial Sequence
<220> FEATURE:
<223> OTHER INFORMATION: Description of Artificial Sequence: hepatitis C virus

<400> SEQUENCE: 86

```
Met Leu Gly Lys Leu Ile Asp Thr Leu Thr Cys Gly Phe Ala Asp Leu
1               5                   10                  15
```

-continued

```
Met Gly Tyr Ile Pro Leu Val Gly Ala Pro Leu Gly Gly Ala Ala Arg
            20                  25                  30

Ala Leu Ala His Gly Ala Arg Val Leu Glu Asp Gly Val Ile Tyr Ala
        35                  40                  45

Thr Gly Asn Leu Pro Gly Cys Ser Phe Ser Ile Phe Leu Leu Ala Leu
    50                  55                  60

Leu Ser Cys Leu Thr Val Pro Ala Ser Ala Tyr Gln Val Arg Asn Ser
65                  70                  75                  80

Ser Gly Leu Tyr His Val Thr Asn Asp Cys Pro Asn Ser Ser Val Val
                85                  90                  95

Tyr Glu Ala Ala Asp Ala Ile Leu His Thr Pro Gly Cys Val Pro Cys
            100                 105                 110

Val Arg Glu Gly Asn Ala Ser Arg Cys Trp Val Ala Val Thr Pro Thr
        115                 120                 125

Val Ala Thr Arg Asp Gly Lys Leu Pro Thr Thr Gln Leu Arg Arg His
    130                 135                 140

Ile Asp Leu Leu Val Gly Ser Ala Thr Leu Cys Ser Ala Leu Tyr Val
145                 150                 155                 160

Gly Asp Leu Cys Gly Ser Val Phe Leu Val Gly Gln Leu Phe Thr Phe
                165                 170                 175

Ser Pro Arg His His Trp Thr Thr Gln Asp Cys Asn Cys Ser Ile Tyr
            180                 185                 190

Pro Gly His Ile Thr Gly His Arg Met Ala Trp Asp Met Met Met Asn
        195                 200                 205

Trp
```

```
<210> SEQ ID NO 87
<211> LENGTH: 192
<212> TYPE: PRT
<213> ORGANISM: Artificial Sequence
<220> FEATURE:
<223> OTHER INFORMATION: Description of Artificial Sequence:
      hepatitis C virus

<400> SEQUENCE: 87

Tyr Glu Val Arg Asn Val Ser Gly Met Tyr His Val Thr Asn Asp Cys
1               5                   10                  15

Ser Asn Ser Ser Ile Val Tyr Glu Ala Ala Asp Met Ile Met His Thr
            20                  25                  30

Pro Gly Cys Val Pro Cys Val Arg Glu Asn Asn Ser Ser Arg Cys Trp
        35                  40                  45

Val Ala Leu Thr Pro Thr Leu Ala Ala Arg Asn Ala Ser Val Pro Thr
    50                  55                  60

Thr Thr Ile Arg Arg His Val Asp Leu Leu Val Gly Ala Ala Ala Phe
65                  70                  75                  80

Cys Ser Ala Met Tyr Val Gly Asp Leu Cys Gly Ser Val Phe Leu Val
                85                  90                  95

Ser Gln Leu Phe Thr Ile Ser Pro Arg Arg His Glu Thr Val Gln Asp
            100                 105                 110

Cys Asn Cys Ser Ile Tyr Pro Gly His Ile Thr Gly His Arg Met Ala
        115                 120                 125

Trp Asp Met Met Met Asn Trp Ser Pro Thr Thr Ala Leu Val Val Ser
    130                 135                 140

Gln Leu Leu Arg Ile Pro Gln Ala Val Val Asp Met Val Ala Gly Ala
145                 150                 155                 160
```

-continued

```
His Trp Gly Val Leu Ala Gly Leu Ala Tyr Tyr Ser Met Val Gly Asn
                165                 170                 175

Trp Ala Lys Val Leu Val Val Met Leu Leu Phe Ala Gly Val Asp Gly
            180                 185                 190


<210> SEQ ID NO 88
<211> LENGTH: 209
<212> TYPE: PRT
<213> ORGANISM: Artificial Sequence
<220> FEATURE:
<223> OTHER INFORMATION: Description of Artificial Sequence:
      hepatitis C virus

<400> SEQUENCE: 88

Met Leu Gly Lys Val Ile Asp Thr Leu Thr Cys Gly Phe Ala Asp Leu
1               5                   10                  15

Met Gly Tyr Ile Pro Leu Val Gly Ala Pro Leu Gly Gly Ala Ala Arg
            20                  25                  30

Ala Leu Ala His Gly Val Arg Val Leu Glu Asp Gly Val Asn Tyr Ala
        35                  40                  45

Thr Gly Asn Leu Pro Gly Cys Ser Phe Ser Ile Phe Leu Leu Ala Leu
    50                  55                  60

Leu Ser Cys Leu Thr Ile Pro Ala Ser Ala Tyr Glu Val Arg Asn Val
65                  70                  75                  80

Ser Gly Met Tyr His Val Thr Asn Asp Cys Ser Asn Ser Ser Ile Val
                85                  90                  95

Tyr Glu Ala Ala Asp Met Ile Met His Thr Pro Gly Cys Val Pro Cys
            100                 105                 110

Val Arg Glu Asn Asn Ser Ser Arg Cys Trp Val Ala Leu Thr Pro Thr
        115                 120                 125

Leu Ala Ala Arg Asn Ala Ser Val Pro Thr Thr Thr Ile Arg Arg His
    130                 135                 140

Val Asp Leu Leu Val Gly Ala Ala Ala Phe Cys Ser Ala Met Tyr Val
145                 150                 155                 160

Gly Asp Leu Cys Gly Ser Val Phe Leu Val Ser Gln Leu Phe Thr Ile
                165                 170                 175

Ser Pro Arg Arg His Glu Thr Val Gln Asp Cys Asn Cys Ser Ile Tyr
            180                 185                 190

Pro Gly His Ile Thr Gly His Arg Met Ala Trp Asp Met Met Met Asn
        195                 200                 205

Trp


<210> SEQ ID NO 89
<211> LENGTH: 209
<212> TYPE: PRT
<213> ORGANISM: Artificial Sequence
<220> FEATURE:
<223> OTHER INFORMATION: Description of Artificial Sequence:
      hepatitis C virus

<400> SEQUENCE: 89

Met Leu Gly Lys Val Ile Asp Thr Leu Thr Cys Gly Phe Ala Asp Leu
1               5                   10                  15

Met Gly Tyr Ile Pro Val Val Gly Ala Pro Val Gly Gly Val Ala Arg
            20                  25                  30

Ala Leu Ala His Gly Val Arg Val Leu Glu Asp Gly Ile Asn Tyr Ala
        35                  40                  45
```

-continued

```
Thr Gly Asn Leu Pro Gly Cys Ser Phe Ser Ile Phe Leu Leu Ala Leu
    50                  55                  60

Leu Ser Cys Ile Thr Thr Pro Val Ser Ala Val Glu Val Lys Asn Asn
65                  70                  75                  80

Ser Asn Ser Tyr Met Ala Thr Asn Asp Cys Ser Asn Ser Ser Ile Ile
                85                  90                  95

Trp Gln Leu Glu Gly Ala Val Leu His Thr Pro Gly Cys Val Pro Cys
            100                 105                 110

Glu Leu Ala Asp Asn Thr Ser Arg Cys Trp Val Pro Val Thr Pro Asn
        115                 120                 125

Met Ala Ile Arg Gln Pro Gly Glu Leu Thr Lys Gly Leu Arg Ala His
    130                 135                 140

Val Asp Val Ile Val Met Ser Ala Thr Leu Cys Ser Ala Leu Tyr Val
145                 150                 155                 160

Gly Asp Val Cys Gly Ala Leu Met Ile Ala Ala Gln Val Val Val Val
                165                 170                 175

Ser Pro Gln His His His Phe Val Gln Glu Cys Asn Cys Ser Ile Tyr
            180                 185                 190

Pro Gly His Ile Thr Gly His Arg Met Ala Trp Asp Met Met Met Asn
        195                 200                 205

Trp
```

<210> SEQ ID NO 90
<211> LENGTH: 209
<212> TYPE: PRT
<213> ORGANISM: Artificial Sequence
<220> FEATURE:
<223> OTHER INFORMATION: Description of Artificial Sequence: hepatitis C virus

<400> SEQUENCE: 90

```
Met Leu Gly Lys Val Ile Asp Thr Leu Thr Cys Gly Phe Ala Asp Leu
1               5                   10                  15

Met Gly Tyr Ile Pro Val Val Gly Ala Pro Val Gly Gly Val Ala Arg
            20                  25                  30

Ala Leu Ala His Gly Val Arg Val Leu Glu Asp Gly Ile Asn Tyr Ala
        35                  40                  45

Thr Gly Asn Leu Pro Gly Cys Ser Phe Ser Ile Phe Leu Leu Ala Leu
    50                  55                  60

Leu Ser Cys Val Thr Ala Pro Val Ser Ala Val Glu Val Lys Asn Thr
65                  70                  75                  80

Ser Gln Ala Tyr Met Ala Thr Asn Asp Cys Ser Asn Asn Ser Ile Val
                85                  90                  95

Trp Gln Leu Glu Asp Ala Val Leu His Val Pro Gly Cys Val Pro Cys
            100                 105                 110

Glu Asn Ser Ser Gly Arg Phe His Cys Trp Ile Pro Ile Ser Pro Asn
        115                 120                 125

Ile Ala Val Ser Lys Pro Gly Ala Leu Thr Lys Gly Leu Arg Ala Arg
    130                 135                 140

Ile Asp Ala Val Val Met Ser Ala Thr Leu Cys Ser Ala Leu Tyr Val
145                 150                 155                 160

Gly Asp Val Cys Gly Ala Val Met Ile Ala Ala Gln Ala Phe Ile Val
                165                 170                 175

Ala Pro Lys Arg His Tyr Phe Val Gln Glu Cys Asn Cys Ser Ile Tyr
            180                 185                 190
```

-continued

```
Pro Gly His Ile Thr Gly His Arg Met Ala Trp Asp Met Met Met Asn
        195                 200                 205

Trp


<210> SEQ ID NO 91
<211> LENGTH: 209
<212> TYPE: PRT
<213> ORGANISM: Artificial Sequence
<220> FEATURE:
<223> OTHER INFORMATION: Description of Artificial Sequence:
      hepatitis C virus

<400> SEQUENCE: 91

Met Leu Gly Lys Val Ile Asp Thr Leu Thr Cys Gly Phe Ala Asp Leu
1               5                   10                  15

Met Gly Tyr Ile Pro Leu Val Gly Ala Pro Val Gly Gly Val Ala Arg
            20                  25                  30

Ala Leu Ala His Gly Val Arg Ala Leu Glu Asp Gly Ile Asn Phe Ala
        35                  40                  45

Thr Gly Asn Leu Pro Gly Cys Ser Phe Ser Ile Phe Leu Leu Ala Leu
    50                  55                  60

Phe Ser Cys Leu Ile His Pro Ala Ala Ser Leu Glu Trp Arg Asn Thr
65                  70                  75                  80

Ser Gly Leu Tyr Val Leu Thr Asn Asp Cys Ser Asn Ser Ser Ile Val
                85                  90                  95

Tyr Glu Ala Asp Asp Val Ile Leu His Thr Pro Gly Cys Ile Pro Cys
            100                 105                 110

Val Gln Asp Gly Asn Thr Ser Thr Cys Trp Thr Pro Val Thr Pro Thr
        115                 120                 125

Val Ala Val Lys Tyr Val Gly Ala Thr Thr Ala Ser Ile Arg Ser His
    130                 135                 140

Val Asp Leu Leu Val Gly Ala Ala Thr Met Cys Ser Ala Leu Tyr Val
145                 150                 155                 160

Gly Asp Met Cys Gly Ala Val Phe Leu Val Gly Gln Ala Phe Thr Phe
                165                 170                 175

Arg Pro Arg Arg His Gln Thr Val Gln Thr Cys Asn Cys Ser Leu Tyr
            180                 185                 190

Pro Gly His Leu Ser Gly His Arg Met Ala Trp Asp Met Met Met Asn
        195                 200                 205

Trp


<210> SEQ ID NO 92
<211> LENGTH: 209
<212> TYPE: PRT
<213> ORGANISM: Artificial Sequence
<220> FEATURE:
<223> OTHER INFORMATION: Description of Artificial Sequence:
      hepatitis C virus

<400> SEQUENCE: 92

Met Ser Gly Lys Val Ile Asp Thr Leu Thr Cys Gly Phe Ala Asp Leu
1               5                   10                  15

Met Gly Tyr Ile Pro Leu Val Gly Ala Pro Val Gly Gly Val Ala Arg
            20                  25                  30

Ala Leu Ala His Gly Val Arg Ala Val Glu Asp Gly Ile Asn Tyr Ala
        35                  40                  45

Thr Gly Asn Leu Pro Gly Cys Ser Phe Ser Ile Phe Leu Leu Ala Leu
    50                  55                  60
```

-continued

```
Leu Ser Cys Leu Thr Val Pro Thr Ser Ala Val Asn Tyr Arg Asn Ala
65                  70                  75                  80

Ser Gly Val Tyr His Ile Thr Asn Asp Cys Pro Asn Ser Ser Ile Val
                85                  90                  95

Tyr Glu Thr Glu His His Ile Leu His Leu Pro Gly Cys Leu Pro Cys
            100                 105                 110

Val Arg Val Gly Asn Gln Ser Arg Cys Trp Val Ala Leu Thr Pro Thr
        115                 120                 125

Val Ala Ala Pro Tyr Ile Gly Ala Pro Leu Glu Ser Leu Arg Ser His
    130                 135                 140

Val Asp Leu Met Val Gly Ala Ala Thr Ala Cys Ser Ala Leu Tyr Ile
145                 150                 155                 160

Gly Asp Leu Cys Gly Gly Val Phe Leu Val Gly Gln Met Phe Ser Phe
                165                 170                 175

Gln Pro Arg Arg His Trp Thr Thr Gln Asp Cys Asn Cys Ser Ile Tyr
            180                 185                 190

Ala Gly His Val Thr Gly His Arg Met Ala Trp Asp Met Met Met Asn
        195                 200                 205

Trp


<210> SEQ ID NO 93
<211> LENGTH: 209
<212> TYPE: PRT
<213> ORGANISM: Artificial Sequence
<220> FEATURE:
<223> OTHER INFORMATION: Description of Artificial Sequence:
      hepatitis C virus

<400> SEQUENCE: 93

Met Leu Gly Lys Val Ile Asp Thr Leu Thr Cys Gly Phe Ala Asp Leu
1               5                   10                  15

Met Gly Tyr Ile Pro Leu Val Gly Gly Pro Ile Gly Gly Val Ala Arg
            20                  25                  30

Ala Leu Ala His Gly Val Arg Val Leu Glu Asp Gly Val Asn Tyr Ala
        35                  40                  45

Thr Gly Asn Leu Pro Gly Cys Ser Phe Ser Ile Phe Ile Leu Ala Leu
    50                  55                  60

Leu Ser Cys Leu Thr Val Pro Ala Ser Ala Val Pro Tyr Arg Asn Ala
65                  70                  75                  80

Ser Gly Ile Tyr His Val Thr Asn Asp Cys Pro Asn Ser Ser Ile Val
                85                  90                  95

Tyr Glu Ala Asp Asn Leu Ile Leu His Ala Pro Gly Cys Val Pro Cys
            100                 105                 110

Val Met Thr Gly Asn Val Ser Arg Cys Trp Val Gln Ile Thr Pro Thr
        115                 120                 125

Leu Ser Ala Pro Ser Leu Gly Ala Val Thr Ala Pro Leu Arg Arg Ala
    130                 135                 140

Val Asp Tyr Leu Ala Gly Gly Ala Ala Leu Cys Ser Ala Leu Tyr Val
145                 150                 155                 160

Gly Asp Ala Cys Gly Ala Leu Phe Leu Val Gly Gln Met Phe Thr Tyr
                165                 170                 175

Arg Pro Arg Gln His Ala Thr Val Gln Asn Cys Asn Cys Ser Ile Tyr
            180                 185                 190

Ser Gly His Val Thr Gly His Arg Met Ala Trp Asp Met Met Met Asn
        195                 200                 205
```

-continued

Trp

<210> SEQ ID NO 94
<211> LENGTH: 209
<212> TYPE: PRT
<213> ORGANISM: Artificial Sequence
<220> FEATURE:
<223> OTHER INFORMATION: Description of Artificial Sequence:
hepatitis C virus

<400> SEQUENCE: 94

Met Leu Gly Lys Val Ile Asp Thr Leu Thr Cys Gly Phe Ala Asp Leu
1 5 10 15

Met Gly Tyr Ile Pro Val Val Gly Ala Pro Leu Gly Gly Val Ala Ala
20 25 30

Ala Phe Ala His Gly Val Arg Ala Leu Glu Asp Gly Ile Asn Tyr Ala
35 40 45

Thr Gly Asn Leu Pro Gly Cys Ser Phe Ser Ile Phe Leu Leu Ala Leu
50 55 60

Leu Ser Cys Leu Thr Thr Pro Ala Ser Ala Leu Thr Tyr Gly Asn Ser
65 70 75 80

Ser Gly Leu Tyr His Leu Thr Asn Asp Cys Pro Asn Ser Ser Ile Val
85 90 95

Leu Glu Ala Asp Ala Met Ile Leu His Leu Pro Gly Cys Leu Pro Cys
100 105 110

Val Arg Val Asn Asn Gln Ser Thr Cys Trp His Ala Val Ser Pro Thr
115 120 125

Leu Ala Ile Pro Asn Ala Ser Thr Pro Ala Thr Gly Phe Arg Arg His
130 135 140

Val Asp Leu Leu Ala Gly Ala Ala Val Val Cys Ser Ser Leu Tyr Ile
145 150 155 160

Gly Asp Leu Cys Gly Ser Leu Phe Leu Ala Gly Gln Leu Phe Thr Phe
165 170 175

Gln Pro Arg Arg His Trp Thr Val Gln Asp Cys Asn Cys Ser Ile Tyr
180 185 190

Thr Gly His Val Thr Gly His Arg Met Ala Trp Asp Met Met Met Asn
195 200 205

Trp

<210> SEQ ID NO 95
<211> LENGTH: 209
<212> TYPE: PRT
<213> ORGANISM: Artificial Sequence
<220> FEATURE:
<223> OTHER INFORMATION: Description of Artificial Sequence:
hepatitis C virus

<400> SEQUENCE: 95

Met Leu Gly Lys Val Ile Asp Thr Leu Thr Cys Gly Phe Ala Asp Leu
1 5 10 15

Met Gly Tyr Ile Pro Val Val Gly Ala Pro Leu Gly Gly Ile Ala Ala
20 25 30

Ala Leu Ala His Gly Val Arg Ala Val Glu Asp Gly Ile Asn Tyr Ala
35 40 45

Thr Gly Asn Leu Pro Gly Cys Ser Phe Ser Ile Phe Leu Leu Ala Leu
50 55 60

Leu Ser Cys Leu Thr Thr Pro Ala Ser Ala Val His Tyr Ala Asn Lys

-continued

```
65                  70                  75                  80

Ser Gly Leu Tyr His Leu Thr Asn Asp Cys Pro Asn Ser Ser Ile Val
                85                  90                  95

Tyr Glu Ala Pro Ala Val Ile Met His Leu Pro Gly Cys Val Pro Cys
            100                 105                 110

Val Lys Val Gly Asn Gln Ser Thr Cys Trp Leu Pro Ala Ser Pro Thr
        115                 120                 125

Leu Ala Val Pro Asn Ala Ser Thr Pro Leu Thr Arg Phe Arg Lys His
    130                 135                 140

Val Asp Leu Met Val Gly Ala Ala Ala Phe Cys Ser Ala Met Tyr Val
145                 150                 155                 160

Gly Asp Ile Cys Gly Gly Leu Phe Leu Leu Gly Gln Val Val Thr Ile
                165                 170                 175

Arg Pro Arg Leu His Gln Thr Val Gln Glu Cys Asn Cys Ser Ile Tyr
            180                 185                 190

Thr Gly Lys Ile Thr Gly His Arg Met Ala Trp Asp Ile Met Met Asn
        195                 200                 205

Trp


<210> SEQ ID NO 96
<211> LENGTH: 209
<212> TYPE: PRT
<213> ORGANISM: Artificial Sequence
<220> FEATURE:
<223> OTHER INFORMATION: Description of Artificial Sequence:
      hepatitis C virus

<400> SEQUENCE: 96

Met Leu Gly Lys Val Ile Asp Thr Leu Thr Cys Gly Leu Ala Asp Leu
1               5                   10                  15

Met Gly Tyr Ile Pro Val Leu Gly Gly Pro Leu Gly Gly Val Ala Ala
            20                  25                  30

Ala Leu Ala His Gly Val Arg Ala Ile Glu Asp Gly Val Asn Tyr Ala
        35                  40                  45

Thr Gly Asn Leu Pro Gly Cys Ser Phe Ser Ile Leu Leu Leu Ala Leu
    50                  55                  60

Leu Ser Cys Leu Thr Ile Pro Ala Ser Ala Ile Gln Val Lys Asn Ala
65                  70                  75                  80

Ser Gly Ile Tyr His Leu Thr Asn Asp Cys Ser Asn Asn Ser Ile Val
                85                  90                  95

Phe Glu Ala Glu Thr Met Ile Leu His Leu Pro Gly Cys Val Pro Cys
            100                 105                 110

Ile Lys Ala Gly Asn Glu Ser Arg Cys Trp Leu Pro Val Ser Pro Thr
        115                 120                 125

Leu Ala Val Pro Asn Ser Ser Val Pro Ile His Gly Phe Arg Arg His
    130                 135                 140

Val Asp Leu Leu Val Gly Ala Ala Ala Phe Cys Ser Ala Met Tyr Ile
145                 150                 155                 160

Gly Asp Leu Cys Gly Ser Ile Phe Leu Val Gly Gln Leu Phe Thr Phe
                165                 170                 175

Arg Pro Lys Tyr His Gln Val Thr Gln Asp Cys Asn Cys Ser Ile Tyr
            180                 185                 190

Ala Gly His Ile Thr Gly His Arg Met Ala Trp Asp Met Met Met Asn
        195                 200                 205

Trp
```

-continued

<210> SEQ ID NO 97
<211> LENGTH: 363
<212> TYPE: PRT
<213> ORGANISM: Artificial Sequence
<220> FEATURE:
<223> OTHER INFORMATION: Description of Artificial Sequence:
hepatitis C virus

<400> SEQUENCE: 97

```
Glu Thr His Val Thr Gly Gly Asn Ala Gly Arg Thr Thr Ala Gly Pro
1               5                   10                  15

Val Gly Leu Leu Thr Pro Gly Ala Lys Gln Asn Ile Gln Leu Ile Asn
            20                  25                  30

Thr Asn Gly Ser Trp His Ile Asn Ser Thr Ala Leu Asn Cys Asn Glu
        35                  40                  45

Ser Leu Asn Thr Gly Trp Leu Ala Gly Leu Phe Tyr Gln His Lys Phe
    50                  55                  60

Asn Ser Ser Gly Cys Pro Glu Arg Leu Ala Ser Cys Arg Arg Leu Thr
65                  70                  75                  80

Asp Phe Ala Gln Gly Trp Gly Pro Ile Ser Tyr Ala Asn Gly Ser Gly
                85                  90                  95

Leu Asp Glu Arg Pro Tyr Cys Trp His Tyr Pro Pro Arg Pro Cys Gly
            100                 105                 110

Ile Val Pro Ala Lys Ser Val Cys Gly Pro Val Tyr Cys Phe Thr Pro
        115                 120                 125

Ser Pro Val Val Val Gly Thr Thr Asp Arg Ser Gly Ala Pro Thr Tyr
    130                 135                 140

Ser Trp Gly Ala Asn Asp Thr Asp Val Phe Val Leu Asn Asn Thr Arg
145                 150                 155                 160

Pro Pro Leu Gly Asn Trp Phe Gly Cys Thr Trp Met Asn Ser Thr Gly
                165                 170                 175

Phe Thr Lys Val Cys Gly Ala Pro Pro Cys Val Ile Gly Gly Val Gly
            180                 185                 190

Asn Asn Thr Leu Leu Cys Pro Thr Asp Cys Phe Arg Lys His Pro Glu
        195                 200                 205

Ala Thr Tyr Ser Arg Cys Gly Ser Gly Pro Trp Ile Thr Pro Arg Cys
    210                 215                 220

Met Val Asp Tyr Pro Tyr Arg Leu Trp His Tyr Pro Cys Thr Ile Asn
225                 230                 235                 240

Tyr Thr Ile Phe Lys Val Arg Met Tyr Val Gly Gly Val Glu His Arg
                245                 250                 255

Leu Glu Ala Ala Cys Asn Trp Thr Arg Gly Glu Arg Cys Asp Leu Glu
            260                 265                 270

Asp Arg Asp Arg Ser Glu Leu Ser Pro Leu Leu Leu Ser Thr Thr Gln
        275                 280                 285

Trp Gln Val Leu Pro Cys Ser Phe Thr Thr Leu Pro Ala Leu Ser Thr
    290                 295                 300

Gly Leu Ile His Leu His Gln Asn Ile Val Asp Val Gln Tyr Leu Tyr
305                 310                 315                 320

Gly Val Gly Ser Ser Ile Ala Ser Trp Ala Ile Lys Trp Glu Tyr Val
                325                 330                 335
```

-continued

```
Val Leu Leu Phe Leu Leu Leu Ala Asp Ala Arg Val Cys Ser Glu Phe
            340                 345                 350

Trp Met Met Leu Leu Ile Ser Gln Ala Glu Ala
        355                 360


<210> SEQ ID NO 98
<211> LENGTH: 363
<212> TYPE: PRT
<213> ORGANISM: Artificial Sequence
<220> FEATURE:
<223> OTHER INFORMATION: Description of Artificial Sequence:
      hepatitis C virus

<400> SEQUENCE: 98

His Thr Arg Val Ser Gly Gly Ala Ala Ala Ser Asp Thr Arg Gly Leu
1               5                   10                  15

Val Ser Leu Phe Ser Pro Gly Ser Ala Gln Lys Ile Gln Leu Val Asn
            20                  25                  30

Thr Asn Gly Ser Trp His Ile Asn Arg Thr Ala Leu Asn Cys Asn Asp
        35                  40                  45

Ser Leu Gln Thr Gly Phe Phe Ala Ala Leu Phe Tyr Lys His Lys Phe
    50                  55                  60

Asn Ser Ser Gly Cys Pro Glu Arg Leu Ala Ser Cys Arg Ser Ile Asp
65                  70                  75                  80

Lys Phe Ala Gln Gly Trp Gly Pro Leu Thr Tyr Thr Glu Pro Asn Ser
                85                  90                  95

Ser Asp Gln Arg Pro Tyr Cys Trp His Tyr Ala Pro Arg Pro Cys Gly
            100                 105                 110

Ile Val Pro Ala Ser Gln Val Cys Gly Pro Val Tyr Cys Phe Thr Pro
        115                 120                 125

Ser Pro Val Val Val Gly Thr Thr Asp Arg Phe Gly Val Pro Thr Tyr
    130                 135                 140

Asn Trp Gly Ala Asn Asp Ser Asp Val Leu Ile Leu Asn Asn Thr Arg
145                 150                 155                 160

Pro Pro Arg Gly Asn Trp Phe Gly Cys Thr Trp Met Asn Gly Thr Gly
                165                 170                 175

Phe Thr Lys Thr Cys Gly Gly Pro Pro Cys Asn Ile Gly Gly Ala Gly
            180                 185                 190

Asn Asn Thr Leu Thr Cys Pro Thr Asp Cys Phe Arg Lys His Pro Glu
        195                 200                 205

Ala Thr Tyr Ala Arg Cys Gly Ser Gly Pro Trp Leu Thr Pro Arg Cys
    210                 215                 220

Met Val His Tyr Pro Tyr Arg Leu Trp His Tyr Pro Cys Thr Val Asn
225                 230                 235                 240

Phe Thr Ile Phe Lys Val Arg Met Tyr Val Gly Gly Val Glu His Arg
                245                 250                 255

Phe Glu Ala Ala Cys Asn Trp Thr Arg Gly Glu Arg Cys Asp Leu Glu
            260                 265                 270

Asp Arg Asp Arg Ser Glu Leu Ser Pro Leu Leu Leu Ser Thr Thr Glu
        275                 280                 285

Trp Gln Ile Leu Pro Cys Ser Phe Thr Thr Leu Pro Ala Leu Ser Thr
    290                 295                 300

Gly Leu Ile His Leu His Gln Asn Ile Val Asp Val Gln Tyr Leu Tyr
305                 310                 315                 320

Gly Val Gly Ser Ala Val Val Ser Leu Val Ile Lys Trp Glu Tyr Val
                325                 330                 335
```

-continued

```
Leu Leu Leu Phe Leu Leu Leu Ala Asp Ala Arg Ile Cys Ala Cys Leu
            340                 345                 350

Trp Met Met Leu Leu Ile Ala Gln Ala Glu Ala
        355                 360
```

CONSTRUCTS AND METHODS FOR EXPRESSION OF RECOMBINANT HCV ENVELOPE PROTEINS

The present application claims benefit of U.S. Provisional Patent Application No. 60/305,604, filed Jul. 17, 2001

FIELD OF THE INVENTION

The present invention relates to the general field of recombinant protein expression. More particularly, the present invention relates to the expression of hepatitis C virus envelope proteins in a eukaryote such as yeast. Constructs and methods are disclosed for the expression of core-glycosylated viral envelope proteins in yeast.

BACKGROUND OF THE INVENTION

Hepatitis C virus (HCV) infection is a major health problem in both developed and developing countries. It is estimated that about 1 to 5% of the world population is affected by the virus. HCV infection appears to be the most important cause of transfusion-associated hepatitis and frequently progresses to chronic liver damage. Moreover, evidence exists implicating HCV in induction of hepatocellular carcinoma. Consequently, the demand for reliable diagnostic methods and effective therapeutic agents is high. Also sensitive and specific screening methods of HCV-contaminated blood-products and improved methods to culture HCV are needed.

HCV is a positive stranded RNA virus of approximately 9,600 bases which encode a single polyprotein precursor of about 3000 amino acids. Proteolytic cleavage of the precursor coupled to co- and post translational modifications has been shown to result in at least three structural and six non-structural proteins. Based on sequence homology, the structural proteins have been functionally assigned as one single core protein and two envelope glycoproteins: E1 and E2. The E1 protein consists of 192 amino acids and contains 5 to 6 N-glycosylation sites, depending on the HCV genotype. The E2 protein consists of 363 to 370 amino acids and contains 9 to 11 N-glycosylation sites, depending on the HCV genotype (for reviews see: Major, M. E. and Feinstone, S. M. 1997, Maertens, G. and Stuyver, L. 1997). The E1 protein contains various variable domains (Maertens, G. and Stuyver, L. 1997). The E2 protein contains three hypervariable domains, of which the major domain is located at the N-terminus of the protein (Maertens, G. and Stuyver, L. 1997). The HCV glycoproteins localize predominantly in the ER where they are modified and assembled into oligomeric complexes.

In eukaryotes, sugar residues are commonly linked to four different amino acid residues. These amino acid residues are classified as O-linked (serine, threonine, and hydroxylysine) and N-linked (asparagine). The O-linked sugars are synthesized in the Golgi or rough Endoplasmic Reticulum (ER) from nucleotide sugars. The N-linked sugars are synthesized from a common precursor, and subsequently processed. It is believed that HCV envelope proteins are N-glycosylated. It is known in the art that addition of N-linked carbohydrate chains is important for stabilization of folding intermediates and thus for efficient folding, prevention of malfolding and degradation in the endoplasmic reticulum, oligomerization, biological activity, and transport of glycoproteins (see reviews by Rose, J. K. and Doms, R. W. 1988, Doms, R. W. et al. 1993, Helenius, A. 1994)). The tripeptide sequences Asn-X-Ser and Asn-X-Thr (in which X can be any amino acid) on polypeptides are the consensus sites for binding N-linked oligosaccharides. After addition of the N-linked oligosaccharide to the polypeptide, the oligosaccharide is further processed into the complex type (containing N-acetylglucosamine, mannose, fucose, galactose and sialic acid) or the high-mannose type (containing N-acetylglucosamine and mannose). HCV envelope proteins are believed to be of the high-mannose type. N-linked oligosaccharide biosynthesis in yeast is very different from the biosynthesis in mammalian cells. In yeast the oligosaccharide chains are elongated in the Golgi through stepwise addition of mannose, leading to elaborate high mannose structures, leading to elaborate high mannose structures, referred to as hyperglycosylation. In contrast therewith, proteins expressed in prokaryotes are never glycosylated.

To date, vaccination against disease has been proven to be the most cost effective and efficient method for controlling diseases. Despite promising results, efforts to develop an efficacious HCV vaccine, however, have been plagued with difficulties. A conditio sine qua non for vaccines is the induction of an immune response in patients. Consequently, HCV antigenic determinants should be identified, and administered to patients in a proper setting. Antigenic determinants can be divided in at least two forms, i.e. lineair and conformational epitopes. Conformational epitopes result from the folding of a molecule in a three-dimensional space, including co- and post translational modifications, such as glycosylation. In general, it is believed that conformational epitopes will realize the most efficacious vaccines, since they represent epitopes which resemble native-like HCV epitopes, and which may be better conserved than the actual linear amino acid sequence. Hence, the eventual degree of glycosylation of the HCV envelope proteins is of the utmost importance for generating native-like HCV antigenic determinants. However, there are seemingly insurmountable problems with culturing HCV, that result in only minute amounts of virions. In addition, there are vast problems with the expression and purification of recombinant proteins, that result in either low amounts of proteins, hyperglycosylated proteins, or proteins that are not glycosylated.

In order to obtain glycosylation of an expressed protein, said protein needs to be targeted to the endoplasmic reticulum (ER). This process requires the presence of a pre-pro-or pre-sequence, the latter also known as signal peptide or leader peptide, at the amino-terminal end of the expressed protein. Upon translocation of the protein into the lumen of the ER, the pre-sequence is removed by means of a signal peptidase complex. A large number of pre-pro- and pre-sequences is currently known in the art. These include the *S. cerevisiae* α-mating factor leader (pre-pro; αMF or MFα), the *Carcinus maenas* hyperglycemic hormone leader sequence (pre; CHH), the *S. occidentalis* amylase leader sequence (pre; Amy1), the *S. occidentalis* glucoamylase Gam1 leader sequence (pre; Gam1), the fungal phytase leader sequence (pre; Phy5), the *Pichia pastoris* acid phosphatase leader sequence (pre; pho1), the yeast aspartic protease 3 signal peptide (pre; YAP3), the mouse salivary amylase signal peptide (pre) and the chicken lysozyme leader sequence (pre; CL).

The CHH leader has been coupled with hirudin and G-CSF (granulocyte colony stimulating factor) and expression of the CHH-hirudin and CHH-G-CSF proteins in *Hansenula polymorpha* results in correct removal of the leader sequence (Weydemann, U. et al. 1995, Fischer et al. in WO00/40727). The chicken lysozyme leader sequence has been fused to human interferonα2b (IFNα2b), human serum albumin and human lysozyme or 1,4-β-N-acetylmuramidase and expressed in *S. cerevisiae* (Rapp in GenBank accession number AF405538, Okabayashi, K. et al. 1991, de Baetselier et al. in EP0362183, Oberto and Davison in EP0184575). Mustilli and coworkers (Mustilli, A. C. et al. 1999) have utilized the *Kluyveromyces lactis* killer toxin leader peptide for expression of HCV E2 in *S. cerevisiae* and *K. lactis*.

The HCV envelope proteins have been produced by recombinant techniques in *Escherichia coli*, insect cells, yeast cells and mammalian cells. However, expression in higher eukaryotes has been characterised by the difficulty of obtaining large amounts of antigens for eventual vaccine production. Expression in prokaryotes, such as *E. coli* results in HCV envelope proteins that are not glycosylated. Expression of HCV envelope proteins in yeast resulted in hyperglycosylation. As already demonstrated in WO 96/04385, the expression of HCV envelope protein E2 in *Saccharomyces cerevisiae* leads to proteins which are heavily glycosylated. This hyperglycosylation leads to shielding of protein epitopes. Although Mustilli and coworkers (Mustilli, A. C. et al. 1999) claims that expression of HCV E2 in *S. cerevisiae* results in core-glycosylation, the analysis of the intracellularly expressed material demonstrates that part of it is at least hyperglycosylated, while the correct processing of the remainder of this material has not been shown. The need for HCV envelope proteins derived from an intracellular source is well accepted (WO 96/04385 to Maertens et al. and Heile, J. M. et al. 2000). This need is further exemplified by the poor reactivity of the secreted yeast derived E2 with sera of chimpanzee immunized with mammalian cell culture derived E2 proteins as evidenced in FIG. 5 of Mustilli and coworkers (Mustilli, A. C. et al. 1999). This is further documented by Rosa and colleagues (Rosa, D. et al. 1996) who show that immunization with yeast derived HCV envelope proteins fails to protect from challenge.

Consequently, there is a need for efficient expression systems resulting in large and cost-effective amounts of proteins and, in particular, such systems are needed for production of HCV envelope proteins. If a pre- or pre-pro-sequence is used to direct the protein of interest to the ER, then efficiency of the expression system is, amongst others, dependent on the efficiency and fidelity with which the pre- or pre-pro-sequences are removed from the protein of interest.

SUMMARY OF THE INVENTION

A first aspect of the present invention relates to recombinant nucleic acids comprising a nucleotide sequence encoding a protein comprising an avian lysozyme leader peptide or a functional equivalent thereof joined to an HCV envelope protein or a part thereof. More specifically said protein is characterized by the structure CL-[$(A1)_a$-$(PS1)_b$-$(A2)_c$]-HCVENV-[$(A3)_d$-$(PS2)_e$-$(A4)_f$]

wherein:

- CL is an avian lysozyme leader peptide or a functional equivalent thereof,
- A1, A2, A3 and A4 are adaptor peptides which can be different or the same,
- PS1 and PS2 are processing sites which can be the different or the same,
- HCVENV is a HCV envelope protein or a part thereof,
- a, b, c, d, e and f are 0 or 1, and
- wherein, optionally, A1 and/or A2 are part of PS1 and/or wherein A3 and/or A4 are part of PS2.

The recombinant nucleic acids according to the invention may further comprise regulatory elements allowing expression of said protein in a eukaryotic host cell.

Another aspect of the invention relates to a recombinant nucleic acid according to the invention which are comprised in a vector. Said vector may be an expression vector and/or an autonomously replicating vector or an integrative vector.

A further aspect of the invention relates to a host cell harboring a recombinant nucleic acid according to the invention or a vector according to the invention. More particularly, said host cell is capable of expressing the protein comprising an avian lysozyme leader peptide or a functional equivalent thereof joined to an HCV envelope protein or a part thereof. More specifically, said protein is characterized by the structure CL-[$(A1)_a$-$(PS1)_b$-$(A2)_c$]-HCVENV-[$(A3)_d$-$(PS2)_e$-$(A4)_f$]

wherein:

- CL is an avian lysozyme leader peptide or a functional equivalent thereof,
- A1, A2, A3 and A4 are adaptor peptides which can be different or the same,
- PS1 and PS2 are processing sites which can be the different or the same,
- HCVENV is a HCV envelope protein or a part thereof,
- a, b, c, d, e and fare 0 or 1, and
- wherein, optionally, A1 and/or A2 are part of PS1 and/or wherein A3 and/or A4 are part of PS2.

The host cell according to the invention may be capable of removing the avian lysozyme leader peptide with high efficiency and fidelity and may be capable of processing the processing sites PS1 and/or PS2 in said protein translocated to the endoplasmic reticulum. Said host cell may further be capable of N-glycosylating said protein translocated to the endoplasmic reticulum or said protein translocated to the endoplasmic reticulum and processed at said sites PS1 and/or PS2. The host cell may be an eukaryotic cell such as a yeast cell.

A next aspect of the invention relates to a method for producing an HCV envelope protein or part thereof in a host cell, said method comprising transforming said host cell with a recombinant nucleic acid according to the invention or with a vector according to the invention, and wherein said host cell is capable of expressing a protein comprising the avian lysozyme leader peptide or a functional equivalent thereof joined to an HCV envelope protein or a part thereof. More particularly, said protein is characterized by the structure CL-[$(A1)_a$-$(PS1)_b$-$(A2)_c$]-HCVENV-[$(A3)_d$-$(PS2)_e$-$(A4)_f$]

wherein:

- CL is an avian lysozyme leader peptide or a functional equivalent thereof,
- A1, A2, A3 and A4 are adaptor peptides which can be different or the same,
- PS1 and PS2 are processing sites which can be the different or the same,
- HCVENV is a HCV envelope protein or a part thereof,
- a, b, c, d, e and f are 0 or 1, and
- wherein, optionally, A1 and/or A2 are part of PS1 and/or wherein A3 and/or A4 are part of PS2.

The method according to the invention may further comprise cultivation of said host cells in a suitable medium to obtain expression of said protein, isolation of the expressed protein from a culture of said host cells, or from said host cells. Said isolation may include one or more of (i) lysis of said host cells in the presence of a chaotropic agent, (ii) chemical modification of the cysteine thiol-groups in the isolated proteins wherein said chemical modification may be reversible or irreversible and (iii) heparin affinity chromatography.

FIGURE LEGENDS

FIG. 1. Schematic map of the vector pGEMT-E1sH6RB which has the sequence as defined in SEQ ID NO:6.

Figure 2:
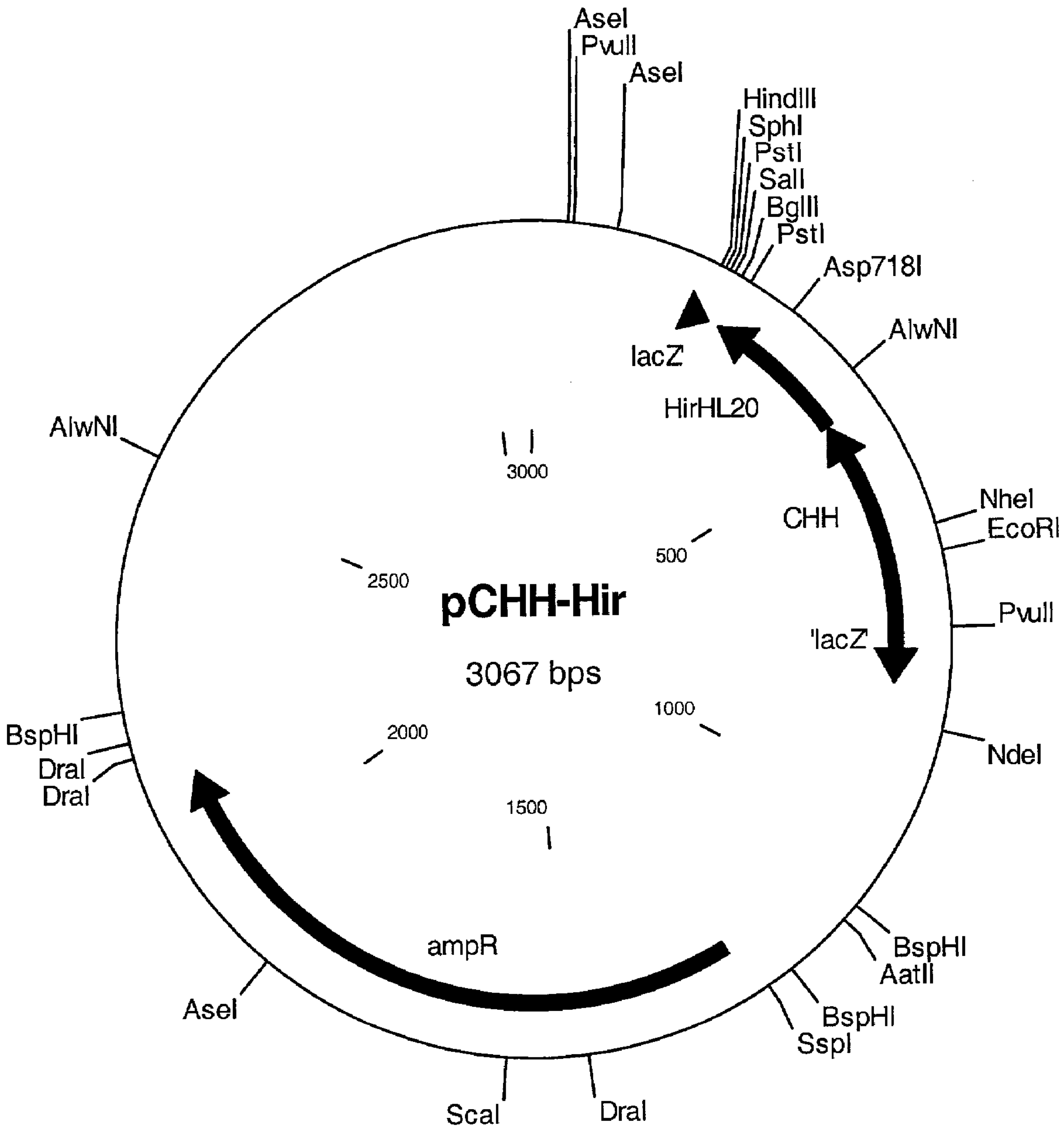

FIG. 2. Schematic map of the vector pCHH-Hir which has the sequence as defined in SEQ ID NO:9.

Figure 3:
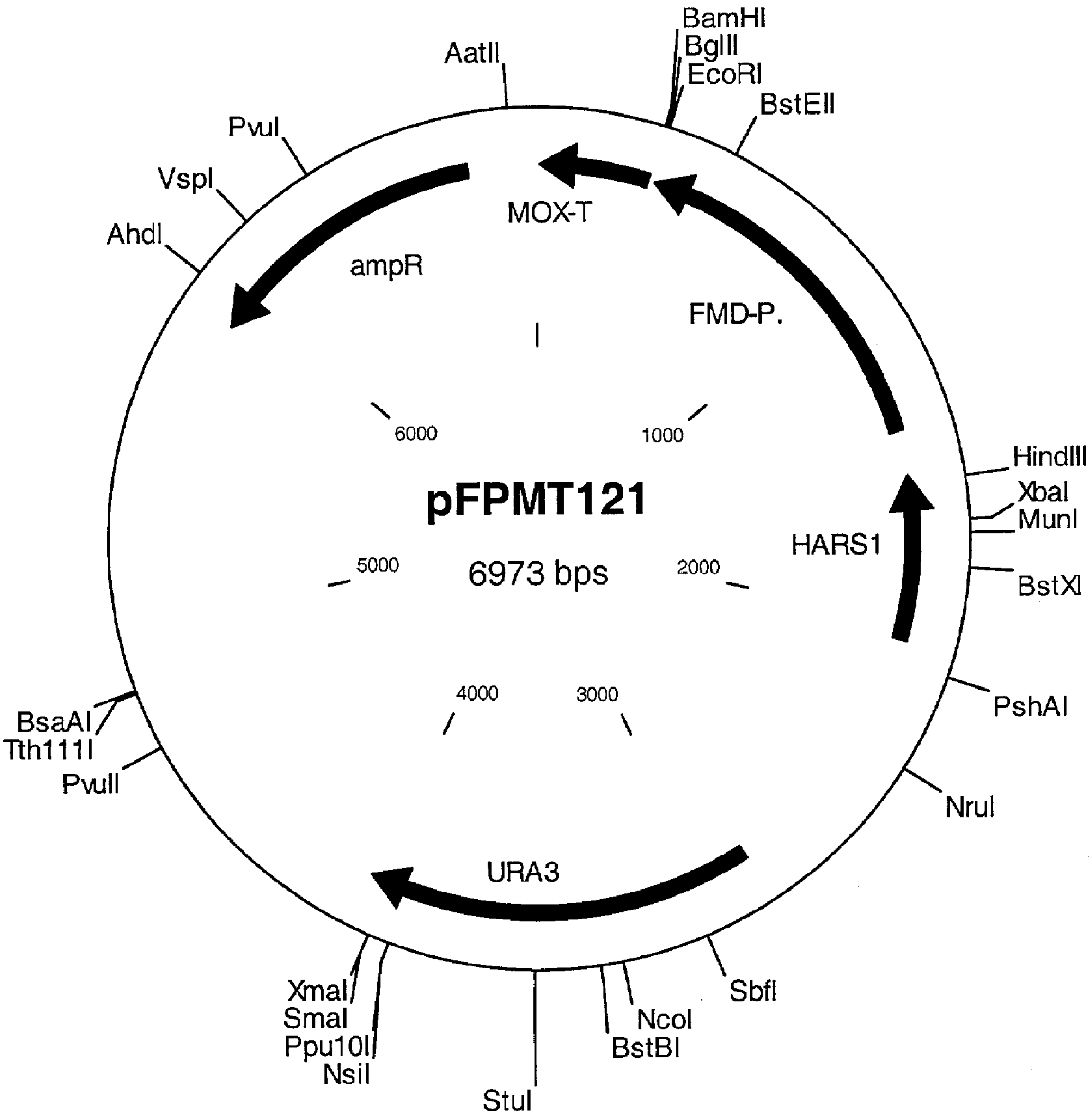

FIG. 3. Schematic map of the vector pFPMT121 which has the sequence as defined in SEQ ID NO:12.

Figure 4:
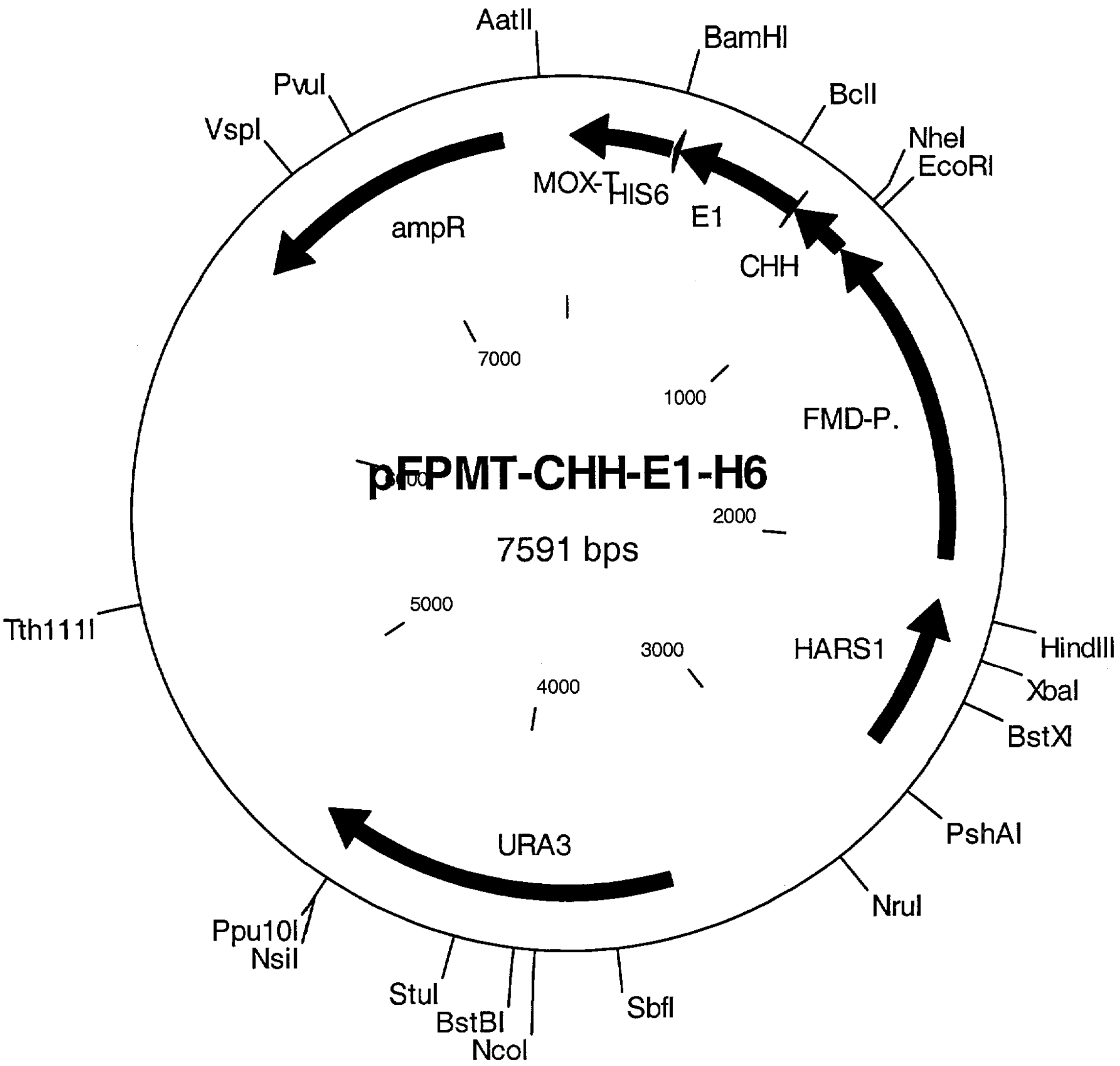

FIG. 4. Schematic map of the vector pFPMT-CHH-E1-H6 which has the sequence as defined in SEQ ID NO:13.

Figure 5:
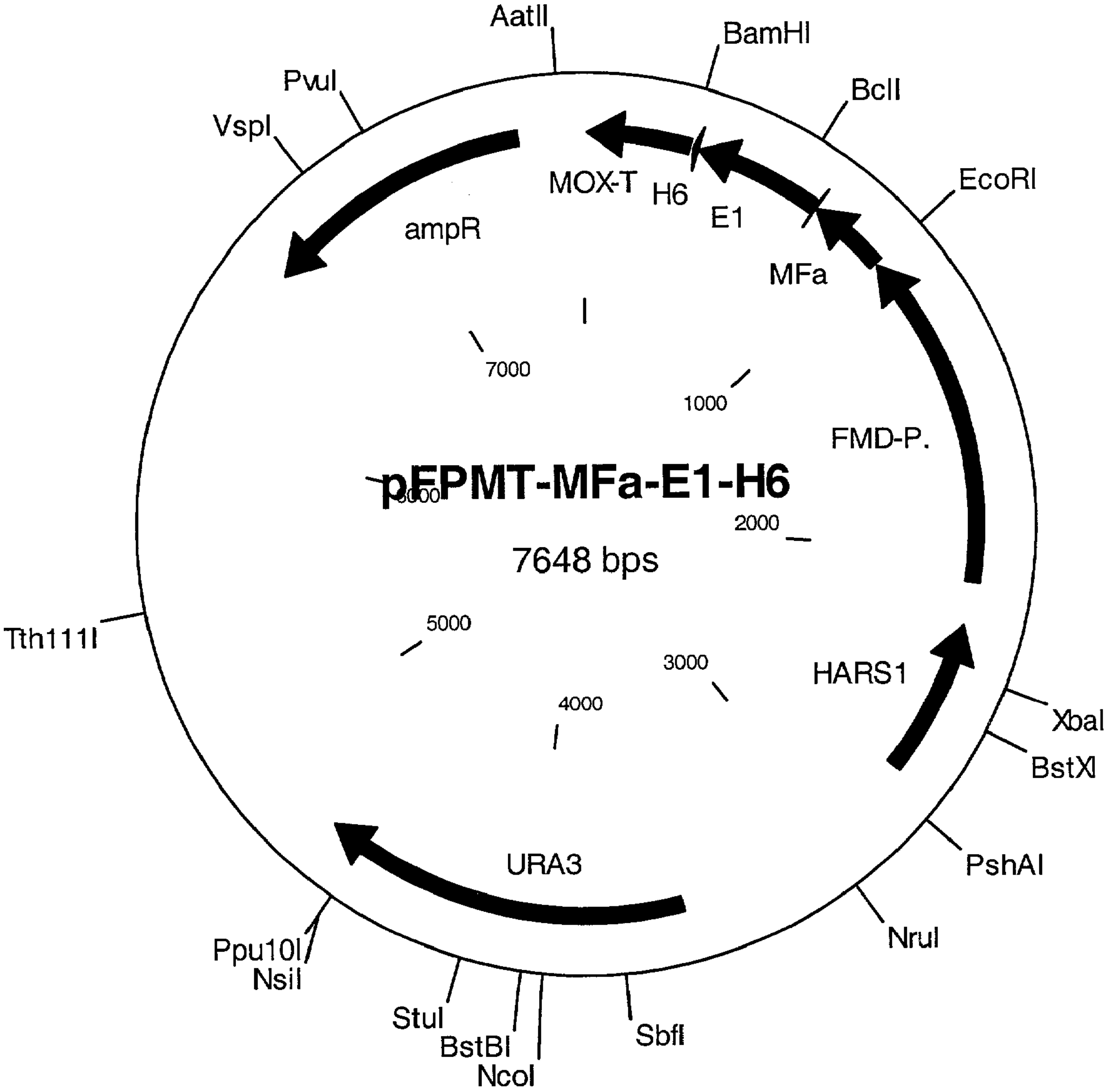

FIG. 5. Schematic map of the vector pFPMT-MFa-E1-H6 which has the sequence as defined in SEQ ID NO:16.

Figure 6:
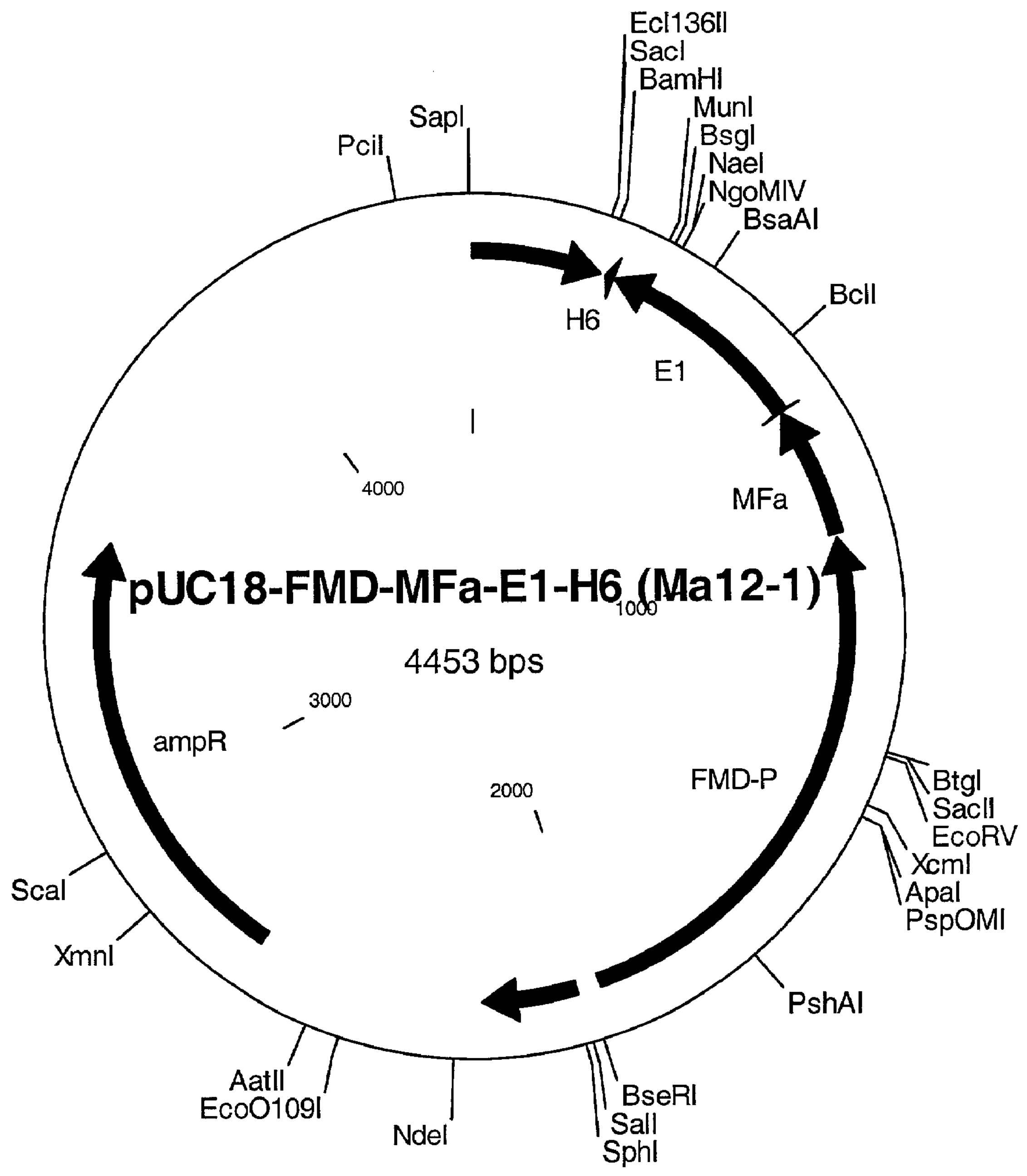

FIG. 6. Schematic map of the vector pUC18-FMD-MFa-E1-H6 which has the sequence as defined in SEQ ID NO:17.

Figure 7:
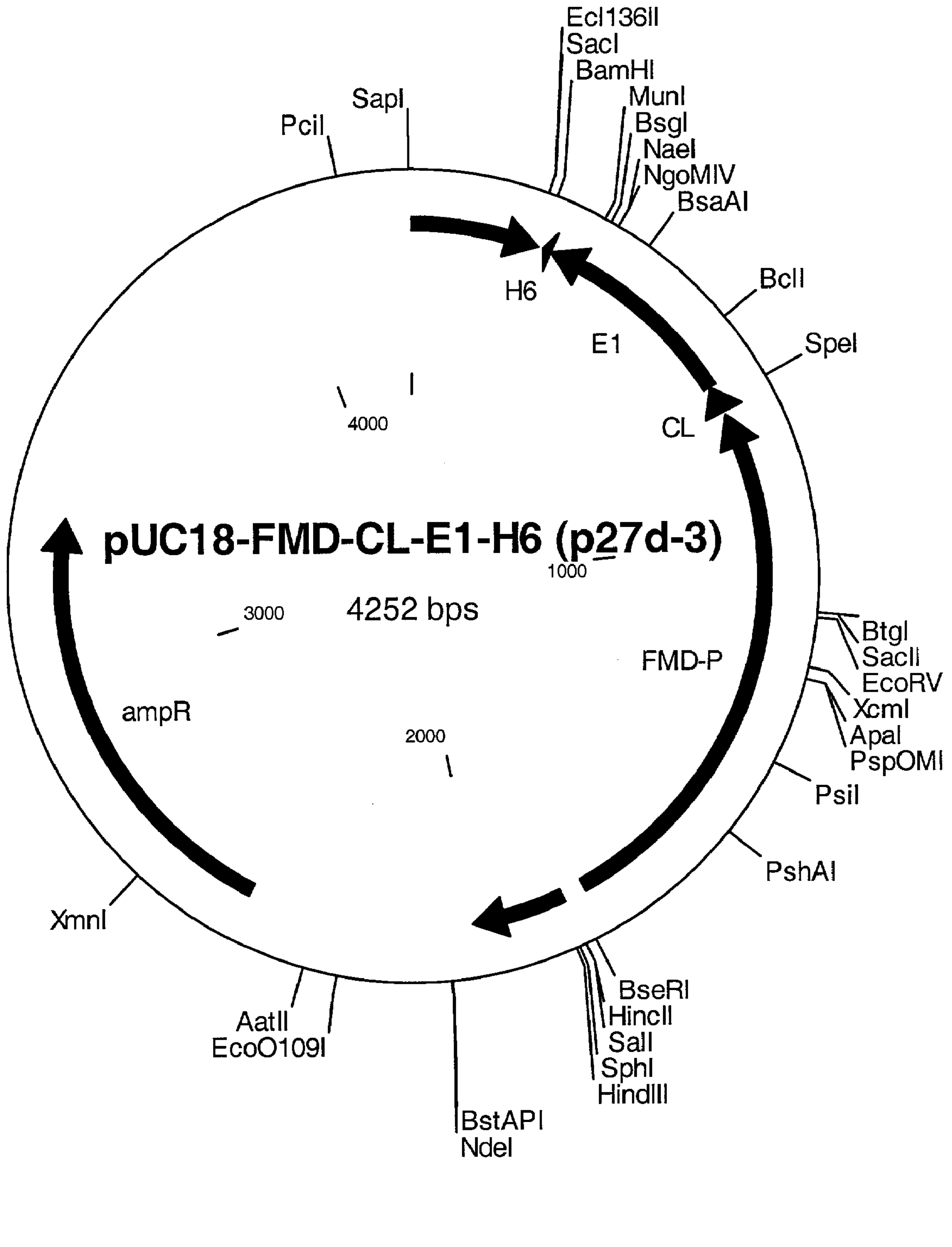

FIG. 7. Schematic map of the vector pUC18-FMD-CL-E1-H6 which has the sequence as defined in SEQ ID NO:20.

Figure 8:
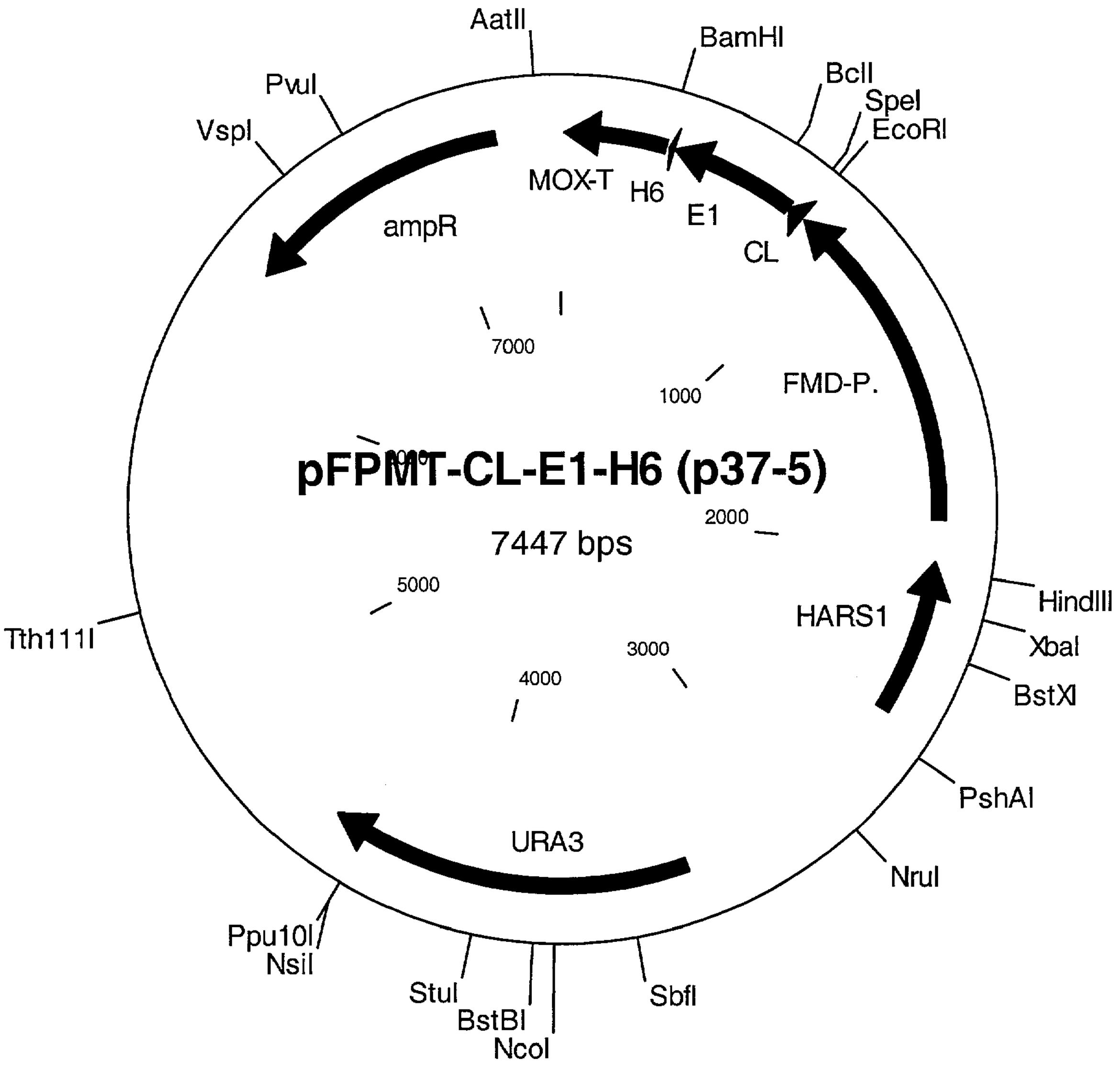

FIG. 8. Schematic map of the vector pFPMT-CL-E1-H6 which has the sequence as defined in SEQ ID NO:21.

Figure 9:
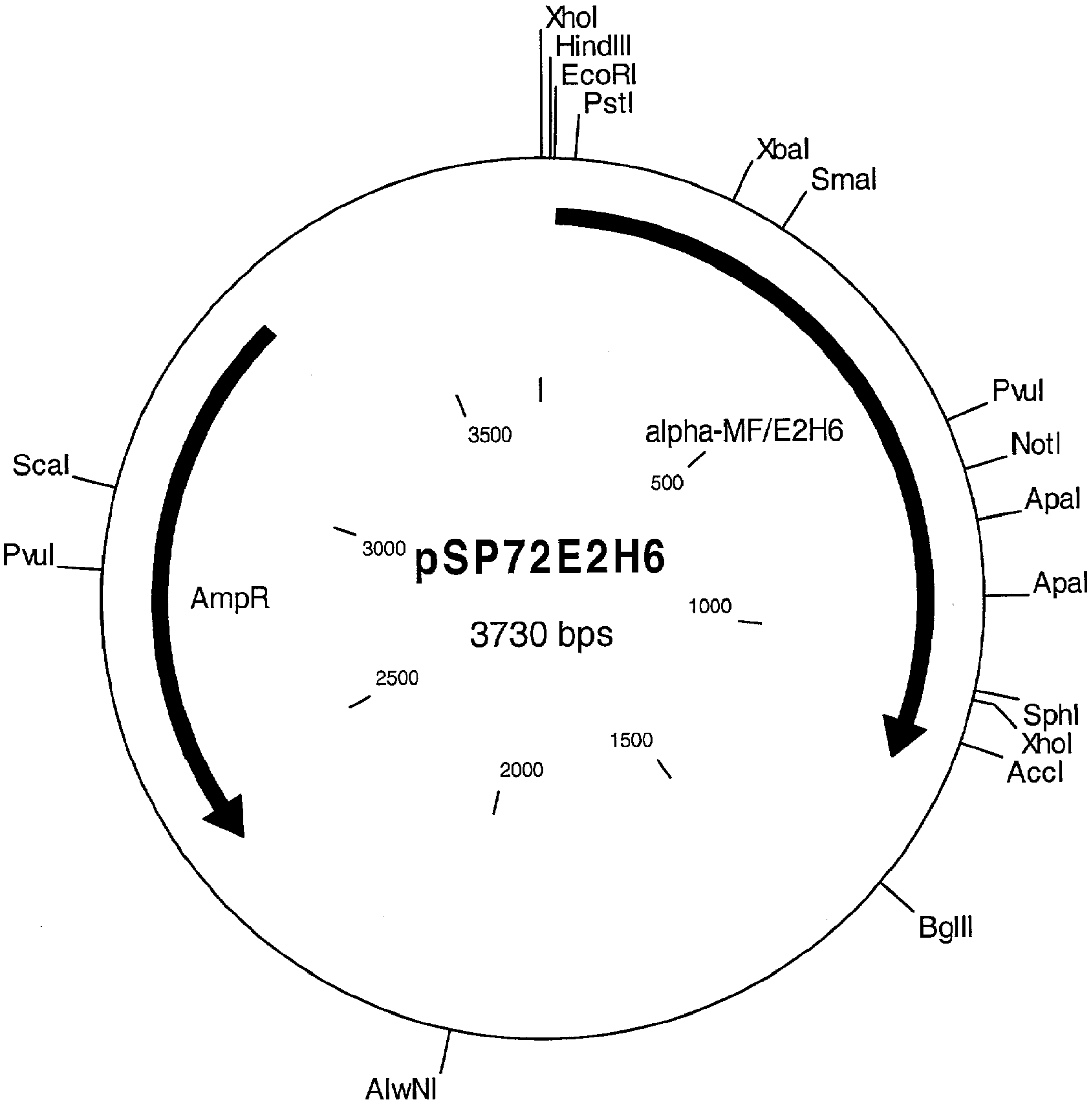

FIG. 9. Schematic map of the vector pSP72E2H6 which has the sequence as defined in SEQ ID NO:22.

Figure 10:
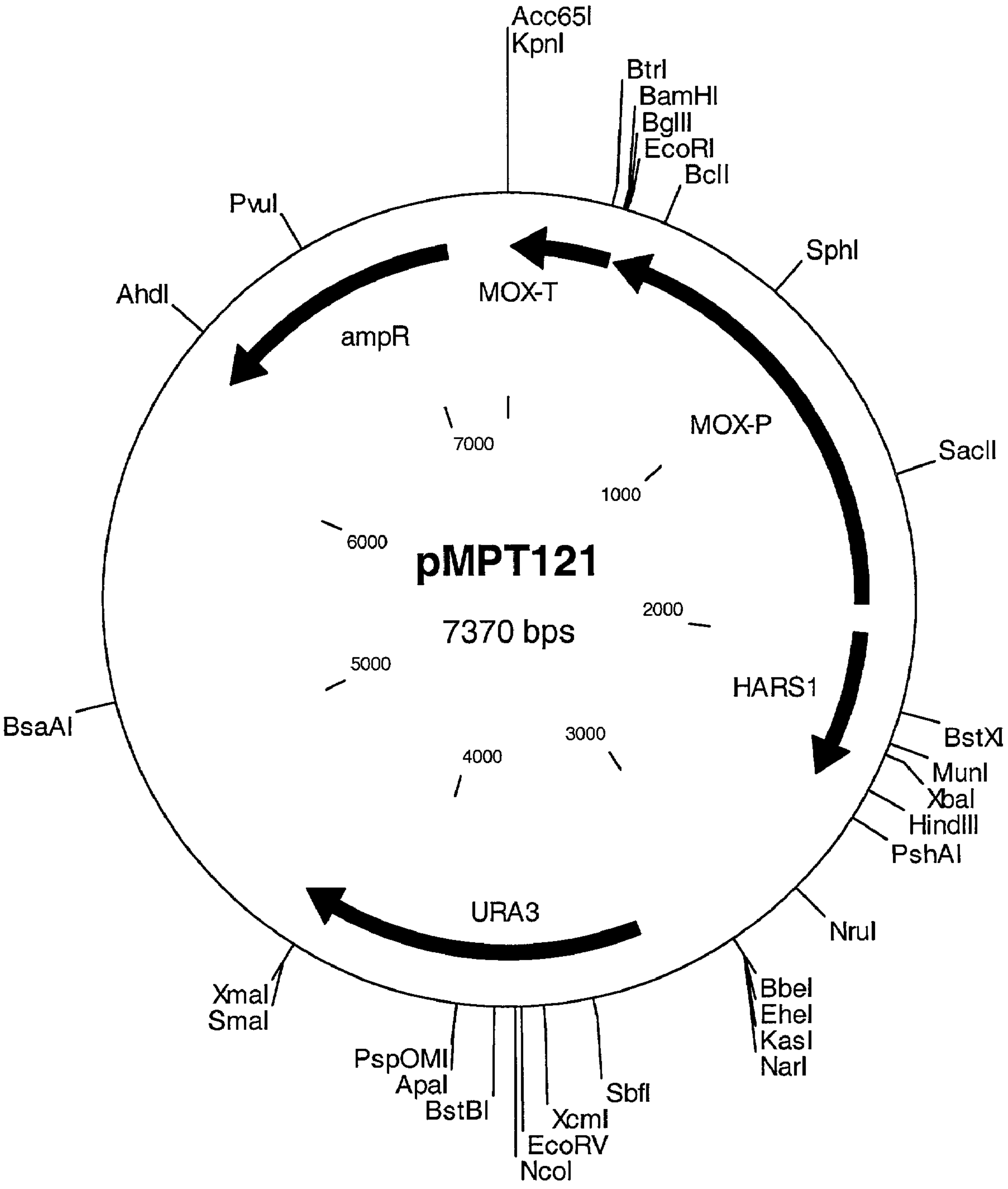

FIG. 10. Schematic map of the vector pMPT121 which has the sequence as defined in SEQ ID NO:23.

Figure 11:
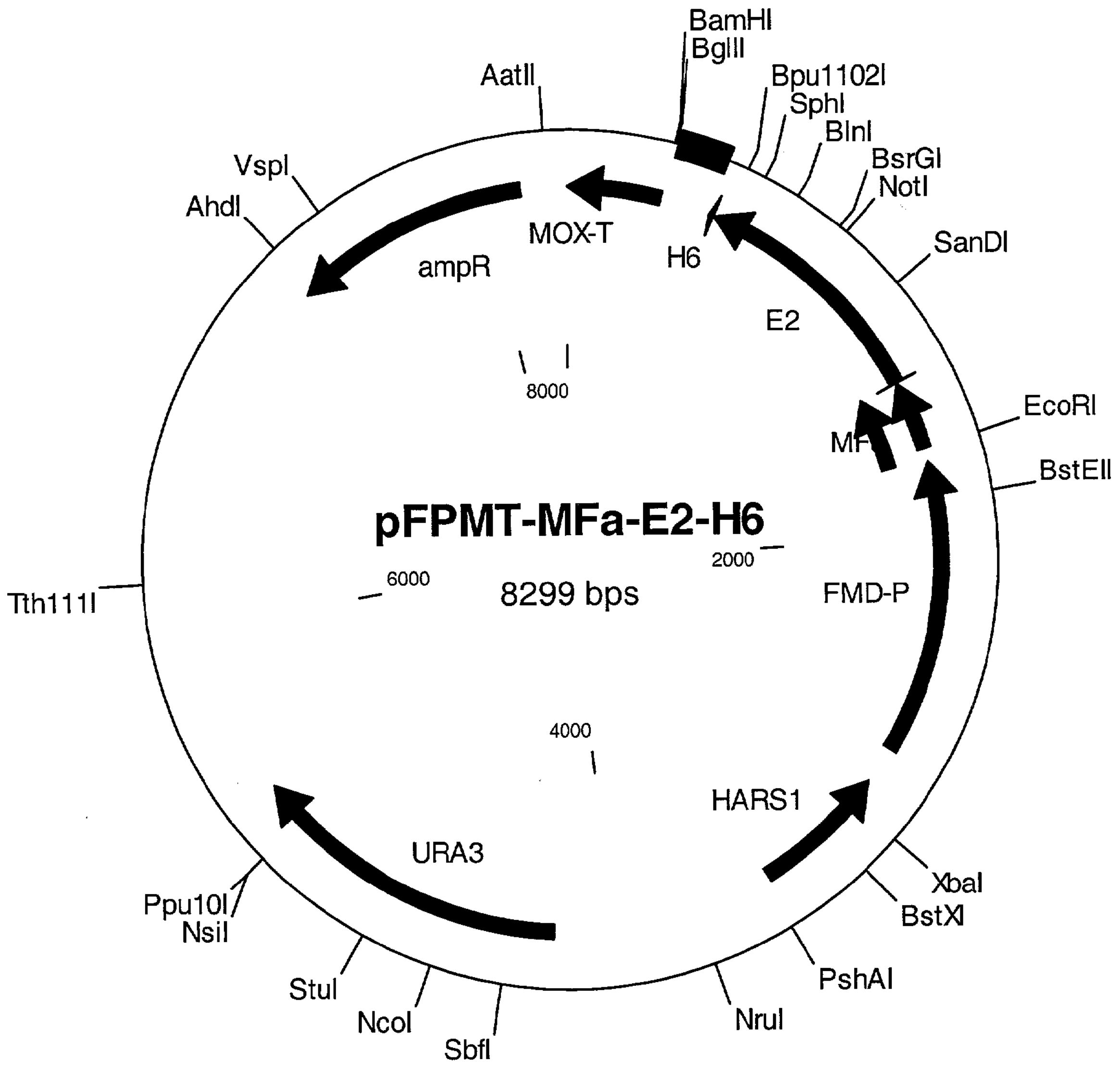

FIG. 11. Schematic map of the vector pFPMT-MFa-E2-H6 which has the sequence as defined in SEQ ID NO:24.

Figure 12:
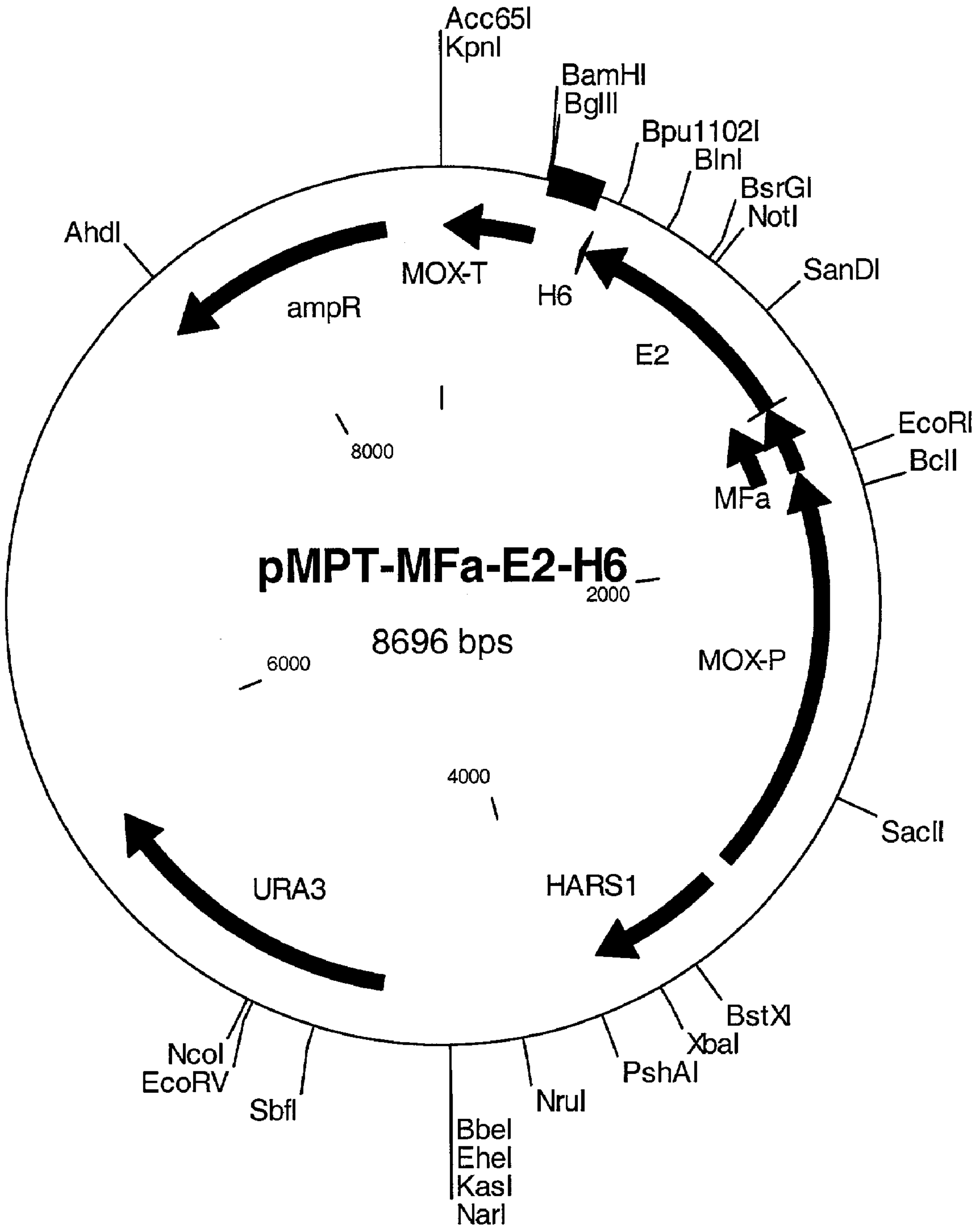

FIG. 12. Schematic map of the vector pMPT-MFa-E2-H6 which has the sequence as defined in SEQ ID NO:25.

Figure 13:
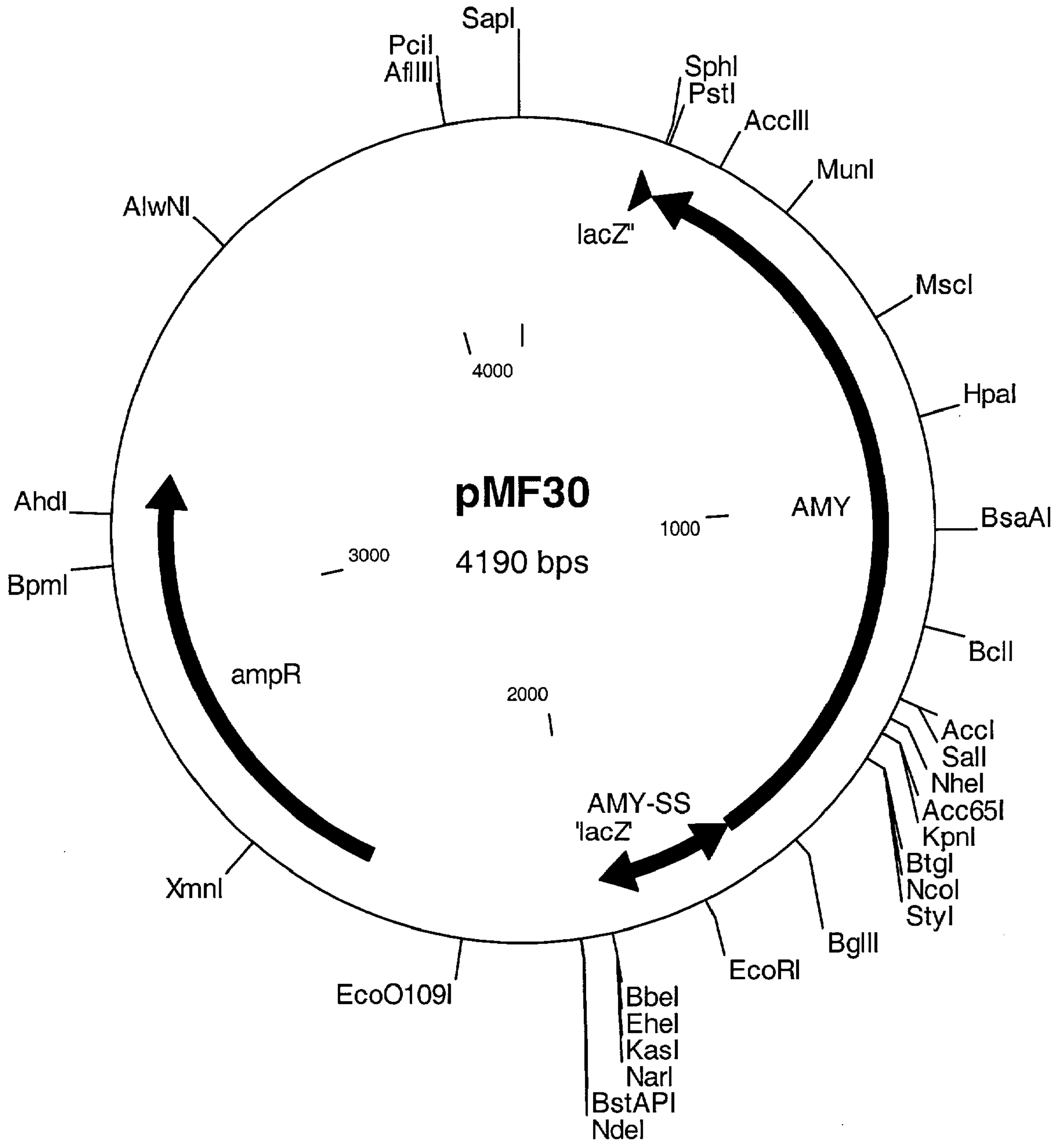

FIG. 13. Schematic map of the vector pMF30 which has the sequence as defined in SEQ ID NO:28.

Figure 14:
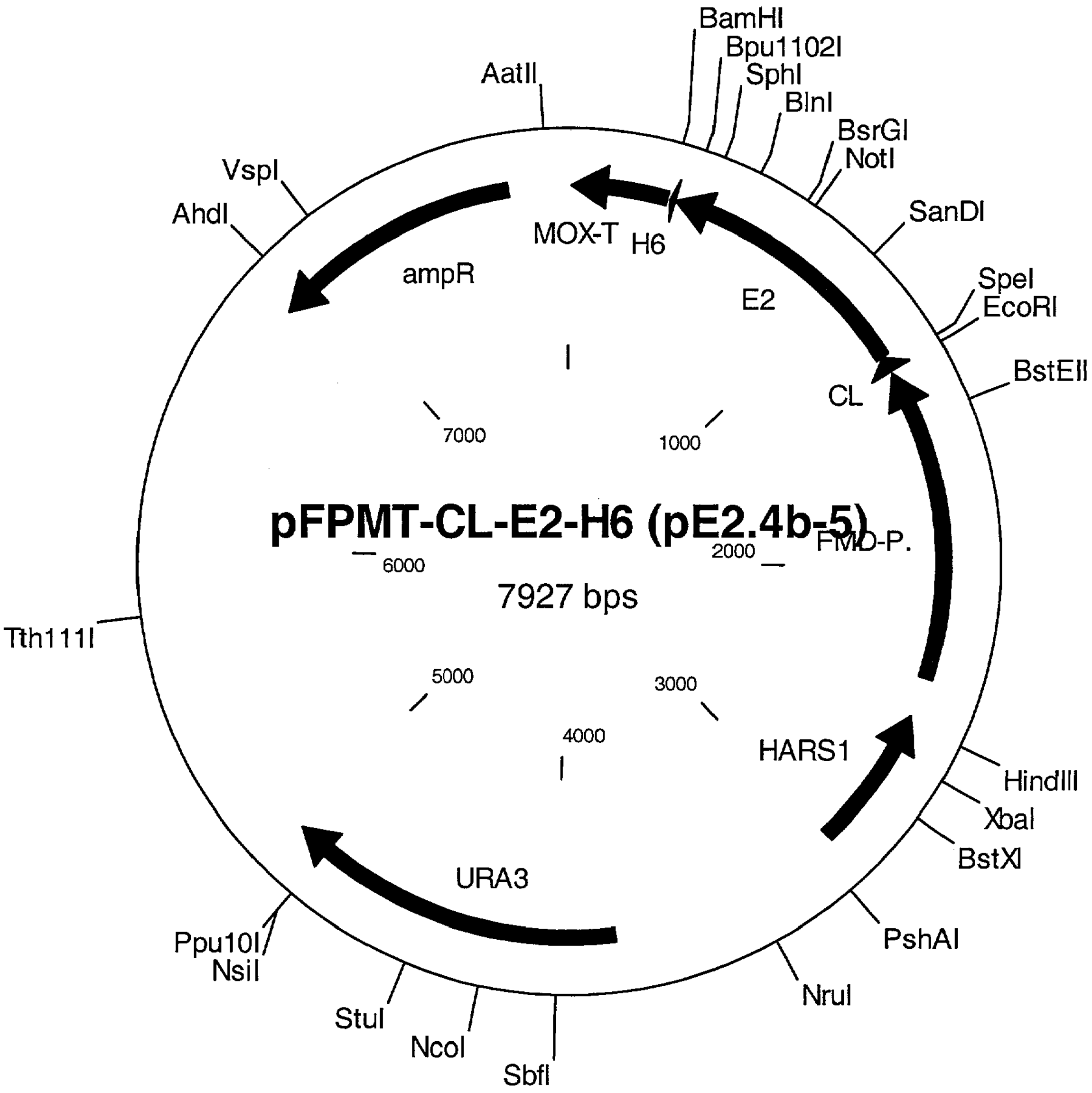

FIG. 14. Schematic map of the vector pFPMT-CL-E2-H6 which has the sequence as defined in SEQ ID NO:32.

Figure 15:
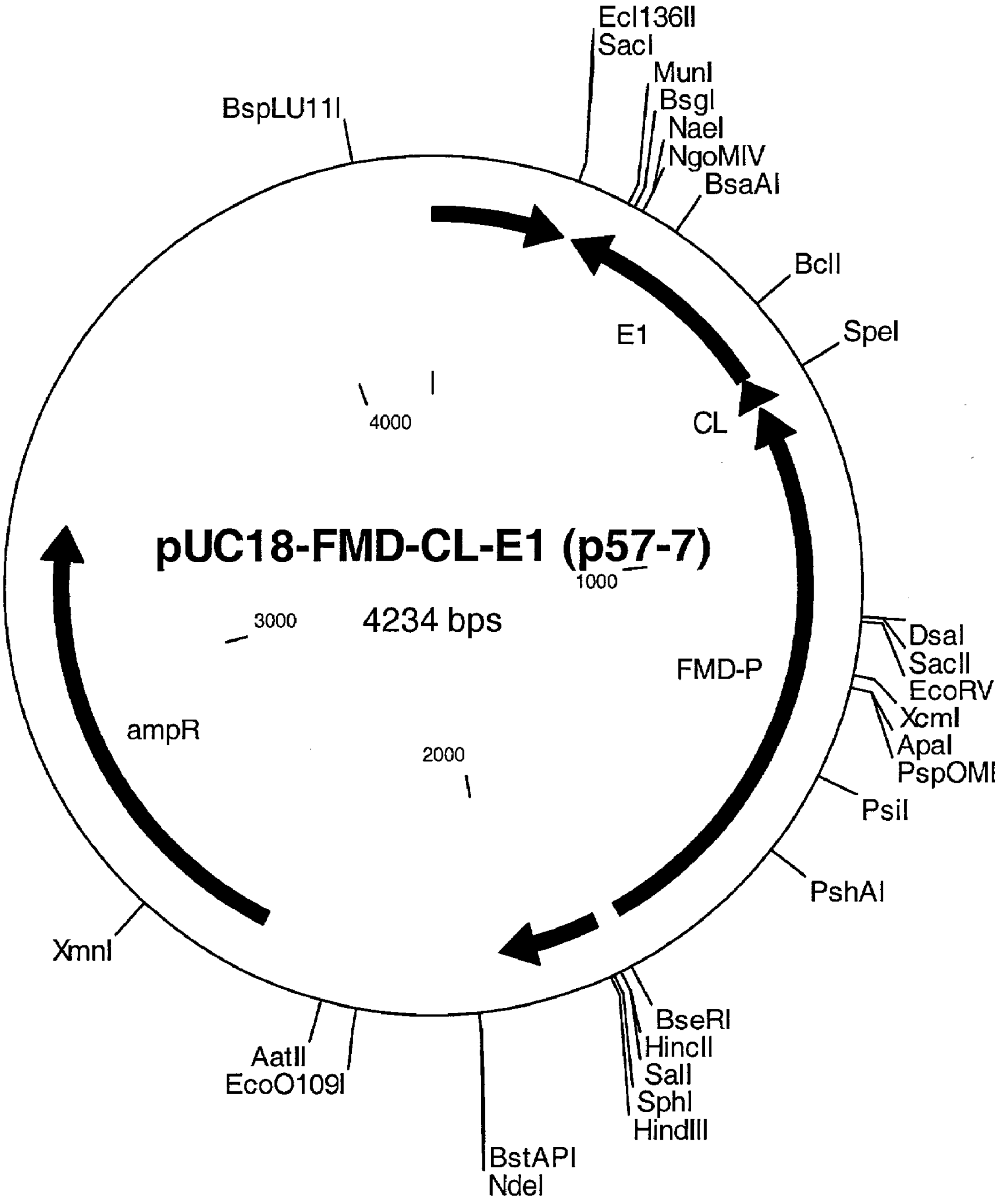

FIG. 15. Schematic map of the vector pUC18-FMD-CL-E1 which has the sequence as defined in SEQ ID NO:35.

Figure 16:
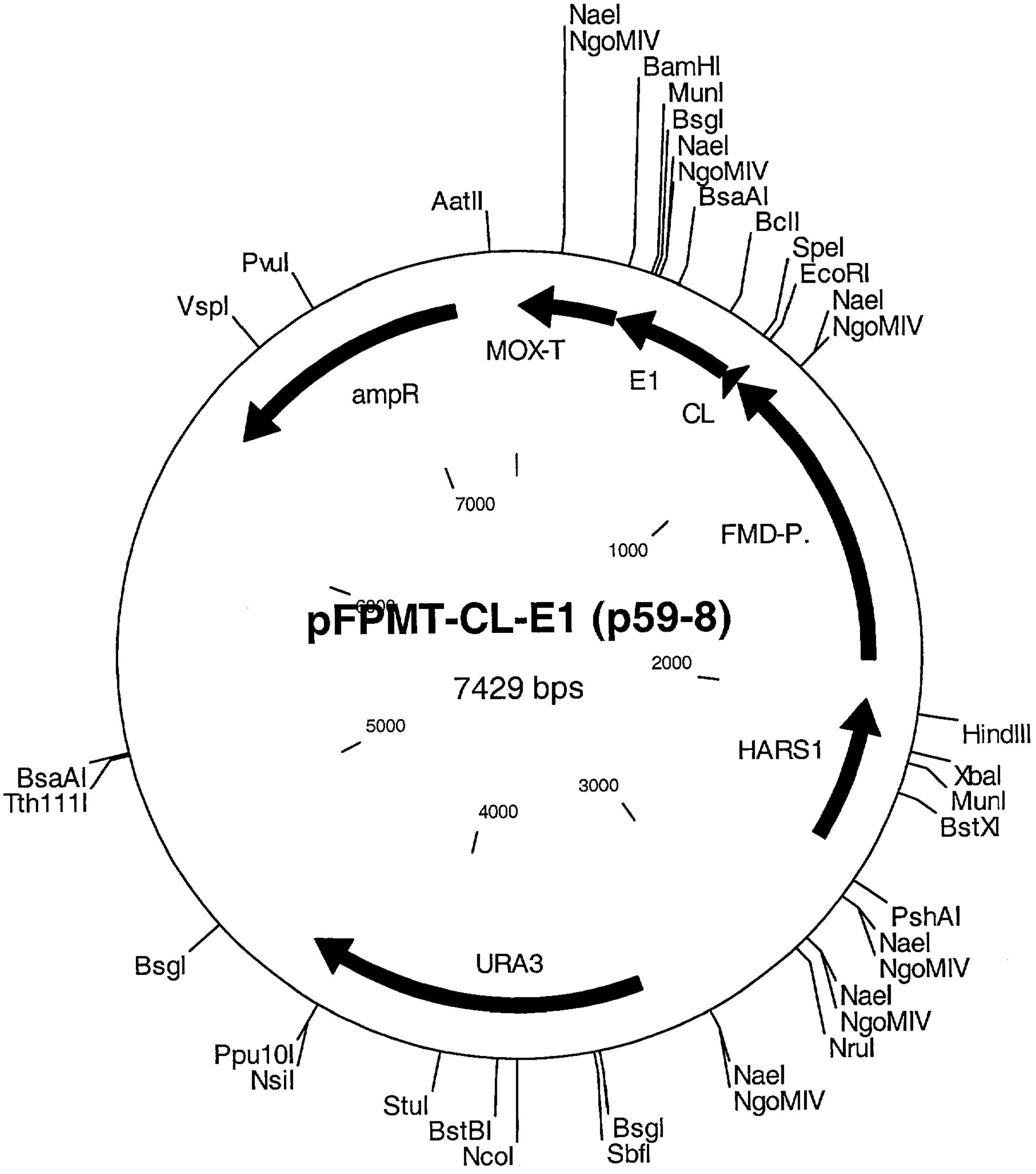

FIG. 16. Schematic map of the vector pFPMT-CL-E1 which has the sequence as defined in SEQ ID NO:36.

Figure 17:
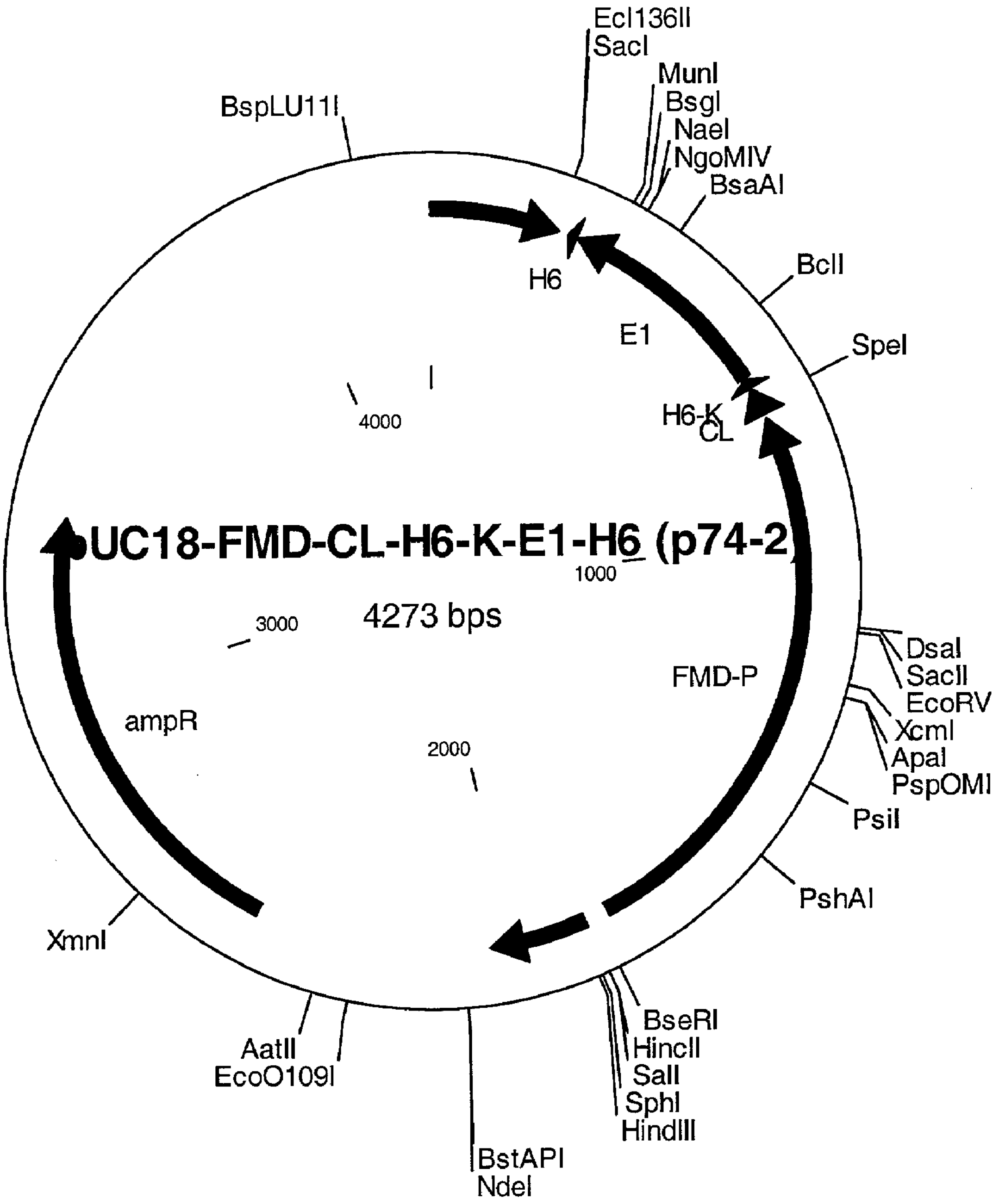

FIG. 17. Schematic map of the vector pUC18-FMD-CL-H6-E1-K-H6 which has the sequence as defined in SEQ ID NO:39.

Figure 18:
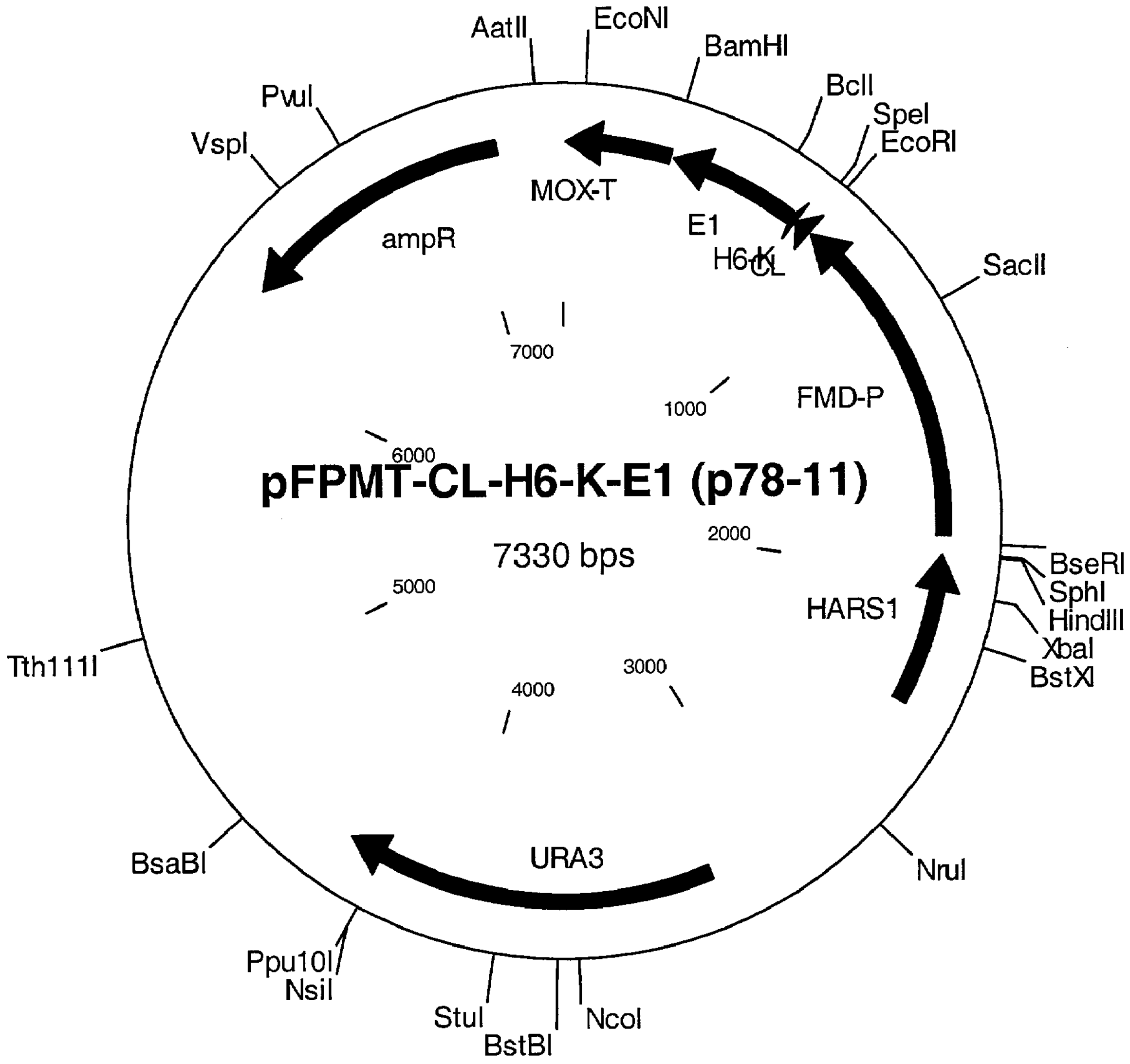

FIG. 18. Schematic map of the vector pFPMT-CL-H6-K-E1 which has the sequence as defined in SEQ ID NO:40.

Figure 19:
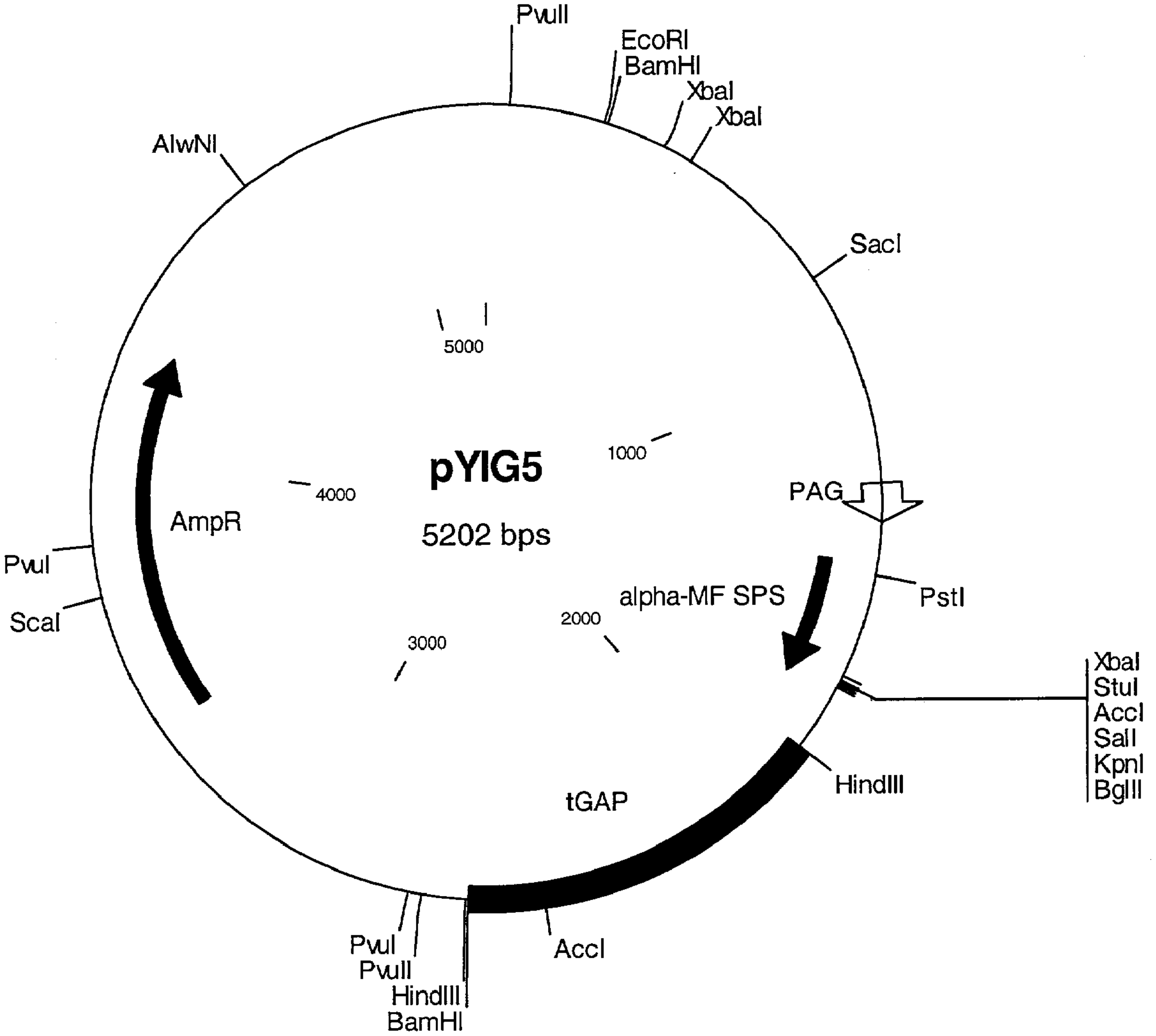

FIG. 19. Schematic map of the vector pYIG5 which has the sequence as defined in SEQ ID NO:41.

Figure 20:
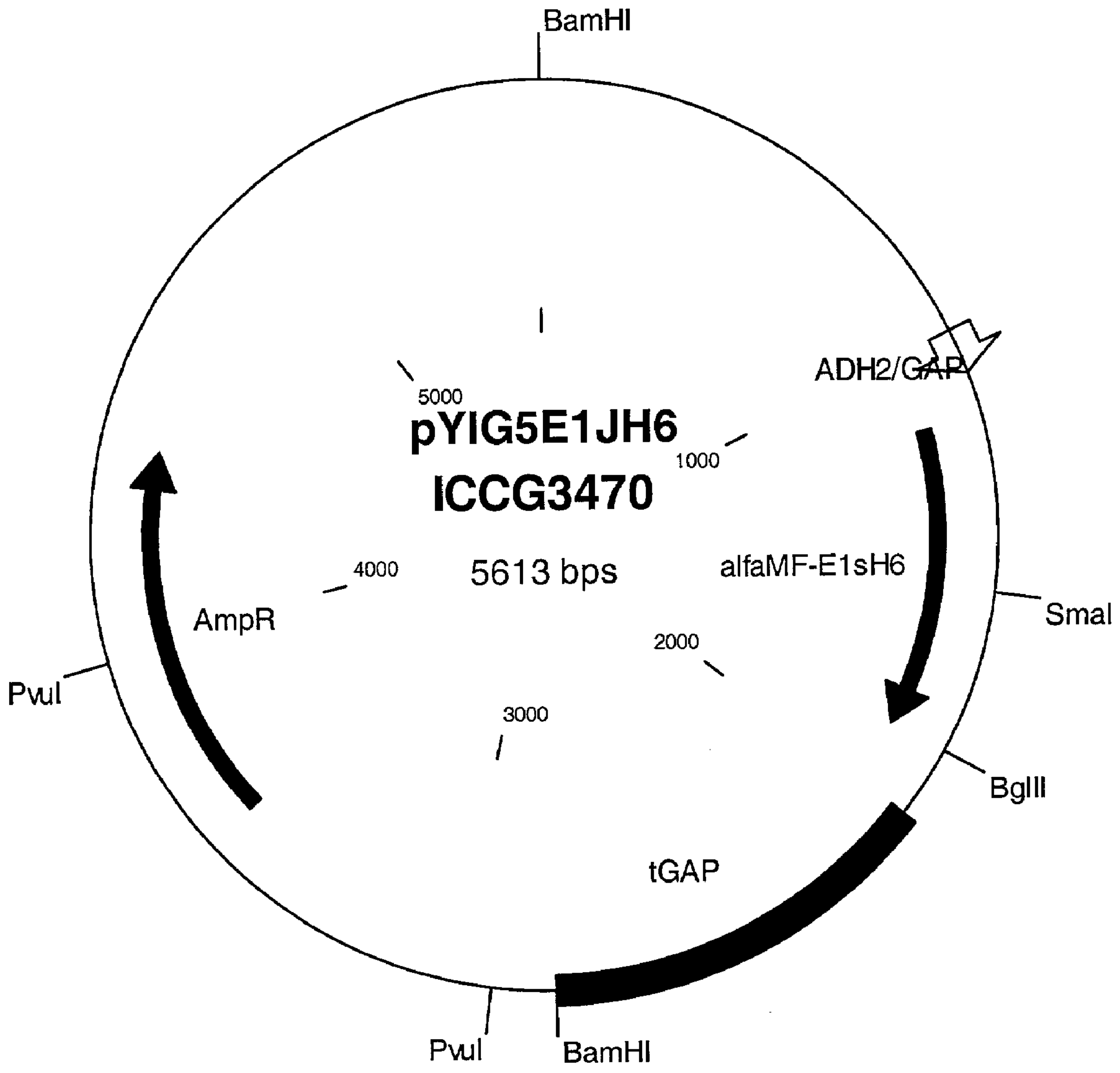

FIG. 20. Schematic map of the vector pYIG5E1H6 which has the sequence as defined in SEQ ID NO:42.

Figure 21:
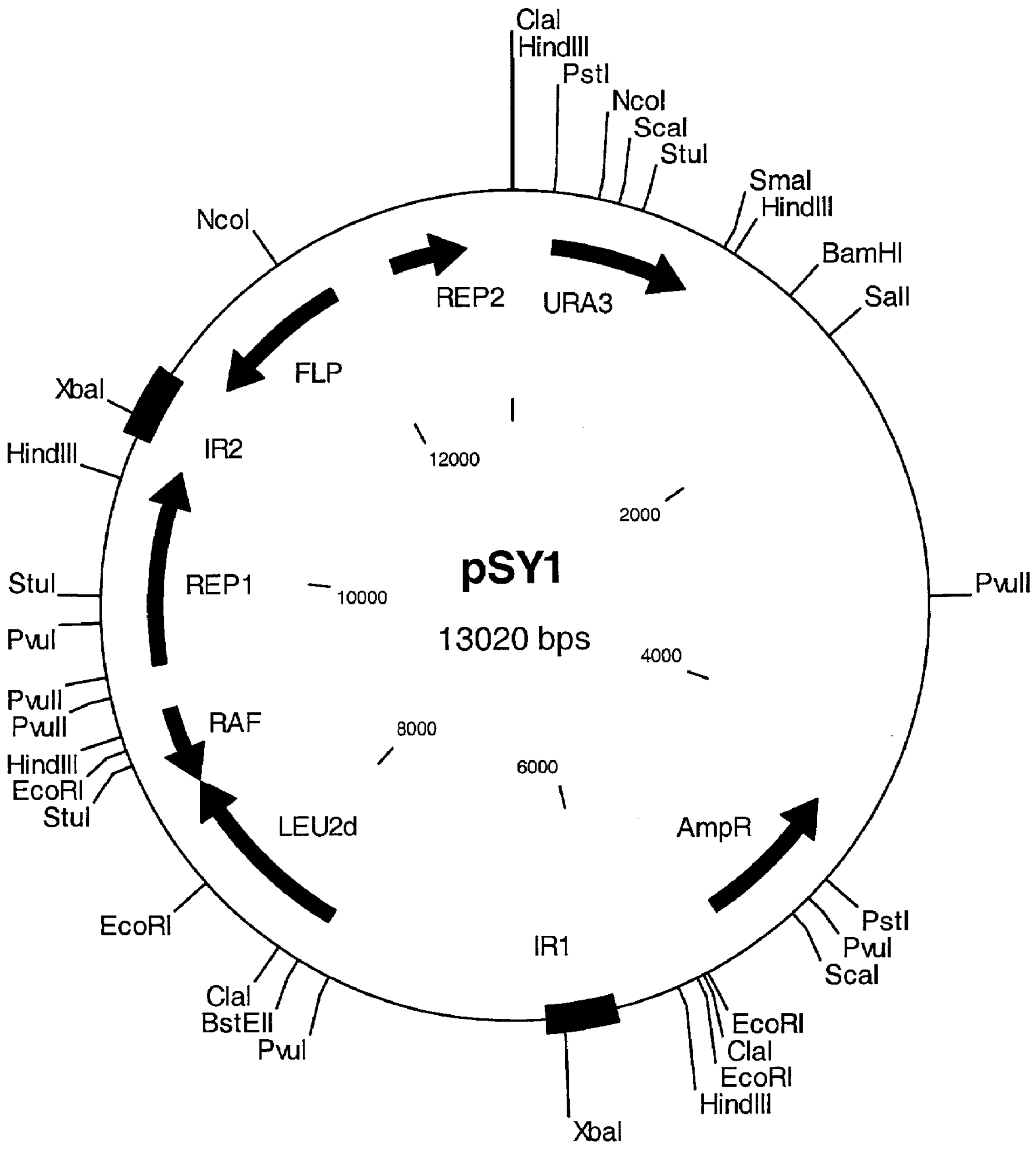

FIG. 21. Schematic map of the vector pSY1 which has the sequence as defined in SEQ ID NO:43.

Figure 22:
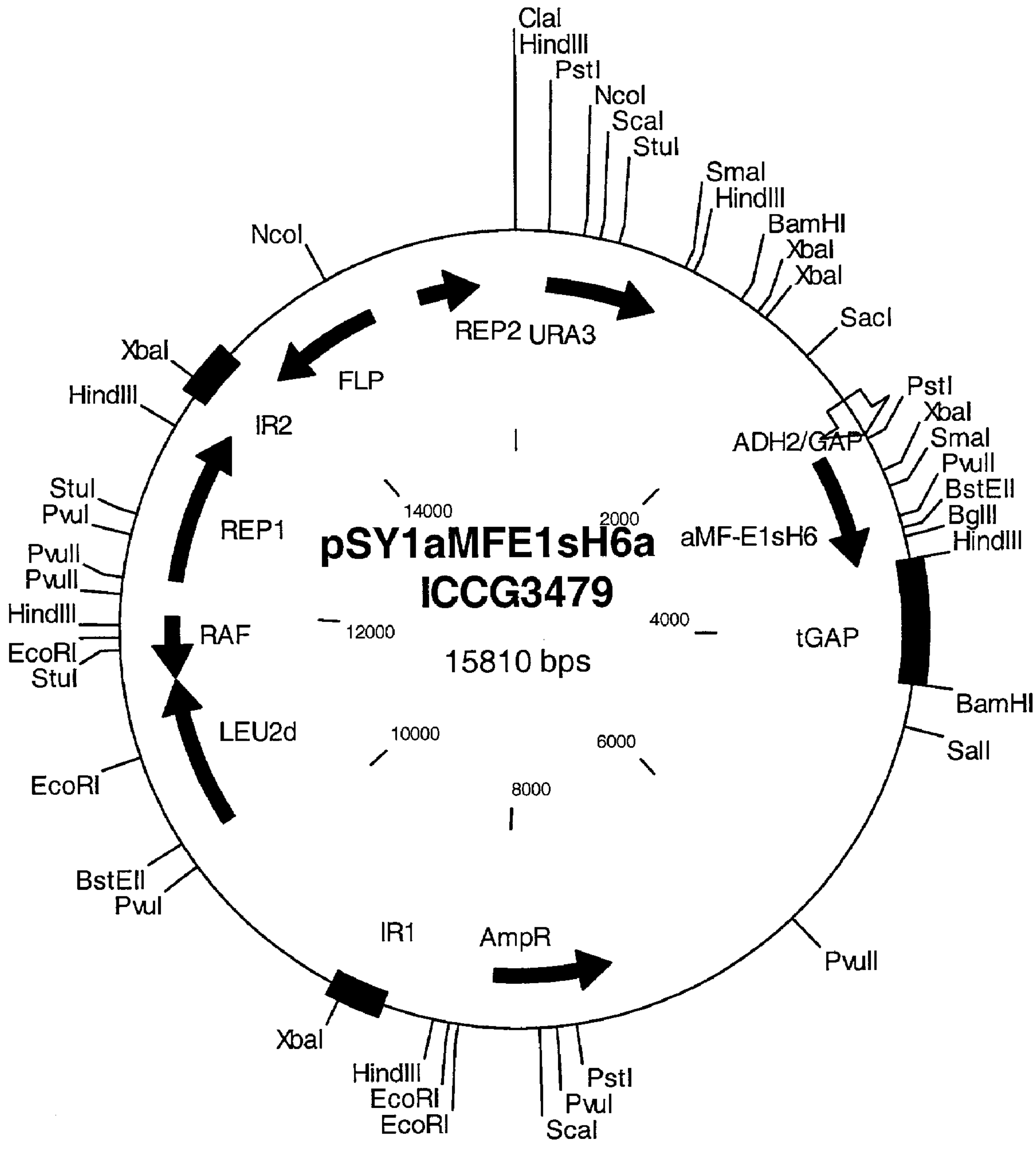

FIG. 22. Schematic map of the vector pSY1aMFE1sH6a which has the sequence as defined in SEQ ID NO:44.

Figure 23:
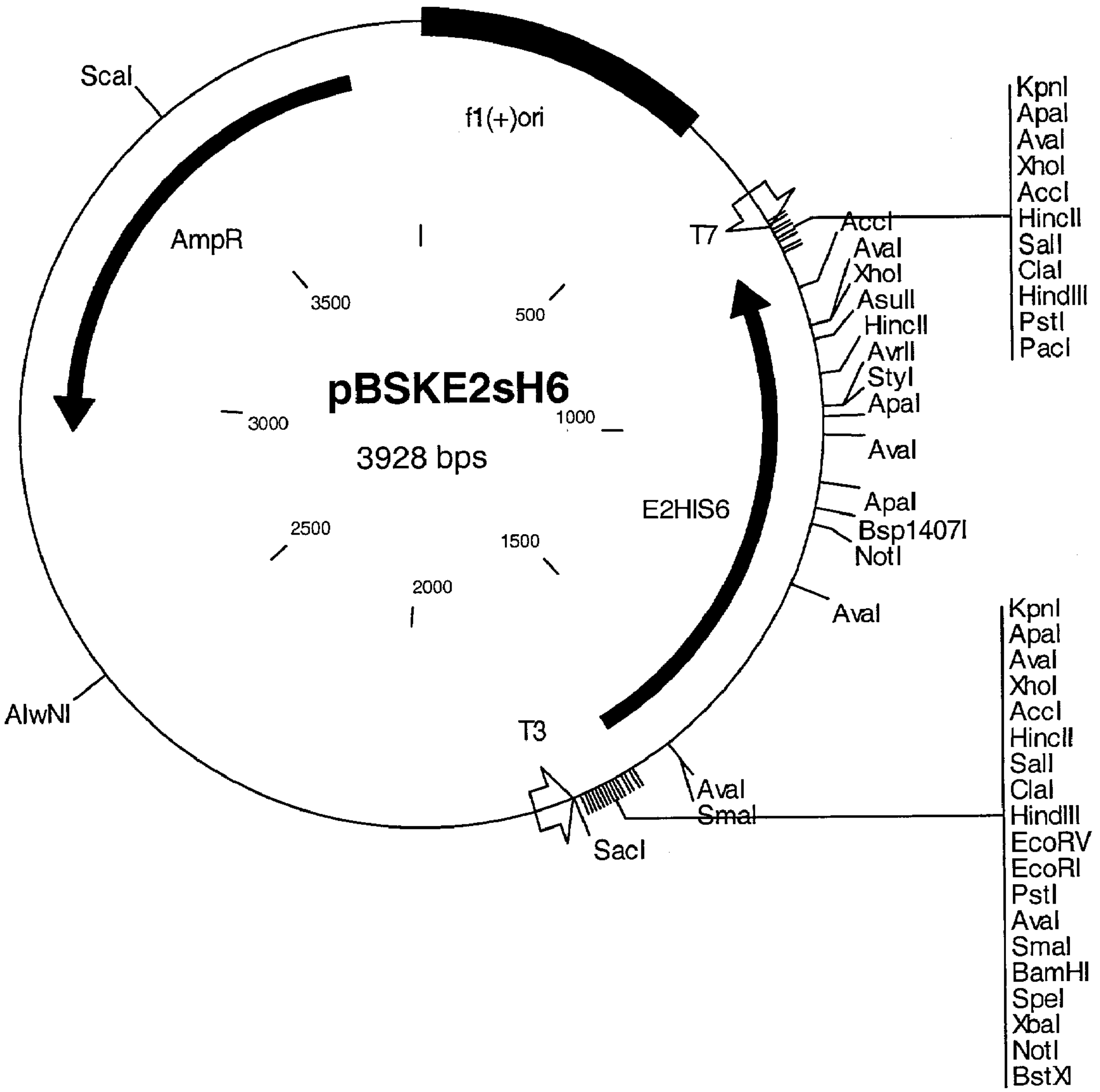

FIG. 23. Schematic map of the vector pBSK-E2sH6 which has the sequence as defined in SEQ ID NO:45.

Figure 24:
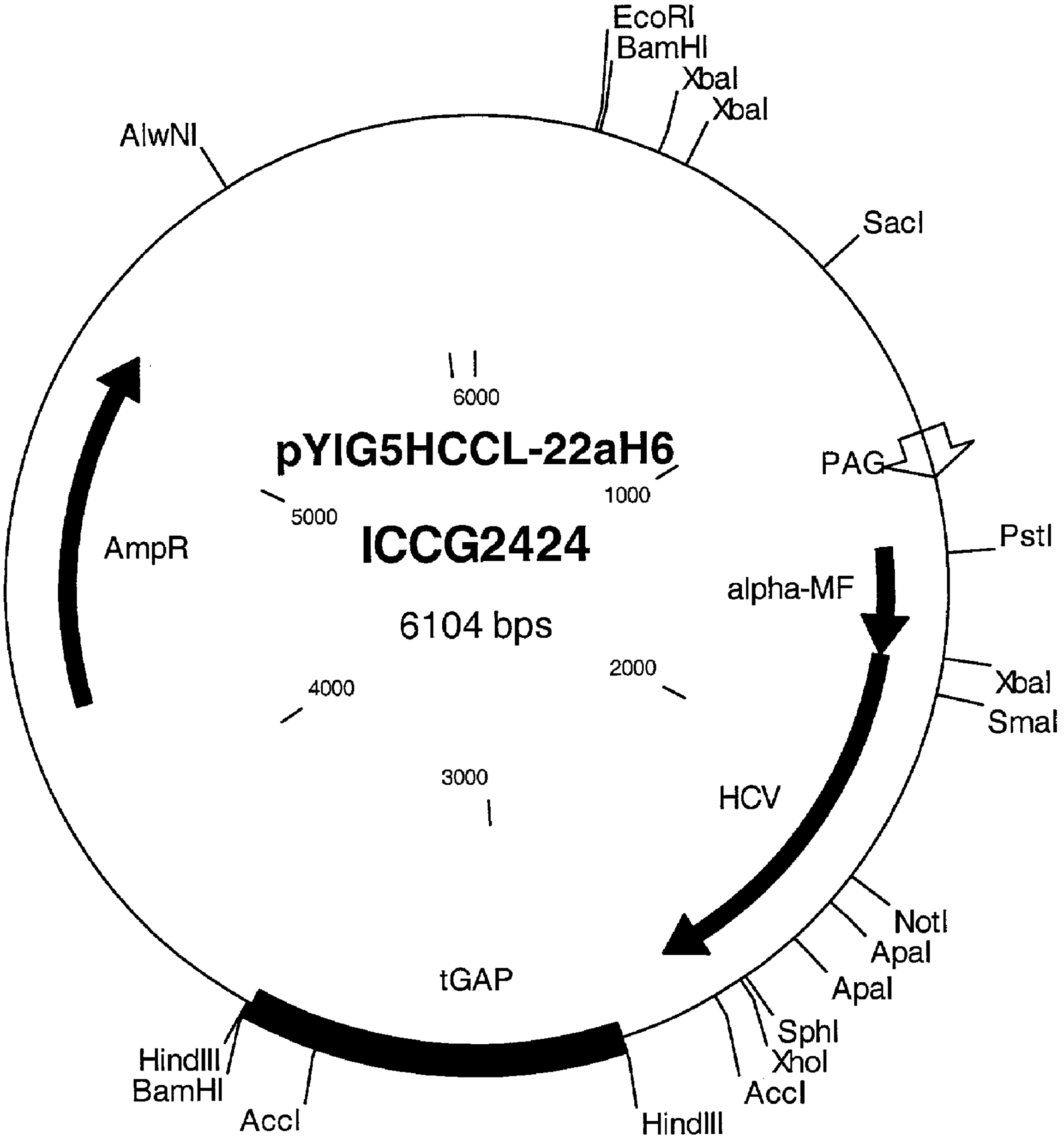

FIG. 24. Schematic map of the vector pYIG5HCCL-22aH6 which has the sequence as defined in SEQ ID NO:46.

Figure 25:
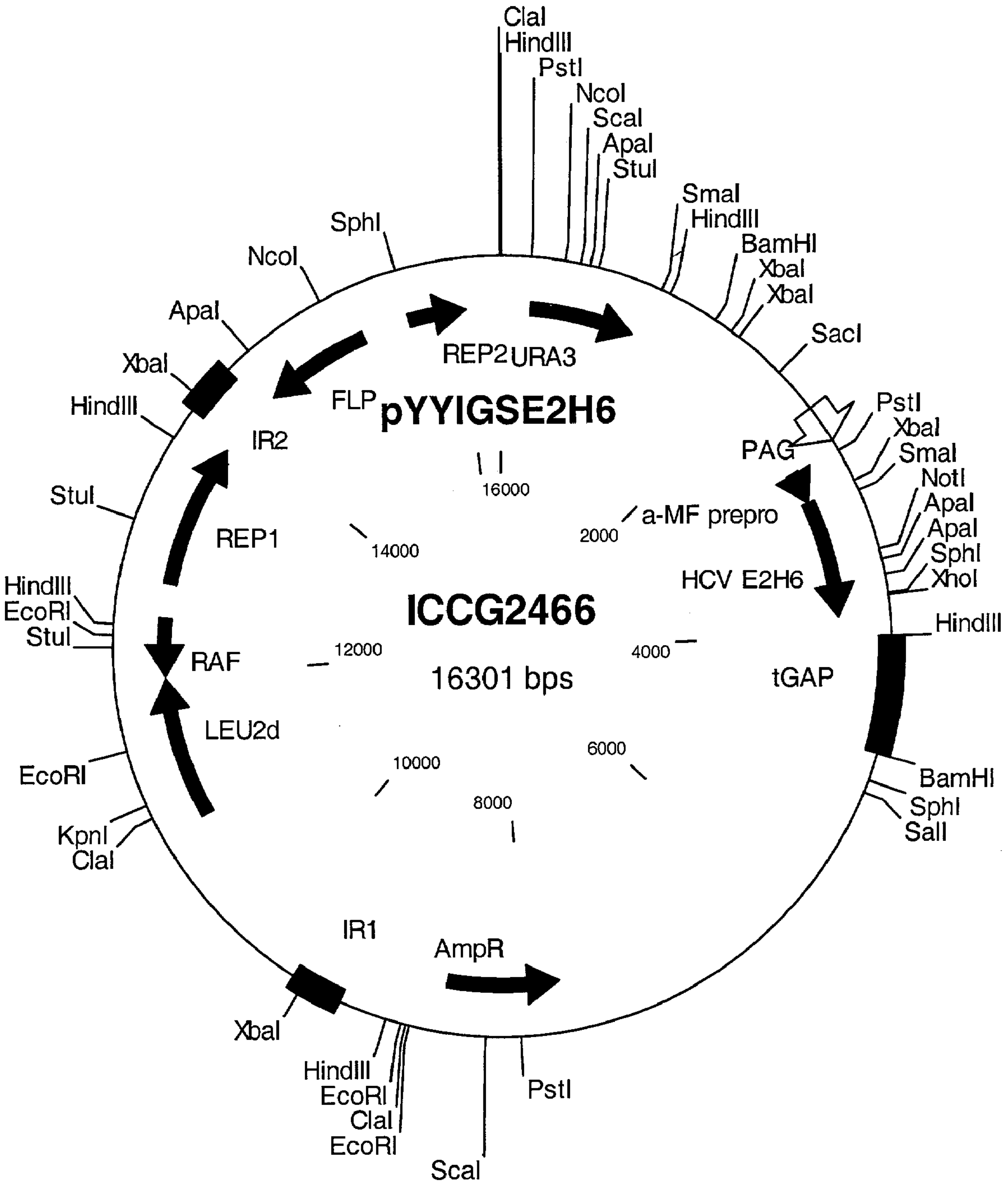

FIG. 25. Schematic map of the vector pYYIGSE2H6 which has the sequence as defined in SEQ ID NO:47.

Figure 26:
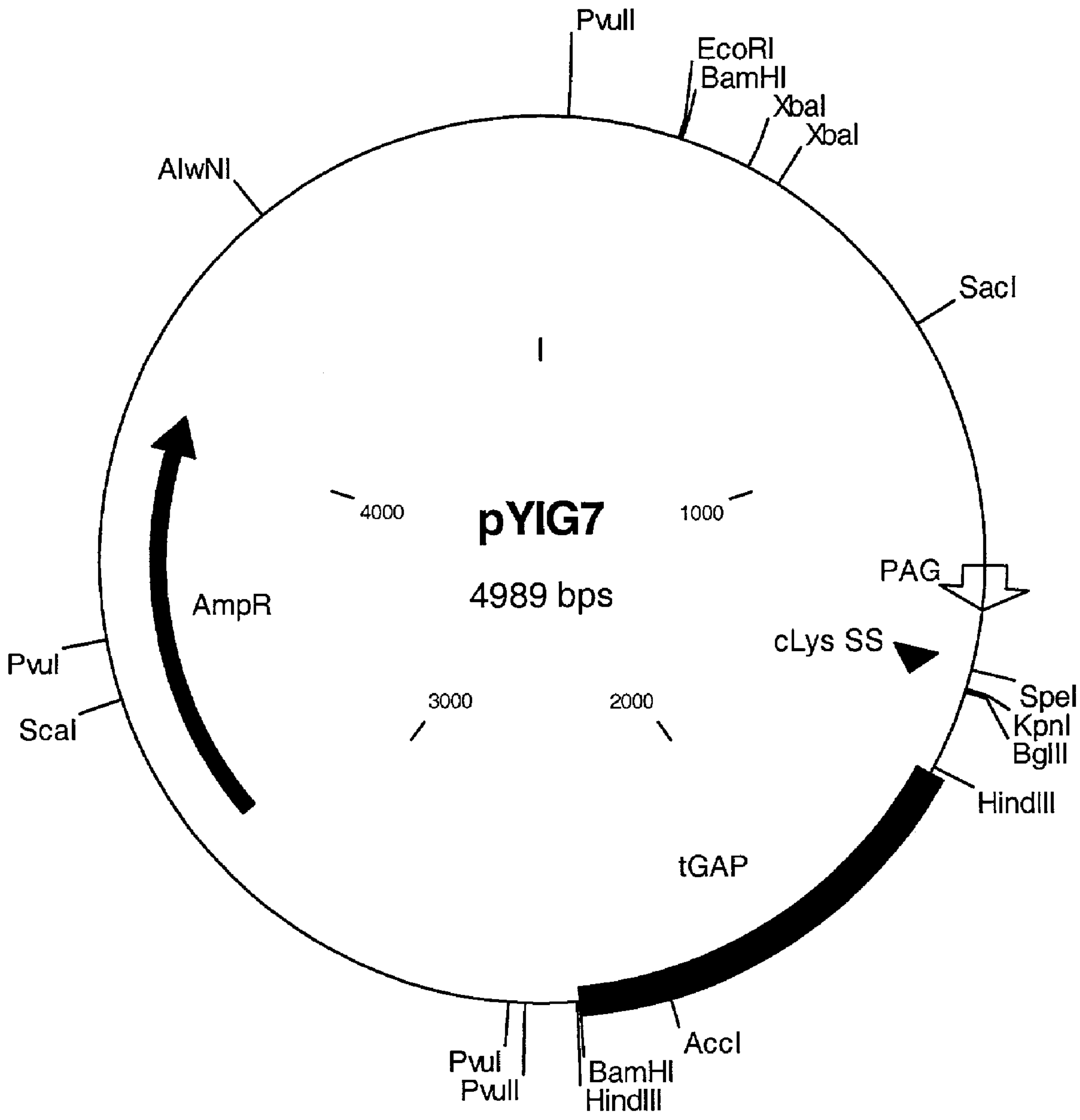

FIG. 26. Schematic map of the vector pYIG7 which has the sequence as defined in SEQ ID NO:48.

Figure 27:
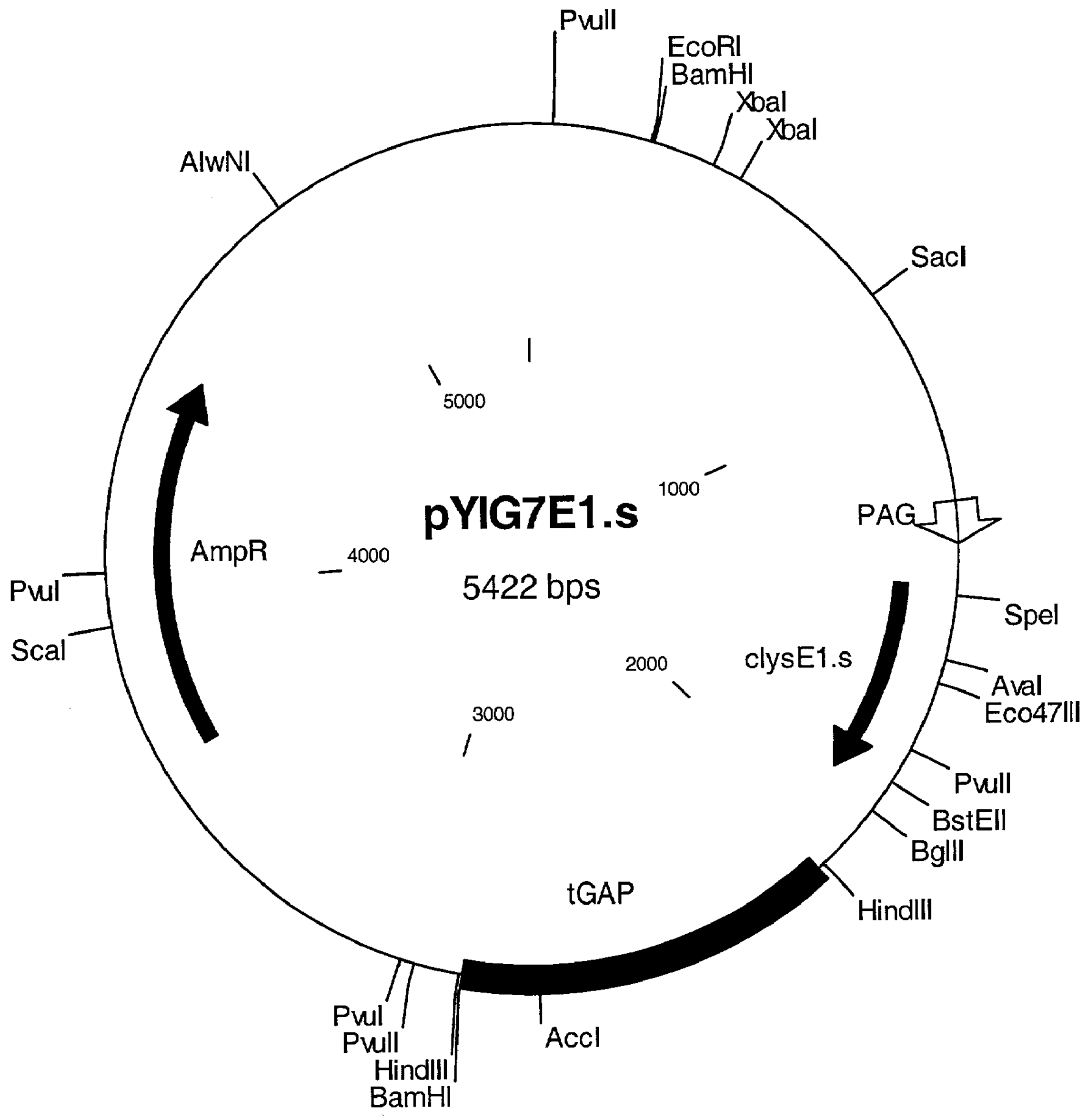

FIG. 27. Schematic map of the vector pYIG7E1 which has the sequence as defined in SEQ ID NO:49.

Figure 28:
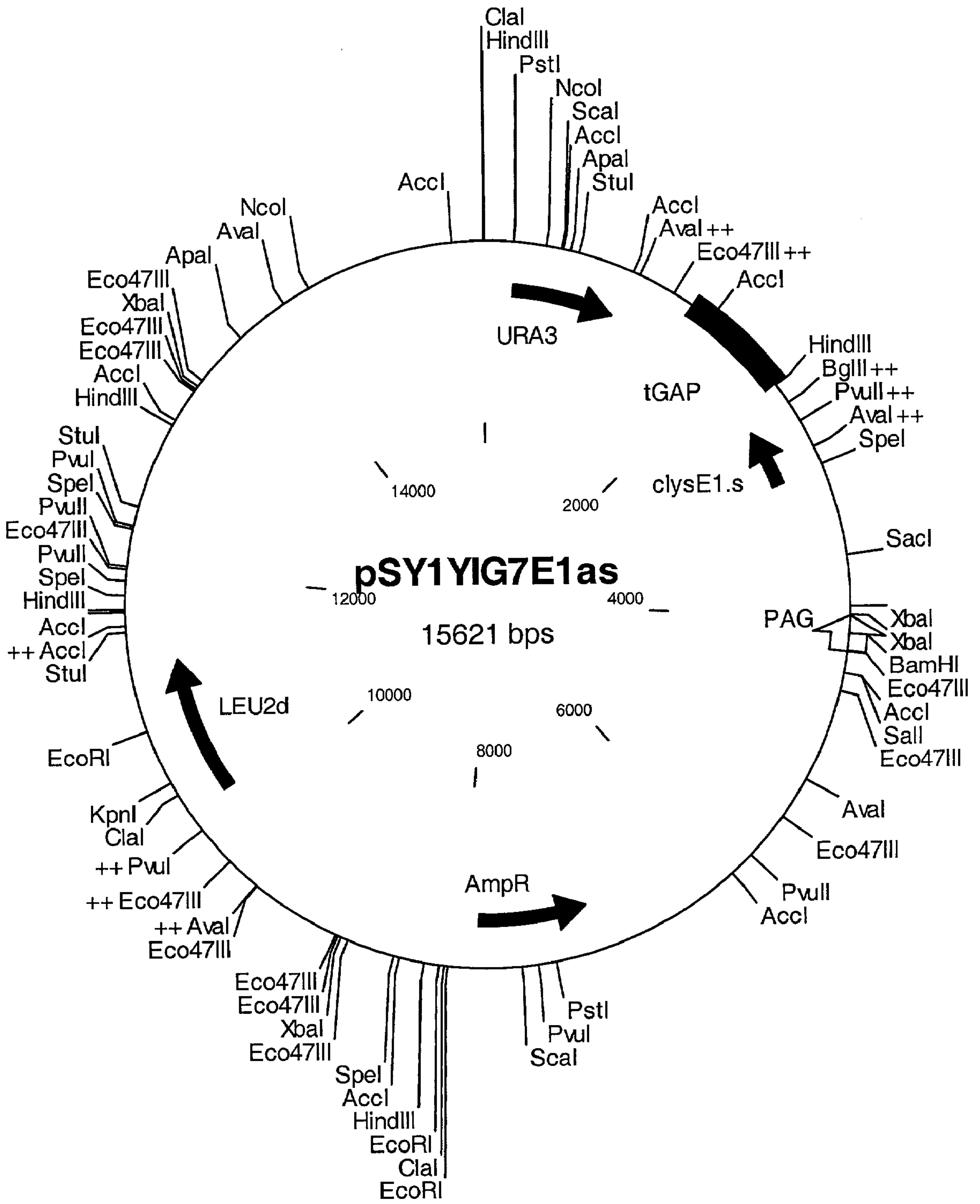

FIG. 28. Schematic map of the vector pSY1YIG7E1s which has the sequence as defined in SEQ ID NO:50.

Figure 29:
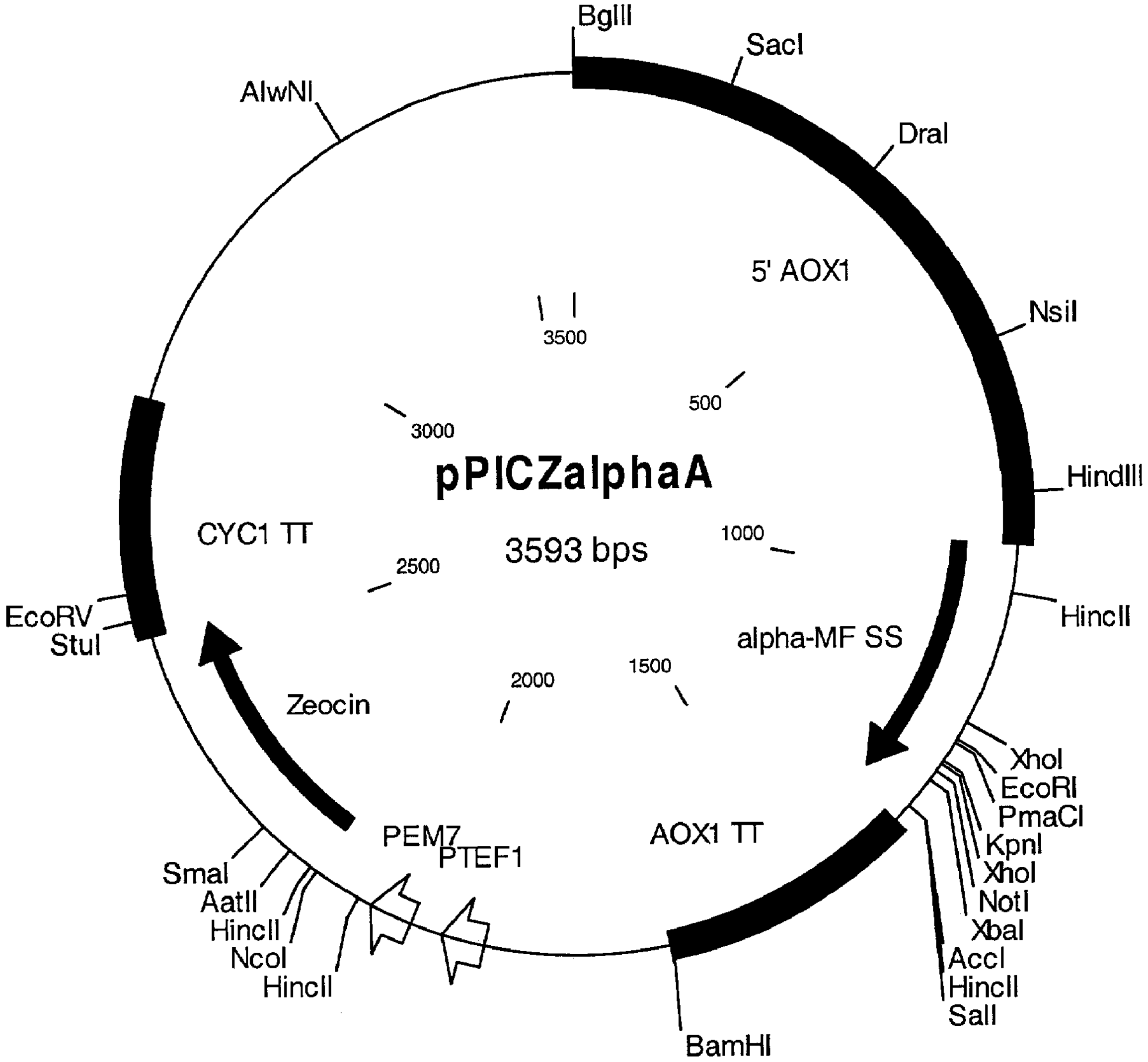

FIG. 29. Schematic map of the vector pPICZalphaA which has the sequence as defined in SEQ ID NO:51.

Figure 30:
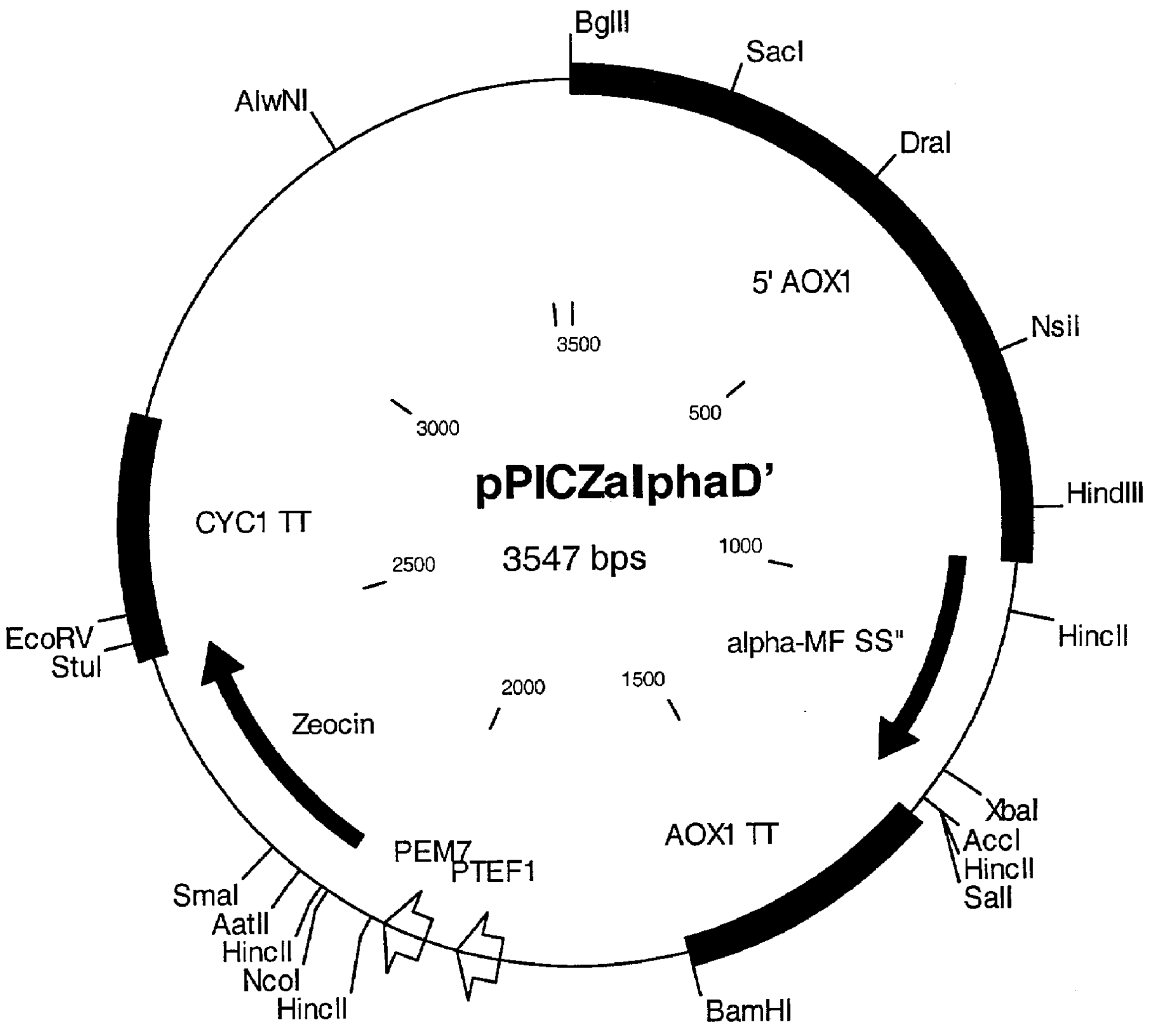

FIG. 30. Schematic map of the vector pPICZalphaD' which has the sequence as defined in SEQ ID NO:52.

Figure 31:
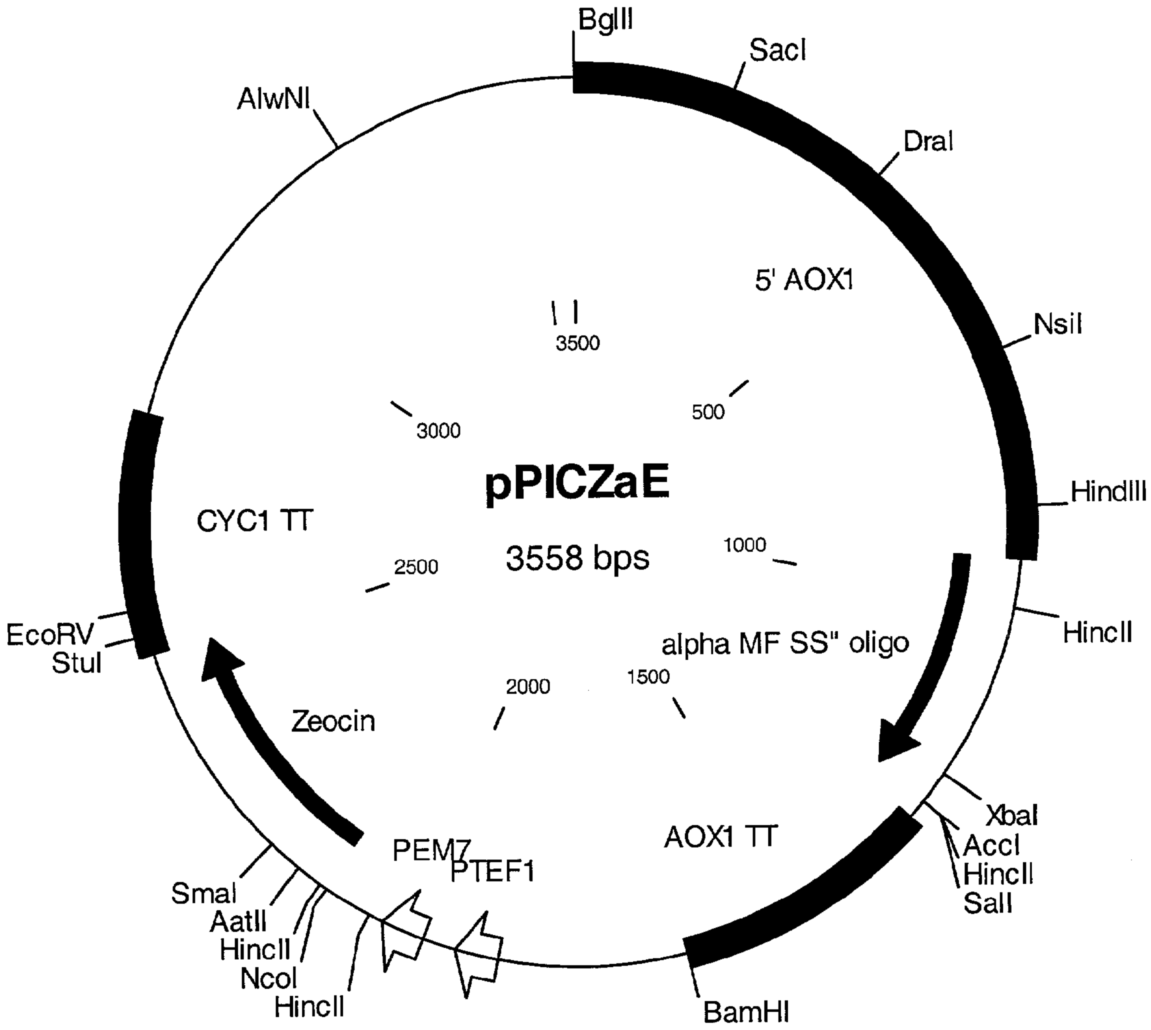

FIG. 31. Schematic map of the vector pPICZalphaE' which has the sequence as defined in SEQ ID NO:53.

Figure 32:
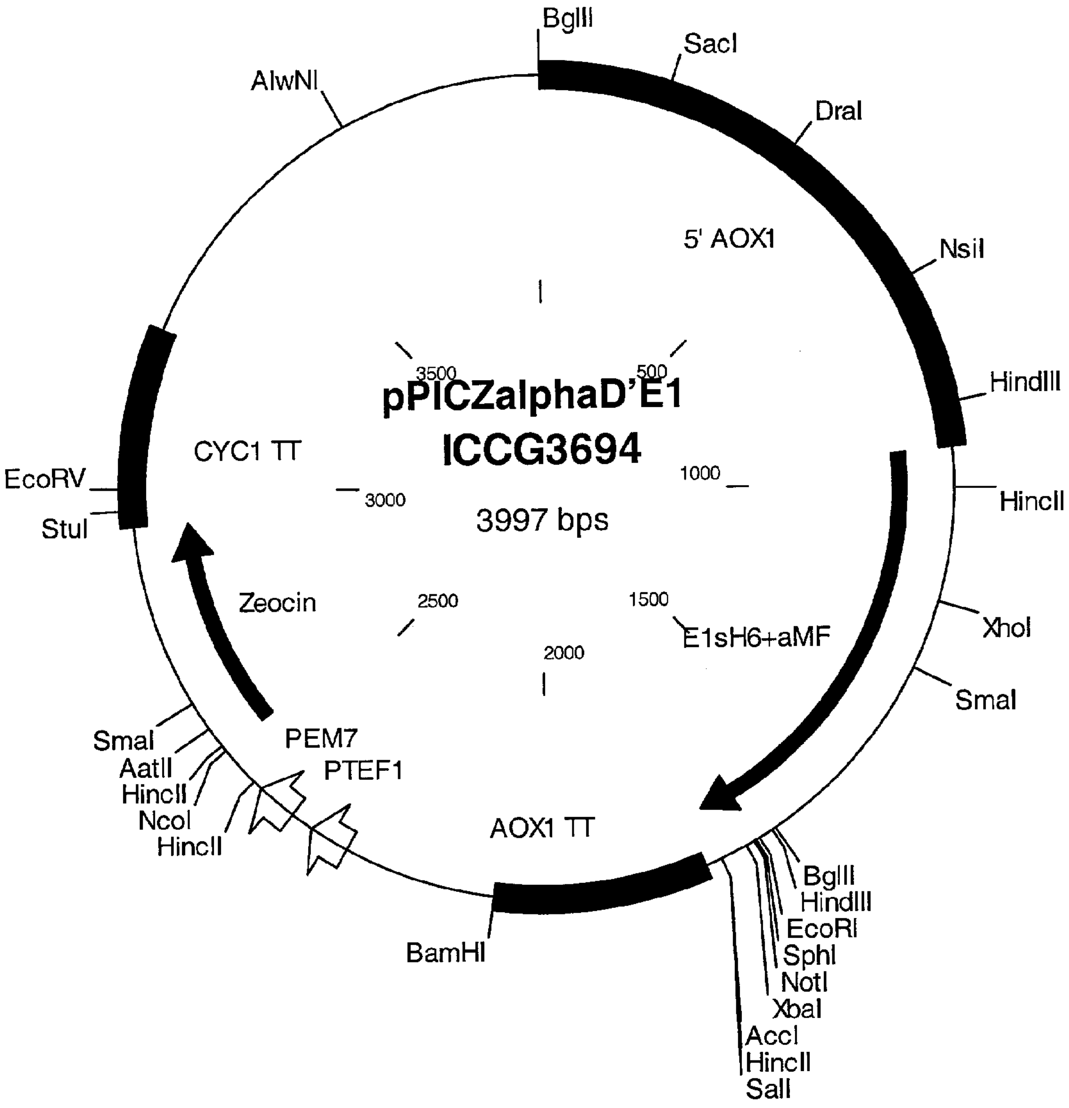

FIG. 32. Schematic map of the vector pPICZalphaD'E1sH6 which has the sequence as defined in SEQ ID NO:58.

Figure 33:
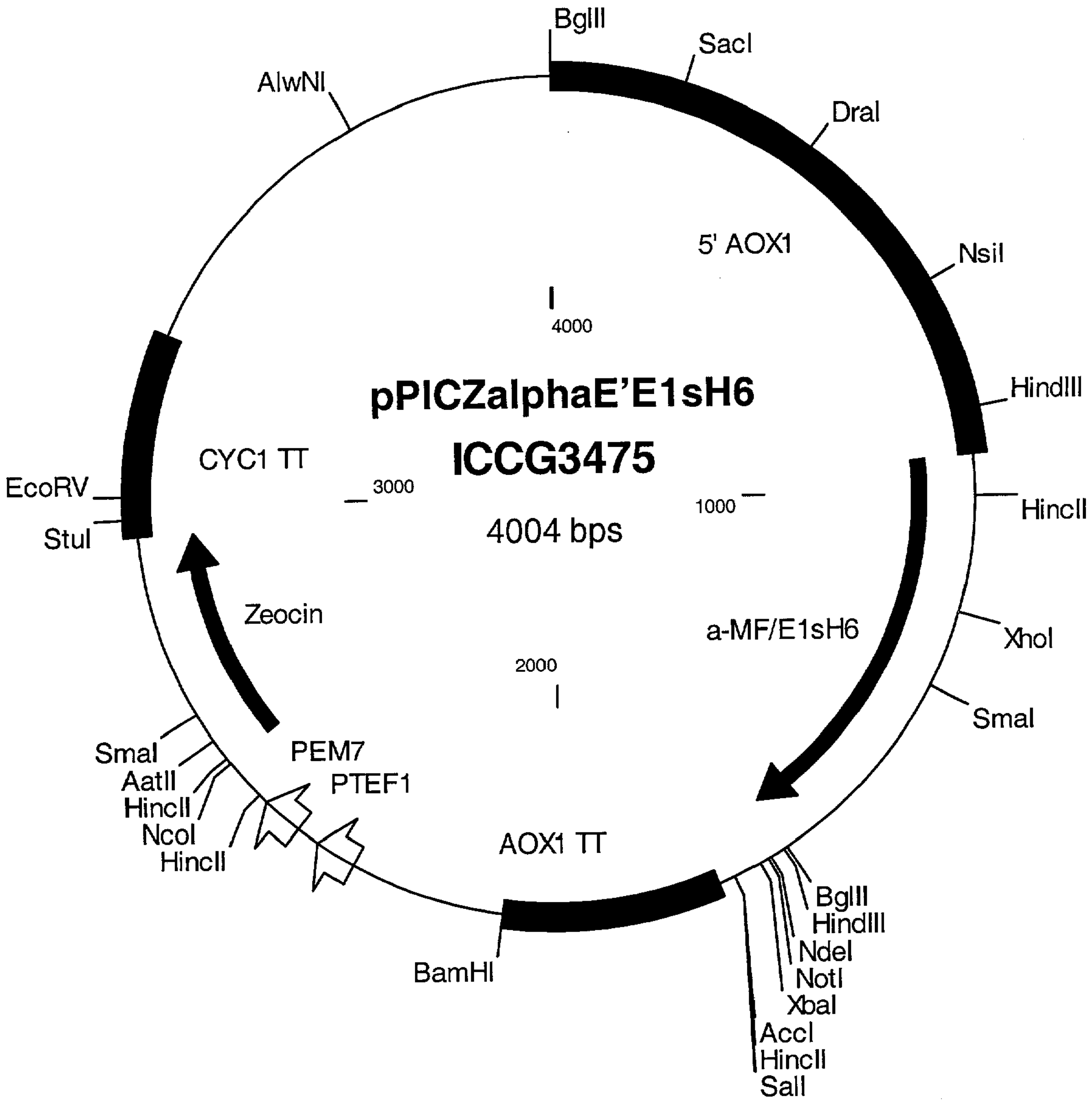

FIG. 33. Schematic map of the vector pPICZalphaE'E1sH6 which has the sequence as defined in SEQ ID NO:59.

Figure 34:
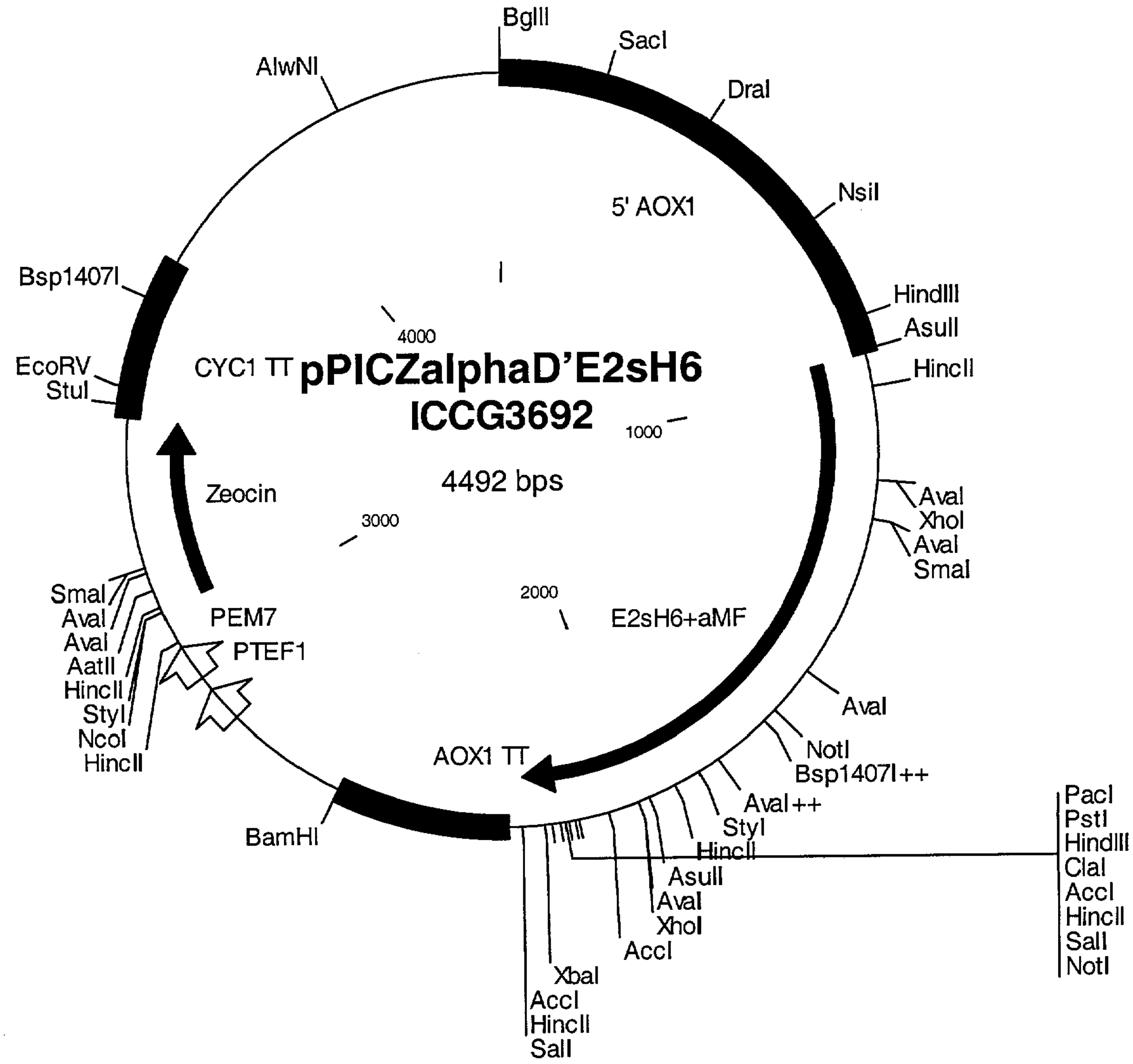

FIG. 34. Schematic map of the vector pPICZalphaD'E2sH6 which has the sequence as defined in SEQ ID NO:60.

Figure 35:
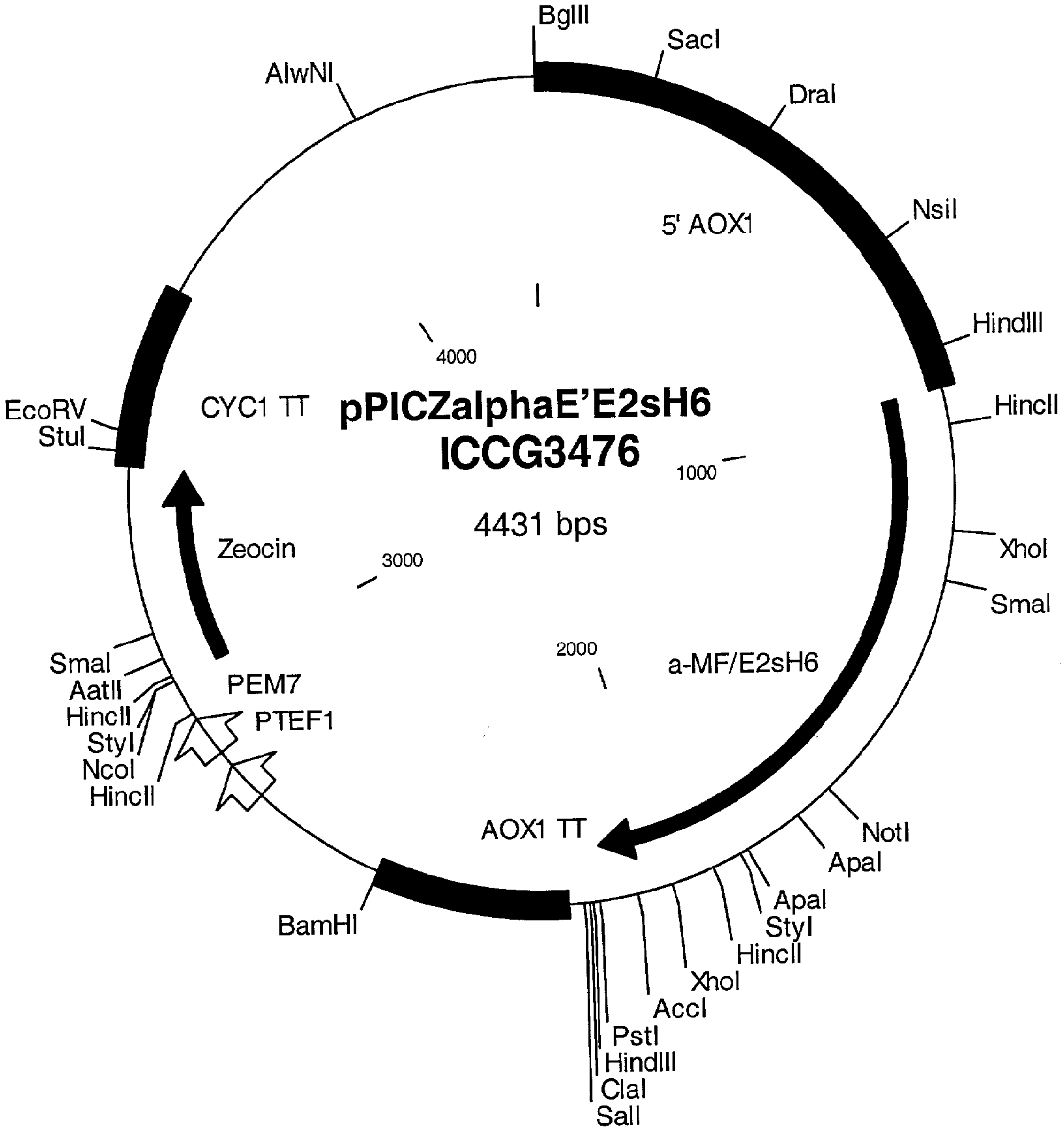

FIG. 35. Schematic map of the vector pPICZalphaE'E2sH6 which has the sequence as defined in SEQ ID NO:61.

Figure 36:
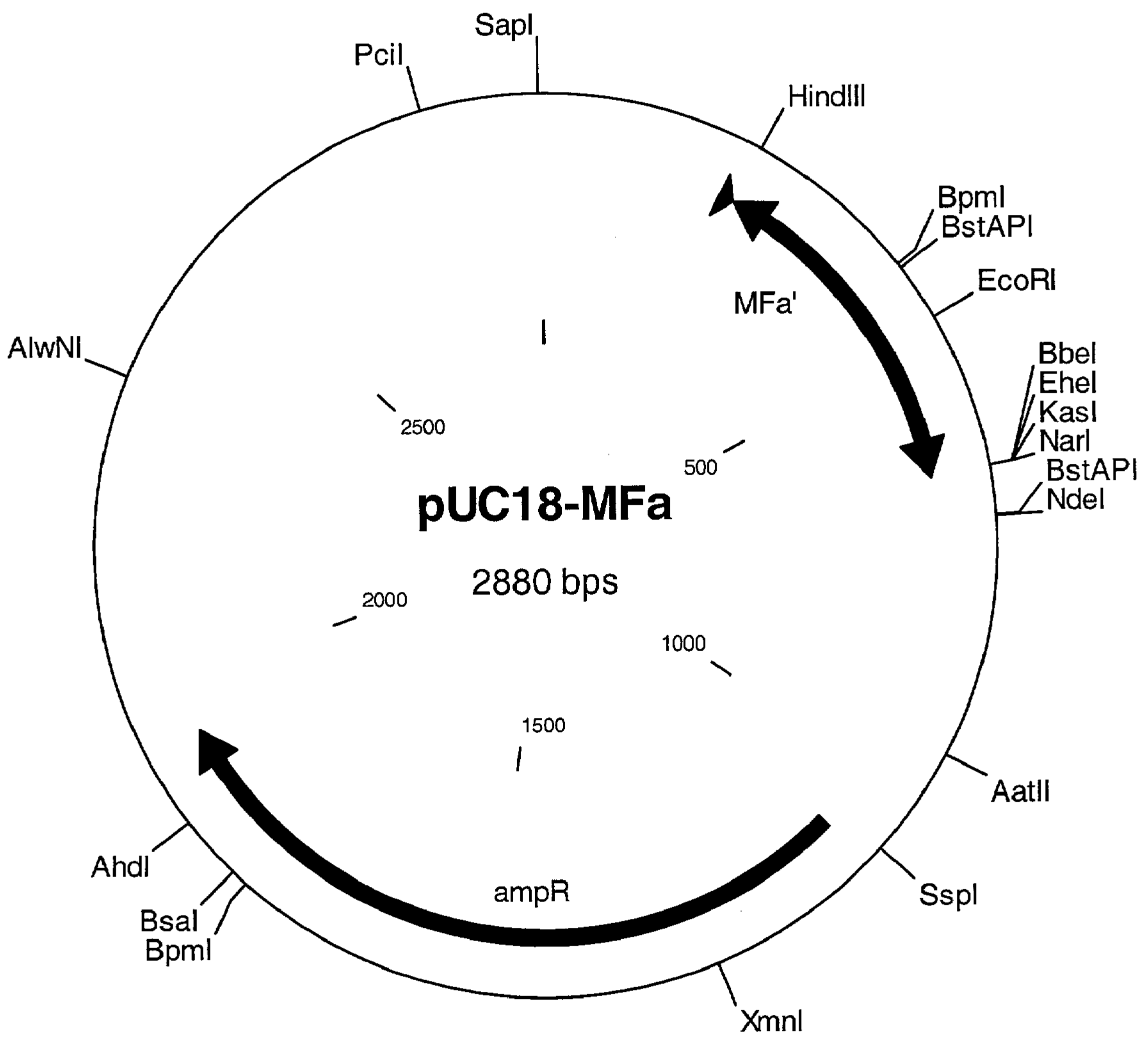

FIG. 36. Schematic map of the vector pUC18MFa which has the sequence as defined in SEQ ID NO:62.

Figure 37:
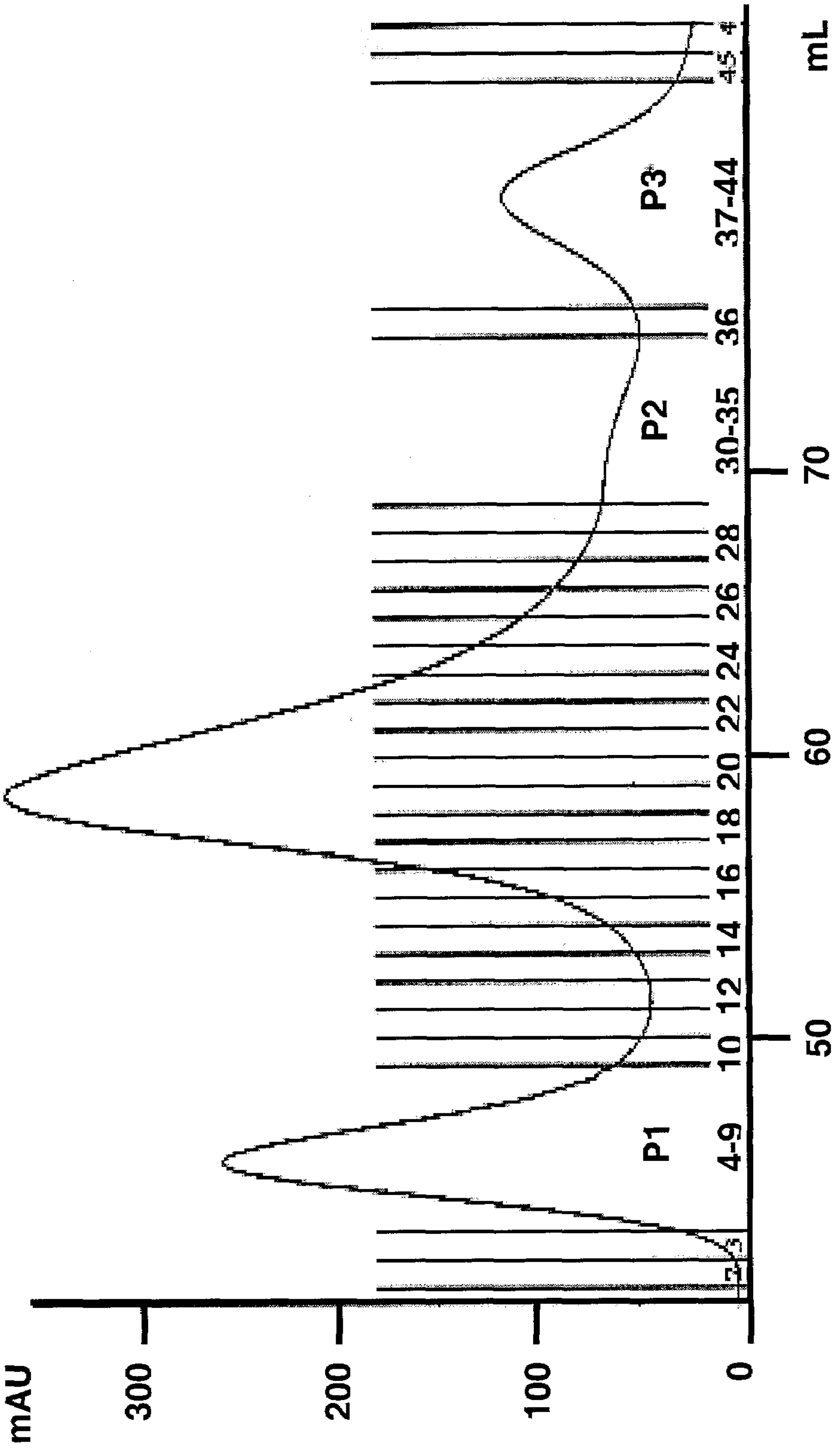

FIG. 37. Elution profile of size exclusion chromatography of IMAC-purified E2-H6 protein expressed from the MFα-E2-H6-expressing *Hansenula polymorpha* (see Example 15). The X-axis indicates the elution volume (in mL). The vertical lines through the elution profile indicate the fractions collected. “P1”=pooled fractions 4 to 9, “P2”=pooled fractions 30 to 35, and “P3”=pooled fractions 37 to 44. The Y-axis indicates absorbance given in mAU (milli absorbance units). The X-axis indicates the elution volume in mL.

Figure 38:
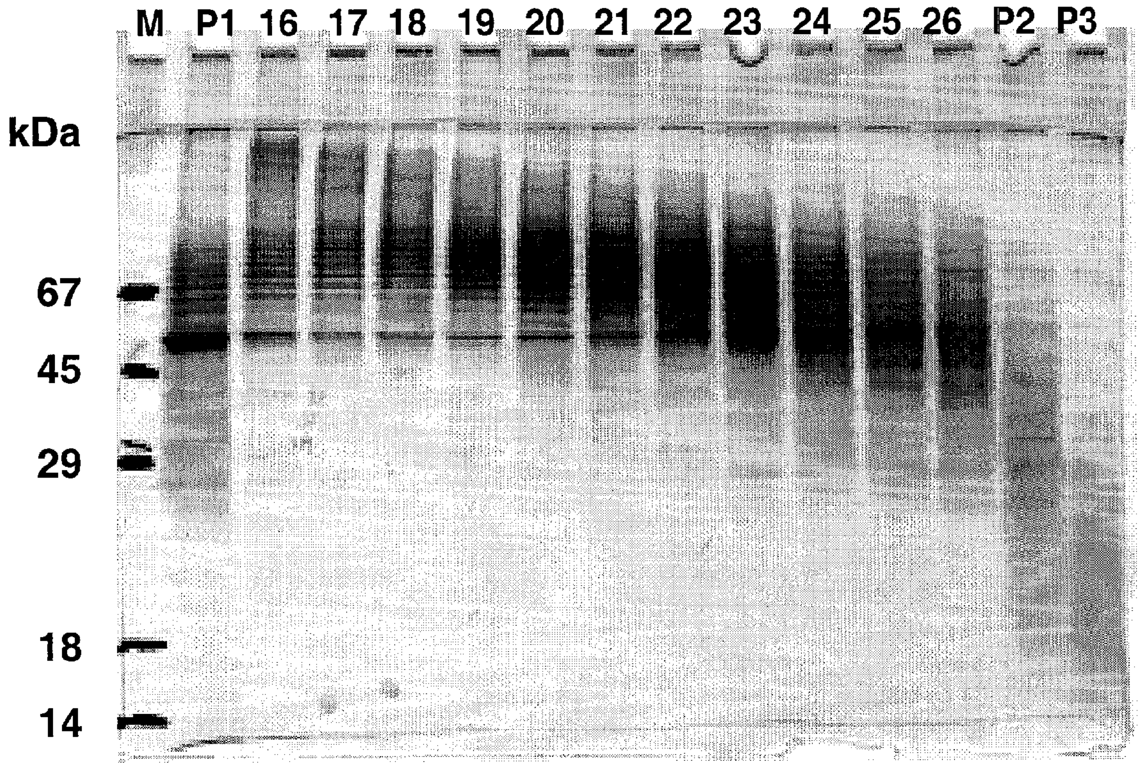

FIG. 38. The different pools and fractions collected after size exclusion chromatography (see FIG. 37) were analyzed by non-reducing SDS-PAGE followed by silver staining of the polyacrylamide gel. The analyzed pools (“P1”, “P2”, and “P3”) and fractions (16 to 26) are indicated on top of the picture of the silver-stained gel. At the left (lane “M”) are indicated the sizes of the molecular mass markers.

Figure 39:
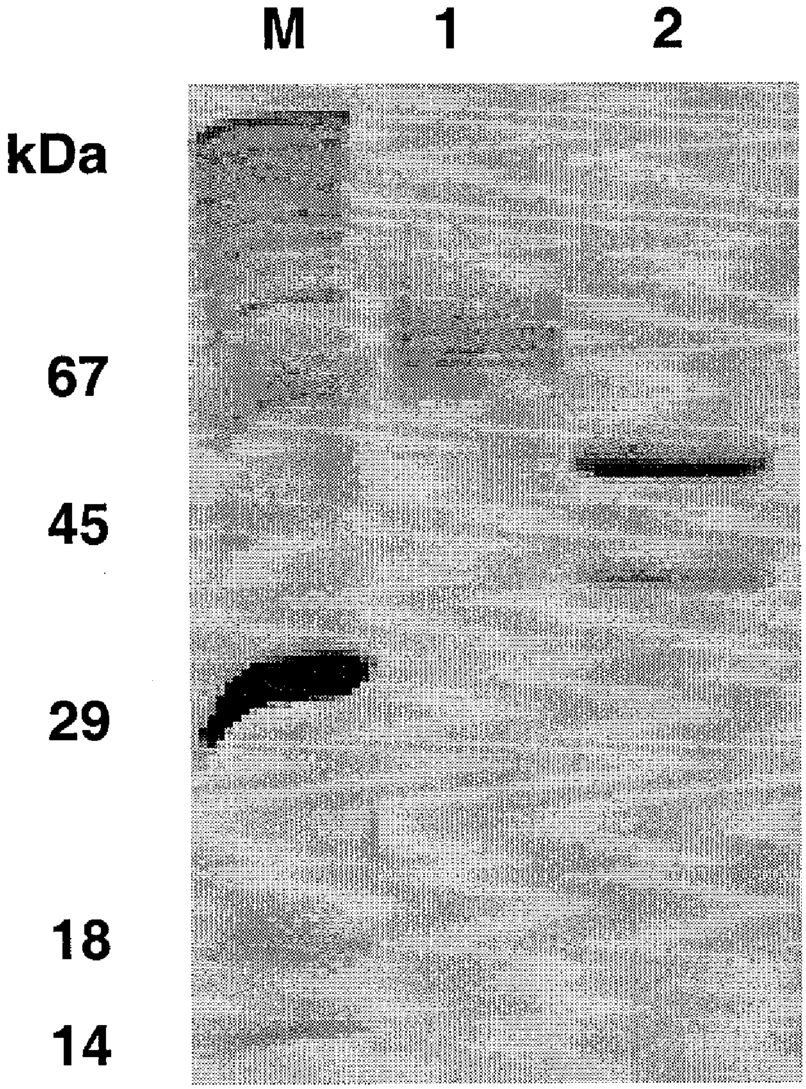

FIG. 39. Fractions 17 to 23 of the size exclusion chromatographic step as shown in FIG. 37 were pooled and alkylated. Thereafter, the protein material was subjected to Endo H treatment for deglycosylation. Untreated material and Endo H-treated material were separated on an SDS-PAGE gel and blotted to a PVDF membrane. The blot was stained with amido black.

Lane 1: Alkylated E2-H6 before Endo H-treatment

Lane 2: Alkylated E2-H6 after Endo H-treatment.

Figure 40:
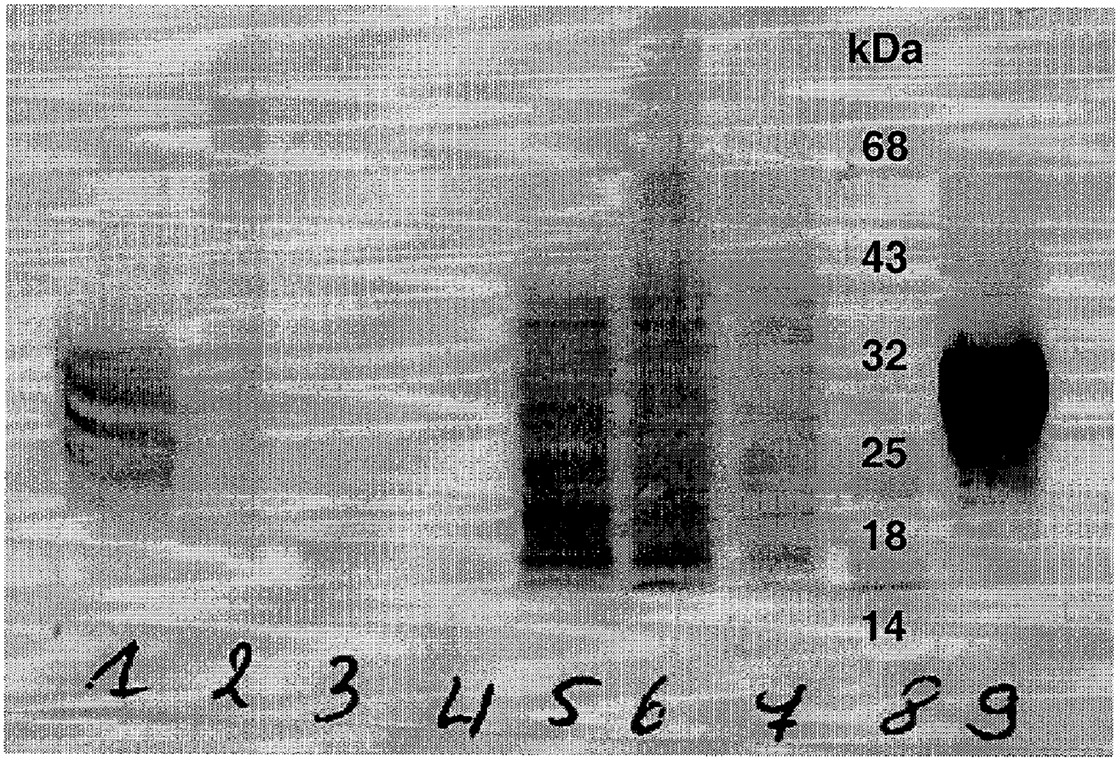

FIG. 40. Western-blot analysis of cell lysates of E1 expressed in *Saccharomyces cerevisiae*. The Western-blot was developed using the E1-specific monoclonal antibody IGH 201.

Lanes 1-4: expression product after 2, 3, 5 or 7 days expression, respectively, in a *Saccharomyces* clone transformed with pSY1YIG7E1s (SEQ ID NO:50, FIG. 28) comprising the nucleotide sequence encoding the chicken lysozyme leader peptide joined to E1-H6.

Lanes 5-7: expression product after 2, 3 or 5 days expression, respectively, in a *Saccharomyces* clone transformed with pSY1aMFE1sH6aYIG1 (SEQ ID NO:44, FIG. 22) comprising the nucleotide sequence encoding the α-mating factor leader peptide joined to E1-H6.

Lane 8: molecular weight markers with sizes as indicated.

Lane 9: purified E1s produced by HCV-recombinant *vaccinia* virus-infected mammalian cells.

Figure 41:
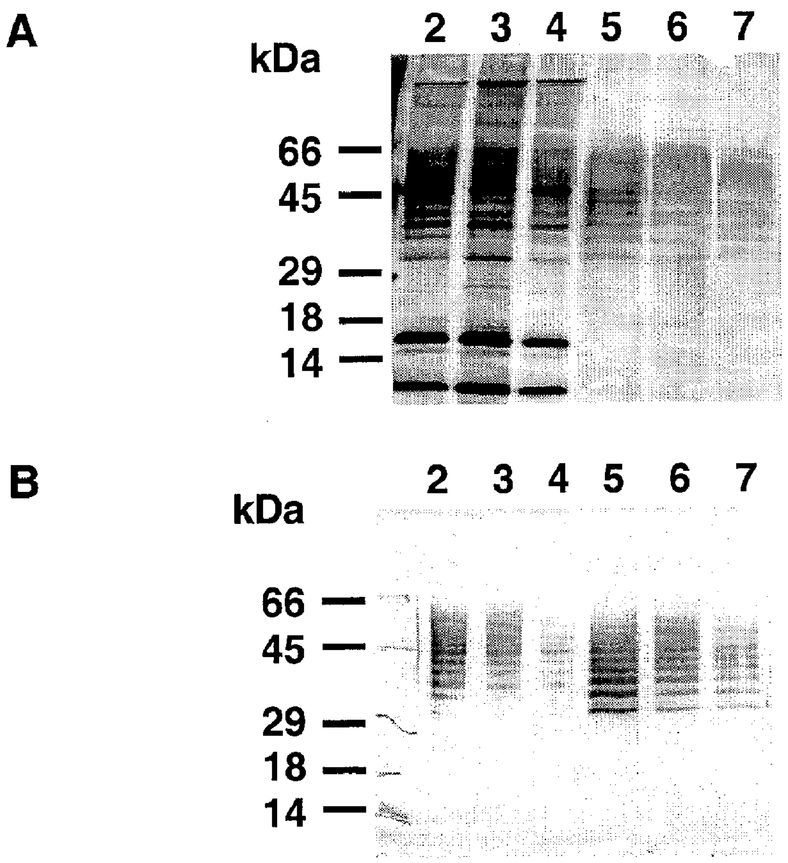

FIG. 41. Analysis of the immobilized metal ion affinity chromatography (IMAC)-purified E2-H6 protein expressed by and processed from CL-E2-H6 to E2-H6 by *H. polymorpha* (see Example 17). Proteins in different wash fractions (lanes 2 to 4) and elution fractions (lanes 5 to 7) were analyzed by reducing SDS-PAGE followed by silver staining of the gel (A, top picture) or by western blot using using a specific monoclonal antibody directed against E2 (B, bottom picture). The sizes of the molecular mass markers are indicated at the left.

Figure 42:
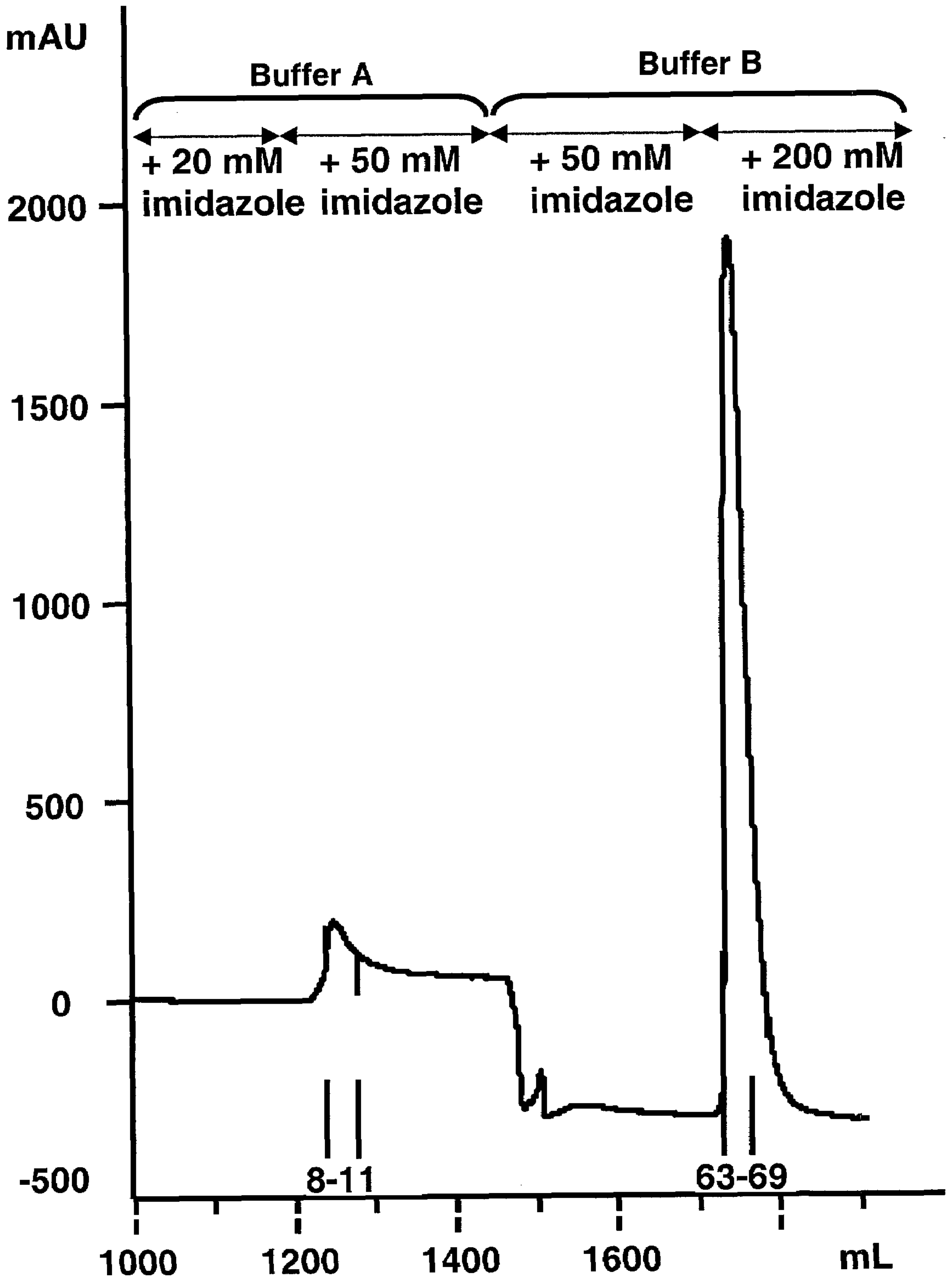

FIG. 42. Elution profile of the first IMAC chromatography step on a Ni-IDA column (Chelating Sepharose FF loaded with $Ni^{2+}$, Pharmacia) for the purification of the sulfonated H6-K-E1 protein produced by *H. polymorpha* (see Example 18). The column was equilibrated with buffer A (50 mM phosphate, 6 M GuHCl, 1% Empigen BB (v/v), pH 7.2) supplemented with 20 mM imidazole. After sample application, the column was washed sequentially with buffer A containing 20 mM and 50 mM imidazole, respectively (as indicated on chromatogram). A further washing and elution step of the His-tagged products was performed by the sequential application of buffer B (PBS, 1% empigen BB, pH 7.2) supplemented with 50 mM imidazole and 200 mM imidazole respectively (as indicated on chromatogram). Following fractions were pooled: the wash pool 1 (fractions 8 to 11, wash with 50 mM imidazole). The eluted material was collected as separate fractions 63 to 72 or an elution pool (fractions 63 to 69) was made. The Y-axis indicates absorbance given in mAU (milli absorbance units). The X-axis indicates the elution volume in mL FIG. 43. Analysis of the IMAC-purified H6-K-E1 protein (see FIG. 42) expressed by and processed from CL-H6-K-E1 to H6-K-E1 by *H. polymorpha*. Proteins in the wash pool 1 (lane 12) and elution fractions 63 to 72 (lanes 2 to 11) were analyzed by reducing SDS-PAGE followed by silver staining of the gel (A, top picture). Proteins present in the sample before IMAC (lane 2), in the flow-through pool (lane 4), in wash pool 1 (lane 5) and in the elution pool (lane 6) were analyzed by western blot using a specific monoclonal antibody directed against E1 (IGH201) (B, bottom picture; no sample was loaded in lane 3). The sizes of the molecular mass markers (lanes M) are indicated at the left.

Figure 44:
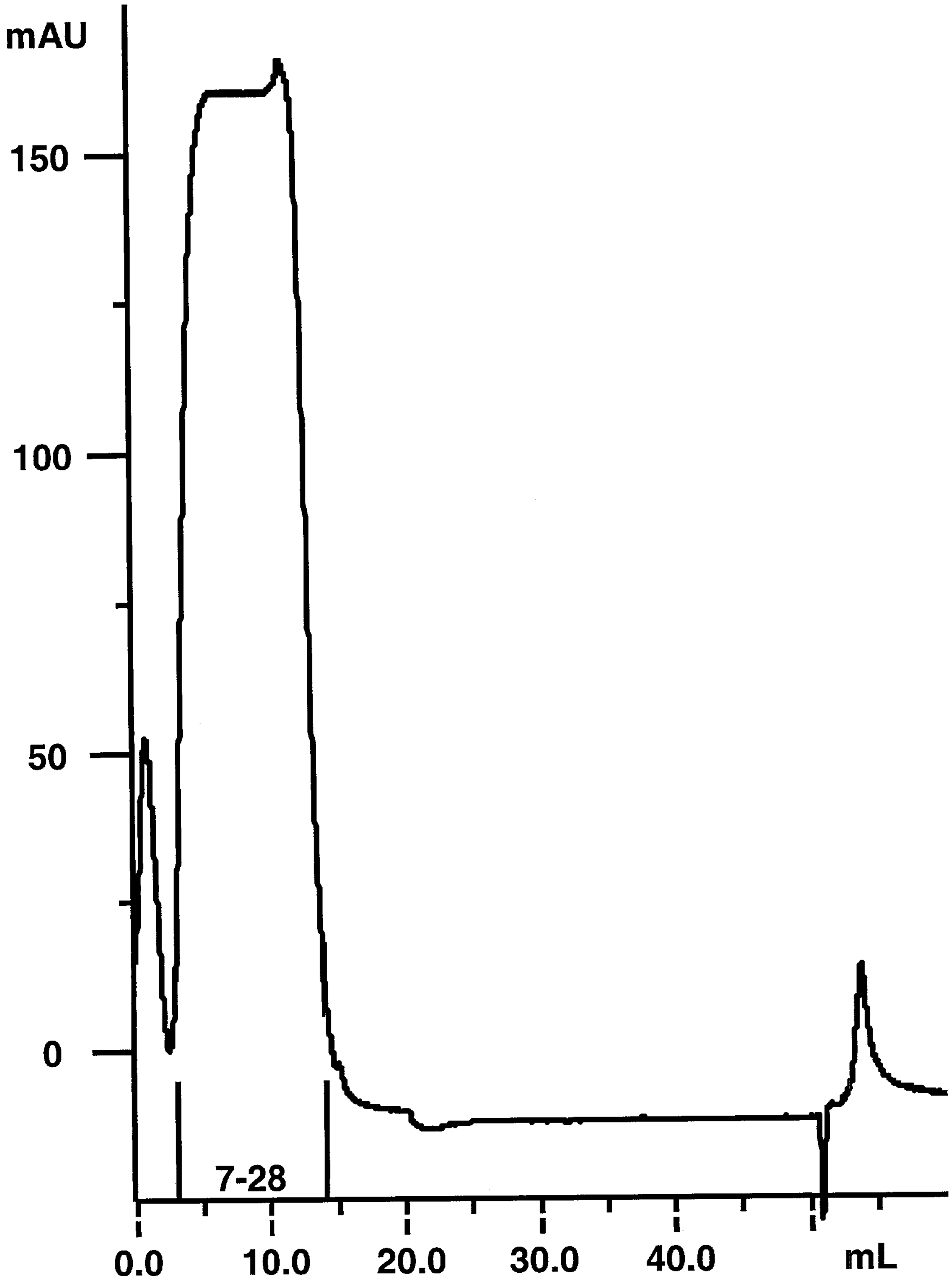

FIG. 44. Elution profile of the second IMAC chromatography step on a Ni-IDA column (Chelating Sepharose FF loaded with $Ni^{2+}$, Pharmacia) for the purification of E1 resulting from the in vitro processing of H6-K-E1 (purification: see FIG. 42) with Endo Lys-C. The flow through was collected in different fractions (1 to 40) that were screened for the presence of E1s-products. The fractions (7 to 28), containing intact E1 processed from H6-K-E1 were pooled. The Y-axis indicates absorbance given in mAU (milli absorbance units). The X-axis indicates the elution volume in mL FIG. 45. Western-blot analysis indicating specific E1s proteins bands reacting with biotinylated heparin (see also Example 19). E1s preparations purified from HCV-recombinant *vaccinia* virus-infected mammalian cell culture or expressed by *H. polymorpha* were analyzed. The panel right from the vertical line shows a Western-blot developed with the biotinylated E1 specific monoclonal IGH 200. The panel left from the vertical line shows a Western-blot developed with biotinylated heparin. From these results it is concluded that mainly the lower-glycosylated E1s has high affinity for heparin.

Lanes M: molecular weight marker (molecular weights indicated at the left).

Lanes 1: E1s from mammalian cells and alkylated during isolation.

Lanes 2: E1s-H6 expressed by *H. polymorpha* and sulphonated during isolation.

Lanes 3: E1s-H6 expressed by *H. polymorpha* and alkylated during isolation.

Lanes 4: same material as loaded in lane 2 but treated with dithiotreitol to convert the sulphonated Cys-thiol groups to Cys-thiol.

Figure 46:
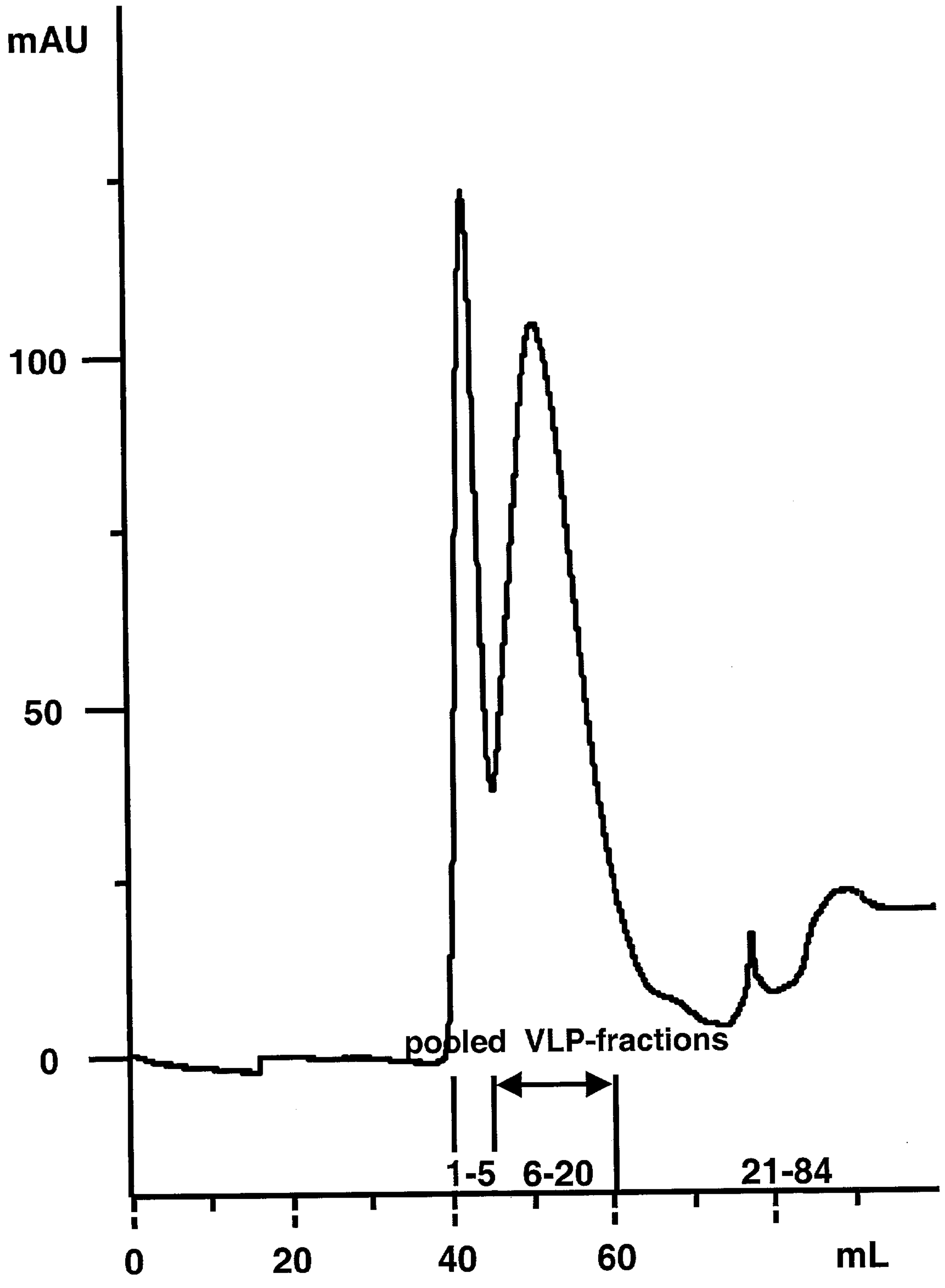

FIG. 46. Size exclusion chromatography (SEC) profile of the purified *H. polymorpha*-expressed E2-H6 in its sulphonated form, submitted to a run in PBS, 3% betain to force virus-like particle formation by exchange of Empigen BB for betain. The pooled fractions containing the VLPs used for further study are indicated by "⇆". The Y-axis indicates absorbance given in mAU (milli absorbance units). The X-axis indicates the elution volume in mL. See also Example 20.

Figure 47:
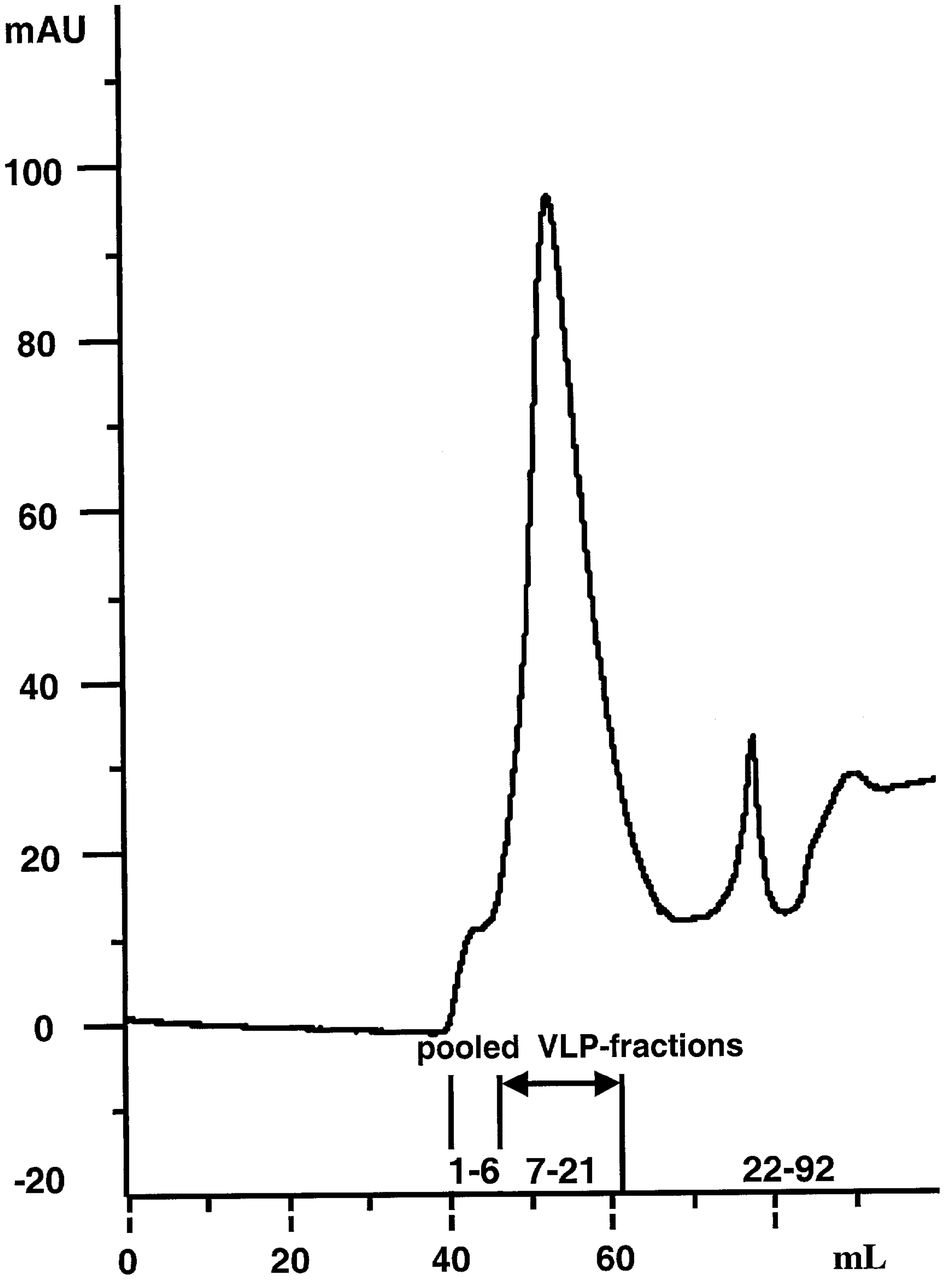

FIG. 47. Size exclusion chromatography (SEC) profile of the purified *H. polymorpha*-expressed E2-H6 in its alkylated form, submitted to a run in PBS, 3% betain to force virus-like particle formation by exchange of Empigen BB for betain. The pooled fractions containing the VLPs are indicated by "⇆". The Y-axis indicates absorbance given in mAU (milli absorbance units). The X-axis indicates the elution volume in mL. See also Example 20.

Figure 48:
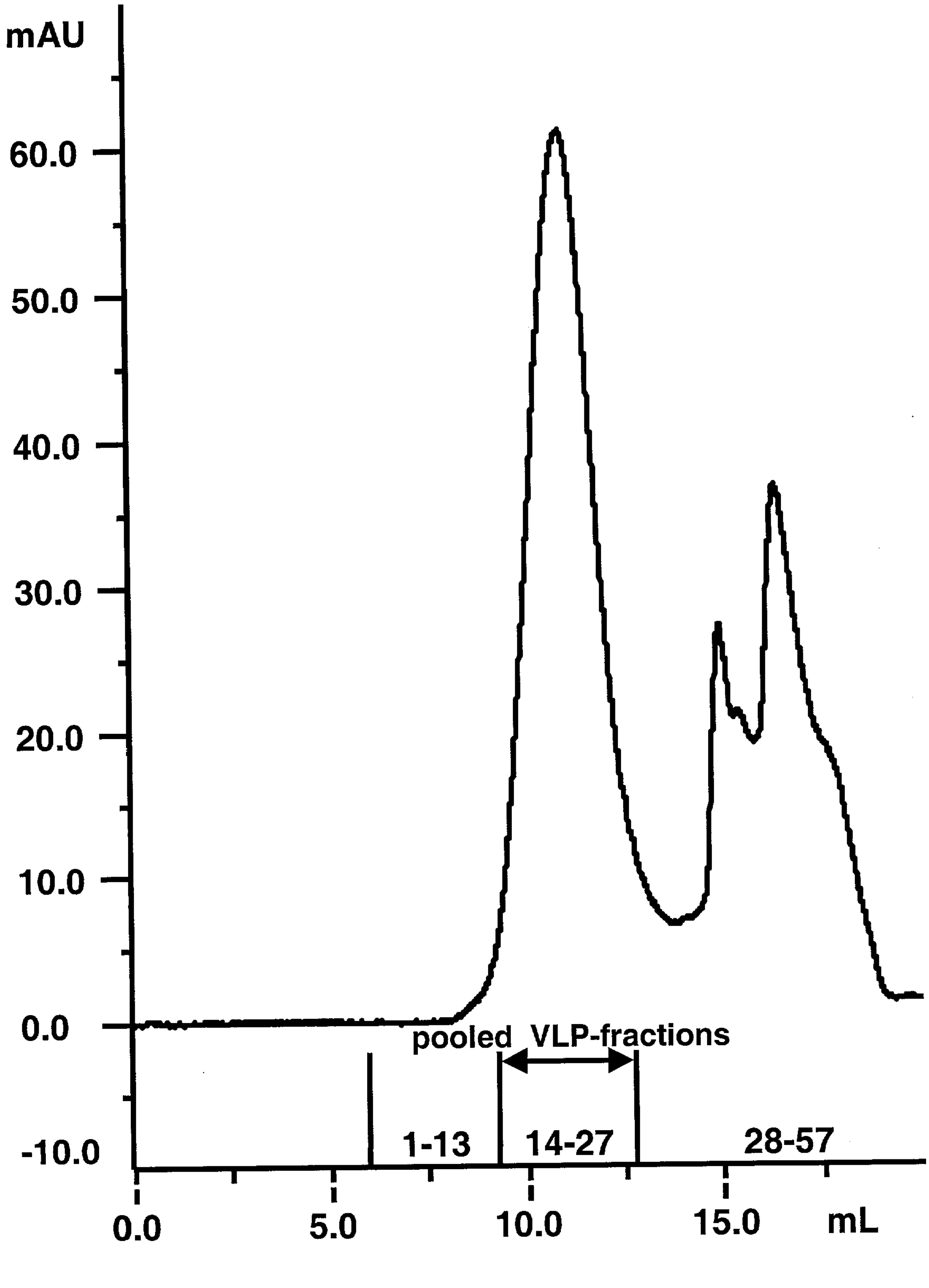

FIG. 48. Size exclusion chromatography (SEC) profile of the purified *H. polymorpha*-expressed E1 in its sulphonated form, submitted to a run in PBS, 3% betain to force virus-like particle formation by exchange of Empigen BB for betain. The pooled fractions containing the VLPs are indicated by "⇆". The Y-axis indicates absorbance given in mAU (milli absorbance units). The X-axis indicates the elution volume in mL. See also Example 20.

Figure 49:
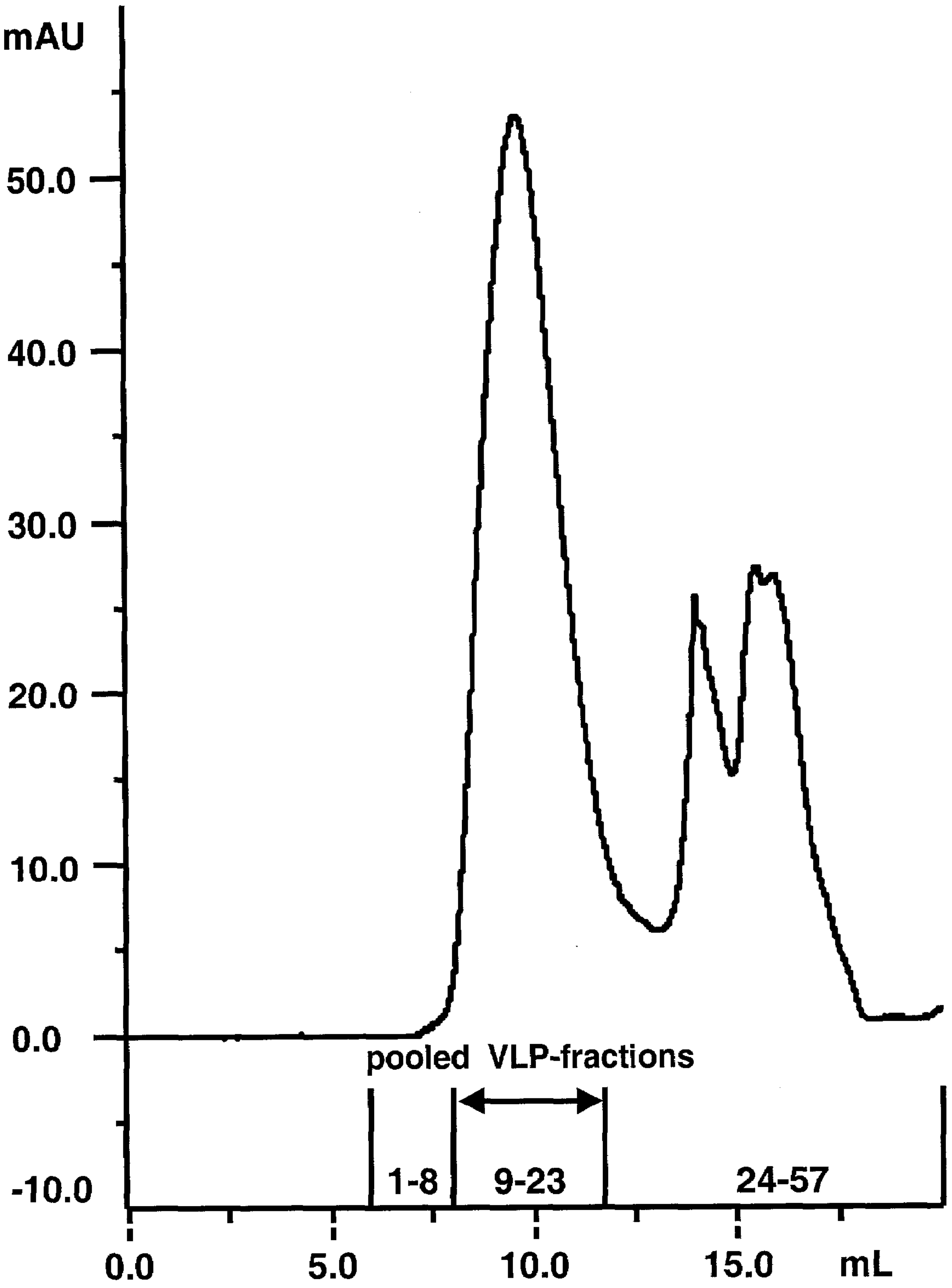

FIG. 49. Size exclusion chromatography (SEC) profile of the purified *H. polymorpha*-expressed E1 in its alkylated form, submitted to a run in PBS, 3% betain to force virus-like particle formation by exchange of Empigen BB for betain. The pooled fractions containing the VLPs are indicated by "⇆". The Y-axis indicates absorbance given in mAU (milli absorbance units). The X-axis indicates the elution volume in mL. See also Example 20.

Figure 50:
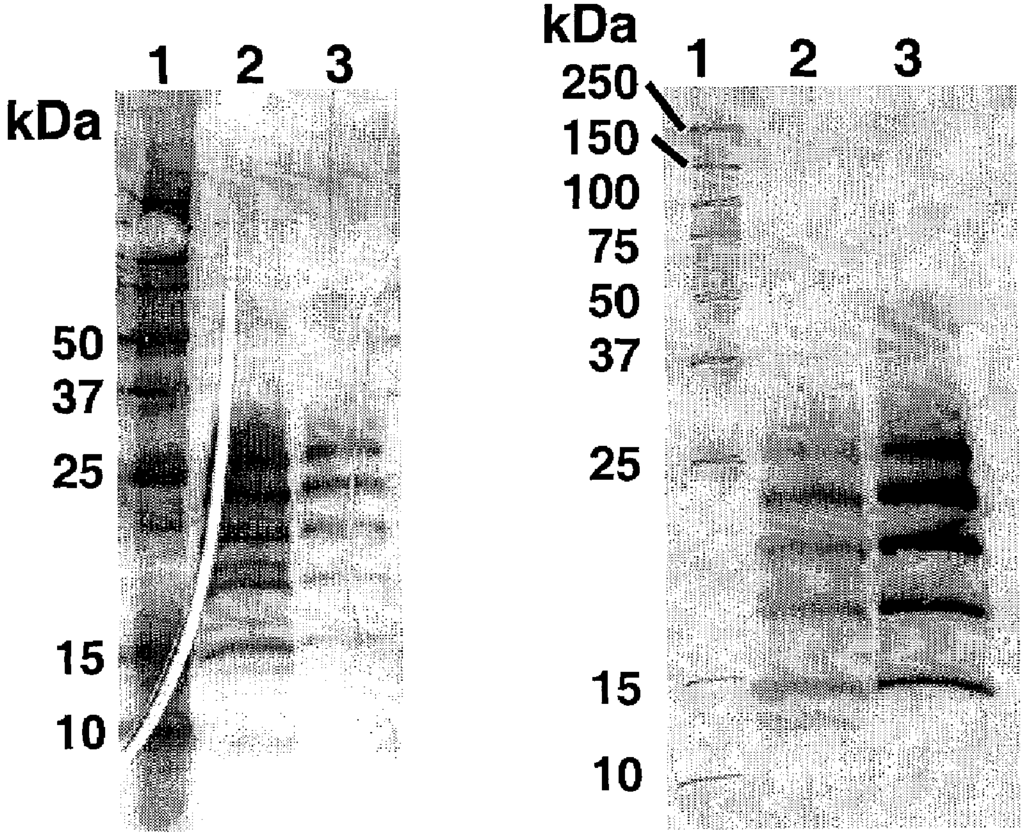

FIG. 50. SDS-PAGE (under reducing conditions) and western blot analysis of VLPs as isolated after size exclusion chromatography (SEC) as described in FIGS. 48 and 49. Left panel: silver-stained SDS-PAGE gel. Right panel: western blot using a specific monoclonal antibody directed against E1 (IGH201). Lanes 1: molecular weight markers (molecular weights indicated at the left); lanes 2: pool of VLPs containing sulphonated E1 (cfr. FIG. 48); lanes 3: pool of VLPs containing alkylated E1 (cfr. FIG. 49). See also Example 20.

Figure 51:
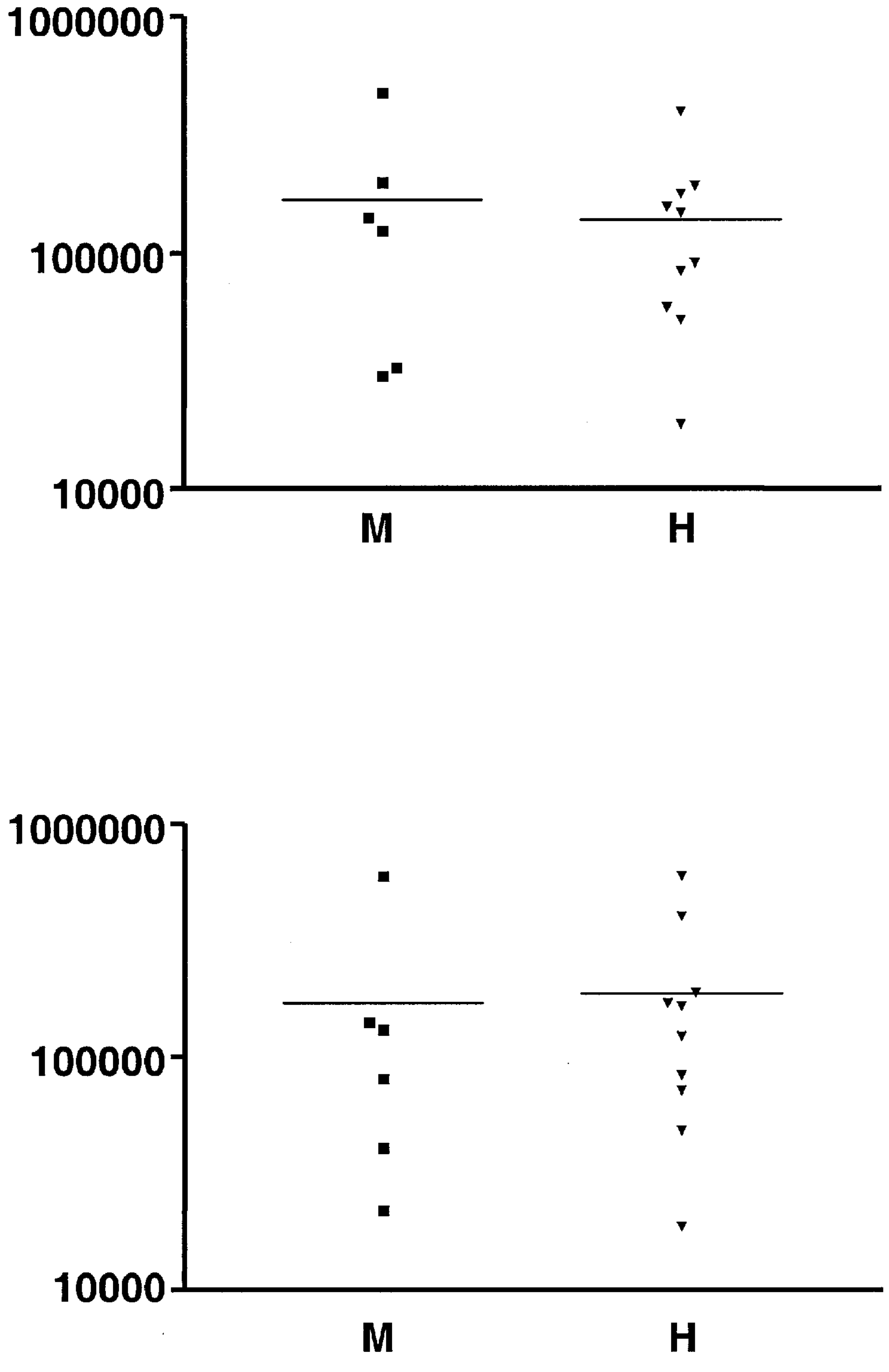

FIG. 51. E1 produced in mammalian cells ("M") or *Hansenula*-produced E1 ("H") were coated on a ELISA solid support to determine the end point titer of antibodies present in sera after vaccination of mice with E1 produced in mammalian cells (top panel), or after vaccination of mice with *Hansenula*-produced E1 (bottom panel). The horizontal bar represents the mean antibody titer. The end-point titers (fold-dilution) are indicated on the Y-axis. See also Example 22.

Figure 52:
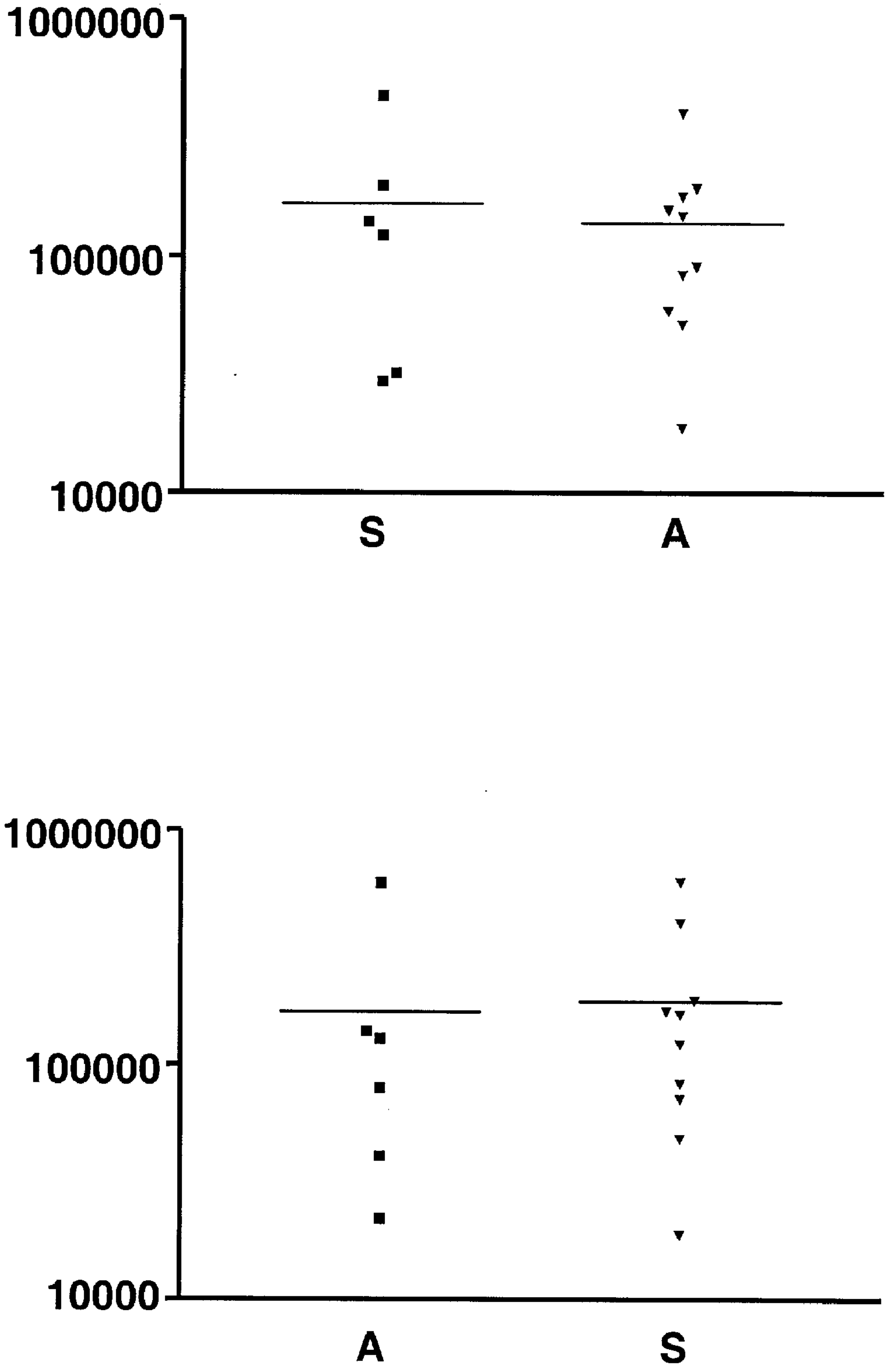

FIG. 52. *Hansenula*-produced E1 was alkylated ("A") or sulphonated ("S") and coated on a ELISA solid support to determine the end point titer of antibodies present in sera after vaccination of mice with *Hansenula*-produced E1 that was alkylated (top panel), or after vaccination of mice with *Hansenula*-produced E1 that was sulphonated (bottom panel). The horizontal bar represents the mean antibody titer. The end-point titers (fold-dilution) are indicated on the Y-axis. See also Example 23.

Figure 53:
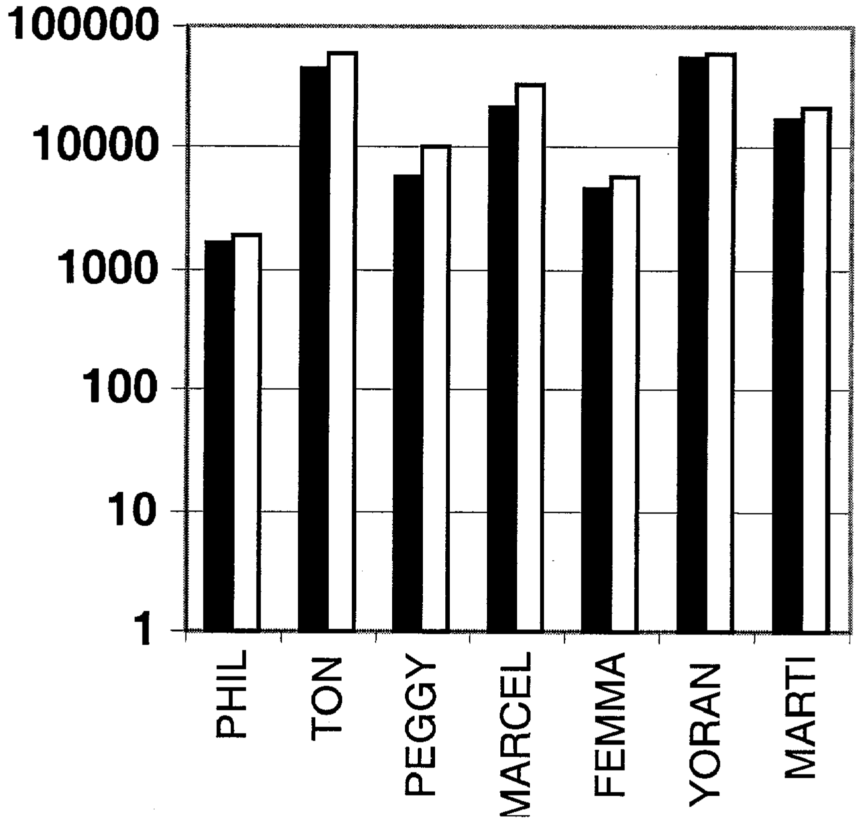
Figure 53:
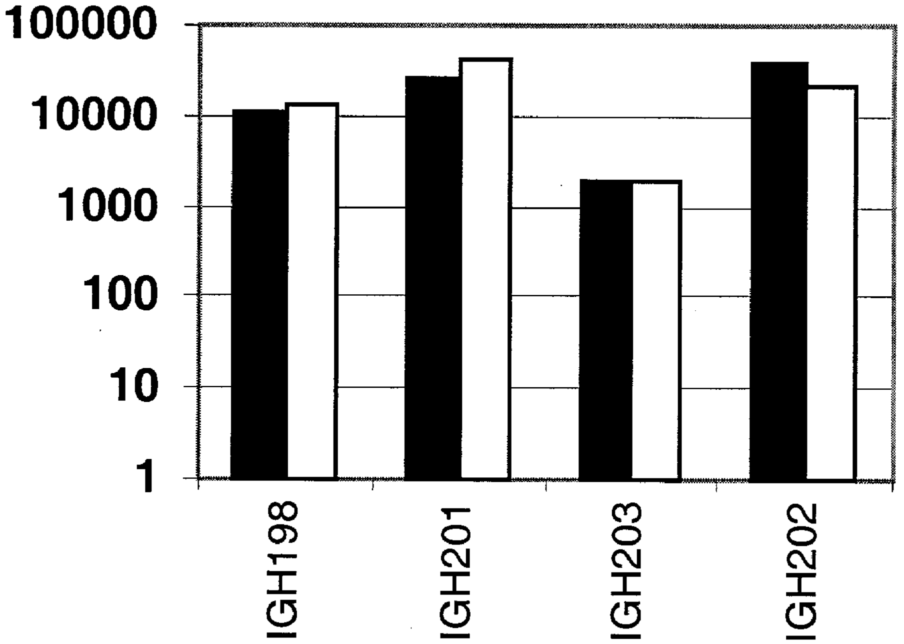

FIG. 53. HCV E1 produced by HCV-recombinant *vaccinia* virus-infected mammalian cells and HCV E1 produced by *H. polymorpha* were coated directly to ELISA plates. End point titers of antibodies were determined in sera of chimpanzees vaccinated with E1 produced by mammalian cells (top panel) and of murine monoclonal antibodies raised against E1 produced by mammalian cells (bottom panel). Chimpanzees Yoran and Marti were prophylactically vaccinated. Chimpanzees Ton, Phil, Marcel, Peggy and Femma were therapeutically vaccinated. Black filled bars: ELISA plate coated with E1 produced by mammalian cells. Open bars: ELISA plate coated with E1 produced by *Hansenula*. The end-point titers (fold-dilution) are indicated on the Y-axis. See also Example 24.

Figure 54:
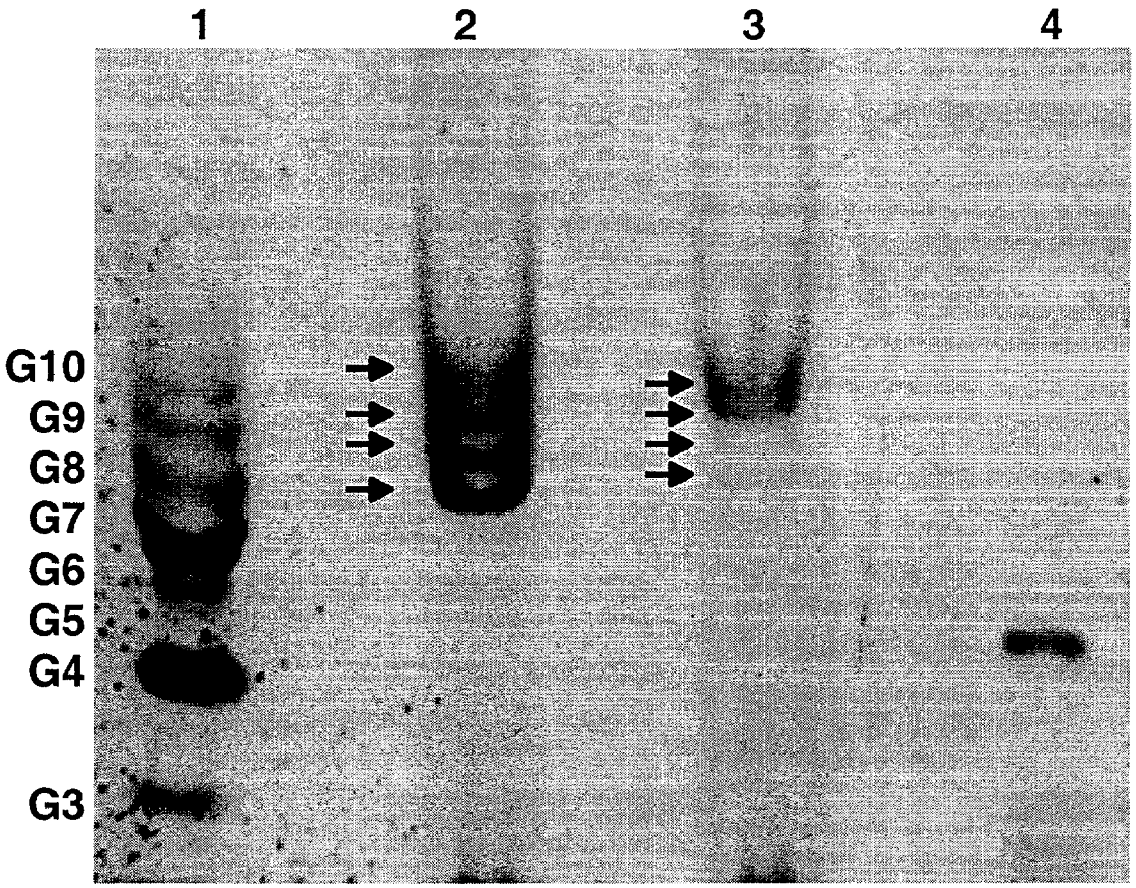

FIG. 54. Fluorophore-assisted carbohydrate gelelectrophoresis of oligosaccharides released from E1 produced by recombinant *vaccinia* virus-infected mammalian cells and from E1-H6 protein produced by *Hansenula*.

Lane 1: Glucose ladder standard with indication at the left of the number of monosaccharides (3 to 10, indicated by G3 to G10).

Lane 2: 25 μg N-linked oligosaccharides released from (alkylated) E1 produced by mammalian cells.

Lane 3: 25 μg N-linked oligosaccharides released from (alkylated) E1-H6 produced by *Hansenula*.

Lane 4: 100 pmoles maltotetraose. See also Example 25.

DETAILED DESCRIPTION OF THE INVENTION

In work leading to the present invention, it was observed that expression of HCV envelope proteins as αMF-HCVENV (α mating factor-HCV envelope protein) pre-proproteins in *Saccharomyces cerevisiae, Pichia pastoris* and *Hansenula polymorpha* was possible but that the extent of removal of the pre-pro- or pre-sequences was unacceptably low and that removal of pre-pro- or pre-sequences is very often not occurring with high fidelity. As a result, many different HCV envelope proteins are produced in these yeasts which do not have a natural amino-terminus (see Example 15). The majority of the HCV envelope proteins expressed in these yeast species were glycosylated (see Examples 6, 10, 13 and 25). More specifically the *S. cerevisiae* (glycosylation deficient mutant)- and *H. polymorpha*-expressed HCV envelope proteins were glycosylated in a manner resembling core-glycosylation. The HCV envelope proteins expressed in *Pichia pastoris* were hyperglycosylated despite earlier reports that proteins expressed in this yeast are normally not hyperglycosylated (Gellissen, G. 2000, Sugrue, R. J. et al. 1997).

Constructs were made for expression of the HCV envelope proteins as pre-pro- or pre-proteins wherein these pre-pro- or pre-sequences were either the *Carcinus maenas* hyperglycemic hormone leader sequence (pre; CHH), the *S. occidentalis* amylase leader sequence (pre; Amyl), the *S. occidentalis* glucoamylase Gam1 leader sequence (pre; Gam1), the fungal phytase leader sequence (pre; Phy5), the *Pichia pastoris* acid phosphatase leader sequence (pre; phol), the yeast aspartic protease 3 signal peptide (pre; YAP3), the mouse salivary amylase signal peptide (pre) and the chicken lysozyme leader sequence (pre; CL). Only for one of these pre-pro-HCVENV or pre-HCVENV proteins, removal of the pre-pro- or pre-sequence with high frequency and high fidelity was observed. This was surprisingly found for the chicken lysozyme leader sequence (CL) and was confirmed both in *S. cerevisiae* and *H. polymorpha* (see Example 16). The CL signal peptide is thus performing very well for expression of glycosylated HCV envelope proteins in eukaryotic cells. This unexpected finding is reflected in the different aspects and embodiments of the present invention as presented below.

A first aspect of the current invention relates to a recombinant nucleic acid comprising a nucleotide sequence encoding a protein comprising an avian lysozyme leader peptide or a functional equivalent thereof joined to an HCV envelope protein or a part thereof.

In one embodiment thereto, the recombinant nucleic acid comprising nucleotide sequence encodes characterized by the structure CL-[$(A1)_a$-$(PS1)_b$ $(A2)_c$]-HCVENV-[$(A3)_d$-$(PS2)_e$-$(A4)_f$]

wherein:

- CL is an avian lysozyme leader peptide or a functional equivalent thereof,
- A1, A2, A3 and A4 are adaptor peptides which can be different or the same,
- PS1 and PS2 are processing sites which can be the different or the same,
- HCVENV is a HCV envelope protein or a part thereof,
- a, b, c, d, e and fare 0 or 1, and
- wherein, optionally, A1 and/or A2 are part of PS1 and/or wherein A3 and/or A4 are part of PS2.

In a further embodiment, the recombinant nucleic acids according to the invention further comprise regulatory elements allowing expression in a eukaryotic host cell of said protein comprising an avian lysozyme leader peptide or a functional equivalent thereof joined to an HCV envelope protein or a part thereof, or of said protein characterized by the structure CL-[$(A1)_a$-$(PS1)_b$-$(A2)_c$]-HCVENV-[$(A3)_d$-$(PS2)_e$-$(A4)_f$].

The terms "polynucleotide", "polynucleic acid", "nucleic acid sequence", "nucleotide sequence", "nucleic acid molecule", "oligonucleotide", "probe" or "primer", when used herein refer to nucleotides, either ribonucleotides, deoxyribonucleotides, peptide nucleotides or locked nucleotides, or a combination thereof, in a polymeric form of any length or any shape (e.g. branched DNA). Said terms furthermore include double-stranded (ds) and single-stranded (ss) polynucleotides as well as triple-stranded polynucleotides. Said terms also include known nucleotide modifications such as methylation, cyclization and 'caps' and substitution of one or more of the naturally occurring nucleotides with an analog such as inosine or with non-amplifiable monomers such as HEG (hexethylene glycol). Ribonucleotides are denoted as NTPs, deoxyribonucleotides as dNTPs and dideoxyribonucleotides as ddNTPs.

Nucleotides can generally be labeled radioactively, chemiluminescently, fluorescently, phosphorescently or with infrared dyes or with a surface-enhanced Raman label or plasmon resonant particle (PRP).

Said terms "polynucleotide", "polynucleic acid", "nucleic acid sequence", "nucleotide sequence", "nucleic acid molecule", "oligonucleotide", "probe" or "primer" also encompass peptide nucleic acids (PNAs), a DNA analogue in which the backbone is a pseudopeptide consisting of N-(2-aminoethyl)-glycine units rather than a sugar. PNAs mimic the behavior of DNA and bind complementary nucleic acid strands. The neutral backbone of PNA results in stronger binding and greater specificity than normally achieved. In addition, the unique chemical, physical and biological properties of PNA have been exploited to produce powerful biomolecular tools, antisense and antigene agents, molecular probes and biosensors. PNA probes can generally be shorter than DNA probes and are generally from 6 to 20 bases in length and more optimally from 12 to 18 bases in length (Nielsen, P. E. 2001). Said terms further encompass locked nucleic acids (LNAs) which are RNA derivatives in which the ribose ring is constrained by a methylene linkage between the 2'-oxygen and the 4'-carbon. LNAs display unprecedented binding affinity towards DNA or RNA target sequences. LNA nucleotides can be oligomerized and can be incorporated in chimeric or mix-meric LNA/DNA or LNA/RNA molecules. LNAs seem to be nontoxic for cultured cells (Orum, H. and Wengel, J. 2001, Wahlestedt, C. et al. 2000). In general, chimeras or mix-mers of any of DNA, RNA, PNA and LNA are considered as well as any of these wherein thymine is replaced by uracil.

The term "protein" refers to a polymer of amino acids and does not refer to a specific length of the product; thus, peptides, oligopeptides, and polypeptides are included within the definition of protein. This term also does not refer to or exclude post-expression modifications of the protein, for example, glycosylations, acetylations, phosphorylations and the like. Included within the definition are, for example, polypeptides containing one or more analogues of an amino acid (including, for example, unnatural amino acids, PNA, etc.), polypeptides with substituted linkages, as well as other modifications known in the art, both naturally occurring and non-naturally occurring.

With "pre-pro-protein" or "pre-protein" is, when used herein, meant a protein comprising a pre-pro-sequence joined to a protein of interest or a protein comprising a pro-sequence joined to a protein of interest, respectively. As alternatives for "pre-sequence", the terms "signal sequence", "signal peptide", "leader peptide", or "leader sequence" are used; all refer to an amino acid sequence that targets a pre-protein to the rough endoplasmic reticulum (ER) which is a prerequisite for (N-)glycosylation. The "signal sequence", "signal peptide", "leader peptide", or "leader sequence" is cleaved off, i.e. "removed" from the protein comprising the signal sequence joined to a protein of interest, at the on the luminal side of this ER by host specific proteases referred to as signal peptidases. Likewise, a pre-pro-protein is converted to a pro-protein upon translocation to the lumen of the ER. Depending on the nature of the "pro" amino acid sequence, it can or can not be removed by the host cell expressing the pre-pro-protein. A well known pre-pro-amino acid sequence is the α mating factor pre-pro-sequence of the *S. cerevisiae* α mating factor.

With "recombinant nucleic acid" is intended a nucleic acid of natural or synthetic origin which has been subjected to at least one recombinant DNA technical manipulation such as restriction enzyme digestion, PCR, ligation, dephosphorylation, phosphorylation, mutagenesis, adaptation of codons for expression in a heterologous cell etc. In general, a recombinant nucleic acid is a fragment of a naturally occurring nucleic acid or comprises at least two nucleic acid fragments not naturally associated or is a fully synthetic nucleic acid.

With "an avian leader peptide or a functional equivalent thereof joined to a HCV envelope protein or a part thereof" is meant that the C-terminal amino acid of said leader peptide is covalently linked via a peptide bond to the N-terminal amino acid of said HCV envelope protein or part thereof. Alternatively, the C-terminal amino acid of said leader peptide is separated from the N-terminal amino acid of said HCV envelope protein or part thereof by a peptide or protein. Said peptide or protein may have the structure $-[(A1)_a-(PS1)_b-(A2)_c]$ as defined above.

The derivation of the HCV envelope protein of interest from the protein comprising an avian lysozyme leader peptide or a functional equivalent thereof joined to an HCV envelope protein or a part thereof or of the protein characterized by the structure $CL-[(A1)_a-(PS1)_b-(A2)_c]-HCVENV-[(A3)_d-(PS2)_e-(A4)_f]$ can be performed in vivo by the proteolytic machinery of the cells in which the pre-protein protein is expressed. More specifically, the step consisting of removal of the avian leader peptide is preferably performed in vivo by the proteolytic machinery of the cells in which the pre-protein is expressed. Derivation may, however, also be performed solely in vitro after and/or during isolation and/or purification of the pre-protein and/or protein from the cells expressing the pre-protein and/or from the culture fluid in which the cells expressing the pre-protein are grown. Alternatively, said in vivo derivation is performed in combination with said in vitro derivation. Derivation of the HCV protein of interest from a recombinantly expressed pre-protein can further comprise the use of (an) proteolytic enzyme(s) in a polishing step wherein all or most of the contaminating proteins co-present with the protein of interest are degraded and wherein the protein of interest is resistant to the polishing proteolytic enzyme(s). Derivation and polishing are not mutually exclusive processes and may be obtained by using the same single proteolytic enzyme. As an example is given here the HCV E1s protein of HCV genotype 1b (SEQ ID NO:2) which is devoid of Lys-residues. By digesting of a protein extract containing said HCV E1 proteins with the Endoproteinase Lys-C (endo-lys C), the E1 proteins will not be degraded whereas contaminating proteins containing one or more Lys-residues are degraded. Such a process may significantly simplify or enhance isolation and/or purification of the HCV E1 proteins. Furthermore, by including in a pre-protein an additional Lys-residue, e.g. between a leader peptide and a HCV E1 protein, the additional advantageous possibility of correct in vitro separation of the leader peptide from the HCV E1 pre-protein is obtainable. Other HCV E1 proteins may comprise a Lys-residue at either one or more of the positions 4, 40, 42, 44, 61, 65 or 179 (wherein position 1 is the first, N-termninal natural amino acid of the E1 protein, i.e. position 192 in the HCV polyprotein). In order to enable the use of endo-lys C as described above, said Lys-residues may be mutated into another amino acid residue, preferably into an Arg-residue.

With a "correctly removed" leader peptide is meant that said leader peptide is removed from the protein comprising the signal sequence joined to a protein of interest with high efficiency, i.e. a large number of pre-(pro-)proteins is converted to pro-proteins or proteins, and with high fidelity, i.e. only the pre-amino acid sequence is removed and not any amino acids of the protein of interest joined to said pre-amino acid sequence. With "removal of a leader peptide with high efficiency" is meant that at least about 40%, but more preferentially about 50%, 55%, 60%, 65%, 70%, 75%, 80%, 85%, 90%, 95%, 96%, 97%, 98% or even 99% of the pre-proteins is converted to the protein from which the pre-sequence is removed. Alternatively, if a substantial part of the expressed pre-proteins is not converted to the protein from which the pre-sequence is removed, these pre-proteins may still be purified.

With "functional equivalent of the avian lysozyme (CL) leader peptide" is meant a CL leader peptide wherein one or more amino acids have been substituted for another amino acid and whereby said substitution is a conservative amino acid substitution. With "conservative amino acid substitution" is meant a substitution of an amino acid belonging to a group of conserved amino acids with another amino acid belonging to the same group of conserved amino acids. As groups of conserved amino acids are considered: the group consisting of Met, Ile, Leu and Val; the group consisting of Arg, Lys and His; the group consisting of Phe, Trp and Tyr; the group consisting of Asp and Glu; the group consisting of Asn and Gln; the group consisting of Cys, Ser and Thr; and the group consisting of Ala and Gly. An exemplary conservative amino acid substitution in the CL leader peptide is the naturally variation at position 6, the amino acid at this position being either Val or Ile; another variation occurs at position 17, the amino acid at this position being, amongst others, Leu or Pro (see SEQ ID NO:1). The resulting CL leader peptides are thus to be considered as functional equivalents. Other functional equivalents of the CL leader peptides include those leader peptides reproducing the same technical aspects as the CL leader peptides as described throughout the current invention, including deletion variants and insertion variants.

With "A" or "adaptor peptide" is meant a peptide (e.g. 1 to 30 amino acids) or a protein which may serve as a linker between e.g. a leader peptide and a processing site (PS), a leader peptide and a protein of interest, a PS and a protein of interest, and/or a protein of interest and a PS; and/or may serve as a linker N- or C-terminal of e.g. a leader peptide, a PS or a protein of interest. The adaptor peptide "A" may have a certain three-dimensional structure, e.g. an α-helical or β-sheet structure or a combination thereof. Alternatively the three-dimensional structure of A is not well defined, e.g. a coiled-coil structure. The adaptor A may be part of e.g. a pre-sequence, a pro-sequence, a protein of interest sequence or a processing site. The adaptor A may serve as a tag enhancing or enabling detection and/or purification and/or processing of the protein of which A is a part. One examples of an A peptide is the his-tag peptide (HHHHHH; SEQ ID NO:63) $H_n$ wherein n usually is six, but may be 7, 8, 9, 10, 11, or 12. Other examples of A-peptides include the peptides EEGEPK (Kjeldsen et al. in WO98/28429; SEQ ID NO:64) or EEAEPK (Kjeldsen et al. in WO97/22706; SEQ ID NO:65) which, when present at the N-terminal of the a protein of interest, were reported to increase fermentation yield but also to protect the N-terminus of the protein of interest against processing by dipeptidyl aminopeptidase and thus resulting in a homogenous N-terminus of the polypeptide. At the same time, in vitro maturation of the protein of interest, i.e. removal of said peptides EEGEPK (SEQ ID NO:64) and EEAEPK (SEQ ID NO:65) from the protein of interest can be achieved by using e.g. endo-lys C which cleaves C-terminal of the Lys-residue in said peptides. Said peptides thus serve the function of adaptor peptide (A) as well as processing site (PS), (see below). Adaptor peptides are given in SEQ ID NOs:63-65, 70-72 and 74-82. Another example of an adaptor peptide is the G4S immunosilent linker. Other examples of adaptor peptides or adaptor proteins are listed in Table 2 of Stevens (Stevens et al. 2000).

With "PS" or "processing site" is meant a specific protein processing or processable site. Said processing may occur enzymatically or chemically. Examples of processing sites prone to specific enzymatic processing include IEGR↓X (SEQ ID NO:66), IDGR↓X (SEQ ID NO:67), AEGR↓X (SEQ ID NO:68), all recognized by and cleaved between the Arg and Xaa (any amino acid) residues as indicated by the "↓" by the bovine factor Xa protease (Nagai, K. and Thogersen, H. C. 1984). Another example of a PS site is a dibasic site, e.g. Arg-Arg, Lys-Lys, Arg-Lys or Lys-Arg, which is cleavable by the yeast Kex2 protease (Julius, D. et al. 1984). The PS site may also be a monobasic Lys-site. Said monobasic Lys-PS-site may also be included at the C-terminus of an A peptide. Examples of A adaptor peptides comprising a C-terminal monobasic Lys-PS-site are given by SEQ ID NOs:64-65 and 74-76. Exoproteolytic removal of a His-tag (HHHHHH; SEQ ID NO:63) is possible by using the dipeptidyl aminopeptidase I (DAPase) alone or in combination with glutamine cyclotransferase (Qcyclase) and pyroglutamic aminopeptidase (pGAPase) (Pedersen, J. et al. 1999). Said exopeptidases comprising a recombinant His-tag (allowing removal of the peptidase from the reaction mixture by immobilize metal-affinity chromatography, IMAC) are commercially available, e.g. as the TAGZyme System of Unizyme Laboratories (Hørsholm, DK). With "processing" is thus generally meant any method or procedure whereby a protein is specifically cleaved or cleavable at at least one processing site when said processing site is present in said protein. A PS may be prone to endoproteolytic cleavage or may be prone to exproteolytic cleavage, in any case the cleavage is specific, i.e. does not extend to sites other than the sites recognized by the processing proteolytic enzyme. A number of PS sites are given in SEQ ID NOs:66-68 and 83-84.

The versatility of the $[(A1/3)_{a/d}\text{-}(PS1/2)_{b/e}\text{-}(A2/4)_{c/f}]$ structure as outlined above demonstrated by means of some examples. In a first example, said structure is present at the C-terminal end of a protein of interest comprised in a pre-protein and wherein A3 is the "VIEGR" peptide (SEQ ID NO:69) which is overlapping with the factor Xa "IEGRX" PS site (SEQ ID NO:66) and wherein X=A4 is the histidine-tag (SEQ ID NO:63) (d, e and f thus are all 1 in this case). The HCV protein of interest can (optionally) be purified by IMAC. After processing with factor Xa, the (optionally purified) HCV protein of interest will carry at its C-terminus a processed PS site which is "IEGR" (SEQ ID NO:70). Variant processed factor Xa processing site, can be IDGR (SEQ ID NO:71) or AEGR (SEQ ID NO:72). In a further example, the $[(A1/3)_{a/d}\text{-}(PS1/2)_{b/e}\text{-}(A2/4)_{c/f}]$ structure is present at the N-terminus of the HCV protein of interest. Furthermore, A1 is the histidine-tag (SEQ ID NO:63), PS is the factor Xa recognition site (any of SEQ ID NOs:66-68) wherein X is the protein of interest, and wherein a=b=1 and c=0. Upon correct removal of a leader peptide, e.g. by the host cell, the resulting HCV protein of interest can be purified by IMAC (optional). After processing with factor Xa, the protein of interest will be devoid of the $[(A1)_a\text{-}(PS1)_b\text{-}(A2)_c]$ structure.

It will furthermore be clear that any of A1, A2, A3, A4, PS1 and PS2, when present, may be present in a repeat structure. Such a repeat structure, when present, is in this context still counted as 1, i.e. a, b, c, d, e, or f are 1 even if e.g. A1 is occurring as e.g. 2 repeats (A1-A1).

With "HCV envelope protein" is meant a HCV E1 or HCV E2 envelope protein or a part thereof whereby said proteins may be derived from a HCV strain of any genotype. More specifically, HCVENV is chosen from the group of amino acid sequences consisting of SEQ ID NOs:85 to 98, amino acid sequences which are at least 90% identical to SEQ ID NOs:85 to 98, and fragments of any thereof. As "identical" amino acids are considered the groups of conserved amino acids as described above, i.e. the group consisting of Met, Ile, Leu and Val; the group consisting of Arg, Lys and His; the group consisting of Phe, Trp and Tyr; the group consisting of Asp and Glu; the group consisting of Asn and Gln; the group consisting of Cys, Ser and Thr; and the group consisting of Ala and Gly.

More specifically, the term "HCV envelope proteins" relates to a polypeptide or an analogue thereof (e.g. mimotopes) comprising an amino acid sequence (and/or amino acid analogues) defining at least one HCV epitope of either the E1 or the E2 region, in addition to a glycosylation site. These envelope proteins may be both monomeric, hetero-oligomeric or homo-oligomeric forms of recombinantly expressed envelope proteins. Typically, the sequences defining the epitope correspond to the amino acid sequences of either the E1 or the E2 region of HCV (either identically or via substitutions of analogues of the native amino acid residue that do not destroy the epitope).

It will be understood that the HCV epitope may co-locate with the glycosylation site. In general, the epitope-defining sequence will be 3 or 4 amino acids in length, more typically, 5, 6, or 7 amino acids in length, more typically 8 or 9 amino acids in length, and even more typically 10 or more amino acids in length. With respect to conformational epitopes, the length of the epitope-defining sequence can be subject to wide variations, since it is believed that these epitopes are formed by the three-dimensional shape of the antigen (e.g. folding). Thus, the amino acids defining the epitope can be relatively few in number, but widely dispersed along the length of the molecule being brought into the correct epitope conformation via folding. The portions of the antigen between the residues defining the epitope may not be critical to the conformational structure of the epitope. For example, deletion or substitution of these intervening sequences may not affect the conformational epitope provided sequences critical to epitope conformation are maintained (e.g. cysteines involved in disulfide bonding, glycosylation sites, etc.). A conformational epitope may also be formed by 2 or more essential regions of subunits of a homo-oligomer or hetero-oligomer.

As used herein, an epitope of a designated polypeptide denotes epitopes with the same amino acid sequence as the epitope in the designated polypeptide, and immunologic equivalents thereof. Such equivalents also include strain, subtype (=genotype), or type(group)-specific variants, e.g. of the currently known sequences or strains belonging to genotypes 1a, 1b, 1c, 1d, 1e, 1f, 2a, 2b, 2c, 2d, 2e, 2f, 2g, 2h, 2i, 3a, 3b, 3c, 3d, 3e, 3f, 3g, 4a, 4b, 4c, 4d, 4e, 4f, 4g, 4h, 4i, 4j, 4k, 4l, 5a, 5b, 6a, 6b, 6c, 7a, 7b, 7c, 8a, 8b, 9a, 9b, 10a, 11 (and subtypes thereof), 12 (and subtypes thereof) or 13 (and subtypes thereof) or any other newly defined HCV (sub)type. It is to be understood that the amino acids constituting the epitope need not be part of a linear sequence, but may be interspersed by any number of amino acids, thus forming a conformational epitope.

The HCV antigens of the present invention comprise conformational epitopes from the E1 and/or E2 (envelope) domains of HCV. The E1 domain, which is believed to correspond to the viral envelope protein, is currently estimated to span amino acids 192-383 of the HCV polyprotein (Hijikata, M. et al. 1991). Upon expression in a mammalian system (glycosylated), it is believed to have an approximate molecular weight of 35 kDa as determined via SDS-PAGE. The E2 protein, previously called NS1, is believed to span amino acids 384-809 or 384-746 (Grakoui, A. et al. 1993) of the HCV polyprotein and also to be an envelope protein. Upon expression in a *vaccinia* system (glycosylated), it is believed to have an apparent gel molecular weight of about 72 kDa. It is understood that these protein endpoints are approximations (e.g. the carboxy terminal end of E2 could lie somewhere in the 730-820 amino acid region, e.g. ending at amino acid 730, 735, 740, 742, 744, 745, preferably 746, 747, 748, 750, 760, 770, 780, 790, 800, 809, 810, 820). The E2 protein may also be expressed together with E1, and/or core (aa 1-191), and/or P7 (aa 747-809), and/or NS2 (aa 810-1026), and/or NS3 (aa 1027-1657), and/or NS4A (aa 1658-1711) and/or NS4B (aa 1712-1972) and/or NS5A (aa 1973-2420), and/or NS5B (aa 2421-3011), and/or any part of any of these HCV proteins different from E2. Likewise, the E1 protein may also be expressed together with the E2, and/or core (aa 1-191), and/or P7 (aa 747-809), and/or NS2 (aa 810-1026), and/or NS3 (aa 1027-1657), and/or NS4A (aa 1658-1711) and/or NS4B (aa 1712-1972), and/or NS5A (aa 1973-2420), and/or NS5B (aa 2421-3011), and/or any part of any of these HCV proteins different from E1. Expression together with these other HCV proteins may be important for obtaining the correct protein folding.

The term "E1" as used herein also includes analogs and truncated forms that are immunologically cross-reactive with natural E1, and includes E1 proteins of genotypes 1, 2, 3, 4, 5, 6, 7, 8, 9, 10, 11, 12 or 13 or any other newly identified HCV type or subtype. The term 'E2' as used herein also includes analogs and truncated forms that are immunologically cross-reactive with natural E2, and includes E2 proteins of genotypes 1, 2, 3, 4, 5, 6, 7, 8, 9, 10, 11, 12 or 13 or any other newly identified HCV type or subtype. For example, insertions of multiple codons between codon 383 and 384, as well as deletions of amino acids 384-387 have been reported (Kato, N. et al. 1992). It is thus also understood that the isolates used in the examples section of the present invention were not intended to limit the scope of the invention and that any HCV isolate from type 1, 2, 3, 4, 5, 6, 7, 8, 9, 10, 11, 12 or 13 or any other new genotype of HCV is a suitable source of E1 and/or E2 sequence for the practice of the present invention. Similarly, as described above, the HCV proteins that are co-expressed with the HCV envelope proteins of the present invention, can be derived from any HCV type, thus also from the same type as the HCV envelope proteins of the present invention.

"E1/E2" as used herein refers to an oligomeric form of envelope proteins containing at least one E1 component and at least one E2 component.

The term "specific oligomeric" E1 and/or E2 and/or E1/E2 envelope proteins refers to all possible oligomeric forms of recombinantly expressed E1 and/or E2 envelope proteins which are not aggregates. E1 and/or E2 specific oligomeric envelope proteins are also referred to as homo-oligomeric E1 or E2 envelope proteins (see below). The term 'single or specific oligomeric' E1 and/or E2 and/or E1/E2 envelope proteins refers to single monomeric E1 or E2 proteins (single in the strict sense of the word) as well as specific oligomeric E1 and/or E2 and/or E1/E2 recombinantly expressed proteins. These single or specific oligomeric envelope proteins according to the present invention can be further defined by the following formula $(E1)_x(E2)_y$ wherein x can be a number between 0 and 100, and y can be a number between 0 and 100, provided that x and y are not both 0. With x=1 and y=0 said envelope proteins include monomeric E1.

The term "homo-oligomer" as used herein refers to a complex of E1 or E2 containing more than one E1 or E2 monomer, e.g. E1/E1 dimers, E1/E1/E1 trimers or E1/E1/E1/E1 tetramers and E2/E2 dimers, E2/E2/E2 trimers or E2/E2/E2/E2 tetramers, E1 pentamers and hexamers, E2 pentamers and hexamers or any higher-order homo-oligomers of E1 or E2 are all 'homo-oligomers' within the scope of this definition. The oligomers may contain one, two, or several different monomers of E1 or E2 obtained from different types or subtypes of hepatitis C virus including for example those described by Maertens et al. in WO 94/25601 and WO 96/13590 both by the present applicants. Such mixed oligomers are still homo-oligomers within the scope of this invention, and may allow more universal diagnosis, prophylaxis or treatment of HCV.

The E1 and E2 antigens used in the present invention may be full-length viral proteins, substantially full-length versions thereof, or functional fragments thereof (e.g. fragments comprising at least one epitope and/or glycosylation site). Furthermore, the HCV antigens of the present invention can also include other sequences that do not block or prevent the formation of the conformational epitope of interest. The presence or absence of a conformational epitope can be readily determined through screening the antigen of interest with an antibody (polyclonal serum or monoclonal to the conformational epitope) and comparing its reactivity to that of a denatured version of the antigen which retains only linear epitopes (if any). In such screening using polyclonal antibodies, it may be advantageous to adsorb the polyclonal serum first with the denatured antigen and see if it retains antibodies to the antigen of interest.

The HCV proteins of the present invention may be glycosylated. Glycosylated proteins intend proteins that contain one or more carbohydrate groups, in particular sugar groups. In general, all eukaryotic cells are able to glycosylate proteins. After alignment of the different envelope protein sequences of HCV genotypes, it may be inferred that not all 6 glycosylation sites on the HCV E1 protein are required for proper folding and reactivity. For instance, HCV subtype 1b E1 protein contains 6 glycosylation sites, but some of these glycosylation sites are absent in certain other (sub)types. The fourth carbohydrate motif (on Asn250), present in types 1b, 6a, 7, 8, and 9, is absent in all other types know today. This sugar-addition motif may be mutated to yield a type 1b E1 protein with improved reactivity. Also, the type 2b sequences show an extra glycosylation site in the V5 region (on Asn299). The isolate S83, belonging to genotype 2c, even lacks the first carbohydrate motif in the VI region (on Asn), while it is present on all other isolates (Stuyver, L. et al. 1994). However, even among the completely conserved sugar-addition motifs, the presence of the carbohydrate may not be required for folding, but may have a role in evasion of immune surveillance. Thus, the identification of the role of glycosylation can be further tested by mutagenesis of the glycosylation motifs. Mutagenesis of a glycosylation motif (NXS or NXT sequences) can be achieved by either mutating the codons for N, S, or T, in such a way that these codons encode amino acids different from N in the case of N, and/or amino acids different from S or T in the case of S and in the case of T. Alternatively, the X position may be mutated into P, since it is known that NPS or NPT are not frequently modified with carbohydrates. After establishing which carbohydrate-addition motifs are required for folding and/or reactivity and which are not, combinations of such mutations may be made. Such experiments have been described extensively by Maertens et al. in WO 96/04385 (Example 8), which is included herein specifically by reference. The term glycosylation as used in the present invention refers to N-glycsoylation unless otherwise specified.

In particular, the present invention relates to HCV envelope proteins, or parts thereof that are core-glycosylated. In this respect, the term "core-glycosylation" refers to a structure "similar" to the structure as depicted in the boxed structure in FIG. 3 of Herscovics and Orlean (Herscovics, A. and Orlean, P. 1993). Thus, the carbohydrate structure referred to contains 10 or 11 mono-saccharides. Notably, said disclosure is herein incorporated by reference. The term "similar" intends that not more than about 4 additional mono-saccharides have been added to the structure or that not more than about 3 mono-saccharides have been removed from the structure. Consequently, a carbohydrate structure consists most preferentially of 10 mono-saccharides, but minimally of 7, and more preferentially of 8 or 9 mono-saccchariden, and maximally of 15 mono-saccharides, and more preferentially of 14, 13, 12, or 11 mono-saccharides. The mono-saccharides connoted are preferentially glucose, mannose or N-acetyl glucosamine.

Another aspect of the present invention covers vectors comprising a polynucleic acid, or a part thereof, of the invention. Such vectors comprise universal cloning vectors such as the pUC-series or pEMBL-series vectors and furthermore include other cloning vectors such as cloning vectors requiring a DNA topoisomerase reaction for cloning, TA-cloning vectors and recombination-based cloning vectors such as those used in the Gateway system (InVitrogen). Vectors comprise plasmids, phagemids, cosmids, bacmids (baculovirus vectors) or may be viral or retroviral vectors. A vector can merely function as a cloning tool and/or -vehicle or may additionally comprise regulatory sequences such as promoters, enhancers and terminators or polyadenylation signals. Said regulatory sequences may enable expression of the information contained within the DNA fragment of interest cloned into a vector comprising said regulatory sequences. Expression may be the production of RNA molecules or mRNA molecules and, optionally, the production of protein molecules thereof. Expression may be the production of an RNA molecule by means of a viral polymerase promoter (e.g. SP6, T7 or T3 promoter) introduced to the 5'- or 3'- end of the DNA of interest. Expression may furthermore be transient expression or stable expression or, alternatively, controllable expression. Controllable expression comprises inducible expression, e.g. using a tetracyclin-regulatable promoter, a stress-inducible (e.g. human hsp70 gene promoter), a methallothionine promoter, a glucocorticoid promoter or a progesterone promoter. Expression vectors are known in the art that mediate expression in bacteria (e.g. *Escherichia coli, Streptomyces* species), insect cells (*Spodoptera frugiperda* cells, Sf9 cells), plant cells (e.g. potato virus X-based expression vectors, see e.g. Vance et al. 1998 in WO98/44097) and mammalian cells (e.g. CHO or COS cells, Vero cells, cells from the HeLa cell line).

This aspect of the invention thus specifically relates to a vector comprising the recombinant nucleic acids according to the invention encoding a protein comprising an avian lysozyme leader peptide or a functional equivalent thereof joined to an HCV envelope protein or a part thereof, or a protein characterized by the structure CL-$[(A1)_a$-$(PS1)_b$-$(A2)_c]$-HCVENV-$[(A3)_d$-$(PS2)_e$-$(A4)_f]$.

Embodied in the present invention are also said vectors further comprising regulatory sequences allowing expression of said protein.

In a specific embodiment, said vector according to the invention is an expression vector.

In another specific embodiment, said vector according to the invention is an autonomously replicating vector or an integrative vector.

In yet another specific embodiment, said vector according to the invention is chosen from any of SEQ ID NOs: 20, 21, 32, 35, 36, 39, 40.

Suitable vectors or expression vectors of the invention are yeast vectors. A yeast vector may comprise a DNA sequence enabling the vector to replicate autonomously. Examples of such sequences are the yeast plasmid 2μ replication genes REP 1-3 and origin of replication. Other vectors are integrating partially or completely in the yeast genome. Such integrative vectors are either targeted to specific genomic loci or integrate randomly. In *P. pastoris*, foreign DNA is targeted to the AOX1 and the HIS4 genes (Cregg, J. M. 1999), in *P. methanolica* to the AUG1 gene (Raymond, C. K. 1999). In most recombinant *H. polymorpha* strains, foreign DNA can be randomly integrated using HARS-sequence-harboring circular plasmids for transformation (Hollenberg, C. P. and Gellissen, G. 1997). Targeted integration can be achieved by homologous recombination using the MOX/

TRP3 locus for disruption/integration (Agaphonov, M. O. et al. 1995, Sohn, J. H. et al. 1999), the LEU2 gene (Agaphonov, M. O. et al. 1999) or the rDNA cluster (Cox, H. et al. 2000). Transformations in *H. polymorpha* typically result in a variety of individual, mitotically stable strains containing single to multiple copies of the expression cassette in a head-to-tail arrangement. Strains with up to 100 copies have been identified (Hollenberg, C. P. and Gellissen, G. 1997). Random multiple-copy integration can be forced in the uracil-auxotroph *H. polymorpha* strain RB11 by a sequence of passages under selective conditions if a *H. polymorpha* or *S. cerevisiae*-derived URA3 gene is present. A HARS sequence can be excluded (Gatzke, R. et al. 1995) or can be present (Hollenberg, C. P. and Gellissen, G. 1997). This passaging furthermore leads to mitotically stable strains. The vector may also comprise a selectable marker, e.g. the *Schizosaccharomyces pombe* TPI gene as described by Russell (Russell, P. R. 1985), or the yeast URA3 gene. Other marker genes so far used for transformation of *Saccharomyces*, for example TRP5, LEU2, ADE1, ADE2, HIS3, HIS4, LYS2, may be obtained from e.g. *Hansenula, Pichia* or *Schwanniomyces.*

"Regulatory elements (or sequences) allowing expression of a protein in a eukaryotic host" are to be understood to comprise at least a genetic element displaying promoter activity and a genetic element displaying terminator activity whereby said regulatory elements are operably linked to the open reading frame encoding the protein to be expressed.

The term "promoter" is a nucleotide sequence which is comprised of consensus sequences which allow the binding of RNA polymerase to the DNA template in a manner such that mRNA production initiates at the normal transcription initiation site for the adjacent structural gene.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide and does not contain stop codons; this region may represent a portion of a coding sequence or a total coding sequence.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include but is not limited to mRNA, DNA (including cDNA), and recombinant polynucleotide sequences.

Many regulatory elements are known in the art. Examples of suitable yeast promoters are the *Saccharomyces cerevisiae* MF$\alpha$1, TPI, ADH I, ADH II or PGK promoters, or corresponding promoters from other yeast species, e.g. *Schizosaccharomyces pombe*. Examples of suitable promoters are described by, for instance, (Alber, T. and Kawasaki, G. 1982, Ammerer, G. 1983, Ballou, L. et al. 1991, Hitzeman, R. A. et al. 1980, Kawasaki, G. and Fraenkel, D. G. 1982, Russell, D. W. et al. 1983, Russell, P. R. 1983, Russell, P. R. and Hall, B. D. 1983). A suitable yeast terminator is, e.g. the TPI terminator (Alber, T. and Kawasaki, G. 1982), or the yeast CYC1 terminator. For methylotrophic or facultative methylotrophic yeast species, the strong and regulatable promoters of the enzymes involved in the methanol utilization pathway are good candidate promoters and include the promoters of the alcohol oxidase genes (AOX1 of *Pichia pastoris*, AUG1 of *P. methanolica*, AOD1 of *Candida boidinii*, and MOX of *Hansenula polymorpha*), the formaldehyde dehydrogenase promoter (FLD1 of *P. pastoris*), the dihydroxyacetone synthase promoter (DAS1 of *C. boidinii*) and the formate dehydrogenase promoter (FMD of *H. polymorpha*). Other promoters include the GAP1 promoter of *P. pastoris* or *H. polymorpha* and the PMA1 and TPS1 promoter of *H. polymorpha* ((Gellissen, G. 2000), and references cited therein). The terminator element derived from any of these genes are examples of suitable terminator elements, more specifically suitable terminator elements include the AOD1, AOX1 and MOX terminator elements.

A further aspect of the current invention covers host cells comprising a recombinant nucleic acid or a vector according to the invention.

In a specific embodiment thereto, said host cells comprising a recombinant nucleic acid or a vector according to the invention are capable of expressing the protein according to the invention comprising the avian leader lysozyme leader peptide or a functional variant thereof joined to an HCV envelope protein or a part thereof.

In an alternative embodiment, said host cells are capable of expressing the protein characterized by the structure CL-$[(A1)_a$-$(PS1)_b$-$(A2)_c]$-HCVENV-$[(A3)_d$-$(PS2)_e$-$(A4)_f]$ wherein:

CL is an avian lysozyme leader peptide or a functional equivalent thereof,

A1, A2, A3 and A4 are adaptor peptides which can be different or the same,

PS1 and PS2 are processing sites which can be the different or the same,

HCVENV is a HCV envelope protein or a part thereof, a, b, c, d, e and f are 0 or 1, and wherein, optionally, A1 and/or A2 are part of PS1 and/or wherein A3 and/or A4 are part of PS2.

In a further specific embodiment thereto, said host cells comprising a recombinant nucleic acid or a vector according to the invention are capable of translocating the protein comprising the avian lysozyme leader peptide or a functional equivalent thereof joined to an HCV envelope protein or a part thereof to the endoplasmic reticulum upon removal of the avian lysozyme leader peptide.

In a further specific embodiment thereto, said host cells comprising a recombinant nucleic acid or a vector according to the invention are capable of translocating the protein $[(A1)_x$-$(PS1)_y$-$(A2)_z]$-HCVENV-$[(A3)_x$-$(PS2)_y$-$(A4)_z]$ to the endoplasmic reticulum upon removal of the CL peptide wherein said protein and said CL peptide are derived from the protein characterized by the structure CL-$[(A1)_a$-$(PS1)_b$-$(A2)_c]$-HCVENV-$[(A3)_d$-$(PS2)_e$-$(A4)_f]$ wherein:

CL is an avian lysozyme leader peptide or a functional equivalent thereof,

A1, A2, A3 and A4 are adaptor peptides which can be different or the same,

PS1 and PS2 are processing sites which can be the different or the same,

HCVENV is a HCV envelope protein or a part thereof, a, b, c, d, e and f are 0 or 1, and wherein, optionally, A1 and/or A2 are part of PS1 and/or wherein A3 and/or A4 are part of PS2.

Also embodied are host cells comprising a recombinant nucleic acid or a vector according to the invention which are capable of processing the processing sites PS1 and/or PS2 in said protein translocated to the endoplasmic reticulum.

Also embodied are host cells comprising a recombinant nucleic acid or a vector according to the invention which are capable of N-glycosylating said protein translocated to the endoplasmic reticulum.

Also embodied are host cells comprising a recombinant nucleic acid or a vector according to the invention which are capable of N-glycosylating said protein translocated to the endoplasmic reticulum and processed at said sites PS1 and/or PS2.

More specifically, the host cells comprising a recombinant nucleic acid or a vector according to the invention are eukaryotic cells and, more particularly, yeast cells such as cells of strains of *Saccharomyces*, such as *Saccharomyces cerevisiae, Saccharomyces kluyveri*, or *Saccharomyces uvarum, Schizosaccharomyces*, such as *Schizosaccharomyces pombe, Kluyveromyces*, such as *Kluyveromyces lactis, Yarrowia*, such as *Yarrowia lipolytica, Hansenula*, such as *Hansenula polymorpha, Pichia*, such as *Pichia pastoris, Aspergillus* species, *Neurospora*, such as *Neurospora crassa*, or *Schwanniomyces*, such as *Schwanniomyces occidentalis*, or mutant cells derived from any thereof.

The term "eukaryotic cells" includes lower eukaryotic cells as well as higher eukaryotic cells. Lower eukaryotic cells are cells such as yeast cells, fungal cells and the like. Particularly suited host cells in the context of the present invention are yeast cells or mutant cells derived from any thereof as described above. Mutant cells include yeast glycosylation minus strains, such as *Saccharomyces* glycosylation minus strains as used in the present invention. Glycosylation minus strains are defined as strains carrying a mutation, in which the nature of the mutation is not necessarily known, but resulting in a glycosylation of glycoproteins comparable to the core-glycosylation In particular, it is contemplated that *Saccharomyces* glycosylation minus strains carry a mutation resulting in a significant shift in mobility on PAGE of the invertase protein. Invertase is a protein which is normally present in *Saccharomyces* in a hyperglycosylated form only (Ballou, L. et al. 1991). Glycosylation minus strains include mnn2, and/or och1 and/or mnn9 deficient strains. The mutant host cells of the invention do not include cells which, due to the mutation, have lost their capability to remove the avian lysozyme leader peptide from a protein comprising said leader peptide joined to a protein of interest.

Higher eukaryotic cells include host cells derived from higher animals, such as mammals, reptiles, insects, and the like. Presently preferred higher eukaryote host cells are derived from Chinese hamster (e.g. CHO), monkey (e.g. COS and Vero cells), baby hamster kidney (BHK), pig kidney (PK15), rabbit kidney 13 cells (RK13), the human osteosarcoma cell line 143 B, the human cell line HeLa and human hepatoma cell lines like Hep G2, and insect cell lines (e.g. *Spodoptera frugiperda*). The host cells may be provided in suspension or flask cultures, tissue cultures, organ cultures and the like. Alternatively the host cells may also be transgenic animals or transgenic plants.

Introduction of a vector, or an expression vector, into a host cell may be effectuated by any available transformation or transfection technique applicable to said host cell as known in the art. Such transformation or transfection techniques comprise heat-shock mediated transformation (e.g. of *E. coli*), conjugative DNA transfer, electroporation, PEG-mediated DNA uptake, liposome-mediated DNA uptake, lipofection, calcium-phosphate DNA coprecipitation, DEAE-dextran mediated transfection, direct introduction by e.g. microinjection or particle bombardment, or introduction by means of a virus, virion or viral particle.

Yet another aspect of the invention relates to methods for producing a HCV envelope protein or part thereof in a host cell, said method comprising transforming said host cell with the recombinant nucleic acid according to the invention or with the vector according to the invention, and wherein said host cell is capable of expressing a protein comprising the avian lysozyme leader peptide or a functional equivalent thereof joined to a HCV envelope protein or a part thereof.

In a specific embodiment thereto, said method for producing a HCV envelope protein or part thereof in a host cell is comprising the step of transforming said host cell with the recombinant nucleic acid according to the invention or with the vector according to the invention, and wherein said host cell is capable of expressing the protein characterized by the structure CL-[$(A1)_a$-$(PS1)_b$-$(A2)_c$]-HCVENV-[$(A3)_d$-$(PS2)_e$-$(A4)_f$]

wherein:

CL is an avian lysozyme leader peptide or a functional equivalent thereof,

A1, A2, A3 and A4 are adaptor peptides which can be different or the same,

PS1 and PS2 are processing sites which can be the different or the same,

HCVENV is a HCV envelope protein or a part thereof, a, b, c, d, e and f are 0 or 1, and wherein, optionally, A1 and/or A2 are part of PS1 and/or wherein A3 and/or A4 are part of PS2.

In another specific embodiment thereto, the host cell in said method is capable of translocating the protein CL-[$(A1)_a$-$(PS1)_b$-$(A2)_c$]-HCVENV-[$(A3)_d$-$(PS2)_e$-$(A4)_f$] to the endoplasmic reticulum upon removal of the CL peptide wherein said protein and said CL peptide are derived from the protein characterized by the structure CL-[$(A1)_a$-$(PS1)_b$-$(A2)_c$]-HCVENV-[$(A3)_d$-$(PS2)_e$-$(A4)_f$]

wherein:

CL is an avian lysozyme leader peptide or a functional equivalent thereof,

A1, A2, A3 and A4 are adaptor peptides which can be different or the same,

PS1 and PS2 are processing sites which can be the different or the same,

HCVENV is a HCV envelope protein or a part thereof, a, b, c, d, e and f are 0 or 1, and wherein, optionally, A1 and/or A2 are part of PS1 and/or wherein A3 and/or A4 are part of PS2.

Also embodied is the method for producing a HCV envelope protein or part thereof wherein said host cell is capable of N-glycosylating said protein translocated to the endoplasmic reticulum.

Further embodied is the method for producing a HCV envelope protein or part thereof wherein said host cell is capable of N-glycosylating said protein translocated to the endoplasmic reticulum and processed at said sites PS1 and/or PS2.

More specifically, the host cell in any of said methods for producing a HCV envelope protein or part thereof is an eukaryotic cell and, more particularly, a yeast cell such as a cell of strains of *Saccharomyces*, such as *Saccharomyces cerevisiae, Saccharomyces kluyveri*, or *Saccharomyces uvarum, Schizosaccharomyces*, such as *Schizosaccharomyces pombe, Kluyveromyces*, such as *Kluyveromyces lactis, Yarrowia*, such as *Yarrowia lipolytica, Hansenula*, such as *Hansenula polymorpha, Pichia*, such as *Pichia pastoris, Aspergillus* species, *Neurospora*, such as *Neurospora crassa*, or *Schwanniomyces*, such as *Schwanniomyces occidentalis*, or mutant cells derived from any thereof.

Any of the methods according to the invention for producing a HCV envelope protein or part thereof may further comprise cultivation of the host cells comprising a recombinant nucleic acid or a vector according to the invention in a suitable medium to obtain expression of said protein.

A further embodiment thereto comprises isolation of the produced HCV envelope protein or part thereof from a culture of said host cells, or, alternatively, from said host cells. Said isolation step may include one or more of (i) lysis of said host cells in the presence of chaotropic agent, (ii) chemical and/or enzymatic modification of the cysteine thiol-groups in the isolated proteins wherein said modification may be reversible or irreversible, and producing a HCV envelope protein or part thereof (iii) heparin affinity chromatography.

Exemplary "chaotropic agents" are guanidinium chloride and urea. In general, a chaotropic agent is a chemical that can disrupt the hydrogen bonding structure of water. In concentrated solutions they can denature proteins because they reduce the hydrophobic effect In the HCV envelope proteins or parts thereof as described herein comprising at least one cysteine residue, but preferably 2 or more cysteine residues, the cysteine thiol-groups can be irreversibly protected by chemical or enzymatic means. In particular, "irreversible protection" or "irreversible blocking" by chemical means refers to alkylation, preferably alkylation of the HCV envelope proteins by means of alkylating agents, such as, for example, active halogens, ethylenimine or N-(iodoethyl)trifluoro-acetamide. In this respect, it is to be understood that alkylation of cysteine thiol-groups refers to the replacement of the thiol-hydrogen by $(CH_2)_nR$, in which n is 0, 1, 2, 3 or 4 and R=H, COOH, $NH_2$, $CONH_2$, phenyl, or any derivative thereof. Alkylation can be performed by any method known in the art, such as, for example, active halogens $X(CH_2)_nR$ in which X is a halogen such as I, Br, Cl or F. Examples of active halogens are methyliodide, iodoacetic acid, iodoacetamide, and 2-bromoethylamine. Other methods of alkylation include the use of NEM (N-ethylmaleimide) or Biotin-NEM, a mixture thereof, or ethylenimine or N-(iodoethyl) trifluoroacetamide both resulting in substitution of —H by $—CH_2—CH_2—NH_2$ (Hermanson, G. T. 1996). The term "alkylating agents" as used herein refers to compounds which are able to perform alkylation as described herein. Such alkylations finally result in a modified cysteine, which can mimic other amino acids. Alkylation by an ethylenimine results in a structure resembling lysine, in such a way that new cleavage sites for trypsine are introduced (Hermanson, G. T. 1996). Similarly, the usage of methyliodide results in an amino acid resembling methionine, while the usage of iodoacetate and iodoacetamide results in amino acids resembling glutamic acid and glutamine, respectively. In analogy, these amino acids are preferably used in direct mutation of cysteine. Therefore, the present invention pertains to HCV envelope proteins as described herein, wherein at least one cysteine residue of the HCV envelope protein as described herein is mutated to a natural amino acid, preferentially to methionine, glutamic acid, glutamine or lysine. The term "mutated" refers to site-directed mutagenesis of nucleic acids encoding these amino acids, ie to the well know methods in the art, such as, for example, site-directed mutagenesis by means of PCR or via oligonucleotide-mediated mutagenesis as described in (Sambrook, J. et al. 1989). It should be understood that for the Examples section of the present invention, alkylation refers to the use of iodo-acetamide as an alkylating agent unless otherwise specified.

It is further understood that in the purification procedure, the cysteine thiol-groups of the HCV proteins or the parts thereof of the present invention can be reversibly protected. The purpose of reversible protection is to stabilize the HCV protein or part thereof. Especially, after reversible protection the sulfur-containing functional group (eg thiols and disulfides) is retained in a non-reactive condition. The sulfur-containing functional group is thus unable to react with other compounds, e.g. have lost their tendency of forming or exchanging disulfide bonds, such as, for example $R_1—SH+R_2—SH—X—>R_1—S—S—R_2$;

$R_1—S—S—R_2+R_3—SH—X—>R_1—S—S—R_3+R_2—SH$;

$R_1—S—S—R_2+R_3—S—S—R_4—X—>R_1—S—S—R_3+R_2—S—S—R_4$.

The described reactions between thiols and/or disulphide residues are not limited to intermolecular processes, but may also occur intramolecularly.

The term "reversible protection" or "reversible blocking" as used herein contemplates covalently binding of modification agents to the cysteine thiol-groups, as well as manipulating the environment of the HCV protein such, that the redox state of the cysteine thiol-groups remains unaffected throughout subsequent steps of the purification procedure (shielding). Reversible protection of the cysteine thiol-groups can be carried out chemically or enzymatically.

The term "reversible protection by enzymatical means" as used herein contemplates reversible protection mediated by enzymes, such as for example acyl-transferases, e.g. acyl-tranferases that are involved in catalysing thio-esterification, such as palmitoyl acyltransferase (see below).

The term "reversible protection by chemical means" as used herein contemplates reversible protection:

1. by modification agents that reversibly modify cysteinyls such as for example by sulphonation and thio-esterification;

Sulphonation is a reaction where thiol or cysteines involved in disulfide bridges are modified to S-sulfonate: $RSH \rightarrow RS—SO_3^-$ (Darbre, A. 1986) or $RS—SR \rightarrow 2\ RS—SO_3^-$ (sulfitolysis; (Kumar, N. et al. 1986)). Reagents for sulfonation are e.g. $Na_2SO_3$, or sodium tetrathionate. The latter reagents for sulfonation are used in a concentration of 10-200 mM, and more preferentially in a concentration of 50-200 mM. Optionally sulfonation can be performed in the presence of a catalysator such as, for example $Cu^{2+}$ (100 μM-1 mM) or cysteine (1-10 mM).

The reaction can be performed under protein denaturing as well as native conditions (Kumar, N. et al. 1985, Kumar, N. et al. 1986).

Thioester bond formation, or thio-esterification is characterised by:

$RSH+R'COX \rightarrow RS—COR'$ in which X is preferentially a halogenide in the compound R'CO—X.

2. by modification agents that reversibly modify the cysteinyls of the present invention such as, for example, by heavy metals, in particular $Zn^{2+}$, $Cd^{2+}$, mono-, dithio- and disulfide-compounds (e.g. aryl- and alkylmethanethiosulfonate, dithiopyridine, dithiomorpholine, dihydrolipoamide, Ellmann reagent, aldrothiol™ (Aldrich) (Rein, A. et al. 1996), dithiocarbamates), or thiolation agents (e.g. gluthathion, N-Acetyl cysteine, cysteineamine). Dithiocarbamate comprise a broad class of molecules possessing an $R_1R_2NC(S)SR_3$ functional group, which gives them the ability to react with sulphydryl groups. Thiol containing compounds are preferentially used in a concentration of 0.1-50 mM, more preferentially in a concentration of 1-50 mM, and even more preferentially in a concentration of 10-50 mM;

3. by the presence of modification agents that preserve the thiol status (stabilise), in particular antioxidantia, such as for example DTT, dihydroascorbate, vitamins and derivates, mannitol, amino acids, peptides and derivates (e.g. histidine, ergothioneine, carnosine, methionine), gallates, hydroxyanisole, hydoxytoluene, hydroquinon, hydroxymethylphenol and their derivates in concentration range of 10 μM-10 mM, more preferentially in a concentration of 1-10 mM;
4. by thiol stabilising conditions such as, for example, (i) cofactors as metal ions ($Zn^{2+}$, $Mg^{2+}$), ATP, (ii) pH control (e.g. for proteins in most cases pH~5 or pH is preferentially thiol $pK_a$-2; e.g. for peptides purified by Reversed Phase Chromatography at pH~2).

Combinations of reversible protection as described in (1), (2), (3) and (4) may result in similarly pure and refolded HCV proteins. In effect, combination compounds can be used, such as, for example Z103 (Zn camosine), preferentially in a concentration of 1-10 mM. It should be clear that reversible protection also refers to, besides the modification groups or shielding described above, any cysteinyl protection method which may be reversed enzymatically or chemically, without disrupting the peptide backbone. In this respect, the present invention specifically refers to peptides prepared by classical chemical synthesis (see above), in which, for example, thioester bounds are cleaved by thioesterase, basic buffer conditions (Beekman, N. J. et al. 1997) or by hydroxylamine treatment (Vingerhoeds, M. H. et al. 1996).

Thiol containing HCV proteins can be purified, for example, on affinity chromatography resins which contain (1) a cleavable connector arm containing a disulfide bond (e.g. immobilised 5,5' dithiobis(2-nitrobenzoic acid) (Jayabaskaran, C. et al. 1987) and covalent chromatography on activated thiol-Sepharose 4B (Pharmacia)) or (2) a aminohexanoyl-4-aminophenylarsine as immobilised ligand. The latter affinity matrix has been used for the purification of proteins, which are subject to redox regulation and dithiol proteins that are targets for oxidative stress (Kalef, E. et al. 1993).

Reversible protection may also be used to increase the solubilisation and extraction of peptides (Pomroy, N. C. and Deber, C. M. 1998).

The reversible protection and thiol stabilizing compounds may be presented under a monomeric, polymeric or liposomic form.

The removal of the reversibly protection state of the cysteine residues can chemically or enzymatically accomplished by e.g.:

- a reductant, in particular DTT, DTE, 2-mercaptoethanol, dithionite, $SnCl_2$, sodium borohydride, hydroxylamine, TCEP, in particular in a concentration of 1-200 mM, more preferentially in a concentration of 50-200 mM;
- removal of the thiol stabilising conditions or agents by e.g. pH increase;
- enzymes, in particular thioesterases, glutaredoxine, thioredoxine, in particular in a concentration of 0.01-5 μM, even more particular in a concentration range of 0.1-5 μM.;
- combinations of the above described chemical and/or enzymatical conditions.

The removal of the reversibly protection state of the cysteine residues can be carried out in vitro or in vivo, e.g. in a cell or in an individual.

It will be appreciated that in the purification procedure, the cysteine residues may or may not be irreversibly blocked, or replaced by any reversible modification agent, as listed above.

A reductant according to the present invention is any agent which achieves reduction of the sulfur in cysteine residues, e.g. "S—S" disulfide bridges, desulphonation of the cysteine residue ($RS—SO_3^-$→RSH). An antioxidant is any reagent which preserves the thiol status or minimises "S—S" formation and/or exchanges. Reduction of the "S—S" disulfide bridges is a chemical reaction whereby the disulfides are reduced to thiol (–SH). The disulfide bridge breaking agents and methods disclosed by Maertens et al. in WO 96/04385 are hereby incorporated by reference in the present description. "S—S" Reduction can be obtained by (1) enzymatic cascade pathways or by (2) reducing compounds. Enzymes like thioredoxin, glutaredoxin are known to be involved in the in vivo reduction of disulfides and have also been shown to be effective in reducing "S—S" bridges in vitro. Disulfide bonds are rapidly cleaved by reduced thioredoxin at pH 7.0, with an apparent second order rate that is around $10^4$ times larger than the corresponding rate constant for the reaction with DTT. The reduction kinetic can be dramatically increased by preincubation the protein solution with 1 mM DTT or dihydrolipoamide (Holmgren, A. 1979). Thiol compounds able to reduce protein disulfide bridges are for instance Dithiothreitol (DTT), Dithioerythritol (DTE), β-mercaptoethanol, thiocarbamates, bis(2-mercaptoethyl) sulfone and N,N'-bis(mercaptoacetyl)hydrazine, and sodium-dithionite. Reducing agents without thiol groups like ascorbate or stannous chloride ($SnCl_2$), which have been shown to be very useful in the reduction of disulfide bridges in monoclonal antibodies (Thakur, M. L. et al. 1991), may also be used for the reduction of HCV proteins. In addition, changes in pH values may influence the redox status of HCV proteins. Sodium borohydride treatment has been shown to be effective for the reduction of disulfide bridges in peptides (Gailit, J. 1993). Tris (2-carboxyethyl) phosphine (TCEP) is able to reduce disulfides at low pH (Burns, J. et al. 1991). Selenol catalyses the reduction of disulfide to thiols when DTT or sodium borohydride is used as reductant. Selenocysteamine, a commercially available diselenide, was used as precursor of the catalyst (Singh, R. and Kats, L. 1995).

Heparin is known to bind to several viruses and consequently binding to the HCV envelope has already been suggested (Garson, J. A. et al. 1999). In this respect, in order to analyze potential binding of HCV envelope proteins to heparin, heparin can be biotinylated and subsequently the interaction of heparin with HCV envelope proteins can be analyzed, e.g. on microtiterplates coated with HCV envelope proteins. In this way different expression systems can be scrutinized. For example, a strong binding is observed with part of the HCV E1 expressed in *Hansenula*, while binding with HCV E1 from mammalian cell culture is absent. In this respect, the term "heparin affinity chromatography" relates to an immobilized heparin, which is able to specifically bind to HCV envelope proteins. Proteins of the high-mannose type bind agglutinins such as *Lens culinaris, Galanthus nivalis, Narcissus pseudonarcissus Pisum sativum* or *Allium ursinum*. Moreover, N-acetylglucosamine can be bound by lectins, such as WGA (wheat germ agglutinin) and its equivalents. Therefore, one may employ lectins bound to a solid phase to separate the HCV envelope proteins of the present invention from cell culture supernatants, cell lysates and other fluids, e.g. for purification during the production of antigens for vaccine or immunoassay use.

With "HCV-recombinant *vaccinia* virus" is meant a *vaccinia* virus comprising a nucleic acid sequence encoding a HCV protein or part thereof.

A further aspect of the invention relates to an isolated HCV envelope protein or part thereof resulting from the method of production as described herein. In particular, the invention relates to an isolated HCV envelope protein or part thereof resulting from the expression in an eukaryotic cell of a recombinant nucleic acid comprising a nucleotide sequence encoding a protein comprising an avian lysozyme leader peptide or a functional equivalent thereof joined to said HCV envelope protein or a part thereof. More specifically, said recombinant nucleic acid is encoding a protein which is characterized by the structure CL-[$(A1)_a$-$(PS1)_b$-$(A2)_c$]-HCVENV-[$(A3)_d$-$(PS2)_3$-$(A4)_f$]

wherein:

- CL is an avian lysozyme leader peptide or a functional equivalent thereof,
- A1, A2, A3 and A4 are adaptor peptides which can be different or the same,
- PS1 and PS2 are processing sites which can be the different or the same,
- HCVENV is a HCV envelope protein or a part thereof,
- a, b, c, d, e and f are 0 or 1, and
- wherein, optionally, A1 and/or A2 are part of PS1 and/or wherein A3 and/or A4 are part of PS2.

In a specific embodiment, the isolated HCV envelope protein or part thereof is derived from said protein comprising an avian lysozyme leader peptide or a functional equivalent thereof joined to said HCV envelope protein or a part thereof. In another specific embodiment, the isolated HCV envelope protein or part thereof is derived from said protein which is characterized by the structure CL-[$(A1)_a$-$(PS1)_b$-$(A2)_c$]-HCVENV-[$(A3)_d$-$(PS2)_e$-$(A4)_f$]

wherein:

- CL is an avian lysozyme leader peptide or a functional equivalent thereof,
- A1, A2, A3 and A4 are adaptor peptides which can be different or the same,
- PS1 and PS2 are processing sites which can be the different or the same,
- HCVENV is a HCV envelope protein or a part thereof,
- a, b, c, d, e and f are 0 or 1, and
- wherein, optionally, A1 and/or A2 are part of PS1 and/or wherein A3 and/or A4 are part of PS2.

Another aspect of the current invention relates to the use of the avian lysozyme leader peptide to direct a recombinantly expressed protein to the endoplasmic reticulum of *Hansenula polymorpha* or any mutant thereof.

Thus, all aspects and embodiments of the current invention as described above and relating to a HCV envelope protein can, specific for *H. polymorpha* or any mutant thereof as host cell, be read as relating to a protein instead of relating to a HCV envelope protein.

More specifically, the current invention also relates to a recombinant nucleic acid comprising a nucleotide sequence encoding a protein comprising an avian lysozyme leader peptide or a functional equivalent thereof joined to a protein of interest or a part thereof.

In one embodiment thereto, the recombinant nucleic acid comprising nucleotide sequence encodes characterized by the structure CL-[$(A1)_a$-$(PS1)_b$-$(A2)_c$]-PROT-[$(A3)_d$-$(PS2)_e$-$(A4)_f$]

wherein:

- CL is an avian lysozyme leader peptide or a functional equivalent thereof,
- A1, A2, A3 and A4 are adaptor peptides which can be different or the same,
- PS1 and PS2 are processing sites which can be the different or the same,
- PROT is a protein of interest or a part thereof,
- a, b, c, d, e and f are 0 or 1, and
- wherein, optionally, A1 and/or A2 are part of PS1 and/or wherein A3 and/or A4 are part of PS2.

In a further embodiment, the recombinant nucleic acids according to the invention further comprise regulatory elements allowing expression in a *H. polymorpha* cell or any mutant thereof of said protein comprising an avian lysozyme leader peptide or a functional equivalent thereof joined to a protein of interest or a part thereof, or of said protein characterized by the structure CL-[$(A1)_x$-$(PS1)_y$-$(A2)_z$]-PROT-[$(A3)_x$-$(PS2)_y$-$(A4)_z$]. Further included are vectors comprising said recombinant nucleic acids, host cells comprising said recombinant nucleic acids or said vectors, said host cells expressing the protein comprising an avian lysozyme leader peptide or a functional variant thereof joined to a protein of interest and methods for producing said protein of interest in said host cells.

A further aspect of the invention relates to an isolated protein of interest or part thereof resulting from the expression in a *Hansenula* cell of a recombinant nucleic acid comprising a nucleotide sequence encoding a protein comprising an avian lysozyme leader peptide or a functional equivalent thereof joined to said protein of interest or a part thereof. More specifically, said recombinant nucleic acid is encoding a protein which is characterized by the structure CL-[$(A1)_a$-$(PS1)_b$-$(A2)_c$]-PROT-[$(A3)_d$-$(PS2)_e$-$(A4)_f$]

wherein:

- CL is an avian lysozyme leader peptide or a functional equivalent thereof,
- A1, A2, A3 and A4 are adaptor peptides which can be different or the same,
- PS1 and PS2 are processing sites which can be the different or the same,
- PROT is a protein of interest or a part thereof,
- a, b, c, d, e and f are 0 or 1, and
- wherein, optionally, A1 and/or A2 are part of PS1 and/or wherein A3 and/or A4 are part of PS2.

In a specific embodiment, the isolated protein of interest or part thereof is derived from said protein comprising an avian lysozyme leader peptide or a functional equivalent thereof joined to said protein of interest or a part thereof. In another specific embodiment, the isolated protein of interest or part thereof is derived from said protein which is characterized by the structure CL-[$(A1)_a$-$(PS1)_b$-$(A2)_c$]-PROT-[$(A3)_d$-$(PS2)_e$-$(A4)_f$]

wherein:

- CL is an avian lysozyme leader peptide or a functional equivalent thereof,
- A1, A2, A3 and A4 are adaptor peptides which can be different or the same,
- PS1 and PS2 are processing sites which can be the different or the same,
- PROT is a protein of interest or a part thereof,
- a, b, c, d, e and f are 0 or 1, and
- wherein, optionally, A1 and/or A2 are part of PS1 and/or wherein A3 and/or A4 are part of PS2.

In a specific embodiment of the invention, said protein of interest or fragment thereof can e.g. be a viral envelope protein or a fragment thereof such as a HCV envelope protein or HBV (hepatitis B) envelope protein, or fragments thereto. In general, said protein of interest or fragment thereof can be any protein needing the N-glycosylation characteristics of the current invention. Other exemplary viral envelope proteins include the HIV (human immunodeficiency virus) envelope protein gp120 and viral envelope proteins of a virus belonging to the Flavirideae.

The terms "HCV virus-like particle formed of a HCV envelope protein" "oligomeric particles formed of HCV envelope proteins" are herein defined as structures of a specific nature and shape containing several basic units of the HCV E1 and/or E2 envelope proteins, which on their own are thought to consist of one or two E1 and/or E2 monomers, respectively. It should be clear that the particles of the present invention are defined to be devoid of infectious HCV RNA genomes. The particles of the present invention can be higher-order particles of spherical nature which can be empty, consisting of a shell of envelope proteins in which lipids, detergents, the HCV core protein, or adjuvant molecules can be incorporated. The latter particles can also be encapsulated by liposomes or apolipoproteins, such as, for example, apolipoprotein B or low density lipoproteins, or by any other means of targeting said particles to a specific organ or tissue. In this case, such empty spherical particles are often referred to as "virus-like particles" or VLPs. Alternatively, the higher-order particles can be solid spherical structures, in which the complete sphere consists of HCV E1 or E2 envelope protein oligomers, in which lipids, detergents, the HCV core protein, or adjuvant molecules can be additionally incorporated, or which in turn may be themselves encapsulated by liposomes or apolipoproteins, such as, for example, apolipoprotein B, low density lipoproteins, or by any other means of targeting said particles to a specific organ or tissue, e.g. asialoglycoproteins. The particles can also consist of smaller structures (compared to the empty or solid spherical structures indicated above) which are usually round (see further)-shaped and which usually do not contain more than a single layer of HCV envelope proteins. A typical example of such smaller particles are rosette-like structures which consist of a lower number of HCV envelope proteins, usually between 4 and 16. A specific example of the latter includes the smaller particles obtained with E1s in 0.2% CHAPS as exemplified herein which apparently contain 8-10 monomers of E1s. Such rosette-like structures are usually organized in a plane and are round-shaped, e.g. in the form of a wheel. Again lipids, detergents, the HCV core protein, or adjuvant molecules can be additionally incorporated, or the smaller particles may be encapsulated by liposomes or apolipoproteins, such as, for example, apolipoprotein B or low density lipoproteins, or by any other means of targeting said particles to a specific organ or tissue. Smaller particles may also form small spherical or globular structures consisting of a similar smaller number of HCV E1 or E2 envelope proteins in which lipids, detergents, the HCV core protein, or adjuvant molecules could be additionally incorporated, or which in turn may be encapsulated by liposomes or apolipoproteins, such as, for example, apolipoprotein B or low density lipoproteins, or by any other means of targeting said particles to a specific organ or tissue. The size (i.e. the diameter) of the above-defined particles, as measured by the well-known-in-the-art dynamic light scattering techniques (see further in examples section), is usually between 1 to 100 nm, more preferentially between 2 to 70 nm, even more preferentially between 2 and 40 nm, between 3 to 20 nm, between 5 to 16 nm, between 7 to 14 nm or between 8 to 12 nm.

In particular, the present invention relates to a method for purifying hepatitis C virus (HCV) envelope proteins, or any part thereof, suitable for use in an immunoassay or vaccine, which method comprising:

(i) growing *Hansenula* or *Saccharomyces* glycosylation minus strains transformed with an envelope gene encoding an HCV E1 and/or HCV E2 protein, or any part thereof, in a suitable culture medium;
(ii) causing expression of said HCV E1 and/or HCV E2 gene, or any part thereof; and
(iii) purifying said HCV E1 and/or HCV E2 protein, or any part thereof, from said cell culture.

The invention further pertains to a method for purifying hepatitis C virus (HCV) envelope proteins, or any part thereof, suitable for use in an immunoassay or vaccine, which method comprising:

(i) growing *Hansenula* or *Saccharomyces* glycosylation minus strains transformed with an envelope gene encoding an HCV E1 and/or HCV E2 protein, or any part thereof, in a suitable culture medium;
(ii) causing expression of said HCV E1 and/or HCV E2 gene, or any part thereof; and
(iii) purifying said intracellularly expressed HCV E1 and/or HCV E2 protein, or any part thereof, upon lysing the transformed host cell.

The invention further pertains to a method for purifying hepatitis C virus (HCV) envelope proteins, or any part thereof, suitable for use in an immunoassay or vaccine, which method comprising:

(i) growing *Hansenula* or *Saccharomyces* glycosylation minus strains transformed with an envelope gene encoding an HCV E1 and/or HCV E2 protein, or any part thereof, in a suitable culture medium, in which said HCV E1 and/or HCV E2 protein, or any part thereof, comprises at least two Cys-amino acids;
(ii) causing expression of said HCV E1 and/or HCV E2 gene, or any part thereof; and
(iii) purifying said HCV E1 and/or HCV E2 protein, or any part thereof, in which said Cys-amino acids are reversibly protected by chemical and/or enzymatic means, from said culture.

The invention further pertains to a method for purifying hepatitis C virus (HCV) envelope proteins, or any part thereof, suitable for use in an immunoassay or vaccine, which method comprising:

(i) growing *Hansenula* or *Saccharomyces* glycosylation minus strains transformed with an envelope gene encoding an HCV E1 and/or HCV E2 protein, or any part thereof, in a suitable culture medium, in which said HCV E1 and/or HCV E2 protein, or any part thereof, comprises at least two Cys-amino acids;
(ii) causing expression of said HCV E1 and/or HCV E2 gene, or any part thereof; and,
(iii) purifying said intracellulary expressed HCV E1 and/or HCV E2 protein, or any part thereof, upon lysing the transformed host cell, in which said Cys-amino acids are reversibly protected by chemical and/or enzymatic means.

The present invention specifically relates to a method for purifying recombinant HCV yeast proteins, or any part thereof, as described herein, in which said purification includes heparin affinity chromatography.

Hence, the present invention also relates to a method for purifying recombinant HCV yeast proteins, or any part thereof, as described above, in which said chemical means is sulfonation.

Hence, the present invention also relates to a method for purifying recombinant HCV yeast proteins, or any part thereof, as described above, in which said reversibly protection of Cys-amino acids is exchanged for an irreversible protection by chemical and/or enzymatic means.

Hence, the present invention also relates to a method for purifying recombinant HCV yeast proteins, or any part thereof, as described above, in which said irreversible protection by chemical means is iodo-acetamide.

Hence, the present invention also relates to a method for purifying recombinant HCV yeast proteins, or any part thereof, as described above, in which said irreversible protection by chemical means is NEM or Biotin-NEM or a mixture thereof.

The present invention also relates to a composition as defined above which also comprises HCV core, E1, E2, P7, NS2, NS3, NS4A, NS4B, NS5A and/or NS5B protein, or parts thereof. The core-glycosylated proteins E1, E2, and/or E1/E2 of the present invention may, for example, be combined with other HCV antigens, such as, for example, core, P7, NS3, NS4A, NS4B, NS5A and/or NS5B. The purification of these NS3 proteins will preferentially include a reversible modification of the cysteine residues, and even more preferentially sulfonation of cysteines. Methods to obtain such a reversible modification, including sulfonation have been described for NS3 proteins in Maertens et al. (PCT/EP99/02547). It should be stressed that the whole content, including all the definitions, of the latter document is incorporated by reference in the present application.

Also, the present invention relates to the use of a envelope protein as described herein for inducing immunity against HCV, characterized in that said HCV envelope protein is used as part of a series of time and compounds. In this regard, it is to be understood that the term "a series of time and compounds" refers to administering with time intervals to an individual the compounds used for eliciting an immune response. The latter compounds may comprise any of the following components: a HCV envelope protein according to the invention, HCV DNA vaccine composition, HCV polypeptides.

In this respect, a series comprises administering, either:

(i) an HCV antigen, such as, for example, a HCV envelope protein according to the invention, with time intervals, or (ii) an HCV antigen, such as, for example, a HCV envelope protein according to the invention in combination with a HCV DNA vaccine composition, in which said envelope protein and said HCV DNA vaccine composition, can be administered simultaneously, or at different time intervals, including at alternating time intervals, or (iii) either (i) or (ii), possibly in combination with other HCV peptides, with time intervals.

In this regard, it should be clear that a HCV DNA vaccine composition comprises nucleic acids encoding HCV envelope peptide, including E1-, E2-, E1/E2-peptides, NS3 peptide, other HCV peptides, or parts of said peptides. Moreover, it is to be understood that said HCV peptides comprises HCV envelope peptides, including E1-, E2-, E1/E2-peptides, other HCV peptides, or parts thereof. The term "other HCV peptides" refers to any HCV peptide or fragment thereof. In item (ii) of the above scheme, the HCV DNA vaccine composition comprises preferentially nucleic acids encoding HCV envelope peptides. In item (ii) of the above scheme, the HCV DNA vaccine composition consists even more preferentially of nucleic acids encoding HCV envelope peptides, possibly in combination with a HCV-NS3 DNA vaccine composition. In this regard, it should be clear that an HCV DNA vaccine composition comprises a plasmid vector comprising a polynucleotide sequence encoding an HCV peptide as described above, operably linked to transcription regulatory elements. As used herein, a "plasmid vector" refers to a nucleic acid molecule capable of transporting another nucleic acid to which it has been linked. Preferred vectors are those capable of autonomous replication and/or expression of nucleic acids to which they have been linked. In general, but not limited to those, plasmid vectors are circular double stranded DNA loops which, in their vector form, are not bound to the chromosome. As used herein, a "polynucleotide sequence" refers to polynucleotides such as deoxyribonucleic acid (DNA), and, where appropriate, ribonucleic acid (RNA). The term should also be understood to include, as equivalents, analogs of either RNA or DNA made from nucleotide analogs, and single (sense or antisense) and double-stranded polynucleotides. As used herein, the term "transcription regulatory elements" refers to a nucleotide sequence which contains essential regulatory elements, such that upon introduction into a living vertebrate cell it is able to direct the cellular machinery to produce translation products encoded by the polynucleotide. The term "operably linked" refers to a juxtaposition wherein the components are configured so as to perform their usual function. Thus, transcription regulatory elements operably linked to a nucleotide sequence are capable of effecting the expression of said nucleotide sequence. Those skilled in the art can appreciate that different transcriptional promoters, terminators, carrier vectors or specific gene sequences may be used successfully. Alternatively, the DNA vaccine may be delivered through a live vector such as adenovirus, canary pox virus, MVA, and the like.

The HCV envelope proteins of the present invention, or the parts thereof, are particularly suited for incorporation into an immunoassay for the detection of anti-HCV antibodies, and/or genotyping of HCV, for prognosing/monitoring of HCV disease, or as a therapeutic agent.

A further aspect of the invention relates to a diagnostic kit for the detection of the presence of anti-HCV antibodies in a sample suspected to comprise anti-HCV antibodies, said kit comprising a HCV envelope protein or part thereof according to the invention. In a specific embodiment thereto, said HCV envelope protein or part thereof is attached to a solid support. In a further embodiment, said sample suspected to comprise anti-HCV antibodies is a biological sample.

The term "biological sample" as used herein, refers to a sample of tissue or fluid isolated from an individual, including but not limited to, for example, serum, plasma, lymph fluid, the external sections of the skin, respiratory-, intestinal- or genito-urinary tracts, oocytes, tears, saliva, milk, blood cells, tumors, organs, gastric secretions, mucus, spinal cord fluid, external secretions such as, for example, excrement, urine, sperm, and the like.

Another aspect of the invention refers to a composition comprising an isolated HCV envelope protein or fragment thereof according to the invention. Said composition may further comprise a pharmaceutically acceptable carrier and can be a medicament or a vaccine.

A further aspect of the invention covers a medicament or a vaccine comprising a HCV envelope protein or part thereof according to the invention.

Yet another aspect of the invention comprises a pharmaceutical composition for inducing a HCV-specific immune response in a mammal, said composition comprising an effective amount of a HCV envelope protein or part thereof according to the invention and, optionally, a pharamaceutically acceptable adjuvant. Said pharmaceutical composition comprising an effective amount of a HCV envelope protein or part thereof according to the invention may also be capable of inducing HCV-specific antibodies in a mammal, or capable of inducing a T-cell function in a mammal. Said pharmaceutical compostion comprising an effective amount of a HCV envelope protein or part thereof according to the invention may be prophylactic composition or a therapeutic composition. In a specific embodiment said mammal is a human.

A "mammal" is to be understood as any member of the higher vertebrate class Mammalia, including humans; characterized by live birth, body hair, and mammary glands in the female that secrete milk for feeding the young. Mammals thus also include non-human primates and trimera mice (Zauberman et al. 1999).

A "vaccine" or "medicament" is a composition capable of eliciting protection against a disease, whether partial or complete, whether against acute or chronic disease; in this case the vaccine or medicament is a prophylactic vaccine or medicament. A vaccine or medicament may also be useful for treatment of an already ill individual, in which case it is called a therapeutic vaccine or medicament. Likewise, a pharmaceutical composition can be used for either prophylactic and/or therapeutic purposes in which cases it is a prophylactic and/or therapeutic composition, respectively.

The HCV envelope proteins of the present invention can be used as such, in a biotinylated form (as explained in WO 93/18054) and/or complexed to *Neutralite Avidin* (Molecular Probes Inc., Eugene, Oreg., USA), avidin or streptavidin. It should also be noted that "a vaccine" or "a medicament" may comprise, in addition to an active substance, a "pharmaceutically acceptable carrier" or "pharmaceutically acceptable adjuvant" which may be a suitable excipient, diluent, carrier and/or adjuvant which, by themselves, do not induce the production of antibodies harmful to the individual receiving the composition nor do they elicit protection. Suitable carriers are typically large slowly metabolized macromolecules such as proteins, polysaccharides, polylactic acids, polyglycolic acids, polymeric amino acids, amino acid copolymers and inactive virus particles. Such carriers are well known to those skilled in the art. Preferred adjuvants to enhance effectiveness of the composition include, but are not limited to: aluminium hydroxide, aluminium in combination with 3-0-deacylated monophosphoryl lipid A as described in WO 93/19780, aluminium phosphate as described in WO 93/24148, N-acetyl-muramyl-L-threonyl-D-isoglutamine as described in U.S. Pat. No. 4,606,918, N-acetyl-normuramyl-L-alanyl-D-isoglutamine, N-acetyl-muramyl-L-alanyl-D-isoglutamyl-L-alanine2-(1'2'dipalmitoyl-sn-glycero-3-hydroxyphosphoryloxy) ethylamine, RIBI (ImmunoChem Research Inc., Hamilton, Mont., USA) which contains monophosphoryl lipid A, detoxified endotoxin, trehalose-6,6-dimycolate, and cell wall skeleton (MPL+TDM+CWS) in a 2% squalene/Tween 80 emulsion. Any of the three components MPL, TDM or CWS may also be used alone or combined 2 by 2. The MPL may also be replaced by its synthetic analogue referred to as RC-529. Additionally, adjuvants such as Stimulon (Cambridge Bioscience, Worcester, Mass., USA), SAF-1 (Syntex) or bacterial DNA-based adjuvants such as ISS (Dynavax) or CpG (Coley Pharmaceuticals) may be used, as well as adjuvants such as combinations between QS21 and 3-de-O-acetylated monophosphoryl lipid A (WO94/00153), or MF-59 (Chiron), or poly[di(carboxylatophenoxy) phosphazene] based adjuvants (Virus Research Institute), or blockcopolymer based adjuvants such as Optivax (Vaxcel, Cythx) or insulin-based adjuvants, such as Algammulin and Gammalnulin (Anutech), Incomplete Freund's Adjuvant (IFA) or Gerbu preparations (Gerbu Biotechnik). It is to be understood that Complete Freund's Adjuvant (CFA) may be used for non-human applications and research purposes as well. "A vaccine composition" may further contain excipients and diluents, which are inherently non-toxic and non-therapeutic, such as water, saline, glycerol, ethanol, wetting or emulsifying agents, pH buffering substances, preservatives, and the like. Typically, a vaccine composition is prepared as an injectable, either as a liquid solution or suspension. Injection may be subcutaneous, intramuscular, intravenous, intraperitoneal, intrathecal, intradermal. Other types of administration comprise implantation, suppositories, oral ingestion, enteric application, inhalation, aerosolization or nasal spray or drops. Solid forms, suitable for solution on, or suspension in, liquid vehicles prior to injection may also be prepared. The preparation may also be emulsified or encapsulated in liposomes for enhancing adjuvant effect. The polypeptides may also be incorporated into Immune Stimulating Complexes together with saponins, for example Quil A (ISCOMS). Vaccine compositions comprise an effective amount of an active substance, as well as any other of the above-mentioned components. "Effective amount" of an active substance means that the administration of that amount to an individual, either in a single dose or as part of a series, is effective for prevention or treatment of a disease or for inducing a desired effect. This amount varies depending upon the health and physical condition of the individual to be treated, the taxonomic group of the individual to be treated (e.g. human, non-human primate, primate, etc.), the capacity of the individual's immune system to mount an effective immune response, the degree of protection desired, the formulation of the vaccine, the treating doctor's assessment, the strain of the infecting pathogen and other relevant factors. It is expected that the amount will fall in a relatively broad range that can be determined through routine trials. Usually, the amount will vary from 0.01 to 1000 μg/dose, more particularly from 0.1 to 100 μg/dose. Dosage treatment may be a single dose schedule or a multiple dose schedule. The vaccine may be administered in conjunction with other immunoregulatory agents.

The present invention is illustrated by the Examples as set forth below. These Examples are merely illustrative and are not construed to restrict or limit the invention in any way.

EXAMPLES

Example 1

Construction of pFPMT-MFα-E1-H6 Shuttle Vector

Plasmids for *Hansenula polymorpha* transformation were constructed as follows. The pFPMT-MFα-E1-H6 shuttle vector has been constructed in a multi-step procedure. Initially the nucleic acid sequence encoding the HCV E1s protein (SEQ ID NO:2) was cloned after a CHH leader sequence (CHH=*Carcinus maenas* hyperglycemic hormone) which was subsequently changed for a MFα leader sequence (MFα=*Saccharomyces cerevisiae* α-mating factor).

At first a pUC18 derivative has been constructed harboring the CHH-E1-H6 unit as a EcoRI/BamHI fragment by the seamless cloning method (Padgett, K. A. and Sorge, J. A. 1996). Thereto, the E1s-H6-encoding DNA fragment and the pCHH-Hir-derived acceptor plasmid were generated by PCR as described below.

Generation of E1s-H6-encoding DNA Fragment

The E1-H6 DNA fragment (coding for HCV type 1b E1s protein consisting of the amino acids 192 to 326 of E1s elongated with 6 His-residues; SEQ ID NO:4) was isolated by PCR from the plasmid pGEMTE1sH6 (SEQ ID NO:6; FIG. 1). The following primers were used thereto:

CHHE1-F:5'-agttactcttca.aggtatgaggtgcgcaacgtgtccg-3' (SEQ ID NO:7);

The Eam1104I site is underlined, the dot marks the cleavage site. The bold printed bases are complementary to those of primer CHH-links. The non-marked bases anneal within the start region of E1 (192-326) in sense direction; and CHHE1-R: 5'-agtta ctcttca.cagggatcctccttaatggtgatggtggtggtgcc-3' (SEQ ID NO: 8);

The Eam1104I site is underlined, the dot marks the cleavage site. The bold printed bases are complementary to those of primer MF30-rechts. The bases forming the BamHI site usefull for later cloning procedures are printed in italics. The non-marked bases anneal in antisense direction within the end of the E1-H6 unit, including the stop codon and three additional bases between the stop codon and the BamHI site.

The reaction mixture was constituted as follows: total volume of 50 μL containing 20 ng of Eco311-linearized pGEMTE1sH6, each 0.2 μM of primers CHHE1-F and CHHE1-R, dNTP's (each at 0.2 μM), 1× buffer 2 (Expand Long Template PCR System; Boehringer; Cat No 1681 834), 2.5 U polymerase mix (Expand Long Template PCR System; Boehringer; Cat No 1681 834).

Program 1 was used, said program consisting of the following steps:

1. denaturation: 5 min 95° C.;
2. 10 cycles of 30 sec denaturation at 95° C., 30 sec annealing at 65° C., and 130 sec elongation at 68° C.
3. termination at 4° C.

Then 5 μL 10× buffer 2 (Expand Long Template PCR System; Boeringer; Cat No 1681 834), 40 μL $H_2O$, and 5 μL of [dATP, dGTP, and dTTP (2 mM each); 10 mM 5-methyl-dCTP] were added to the sample derived from program 1, and further amplification was performed following program 2 consisting of the following steps:

1. denataruation: 5 min at 95° C.
2. 5 cycles of 45 sec denaturation at 95° C., 30 sec annealing at 65° C., and 130 sec at 68° C.
3. termination at 4° C.

Generation of pCHH-Hir-derived Acceptor Plasmid

The acceptor fragment was made by PCR from the pCHH-Hir plasmid (SEQ ID NO:9; FIG. 2) and consists of almost the complete pCHH-Hir plasmid, except that the Hir-coding sequence is not present in the PCR product. Following primers were used for this PCR:

1. CHH-links: 5'-agttactcttca.cctcttttccaacgggtgtgtag-3' (SEQ ID NO:10);

The Eam1104I site is underlined, the dot marks the cleavage site. The bold printed bases are complementary to those of primer CHHE1-F. The non-marked bases anneal within the end of the CHH sequence in antisense direction; and 2. MF30-rechts: 5'-agtcactcttca.ctgcaggcatgcaagcttggcg-3' (SEQ ID NO:11);

The Eam1104I site is underlined, the dot marks the cleavage site. The bold printed bases are complementary to those of primer CHHE1-R. The non-marked bases anneal within the pUC18 sequences behind the cloned CHH-Hirudin HL20 of pCHH-Hir, pointing away from the insert.

The reaction mixture was constituted as follows: total volume of 50 μL containing 20 ng of Asp718I-linearized pCHH-Hir, each 0.2 μM of primers CHH-links and MF30-rechts, dNTP's (each at 0.2 μM), 1× buffer 2 (Expand Long Template PCR System; Boeringer; Cat No 1681 834), 2.5 U polymerase mix (Expand Long Template PCR System; Boeringer; Cat No 1681 834).

Program 1 was as described above was used.

Then 5 μL 10× buffer 2 (Expand Long Template PCR System; Boeringer; Cat No 1681 834), 40 μL $H_2O$, and 5 μL of [DATP, dGTP, and dTTP (2 mM each); 10 mM 5-methyl-dCTP] were added to the sample derived from program 1, and further amplification was performed following program 2 as described above.

Generation of Vector pCHHE1

The E1s-H6-encoding DNA fragment and the pCHH-Hir-derived acceptor plasmid generated by PCR as described above were purified using the PCR product purification kit (Qiagen) according to the supplier's specifications. Subsequently the purified fragments were digested separately with Eam1104I. Subsequently, the E1s-H6 DNA fragment was ligated into the pCHH-Hir-derived acceptor plasmid using T4 ligase (Boehringer) following the specifications of the supplier.

*E. coli* XL-Gold cells were transformed with the ligation mixture and the plasmid DNA of several ampicillin-resistant colonies were analyzed by digestion with EcoRI and BamHI. A positive clone was selected and denominated as pCHHE1.

Generation of Vector pFPMT-CHH-EIH6

The EcoRI/BamHI fragment of pCHHE1 was ligated with the EcoRI/BamHI digested vector pFPMT121 (SEQ ID NO:12; FIG. 3). T4 ligase (Boehringer) was used according to the supplier's instructions. The ligation mixture was used to transform *E. coli* DH5αF' cells. Several transformants were analyzed on restriction pattern of the plasmid DNA and a positive clone was withheld which was denominated pFPMT-CHH-E1H6 (SEQ ID NO: 13; FIG. 4).

Generation of pFPMT-MFα-E1-H6

Finally the shuttle vector pFPMT-MFα-E1-H6 was generated by ligation of three fragments, said fragments being:

1. the 6.961 kb EcoRI/BamHI digested pFPMT121 (SEQ ID NO:12; FIG. 3),
2. the 0.245 EcoRI/HindIII fragment of pUC18-MFa (SEQ ID NO:62; FIG. 36), and
3. the 0.442 kb HindIII/BamHI fragment of a 0.454 kb PCR product derived from pFPMT-CHH-E1H6.

The 0.454 kb PCR product giving rise to fragment No. 3 was obtained by PCR using the following primers:

```
1. primer MFa-E1 f-Hi:
   5'-aggggtaagcttggataaaaggtatgaggtgcgcaacgtgtccgggatgt-3'; and   (SEQ ID NO:14)

2. primer E1 back-Bam:
   5'-agttacggatccttaatggtgatggtggtggtgccagttcat-3'.               (SEQ ID NO:15)
```

The reaction mixture was constituted as follows: Reaction mixture volume 50 μL, pFPMT-CHH-E1-H6 (EcoRI-linearized; 15 ng/μL), 0.5 μL; primer MFa-E1 f-Hi (50 μM), 0.25 μL; primer E1 back-Bam (50 μM), 0.25 μL; dNTP's (all at 2 mM), 5 μL; DMSO, 5 μL; $H_2O$, 33.5 μL; Expand Long Template PCR System (Boeringer Mannheim; Cat No 1681 834) Buffer 2 (10× concentrated), 5 μL; Expand Long Template PCR System Polymerase mixture (1 U/μL), 0.5 μL.

The PCR program consisting of the following steps was used:

1. denaturation: 5 min at 95° C.
2. 29 cycles of 45 sec denaturation at 95° C., 45 sec annealing at 55° C., and 40 sec elongation at 68° C.
3. termination at 4° C.

Based on the primers used, the resulting 0.454 kb PCR product contained the codons of E1(192-326) followed by six histidine codons and a "taa" stop codon, upstream flanked by the 22 3'-terminal base pairs of the MFα prepro sequence (including the cloning relevant HindIII site plus a six base pairs overhang) and downstream flanked by a (cloning relevant) BamHI site and a six base pairs overhang.

For the ligation reaction, T4 DNA ligase (Boehringer Mannheim) has been used according to the supplier's conditions (sample volume 20 μL). *E.coli* HB101 cells were transformed with the ligation mixture and positive clones withheld after restriction analysis of the plasmids isolated from several transformants. A positive plasmid was selected and denominated as pFPMT-MFα-E1-H6 (SEQ ID NO:16; FIG. 5).

Example 2

Construction of pFPMT-CL-E1-H6 Shuttle Vector

Plasmids for *Hansenula polymorpha* transformation were constructed as follows. The pFPMT-CL-E1-H6 shuttle vector was constructed in three steps starting from pFPMT-MFα-E1-H6 (SEQ ID NO: 16, FIG. 5).

In a first step, the MFα-E1-H6 reading frame of pFPMT-MFα-E1-H6 was subcloned into the pUC18 vector. Therefore a 1.798 kb SalI/BamHI fragment of pFPMT-MFα-E1-H6 (containing the FMD promotor plus MFα-E1-H6) was ligated to the SalI/BamHI vector fragment of pUC18 with T4 ligase (Boehringer) according to the supplier's conditions. This resulted in plasmid that is depicted in FIG. 6 (SEQ ID NO: 17), and further denominated as pMa12-1 (pUC18-FMD-MFα-E1-H6). The ligation mixture was used to transform *E.coli* DH5αF' cells. Several ampicillin-resistant colonies were picked and analyzed by restriction enzyme digestion of plasmid DNA isolated from the picked clones. A positive clone was further analyzed by determining the DNA sequence of the MFα-E1-H6 coding sequence. A correct clone was used for PCR directed mutagenesis to replace the MFα pre-pro-sequence with the codons of the avian lysozyme pre-sequence ("CL"; corresponding to amino acids 1 to 18 of avian lysozyme; SEQ ID NO: 1). The principle of the applied PCR-directed mutagenesis method is based on the amplification of an entire plasmid with the desired alterations located at the 5'-ends of the primers. In downstream steps, the ends of the linear PCR product are modified prior to self-ligation resulting in the desired altered plasmid.

The following primers were used for the PCR reaction:

```
                                                              (SEQ ID NO:18)
1. primer CL hin: 5'-tgcttcctaccactagcagcactaggatatgaggtgcgcaacgtgtccggg-3';

                                                              (SEQ ID NO:19)
2. primer CL her neu: 5'-tagtactagtattagtaggcttcgcatgaattcccgatgaaggcagagagcg-3'.
```

The underlined 5' regions of the primers contain the codons of about half of the avian lysozyme pre-sequence. Primer CL her neu includes a SpeI restriction site (italic). The non-underlined regions of the primers anneal with the codons for amino acid residues 192 to 199 of E1 (CL hin) or the with the "atg" start codon over the EcoRI site up to position-19 (counted from the EcoRI site) of FMD promoter. The primers are designed to amplify the complete pMa12-1 thereby replacing the codons of the MFα pre-pro-sequence with the codons of the avian lysozyme pre sequence.

The reaction mixture was constituted as follows: pUC18-FMD-Mfα-E1-H6 (pMa12-1; 1.3 ng/μL), 1 μL; primer CL hin (100 μM), 2 μL; primer CL her neu (100 μM), 2 μL; dNTP's (all at 2.5 mM), 8 μL; $H_2O$, 76 μL; Expand Long Template PCR System (Boeringer; Cat No 1681 834) Buffer 2 (10× concentrated), 10 μL; Expand Long Template PCR System Polymerase mixture (1 U/μL), 0.75 μL.

The PCR program consisting of the following steps was applied:

1. denaturation: 15 min at 95° C.
2. 35 cycles of 30 sec denaturation at 95° C., 1 min annealing at 60° C., and 1 min elongation at 72° C.
3. termination at 4° C.

The resulting PCR product was checked by agarose gel electrophoresis for its correct size (3.5 kb). Thereafter the 3'-A overhangs form the PCR product were removed by a T4 polymerase reaction resulting in blunt ends with 3'- and 5'-OH-groups. Therefore, the PCR product was treated with T4 polymerase (Boehringer; 1 U/μL): to the remaining 95 μL of PCR reaction mix were added 1 μL T4 polymerase and 4 μL dNTP's (all at 2.5 mM). The sample was incubated for 20 min at 37° C. Subsequently, the DNA was precipitated with ethanol and taken up in 16 μL $H_2O$.

Subsequently 5'-phosphates were added to the blunt-ended PCR product by a kinase reaction. Therefore, to the 16 μL blunt-ended PCR product were added 1 μL T4 polynucleotide kinase (Boehringer; 1U/μL), 2 μL 10-fold concentrated T4 polynucleotide kinase reaction buffer (Boehringer), and 1 μL ATP (10 mM). The sample was incubated for 30 min at 37° C. Subsequently the DNA was applied onto a 1% agarose gel and the correct product band was isolated by means of the gel extraction kit (Qiagen) according to the supplier's conditions. Fifty (50) ng of the purified product was then self-ligated by use of T4 ligase (Boehringer) according to the supplier's conditions. After 72 h incubation at 16° C., the DNA in the ligation mix was precipitated with ethanol and dissolved in 20 μL water. *E.coli* DH5α-F' cells were subsequently transformed with 10 μL of the ligation sample. The plasmid DNA of several ampicillin-resistant clones was checked by means of restriction enzyme digestion. A positive clone was withheld and denominated p27d-3

(pUC18-FMD-CL-E1-H6, SEQ ID NO:20, FIG. 7). Subsequently the CL-E1-H6 reading frame was verified by DNA sequencing.

In a last step the pFPMT-CL-E1-H6 shuttle vector was constructed as described below. The 0.486 kb EcoRI/BamHI fragment of p27d-3 (harboring CL-E1(192-326)-H6) was ligated with EcoRI/BamHI-digested pFPMT121 (SEQ ID NO:12, FIG. 3). For the reaction, T4 ligase (Boehringer) has been used according to the supplier's recommendations. The DNA in the ligation sample was precipitated with ethanol and dissolved in 10 μL $H_2O$. *E. coli* DH5αF' cells were transformed with 10 μL of the ligation sample, and the plasmid DNA of several ampicillin-resistant colonies were analyzed by digestion with EcoRI and BamHI. Plasmid clone p37-5 (pFPMT-CL-E1-H6; SEQ ID NO:21, FIG. 8) showed the desired fragment sizes of 0.486 kb and 6.961 kb. The correct sequence of CL-E1-H6 of p37-5 was verified by sequencing.

Example 3

Construction of pFPMT-MFα-E2-H6 and pMPT-MFα-E2-H16 Shuttle Vectors

Plasmids for *Hansenula polymorpha* transformation were constructed as follows. The DNA sequence encoding the MTα-E2s (amino acids 384-673 of HCV E2)-VIEGR-His6 (SEQ ID NO:5) was isolated as a 1.331 kb EcoRI/BglII fragment from plasmid pSP72E2H6 (SEQ ID NO:22, FIG. 9). This fragment was ligated with either the EcoRI/BglII-digested vectors pFPMT121 (SEQ ID NO: 12, FIG. C+2) or pMPT121 (SEQ ID NO:23, FIG. 10) using T4 DNA ligase (Boehringer Mannheim) according to the supplier's recommendations. After transformation of *E. coli* and checking of plasmid DNA isolated from different transformants by restriction enzyme digestion, positive clones were withheld and the resulting shuttle vectors are denominated pFPMT-MFα-E2-H6 (SEQ ID NO:22, FIG. 11) and pMPT-MFα-E2-H6 (SEQ ID NO:23, FIG. 12), respectively.

Example 4

Construction of pFPMT-CL-E2-H6 Shuttle Vector

The shuttle vector pFPMT-CL-E2-H6 was assembled in a three-step procedure. An intermediate construct was prepared in which the E2 coding sequence was cloned behind the signal sequence of α-amylase of *Schwanniomyces occidentalis*. This was done by the seamless cloning method (Padgett, K. A. and Sorge, J. A. 1996).

Generation of E2s-H6 Encoding DNA Fragment

At first the DNA sequence encoding E2-H6 (amino acids 384 to 673 of HCV E2 extended with the linker peptide "VIEGR" and with 6 His residues, SEQ ID NO:5) was amplified from the pSP72E2H6 plasmid (SEQ ID NO:24, FIG. 11) by PCR. The used primers were denoted MF30E2/F and MF30E2/R and have the following sequences:

- primer MF30E2/F: 5'-agtca <u>ctcttc</u>a.aggcatacccgcgtgtcaggaggg-3' (SEQ ID NO:26; the Eam1104I site is underlined, the dot marks the enzyme's cleavage site; the last codon of the *S. occidentalis* signal sequence is printed in bold; the non-marked bases anneal with the codons of E2 (amino acids 384-390 of HCV E2);
- primer MF30E2/R: 5'-agt <u>cactcttc</u>a.cagggatccttagtgatggtggtgatg-3' (SEQ ID NO:27; the Eam1104I site is underlined, the dot marks the enzyme's cleavage site; the bold printed bases are complementary to the bold printed bases of primer MF30-Rechts (see below); a BamHI site to be introduced into the construct is printed in italic; the non-marked sequence anneals with the stop codon and the six terminal His codons of E2 (384-673)-VIEGR-H6 (SEQ ID NO:5).

The reaction mixture was constituted as follows: total volume of 50 μL containing 20 ng of the 1.33 kb EcoRI/BglII fragment of pSP72E2H6, each 0.2 μM of primers MF30E2/F and MF30E2/R, dNTP's (each 0.2 μM), 1× buffer 2 (Expand Long Template PCR System; Boeringer; Cat No 1681 834), 2.5 U polymerase mix (Expand Long Template PCR System; Boeringer; Cat No 1681 834).

The PCR program 3 consisting of the following steps was used:

1. denaturation: 5 min at 95° C.
2. 10 cycles of 30 sec denaturation at 95° C., 30 sec annealing at 65° C., and 1 min elongation at 68° C.
3. termination at 4° C.

Then 10 μL 10× buffer 2 (Expand Long Template PCR System; Boeringer; Cat No 1681 834), 40 μL $H_2O$, and 5 μL of [dATP, dGTP, and dTTP (2 mM each); 10 mM 5-methyl-dCTP] have been added to the sample derived from PCR program 3, and it has been continued with PCR program 4 consisting of the following steps:

1. denaturation: 5 min at 95° C.
2. 5 cycles of 45 sec denaturation at 95° C., 30 sec annealing at 65° C., and 1 min elongation at 68° C.
3. termination at 4° C.

Generation of pMF30-derived Acceptor Plasmid

The second fragment originated from the plasmid pMF30 (SEQ ID NO:28, FIG. 13), the amplicon was almost the complete pMF30 plasmid excluding the codons of the mature α-amylase of *S. occidentalis*, modifications relevant for cloning were introduced by primer design. The following set of primers was used:

- primer MF30-Links: 5'-agtca <u>ctcttc</u>a.cctcttgtcaaaaataatcggttgag-3' (SEQ ID NO:29; the Eam1104I site is underlined, the dot marks the enzyme's cleavage site; the bold printed "cct" is complementary to the bold printed "agg" of primer MF30E2/F (see above); the non-marked and the bold printed bases anneal with the 26 terminal bases of the codons of the α-Amylase of *S. occidentalis* in pMF30);
- primer MF30-Rechts: 5'-agtca <u>ctcttc</u>a.ctgcaggcatgcaagcttggcg-3' (SEQ ID NO: 11; the Eam1104I site is underlined, the dot marks the enzyme's cleavage site; the bold printed "ctg" is complementary to the bold printed "cag" of primer MF30E2/R (see above); the non-marked bases anneal with pUC18 sequences downstream of the stop codon of the α-Amylase of *S. occidentalis* in pMF30).

The reaction mixture was constituted as follows: total volume of 50 μL containing 20 ng of the BglII-linearized pMF30, each 0.2 MM of primers MF30-Links and MF30-Rechts, dNTP's (each 0.2 μM), 1× buffer 1 (Expand Long Template PCR System; Boeringer; Cat No 1681 834), 2.5 U polymerase mix (Expand Long Template PCR System; Boeringer; Cat No 1681 834). The same PCR programs (programs 3 and 4) as described above were used, except for the elongation times which were extended from 1 minute to 4 minutes in both programs.

Generation of Vector pAMY-E2

The E2s-H6 encoding DNA fragment and pMF30-derived acceptor plasmid obtained by PCR were controlled on their respective size by gel electrophoresis on a 1% agarose gel. The PCR products were purified with a PCR product purification kit (Qiagen) according to the supplier's instructions. Subsequently the purified fragments were digested separately with Eam11004I. Ligation of the E2s-H6 fragment with the pMF30-derived acceptor plasmid was performed by using T4 ligase (Boehringer) according to the supplier's recommendations. The ligation mixture was used to transform E.coli DH5αF' cells and the plasmid DNA of several clones was analyzed by EcoRI/BamHI digestion. A positive clone was selected, its plasmid further denominated as pAMY-E2, and utilized for further modifications as described below.

Generation of Vector pUC18-CL-E2-H6

The pAMY-E2 was subjected to PCR-directed mutagenesis in order to replace the codons of the α-amylase signal sequence with the codons of the avian lysozyme pre sequence. This is further denominated as "CL", corresponding to the first 18 amino acids of avian lysozyme ORF (SEQ ID NO:1). For this mutagenesis following primers were used:

```
primer CL2 hin:
5'-tgcttcctaccactagcagcactaggacatacccgcgtgtcaggaggggcag-3'; and    (SEQ ID NO:30)

primer CL2 her:
5'-tagtactagtattagtaggcttcgcatggaattcactggccgtcgttttacaacgtc-3'.    (SEQ ID NO:31)
```

The underlined 5'-regions of the primers contain the DNA sequence of about half of the avian lysozyme pre sequence. Primer CL2 her includes SpeI (italic) and EcoRI (italic, double underlined) restriction sites. The non-underlined regions of the primers anneal with the codons of amino acid residues 384 to 392 of E2 (CL2 hin) or the with the "atg" start codon over the EcoRI site up to position -19 (counted from the EcoRI site) of FMD promoter. The primers are designed to amplify the complete pAMY-E2 vector thereby replacing the codons of the α-amylase signal sequence with the codons of the avian lysozyme pre-sequence.

The PCR reaction was performed according to the following program:
1. denaturation: 15 min at 95° C.
2. 35 cycles of 30 sec denaturation at 95° C., 1 min annealing at 60° C., and 1 min elongation at 72° C.
3. termination at 4° C.

The following reaction mixture was used: pAMY-E2 (1 ng/μL), 1 μL; primer CL2 hin (100 μM), 2 μL; primer CL2 her (100 μM), 2 μL; dNTP's (2.5 mM each), 8 μL; H₂O, 76 μL; Expand Long Template PCR System (Boeringer; Cat No 1681 834) Buffer 2 (10× concentrated), 10 μL; Expand Long Template PCR System Polymerase mixture (1U/μL), 0.75 μL.

The resulting PCR product was checked by gel electrophoresis on a 1% agarose gel. Prior to ligation the PCR fragment was modified as follows. The 3'-A overhangs were removed by T4 polymerase resulting in blunt ends with 3'- and 5'-OH-groups. Thereto 1 μL T4 polymerase (Boehringer, 1U/μL) was added to the residual 95 μL PCR reaction mixture along with 4 μL dNTP's (2.5 mM each). The sample was incubated for 20 min at 37° C. Subsequently the DNA was precipitated with ethanol and dissolved in 16 μL deionized water. This was followed by a kinase treatment to add 5'-phosphates to the blunt-ended PCR product. To the 16 μL dissolved blunt-ended PCR product were added 1 μL T4 polynucleotide kinase (Boehringer, 1U/μL), 2 μL 10-fold concentrated T4 polynucleotide kinase reaction buffer (Boehringer) and 1 μL ATP (10 mM). The sample was incubated for 30 min at 37° C.

The kinase treated sample was subsequently separated on a 1% agarose gel. The product band was isolated. The DNA was extracted from the agarose slice by means of the Gel Extraction kit (Qiagen) according to the supplier's recommendations. Fifty (50) ng of the purified product was then self-ligated by use of T4 ligase (Boehringer) according to the supplier's conditions. After 16 h incubation at 16° C., the DNA in the ligation mix was precipitated with ethanol and dissolved in 20 μL H₂O (ligation sample).

E.coli DH5αF' cells were transformed with 10 μL of the ligation sample. Several ampicillin-resistant clones were further characterized via restriction analysis of the isolated plasmid DNA. A positive clone was denominated as pUC18-CL-E2-H6 and was used for further modifications as described below.

Generation of Shuttle Vector pFPMT-CL-E2-H6

A 0.966 kb EcoRI/BamHI fragment was isolated from pUC18-CL-E2-H6 (harboring CL-E2(384-673)-VIEGR-H6 and was ligated into the EcoRI/BamHI-digested pFPMT121 (SEQ ID NO:12, FIG. 3). For the reaction, T4 ligase (Boehringer) was used according to the supplier's conditions. The ligation sample was precipitated with ethanol and dissolved in 10 μL water. This was used to transform E.coli DH5αF' cells, a positive clone was withheld after restriction analysis and the respective plasmid is denominated pFPMT-CL-E2-H6 (SEQ ID NO:32, FIG. 14).

Example 5

Construction of pFPMT-CL-K-H6-E1 Shuttle Vector

The construction of the shuttle vector was comprised of two steps.

In a first step the pUC18-FMD-CL-H6-K-E1-H6 construct was constructed by site-directed mutagenesis. The pUC18-FMD-CL-E1-H6 was used as template (SEQ ID NO:20; FIG. 7). The following primers were used:

Primer H6K hin neu: 5'-catcacaaatatgaggtgcgcaacgtgtccgggatgtac-3' (SEQ ID NO:37).

Primer H6KRK her neu: 5'-gtgatggtggtgtcctagtgctgctagtggtaggaagcatag-3' (SEQ ID NO:38).

(The bases providing additional codons are underlined.)

The PCR reaction mixture was constituted as follows: pUC18-FMD-CL-E1-H6 (2 ng/μL), 1 μL; primer H6K hin neu (100 μM), 2 μL; primer H6KRK her neu (100 μM), 2 μL; dNTP's (2.5 mM each), 8 μL; H₂O, 76 μL; Expand Long Template PCR System (Boeringer; Cat No 1681 834) Buffer 2 (10× concentrated), 10 μL; Expand Long Template PCR System Polymerase mixture (1 U/μL), 0.75 μL.

The PCR program used consisted of the following steps:

denaturation step: 15 min at 95° C.

35 cycles of 30 sec denaturation at 95° C., 1 min annealing at 60° C., and 5 min elongation at 72° C.

termination at 4° C.

An aliquot of the PCR sample was analyzed on a 1% agarose gel to check its size, which was correct (~4.2 kb).

Thereafter the 3'-A overhangs from the PCR product were removed by a T4 polymerase reaction resulting in blunt ends with 3'- and 5'-OH groups. Therefore, to the remaining 95 μL of the PCR reaction were added 1 μL T4 polymerase (Boehringer; 1 U/μL) and 4 μL dNTP's (2.5mM each). The sample was incubated for 20 min at 37° C. Subsequently, the DNA in the sample was precipitated with ethanol and dissolved in 16 μL $H_2O$.

Subsequently 5'-phosphates were added to the blunt-ended PCR product by a kinase reaction. Therefore, to the 16 μL dissolved blunt-ended PCR product were added 1 μL T4 polynucleotide kinase (Boehringer; 1 U/μL), 2 μL 10-fold concentrated T4 polynucleotide kinase reaction buffer (Boehringer), and 1 μL ATP (10 mM). The sample was incubated for 30 min at 37° C.

Subsequently the sample was applied onto a 1% agarose gel and the correct product band was isolated, by means of the gel extraction kit (Qiagen) according to the supplier's conditions. Fifty (50) ng of the purified product has then been self-ligated by use of T4 ligase (Boehringer) according to the supplier's recommendations. After 72 h incubation at 16° C. the DNA in the ligation sample was precipitated with ethanol and dissolved in 10 μL water. *E.coli* DH5αF' cells were transformed with 5 μL of the ligation sample. The plasmid DNA of several ampicillin-resistant colonies was analyzed by restriction enzyme digestion, a positive clone was withheld and the corresponding plasmid denominated: pUC18-FMD-CL-H6-E1-K-H6 (SEQ ID NO:39, FIG. 17).

In a second step the transfer vector was constructed by a two-fragment ligation. In the following construction fragments with BclI cohesive ends were involved. Since BclI can cleave its site only on unmethylated DNA, an *E. coli* dam strain was transformed with the involved plasmids pUC18-FMD-CL-H6-K-E1-H6 (SEQ ID NO:39, FIG. 17) and pFPMT-CL-E1 (SEQ ID NO:36, FIG. 16). From each transformation, an ampicillin-resistant colony was picked, grown in a liquid culture and the unmethylated plasmid DNAs were prepared for the further use. The 1.273 kb BclI/HindIII fragment of the unmethylated plasmid pUC18-FMD-CL-H6-K-E1-H6 (harbouring the FMD promoter, the codons of the CL-H6-K unit, and the start of E1) and the 6.057 kb BclI/HindIII fragment of plasmid pFPMT-CL-E1 (harbouring the missing part of the E1 reading frame starting from the BclI site, without C-terminal His tag, as well as the pFPMT121-located elements except for the FMD promoter) were prepared and ligated together for 72 h at 16° C. by use of T4 ligase (Boehringer) in a total volume of 20 μL according to the supplier's specifications. Subsequently, the ligation mixture was placed on a piece of nitrocellulose membrane floating on sterile deionized water in order to desalt the ligation mixture (incubation for 30 min at room temperature). *E. coli* TOP10 cells were transformed by electroporation with 5 μL of the desalted sample. The plasmid DNA of several resulting ampicillin-resistant colonies was analyzed by restriction enzyme digestion. A positive clone was withheld and denominated pFPMT-CL-H6-K-E1 (SEQ ID NO:40, FIG. 18).

Example 6

Transformation of *Hansenula Polymorpha* and Selection of Transformants

*H. polymorpha* strain RB11 was been transformed (PEG-mediated DNA uptake protocol essentially as described by (Klebe, R. J. et al. 1983) with the modification of (Roggenkamp, R. et al. 1986) with the different parental shuttle vectors as described in Examples 1 to 5. For each transformation, 72 uracil-prototrophic colonies were selected and used for strain generation by the following procedure. For each colony, a 2 mL liquid culture was inoculated and grown in test tubes for 48 h (37° C.; 160 rpm; angle 45°) in selective medium (YNB/glucose, Difco). This step is defined as the first passaging step. A 150 μL aliquot of the cultures of the first passaging step were used to inoculate 2 mL fresh YNB/glucose medium. Again, the cultures have been incubated as described above (second passaging step). Together, eight of such passaging steps were carried out. Aliquots of the cultures after the third and the eighth passaging steps were used to inoculate 2 mL of non-selective YPD medium (Difco). After 48 h of incubation at 37° C. (160 rpm; angle 45°; the so-called first stabilization step), 150 μL aliquots of these YPD cultures have been used to inoculate fresh 2 mL YPD cultures which were incubated as described above (second stabilization step). Aliquots of the cultures of the second stabilization step were then streaked on plates containing selective YNB/agar. These plates were incubated for four days until macroscopic colonies became visible. A well-defined single colony of each separation was defined as strain and used for further expression analysis.

Expression analysis was performed on small-scale shake flask cultures. A colony was picked from the above mentioned YNB/agar plate and inoculated in 2 mL YPD and incubated for 48 h as mentioned above. This 2 rnL-aliquot was used as seed culture for 20 mL shake flask culture. YPGlycerol (1%) was used as medium and the shake flask was incubated on a rotary shaker (200 rpm, 37° C.). After 48 h of growth 1% MeOH was added to the culture for induction of the expression cassette. At different time intervals cell pellets of 1 mL aliquots were collected and stored at −20° C. until further analysis. Specific protein expression was analyzed by SDS-PAGE/Western blotting. Therefore cell pellets were solubilized in sample-buffer (TrisHCl-SDS) and incubated for >15 minutes at 95° C. Proteins were separated on a 15% polyacryl-amide gel and blotted (wet-blot; bicarbonate buffer) onto nitrocellulose membranes. Blots were developed using a specific murine anti-E1 (IGH 201) or murine anti-E2 (IGH 216, described by Maertens et al. in WO96/04385) as first antibody, Rabbit-Anti-Mouse-AP was used as second antibody. Staining was performed with NBT-BCIP.

Positive strains were withheld for further investigation.

Five of these positive clones were used in a shake flask expression experiment. A colony of the respective strain was picked from YNB plate and used to inoculate 2 mL YPD. These cultures were incubated as described above. This cell suspension was used to inoculate a second seed culture of 100 mL YPD medium in a 500 mL shake flask. This shake flask was incubated on a rotary shaker for 48 h at 37° C. and 200 rpm. A 25 mL aliquot of this seed culture was used to inoculate 250 mL YPGlycerol (1%) medium and was incubated in a baffled 2-1 shake flask under the above described conditions. 48 h after inoculation 1% MeOH (promotor induction) was added and the shake flasks were further incubated under the above described conditions. 24 h post induction, the experiment was stopped and cell pellets collected by centrifugation. The expression level of the five different clones was analyzed by SDS-PAGE/Western blotting (conditions as above). A titration series of each clone was loaded onto the gel and the most productive strain was selected for further fermentation and purification trials.

Surprisingly, *H. polymorpha*, a yeast strain closely related to *Pichia pastoris* (Gellissen, G. 2000), is able to express HCV proteins essentially without hyperglycosylation and thus with sugar moieties comparable in size to the HCV envelope proteins expressed by HCV-recombinant *vaccinia* virus-infected mammalian cells.

The *Hansenula polymorpha* strain RB11 was deposited on Apr. 19, 2002 under the conditions of the Budapest Treaty at the Mycothèque de l'UCL (MUCL), Universitè Catholique de Louvain, Laboratoire de mycologie, Place Croix du Sud 3 bte 6, B-1348 Louvain-la-Neuve, Belgium and has the MUCL accession number MUCL43805.

Example 7

Construction of pSY1aMFE1sH6a Vector

The *S. cerevisiae* expression plasmid was constructed as follows. An E1-coding sequence was isolated as a NsI1/Eco52I fragment from pGEMT-E1sH6 (SEQ ID NO:6, FIG. 1) which was made blunt-ended (using T4 DNA polymerase) and cloned in the pYIG5 vector (SEQ ID NO:41, FIG. 19) using T4 DNA ligase (Boehringer) according to the supplier's specifications. The cloning was such that the E1s-H6 encoding fragment was joined directly and in frame to the αMF-coding sequence. The ligation mixture was transformed in *E.coli* DH5αF' cells. Subsequently, the plasmid DNA of several ampicilin resistant clones was analyzed by restriction digestion and a positive clone was withheld and denominated as pYIG5E1H6 (ICCG3470; SEQ ID NO:42, FIG. 20).

Figure 43:
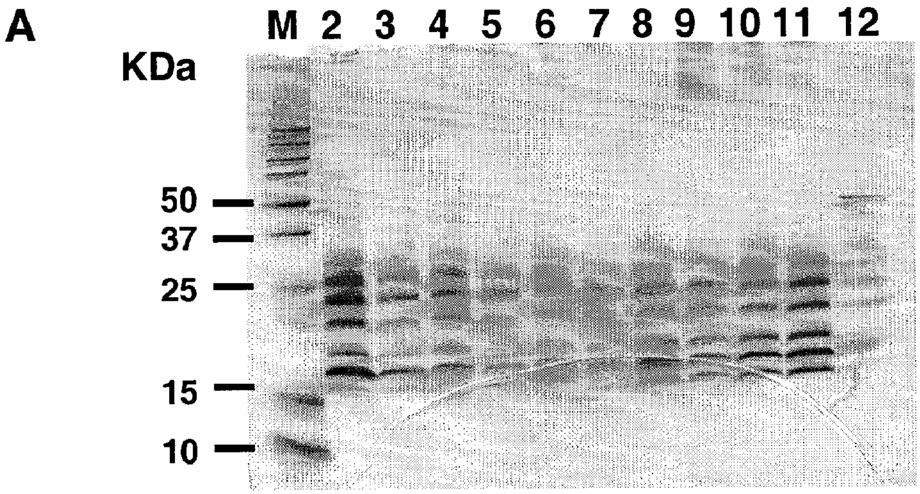
Figure 43:
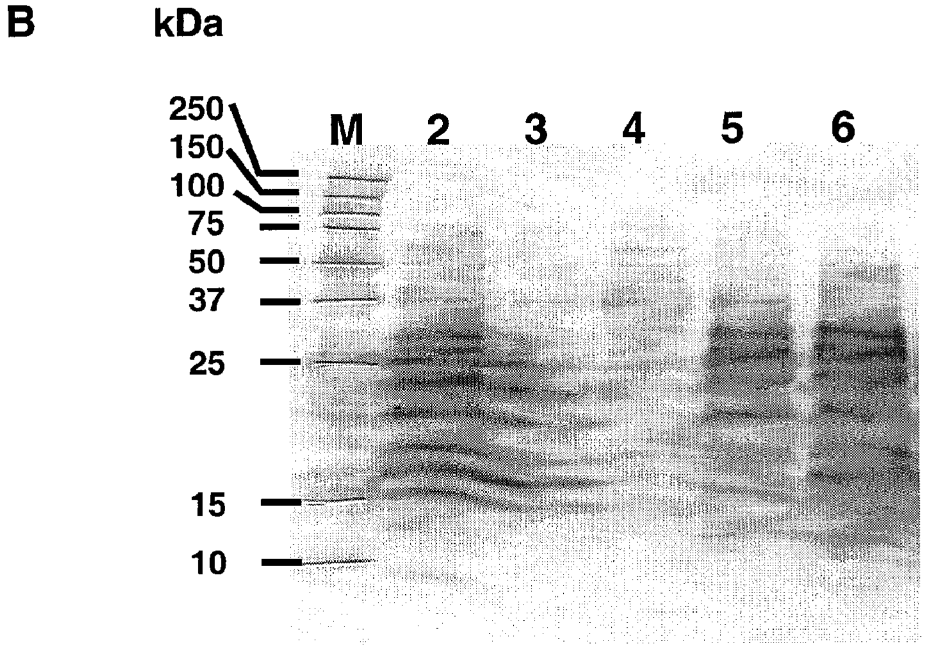

The expression cassette (containing the αMF-sequence and the E1s-coding region with a His-tag) was transferred as a BamHI fragment (2790 bp) of pYIG5E1H6 into the BamHI-digested *E coli/S. cerevisiae* pSY1 shuttle vector (SEQ ID NO:43, FIG. 43). The ligation was performed with T4 DNA ligase (Boehringer) according to supplier's conditions. The ligation mix was transformed to *E. coli* DH5αF' cells, and the plasmid DNA of several ampicilin resistant colonies was analyzed by restriction enzyme digestion. A positive clone was withheld and denominated pSY1aMFE1sH6a (ICCG3479; SEQ ID NO:44, FIG. 22).

Example 8

Construction of pSYYIGSE2H6 Vector

The *S. cerevisiae* expression plasmid pSYYIGSE2H6 was constructed as follows. An E2 coding sequence was isolated as a SalI/KpnI fragment from pBSK-E2sH6 (SEQ ID NO:45, FIG. 23) which was made blunt-ended (using T4 DNA polymerase) and subsequently cloned in the pYIG5 vector (SEQ ID NO:41, FIG. 19) using T4 DNA ligase (Boehringer) according to the supplier's specifications. The cloning was such that the E2-H6 encoding fragment was joined directly and in frame to the αMF-coding sequence. The ligation mixture was then transformed to *E. coli* DH5αF' cells, the plasmid DNA of several ampicilin resistant clones was analyzed by restriction digestion and a positive clone withheld and denominated as pYIG5HCCL-22aH6 (ICCG2424; SEQ ID NO:46, FIG. 24).

The expression cassette (containing the αMF-sequence and the E2 (384-673) coding region with a His-tag) was transferred as a BamHI fragment (3281 bp) of pYIG5HCCL-22aH6 into the BamHI opened *E. coli/S. cerevisiae* pSY1 shuttle vector (SEQ ID NO:43, FIG. 21). The ligation was performed with T4 DNA ligase (Boehringer) according to supplier's conditions. The ligation mix was transformed to *E. coli* DH5αF' cells and the plasmid DNA of several ampicilin resistant colonies was analyzed by restriction enzyme digestion. A restriction positive clone was withheld and denominated pSYYIGSE2H6 (ICCG2466; SEQ ID NO:47, FIG. 25).

Example 9

Construction of pSY1YIG7E1s Vector

The *S. cerevisiae* expression plasmid pSY1YIG7E1s was constructed as follows. An E1 coding sequence was isolated as a NsI1/Eco52I fragment from pGEMT-E1s (SEQ ID NO:6, FIG. 1) which was made blunt-ended and cloned into the pYIG7 vector (SEQ ID NO:48, FIG. 26) using T4 DNA ligase (Boehringer) according to the supplier's specifications. The cloning was such that the E1-encoding fragment was joined directly and in frame to the αMF-coding sequence. The ligation mixture was transformed to *E. coli* DH5αF' cells, the plasmid DNA of several ampicilin resistant clones analyzed by restriction digestion and a positive clone withheld and denominated as pYIG7E1 (SEQ ID NO:49, FIG. 27).

The expression cassette (containing the CL leader sequence and the E1 (192-326) coding region) was transferred as a BamHI fragment (2790 bp) of pYIG7E1 into the BamHI-digested *E. coli/S. cerevisiae* pSY1 shuttle vector (SEQ ID NO:43, FIG. 21). The ligation was performed with T4 DNA ligase (Boehringer) according to supplier's conditions. The ligation mix was transformed to *E. coli* DH5αF' cells and the plasmid DNA of several ampicilin resistant colonies was analyzed by restriction enzyme digestion. A positive clone was withheld and denominated pSY1YIG7E1s (SEQ ID NO:50, FIG. 28).

Example 10

Transformation of *Saccharomyces Cerevisiae* and Selection of Transformants

In order to overcome hyper-glycosylation problems, often reported for proteins over-expressed in *Saccharomyces cerevisiae*, a mutant screening was set-up. This screening was based on the method of Ballou (Ballou, L. et al. 1991), whereby spontaneous recessive orthovanadate-resistant mutants were selected. Initial strain selection was performed based on the glycosylation pattern of invertase, as observed after native gel electrophoresis. A strain, reduced in glycosylation capabilities, was withheld for further recombinant protein expression experiments and denominated strain IYCC155. The nature of mutation has not been further studied.

Said glycosylation-deficient strain IYCC155 was transformed with the plasmids as described in Examples 7 to 9 essentially by to the lithium acetate method as described by Elble (Elble, R. 1992). Several Ura complemented strains were picked from a selective YNB+2% agar plate (Difco) and used to inoculate 2 ml YNB+2% glucose. These cultures were incubated for 72 h, 37° C., 200 rpm on orbital shaker, and the culture supernatant and intracellular fractions were analysed for expression of E1 by western blot developed with a E1 specific murine monoclonal antibody (IGH 201). A high producing clone was withheld for further experiments.

The expression of proteins in the *S. cerivisiae* glycosylation deficient mutant used here is hampered by the suboptimal growth characteristics of such strains which leads to a lower biomass yield and thus a lower yield of the desired proteins compared to wild-type *S. cerivisiae* strains. The yield of the desired proteins was still substantially higher than in mammalian cells.

Example 11

Construction of pPICZalphaD'E1sH6 and pPICZalphaE'E1sH6 Vectors

The shuttle vector pPICZalphaE'E1sH6 was constructed starting from the pPICZalphaA vector (Invitrogen; SEQ ID NO:51, FIG. 29). In a first step said vector was adapted in order to enable cloning of the E1 coding sequence directly behind the cleavage site of the KEX2 or STE13 processing proteases, respectively. Therefore pPICZalphaA was digested with XhoI and NotI. The digest was separated on a 1% agarose gel and the 3519 kb fragment (major part of vector) was isolated and purified by means of a gel extraction kit (Qiagen). This fragment was then ligated using T4 polymerase (Boehringer) according to the supplier's conditions in presence of specific oligonucleotides yielding pPICZalphaD' (SEQ ID NO:52, FIG. 30) or pPICZalphaE' (SEQ ID NO:53, FIG. 31).

The following oligonucleotides were used:

```
for constructing pPICZalphaD':
                                        (SEQ ID NO:54)
8822:    5'-TCGAGAAAAGGGGCCCGAATTCGCATGC-3'; and

                                        (SEQ ID NO:55)
8823:    5'-GGCCGCATGCGAATTCGGGCCCCTTTTC-3'
which yield, after annealing, the linker oligo-
nucleotide:

TCGAGAAAAGGGGCCCGAATTCGCATGC            (SEQ ID NO:54)

    CTTTTCCCCGGGCTTAAGCGTACGCCGG        (SEQ ID NO:55)

for constructing pPICZalphaE'
                                        (SEQ ID NO:56)
8649:    5'-TCGAGAAAAGAGAGGCTGAAGCCTGCAGCATATGC-3'

                                        (SEQ ID NO:57)
8650:    5'-GGCCGCATATGCTGCAGGCTTCAGCCTCTCTTTTC-3'
which yield, after annealing, the linker oligo-
nucleotide:

TCGAGAAAAGAGAGGCTGAAGCCTGCAGCATATGC     (SEQ ID NO:56)

                                        (SEQ ID NO:57)
    CTTTTCTCTCCGACTTCGGACGTCGTATACGCCGG
```

These shuttle vectors pPICZalphaD' and pPICZalphaE' have newly introduced cloning sites directly behind the cleavage site of the respective processing proteases, KEX2 and STE13. The E1-H6 coding sequence was isolated as a NsI1/Eco52I fragment from pGEMT-E1sH6 (SEQ ID NO:6, FIG. 1). The fragment was purified using a gel extraction kit (Qiagen) after separation of the digest on a 1% agarose gel. The resulting fragment was made blunt-ended (using T4 DNA polymerase) and ligated into either pPICZalphaD' or pPICZalphaE' directly behind the respective processing protease cleavage site.

The ligation mixtures were transformed to *E. coli* TOP10F' cells and plasmid DNA of several zeocin resistant colonies analyzed by restriction enzyme digestion. Positive clones were withheld and denominated pPICZalphaD'E1sH6 (ICCG3694; SEQ ID NO:58, FIG. 32) and pPICZalphaE'E1sH6 (ICCG3475; SEQ ID NO:59, FIG. 33), respectively.

Example 12

Construction of pPICZalphaD'E2sH6 and pPICZalphaE'E2sH6 Vectors

The shuttle vectors pPICZalphaD' and pPICZalphaE' were constructed as described in Example 11.

The E2-H6 coding sequence was isolated as a SalI/KpnI fragment from pBSK-E2sH6 (SEQ ID NO:45, FIG. 23). The fragment was purified with a gel extraction kit (Qiagen) after separation of the digest on a 1% agarose gel. The resulting fragment was made blunt-ended (using T4 DNA polymerase) and ligated into either pPICZalphaD' or pPICZalphaE' directly behind the respective processing protease cleavage site.

The ligation mixture was transformed to *E. coli* TOP10F' cellls and the plasmid DNA of several zeocin resistant colonies was analyzed by restriction enzyme digestion. Positive clone were withheld and denominated pPICZalphaD'E2sH6 (ICCG3692; SEQ ID NO:60, FIG. 34) and pPICZalphaE'E2sH6 (ICGG3476; SEQ ID NO:61, FIG. 35), respectively.

Example 13

Transformation of *Pichia Pastoris* and Selection of Transformants

The *P. pastoris* shuttle plasmids as described in Examples 11 and 12 were transformed to *P. pastoris* cells according to the supplier's conditions (Invitrogen). An E1- and an E2-producing strain were withheld for further characterization.

The HCV envelope proteins were expressed in *P. pastoris*, a yeast strain well known for the fact that hyperglycosylation is normally absent (Gellissen, G. 2000) and previously used to express dengue virus E protein as GST fusion (Sugrue, R. J. et al. 1997). Remarkably, the resulting *P. pastoris*-expressed HCV envelope proteins displayed a comparable glycosylation as is observed in wild-type *Saccharomyces* strains. More specifically, the HCV envelope proteins produced by *P. pastoris* are hyperglycosylated (based on the molecular weight of the expression products detected in western-blots of proteins isolated from transformed *P. pastoris* cells).

Example 14

Culture Conditions for *Saccharomyces Cerevisiae, Hansenula Polymorpha* and *Pichia Pastoris*

*Saccharomyces cerevisiae*

Cell banking

Of the selected recombinant clone a master cell bank and working cell bank were prepared. Cryo-vials were prepared from a mid-exponentially grown shake flask culture (incubation conditions as for fermentation seed cultures, see below). Glycerol was added (50% final conc.) as a cryoprotectant.

Fermentation

Seed cultures were started from a cryo-preserved working cell bank vial and grown in 500 mL medium (YNB supplemented with 2% sucrose, Difco) in a 2 L Erlenmeyer shake flasks at 37° C., 200 rpm for 48 h.

Fermentations were typically performed in Biostat C fermentors with a working volume of 15 L (B.Braun Int., Melsungen, Germany). The fermentation medium contained 1% Yeast Extract, 2% Peptone and 2% sucrose as carbon source. Poly-ethylene glycol was used as anti-foam agent.

Temperature, pH and dissolved oxygen were typically controlled during the fermentation, applicable set-points are summarised in Table 1. Dissolved oxygen was cascade controlled by agitation/aeration. pH was controlled by addition of NaOH (0.5 M) or $H_3PO_4$ solution (8.5 %).

TABLE 1

Typical parameter settings for *S. cerevisiae* fermentations

| Parameter | set-point |
|---|---|
| Temperature | 33-37° C. |
| pH | 4.2-5.0 |
| DO (growth phase) | 10-40% air saturation |
| DO (induction) | 0-5% |
| aeration | 0.5-1.8 vvm* |
| agitation | 150-900 rpm |

*volume replacement per minute

The fermentation was started by the addition of 10% seed-culture. During the growth phase the sucrose concentration was monitored off-line by HPLC analysis (Polysphere Column OAKC Merck).

During the growth phase the dissolved oxygen was controlled by cascade control (agitation/aeration). After complete metabolisation of sucrose the heterologous protein production was driven by the endogenous produced ethanol supplemented with stepwise addition of EtOH in order to maintain the concentration at approximately 0.5% (off-line HPLC analysis, polyspher OAKC column) During this induction phase the dissolved oxygen was controlled below 5% air-saturation, by manual adjustment of airflow rate and agitator speed.

Typically the fermentation was harvested 48 to 72 h post induction by concentration via tangential flow filtration followed by centrifugation of the concentrated cell suspension to obtain cell pellets. If not analyzed immediately, cell pellets were stored at −70° C.

*Hansenula polymorpha*

Cell banking

Of the selected recombinant clone a master cell bank and working cell bank were prepared. Cryo-vials were prepared from a mid-exponentially grown shake flask culture (incubation conditions as for fermentation seed cultures, see below). Glycerol was added (50% final conc.) as a cryoprotectant.

Fermentation

Seed cultures were started from a cryo-preserved (−70° C.) working cell bank vial and grown in 500 mL medium (YPD, Difco) in a 2 L Erlenmeyer shake flasks at 37° C., 200 rpm for 48 h. Fermentations were typically performed in Biostat C fermentors with a working volume of 15 L (B.Braun Int., Melsungen, Germany). The fermentation medium contained 1% Yeast Extract, 2% Peptone and 1% glycerol as carbon source. Poly-ethylene glycol was used as anti-foam agent.

Temperature, pH, air-in and dissolved oxygen were typically controlled during the fermentation, applicable set-points are summarised in Table 2. Dissolved oxygen was controlled by agitation. pH was controlled by addition of NaOH (0.5 M) or $H_3PO_4$ solution (8.5%).

TABLE 2

Typical parameter settings for *H. polymorpha* fermentations

| Parameter | set-point |
|---|---|
| Temperature | 30-40° C. |
| pH | 4.2-5.0 |
| DO | 10-40% air saturation |
| aeration | 0.5-1.8 vvm* |
| agitation | 150-900 rpm |

*volume replacement per minute

The fermentation was started by the addition of 10% seed-culture. During the growth phase the glycerol concentration was monitored off-line (Polysphere Column OAKC Merck) and 24 h after complete glycerol consumption 1% methanol was added in order to induce the heterologous protein expression. The fermentation was harvested 24 h post induction by concentration via tangential flow filtration followed by centrifugation of the concentrated cell suspension to obtain cell pellets. If not analyzed immediately, cell pellets were stored at −70° C.

*Pichia pastoris*

Small scale protein production experiments with recombinant *Pichia pastoris* were set up in shake flask cultures. Seed cultures were grown overnight in YPD medium (Difco). Initial medium pH was corrected to 4.5. Shake flasks were incubated on a rotary shaker at 200-250 rpm, 37° C.

The small scale production was typically performed at 500 mL scale in 2 L shake flasks and were started with a 10% inoculation in expression medium, containing 1% Yeast extract, 2% Peptone (both Difco), and 2% glycerol as carbon source. Incubation conditions were as for the seed culture. Induction was started by addition of 1% MeOH approximately 72 h after inoculation. The cells were collected 24 h post induction by centrifugation. If not analyzed immediately, cell pellets were stored at −70° C.

Example 15

Leader Peptide Removal from MFα-E1-H6 and MFα-E2-H6 Proteins Expressed in Selected Yeast Cells The expression products in *Hansenula polymorpha* and a *Saccharomyces cerevisiae* glycosylation minus strain of the HCV E1 and E2 protein constructs with the α-mating factor (αMF) leader sequence of *S. cerevisiae* were further analyzed. Since both genotype 1b HCV E1s (aa 192-326) and HCV E2s (aa 383-673 extended by the VIEGR (SEQ ID NO:69)-sequence) were expressed as C-terminal his-tagged (H6, HHHHHH, SEQ ID NO:63; said HCV proteins are further on in this Example denoted as αMF-E1-H6 and αMF-E2-H6) proteins, a rapid and efficient purification of the expressed products after guanidinium chloride (GuHCl)-solubilization of the yeast cells was performed on Ni-IDA (Ni-iminodiacetic acid). In brief, cell pellets were resuspended in 50 mM phosphate, 6M GuHCl, pH 7.4 (9 vol/g cells). Proteins were sulfonated overnight at room temperature (RT) in the presence of 320 mM (4% w/v) sodium sulfite and 65 mM (2% w/v) sodium tetrathionate. The lysate was cleared after a freeze-thaw cycle by centrifugation (10.000 g, 30 min, 4° C.) and Empigen (Albright & Wilson, UK) and imidazole were added to the supernatant to final concentrations of 1% (w/v) and 20 mM, respectively. The sample was filtrated (0.22 μM) and loaded on a Ni-IDA Sepharose FF column, which was equilibrated with 50 mM phosphate, 6M GuHCl, 1% Empigen (buffer A) supplemented with 20 mM imidazole. The column was washed sequentially with buffer A containing 20 mM and 50 mM imidazole, respectively, till absorbance at 280 nm reached baseline level. The his-tagged products were eluted by applying buffer D, 50 mM phosphate, 6M GuHCl, 0.2% (for E1) or 1% (for E2) Empigen, 200 mM imidazole. The eluted materials were analyzed by SDS-PAGE and western-blot using a specific monoclonal antibodies directed against E1 (IGH201), or E2 (IGH212).

The E1-products were immediately analyzed by Edman degradation.

Since at this stage, SDS-PAGE revealed already a very complex picture of protein bands for HCV E2, a further fractionation by size exclusion chromatography was performed. The Ni-IDA eluate was concentrated by ultrafiltration (MWCO 10 kDa, centriplus, Amicon, Millipore) and loaded on Superdex G200 (10/30 or 16/60; Pharmacia) in PBS, 1% Empigen or PBS, 3% Empigen. Elution fractions, containing E2 products, with a Mr between ~80 kDa and ~45 kDa, i.e. fractions 17-23 of the elution profile in FIG. 37 based on the migration on SDS-PAGE (FIG. 38), were pooled and alkylated (incubation with 10 mM DTT 3 h at RT followed by incubation with 30 mM iodo-acetamide for 3 hours at RT). Samples for amino-terminal sequencing were treated with Endo H (Roche Biochemicals) or left untreated. The glycosylated and deglycosylated E2 products were blotted on PVDF-membranes for amino-terminal sequencing. An amido-black stained blot of glycosylated and deglycosylated E2 is shown in FIG. 39.

The sequencing of both E1 and E2 purified products lead to the disappointing observation that removal of the signal sequence from the HCV envelope proteins is occurring only partially (see Table 3). In addition, the majority of the side products (degradation products and products still containing the leader sequence or part thereof) are glycosylated. This glycosylation resides even in part on the non-cleaved fragment of the signal sequence which contains also an N-glycosylation site. These sites can be mutated in order to result in less glycosylated side products. However, even more problematic is the finding that some alternatively cleaved products have only 1 to 4 amino acids difference compared to the desired intact envelope protein. Consequently, purification of the correctly processed product is virtually impossible due to the lack of sufficiently discriminating biochemical characteristics between the different expression products. Several of the degradation products may be a result of a Kex-2 like cleavage (e.g. the cleavage observed after aa 196 of E1 which is a cleavage after an arginine), which is also required for the cleavage of the α-mating factor leader and which can thus not be blocked without disturbing this essential process.

A high E1 producing clone derived from transformation of *S. cerevisiae* IYCC155 with pSY1YIG7E1s (SEQ ID NO:50; FIG. 28) was compared with a high producing clone derived from transformation of *S. cerevisiae* IYCC155 with pSY1ME1sH6aYIG1E1s (SEQ ID NO:44; FIG. 22). The intracellular expression of the E1 protein was evaluated after 2 up to 7 days after induction, and this by means of Western-blot using the E1 specific monoclonal antibody (IGH 201). As can be judged from FIG. 40, maximal expression was observed after 2 days for both strains but the expression patterns for both strains are completely different. Expression with the α-mating factor leader results in a very complex pattern of bands, which is a consequence from the fact that the processing of the leader is not efficient. This leads to several expression products with a different amino-terminus and of which some are Modified by 1 to 5 N-glycosyiations. However, for the E1 expressed with the CL leader a limited number of distinct bands is visible which reflects the high level of correct CL leader removal and the fact that only this correctly processed material may be modified by N-glycosylation (1 to 5 chains), as observed for *Hansenula*-derived E1 expressed with the same CL leader (see Example 16).

The hybridoma cell line producting the monoclonal antibody directed against E1 (IGH201) was deposited on Mar. 12, 1998 under the conditions of the Budapest Treaty at the European Collection of Cell Cultures, Centre for Applied Microbiology & Research, Salisbury, Wiltshire SP4 0JG, UK, and has the accession number ECACC 98031216. The monoclonal antibody directed against E2 (IGH212) has been described as antibody 12D11F2 in Example 7.4 by Maertens et al. in WO96/04385.

Table 3. Identification of N-termini of αMF-E1-H6 and αMF-E2-H6 proteins expressed in *S. cerevisiae* or *H. polymorpha*. Based on the N-terminal sequencing the amount of N-termini of the mature E1-H6 and E2-H6 proteins could be estimated ("mature" indicating correct removal of the αMF signal sequence). The total amount of protein products was calculated as pmol of protein based on the intensity of the peaks recovered by Edman degradation. Subsequently, for each specific protein (i.e. for each 'detected N-terminus') the mol % versus the total was estimated.

| Yeast | αMF-E1-H6 | αMF-E2-VIEGR-H6 |
|---|---|---|
| *S. cerevisiae* | Experiment 1: | / |
| | 16% of proteins still containing αMF sequences<br>18% of proteins cleaved between aa 195 and 196 of E1<br>66% of proteins with correctly removed αMF | |
| | Experiment 2 | / |
| | 18% of proteins still containing αMF sequences<br>33% of proteins cleaved between aa 195 and 196 of E1<br>8% of other proteins other E1 cleavage products<br>44% of proteins with correctly removed αMF | |
| *H. polymorpha* | 64% of proteins still containing αMF sequences<br>6% of proteins cleaved between aa 192 and 193 of E1<br>30% of proteins with correctly removed αMF | 75% of proteins still containing αMF sequences<br>25% of proteins with correctly removed αMF |

Example 16

Expression of an E1 Construct in Yeast Suitable for Large Scale Production and Purification Several other leader sequences were used to replace the *S. cerevisiae* αMF leader peptide including CHH (leader sequence of *Carcinus maenas* hyperglycemic hormone), Amy1 (leader sequence of amylase from *S. occidentalis*), Gam1 (leader sequence of glucoamylase from *S. occidentalis*), Phy5 (leader sequence from fungal phytase), pho1 (leader sequence from acid phosphatase from *Pichia pastoris*) and CL (leader of avian lysozyme C, 1,4-beta-N-acetylmuramidase C) and linked to E1-H6 (i.e. E1 with C-terminal his-tag). All constructs were expressed in *Hansenula polymorpha* and each of the resulting cell lysates was subjected to western blot analysis. This allowed already to conclude that the extent of removal of the leader or signal sequence or peptide was extremely low, except for the construct wherein CL is used as leader peptide. This was confirmed for the CHH-E1-H6 construct by Edman-degradation of Ni-IDA purified material: no correctly cleaved product could be detected although several different sequences were recovered (see Table 4).

TABLE 4

Identification of N-termini of CHH-E1-H6 proteins expressed in *H. polymorpha*, based on N-terminal amino acid sequencing of different protein bands after separation by SDS-PAGE and blotting to a PVDF membrane.

| Molecular size | Identified N-termini |
|---|---|
| 45 kD | starts at amino acid 27 of CHH leader = only pre-sequence cleaved, pro-sequence still attached |
| 26 kD | partially starts at amino acid 1 of CHH leader = no removal of pre-pro-sequence |
| | partially starts at amino acid 9 of CHH leader = product of alternative translation starting at second AUG codon |
| 24 kD | partially starts at amino acid 1 of CHH leader = no removal of pre-pro-sequence |
| | partially starts at amino acid 9 of CHH leader = product of alternative translation starting at second AUG codon |

As mentioned already, the western-blots of the cell lysates revealed a pattern of E1 specific protein bands, indicative for a higher degree of correct removal of the CL leader peptide. This is surprising since this leader is not derived from a yeast. Amino acid sequencing by Edman degradation of GuHCl solubilized and Ni-IDA purified material indeed confirmed that 84% of the E1 proteins is correctly cleaved and the material is essentially free of degradation products. Still 16% of non-processed material is present but since this material is non-glycosylated it can be easily removed from the mixture allowing specific enrichment of correctly cleaved and glycosylated E1. Such a method for enrichment may be an affinity chromatography on lectins, other alternatives are also given in Example 19. Alternatively, the higher hydrophobic character of the non-glycosylated material may be used to select and optimize other enrichment procedures. The correct removal of the CL leader peptide from the CL-E1-H6 protein was further confirmed by mass spectrometry which also confirmed that up to 4 out of the 5 N-glycosylation sites of genotype 1b E1s can be occupied, whereby the sequence NNSS (amino acids 233 to 236; SEQ ID NO:73) are considered to be a single N-glycosylation site.

Example 17

Purification and Biochemical Characterization of the HCV E2 Protein Expressed in *Hansenula Polymorpha* from the CL-E2-H6 Encoding Construct The efficiency of removal of the CL leader peptide from CL-E2-VIEGR-H6 (further on in this Example denoted as "CL-E2-H6") protein expressed in *Hansenula polymorpha* was analyzed. Since the HCV E2s (aa 383-673) was expressed as a his-tagged protein, a rapid and efficient purification of the expressed protein after GuHCl-solubilization of collected cells was performed on Ni-IDA. In brief, cell pellets were resuspended in 30 mM phosphate, 6 M GuHCl, pH 7.2 (9 mL buffering cells). The protein was sulfonated overnight at room temperature in the presence of 320 mM (4% w/v) sodium sulfite and 65 mM (2% w/v) sodium tetrathionate. The lysate was cleared after a freeze-thaw cycle by centrifugation (10.000 g, 30 min, 4° C.). Empigen BB (Albright & Wilson) and imidazole were added to a final concentration of 1% (w/v) and 20 mM, respectively. All further chromatographic steps were executed on an Akta FPLC workstation (Pharmacia). The sample was filtrated through a 0.22 μm pore size membrane (cellulose acetate) and loaded on a Ni-IDA column (Chelating Sepharose FF loaded with $Ni^{2+}$, Pharmacia), which was equilibrated with 50 mM phosphate, 6 M GuHCl, 1% Empigen BB, pH 7.2 (buffer A) supplemented with 20 mM imidazole. The column was washed sequentially with buffer A containing 20 mM and 50 mM imidazole, respectively, till the absorbance at 280 nm reached the baseline level. The his-tagged products were eluted by applying buffer D, 50 mM phosphate, 6 M GuHCl, 0.2% Empigen BB (pH 7.2), 200 mM imidazole. The purified materials were analysed by SDS-PAGE and western-blot using a specific monoclonal antibody directed against E2 (IGH212) (FIG. 41). The IMAC-purified E2-H6 protein was also subjected to N-terminal sequencing by Edman degradation. Thereto proteins were treated with N-glycosidase F (Roche) (0.2 U/μg E2, 1 h incubation at 37° C. in PBS/3% empigen BB) or left untreated. The glycosylated and deglycosylated E2-H6 proteins were subjected to SDS-PAGE and blotted on a PVDF-membrane for amino acid sequencing (analysis was performed on a PROCISE™ 492 protein sequencer, Applied Biosystems). Since at this stage, SDS-PAGE revealed some degradation products, a further fractionation by size exclusion chromatography was performed. Hereto, the Ni-IDA eluate was concentrated by ultrafiltration (MWCO 10 kDa, centriplus, Amicon, Millipore) and loaded on a Superdex G200 (Pharmacia) in PBS, 1% Empigen BB. Elution fractions, containing mainly intact E2s related products with a Mr between ~30 kda and ~70 kDa based on the migration on SDS-PAGE, were pooled and eventually alkylated (incubation with 5 mM DTT for 30 minutes at 37° C., followed by incubation with 20 mM iodoacetamide for 30 minutes at 37° C.). The possible presence of degradation products after IMAC purification can thus be overcome by a further fractionation of the intact product by means of size exclusion chromotography. An unexpectedly good result was obtained. Based on the N-terminal sequencing the amount of E2 product from which the CL leader peptide is removed could be estimated. The total amount of protein products is calculated as pmol of protein based on the intensity of the peaks recovered by Edman degradation. Subsequently, for each specific protein (i.e. for each 'detected N-terminus') the mol % versus the total is estimated. In the current experiment, only the correct N-terminus of E2-H6 was detected and other variants of E2-H6 lacking amino acid of the E2 protein or containing N-terminal amino acids not comprised in the E2 protein were absent. In conclusion, the E2-H6 protein expressed by *H. polymorpha* as CL-E2-H6 protein was isolated without any further in vitro processing as a >95% correctly cleaved protein. This is in sharp contrast with the fidelity of leader peptide removal by *H. polymorpha* of the αMF-E2-H6 protein to the E2-H6 protein, which was estimated to occur in 25% of the isolated proteins (see Table 3).

Example 18

Purification and Biochemical Characterization of the HCV E1 Protein Expressed in *Hansenula Polymorpha* from the CL-H6-K-E1 Encoding Construct and In Vitro Processing of H6-Containing Proteins The efficiency of removal of the CL leader peptide from the CL-H6-K-E1 protein expressed in *H. polymorpha* was analyzed, as well as the efficiency of subsequent in vitro processing in order to remove the H6 (his-tag)-adaptor peptide and the Endo Lys-C processing site. Since the HCV E1s (aa 192-326) was expressed as a N-terminal His-K-tagged protein CL-H6-K-E1, a rapid and efficient purification could be performed as described in Example 17. The elution profile of the IMAC-chromatographic purification of H6-K-E1 (and possibly residual CL-H6-K E1) proteins is shown in FIG. 42. After SDS-PAGE and silver staining of the gel and western-blot analysis using a specific monoclonal antibody directed against E1 (IGH201) (FIG. 43), the elution fractions (63-69) containing the recombinant E1s products were pooled ('IMAC pool') and subjected to an overnight Endoproteinase Lys-C (Roche) treatment (enzyme/substrate ratio of 1/50 (w/w), 37° C.)in order to remove the H6-K-fusion tail. Removal of non-processed fusion product was performed by a negative IMAC chromatography step on a Ni-IDA column whereby Endo-Lys-C-processed proteins are collected in the flow-through fraction. Hereto the Endoproteinase Lys-C digested protein sample was applied on a Ni-IDA column after a 10-fold dilution with 10 mM $NaH_2PO_4.3H_2O$, 1% (v/v) Empigen B, pH 7.2 (buffer B) followed by washing with buffer B till the absorbance at 280 nm reached the baseline level. The flow through was collected in different fractions (1-40) that were screened for the presence of E1s-products (FIG. 44). The fractions (7-28), containing intact E1 from which the N-terminal H6-K (and possibly residual CL-H6-K) tail is removed (with a Mr between ~15 kDa and ~30 kDa based on the migration on SDS-PAGE followed by silver staining or western blot analysis using a specific monoclonal antibody directed against E1 (IGH201), were pooled and alkylated (incubation with 5 mM DTT for 30 minutes at 37° C., followed by incubation with 20 mM iodoacetamide for 30 minutes at 37° C.).

This material was subjected to N-terminal sequencing (Edman degradation). Hereto, protein samples were treated with N-glycosidase F (Roche) (0.2 U/µg E1, 1 h incubation at 37° C. in PBS/3% empigen BB) or left untreated. The glycosylated and deglycosylated E1 proteins were then separated by SDS-PAGE and blotted on a PVDF-membrane for further analysis by Edman degradation (analysis was performed on a PROCISE™ 492 protein sequencer, Applied Biosystems). Based on the N-terminal sequencing the amount of correctly processed E1 product could be estimated (processing includes correct cleavage of the H6-K-sequence). The total amount of protein products is calculated as pmol of protein based on the intensity of the peaks recovered by Edman degradation. Subsequently, for each specific protein (i.e. for each 'detected N-terminus') the mol % versus the total is estimated. In the current experiment, only the correct N-terminus of E1 was detected and not the N-termini of other processing variants of H6-K-E1. Based thereon, in vitro processing by Endo Lys-C of the H6-K-E1 E1 (and possibly residual CL-H6-K-E1) protein to the E1 protein was estimated to occur with a fidelity of more than 95%.

Example 19

Specific Removal of Low-Glycosylated Forms of HCV E1 by Heparin

Figure 45:
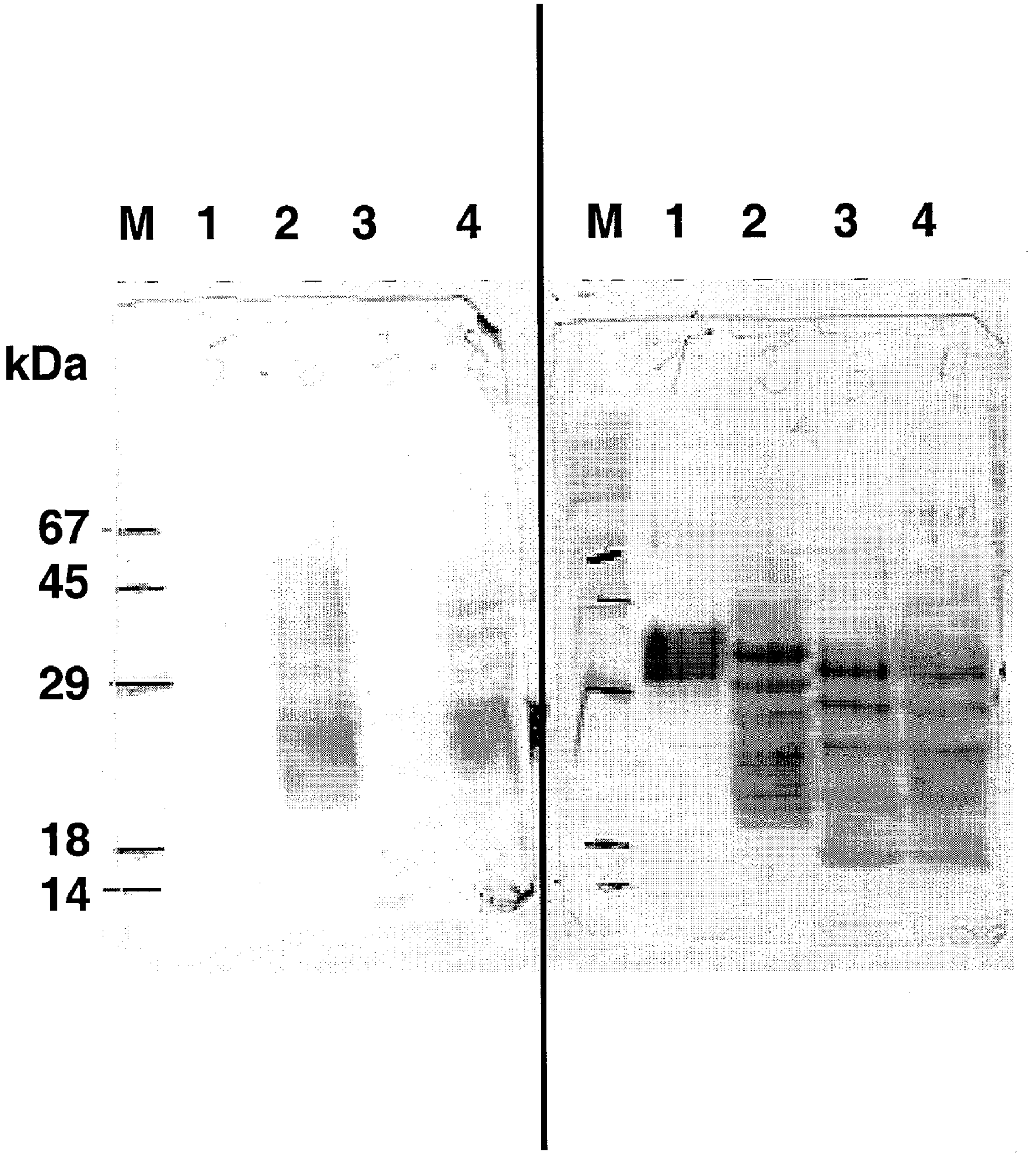

In order to find specific purification steps for HCV envelope proteins from yeast cells binding with heparin was evaluated. Heparin is known to bind to several viruses and consequently binding to the HCV envelope has already been suggested (Garson, J. A. et al. 1999). In order to analyze this potential binding, heparin was biotinylated and interaction with HCV E1 analyzed in microtiterplates coated with either sulfonated HCV E1 from *H. polymorpha*, alkylated HCV E1 from *H. polymorpha* (both produced as described in Example 16) and alkylated HCV E1 from a culture of mammalian cells transfected with a *vaccinia* expression vector. Surprisingly, a strong binding could only be observed with sulfonated HCV E1 from *H. polymorpha*, while binding with HCV E1 from mammalian cell culture was completely absent. By means of western-blot we could show that this binding was specific for the lower molecular weight bands of the HCV E1 protein mixture (FIG. 45), corresponding to low-glycosylated mature HCV E1s. FIG. 45 also reveals that sulfonation is not essential for heparin binding since upon removal of this sulfonation binding is still observed for the low molecular weight E1 (lane 4). Alternatively, alkylation is reducing this binding substantially, however, this may be caused by the specific alkylation agent (iodo-acetamide) used in this example. This finding further demonstrated the industrial applicability of the CL-HCV-envelope expression cassettes for yeast since we specifically can enrich HCV E1 preparations towards a preparation with HCV E1 proteins with a higher degree of glycosylation (i.e. more glycosylation sites occupied).

Example 20

Formation and Analysis of Virus-Like Particles (VLPs)

Conversion of the HCV E1 and E2 envelope proteins expressed in *H. polymorpha* (Examples 16 to 18) to VLPs was done essentially as described by Depla et al. in WO99/67285 and by Bosman et al. in WO01/30815. Briefly, after cultivation of the transformed *H. polymorpha* cells during which the HCV envelope proteins were expressed, cells were harvested, lysed in GuHCl and sulphonated as described in Example 17. His-tagged proteins were subsequently purified by IMAC and concentrated by ultrafiltration as described in Example 17.

VLP-formation of HCV Envelope Proteins with Sulphonated Cys-thiol Groups

The concentrated HCV envelope proteins sulphonated during the isolation procedure were not subjected to a reducing treatment and loaded on a size-exclusion chromatography column (Superdex G200, Pharmacia) equilibrated with PBS, 1% (v/v) Empigen. The eluted fractions were analyzed by SDS-PAGE and western blotting. The fractions with a relative Mr ~29-~15 kD (based on SDS-PAGE migration) were pooled, concentrated and loaded on Superdex G200, equilibrated with PBS, 3% (w/v) betain, to enforce virus like particle formation (VLP). The fractions were pooled, concentrated and desalted to PBS, 0.5% (w/v) betain.

VLP-formation of HCV Envelope Proteins with Irreversibly Modified Cys-thiol Groups The concentrated HCV envelope proteins sulphonated during the isolation procedure were subjected to a reducing treatment (incubation in the presence of 5 mM DTT in PBS) to convert the sulphonated Cys-thiol groups to free Cys-thiol groups. Irreversible Cys-thiol modification was performed by (i) incubation for 30 min in the presence of 20 mM iodoacetamide, or by (ii) incubation for 30 min in the presence of 5 mM N-ethylmaleimide (NEM) and 15 mM biotin-N-ethylmaleimide. The proteins were subsequently loaded on a size-exclusion chromatography column (Superdex G200, Pharmacia) equilibrated with PBS, 1% (v/v) Empigen in case of iodoacetarmide-blocking, or with PBS, 0.2% CHAPS in case of blocking with NEM and biotin-NEM. The eluted fractions were analyzed by SDS-PAGE and Western blotting. The fractions with a relative Mr ~29-~15 kD (based on SDS-PAGE migration) were pooled, concentrated and, to force virus-like particle formation, loaded on a Superdex G200 column equilibrated with PBS, 3% (w/v) betain. The fractions were pooled, concentrated and desalted to PBS, 0.5% (w/v) betain in case of iodoacetamide-blocking, or with PBS, 0.05% CHAPS in case of blocking with NEM and biotin-NEM.

VLP-formation of HCV Envelope Proteins with Reversibly Modified Cys-thiol Groups The concentrated HCV envelope proteins sulphonated during the isolation procedure were subjected to a reducing treatment (incubation in the presence of 5 mM DTT in PBS) to convert the sulphonated Cys-thiol groups to free Cys-thiol groups. Reversible Cys-thiol modification was performed by incubation for 30 min in the presence of dithiodipyridine (DTDP), dithiocarbamate (DTC) or cysteine. The proteins were subsequently loaded on a size-exclusion chromatography column (Superdex G200, Pharmacia) equilibrated with PBS, 1% (v/v) Empigen. The eluted fractions were analyzed by SDS-PAGE and Western blotting. The fractions with a relative Mr ~29-~15 kD (based on SDS-PAGE migration) were pooled, concentrated and loaded on Superdex G200, equilibrated with PBS, 3% (w/v) betain, to enforce virus like particle formation (VLP). The fractions were pooled, concentrated and desalted to PBS, 0.5% (w/v) betain.

The elution profiles of size-exclusion chromatography in PBS, 3% (w/v) betain to obtain VLPs of *H. polymorpha*-expressed E2-H6 are shown in FIG. 46 (sulphonated) and FIG. 47 (alkylated with iodoacetamide).

The elution profiles of size-exclusion chromatography in PBS, 3% (w/v) betain to obtain to VLPs of *H. polymorpha*-expressed E1 are shown in FIG. 48 (sulphonated) and FIG. 49 (alkylated with iodoacetamide). The resulting VLPs were analyzed by SDS-PAGE and western blotting as shown in FIG. 50.

Size-analysis of VLPs Formed by *H. Polymorpha*-expressed HCV Envelope Proteins

The VLP particle size was determined by Dynamic Light Scattering. For the light-scattering experiments, a particle-size analyzer (Model Zetasizer 1000 HS, Malvern Instruments Ltd., Malvern, Worcester UK) was used which was controlled by photon correlation spectroscopy (PCS) software. Photon correlation spectroscopy or dynamic light scattering (DLS) is an optical method that measures brownian motion and relates this to the size of particles. Light from a continuous, visible laser beam is directed through an ensemble of macromolecules or particles in suspension and moving under brownian motion. Some of the laser light is scattered by the particles and this scattered light is measured by a photomultiplier. Fluctuations in the intensity of scattered light are converted into electrical pulses which are fed into a correlator. This generates the autocorrelation function which is passed to a computer where the appropriate data analysis is performed. The laser used was a 10 mW monochromatic coherent He—Ne laser with a fixed wavelength of 633 nm. For each sample, three to six consecutive measurements were taken.

The results of these experiments are summarized in Table 5.

TABLE 5

Results of dynamic light scattering analysis on the indicated VLP-compositions of HCV envelope proteins expressed by *H. polymorpha*. The VLP particle sizes are given as mean diameter of the particles.

| Cys-thiol modification | E1-H6 | E2-VIEGR-H6 | E1 |
|---|---|---|---|
| sulphonation | 25-45 nm | 20 nm | 20-26 nm |
| alkylation (iodoacetamide) | 23-56 nm | 20-56 nm | 21-25 nm |

The observation that sulphonated HCV E1 derived from *H. polymorpha* still forms particles with a size in the same range as alkylated HCV E1 from *Hansenula* is surprising. Such an effect was not expected since the high (up to 8 Cys-thiol groups can be modified on HCV E1) net increase of negative charges as a consequence of sulphonation should induce an ionic repulsion between the subunits. The other reversible cysteine modifying agents tested also allowed particle formation, the HCV E1 produced in this way, however, proved to be less stable than the sulphonated material, resulting in disulfide-based aggregation of the HCV E1. In order to use these other reversible blockers, further optimization of the conditions is required.

Example 21

Antigenic Equivalence of *Hansenula*-produced HCV E1-H6 and HCV E1 Produced by Vaccinia-infected Mammalian Cells The reactivity of *Hansenula*-produced HCV E1-H6 with sera from HCV chronic carriers was compared to the reactivity of HCV E1 produced by HCV-recombinant *vaccinia* virus-infected mammalian cells as described by Depla et al. in WO 99/67285. Both HCV-E1 preparations tested consisted of VLP's wherein the HCV E1 proteins were alkylated with NEM and biotin-NEM. The reactivities of both HCV E1 VLP-preparations with sera from HCV chronic carriers was determined by ELISA. The results are summarized in Table 6. As can be derived from Table 6, no differences in reactivity were noted between HCV E1 expressed in HCV-recombinant *vaccinia* virus-infected mammalian cells and HCV E1 expressed in *H. polymorpha*.

TABLE 6

Antigenicity of E1 produced in a mammalian cell culture or produced in *H. polymorpha* were evaluated on a panel of sera from human HCV chronic carriers. For this purpose biotinylated E1 was bound to streptavidin coated ELISA plates. Thereafter human sera were added at a 1/20 dilution and bound immunoglobulins from the sera bound to E1 were detected with a rabbit-anti-human IgG-Fc specific secondary antibody labeled with peroxidase. Results are expressed as OD-values. The average values are the averages of the OD-values of all serum samples tested.

| Serum | *Hansenula* | mammalian | Serum | *Hansenula* | mammalian |
|---|---|---|---|---|---|
| 17766 | 1.218 | 1.159 | 55337 | 1.591 | 1.416 |
| 17767 | 1.513 | 1.363 | 55348 | 1.392 | 1.261 |
| 17777 | 0.806 | 0.626 | 55340 | 1.202 | 0.959 |
| 17784 | 1.592 | 1.527 | 55342 | 1.599 | 1.477 |
| 17785 | 1.508 | 1.439 | 55345 | 1.266 | 1.428 |
| 17794 | 1.724 | 1.597 | 55349 | 1.329 | 1.137 |
| 17798 | 1.132 | 0.989 | 55350 | 1.486 | 1.422 |
| 17801 | 1.636 | 1.504 | 55352 | 0.722 | 1.329 |
| 17805 | 1.053 | 0.944 | 55353 | 1.065 | 1.157 |
| 17810 | 1.134 | 0.999 | 55354 | 1.118 | 1.092 |
| 17819 | 1.404 | 1.24 | 55355 | 0.754 | 0.677 |
| 17820 | 1.308 | 1.4 | 55362 | 1.43 | 1.349 |
| 17826 | 1.163 | 1.009 | 55365 | 1.612 | 1.608 |
| 17827 | 1.668 | 1.652 | 55368 | 0.972 | 0.959 |
| 17849 | 1.595 | 1.317 | 55369 | 1.506 | 1.377 |
| 55333 | 1.217 | 1.168 | average | 1.313 | 1.245 |

Example 22

Immunogenic Equivalence of *Hansenula*-produced HCV E1-H6 and HCV E1 Produced by Vaccinia-infected Mammalian Cells The immunogenecity of *Hansenula*-produced HCV E1-H6 was compared to the immunogenecity of HCV E1 produced by HCV-recombinant *vaccinia* virus-infected mammalian cells as described by Depla et al. in WO99/67285. Both HCV-E1 preparations tested consisted of VLP's wherein the HCV E1 proteins were alkylated with iodoacetamide. Both VLP preparations were formulated with alum and injected in Balb/c mice (3 intramuscular/subcutaneous injections with a three week interval between each and each consisting of 5 µg E1 in 125 µl containing 0.13% Alhydrogel, Superfos, Denmark). Mice were bled ten days after the third immunization.

Results of this experiment are shown in FIG. 51. For the top part of FIG. 51, antibodies raised following immunization with VLPs of E1 produced in mammalian cells were determined. Antibody titers were determined by ELISA (see Example 21) wherein either E1 produced in mammalian cells ("M") or *Hansenula*-produced E1 ("H") were coated directly on the ELISA solid support whereafter the ELISA plates were blocked with casein. For the bottom part of FIG. 51, antibodies raised following immunization with VLPs of *Hansenula*-produced E1 were determined. Antibody titers were determined by ELISA (see Example 21) wherein either E1 produced in mammalian cells ("M") or *Hansenula*-produced E1 ("H") were coated directly on the ELISA solid support whereafter the ELISA plates were blocked with casein.

The antibody titers determined were end point titers. The end point titer is determined as the dilution of serum resulting in an OD (as determined by ELISA) equal to two times the mean of the background of the assay.

FIG. 51 shows that no significant differences were observed between the immunogenic properties of both E1-compositions and that the determined antibody titers are independent of the antigen used in the ELISA to perform the end point titration.

The yeast-derived HCV E1 induced upon vaccination a protective response similar to the protective response obtained upon vaccination with alkylated HCV E1 derived from mammalian cell culture. The latter response was able to prevent chronic evolution of HCV after an acute infection.

Example 23

Antigenic and Immunogenic Profile of *Hansenula*-produced HCV E1-H6 which is Sulphonated The reactivity of *Hansenula*-produced HCV E1-H6 with sera from HCV chronic carriers was compared to the reactivity of HCV E1 produced by HCV-recombinant *vaccinia* virus-infected mammalian cells as described by Depla et al. in WO 99/67285. Both HCV-E1 preparations tested consisted of VLP's wherein the *Hansenula*-produced HCV E1 proteins were sulphonated and the HCV E1 produced by mammalian cells was alkylated. The results are given in Table 7. Although the overall (average) reactivity was identical, some major differences were noted for individual sera. This implies that the sulphonated material presents at least some of its epitopes in a way different from alkylated HCV E1.

The immunogenecity of *Hansenula*-produced HCV E1-H6 which was sulphonated was compared to the immunogenecity of *Hansenula*-produced HCV E1-H6 which was alkylated. Both HCV-E1 preparations tested consisted of VLP's. Both VLP preparations were formulated with alum and injected in Balb/c mice (3 intramuscular/subcutaneous injections with a three week interval between each and each consisting of 5 µg E1 in 125 µl containing 0.13% Alhydrogel, Superfos, Denmark). Mice were bled ten days after the third immunization.

Antibody titers were determined similarly as described in Example 22. Surprisingly, immunization with sulphonated material resulted in higher antibody titers, regardless of the antigen used in ELISA to assess these titers (FIG. 51; top panel: titration of antibodies raised against alkylated E1; bottom panel: titration of antibodies raised against sulphonated E1; "A": alkylated E1 coated on ELISA plate; "S": sulphonated E1 coated on ELISA plate). However, in this experiment individual titers are different dependent on the antigen used for analysis which confirms the observation noted with sera from HCV patients. Consequently, HCV E1 wherein the cysteine thiol-groups are modified in a reversible way may be more immunogenic and thus have an increased potency as a vaccine protecting against HCV (chronic infection). In addition thereto, induction of a response to neo-epitopes induced by irreversible blocking is less likely to occur.

TABLE 7

Antigenicity of alkylated E1 (produced in mammalian cell culture) or sulphonated E1-H6 (produced in *H. polymorpha*) was evaluated on a panel of sera from human HCV chronic carriers ("patient sera") and a panel of control sera ("blood donor sera"). To this purpose E1 was bound to ELISA plates, after which the plates were further saturated with casein. Human sera were added at a 1/20 dilution and bound immunoglobulins were detected with a rabbit-anti-human IgG-Fc specific secondary antibody labeled with peroxidase. Results are expressed as OD-values. The average values are the averages of the OD-values of all serum samples tested.

| patient sera | | | blood donor sera | | |
|---|---|---|---|---|---|
| sernr | *Hansenula* | mammalian | sernr | *Hansenula* | mammalian |
| 17766 | 0.646 | 0.333 | F500 | 0.055 | 0.054 |
| 17777 | 0.46 | 0.447 | F504 | 0.05 | 0.05 |
| 17785 | 0.74 | 0.417 | F508 | 0.05 | 0.054 |
| 17794 | 1.446 | 1.487 | F510 | 0.05 | 0.058 |
| 17801 | 0.71 | 0.902 | F511 | 0.05 | 0.051 |
| 17819 | 0.312 | 0.539 | F512 | 0.051 | 0.057 |
| 17827 | 1.596 | 1.576 | F513 | 0.051 | 0.052 |
| 17849 | 0.586 | 0.964 | F527 | 0.057 | 0.054 |
| 55333 | 0.69 | 0.534 | average | 0.052 | 0.054 |
| 55338 | 0.461 | 0.233 | | | |
| 55340 | 0.106 | 0.084 | | | |
| 55345 | 1.474 | 1.258 | | | |
| 55352 | 1.008 | 0.668 | | | |
| 55355 | 0.453 | 0.444 | | | |
| 55362 | 0.362 | 0.717 | | | |
| 55369 | 0.24 | 0.452 | | | |
| average | 0.706 | 0.691 | | | |

Example 24

Identical Antigenic Reactivity of *Hansenula*-produced HCV E1-H6 and HCV E1 Produced by Vaccinia-infected Mammalian Cells with Sera from Vaccinated Chimpanzees The reactivities of the E1 produced by HCV-recombinant *vaccinia* virus-infected mammalian cells and the E1-H6 produced by *Hansenula* (both alkylated) with sera from vaccinated chimpanzees and with monoclonal antibodies were compared. Thereto, said E1 proteins were coated directly to ELISA plates followed by saturation of the plates with casein. The end point titers of antibodies binding the E1 proteins coated to the ELISA plates was determined for chimpanzee sera and for specific murine monoclonal antibodies, all obtained from animals immunized with E1 produced by mammalian cells. End point titer determination was done as described in Example 22. The murine monoclonal antibodies used were IGH201 (see Example 15), IGH198 (IGH198=23C12 in Maertens et al. in WO96/04385), IGH203 (IGH203=15G6 in Maertens et al. in WO96/04385) and IGH202 (IGH202=3F3 in Maertens et al. in WO99/50301).

As can be derived from FIG. 53, the reactivities of 7 different chimpanzee are identical when tested with E1 protein produced by either *Hansenula* or mammalian cells. The reactivities of the monoclonal antibodies against HCV E1 are also almost equal. Two of the chimpanzees (Yoran and Marti) were involved in a prophylactic vaccine study and were able to clear an acute infection upon challenge while a control animal did not clear the infection. The five other chimpanzees (Ton, Phil, Marcel, Peggy, Femma) were involved in therapeutic vaccination studies and showed a reduction in liver damage, as measured by ALT in serum and/or histological activity index on liver biopsy, upon the HCV E1 immunizations.

The results obtained in this experiment are clearly different from the findings of Mustilli and coworkers (Mustilli, A. C. et al. 1999) who expressed the HCV E2 protein both in *Saccharomyces cerevisiae* and *Kluyveromyces lactis*. The purified yeast-produced E2 was, however, different from the HCV E2 produced by mammalian (CHO) cells in that a lower reactivity was observed with sera from chimpanzees immunized with HCV E2 produced by mammalian cells while reactivity with monoclonal antibodies was higher for the yeast-produced HCV E2.

Example 25

Glycoprofiling of HCV E1 by Fluorophore-assisted Carbohydrote Electrophoresis (FACE)

The glycosylation profiles were compared of *Hansenula*-produced HCV E1 and HCV E1 produced by HCV-recombinant *vaccinia* virus-infected mammalian cells as described by Depla et al. in WO99/67285. This was done by means of fluorophore-assisted carbohydrate electrophoresis (FACE). Thereto, oligosaccharides were released from E1s produced by mammalian cells or *Hansenula* by peptide-N-glycosidase (PNGase F) and labelled with ANTS (the E1 proteins were alkylated with iodoacetamide prior to PNGase F digestion). ANTS-labeled oligosaccharides were separated by PAGE on a 21% polyacrylamide gel at a current of 15 mA at 4° C. for 2-3 h. From FIG. 54, it was concluded that the oligosaccharides on E1 produced by mammalian cells and E1-H6 produced by *Hansenula* migrate like oligomaltose with a degree of polymerization between 7 and 11 monosaccharides. This indicates that the *Hansenula* expression system surprisingly leads to an E1 protein which is not hyperglycosylated and which has sugar chains with a length similar to the sugar chains added to E1 proteins produced in mammalian cells.

REFERENCE LIST

Agaphonov, M. O., Beburov, M. Y., Ter Avanesyan, M. D., and Smirnov, V. N. (1995) A disruption-replacement approach for the targeted integration of foreign genes in *Hansenula polymorpha*. Yeast 11:1241-1247.

Agaphonov, M. O., Trushkina, P. M., Sohn, J. H., Choi, E. S., Rhee, S. K., and Ter Avanesyan, M. D. (1999) Vectors for rapid selection of integrants with different plasmid copy numbers in the yeast *Hansenula polymorpha* DL1. Yeast 15:541-551.

Alber, T. and Kawasaki, G. (1982) Nucleotide sequence of the triose phosphate isomerase gene of *Saccharomyces cerevisiae*. J. Mol Appl. Genet 1:419-434.

Ammerer, G. (1983) Expression of genes in yeast using the ADCI promoter. Methods Enzymol. 101:192-201.

Ballou, L., Hitzeman, R. A., Lewis, M. S., and Ballou, C. E. (1991) Vanadate-resistant yeast mutants are defective in protein glycosylation. Proc. Natl. Acad. Sci. U.S.A 88:3209-3212.

Beekman, N. J., Schaaper, W. M., Tesser, G. I., Dalsgaard, K., Kamstrup, S., Langeveld, J. P., Boshuizen, R. S., and Meloen, R. H. (1997) Synthetic peptide vaccines: palmitoylation of peptide antigens by a thioester bond increases immunogenicity. J. Pept. Res. 50:357-364.

Burns, J., Butler, J., and Whitesides, G. (1991) Selective reduction of disulfides by Tris (2-carboxyethyl)phosphine. J. Org. Chem. 56:2648-2650.

Cox, H., Mead, D., Sudbery, P., Eland, R. M., Mannazzu, I., and Evans, L. (2000) Constitutive expression of recombinant proteins in the methylotrophic yeast *Hansenula polymorpha* using the PMA1 promoter. Yeast 16:1191-1203.

Cregg, J. M. (1999) Expression in the methylotophic yeast *Pichia pastoris*. In Gene expression systems: using nature for the art of expression, J. M. Fernandez and J. P. Hoeffler, eds (San Diego: Academic Press), pp. 157-191.

Darbre, A. (1986) *Practical protein chemistry: a handbook*. Whiley & Sons Ltd.

Doms, R. W., Lamb, R. A., Rose, J. K., and Helenius, A. (1993) Folding and assembly of viral membrane proteins. Virology 193:545-562.

Elble, R. (1992) A simple and efficient procedure for transformation of yeasts. Biotechniques 13:18-20.

Gailit, J. (1993) Restoring free sulfhydryl groups in synthetic peptides. Anal. Biochem. 214:334-335.

Garson, J. A., Lubach, D., Passas, J., Whitby, K., and Grant, P. R. (1999) Suramin blocks hepatitis C binding to human hepatoma cells in vitro. J. Med. Virol. 57:238-242.

Gatzke, R., Weydemann, U., Janowicz, Z. A., and Hollenberg, C. P. (1995) Stable multicopy integration of vector sequences in *Hansenula polymorpha*. Appl. Microbiol. Biotechnol. 43:844-849.

Gellissen, G. (2000) Heterologous protein production in methylotrophic yeasts. Appl. Microbiol. Biotechnol. 54:741-750.

Grakoui, A., Wychowski, C., Lin, C., Feinstone, S. M., and Rice, C. M. (1993) Expression and identification of hepatitis C virus polyprotein cleavage products. J. Virol. 67:1385-1395.

Heile, J. M., Fong, Y. L., Rosa, D., Berger, K., Saletti, G., Campagnoli, S., Bensi, G., Capo, S., Coates, S., Crawford, K., Dong, C., Wininger, M., Baker, G., Cousens, L., Chien, D., Ng, P., Archangel, P., Grandi, G., Houghton, M., and Abrignani, S. (2000) Evaluation of hepatitis C virus glycoprotein E2 for vaccine design: an endoplasmic reticulum-retained recombinant protein is superior to secreted recombinant protein and DNA-based vaccine candidates. J. Virol. 74:6885-6892.

Helenius, A. (1994) How N-linked oligosaccharides affect glycoprotein folding in the endoplasmic reticulum. Mol Biol. Cell 5:253-265.

Hermanson, G. T. (1996) *Bioconjugate techniques*. San Diego: Academic Press.

Herscovics, A. and Orlean, P. (1993) Glycoprotein biosynthesis in yeast. FASEB J. 7:540-550.

Hijikata, M., Kato, N., Ootsuyama, Y., Nakagawa, M., and Shimotohno, K. (1991) Gene mapping of the putative structural region of the hepatitis C virus genome by in vitro processing analysis. Proc. Natl. Acad. Sci. U.S.A 88:5547-5551.

Hitzeman, R. A., Clarke, L., and Carbon, J. (1980) Isolation and characterization of the yeast 3-phosphoglycerokinase gene (PGK) by an immunological screening technique. J. Biol. Chem. 255:12073-12080.

Hollenberg, C. P. and Gellissen, G. (1997) Production of recombinant proteins by methylotrophic yeasts. Curr. Opin. Biotechnol. 8:554-560.

Holmgren, A. (1979) Thioredoxin catalyzes the reduction of insulin disulfides by dithiothreitol and dihydrolipoamide. J. Biol. Chem. 254:9627-9632.

Jayabaskaran, C., Davison, P. F., and Paulus, H. (1987) Facile preparation and some applications of an affinity matrix with a cleavable connector arm containing a disulfide bond. Prep. Biochem. 17:121-141.

Julius, D., Brake, A., Blair, L., Kunisawa, R., and Thorner, J. (1984) Isolation of the putative structural gene for the lysine-arginine-cleaving endopeptidase required for processing of yeast prepro-alpha-factor. Cell 37:1075-1089.

Kalef, E., Walfish, P. G., and Gitler, C. (1993) Arsenical-based affinity chromatography of vicinal dithiol-containing proteins: purification of L1210 leukemia cytoplasmic proteins and the recombinant rat c-erb A beta 1 T3 receptor. Anal. Biochem. 212:325-334.

Kato, N., Ootsuyama, Y., Tanaka, T., Nakagawa, M., Nakazawa, T., Muraiso, K., Ohkoshi, S., Hijikata, M., and Shimotohno, K. (1992) Marked sequence diversity in the putative envelope proteins of hepatitis C viruses. Virus Res. 22:107-123.

Kawasaki, G. and Fraenkel, D. G. (1982) Cloning of yeast glycolysis genes by complementation. Biochem. Biophys. Res. Commun. 108:1107-1122.

Klebe, R. J., Harriss, J. V., Sharp, Z. D., and Douglas, M. G. (1983) A general method for polyethylene-glycol-induced genetic transformation of bacteria and yeast. Gene 25:333-341.

Kumar, N., Kella, D., and Kinsella, J. E. (1985) A method for the controlled cleavage of disulfide bonds in proteins in the absence of denaturants. J. Biochem. Biophys. Methods 11:251-263.

Kumar, N., Kella, D., and Kinsella, J. E. (1986) Anomalous effects of denaturants on sulfitolysis of protein disulfide bonds. Int. J. Peptide Prot. Res. 28:586-592.

Maertens, G. and Stuyver, L. (1997) Genotypes and genetic variation of hepatitis C virus. In The molecular medicine of viral hepatitis, T. J. Harrison and A. J. Zuckerman, eds John Wiley & Sons), pp. 183-233.

Major, M. E. and Feinstone, S. M. (1997) The molecular virology of hepatitis C. Hepatology 25:1527-1538.

Mustilli, A. C., Izzo, E., Houghton, M., and Galeotti, C. L. (1999) Comparison of secretion of a hepatitis C virus glycoprotein in *Saccharomyces cerevisiae* and *Kluyveromyces lactis*. Res. Microbiol. 150:179-187.

Nagai, K. and Thogersen, H. C. (1984) Generation of beta-globin by sequence-specific proteolysis of a hybrid protein produced in *Escherichia coli*. Nature 309:810-812.

Nielsen, P. E. (2001) Targeting double stranded DNA with peptide nucleic acid (PNA). Curr Med Chem 8:545-550.

Okabayashi, K., Nakagawa, Y., Hayasuke, N., Ohi, H., Miura, M., Ishida, Y., Shimizu, M., Murakami, K., Hirabayashi, K., Minamino, H., and. (1991) Secretory expression of the human serum albumin gene in the yeast, *Saccharomyces cerevisiae*. J. Biochem. (Tokyo) 110:103-110.

Orum, H. and Wengel, J. (2001) Locked nucleic acids: a promising molecular family for gene-function analysis and antisense drug development. Curr Opin. Mol. Ther. 3:239-243.

Padgett, K. A. and Sorge, J. A. (1996) Creating seamless junctions independent of restriction sites in PCR cloning. Gene 168:31-35.

Pedersen, J., Lauritzen, C., Madsen, M. T., and Weis, D. S. (1999) Removal of N-terminal polyhistidine tags from recombinant proteins using engineered aminopeptidases. Protein Expr. Purif. 15:389-400.

Pomroy, N. C. and Deber, C. M. (1998) Solubilization of hydrophobic peptides by reversible cysteine PEGylation. Biochem. Biophys. Res. Commun. 245:618-621.

Raymond, C. K. (1999) Recombinant protein expression in *Pichia methanolica*. In Gene expression systems: using nature for the art of expression, J. M. Fernandez and J. P. Hoeffler, eds (San Diego: Academic Press), pp. 193-209.

Rein, A., Ott, D. E., Mirro, J., Arthur, L. O., Rice, W., and Henderson, L. E. (1996) Inactivation of murine leukemia virus by compounds that react with the zinc finger in the viral nucleocapsid protein. J. Virol. 70:4966-4972.

Roggenkamp, R., Hansen, H., Eckart, M., Janowicz, Z., and Hollenberg, C. P. (1986) Transformation of the methylotrophic yeast *Hansenula polymorpha* by autonomous replication and integration vectors. Mol Gen Genet 202: 302-308.

Rosa, D., Campagnoli, S., Moretto, C., Guenzi, E., Cousens, L., Chin, M., Dong, C., Weiner, A. J., Lau, J. Y., Choo, Q. L., Chien, D., Pileri, P., Houghton, M., and Abrignani, S. (1996) A quantitative test to estimate neutralizing antibodies to the hepatitis C virus: cytofluorimetric assessment of envelope glycoprotein 2 binding to target cells. Proc. Natl. Acad. Sci. U.S.A 93:1759-1763.

Rose, J. K. and Doms, R. W. (1988) Regulation of protein export from the endoplasmic reticulum. Annu. Rev. Cell Biol. 4:257-288.

Russell, D. W., Smith, M., Williamson, V. M., and Young, E. T. (1983) Nucleotide sequence of the yeast alcohol dehydrogenase II gene. J. Biol. Chem. 258:2674-2682.

Russell, P. R. (1983) Evolutionary divergence of the mRNA transcription initiation mechanism in yeast. Nature 301: 167-169.

Russell, P. R. (1985) Transcription of the triose-phosphate-isomerase gene of *Schizosaccharomyces pombe* initiates from a start point different from that in *Saccharomyces cerevisiae*. Gene 40:125-130.

Russell, P. R. and Hall, B. D. (1983) The primary structure of the alcohol dehydrogenase gene from the fission yeast *Schizosaccharomyces pombe*. J. Biol. Chem. 258:143-149.

Sambrook, J., Fritsch, E. F., and Maniatis, T. (1989) *Molecular Cloning: A Laboratory Manual*. Cold Spring Harbor Laboratory Press.

Singh, R. and Kats, L. (1995) Catalysis of reduction of disulfide by selenol. Anal. Biochem. 232:86-91.

Sohn, J. H., Choi, E. S., Kang, H. A., Rhee, J. S., and Rhee, S. K. (1999) A family of telomere-associated autonomously replicating sequences and their functions in targeted recombination in *Hansenula polymorpha* DL-1. J. Bacteriol. 181:1005-1013.

Stevens, R. C. (2000) Design of high-throughput methods of protein production for structural biology. Structure. Fold. Des 8:R177-R185.

Stuyver, L., van Arnhem, W., Wyseur, A., Hernandez, F., Delaporte, E., and Maertens, G. (1994) Classification of hepatitis C viruses based on phylogenetic analysis of the envelope 1 and nonstructural 5B regions and identification of five additional subtypes. Proc. Natl. Acad. Sci. U.S.A 91:10134-10138.

Sugrue, R. J., Cui, T., Xu, Q., Fu, J., and Chan, Y. C. (1997) The production of recombinant dengue virus E protein using *Escherichia coli* and *Pichia pastoris*. J. Virol. Methods 69:159-169.

Thakur, M. L., DeFulvio, J., Richard, M. D., and Park, C. H. (1991) Technetium-99m labeled monoclonal antibodies: evaluation of reducing agents. Int. J. Rad. Appl. Instrum. B 18:227-233.

Vingerhoeds, M. H., Haisma, H. J., Belliot, S. O., Smit, R. H., Crommelin, D. J., and Storm, G. (1996) Immunoliposomes as enzyme-carriers (immuno-enzymosomes) for antibody-directed enzyme prodrug therapy (ADEPT): optimization of prodrug activating capacity. Pharm. Res. 13:604-610.

Wahlestedt, C., Salmi, P., Good, L., Kela, J., Johnsson, T., Hokfelt, T., Broberger, C., Porreca, F., Lai, J., Ren, K., Ossipov, M., Koshkin, A., Jakobsen, N., Skouv, J., Oerum, H., Jacobsen, M. H., and Wengel, J. (2000) Potent and nontoxic antisense oligonucleotides containing locked nucleic acids. Proc Natl Acad Sci U S A 97:5633-5638.

Weydemann, U., Keup, P., Piontek, M., Strasser, A. W., Schweden, J., Gellissen, G., and Janowicz, Z. A. (1995) High-level secretion of hirudin by *Hansenula polymorpha*—authentic processing of three different preprohirudins. Appl. Microbiol. Biotechnol. 44:377-385.

The invention claimed is:

1. A recombinant nucleic acid comprising a nucleotide sequence encoding a protein comprising a leader peptide defined by the amino acid sequence MRSLLILVLCFLP-LAALG (SEQ ID NO:99) joined to an HCV envelope protein or to the sequence of SEQ ID NO:2 or a corresponding sequence from another HCV.

2. The recombinant nucleic acid according to claim 1 wherein said leader peptide is joined to a protein of the formula $[(A1)_a-(PS1)_b-(A2)_c]$-HCVENV-$[(A3)_d-(PS2)_e-(A4)_f]$ wherein:

A1, A2, A3 and A4 are adaptor peptides which can be different or the same,

PS1 and PS2 are processing sites which can be the different or the same,

HCVENV is the HCV envelope protein or to the sequence of SEQ ID NO:2 or a corresponding sequence from another HCV, a, b, c, d, e and f are 0 or 1, and wherein, optionally, A1 and/or A2 are part of PS1 and/or wherein A3 and/or A4 are part of PS2.

3. The recombinant nucleic acid according to claim 2 wherein A has an amino acid sequence chosen from SEQ ID NOs:63-65, 70-72 and 74-82, wherein PS has an amino acid sequence chosen from SEQ ID NOs:66-68 and 83-84 or wherein PS is a dibasic site chosen from Lys-Lys, Arg-Arg, Lys-Arg and Arg-Lys or the monobasic site Lys, and wherein HCVENV is chosen from SEQ ID NOs:85-98 and fragments thereof.

4. The recombinant nucleic acids according to claim 1 or 2 further comprising regulatory elements allowing expression of said protein in a eukaryotic host cell.

5. A vector comprising the recombinant nucleic acid according to claim 1.

6. The vector according to claim 5 which is an expression vector.

7. The vector according to claim 5 or 6 which is an autonomously replicating vector or an integrative vector.

8. The vector according to claim 6 which is chosen from SEQ ID NOs: 20, 21, 32, 35, 36, 39, 40, 49 and 50.

9. An isolated yeast cell comprising the recombinant nucleic acid according to claim 1.

10. An isolated yeast cell according to claim 9, which is expressing the recombinant nucleic acid.

11. An isolated yeast cell according to claim 9 or 10 which is expressing the protein characterized by the structure CL-$[(A1)_a-(PS1)_b-(A2)_c]$-HCVENV$[(A3)_d-(PS2)_e-(A4)_f]$ wherein:

CL is the leader peptide,

A1, A2, A3 and A4 are adaptor peptides which can be different or the same,

PS1 and PS2 are processing sites which can be the different or the same,

HCVENV is a HCV envelope protein or to the sequence of SEQ ID NO:2 or a corresponding sequence from another HCV, a, b, c, d, e and f are 0 or 1 and wherein, optionally, A1 and/or A2 are part of PS1 and/or wherein A3 and/or A4 are part of PS2.

12. An isolated yeast cell according to any of claims 9 to 10 which is translocating the protein CL-$[(A1)_a-(PS1)_b(A2)_c]$-HCVENV-$[(A3)_d-(PS2)_e-(A4)_f]$ to the endoplasmic reticulum upon removal of the CL peptide wherein said protein and said CL peptide are derived from the protein characterized by the structure CL-[(A1)a-(PS1)b-(A2)c]-HCVENV-[(A3)d-(PS2)e-(A4)f]

wherein:

CL is the leader peptide,

A1, A2, A3 and A4 are adaptor peptides which can be different or the same,

PS1 and PS2 are processing sites which can be the different or the same,

HCVENV is a HCV envelope protein or to the sequence of SEQ ID NO:2 or a corresponding sequence from another HCV, a, b, c, d, e and f are 0 or 1, and wherein, optionally, A1 and/or A2 are part of PS1 and/or wherein A3 and/or A4 are part of PS2.

13. An isolated yeast cell according to any of claims 9 to 10 which is processing the processing sites PS1 and/or P82 in said protein translocated to the endoplasmic reticulum.

14. An isolated yeast cell according to claim 13 which is N-glycosylating said protein translocated to the endoplasmic reticulum and processed at said sites PS1 and/or PS2.

15. An isolated yeast cell according to any of claims 9 to 10 which is N-glycosylating said protein translocated to the endoplasmic reticulum.

16. The yeast cell according to any one of claims 9-10 which is a *Saccharomyces* cell, a *Schizosaccharomyces* cell, a *Kluyveromyces* cell, a *Yarrowia* cell, a *Hansenula* cell, a *Pichia* cell, an *Aspergillus* cell, a *Neurospora* cell, or a *Schwanniomyces* cell, or a mutant cell derived from any thereof.

17. The yeast cell according to claim 16 wherein said *Saccharomyces* cell is chosen from a *Saccharomyces cerevisiae* cell, a *Saccharomyces kluyveri* cell, or a *Saccharomyces uvarum* cell; wherein said *Schizosaccharomyces* cell is a *Schizosaccharomyces pombe* cell; wherein said *Kluyveromyces* cell is a *Kluyveromyces lactis* cell; wherein said *Yarrowia* cell is a *Yarrowia lipolytica* cell; wherein said *Hansenula* cell is a *Hansenula polymorpha* cell; wherein said *Pichia* cell is a *Pichia pastoris* cell; wherein said *Neurospora* cell is a *Neurospora crassa* cell; wherein said *Schwanniomyces* cell is a *Schwanniomyces occidentalis* cell.

18. A method for producing a HCV envelope protein or to the sequence of SEQ ID NO:2 or a corresponding sequence from another HCV in a yeast cell, said method comprising transforming said yeast cell with the recombinant nucleic acid according to any of claims 1 to 2 or with the vector according to any of claims 5 to 8, and expressing said protein comprising the leader peptide joined to a HCV envelope protein or to the sequence of SEQ ID NO:2 or a corresponding sequence from another HCV in said yeast cell.

19. The method according to claim 18 wherein said yeast cell is translocating the protein CL-[(A1)$_a$-(PS1)$_b$-(A2)$_c$]-HCVENV-[(A3)$_d$-(PS2)$_e$-(A4)$_f$] to the endoplasmic reticulum upon removal of the CL peptide wherein said protein and said CL peptide are derived from the protein characterized by the structure CL-[(A1 )$_a$-(PS1)$_b$-(A2)$_c$]-HCVENV-[(A3)$_d$-(PS2)$_e$-(A4)$_f$]

wherein:

CL is a leader peptide,

A1, A2, A3 and A4 are adaptor peptides which can be different or the same,

PS1 and P82 are processing sites which can be the different or the same,

HCVENV is a HCV envelope protein or to the sequence of SEQ ID NO:2 or a corresponding sequence from another HCV, a, b, a, d, e and f are 0 or 1, and wherein, optionally, A1 and/or A2 are part of PS1 and/or wherein A3 and/or A4 are part of PS2.

20. The method according to claim 18 wherein said yeast cell is processing the processing sites PS1 and/or PS2 in said protein translocated to the endoplasmic reticulum.

21. The method according to claim 20 wherein said yeast cell is N-glycosylating said protein translocated to the endoplasmic reticulum and processed at said sites PS1 and/or PS2.

22. The method according to claim 18 further comprising in vitro processing of the processing sites PS1 and/or PS2.

23. The method according to claim 18 wherein said yeast cell is N-glycosylating said protein translocated to the endoplasmic reticulum.

24. The method according to claim 18 wherein said yeast cell is a *Saccharomyces* cell, a *Schizosaccharomyces* cell, a *Kluyveromyces* cell, a *Yarrowia* cell, a *Hansenula* cell, a *Pichia* cell, an *Aspergillus* cell, a *Neurospora* cell, or a *Schwanniomyces* cell, or a mutant cell derived from any thereof.

25. The method according to claim 18 further comprising cultivation of said yeast cells in a suitable medium to obtain expression of said protein.

26. The method according to claim 25 further comprising isolation of the expressed protein from a culture of said yeast cells, or from said yeast cells.

27. The method according to claims 26 wherein said isolation step involves lysis of said yeast cells in the presence of a chaotropic agent.

28. The method according to claim 26 wherein the cysteine thiol-groups in the isolated proteins are chemically modified and wherein said chemical modification is reversible or irreversible.

29. The method according to claim 25 involving heparin affinity chromatography.

30. A method for producing a HCV envelope protein or to the sequence of SEQ ID NO:2 or a corresponding sequence from another HCV in a yeast cell, said method comprising transforming said yeast cell with the recombinant nucleic acid according to any of claims 1 to 2 or with the vector according to any of claims 5 to 8, and expressing said protein characterized by the structure CL-[(A1)$_a$-(PS1)$_b$(A2)$_c$]-HCVENV-[(A3)$_d$-(PS2)$_e$-(A4)$_f$] in said host cell wherein:

CL is a leader peptide,

A1, A2, A3 and A4 are adaptor peptides which can be different or the same,

PS1 and PS2 are processing sites which can be the different or the same,

HCVENV is a HCV envelope protein or to the sequence of SEQ ID NO:2 or a corresponding sequence from another HCV, a, b, c, d, e and f are 0 or 1, and wherein, optionally, A1 and/or A2 are part of PS1 and/or wherein A3 and/or A4 are part of PS2.

31. A method for producing a HCV envelope protein or the sequence of SEQ ID NO: 2 or a corresponding sequence from another HCV in a yeast cell, said method comprising transforming said yeast cell with the vector according to claim 7, and expressing said protein comprising the leader peptide joined to a HCV envelope protein or to the sequence of SEQ ID NO: 2 or a corresponding sequence from another HCV in said yeast cell.

32. A method for producing a HCV envelope protein or the sequence of SEQ ID NO: 2 or a corresponding sequence from another HCV in a yeast cell, said method comprising transforming said yeast cell with the vector according to claim 7, and expressing said protein characterized by the structure CL-[(A1)a-(PS1)b-(A2)c]-HCVENV-[(A3)d-(PS2)e-(A4)f] in said yeast cell wherein:

CL is a leader peptide,

A1, A2, A3 and A4 are adaptor peptides which can be different or the same,

PS1 and PS2 are processing sites which can be the different or the same,

HCVENV is a HCV envelope protein or the sequence of SEQ ID NO: 2 or a corresponding sequence from another HCV, a, b, c, d, e and f are 0 or 1, and wherein, optionally, A1 and/or A2 are part of PS1 and/or wherein A3 and/or A4 are part of PS2.

* * * * *